US011261162B2

(12) United States Patent
Bozik et al.

(10) Patent No.: US 11,261,162 B2
(45) Date of Patent: *Mar. 1, 2022

(54) KV7 CHANNEL ACTIVATORS COMPOSITIONS AND METHODS OF USE

(71) Applicant: Knopp Biosciences LLC, Pittsburgh, PA (US)

(72) Inventors: Michael E. Bozik, Wexford, PA (US); Scott S. Harried, Sun Prairie, WI (US); Lynn Resnick, Pittsburgh, PA (US); George T. Topalov, Pittsburgh, PA (US); Justin K. Belardi, Pittsburgh, PA (US); Charles A. Flentge, Mars, PA (US); David A. Mareska, McMurray, PA (US); James S. Hale, Pittsburgh, PA (US)

(73) Assignee: KNOPP BIOSCIENCES, LLC, Pittsburgh, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/077,068

(22) Filed: Oct. 22, 2020

(65) Prior Publication Data

US 2021/0130299 A1 May 6, 2021

Related U.S. Application Data

(63) Continuation of application No. 16/358,642, filed on Mar. 19, 2019, now Pat. No. 10,851,067.

(60) Provisional application No. 62/697,198, filed on Jul. 12, 2018, provisional application No. 62/663,438, filed on Apr. 27, 2018, provisional application No. 62/644,902, filed on Mar. 19, 2018, provisional application No. 62/644,932, filed on Mar. 19, 2018.

(51) Int. Cl.
*C07D 235/30* (2006.01)
*C07D 471/04* (2006.01)
*C07D 405/04* (2006.01)

(52) U.S. Cl.
CPC ......... *C07D 235/30* (2013.01); *C07D 405/04* (2013.01); *C07D 471/04* (2013.01)

(58) Field of Classification Search
CPC .................................................. C07D 235/30
See application file for complete search history.

(56) References Cited

U.S. PATENT DOCUMENTS

| | | |
|---|---|---|
| 6,855,714 B2 | 2/2005 | Blume et al. |
| 7,501,447 B2 | 3/2009 | Liu et al. |
| 8,466,201 B2 | 6/2013 | Edwards et al. |
| 9,481,653 B2 | 11/2016 | Resnick et al. |
| 9,914,708 B2 | 3/2018 | Harried et al. |
| 10,385,025 B2 | 8/2019 | Resnick et al. |
| 10,851,067 B2 * | 12/2020 | Bozik ................. C07D 401/04 |
| 2008/0214613 A1 | 9/2008 | Renton et al. |
| 2011/0124858 A1 | 5/2011 | Iwata et al. |
| 2017/0114022 A1 | 4/2017 | Harried et al. |
| 2018/0148419 A1 | 5/2018 | Resnick et al. |

FOREIGN PATENT DOCUMENTS

| | | |
|---|---|---|
| EP | 2218718 A1 | 8/2010 |
| JP | 07072181 | 8/2015 |
| WO | 1996001833 A1 | 1/1996 |
| WO | 2004108712 A1 | 12/2004 |
| WO | 2009085230 A1 | 7/2009 |
| WO | 2010051819 A1 | 5/2010 |
| WO | 2010080503 A1 | 7/2010 |
| WO | 2012004698 A1 | 1/2012 |
| WO | 2012018668 A1 | 2/2012 |
| WO | 2016040952 A3 | 5/2016 |

OTHER PUBLICATIONS

Chemical Abstracts Registry No. 1298059-85-4, indexed in the Registry file on STN CAS Online May 20, 2011.
Chemical Abstracts Registry No. 1370729-32-0, indexed in the Registry file on STN CAS Online Apr. 27, 2012.
Chemical Abstracts Registry No. 1390407-52-9, indexed in the Registry file on STN CAS Online Aug. 13, 2012.
Chemical Abstracts Registry No. 1445709-80-7, indexed in the Registry file on STN CAS Online Jul. 19, 2013.
Chemical Abstracts Registry No. 689297-99-2, indexed in the Registry file on STN CAS Online Jun. 4, 2004.
Dadiboyena, et al. "Parallel synthesis of aminobenzimidazole-tethered thiazoles." Synthesis 44, No. 02 (2012): 215-218.
Ding Kejia et al: "Aryl-substituted aminobenzimidazoles targeting the hepatitis C virus internal ribosome entry site", Bioorganic & Medicinal Chemistry Letters, vol. 24, No. 14, May 14, 2014 (May 14, 2014), pp. 3113-3117, XP029033865, ISSN: 0960-894X, DOI: 10.1016/J.BMCL.2014.05.009; compounds 4ba, 4ca.
International Search Report and Written Opinion for PCT/US2015/050027 dated Mar. 2, 2016.
International Search Report and Written Opinion for PCT/US2017/059393 dated Feb. 28, 2018.
International Search Report and Written Opinion for PCT/US2019/023039 dated Jul. 29, 2019.
Internet Archive WayBack Machine, Dec. 4, 2011, https://web.archive.org/web/20111204050304/http://www.uorsy.com:80/screening.php—accessed Dec. 13, 2018.
PubChem CID 118938248, National Center for Biotechnology Information, Pub Chem Compound Database, CID=118938248, https://pubchem.ncbi.nlm.nih.gov/compound/118938248 (accessed Mar. 11, 2020); created Apr. 9, 2016.

(Continued)

*Primary Examiner* — Laura L Stockton
(74) *Attorney, Agent, or Firm* — Troutman Pepper Hamilton Sanders LLP

(57) ABSTRACT

Provided herein are optionally substituted benzoimidazol-1,2-yl amides, pharmaceutical compositions comprising a therapeutically effective amount of such compounds and a pharmaceutically acceptable excipient, and methods of treating Kv7 associated diseases, such as, epilepsy, amyotrophic lateral sclerosis, various types of pain, hyperexcitability, a dyskinesia, dystonia, mania and tinnitus with such compounds and pharmaceutical compositions.

20 Claims, No Drawings

(56) References Cited

OTHER PUBLICATIONS

PubChem CID 129075695, National Center for Biotechnology Information, Pub Chem Compound Database, CID=129075695, https://pubchem.ncbi.nlm.nih.gov/ compound/129075695 (accessed Mar. 11, 2020); created Aug. 4, 2017.
PubChem CID 129075701, National Center for Biotechnology Information, Pub Chem Compound Database, CID=129075701, https://pubchem.ncbi.nlm.nih.gov/ compound/129075701 (accessed Mar. 11, 2020); created Aug. 4, 2017.
PubChem CID 21428920, National Center for Biotechnology Information. PubChem Compound Database; CID=21428920, https://pubchem.ncbi.nlm.nih.gov/compound/21428920 (accessed Apr. 27, 2016), create date Dec. 5, 2007.
PubChem CID 47251124, National Center for Biotechnology Information. PubChem Compound Database; CID=47251124, https://pubchem.ncbi.nlm.nih.gov/compound/47251124 (accessed Apr. 27, 2016), create date Nov. 26, 2010.
PubChem CID 52655712, National Center for Biotechnology Information. PubChem Compound Database; CID=52655712, https://pubchem.ncbi.nlm.nih.gov/compound/52655712 (accessed Apr. 27, 2016), create date May 20, 2011.
PubChem CID 53531705, National Center for Biotechnology Information. PubChem Compound Database; CID=53531705, https://pubchem.ncbi.nlm.nih.gov/compound/53531705 (accessed Apr. 27, 2016), create date Dec. 3, 2011.
PubChem CID 60339539, National Center for Biotechnology Information. PubChem Compound Database; CID=60339539, https://pubchem.ncbi.nlm.nih.gov/compound/60339539 (accessed Apr. 27, 2016), create date Oct. 18, 2012.
PubChem CID 60339611, National Center for Biotechnology Information. PubChem Compound Database; CID=60339611, https://pubchem.ncbi.nlm.nih.gov/compound/60339611 (accessed Apr. 27, 2016), create date Oct. 18, 2012.
Pubchem. Substance Record for SID 128950369. Deposit Date: Dec. 4, 2011. [retrieved on Oct. 15, 2015]. Retrieved from the Internet. <URL: https://pubchem.ncbi.nlm.nih.gov/substance/128950369/version/1>. entire document.
Pubchem. Substance Record for SID 131669753. Deposit Date: Jan. 24, 2012. [retrieved on Nov. 30, 2015], Retrieved from the Internet. <URL: https://pubchem.ncbi.nlm.nih.gov/substance/131669753/version/1#section=To- p >. entire document.
Pubmed Compound Summary for CID 1111771, "N-(a-Ethylbenzimidazol-2-Yl)acetamide", U.S. National Library of Medicine, Jul. 10, 2005, pp. 1-8 (<https://pubchem.ncbi.nlm.nih.gov/compound/1111771>).
SciFinder Search 2. downloaded 2014.
SciFinder Search 3. downloaded 2014.
SciFinder Search. downloaded 2014.
Supplementary European Search Report and Written Opinion for EP 15840730.4 dated Dec. 22, 2017.
Uorsy, Internet Archive WayBack Machine, Dec. 4, 2011,—https://web.archive.org/web/20111204050304 http://www.uorsy.com:80/screening.php access Dec. 13, 2018.
Palumbo et al. "The Management and Outcomes of Pharmacological Treatments for Tinnitus" 2015, Current Neuropharmology 13:692-700.

* cited by examiner

KV7 CHANNEL ACTIVATORS COMPOSITIONS AND METHODS OF USE

CROSS-REFERENCE TO RELATED APPLICATIONS

The present application is a continuation of U.S. patent application Ser. No. 16/358,642 (U.S. Publication No. 2019-0284142 A1) filed Mar. 19, 2019, which claims the benefit of U.S. Provisional Application No. 62/644,902 filed Mar. 19, 2018 and U.S. Provisional Application No. 62/644,932 filed Mar. 19, 2018 and U.S. Provisional Application No. 62/663,438 filed Apr. 27, 2018 and U.S. Provisional Application No. 62/697,198 filed Jul. 12, 2018. The disclosures of each of these applications are incorporated herein by reference.

GOVERNMENT INTERESTS

This invention was made with United States Government support under Grant No. U44NS093160 awarded by the National Institute of Neurological Disorders and Stroke of the National Institutes of Health. The United States Government has certain rights in the invention.

SUMMARY

Potassium ($K^+$) channels, present on the plasma membranes of most cell types, are the most diverse class of all ion channels and are associated with a wide range of physiological functions including the regulation of the electrical properties of excitable cells. The primary pore-forming (a) subunits of these highly selective cation channels are divided into three primary structural classes based on the number of transmembrane (TM)-spanning regions and pore (P) regions: currently there are known to be 6TM/1P, 2TM/1P and 4TM/2P $K^+$ channels. The Kv7 genes (originally termed KCNQ, a name assigned by the HUGO Gene Nomenclature Committee (HGNC)) were assigned to a subfamily of voltage-gated $K^+$ channels by the International Union of Pharmacology (IUPHAR). The Kv7 subfamily consists of five homologous pore-forming a subunits, Kv7.1-7.5, that have a structure typical of voltage-gated $K^+$ channels with 6TM-spanning regions (S1-S6) flanked by intracellular N-terminal and C-terminal domains, a typical voltage-sensor domain located in S4 comprised of alternating positively-charged residues and a single P region between S5 and S6 of each subunit. The channels are formed as tetramers of the primary a subunits, either as homotetramers or heterotetramers. Neurons are known to express Kv7 channels comprised of Kv7.2-7.5α subunits. Some of these gene products may be exclusively neuronal while others, such as Kv7.4 and Kv7.5, can be found in other tissues such as smooth and skeletal muscle.

Native M-channels, and the corresponding macroscopic M-current, were first characterized in amphibian sympathetic neurons. M-channels were notable because they were slowly activating and non-inactivating, active at membrane potentials at or near the resting membrane potential of neurons and muscarinic cholinergic agonists produced a reduction in the M-current, demonstrating a direct and inhibitory link between G-protein coupled receptors (GPCRs) and a physiological $K^+$ current. It was not until the cloning of this subfamily of genes that the pharmacological and biophysical identity was established between Kv7.2/7.3 (and likely Kv7.5/7.3) heteromultimers and the elusive 'M'-channel, providing significant new evidence for their importance in neuronal regulation.

The distributions of these channels, both regionally and developmentally, as well as their biophysical characteristics, support their role in providing enduring resistance to depolarizing excitatory influences. Under physiological conditions, as was demonstrated with native M-channels, they can be very effective at regulating the sub-threshold excitability of certain neuronal populations with significant roles in regulating the frequency and ultimately the pattern of action potential discharge in many types of neurons. Their importance in neuronal regulation was punctuated by the discovery that neuronal Kv7 mutations lead to benign familial neonatal convulsions (BFNC), indicating that reduction or removal of the influence of Kv7.2 and Kv7.3 channels can dramatically alter neuronal excitability. Mutation analyses demonstrated their involvement in BFNC and suggested their utility as targets for anti-epileptic drugs (AEDs).

Unlike established pharmacological terminology for GPCRs, the mode of action of $K^+$ channel modulators, in particular compounds that activate the channel, is still being refined. The application of voltage-clamp techniques to the study of ion channel pharmacology enabled detailed biophysical studies on either whole-cell currents or single channels, allowing some characterization of the nature of compound-channel interactions but not preventing ongoing confusion around the terminology. The term opener or activator is commonly used throughout the literature but does not adequately describe the mode of action of all these 'positive modulator' compounds. In general, openers or activators are expected to increase the open probability of the channel or increase macroscopic current amplitude, but this nomenclature is really too simplistic. For example, retigabine, the first publicly disclosed Kv7 opener, has a complex and interesting profile in that it has inhibitory activity at higher membrane potentials. Neuronal Kv7 channel openers may work in concert with the activity of a channel over the 'normal' activation-voltage range and enhance currents without significantly affecting the activation threshold while others can significantly alter the activation threshold. In addition, some openers appear to remove the voltage-dependence of activation entirely. Whether these effects represent some continuum is currently unclear since the effects are often concentration-dependent. Clearly, the modes of interaction of compounds that can increase channel current are complex and in most cases not well understood and the implications of these profiles on neuronal responsiveness and systems physiology are also unclear. Retigabine is modestly potent, not highly specific, but it is a very effective opener of Kv7.2, Kv7.5 and heteromultimeric Kv7 channels. Its effects are characterized by a significant increase in channel current over a narrow voltage range. As mentioned above, at more positive voltages the opener is less effective and under some conditions channel current significantly decreases at more positive voltages relative to control currents (this 'crossover' voltage-dependence of opener action is a characteristic of many neuronal Kv7 channel openers). This effect is also concentration-dependent and is more pronounced at higher concentrations.

Provided herein are compounds that can be potent and/or at least biased for the Kv7.2/7.3 heteromultimer over the Kv7.4 homomultimer. These compounds may have reduced untoward side effects as compared to retigabine.

DETAILED DESCRIPTION

Before the present compositions and methods are described, it is to be understood that any invention is not limited to the particular processes, compositions, or methodologies described, as these may vary. Moreover, the processes, compositions, and methodologies described in particular embodiments are interchangeable. Therefore, for example, a composition, dosage regimen, route of administration, and so on described in a particular embodiment may be used in any of the methods described in other particular embodiments. It is also to be understood that the terminology used in the description is for the purpose of describing the particular versions or embodiments only, and is not intended to limit the scope of the present invention, which will be limited only by the appended claims. Unless clearly defined otherwise, all technical and scientific terms used herein have the same meanings as commonly understood by one of ordinary skill in the art. Although any methods similar or equivalent to those described herein can be used in the practice or testing of embodiments of the present invention, the preferred methods are now described. All publications and references mentioned herein are incorporated by reference. Nothing herein is to be construed as an admission that the invention is not entitled to antedate such disclosure by virtue of prior invention.

It must be noted that, as used herein, and in the appended claims, the singular forms "a" "an", and "the" include plural reference unless the context clearly dictates otherwise.

As used herein, the term "about" means plus or minus 10% of the numerical value of the number with which it is being used. Therefore, about 50% means in the range of 45%-55%. Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

"Administering," when used in conjunction with a therapeutic, means to administer a therapeutic directly into or onto a target tissue or to administer a therapeutic to a subject whereby the therapeutic positively impacts the tissue to which it is targeted. "Administering" a composition may be accomplished by oral administration, injection, infusion, absorption or by any method in combination with other known techniques. "Administering" may include the act of self-administration or administration by another person such as a healthcare provider or a device.

As used herein, the terms "comprising," "comprise," "comprises," and "comprised" are inclusive or open-ended and do not exclude additional, unrecited elements or method steps.

As used herein, the term "consists of" or "consisting of" means that the composition or method includes only the elements, steps, or ingredients specifically recited in the particular embodiment or claim.

As used herein, the term "consisting essentially of" or "consists essentially of" means that the composition or method includes only the specified materials or steps and those that do not materially affect the basic and novel characteristics of the claimed invention.

The term "improves" is used to convey that the present invention refers to the overall physical state of an individual to whom an active agent has been administered. For example, the overall physical state of an individual may "improve" if one or more symptoms of a condition, disease or disorder, such as a neurodegenerative disorder, are alleviated by administration of an active agent. "Improves" may also refer to changes in the appearance, form, characteristics, and/or physical attributes of tissue, or any combination thereof, to which it is being provided, applied, or administered.

The term "inhibit," "suppress," "decrease," "interfere," and/or "reduce" (and like terms) generally refers to the act of reducing, either directly or indirectly, a function, activity, or behavior relative to the natural, expected, or average or relative to current conditions.

As used herein, the phrase "Kv7 associated diseases" is a disease, disorder, or condition: associated with a mutation in the KCNQ2 gene; associated with a mutation in the KCNQ3 gene; associated with a mutation in the KCNQ4 gene; associated with a mutation in the KCNQ5 gene; associated with genes encoding Kv7 potassium channels; associated with a non-mutated Kv7 potassium channel, but dysfunctional Kv7 potassium channel; associated with the hyperexcitability of cells that are believed to cause the disease, disorder or condition; or a combination thereof. Regardless of causation, these Kv7 associated diseases, disorders or conditions can be treated by the activation of the Kv7 potassium channel, even though the Kv7 potassium channel may not be a direct or indirect cause of the disease, disorder or condition.

Examples of a Kv7 associated disorder in relation to a mutation in the KCNQ2 gene include but are not limited to benign familial neonatal seizures (BFNS) or KCNQ2 encephalopathy (also known as KCNQ2 neonatal epileptic encephalopathy). Examples of a Kv7 associated disorder in relation to a mutation in the KCNQ3 gene include but are not limited to BFNS or KCNQ3-related developmental disability. Examples of a Kv7 associated disorder in relation to a mutation in the KCNQ4 gene include but are not limited to autosomal dominant nonsyndromic hearing loss. Examples of a Kv7 associated disorder in relation to a mutation in the KCNQ5 gene include but are not limited to nonsyndromic intellectual disability or epileptic encephalopathy. Examples of a disorder associated with the hyperexcitability of cells that are believed to cause the disease, disorder or condition include but are not limited to focal clonic seizures, generalized tonic-clonic seizures, neuropathic pain, overactive bladder; or smooth muscle disorders, or a combination thereof.

In each of the embodiments disclosed herein, the compositions and methods may be utilized with or on a subject in need of such treatment, which may also be referred to as "in need thereof." As used herein, the phrase "in need thereof" means that the subject has been identified as having a need for the particular method or treatment and that the treatment has been given to the subject for that particular purpose.

As used herein, the term "therapeutic" means an agent utilized to treat, combat, ameliorate, or prevent, or any combination thereof, an unwanted condition, disorder or disease of a subject.

As used herein, the term "patient" and "subject" are interchangeable and may be taken to mean any living organism, which may be treated with compounds of the present invention. As such, the terms "patient" and "subject" may include, but are not limited to, any non-human mammal, primate or human. In some embodiments, the "patient" or "subject" is an adult, child, infant, or fetus. In some embodiments, the "patient" or "subject" is a human. In some embodiments, the "patient" or "subject" is a mammal, such as mice, rats, other rodents, rabbits, dogs, cats, swine, cattle, sheep, horses, primates, or humans.

The terms "therapeutically effective amount" or "therapeutic dose" as used herein are interchangeable and may refer to the amount of an active agent or pharmaceutical compound or composition that elicits a clinical, biological or medicinal response in a tissue, system, animal, individual or human that is being sought by a researcher, veterinarian, medical doctor or other clinical professional. A clinical, biological or medical response may include, for example, one or more of the following: (1) preventing a disease, condition or disorder in an individual that may be predisposed to the disease, condition or disorder but does not yet experience or display pathology or symptoms of the disease, condition or disorder, (2) inhibiting a disease, condition or disorder in an individual that is experiencing or displaying the pathology or symptoms of the disease, condition or disorder or arresting further development of the pathology and/or symptoms of the disease, condition or disorder, and (3) ameliorating a disease, condition or disorder in an individual that is experiencing or exhibiting the pathology or symptoms of the disease, condition or disorder or reversing the pathology and/or symptoms experience or exhibited by the individual.

The term "treat," "treated," or "treating" may be taken to mean prophylaxis of a specific disorder, disease or condition, alleviation of the symptoms associated with a specific disorder, disease or condition and/or prevention of the symptoms associated with a specific disorder, disease or condition. In some embodiments, the term refers to slowing the progression of the disorder, disease or condition or alleviating the symptoms associated with the specific disorder, disease or condition. In some embodiments, the term refers to alleviating the symptoms associated with the specific disorder, disease or condition. In some embodiments, the term refers to alleviating the symptoms associated with the specific disorder, disease or condition. In some embodiments, the term refers to restoring function which was impaired or lost due to a specific disorder, disorder or condition.

"Pharmaceutically acceptable salt" is meant to indicate those salts which are, within the scope of sound medical judgment, suitable for use in contact with the tissues of a patient without undue toxicity, irritation, allergic response and the like, and are commensurate with a reasonable benefit/risk ratio. Pharmaceutically acceptable salts are well known in the art. For example, Berge et al. (1977) J. Pharm. Sciences, Vol. 6, 1-19, describes pharmaceutically acceptable salts in detail. A pharmaceutically acceptable "salt" is any acid addition salt, preferably a pharmaceutically acceptable acid addition salt, including, but not limited to, halogenic acid salts such as hydrobromic, hydrochloric, hydrofluoric and hydroiodic acid salt; an inorganic acid salt such as, for example, nitric, perchloric, sulfuric and phosphoric acid salt; an organic acid salt such as, for example, sulfonic acid salts (methanesulfonic, trifluoromethanesulfonic, ethanesulfonic, benzenesulfonic or p-toluenesufonic, acetic, malic, fumaric, succinic, citric, benzonic, gluconic, lactic, mandelic, mucic, pamoic, pantothenic, oxalic and maleic acid salts; and an amino acid salt such as aspartic or glutamic acid salt. The acid addition salt may be a mono- or di-acid addition salt, such as a di-hydrohalogic, di-sulfuric, di-phosphoric or di-organic acid salt. In all cases, the acid addition salt is used as an achiral reagent which is not selected on the basis of any expected or known preference for the interaction with or precipitation of a specific optical isomer of the products of this disclosure.

Unless otherwise indicated, when a compound or chemical structural feature such as aryl is referred to as being "optionally substituted," it includes a feature that has no substituents (i.e. unsubstituted), or a feature that is "substituted," meaning that the feature has one or more substituents. The term "substituent" has the broadest meaning known to one of ordinary skill in the art, and includes a moiety that replaces one or more hydrogen atoms attached to a parent compound or structural feature. In some embodiments, a substituent may be an ordinary organic moiety known in the art, which may have a molecular weight (e.g. the sum of the atomic masses of the atoms of the substituent) of 15 g/mol to 50 g/mol, 15 g/mol to 100 g/mol, 15 g/mol to 150 g/mol, 15 g/mol to 200 g/mol, 15 g/mol to 300 g/mol, or 15 g/mol to 500 g/mol. In some embodiments, a substituent comprises, or consists of: 0-30, 0-20, 0-10, or 0-5 carbon atoms; and 0-30, 0-20, 0-10, or 0-5 heteroatoms, wherein each heteroatom may independently be: N, O, S, Si, F, Cl, Br, or I; provided that the substituent includes one C, N, O, S, Si, F, Cl, Br, or I atom. Examples of substituents include, but are not limited to, alkyl, alkenyl, alkynyl, heteroalkyl, heteroalkenyl, heteroalkynyl, aryl, heteroaryl, hydroxy, alkoxy, aryloxy, acyl, acyloxy, alkylcarboxylate, thiol, alkylthio, cyano, halo, thiocarbonyl, 0-carbamyl, N-carbamyl, O-thiocarbamyl, N-thiocarbamyl, C-amido, N-amido, S-sulfonamido, N-sulfonamido, isocyanato, thiocyanato, isothiocyanato, nitro, silyl, sulfenyl, sulfinyl, sulfonyl, haloalkyl, haloalkoxyl, trihalomethanesulfonyl, trihalomethanesulfonamido, amino, etc.

For convenience, the term "molecular weight" is used with respect to a moiety or part of a molecule to indicate the sum of the atomic masses of the atoms in the moiety or part of a molecule, even though it may not be a complete molecule.

The structures associated with some of the chemical names referred to herein are depicted below. These structures may be unsubstituted, as shown below, or a substituent may independently be in any position normally occupied by a hydrogen atom when the structure is unsubstituted. Unless a point of attachment is indicated by

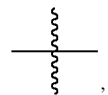

attachment may occur at any position normally occupied by a hydrogen atom.

As used herein, the term "alkyl" has the broadest meaning generally understood in the art, and may include a moiety composed of carbon and hydrogen containing no double or triple bonds. Alkyl may be linear alkyl, branched alkyl, cycloalkyl, or a combination thereof, and in some embodiments, may contain from one to thirty-five carbon atoms. In some embodiments, alkyl may include $C_{1-10}$ linear alkyl, such as methyl (—$CH_3$), methylene (—$CH_2$—), ethyl (—$CH_2CH_3$), ethylene (—$C_2H_4$—), n-propyl (—$CH_2CH_2CH_3$), propylene (—$C_3H_6$—), n-butyl (—$CH_2CH_2CH_2CH_3$), n-pentyl (—$CH_2CH_2CH_2CH_2CH_3$), n-hexyl (—$CH_2CH_2CH_2CH_2CH_2CH_3$), etc.; $C_{3-10}$ branched alkyl, such as $C_3H_7$ (e.g. iso-propyl), $C_4H_9$ (e.g. branched butyl isomers), $C_5H_{11}$ (e.g. branched pentyl isomers), $C_6H_{13}$ (e.g. branched hexyl isomers), $C_7H_{15}$ (e.g. branched heptyl isomers), etc.; $C_{3-10}$ cycloalkyl, such as $C_3H_5$ (e.g. cyclopropyl), $C_4H_7$ (e.g. cyclobutyl isomers such as cyclobutyl, methylcyclopropyl, etc.), $C_5H_9$ (e.g. cyclopentyl isomers such as cyclopentyl, methylcyclobutyl, dimethylcyclopropyl, etc.), $C_6H_{11}$ (e.g. cyclohexyl isomers), $C_7H_{13}$ (e.g. cycloheptyl isomers), bicyclo[1.1.1]pentane, norborane, etc.; and the like.

With respect to an optionally substituted moiety such as optionally substituted alkyl, a phrase such as "optionally substituted $C_{1-12}$ alkyl" refers to a $C_{1-12}$ alkyl that may be unsubstituted, or may have 1 or more substituents, and does not limit the number of carbon atoms in any substituent. Thus, for example, $CH_2(CH_2)_{11}OCH_3$ is optionally substituted $C_{1-12}$ alkyl because the parent alkyl group has 12 carbon atoms. A phrase such as "$C_{1-12}$ optionally substituted alkyl" refers to unsubstituted $C_{1-12}$ alkyl, or substituted alkyl wherein the alkyl parent and all substituents together have from 1-12 carbon atoms. For example, $CH_2CH_2OCH_3$ is $C_{1-12}$ optionally substituted alkyl because the alkyl group (e.g. ethyl) and the substituent (e.g. methoxy) together contain 3 carbon atoms. Similar conventions may be applied to other optionally substituted moieties such as aryl and heterocyclyl.

Substituents on alkyl may be the same as those described generally above. In some embodiments, substituents on alkyl are independently selected from F, Cl, Br, I, CN, $CO_2H$, —O-alkyl, ester groups, acyl, amine groups, amide groups, phenyl (including fused phenyl resulting optionally substituted alkyl such as indenyl, where the phenyl substituent is fused to the parent alkyl moiety), and may have a molecular weight of about 15 to about 100 or about 500.

As used herein, the term "aryl" has the broadest meaning generally understood in the art, and may include an aromatic ring or aromatic ring system such as phenyl, naphthyl, etc.

The term "heterocyclyl" includes any ring or ring system containing a heteroatom such as N, O, S, P, etc. Heterocyclyl includes heteroaryl rings or ring systems (such as those listed below) and non-aromatic rings or ring systems. Examples of non-aromatic heterocyclyl include azetidinyl, oxatanyl, thietanyl, pyrrolidinyl, tetrahydrofuranyl, thiolanyl, imidazolidinyl, pyrazolidinyl, oxazolidinyl, isoxazolidinyl, thiazolidinyl, isothiazolidinyl, dioxalanyl, dithiolanyl, tetrahydropyranyl, piperidinyl, piperazinyl, morpholino, etc.

The term "heteroaryl" also has the meaning understood by a person of ordinary skill in the art, and includes an "aryl" which has one or more heteroatoms in the ring or ring system, such as pyridinyl, furyl, thienyl, oxazolyl, thiazolyl, imidazolyl, triazolyl, oxadiazolyl, isoxazolyl, indolyl, quinolinyl, benzofuranyl, benzothienyl, benzooxazolyl, benzothiazolyl, benzoimidazolyl, etc.

As used herein, the term "carbocyclyl" has the broadest meaning generally understood in the art and includes rings free of heteroatoms, such as cycloalkyl, e.g. cyclopropyl, cyclobutyl, cyclopentyl, cyclohexyl, etc.; cycloalkenyl, e.g. cyclopropenyl, cyclobutenyl, cyclopentenyl, cyclohexenyl; cycloalkynyl, e.g. cyclopropynyl, cyclobutynyl, cyclopentynyl, cyclohexynyl; bridged cycloalkyl, e.g. bicyclo[0.1.1]pentane, norborane, etc.; as well as aryl rings free of heteroatoms.

If stereochemistry is not indicated, a name or structural representation includes any stereoisomer or any mixture of stereoisomers and Applicant reserves the right to specifically identify and claim a compound as a single stereoisomer or any particular mixture of stereoisomers.

Compounds described herein may contain an asymmetric center and may thus exist as enantiomers. Where the compounds according to embodiments herein possess two or more asymmetric centers, they may additionally exist as diastereomers. Embodiments herein include all such possible stereoisomers as substantially pure resolved enantiomers, racemic mixtures thereof, as well as mixtures of diastereomers. In some embodiments, the formulas are shown without a definitive stereochemistry at certain positions. Embodiments herein include all stereoisomers of such formulas and pharmaceutically acceptable salts thereof. Diastereoisomeric pairs of enantiomers may be separated by, for example, fractional crystallization from a suitable solvent, and the pair of enantiomers thus obtained may be separated into individual stereoisomers by conventional means, for example by the use of an optically active acid or base as a resolving agent or on a chiral HPLC column. Further, any enantiomer or diastereomer of a compound of the general formula may be obtained by stereospecific or stereoselective synthesis using optically pure or enantioenriched starting materials or reagents of known configuration. The scope of embodiments herein as described and claimed encompasses the racemic forms of the compounds as well as the individual enantiomers, diastereomers, and stereoisomer-enriched mixtures and Applicant reserves the right to specifically identify and claim a compound in any such form.

The compounds disclosed herein can exist as and therefore include all stereoisomers, conformational isomers and mixtures thereof in all proportions as well as isotopic forms such as deuterated compounds and Applicant reserves the right to specifically identify and claim a compound in any such form.

Disclosed herein are examples of developments in Kv7.2/7.3 structure activity relationships that have resulted in significant gains in potency against this ion channel target. The known Kv7 activator ezogabine has an $EC_{50}$ of 1.1 μM as characterized in the Kv7.2/7.3 FluxOR Potassium Ion Channel Assay (Invitrogen, F20015). Species described in, US 2017/0114022, US 2018/0148419, and WO 2018/081825 that were tested in the thallium flux assay possess a range of Kv7.2/7.3 potencies demonstrated by their $EC_{50}$ values, the majority of which lie in the activity range between 1 and 10 μM and only a few (11%) with $EC_{50}$ values≤0.30 μM. The genera and species described herein distinguish themselves as Kv7 activators from the previous chemical matter as demonstrated by their superior activities on Kv7.2/7.3; the thallium flux $EC_{50}$ values of these compounds range from ≤1 μM to ≤0.3 μM, including a number of these new examples that possess $EC_{50}$ values≤0.05 μM. In certain preferred embodiments, compounds of the present application possess a small non-hydrogen substituent at the $R^2$ position, in combination with increased substitution at the position beta to the carbonyl of the optionally substituted, hydrophobic alkyl group at the

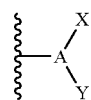

position, as in any of structural formulas 1C, 2C, 8a, 8b, 8c, 9, 10, 11, 12, 13, or 14, often result in a Kv7.2/7.3 $EC_{50}$<1 μM.

Some embodiments include a compound represented by Formula 1C:

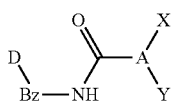

Formula 1C

With respect to Formula 1C, Bz can be optionally substituted benzoimidazol-1,2-yl. If the benzoimidazol-1,2-yl is substituted, it may have 1, 2, 3, or 4 substituents. Any substituent may be included on the benzoimidazol-1,2-yl. In some embodiments, some or all of the substituents on the benzoimidazol-1,2-yl may have: from 0 to 10 carbon atoms and from 0 to 10 heteroatoms, wherein each heteroatom is independently: O, N, S, F, Cl, Br, or I (provided that there is at least 1 non-hydrogen atom); and/or a molecular weight of 15 g/mol to 500 g/mol. In some embodiments, some or all of the substituents may each have a molecular weight of 15 Da to 200 Da, 15 Da to 100 Da, or 15 Da to 50 Da, and consist of 2 to 5 chemical elements, wherein the chemical elements are independently C, H, O, N, S, F, Cl, or Br. In some embodiments, Bz can be optionally substituted benzoimidazol-1,2-diyl. In some embodiments, Bz can be optionally substituted benzoimidazol-1,2,6-triyl.

For example, with respect to Formula 1C, the substituents of Bz may be $C_{1-10}$ optionally substituted alkyl, such as $CH_3$, $C_2H_5$, $C_3H_7$, cyclic $C_3H_5$, $C_4H_9$, cyclic $C_4H_7$, $C_5H_{11}$, cyclic $C_5H_9$, $C_6H_{13}$, cyclic $C_6H_{11}$, etc., which may be optionally substituted; $C_{1-10}$ optionally substituted alkoxy such as $OCH_3$, $OC_2H_5$, $OC_3H_7$, cyclic $OC_3H$, $OC_4H_9$, cyclic $OC_4H_7$, $OC_5H_{11}$, cyclic $OC_5H_9$, $OC_6H_{13}$, cyclic $OC_6H_1$, etc.; halo, such as F, Cl, Br, I; OH; CN; $NO_2$; $C_{1-6}$ fluoroalkyl, such as $CF_3$, $CF_2H$, $C_2F5$, etc.; $C_{1-6}$ fluoroalkoxy, such as $OCF_3$, $OCF_2H$, $OC_2F5$, etc.; a $C_{1-10}$ ester such as $-O_2CCH_3$, $-CO_2CH_3$, $-O_2CC_2H_5$, $-CO_2C_2H_5$, $-O_2C$-phenyl, $-CO_2$-phenyl, etc.; a $C_{1-10}$ ketone such as $-COCH_3$, $-COC_2H_5$, $-COC_3H_7$, $-CO$-phenyl, etc.; or a $C_{1-10}$ amine such as $NH_2$, $NH(CH_3)$, $N(CH_3)_2$, $N(CH_3)C_2H$, etc. In some embodiments, a substituent of Bz may be F, Cl, Br, I, CN, $NO_2$, $C_{1-4}$ alkyl, $C_{1-4}$ alkyl-OH, $C_{1-3}$ O-alkyl, $CF_3$, COH, $C_{1-4}$ CO-alkyl, $CO_2H$, $C_{1-4}$ $CO_2$-alkyl, $NH_2$, or $C_{1-4}$ alkylamino.

Some embodiments of Formula 1C may include a compound represented by Formula 2C:

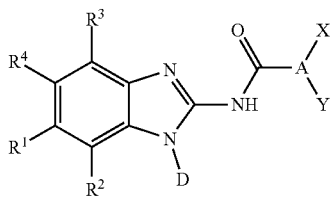

Formula 2C

To any relevant embodiment or structural representation of Formula 1C or 2C herein the following applies, D is optionally substituted $C_{3-6}$ carbocyclyl or $C_{2-5}$ heterocyclyl. If D is substituted cyclobutyl, it may have 1, 2, 3, 4, 5, 6, or 7 substituents. If D is substituted phenyl, it may have 1, 2, 3, 4, or 5 substituents. If D is substituted isoxazolyl, it may have 1 or 2. Substituents. D may include any substituent. In some embodiments, some or all of the substituents of D may have: from 0 to 10 carbon atoms and from 0 to 10 heteroatoms, wherein each heteroatom is independently: O, N, S, F, Cl, Br, or I (provided that there is at least 1 non-hydrogen atom); and/or a molecular weight of 15 g/mol to 500 g/mol. In some embodiments, some or all of the substituents may each have a molecular weight of 15 Da to 200 Da, 15 Da to 100 Da, or 15 Da to 50 Da, and consist of 2 to 5 chemical elements, wherein the chemical elements are independently C, H, O, N, S, F, Cl, or Br.

To any relevant embodiment or structural representation of Formula 1C or 2C herein the following applies, the substituents of D may be $C_{1-10}$ optionally substituted alkyl, such as $CH_3$, $C_2H_5$, $C_3H_7$, cyclic $C_3H_5$, $C_4H_9$, cyclic $C_4H_7$, $C_5H_{11}$, cyclic $C_5H_9$, $C_6H_{13}$, cyclic $C_6H_{11}$, bicyclo[1.1.1]pentane, norborane, etc., which may be optionally substituted; $C_{1-10}$ optionally substituted alkoxy such as $OCH_3$, $OC_2H_5$, $OC_3H_7$, cyclic $OC_3H_5$, $OC_4H_9$, cyclic $OC_4H_7$, $OC_5H_{11}$, cyclic $OC_5H_9$, $OC_6H_{13}$, cyclic $OC_6H_{11}$, etc.; halo, such as F, Cl, Br, I; OH; CN; $NO_2$; $C_{1-6}$ fluoroalkyl, such as $CF_3$, $CF_2H$, $C_2F5$, etc.; $C_{1-6}$ fluoroalkoxy, such as $OCF_3$, $OCF_2H$, $OC_2F5$, etc.; a $C_{1-10}$ ester such as $-O_2CCH_3$, $-CO_2CH_3$, $-O_2CC_2H_5$, $-CO_2C_2H_5$, $-O_2C$-phenyl, $-CO_2$-phenyl, etc.; a $C_{1-10}$ ketone such as $-COCH_3$, $-COC_2H_5$, $-COC_3H_7$, $-CO$-phenyl, etc.; or a $C_{1-10}$ amine such as $NH_2$, $NH(CH_3)$, $N(CH_3)_2$, $N(CH_3)C_2H_5$, etc. In some embodiments, a substituent of D may be F, Cl, Br, I, CN, $NO_2$, $C_{1-4}$ alkyl, $C_{1-4}$ alkyl-OH, $C_{1-3}$ O-alkyl, $CF_3$, COH, $C_{1-4}$ CO-alkyl, $CO_2H$, $C_{1-4}$ $CO_2$-alkyl, $NH_2$, or $C_{1-4}$ alkylamino.

To any relevant embodiment or structural representation of Formula 1C or 2C herein the following applies, in some embodiments, D is:

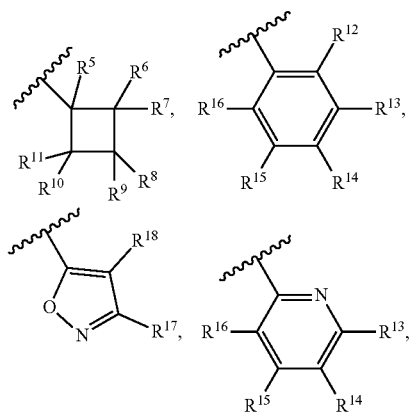

or optionally substituted $C_{2-4}$ alkyl.

To any relevant embodiment or structural representation of Formula 1C or 2C herein the following applies, in some embodiments, D is optionally substituted cyclobutyl, optionally substituted phenyl, optionally substituted isoxazolyl, bicyclo[1.1.1]pentane, norborane, or isopropyl.

To any relevant embodiment or structural representation of Formula 1C or 2C herein the following applies, in some embodiments, D is optionally substituted cyclobutyl. In some embodiments, D is cyclobutyl. In some embodiments, D is

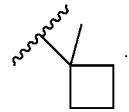 [SMILES: *C1(C)CCC1 ; "."]

To any relevant embodiment or structural representation of Formula 1C or 2C herein the following applies, in some embodiments, D is isopropyl.

To any relevant embodiment or structural representation of Formula 1C or 2C herein the following applies, in some embodiments, D is t-butyl, or tert-butyl.

To any relevant embodiment or structural representation of Formula 1C or 2C herein the following applies, in some embodiments, D is bicyclo[1.1.1]pentane.

To any relevant embodiment or structural representation of Formula 1C or 2C herein the following applies, in some embodiments, D is optionally substituted phenyl. In some embodiments D is

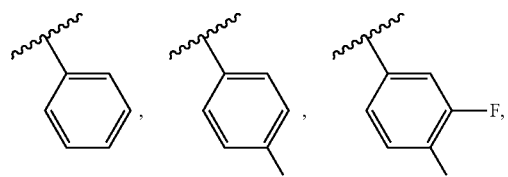

To any relevant embodiment or structural representation of Formula 1C or 2C herein the following applies, in some embodiments, D is optionally substituted pyridinyl, such as optionally substituted pyridin-2-yl, pyridin-3-yl, or pyridin-4-yl. In some embodiments, D is

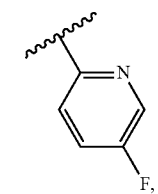

To any relevant embodiment or structural representation of Formula 1C or 2C herein the following applies, in some embodiments, D is optionally substituted isoxazolyl. In some embodiments, D is

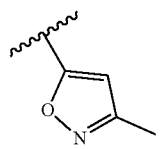

To any relevant embodiment or structural representation of Formula 1C or 2C herein the following applies, A is $C_{1-8}$ alkyl, such as linear or branched

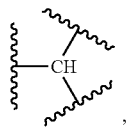

linear or branched

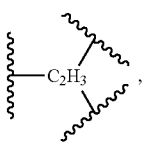

linear or branched

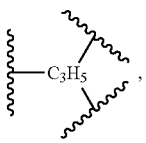

linear or branched

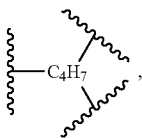

linear or branched

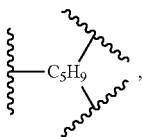

linear or branched

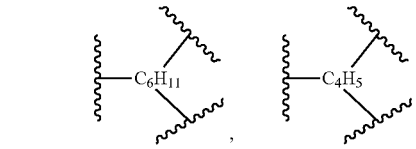

containing one ring,

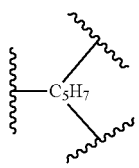

containing one ring,

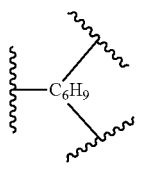

containing one ring,

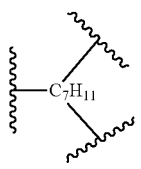

containing one ring, or

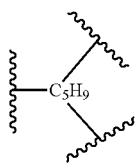

containing a bicyclic ring system.

To any relevant embodiment or structural representation of Formula 1C or 2C herein the following applies, X is H, F, CH$_3$, SCF$_3$, CF$_3$, optionally substituted C$_{2-10}$ alkyl, optionally substituted phenyl, or optionally substituted pyridinyl. In some embodiments, X is H. In some embodiments, X is CH$_3$. In some embodiments, X is F. In some embodiments, X is CF$_3$.

To any relevant embodiment or structural representation of Formula 1C or 2C herein the following applies, if X is substituted phenyl, it may have 1, 2, 3, 4, or 5, substituents. If X is substituted pyridinyl, it may have 1, 2, 3, or 4 substituents. In some embodiments, some or all of the substituents of X may have: from 0 to 10 carbon atoms and from 0 to 10 heteroatoms, wherein each heteroatom is independently: O, N, S, F, Cl, Br, or I (provided that there is at least 1 non-hydrogen atom); and/or a molecular weight of 15 g/mol to 500 g/mol. In some embodiments, some or all of the substituents may each have a molecular weight of 15 Da to 200 Da, 15 Da to 100 Da, or 15 Da to 50 Da, and consist of 2 to 5 chemical elements, wherein the chemical elements are independently C, H, O, N, S, F, Cl, or Br.

To any relevant embodiment or structural representation of Formula 1C or 2C herein the following applies, the substituents of X may be C$_{1-10}$ optionally substituted alkyl, such as CH$_3$, C$_2$H$_5$, C$_3$H$_7$, cyclic C$_3$H$_5$, C$_4$H$_9$, cyclic C$_4$H$_7$, C$_5$H$_{11}$, cyclic CH$_9$, C$_6$H$_{13}$, cyclic C$_6$H$_{11}$, etc., which may be optionally substituted; C$_{1-10}$ optionally substituted alkoxy such as OCH$_3$, OC$_2$H$_5$, OC$_3$H$_7$, cyclic OC$_3$H$_5$, OC$_4$H$_9$, cyclic OC$_4$H$_7$, cyclic OC$_5$H$_{11}$, cyclic OC$_5$H$_9$, OC$_6$H$_{13}$, cyclic OC$_6$H$_{11}$, etc.; halo, such as F, Cl, Br, I; OH; CN; NO$_2$; C$_{1-6}$ fluoroalkyl, such as CF$_3$, CF$_2$H, C$_2$F$_5$, etc.; C$_{1-6}$ fluoroalkoxy, such as OCF$_3$, OCF$_2$H, OC$_2$F$_5$, etc.; a C$_{1-10}$ ester such as —O$_2$CCH$_3$, —CO$_2$CH$_3$, —O$_2$CC$_2$H, —CO$_2$C$_2$H$_5$, —O$_2$C-phenyl, —CO$_2$-phenyl, etc.; a C$_{1-10}$ ketone such as —COCH$_3$, —COC$_2$H$_5$, —COC$_3$H$_7$, —CO-phenyl, etc.; or a C$_{1-10}$ amine such as NH$_2$, NH(CH$_3$), N(CH$_3$)$_2$, N(CH$_3$)C$_2$H$_5$, etc. In some embodiments, a substituent of X may be F, Cl, Br, I, CN, NO$_2$, C$_{1-4}$ alkyl, C$_{1-4}$ alkyl-OH, C$_{1-3}$ O-alkyl, CF$_3$, COH, C$_{1-4}$ CO-alkyl, CO$_2$H, C$_{1-4}$ CO$_2$-alkyl, NH$_2$, SCF$_3$, or C$_{1-4}$ alkylamino.

To any relevant embodiment or structural representation of Formula 1C or 2C herein the following applies, Y is H, F, Cl, Br, I, or a moiety having a molecular weight of 15 Da to 300 Da and consisting of 2 to 5 chemical elements, wherein the chemical elements are independently C, H, O, N, S, F, Cl, or Br. In some embodiments, Y is H, F, Cl, Br, I, CN, —COH, C$_{1-6}$—CO-alkyl, CF$_3$, OH, C$_{1-5}$ O-alkyl, C$_{0-6}$ amino, or C$_{0-6}$ fluoroamino. In some embodiments, Y is H, F, CF$_3$, OH, C$_{1-5}$ O-alkyl, C$_{0-6}$ amino, or C$_{0-6}$ fluoroamino. In some embodiments, Y is H. In some embodiments, Y is OH. In some embodiments, Y is F. In some embodiments, Y is CF$_3$. In some embodiments, Y is C$_{1-3}$ O-alkyl, such as —OCH$_3$, OC$_2$H$_5$, OC$_3$H$_7$, etc. In some embodiments, Y is C$_{0-6}$ fluoroamino. In some embodiments, Y is optionally substituted tetrahydropyranyl, such as

In some embodiments Y may include a C$_{1-8}$ alkyl that may include one or two C$_{3-6}$ carbocyclyl rings. In some embodiments, wherein Y includes at least one carbocyclyl rings, the rings may be connected to each other. In some embodiments, Y is —C(CF$_3$)$_2$OH (or 1,1,1,3,3,3-hexafluoro-2-hydroxypropan-2-yl). In some embodiments Y is

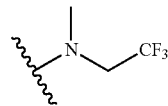

(or methyl(2,2,2-trifluoroethyl)amino). In some embodiments, Y is dimethylamino.

To any relevant embodiment or structural representation of Formula 1C or 2C herein the following applies, in some embodiments

is C$_{2-8}$ alkyl, such as

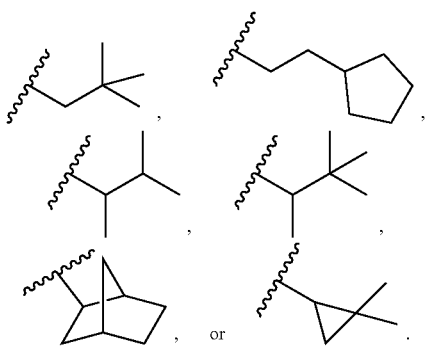

, or .

To any relevant embodiment or structural representation of Formula 1C or 2C herein the following applies, in some embodiments

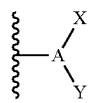

is C$_{2-8}$ hydroxyalkyl, such as

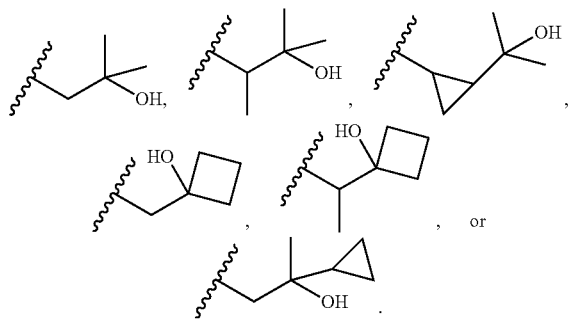

, or .

To any relevant embodiment or structural representation of Formula 1C or 2C herein the following applies, in some embodiments

is C$_{2-8}$ fluoroalkyl such as

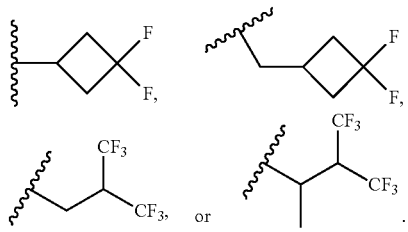

, or .

To any relevant embodiment or structural representation of Formula 1C or 2C herein the following applies, in some embodiments

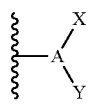

is C$_{2-8}$ alkoxyalkyl, such as

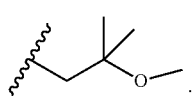 [SMILES: *CC(C)(C)OC]

.

To any relevant embodiment or structural representation of Formula 1C or 2C herein the following applies, in some embodiments

is C$_{2-8}$ hydroxyfluoroalkyl, such as

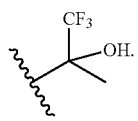 [SMILES: *C(C)(O)C(F)(F)F]

.

To any relevant embodiment or structural representation of Formula 1C or 2C herein the following applies, in some embodiments

is optionally substituted 2-hydroxy-2-phenylethyl, such as

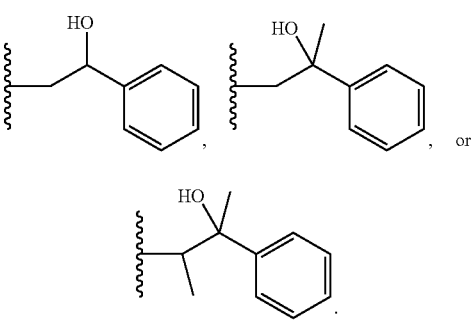

, or .

In some embodiments

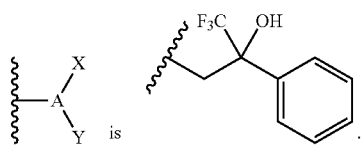 is

To any relevant embodiment or structural representation of Formula 1C or 2C herein the following applies, in some embodiments

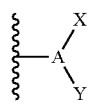

is optionally substituted 2-hydroxy-2-phenylpyridinyl, such as

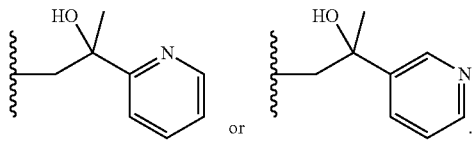 [SMILES: *CC(C)(O)c1ccccn1 ; *CC(C)(O)c1cccnc1]

To any relevant embodiment or structural representation of Formula 1C or 2C herein the following applies, in some embodiments

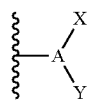

is optionally substituted $C_{2-8}$ fluoroaminoalkyl, such as

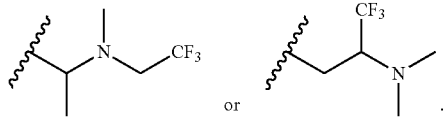

To any relevant embodiment or structural representation of Formula 1C or 2C herein the following applies. Generally $R^{1-18}$ may be H or any substituent, such as a substituent having 0 to 12 atoms or 0 to 6 carbon atoms and 0 to 5 heteroatoms, wherein each heteroatom is independently: O, N, S, F, Cl, Br, or I, and/or having a molecular weight of 15 g/mol to 300 g/mol. Any of $R^{1-18}$ may comprise: a) 1 or more alkyl moieties optionally substituted with, or optionally connected by or to, b) 1 or more functional groups, such as C=C, C≡C, CO, $CO_2$, CON, $NCO_2$, OH, SH, O, S, N, N=C, F, Cl, Br, I, CN, $NO_2$, $CO_2H$, $NH_2$, etc.; or may be a substituent having no alkyl portion, such as F, Cl, Br, I, $NO_2$, CN, $NH_2$, OH, COH, $CO_2H$, etc. In some embodiments, each of $R^{1-18}$ is independently H, F, Cl, Br, I, or a substituent having a molecular weight of 15 Da to 300 Da, 15 Da to 200 Da, 15 Da to 100 Da, or 15 Da to 60 Da, and consisting of 2 to 5 chemical elements, wherein the chemical elements are independently C, H, O, N, S, F, Cl, or Br.

With respect to any relevant structural representation of Formula 1C or 2C, some non-limiting examples of $R^{1-18}$ may include $R^A$, F, Cl, Br, CN, $OR^A$, $C_{1-3}$ fluoroalkyl, $C_{1-5}$ hydroxyalkyl, $NO_2$, $NR^A R^B$, $COR^A$, $CO_2 R^A$, $OCOR^A$, $NR^A COR^B$, $CONR^A R^B$, etc. In some embodiments, $R^{1-18}$ may be H; F; Cl; Br; CN; $C_{1-3}$ fluoroalkyl, such as $CHF_2$, $CF_3$, etc; OH; $NH_2$; $C_{1-6}$ alkyl, such as methyl, ethyl, propyl isomers (e.g. n-propyl and isopropyl), cyclopropyl, butyl isomers, cyclobutyl isomers (e.g. cyclobutyl and methylcyclopropyl), pentyl isomers, cyclopentyl isomers, hexyl isomers, cyclohexyl isomers, etc.; optionally substituted $C_{1-7}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, —O-benzyl, etc.; $C_{1-4}$ hydroxyalkyl, such as —$CH_2OH$, —$C_2H_4$—OH, —$C_3H_6$—OH, $C_4H_8$—OH, etc.; $C_{2-5}$—$CO_2$-alkyl, such as —$CO_2$—$CH_3$, —$CO_2$—$C_2H_5$, —$CO_2$—$C_3H_7$, —$CO_2$—$C_4H_9$, etc.

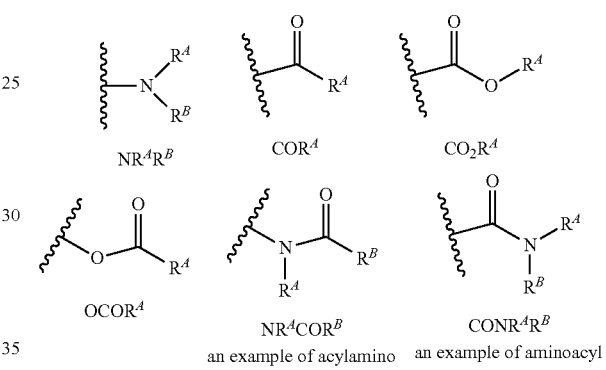

With respect to any relevant structural representation of Formula 1C or 2C, each $R^A$ may independently be H, or $C_{1-12}$ alkyl, including: linear or branched alkyl having a formula $C_a H_{2a+1}$, or cycloalkyl having a formula $C_a H_{2a-1}$, wherein a is 1, 2, 3, 4, 5, 6, 7, 8, 9, 10, 11, or 12, such as linear or branched alkyl of a formula: $CH_3$, $C_2H_5$, $C_3H_7$, $C_4H_9$, $C_5H_{11}$, $C_6H_{13}$, $C_7H_{15}$, $C_8H_{17}$, $C_9H_{19}$, $C_{10}H_{21}$, etc., or cycloalkyl of a formula: $C_3H_5$, $C_4H_7$, $C_5H_9$, $C_6H_{11}$, $C_7H_{13}$, $C_8H_{15}$, $C_9H_{17}$, $C_{10}H_{19}$, etc. In some embodiments, $R^A$ may be H or optionally substituted $C_{1-6}$ alkyl. In some embodiments, $R^A$ may be H or optionally substituted $C_{1-3}$ alkyl. In some embodiments, $R^A$ may be H or $CH_3$. In some embodiments, $R^A$ may be H.

With respect to any relevant structural representation of Formula 1C or 2C, each $R^B$ may independently be H, or $C_{1-12}$ alkyl, including: linear or branched alkyl having a formula $C_a H_{2a+1}$, or cycloalkyl having a formula $C_a H_{2a-1}$, wherein a is 1, 2, 3, 4, 5, 6, 7, 8, 9, 10, 11, or 12, such as linear or branched alkyl of a formula: $CH_3$, $C_2H_5$, $C_3H_7$, $C_4H_9$, $C_5H$, $C_6H_{13}$, $C_7H_{15}$, $C_8H_{17}$, $C_9H_{19}$, $C_{10}H_{21}$, etc., or cycloalkyl of a formula: $C_3H_5$, $C_4H_7$, $C_5H_9$, $C_6H$, $C_7H_{13}$, $C_8H_{15}$, $C_9H_{17}$, $C_{10}H_{19}$, etc. In some embodiments, $R^B$ may be H or $C_{1-3}$ alkyl. In some embodiments, $R^B$ may be H or $CH_3$. In some embodiments, $R^B$ may be H.

With respect to any relevant structural representation of Formula 1C or 2C, such as Formula 2C, in some embodiments $R^1$ is H, F, Cl, Br, CN, $OCH_3$, OH, $CHF_2$, $CF_3$, $C_{1-4}$—$CO_2$-alkyl, $C_{1-4}$ alkyl, or $C_{1-5}$ hydroxyalkyl. In some embodiments, $R^1$ is H, Cl, Br, CN, $OCH_3$, $OCHF_2$, $CHF_2$, $CF_3$, —$CO_2CH_2CH_3$, —$CH_2OH$,

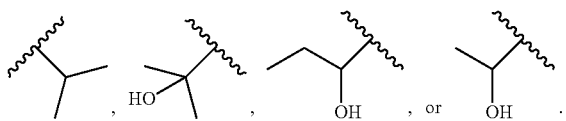

In some embodiments, $R^1$ is H. In some embodiments, $R^1$ is F. In some embodiments, $R^1$ is Cl. In some embodiments, $R^1$ is Br. In some embodiments, $R^1$ is CN. In some embodiments, $R^1$ is $OCH_3$. In some embodiments, $R^1$ is $CHF_2$. In some embodiments, $R^1$ is $CF_3$. In some embodiments, $R^1$ is $-CO_2CH_2CH_3$. In some embodiments, $R^1$ is $-CH_2OH$. In some embodiments, $R^1$ is

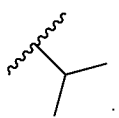 [SMILES: *C(C)C]

In some embodiments, $R^1$ is

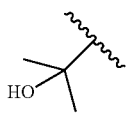

In some embodiments, $R^1$ is

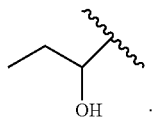

In some embodiments, $R^1$ is

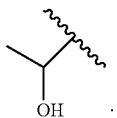

In some embodiments, $R^1$ is $-OCH_3$, $-OH$, $-OCHF_2$, $-O$-benzyl, $-CN$, $-CF_3$, $-CH_2OH$, $-COOCH_2CH_3$, $-C(CH_3)_2OH$, $-CHOHCH_2CH_3$, $-CHOHCH_3$, $-CHF_2$, $-CH(CH_3)_2$, $-C(CH_2CH_3)_2OH$, $-CH_2COOC H_2CH_3$, $-CH_2C(CH_3)_2OH$, $-CH_2COOH$, or $-CH_2CON(CH_3)_2$. With respect to the embodiments recited in this paragraph, in some embodiments, the remaining groups of $R^{1-18}$ may independently be $R^A$, F, Cl, Br, CN, $OR^A$, $C_{1-3}$ fluoroalkyl, $C_{1-5}$ hydroxyalkyl, $NO_2$, $NR^AR^B$ $COR^A$, $CO_2R^A$, $OCOR^A$, $NR^ACOR^B$, $CONR^AR^B$, etc. In some embodiments, the remaining groups of $R^{1-18}$ may be H, F, Cl, Br, CN, $C_{1-3}$ fluoroalkyl, OH, $NH_2$, $C_{1-6}$ alkyl, $C_{1-6}$ alkoxy, $C_{1-4}$—$CO_2$-alkyl, or $C_{1-5}$ hydroxyalkyl.

With respect to any relevant structural representation of Formula 1C or 2C, in some embodiments $R^2$ is H, F, Cl, Br, CN, $OCH_3$, $OCF_3$, $CHF_2$, $CF_3$, $C_{1-4}$—$CO_2$-alkyl, $C_{1-4}$ alkyl, or $C_{1-5}$ hydroxyalkyl. In some embodiments, $R^2$ is H. In some embodiments, $R^2$ is F. In some embodiments, $R^2$ is $CH_2OH$. In some embodiments, $R^2$ is $-CO_2CH_3$. With respect to the embodiments recited in this paragraph, in some embodiments, the remaining groups of $R^{1-18}$ may independently be $R^A$, F, Cl, Br, CN, $OR^A$, $C_{1-3}$ fluoroalkyl, $C_{1-5}$ hydroxyalkyl, $NO_2$, $NR^AR^B$ $COR^A$, $CO_2R^A$, $OCOR^A$, $NR^ACOR^B$, $CONR^AR^B$, etc. In some embodiments, the remaining groups of $R^{1-18}$ may be H, F, Cl, Br, CN, $C_{1-3}$ fluoroalkyl, OH, $NH_2$, $C_{1-6}$ alkyl, $C_{1-6}$ alkoxy, $C_{1-4}$—$CO_2$-alkyl, or $C_{1-4}$ hydroxyalkyl. In some embodiments, $R^2$ is $-CH_2OH$, $-CO_2Me$, or $-C(CH_3)_2OH$.

With respect to any relevant structural representation of Formula 1C or 2C, in some embodiments $R^3$ is H, F, Cl, Br, CN, $OCH_3$, $OCHF_2$, $CHF_2$, $CF_3$, $C_{1-4}$—$CO_2$-alkyl, $C_{1-4}$ alkyl, or $C_{1-5}$ hydroxyalkyl. In some embodiments, $R^3$ is H. In some embodiments, $R^3$ is F. With respect to the embodiments recited in this paragraph, in some embodiments, the remaining groups of $R^{1-18}$ may independently be $R^A$, F, Cl, Br, CN, $OR^A$, $C_{1-3}$ fluoroalkyl, $C_{1-5}$ hydroxyalkyl, $NO_2$, $NR^AR^B$, $COR^A$, $CO_2R^A$, $OCOR^A$, $NR^ACOR^B$, $CONR^AR^B$, etc. In some embodiments, the remaining groups of $R^{1-18}$ may be H, F, Cl, Br, CN, $C_{1-3}$ fluoroalkyl, OH, $NH_2$, $C_{1-6}$ alkyl, optionally substituted $C_{1-6}$ alkoxy, $C_{1-4}$—$CO_2$-alkyl, or $C_{1-4}$ hydroxyalkyl.

With respect to any relevant structural representation of Formula 1C or 2C, in some embodiments $R^4$ is H, F, Cl, Br, CN, $OCH_3$, $CHF_2$, $CF_3$, $C_{1-4}$—$CO_2$-alkyl, $C_{1-4}$ alkyl, or $C_{1-5}$ hydroxyalkyl. In some embodiments, $R^4$ is H. In some embodiments, $R^4$ is F. In some embodiments, $R^4$ is $CH_3$. In some embodiments, $R^4$ is $CF_3$. With respect to the embodiments recited in this paragraph, in some embodiments, the remaining groups of $R^{1-18}$ may independently be $R^A$, F, Cl, Br, CN, $OR^A$, $C_{1-3}$ fluoroalkyl, $C_{1-5}$ hydroxyalkyl, $NO_2$, $NR^AR^B$ $COR^A$, $CO_2R^A$, $OCOR^A$, $NR^ACOR^B$, $CONR^AR^B$, etc. In some embodiments, the remaining groups of $R^{1-18}$ may be H, F, Cl, Br, CN, $C_{1-3}$ fluoroalkyl, OH, $NH_2$, $C_{1-6}$ alkyl, $C_{1-6}$ alkoxy, $C_{1-4}$—$CO_2$-alkyl, or $C_{1-4}$ hydroxyalkyl.

With respect to any relevant structural representation of Formula 1C or 2C, in some embodiments $R^5$ is H, F, Cl, Br, CN, $OCH_3$, $CHF_2$, $CF_3$, $C_{1-4}$—$CO_2$-alkyl, $C_{1-4}$ alkyl, or $C_{1-5}$ hydroxyalkyl. In some embodiments, $R^5$ is H. In some embodiments, $R^5$ is $CH_3$. With respect to the embodiments recited in this paragraph, in some embodiments, the remaining groups of $R^{1-18}$ may independently be $R^A$, F, Cl, Br, CN, $OR^A$, $C_{1-3}$ fluoroalkyl, $C_{1-5}$ hydroxyalkyl, $NO_2$, $NR^AR^B$ $COR^A$, $CO_2R^A$, $OCOR^A$, $NR^ACOR^B$, $CONR^AR^B$, etc. In some embodiments, the remaining groups of $R^{1-18}$ may be H, F, Cl, Br, CN, $C_{1-3}$ fluoroalkyl, OH, $NH_2$, $C_{1-6}$ alkyl, $C_{1-6}$ alkoxy, $C_{1-4}$—$CO_2$-alkyl, or $C_{1-4}$ hydroxyalkyl.

With respect to any relevant structural representation of Formula 1C or 2C, in some embodiments $R^6$ is H, F, Cl, Br, CN, $OCH_3$, $CHF_2$, $CF_3$, $C_{1-4}$—$CO_2$-alkyl, $C_{1-4}$ alkyl, or $C_{1-5}$ hydroxyalkyl. In some embodiments, $R^6$ is H. With respect to the embodiments recited in this paragraph, in some embodiments, the remaining groups of $R^{1-18}$ may independently be $R^A$, F, Cl, Br, CN, $OR^A$, $C_{1-3}$ fluoroalkyl, $C_{1-5}$ hydroxyalkyl, $NO_2$, $NR^AR^B$, $COR^A$, $CO_2R^A$, $OCOR^A$, $NR^A$-$COR^B$, $CONR^AR^B$, etc. In some embodiments, the remaining groups of $R^{1-18}$ may be H, F, Cl, Br, CN, $C_{1-3}$ fluoroalkyl, OH, $NH_2$, $C_{1-6}$ alkyl, $C_{1-6}$ alkoxy, $C_{1-4}$—$CO_2$-alkyl, or $C_{1-4}$ hydroxyalkyl.

With respect to any relevant structural representation of Formula 1C or 2C, in some embodiments $R^7$ is H, F, Cl, Br, CN, $OCH_3$, $CHF_2$, $CF_3$, $C_{1-4}$—$CO_2$-alkyl, $C_{1-4}$ alkyl, or $C_{1-5}$ hydroxyalkyl. In some embodiments, $R^7$ is H. With respect to the embodiments recited in this paragraph, in some embodiments, the remaining groups of $R^{1-18}$ may independently be $R^A$, F, Cl, Br, CN, $OR^A$, $C_{1-3}$ fluoroalkyl, $C_{1-5}$ hydroxyalkyl, $NO_2$, $NR^AR^B$, $COR^A$, $CO_2R^A$, $OCOR^A$, $NR^A$-

$COR^B$, $CONR^AR^B$, etc. In some embodiments, the remaining groups of $R^{1-18}$ may be H, F, Cl, Br, CN, $C_{1-3}$ fluoroalkyl, OH, $NH_2$, $C_{1-6}$ alkyl, $C_{1-6}$ alkoxy, $C_{1-4}$—$CO_2$-alkyl, or $C_{1-4}$ hydroxyalkyl.

With respect to any relevant structural representation of Formula 1C or 2C, in some embodiments $R^8$ is H, F, Cl, Br, CN, $OCH_3$, $CHF_2$, $CF_3$, $C_{1-4}$—$CO_2$-alkyl, $C_{1-4}$ alkyl, or $C_{1-5}$ hydroxyalkyl. In some embodiments, $R^8$ is H. With respect to the embodiments recited in this paragraph, in some embodiments, the remaining groups of $R^{1-18}$ may independently be $R^A$, F, Cl, Br, CN, $OR^A$, $C_{1-3}$ fluoroalkyl, $C_{1-5}$ hydroxyalkyl, $NO_2$, $NR^AR^B$, $COR^A$, $CO_2R^A$, $OCOR^A$, $NR^A$-$COR^B$, $CONR^AR^B$, etc. In some embodiments, the remaining groups of $R^{1-18}$ may be H, F, Cl, Br, CN, $C_{1-3}$ fluoroalkyl, OH, $NH_2$, $C_{1-6}$ alkyl, $C_{1-6}$ alkoxy, $C_{1-4}$—$CO_2$-alkyl, or $C_{1-4}$ hydroxyalkyl.

With respect to any relevant structural representation of Formula 1C or 2C, in some embodiments $R^9$ is H, F, Cl, Br, CN, $OCH_3$, $CHF_2$, $CF_3$, $C_{1-4}$—$CO_2$-alkyl, $C_{1-4}$ alkyl, or $C_{1-5}$ hydroxyalkyl. In some embodiments, $R^9$ is H. With respect to the embodiments recited in this paragraph, in some embodiments, the remaining groups of $R^{1-18}$ may independently be $R^A$, F, Cl, Br, CN, $OR^A$, $C_{1-3}$ fluoroalkyl, $C_{1-5}$ hydroxyalkyl, $NO_2$, $NR^AR^B$, $COR^A$, $CO_2R^A$, $OCOR^A$, $NR^A$-$COR^B$, $CONR^AR^B$, etc. In some embodiments, the remaining groups of $R^{1-18}$ may be H, F, Cl, Br, CN, $C_{1-3}$ fluoroalkyl, OH, $NH_2$, $C_{1-6}$ alkyl, $C_{1-6}$ alkoxy, $C_{1-4}$—$CO_2$-alkyl, or $C_{1-4}$ hydroxyalkyl.

With respect to any relevant structural representation of Formula 1C or 2C, in some embodiments $R^{10}$ is H, F, Cl, Br, CN, $OCH_3$, $CHF_2$, $CF_3$, $C_{1-4}$—$CO_2$-alkyl, $C_{1-4}$ alkyl, or $C_{1-5}$ hydroxyalkyl. In some embodiments, $R^{10}$ is H. With respect to the embodiments recited in this paragraph, in some embodiments, the remaining groups of $R^{1-18}$ may independently be $R^A$, F, Cl, Br, CN, $OR^A$, $C_{1-3}$ fluoroalkyl, $C_{1-5}$ hydroxyalkyl, $NO_2$, $NR^AR^B$, $COR^A$, $CO_2R^A$, $OCOR^A$, $NR^A$-$COR^B$, $CONR^AR^B$, etc. In some embodiments, the remaining groups of $R^{1-18}$ may be H, F, Cl, Br, CN, $C_{1-3}$ fluoroalkyl, OH, $NH_2$, $C_{1-6}$ alkyl, $C_{1-6}$ alkoxy, $C_{1-4}$—$CO_2$-alkyl, or $C_{1-4}$ hydroxyalkyl.

With respect to any relevant structural representation of Formula 1C or 2C, in some embodiments $R^{10}$ is H, F, Cl, Br, CN, $OCH_3$, $CHF_2$, $CF_3$, $C_{1-4}$—$CO_2$-alkyl, $C_{1-4}$ alkyl, or $C_{1-5}$ hydroxyalkyl. In some embodiments, $R^{10}$ is H. With respect to the embodiments recited in this paragraph, in some embodiments, the remaining groups of $R^{1-18}$ may independently be $R^A$, F, Cl, Br, CN, $OR^A$, $C_{1-3}$ fluoroalkyl, $C_{1-5}$ hydroxyalkyl, $NO_2$, $NR^AR^B$, $COR^A$, $CO_2R^A$, $OCOR^A$$NR^A$-$COR^B$, $CONR^AR^B$, etc. In some embodiments, the remaining groups of $R^{1-18}$ may be H, F, Cl, Br, CN, $C_{1-3}$ fluoroalkyl, OH, $NH_2$, $C_{1-6}$ alkyl, $C_{1-6}$ alkoxy, $C_{1-4}$—$CO_2$-alkyl, or $C_{1-4}$ hydroxyalkyl.

With respect to any relevant structural representation of Formula 1C or 2C, in some embodiments $R^{12}$ is H, F, Cl, Br, CN, $OCH_3$, $CHF_2$, $CF_3$, $C_{1-4}$—$CO_2$-alkyl, $C_{1-4}$ alkyl, or $C_{1-5}$ hydroxyalkyl. In some embodiments, $R^{12}$ is H. With respect to the embodiments recited in this paragraph, in some embodiments, the remaining groups of $R^{1-18}$ may independently be $R^A$, F, Cl, Br, CN, $OR^A$, $C_{1-3}$ fluoroalkyl, $C_{1-5}$ hydroxyalkyl, $NO_2$, $NR^AR^B$, $COR^A$, $CO_2R^A$, $OCOR^A$, $NR^A$-$COR^B$, $CONR^AR^B$, etc. In some embodiments, the remaining groups of $R^{1-18}$ may be H, F, Cl, Br, CN, $C_{1-3}$ fluoroalkyl, OH, $NH_2$, $C_{1-6}$ alkyl, $C_{1-6}$ alkoxy, $C_{1-4}$—$CO_2$-alkyl, or $C_{1-4}$ hydroxyalkyl.

With respect to any relevant structural representation of Formula 1C or 2C, in some embodiments $R^{13}$ is H, F, Cl, Br, CN, $OCH_3$, $CHF_2$, $CF_3$, $C_{1-4}$—$CO_2$-alkyl, $C_{1-4}$ alkyl, or $C_{1-5}$ hydroxyalkyl. In some embodiments, $R^{13}$ is H. With respect to the embodiments recited in this paragraph, in some embodiments, the remaining groups of $R^{1-18}$ may independently be $R^A$, F, Cl, Br, CN, $OR^A$, $C_{1-3}$ fluoroalkyl, $C_{1-5}$ hydroxyalkyl, $NO_2$, $NR^AR^B$, $COR^A$, $CO_2R^A$, $OCOR^A$, $NR^A$-$COR^B$, $CONR^AR^B$, etc. In some embodiments, the remaining groups of $R^{1-18}$ may be H, F, Cl, Br, CN, $C_{1-3}$ fluoroalkyl, OH, $NH_2$, $C_{1-6}$ alkyl, $C_{1-6}$ alkoxy, $C_{1-4}$—$CO_2$-alkyl, or $C_{1-4}$ hydroxyalkyl.

With respect to any relevant structural representation of Formula 1C or 2C, in some embodiments $R^{14}$ is H, F, Cl, Br, CN, $OCH_3$, $CHF_2$, $CF_3$, $C_{1-4}$—$CO_2$-alkyl, $C_{1-4}$ alkyl, or $C_{1-5}$ hydroxyalkyl. In some embodiments, $R^{14}$ is H. In some embodiments, $R^{14}$ is F. With respect to the embodiments recited in this paragraph, in some embodiments, the remaining groups of $R^{1-18}$ may independently be $R^A$, F, Cl, Br, CN, $OR^A$, $C_{1-3}$ fluoroalkyl, $C_{1-5}$ hydroxyalkyl, $NO_2$, $NR^AR^B$, $COR^A$, $CO_2R^A$, $OCOR^A$, $NR^ACOR^B$, $CONR^AR^B$, etc. In some embodiments, the remaining groups of $R^{1-18}$ may be H, F, Cl, Br, CN, $C_{1-3}$ fluoroalkyl, OH, $NH_2$, $C_{1-6}$ alkyl, $C_{1-6}$ alkoxy, $C_{1-4}$—$CO_2$-alkyl, or $C_{1-4}$ hydroxyalkyl.

In some embodiments of the invention, one or more hydrogen atoms is replaced by a deuterium. It is well established that deuteration of physiologically active compounds offer the advantage of retaining the pharmacological profile of their hydrogen counterparts while positively impacting their metabolic outcome. Selective replacement of one or more hydrogen with deuterium, in a compound of the present invention, could improve the safety, tolerability and efficacy of the compound when compared to its all hydrogen counterpart.

Methods for incorporation of deuterium into compounds are well established. Using metabolic studies established in the art, the compound of the present invention can be tested to identify sites for selective placement of a deuterium isotope, wherein the isotope will not be metabolized. Moreover these studies identify sites of metabolism as the location where a deuterium atom would be placed.

In certain embodiments, the embodiments expressed herein do not encompass any compound expressly disclosed in U.S. Pat. No. 9,481,653, WO 2016/040952, U.S. Provisional No. 62/579,770, U.S. Provisional No. 62/663,427, or U.S. Provisional No. 62/644,932.

In certain embodiments, the compounds of Formula 1C have a Kv7.2/7.3 Thallium flux $EC_{50}$ of ≤10 µM. In certain embodiments, the compounds of Formula 1C have a Kv7.2/7.3 Thallium flux $EC_{50}$ of ≤1 µM. In certain embodiments, the compounds of Formula 1C have a Kv7.2/7.3 Thallium flux $EC_{50}$ of ≤0.3 µM.

Some embodiments of Formula 1C may include a compound represented by Formula 8a:

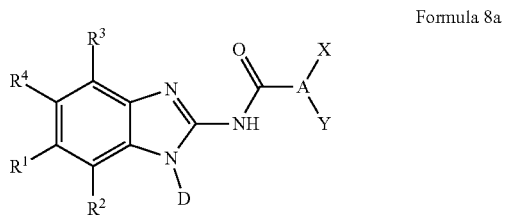

Formula 8a wherein

D is optionally substituted cyclobutyl or t-butyl;

A is $C_1$ alkyl;

X is substituted cyclobutyl, wherein the substituent is F;

Y is H;
R¹ is $C_3$ hydroxyalkyl or CN;
R² and R⁴ are H;
R³ is H or F; and
wherein when X is substituted with 2 fluorine atoms, the fluorine atoms are not geminal;
or a pharmaceutically acceptable salt thereof.

Some embodiments of Formula 1C may include a compound represented by Formula 8b:

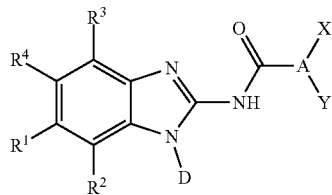

Formula 8b wherein
D is optionally substituted cyclobutyl or t-butyl, wherein the optional substituents are selected from —$CH_3$ and F;
A is $C_1$ alkyl;
X is substituted cyclobutyl, wherein the substituent is F;
Y is H;
R¹ is selected from $C_3$ hydroxyalkyl, CN, or F;
R² is selected from H, F, or —$OCF_3$;
R³ is selected from H, F, or —$OCH_3$;
R⁴ is H or F; and
wherein when X is substituted with 2 fluorine atoms, the fluorine atoms are not geminal;
or a pharmaceutically acceptable salt thereof.

Some embodiments of Formula 1C may include a compound represented by Formula 8c:

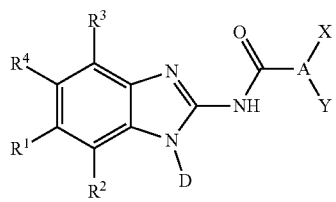

Formula 8c wherein
D is optionally substituted cyclobutyl, optionally substituted phenyl, or t-butyl, wherein the optional substituents are selected from —$CH_3$ and F;
A is $C_1$ alkyl;
X is substituted cyclobutyl, wherein the substituent is F;
Y is H;
R¹ is selected from H, $C_3$ hydroxyalkyl, CN, F, or Cl;
R² is selected from H, CN, F, Br, or —$OCF_3$;
R³ is selected from H, F, or —$OCH_3$;
R⁴ is H or F; and
wherein when X is substituted with 2 fluorine atoms, the fluorine atoms are not geminal;
or a pharmaceutically acceptable salt thereof.

Some embodiments of Formula 1C may include a compound represented by Formula 9:

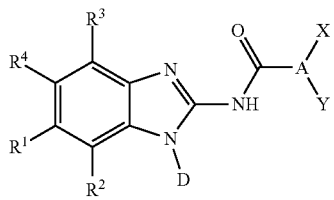

Formula 9 wherein
D is cyclobutyl;
A is $C_1$ alkyl;
X is optionally substituted cyclobutyl, wherein the optional substituent is F;
Y is H;
R¹ is $C_3$ hydroxyalkyl;
R² and R⁴ are H;
R³ is F; and
wherein when X is substituted with 2 fluorine atoms, the fluorine atoms are not geminal;
or a pharmaceutically acceptable salt thereof.

Some embodiments of Formula 1C may include a compound represented by Formula 10:

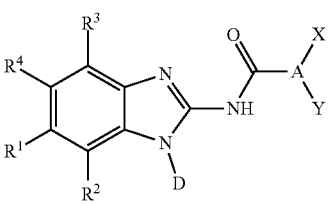

Formula 10 wherein
D is optionally substituted $C_{2-5}$ alkyl, wherein the optional substituents are selected from —$CH_3$ and F;
A is $C_{1-6}$ alkyl;
X is H, F, —$CH_3$, —$CF_3$, —$SCF_3$, pyridinyl, optionally substituted $C_{1-3}$ alkyl, optionally substituted phenyl, or optionally substituted cyclobutyl, wherein the optional substituent is F;
Y is H, F, —OH, or —$CH_3$;
R¹ is H, $C_{3-4}$ hydroxyalkyl, —CN, —OH, —$CF_3$, —$OCHF_2$, optionally substituted $C_{3-5}$ heterocyclyl, optionally substituted $C_{1-5}$ alkyl, optionally substituted $C_{1-7}$ alkoxy, —$NR^A R^B$, or halogen, wherein the optional substituents are selected from —OH and F;
R² is H, halogen, —CN, —$OCH_3$, —$COR^A$, —$CF_3$, —$OCF_3$, optionally substituted $C_1$ alkyl, wherein the optional substituents of R² are selected from —$OCH_3$ and —$COR^A$;
R³ is H, halogen, —$CF_3$, —$OCHF_2$, —$OCF_3$, or —$OCH_3$;
R⁴ is H, halogen, or $C_3$ hydroxyalkyl; and
$R^A$ and $R^B$ are $CH_3$;
or a pharmaceutically acceptable salt thereof.

Some embodiments of Formula 1C may include a compound represented by Formula 11:

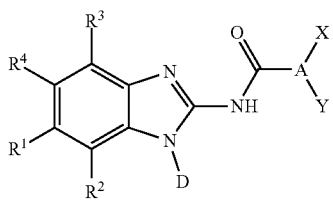

Formula 11 wherein

D is optionally substituted $C_{2-5}$ alkyl or optionally substituted phenyl, wherein the optional substituents are selected from —$CH_3$ and F;

A is $C_{1-6}$ alkyl;

X is H, F, —$CH_3$, —$CF_3$, —$SCF_3$, pyridinyl, optionally substituted $C_{1-3}$ alkyl, optionally substituted phenyl, or optionally substituted cyclobutyl, wherein the optional substituent is F;

Y is H, F, —OH, or —$CH_3$;

$R^1$ is H, $C_{3-4}$ hydroxyalkyl, —CN, —OH, —$CF_3$, —$OCHF_2$, optionally substituted $C_{3-5}$ heterocyclyl, optionally substituted $C_{1-5}$ alkyl, optionally substituted $C_{1-7}$ alkoxy, —$NR^A R^B$, or halogen, wherein the optional substituents are selected from —OH and F;

$R^2$ is H, halogen, —CN, —$OCH_3$, —$COR^A$, —$CF_3$, —$OCF_3$, optionally substituted $C_{1-2}$ alkyl, wherein the optional substituents of $R^2$ are selected from —$OCH_3$ and —$COR^A$;

$R^3$ is H, halogen, —$CF_3$, —$OCHF_2$, —$OCF_3$, or —$OCH_3$;

$R^4$ is H, halogen, or $C_3$ hydroxyalkyl; and $R^A$ and $R^B$ are $CH_3$;

or a pharmaceutically acceptable salt thereof.

Some embodiments of Formula 1C may include a compound represented by Formula 12:

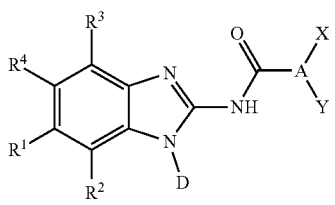

Formula 12 wherein

D is optionally substituted cyclobutyl, wherein the optional substituent is —$CH_3$;

A is $C_3$ alkyl;

X is —$CH_3$;

Y is —$CH_3$;

$R^1$ is CN;

$R^2$ and $R^3$ are F; and $R^4$ and is H;

or a pharmaceutically acceptable salt thereof.

Some embodiments of Formula 1C may include a compound represented by Formula 13:

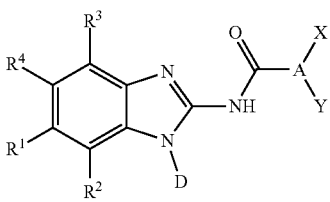

Formula 13 wherein

D is t-butyl;

A is $C_1$ alkyl;

X is optionally substituted cyclobutyl, wherein the optional substituent is F;

Y is H;

$R^1$ and $R^4$ are F;

$R^2$ and $R^3$ are H; and wherein when X is substituted with 2 fluorine atoms, the fluorine atoms are not geminal;

or a pharmaceutically acceptable salt thereof.

Some embodiments of Formula 1C may include a compound represented by Formula 14:

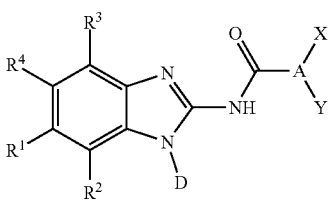

Formula 14 wherein

D is optionally substituted $C_{2-5}$ alkyl, wherein the optional substituents are selected from —$CH_3$;

A is $C_{1-6}$ alkyl;

X is H, F, —$CH_3$, —$CF_3$, optionally substituted $C_{1-3}$ alkyl, optionally substituted phenyl, or optionally substituted cyclobutyl, wherein the optional substituent is F;

Y is H, F, —OH, or —$CH_3$;

$R^1$ is H, $C_{3-4}$ hydroxyalkyl, —CN, —$CF_3$, —$OCH_2CF_3$, —$OCHF_2$, optionally substituted $C_{3-5}$ heterocyclyl, optionally substituted $C_{1-5}$ alkyl, optionally substituted $C_{1-7}$ alkoxy, —$NR^A R^B$, F, or Cl, wherein the optional substituents are selected from —OH and F;

$R^2$ is F, Br, —CN, —$OCH_3$, —$OCF_3$, or —$CF_3$;

$R^3$ is H, halogen, —$CF_3$, —$OCHF_2$, —$OCF_3$, or —$OCH_3$;

$R^4$ is H, fluorine, or chlorine; and $R^A$ and $R^B$ are $CH_3$;

or a pharmaceutically acceptable salt thereof.

In some embodiments of Formula 11, when X is substituted with 2 fluorine atoms, the fluorine atoms are not geminal;

Some embodiments of Formula 11 are further illustrated by the compounds of Group I, Group II, and Group III, or a pharmaceutically acceptable salt thereof.

In some embodiments, provided herein are any one of the following compounds of Group I, or a pharmaceutically acceptable salt thereof:

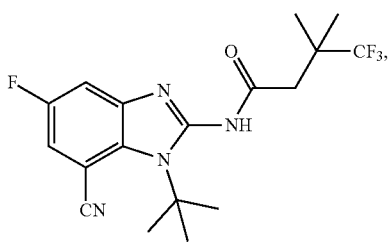
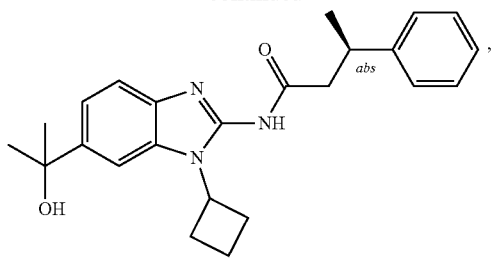
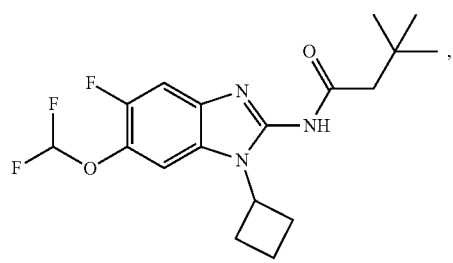
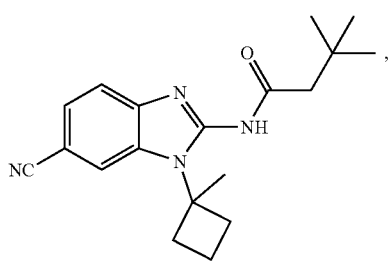
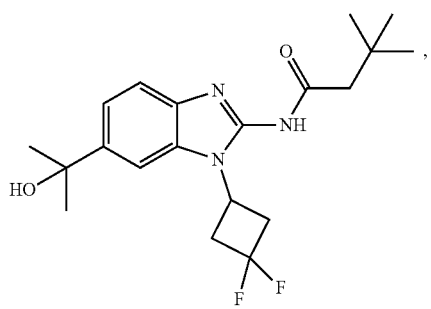
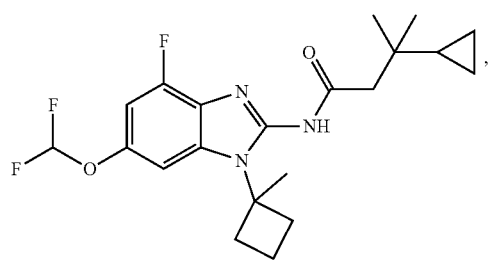
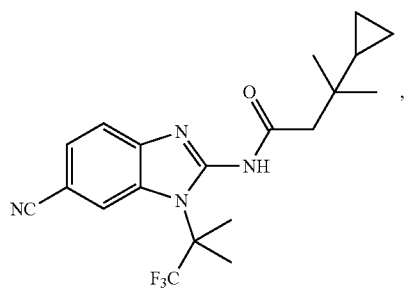
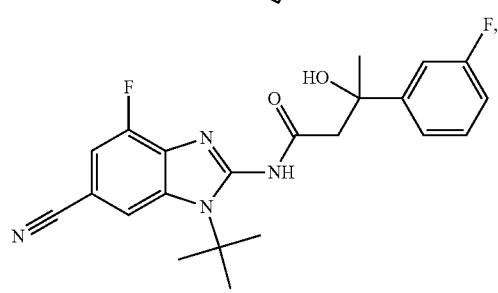
stereoisomer 1
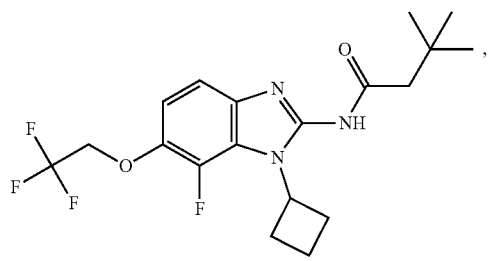
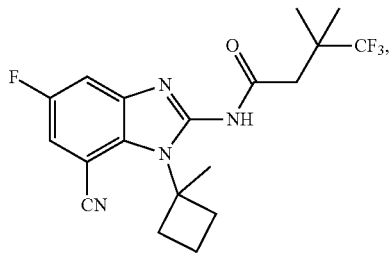
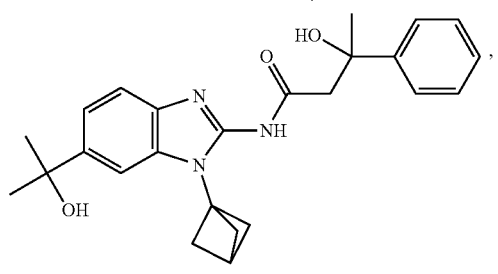
stereoisomer 1
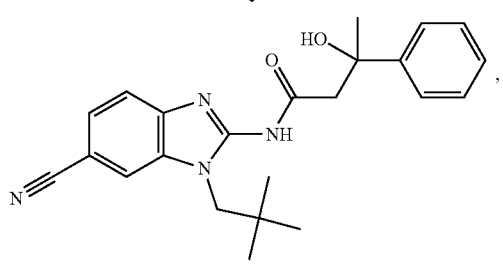
stereoisomer 1

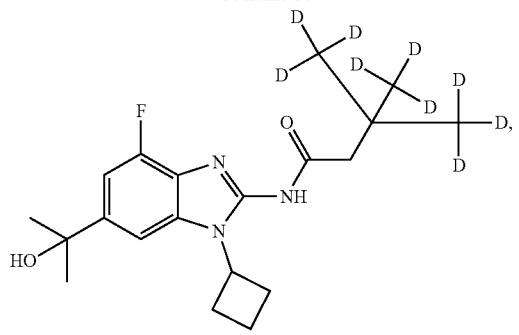
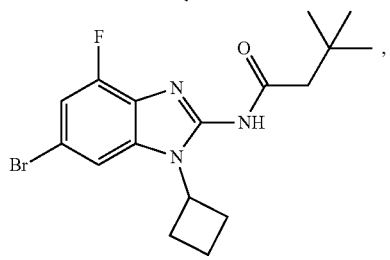
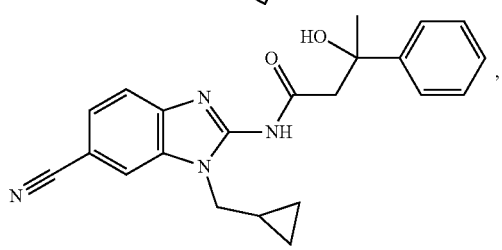
stereoisomer 2
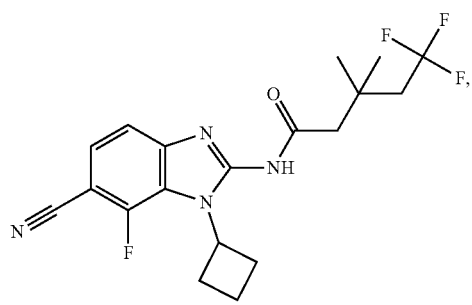
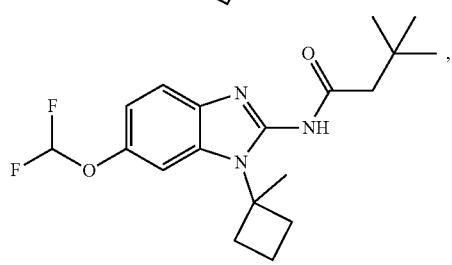
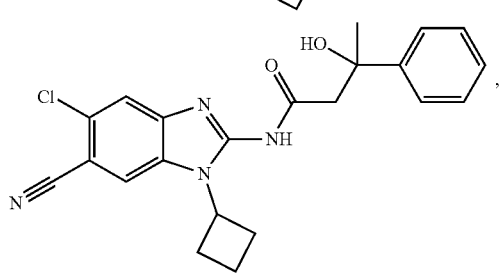
stereoisomer 1
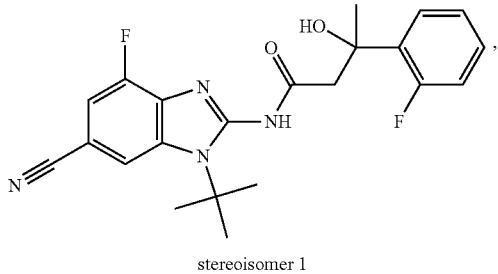
stereoisomer 1
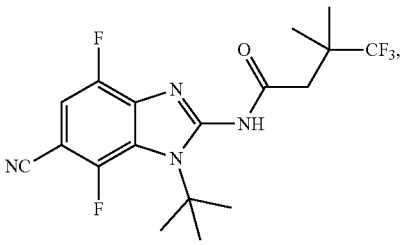
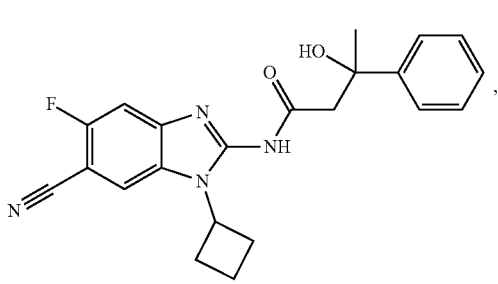
stereoisomer 1
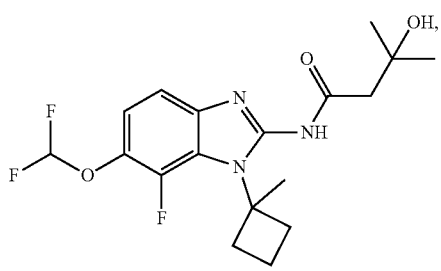
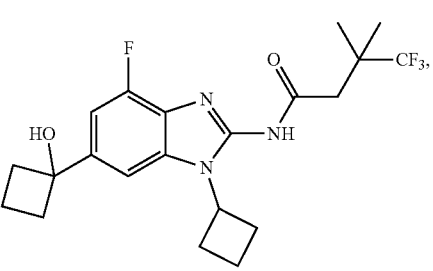
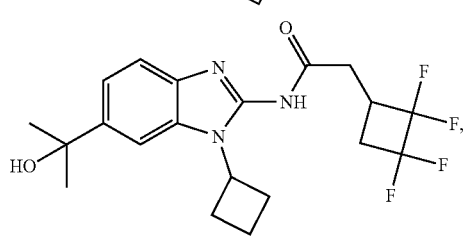

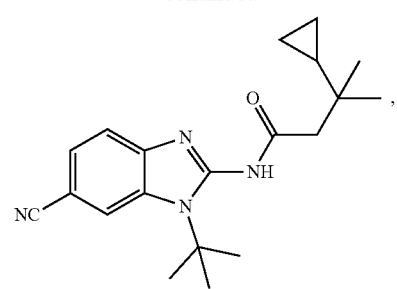
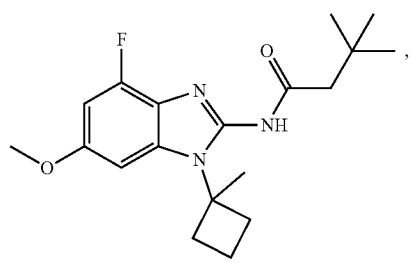
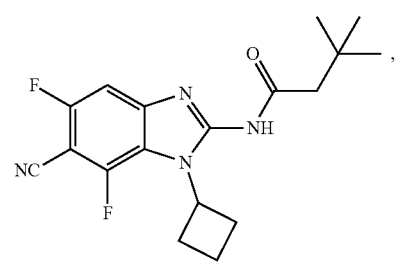
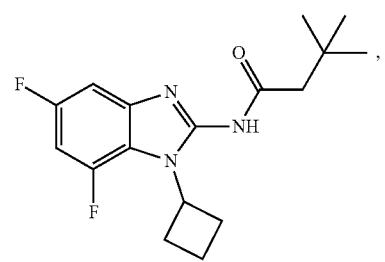
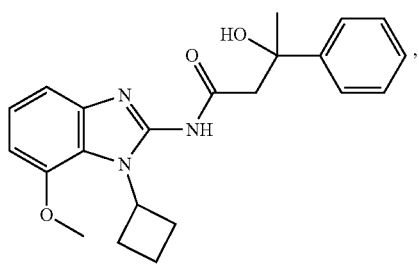
stereoisomer 2
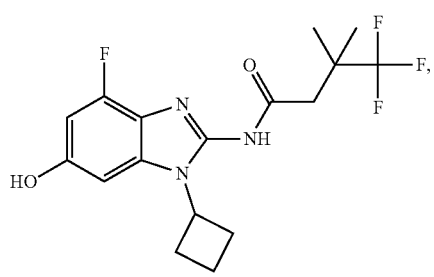
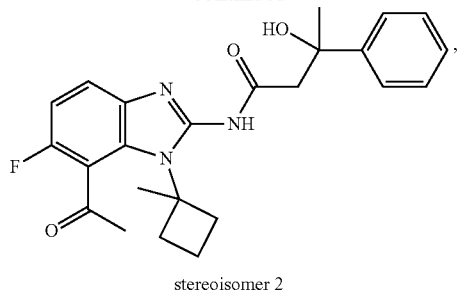
stereoisomer 2
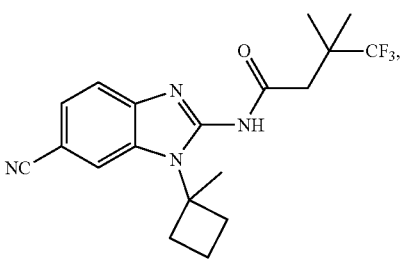
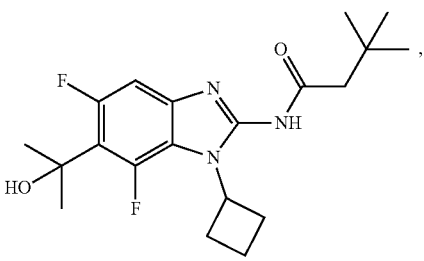
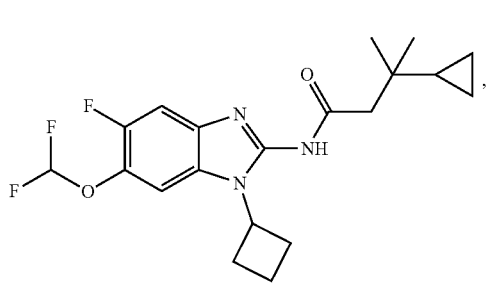
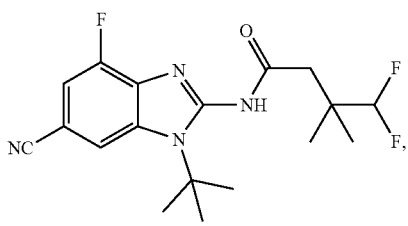
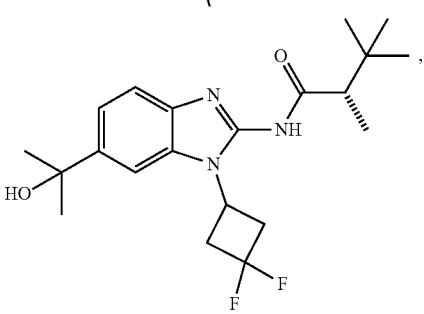

33
-continued
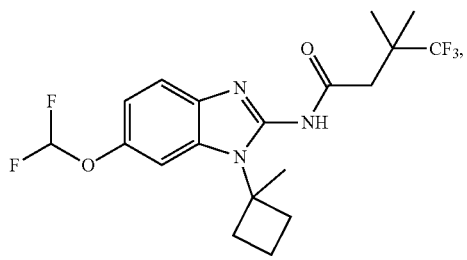
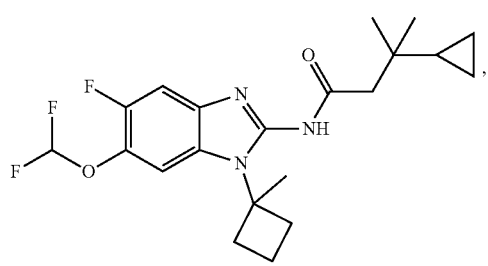
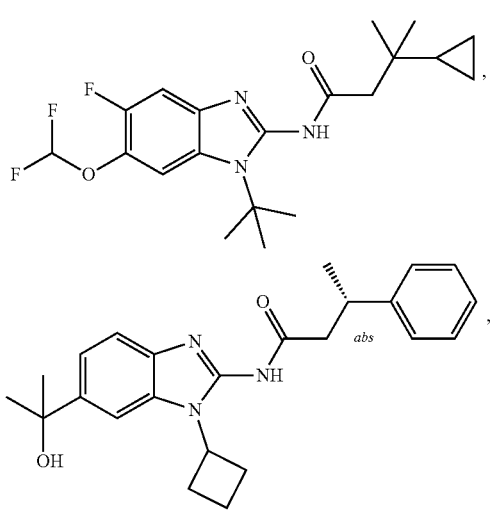
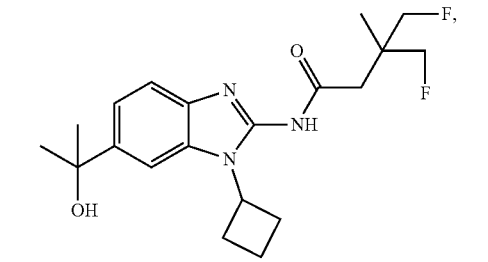
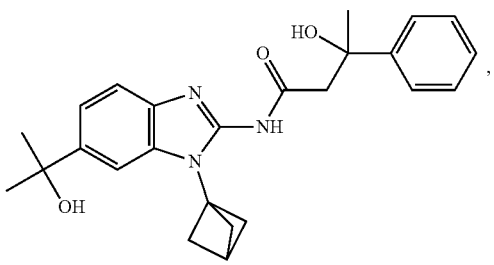
stereoisomer 2
34
-continued
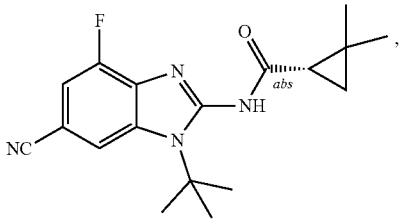
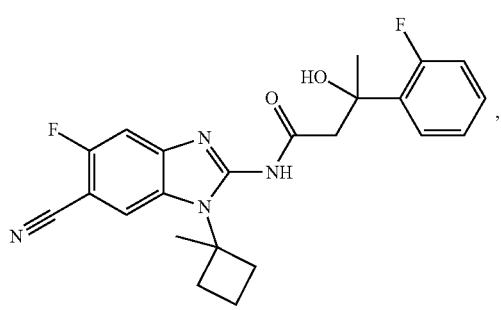
stereoisomer 2
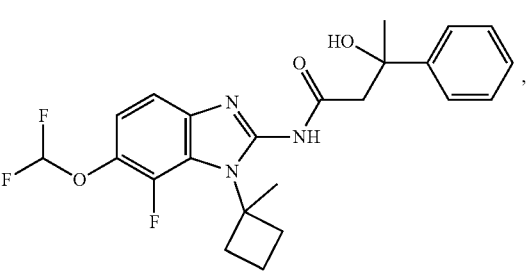
stereoisomer 2
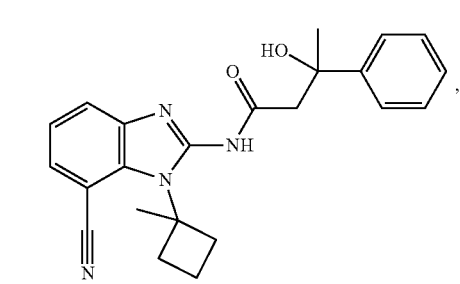
stereoisomer 2
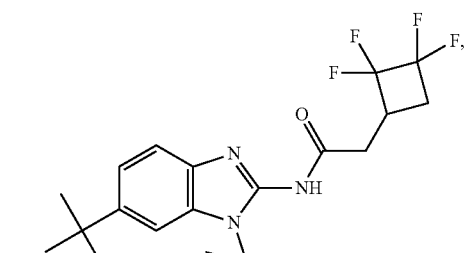
stereoisomer 1

35
-continued
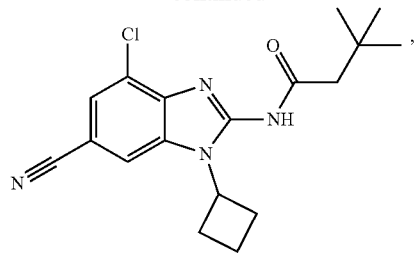
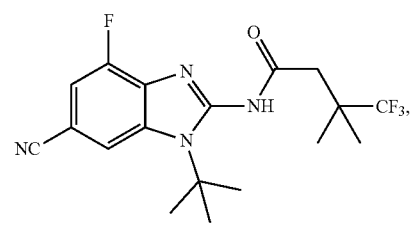
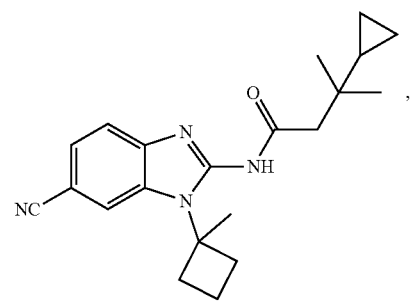
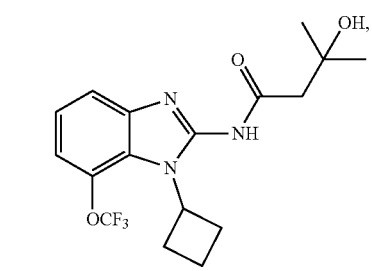
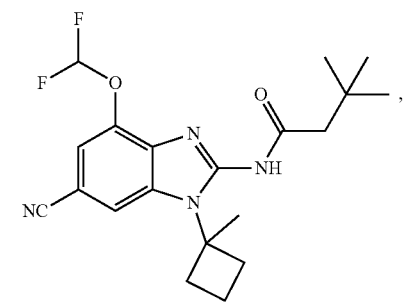
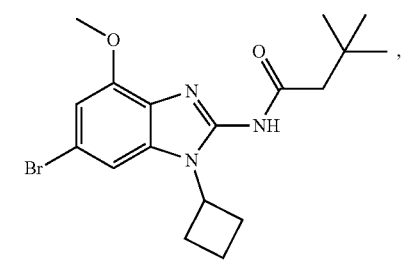
36
-continued
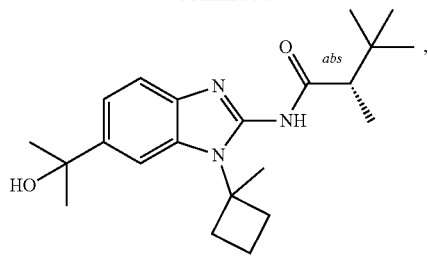
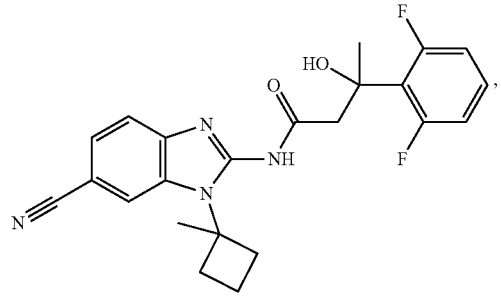
stereoisomer 2
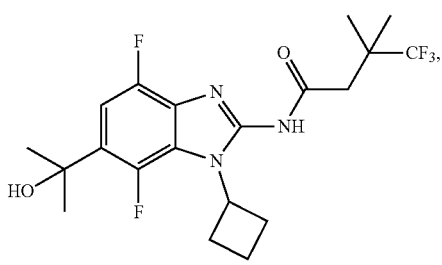
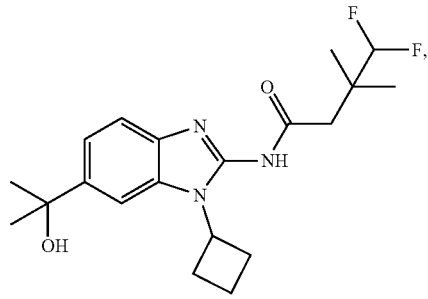
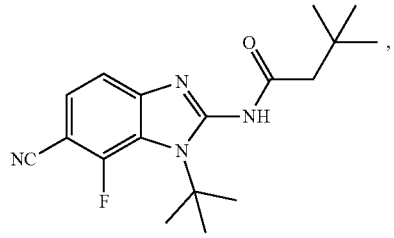
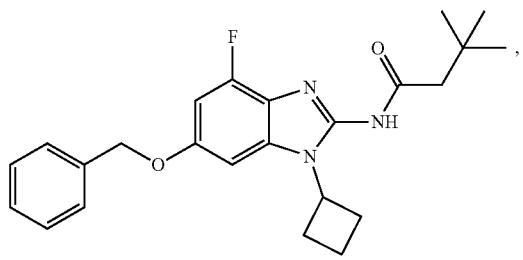

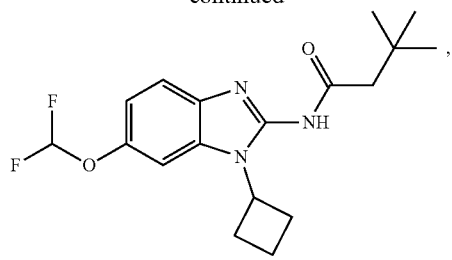
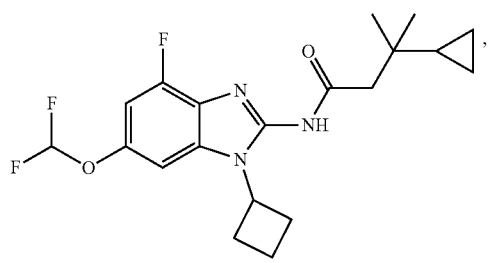
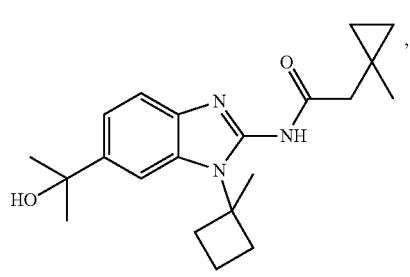
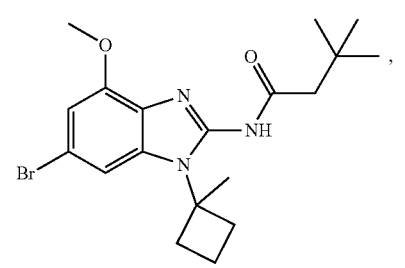
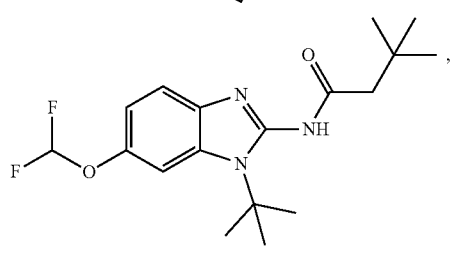
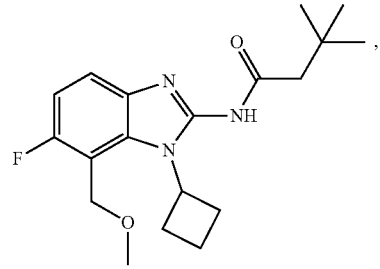
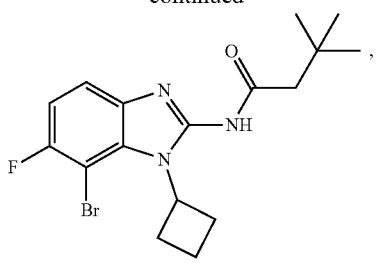
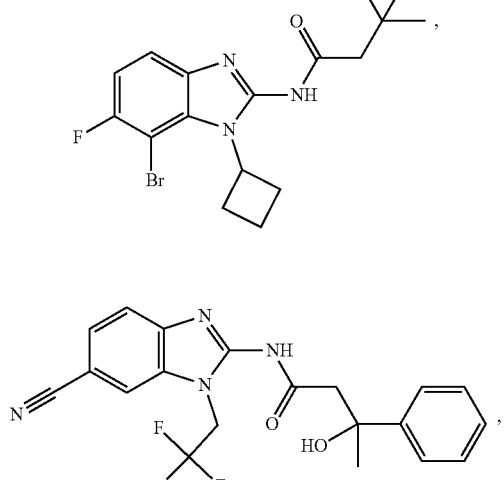
stereoisomer 1
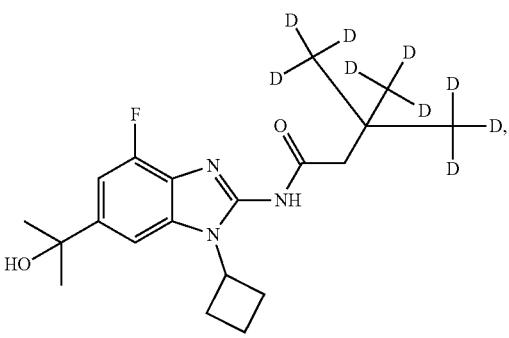
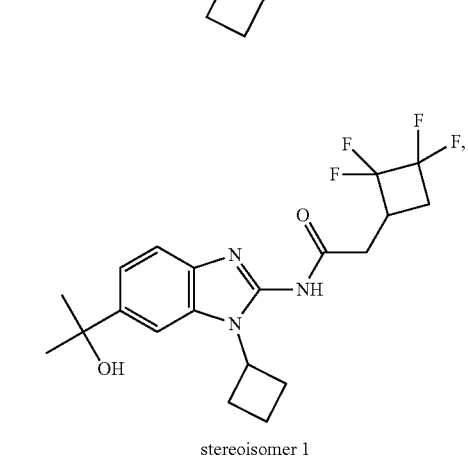
stereoisomer 1
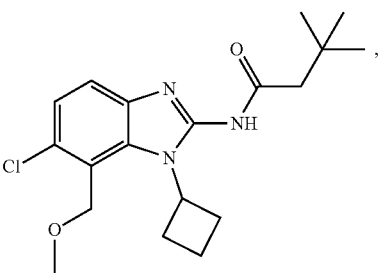

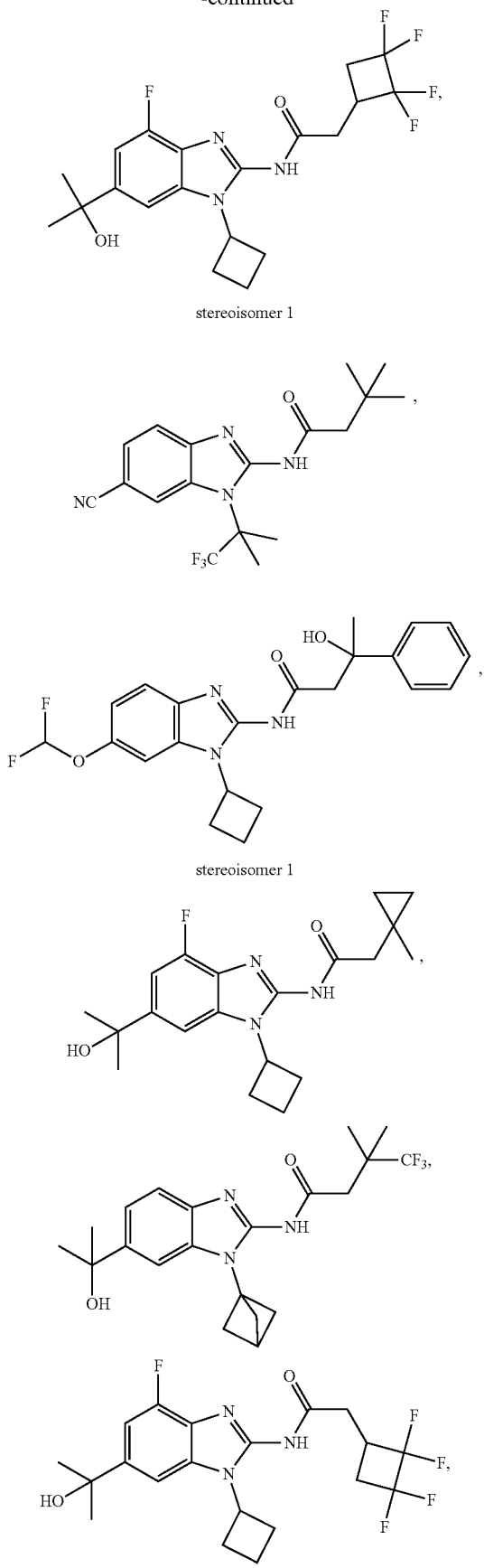
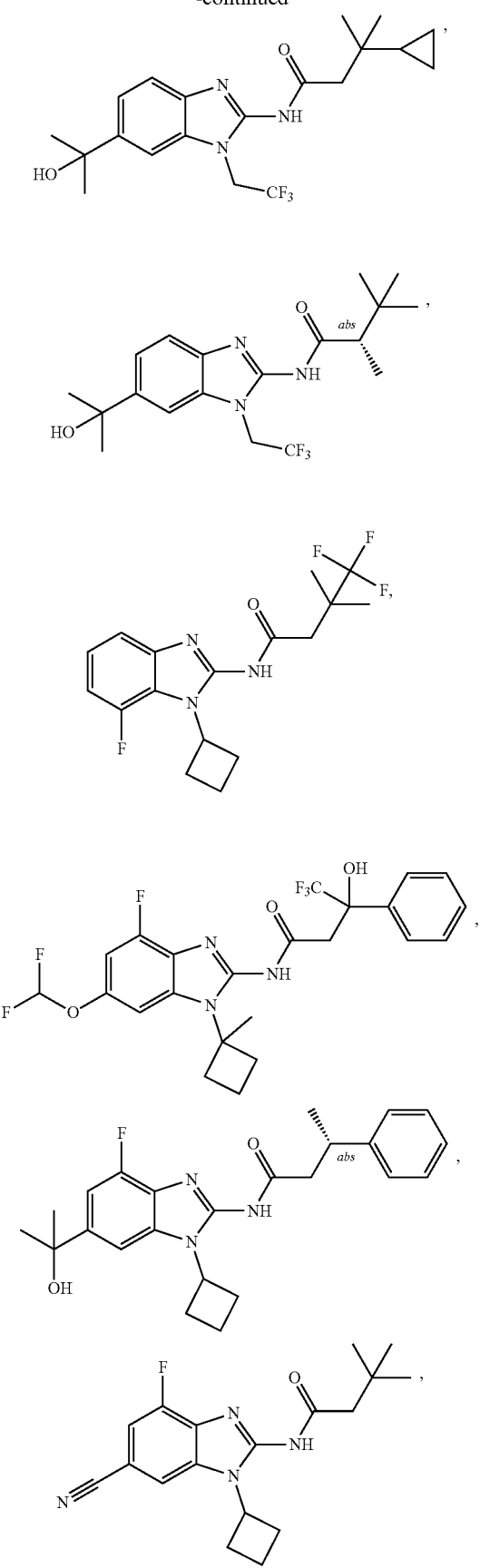

41
-continued
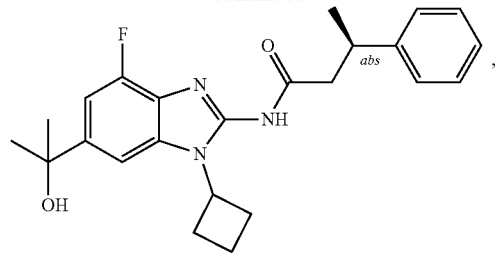
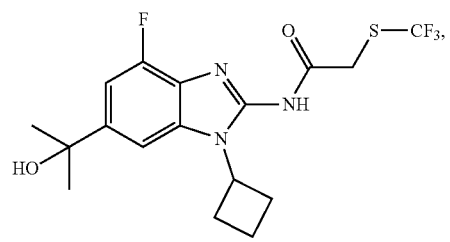
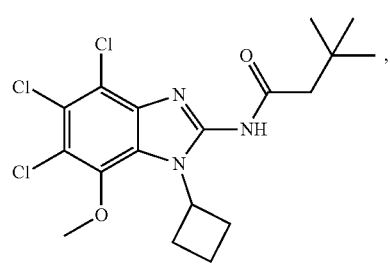
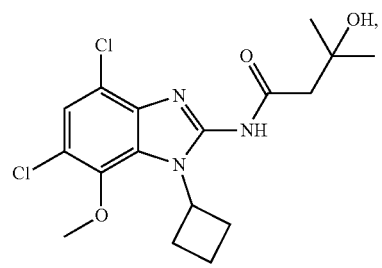
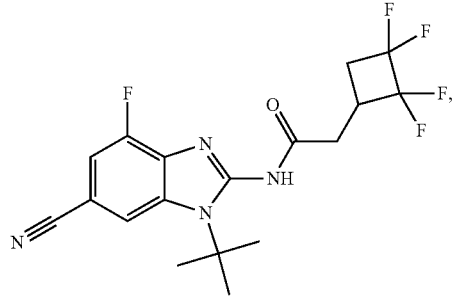
stereoisomer 2
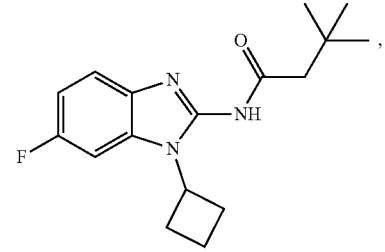
42
-continued
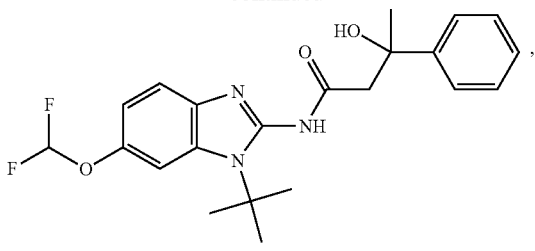
stereoisomer 1
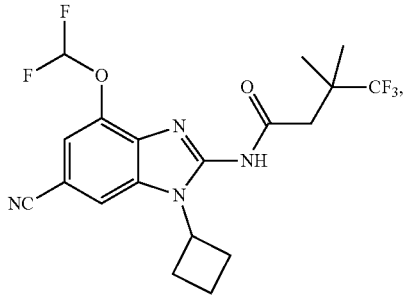
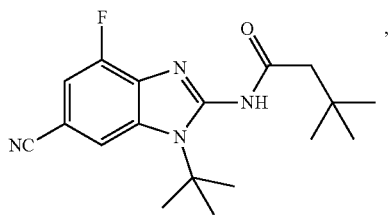
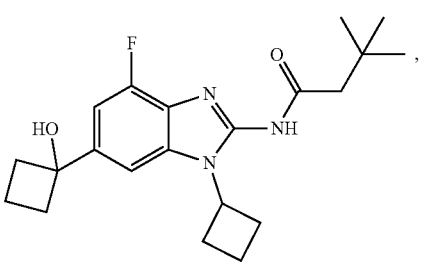
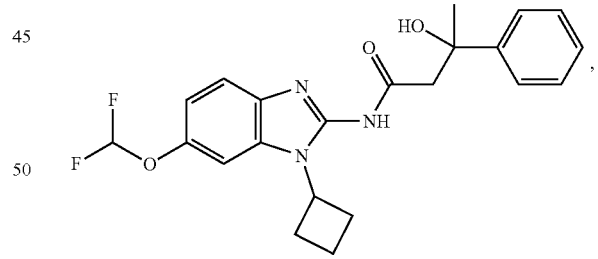
stereoisomer 2
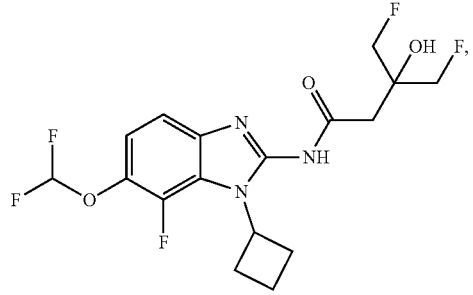

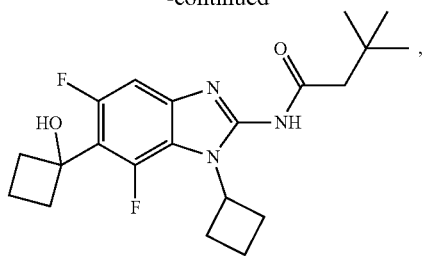
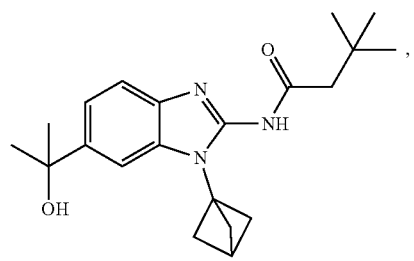
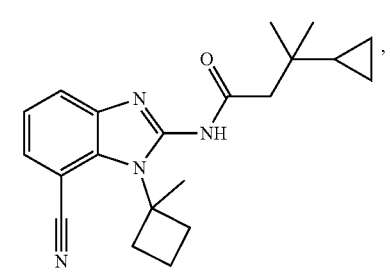
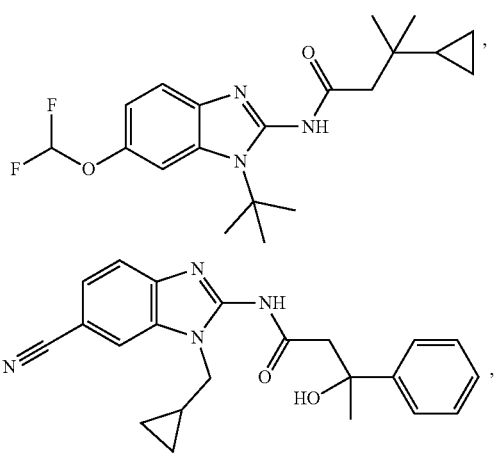
stereoisomer 1
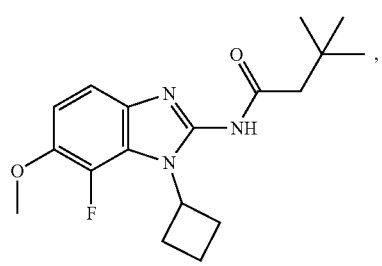
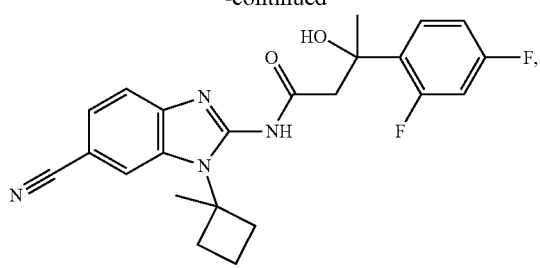
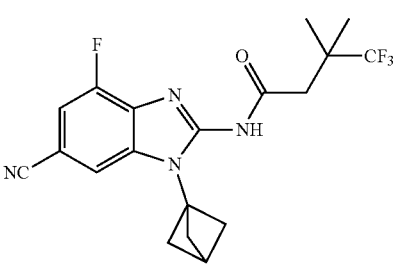
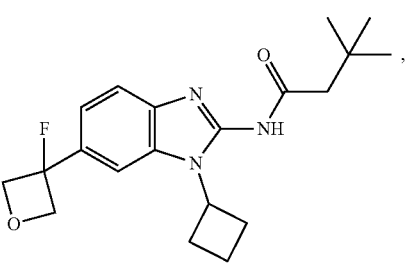
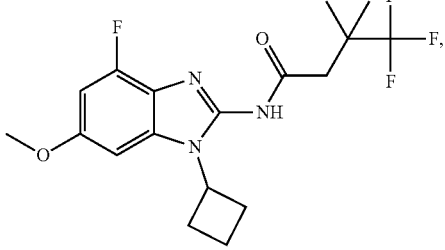
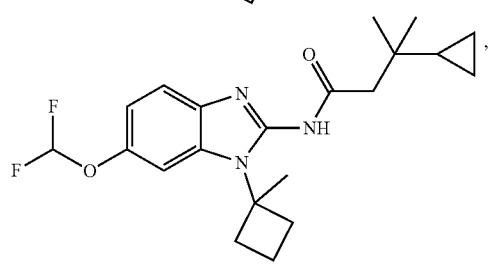
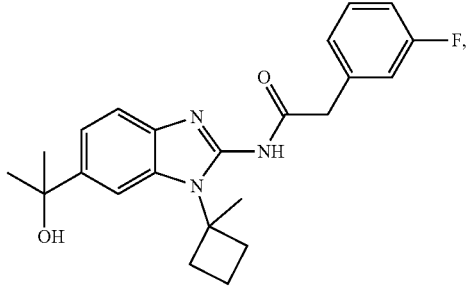

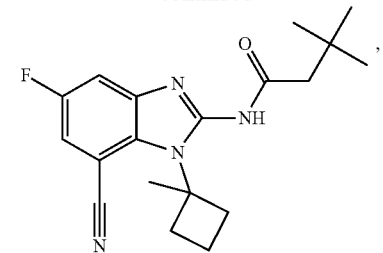
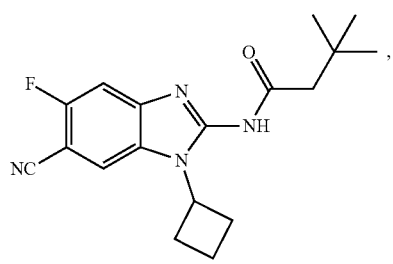
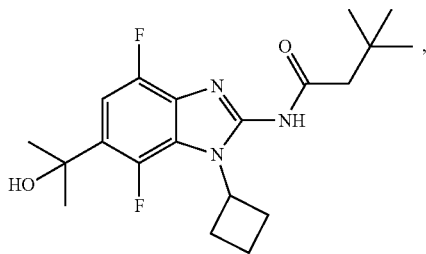
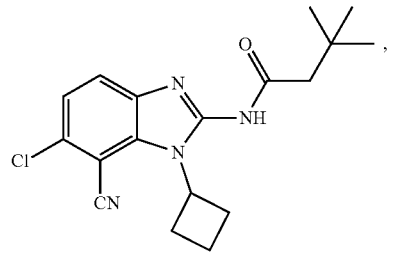
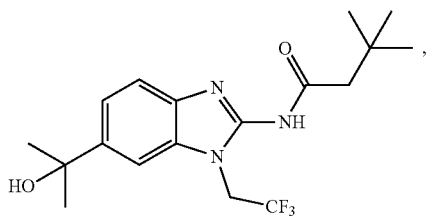
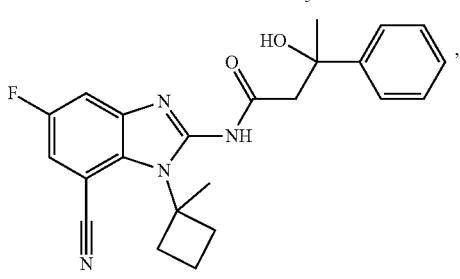
stereoisomer 1
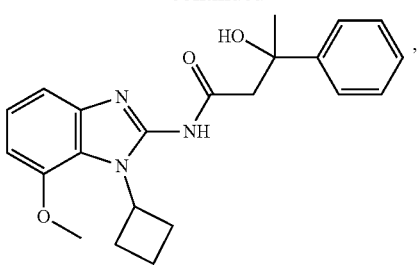
stereoisomer 1
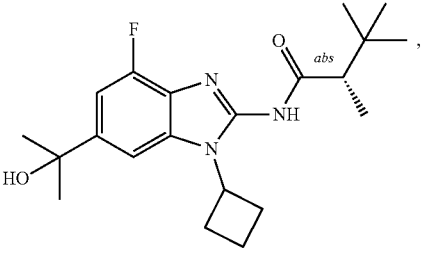
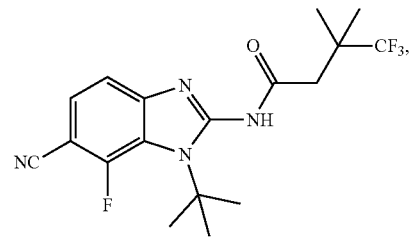
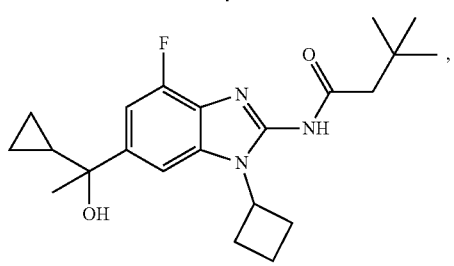
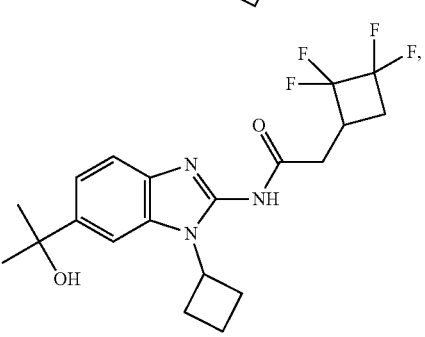
stereoisomer 2
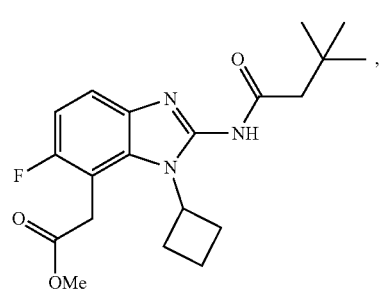

47
-continued
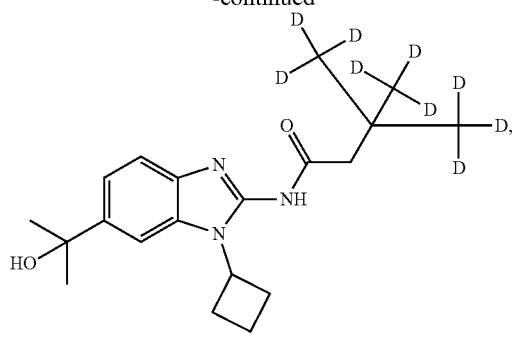
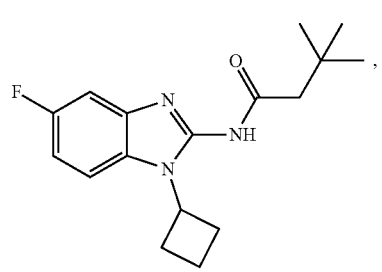
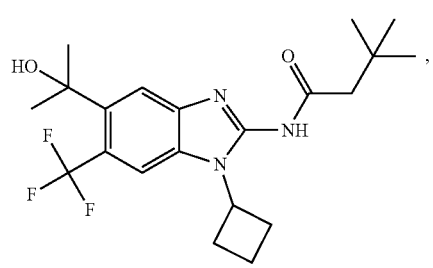
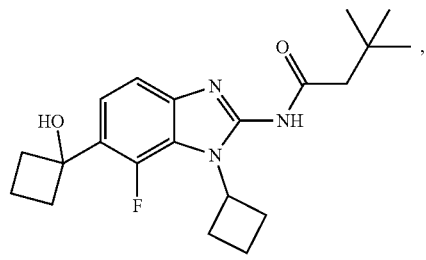
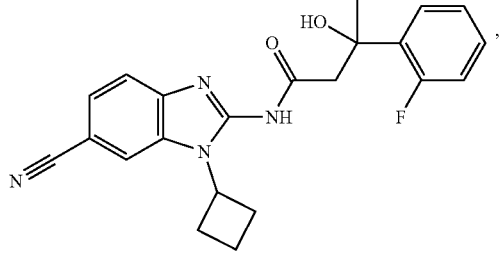
stereoisomer 1
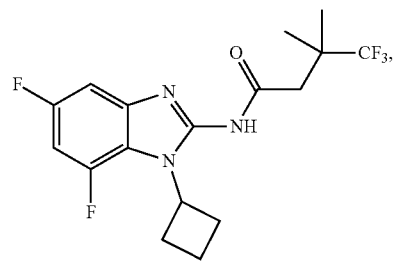
48
-continued
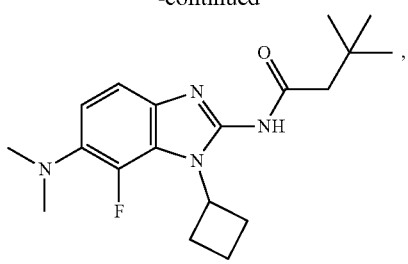
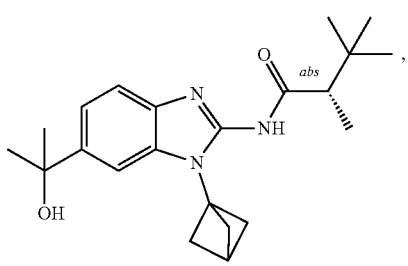
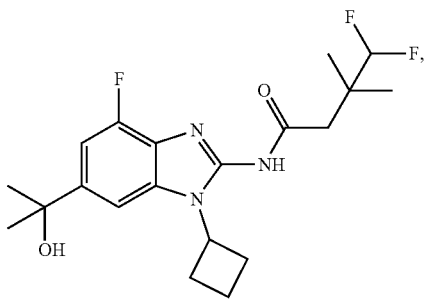
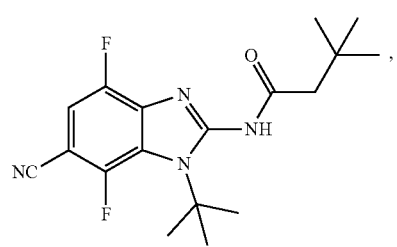
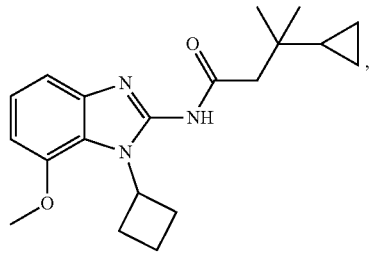
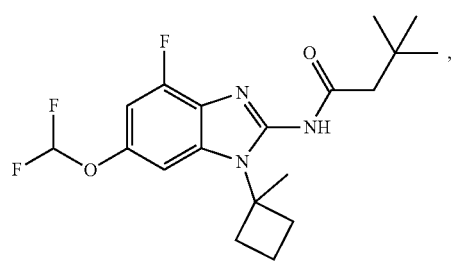

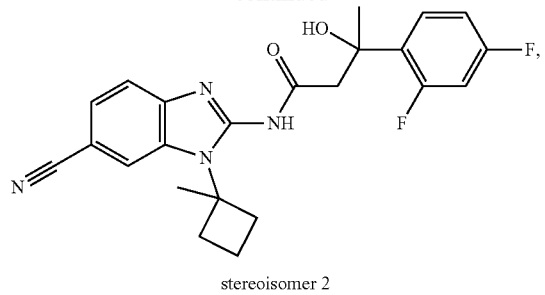
stereoisomer 2
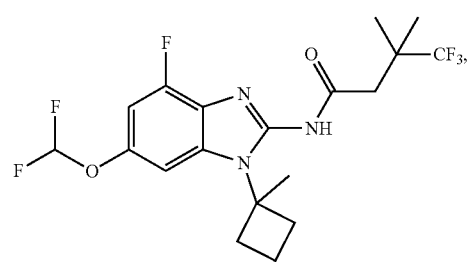
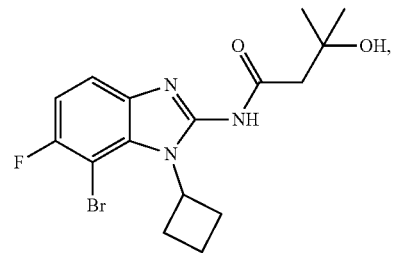
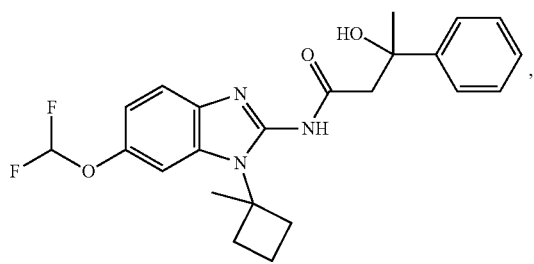
stereoisomer 1
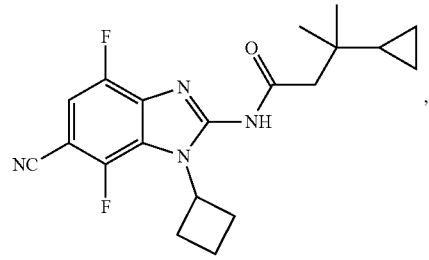
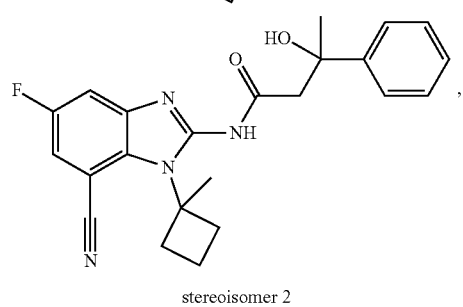
stereoisomer 2
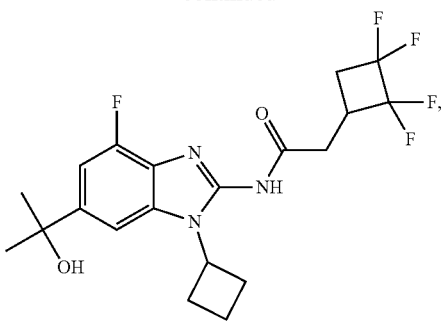
stereoisomer 2
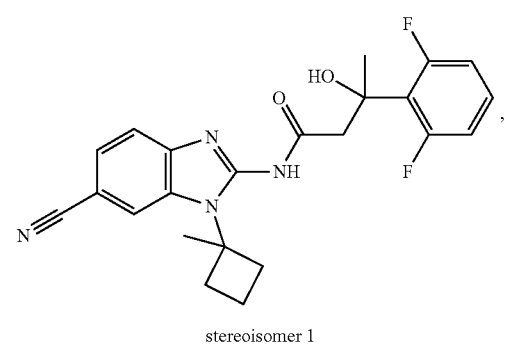
stereoisomer 1
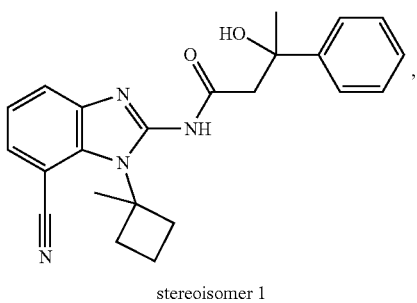
stereoisomer 1
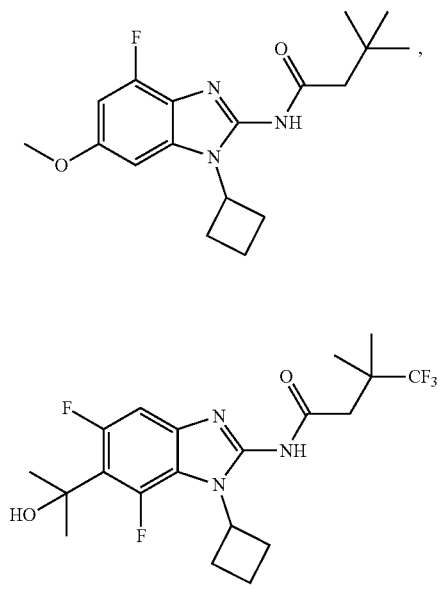

-continued
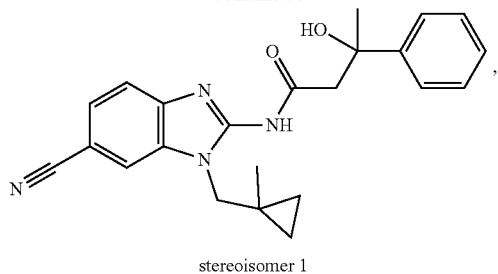
stereoisomer 1
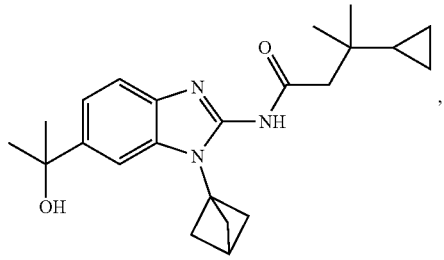
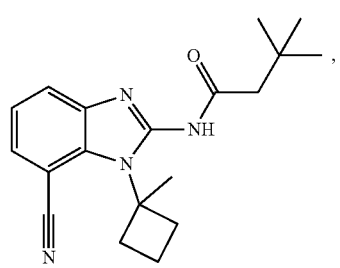
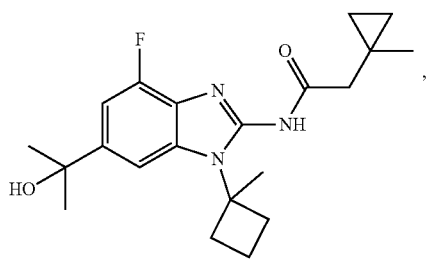
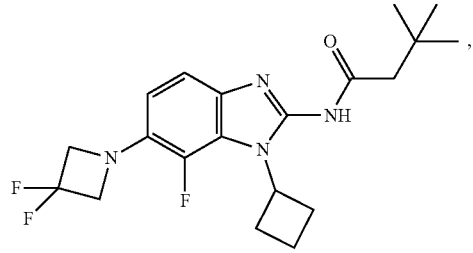
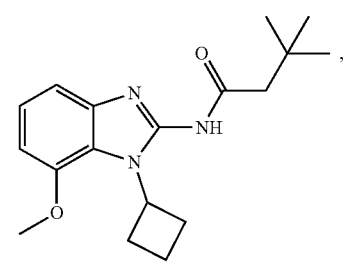
-continued
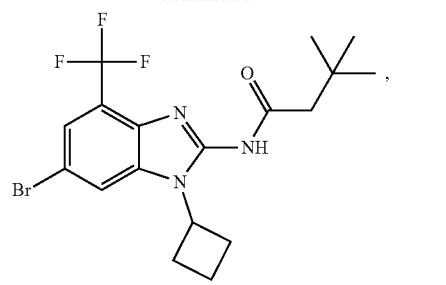
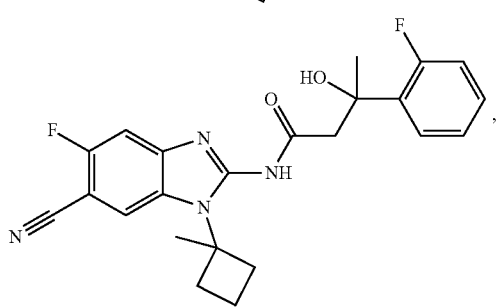
stereoisomer 1
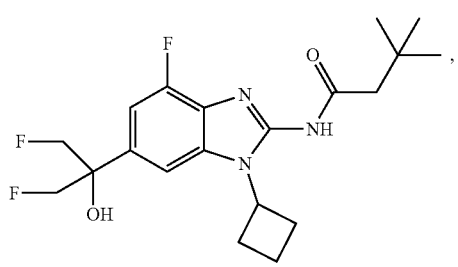
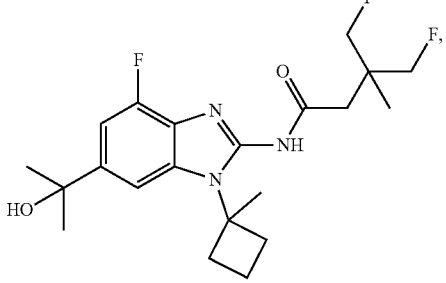
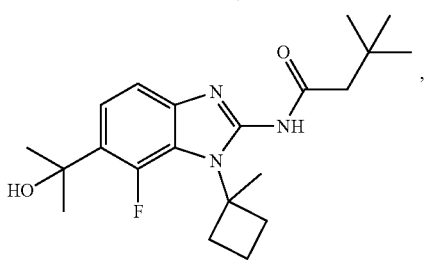
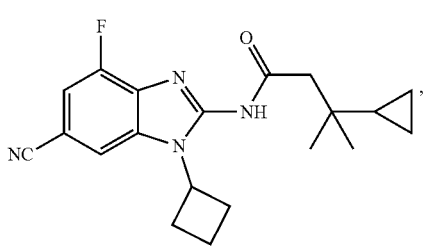

-continued
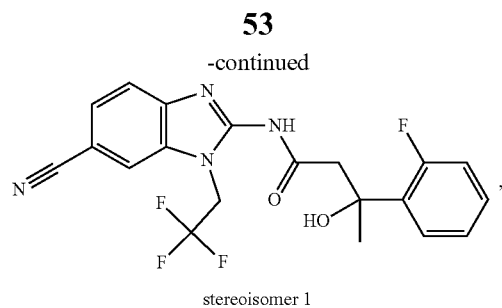
stereoisomer 1
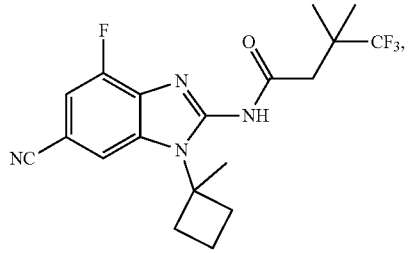
and
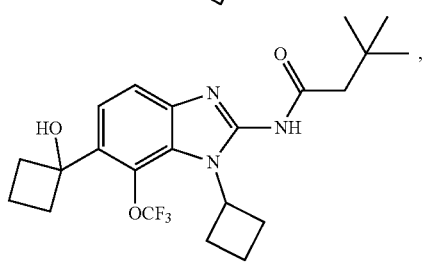
stereoisomer 1
In some embodiments, provided herein are any one of the following compounds of Group II, or a pharmaceutically acceptable salt thereof:
-continued
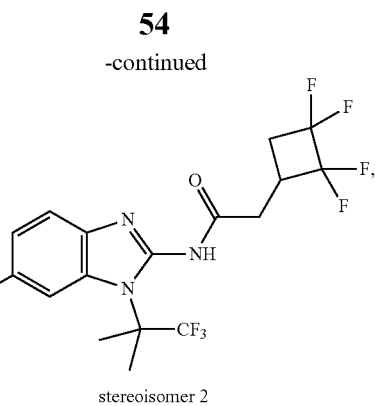
stereoisomer 2
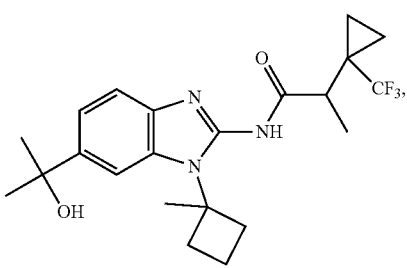
stereoisomer 1
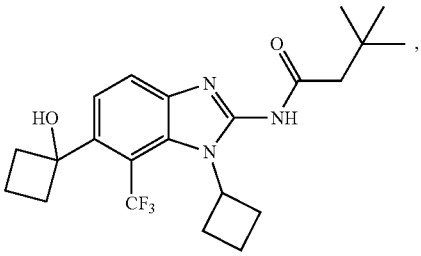
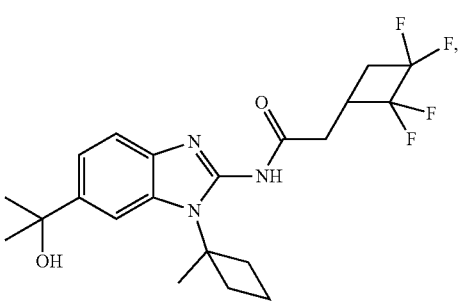
stereoisomer 1

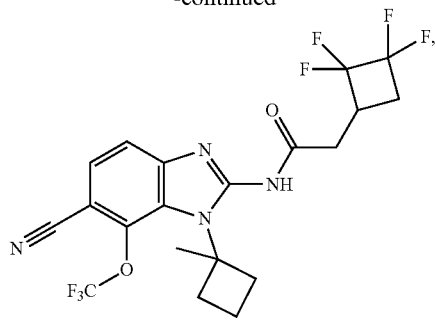
stereoisomer 1
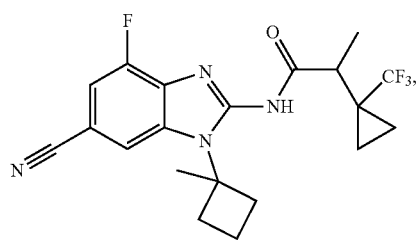
stereoisomer 1
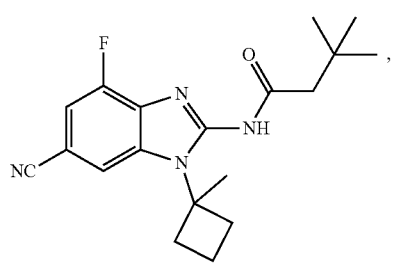
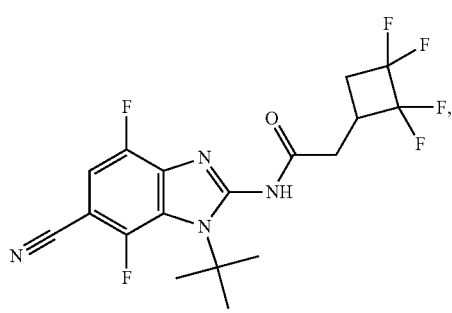
stereoisomer 1
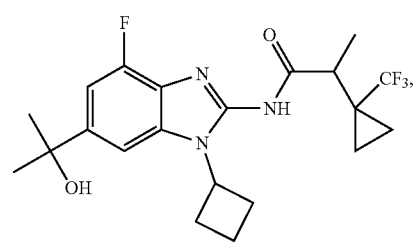
stereoisomer 1
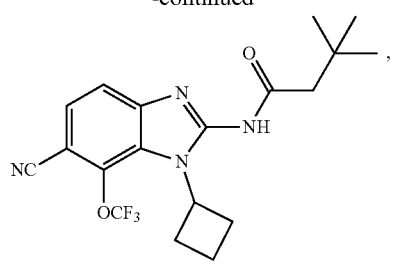
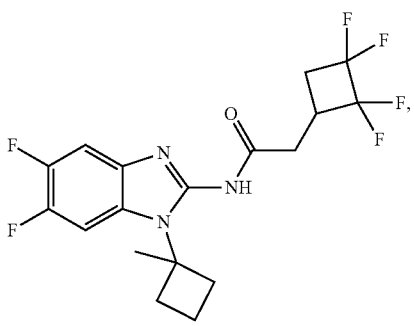
stereoisomer 2
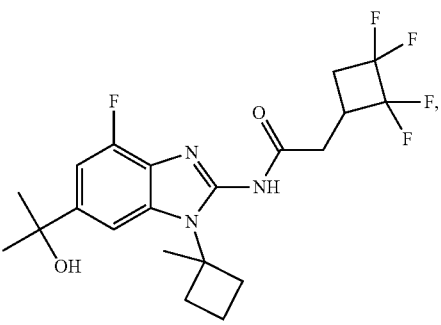
stereoisomer 2
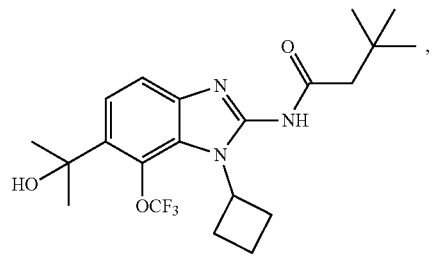
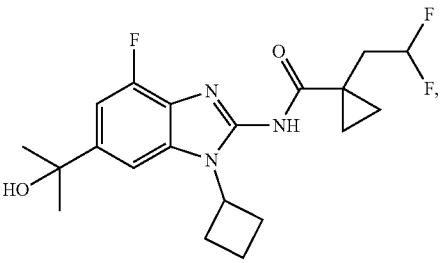

57
-continued
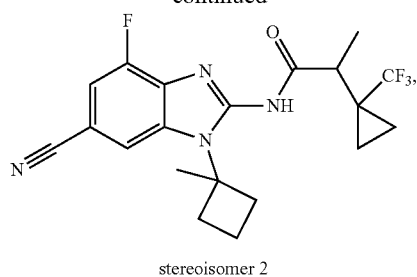
stereoisomer 2
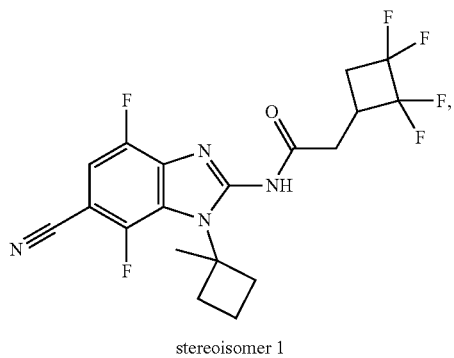
stereoisomer 1
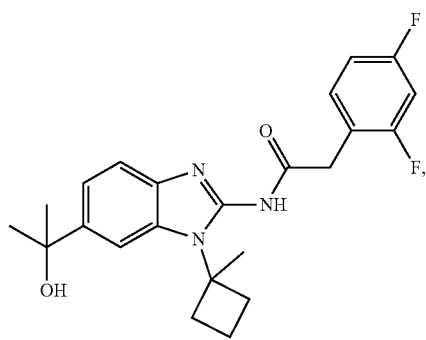
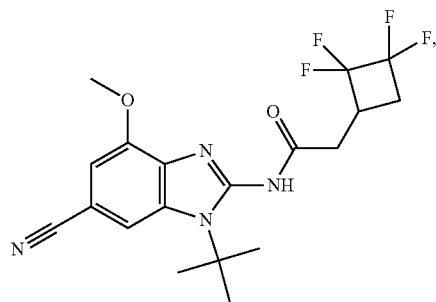
stereoisomer 2
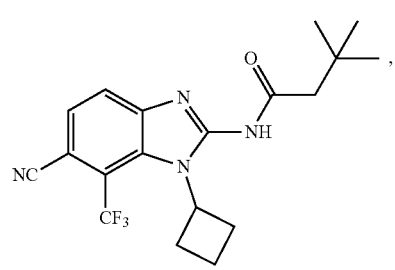
58
-continued
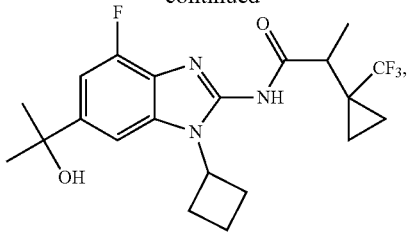
stereoisomer 2
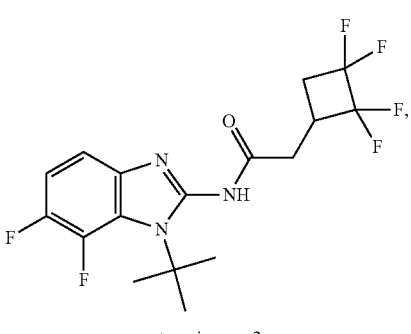
stereoisomer 2
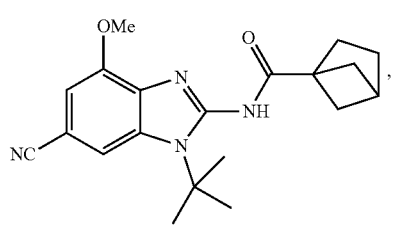
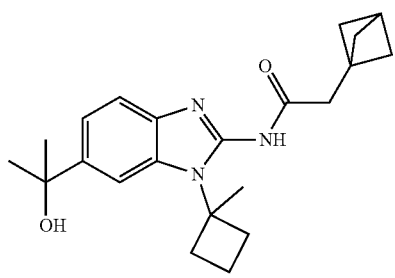
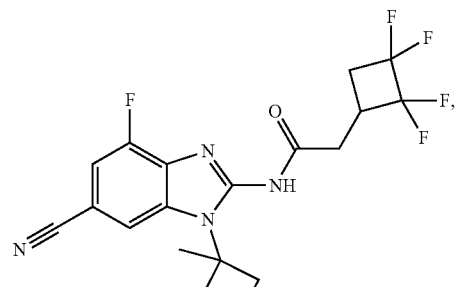
stereoisomer 2

-continued
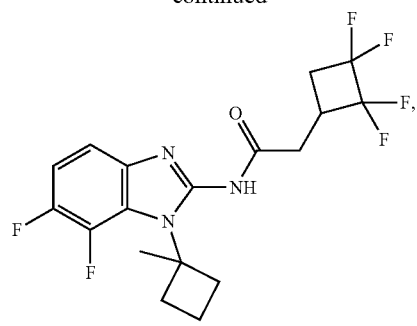
stereoisomer 2
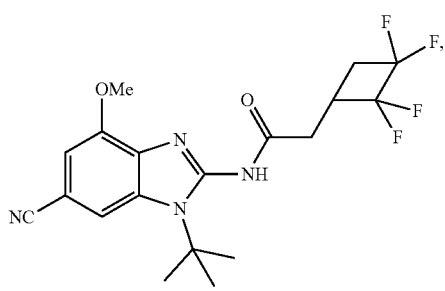
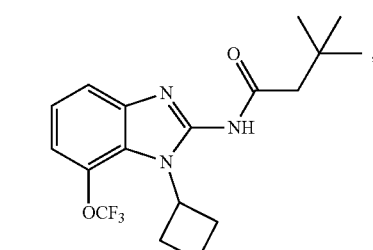
stereoisomer 1
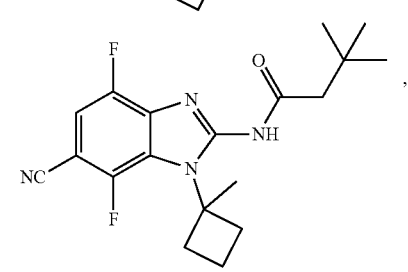
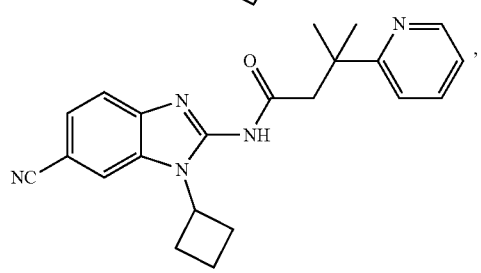
-continued
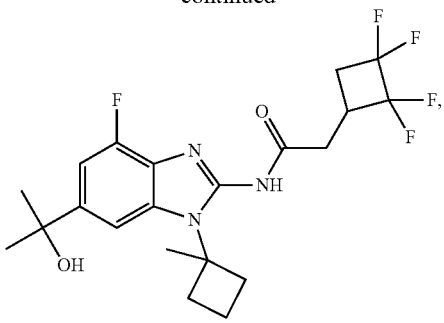
stereoisomer 1
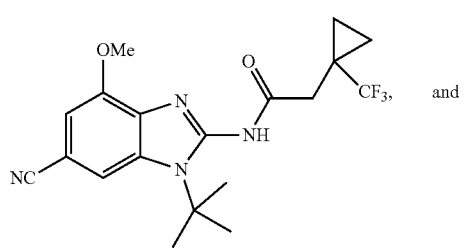
and
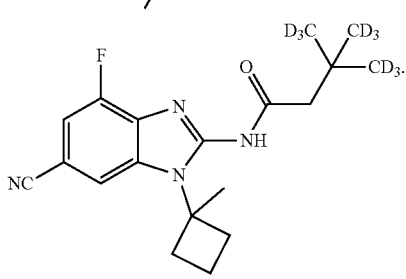
In some embodiments, provided herein are any one of the following compounds of Group III, or a pharmaceutically acceptable salt thereof:
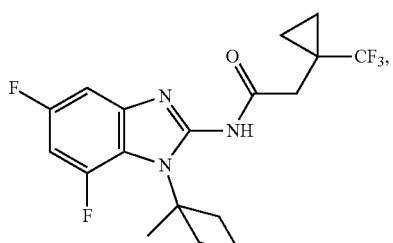
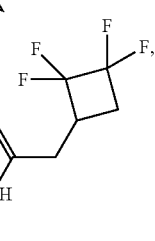
stereoisomer 1

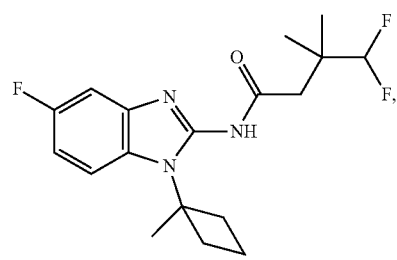
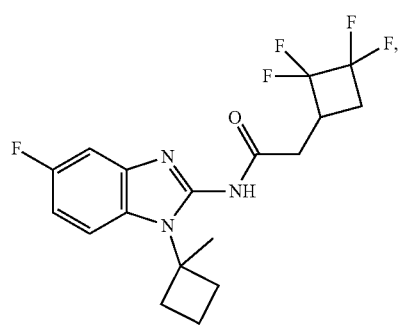
stereoisomer 1
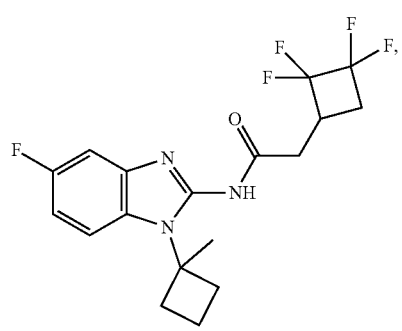
stereoisomer 2
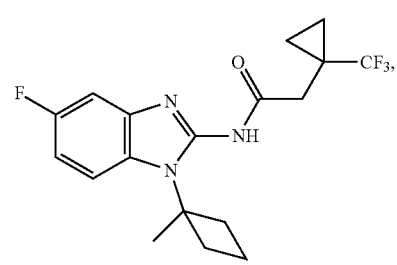
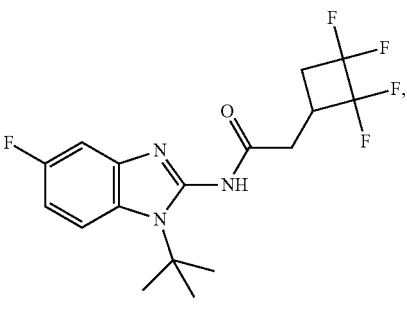
stereoisomer 1
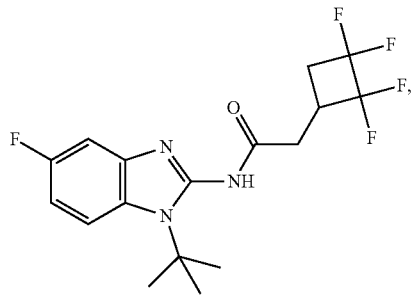
stereoisomer 2
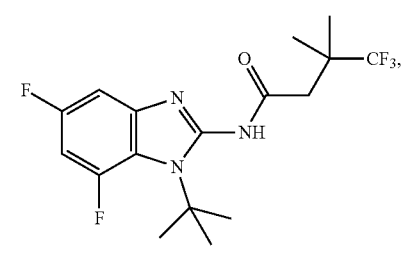
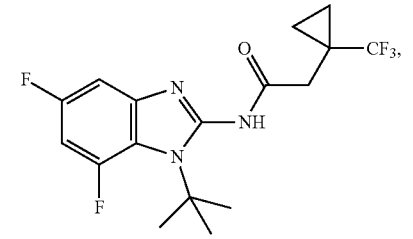
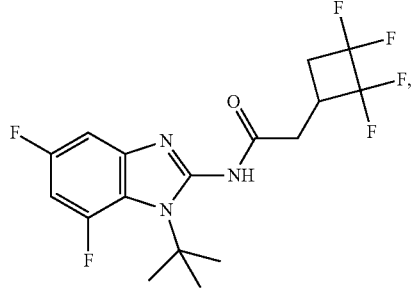
stereoisomer 2
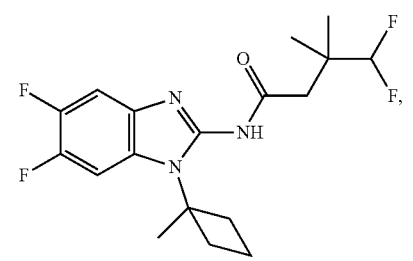
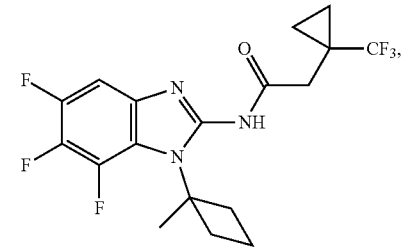

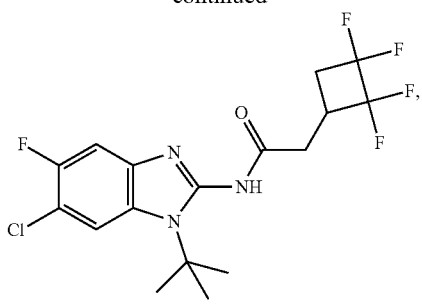
stereoisomer 2
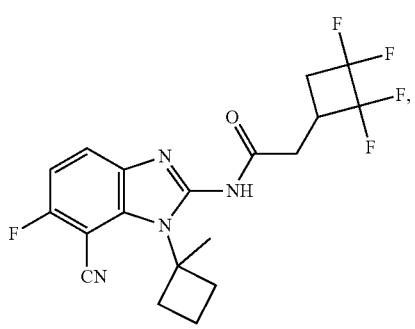
stereoisomer 1
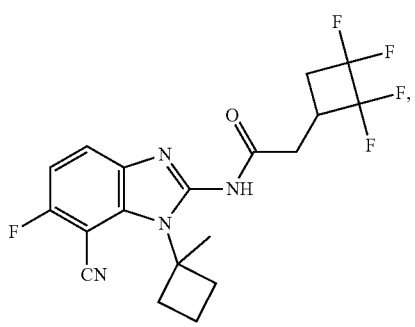
stereoisomer 2
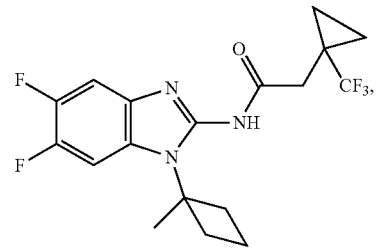
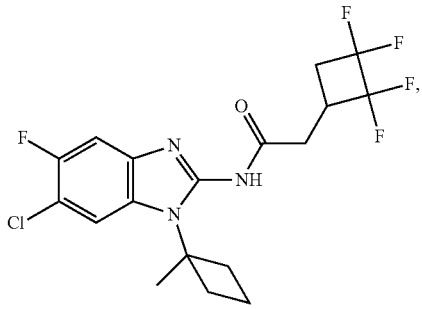
stereoisomer 2
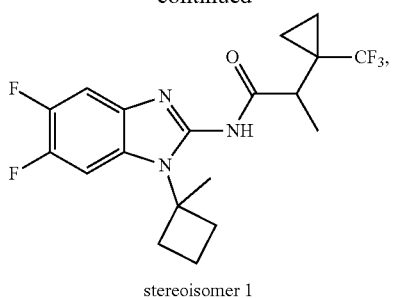
stereoisomer 1
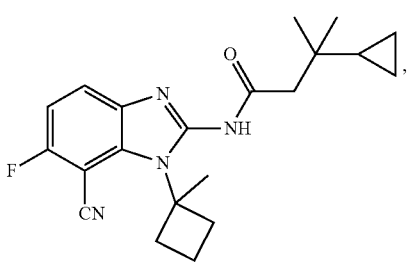
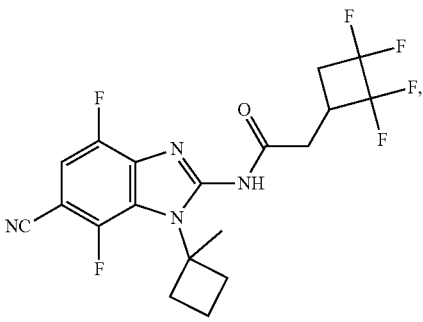
stereoisomer 2
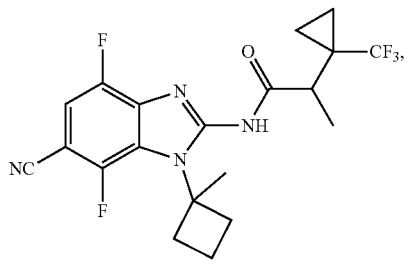
stereoisomer 2
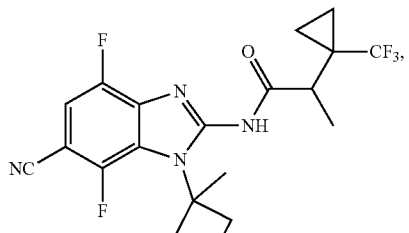
stereoisomer 1

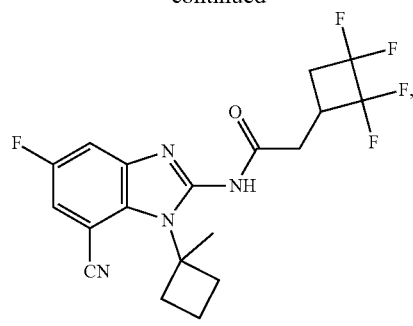
stereoisomer 1
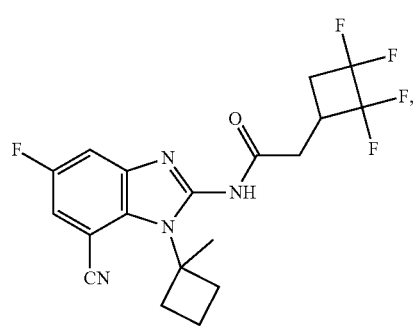
stereoisomer 2
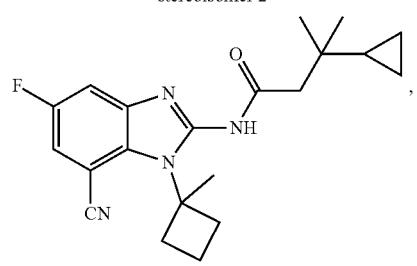
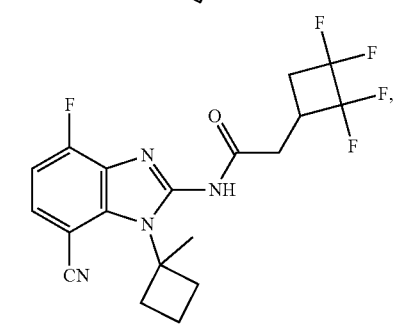
stereoisomer 2
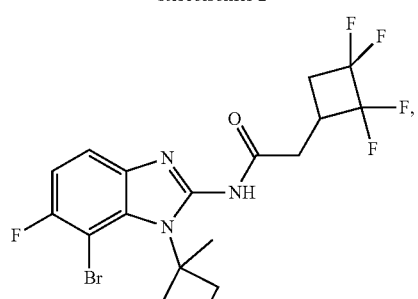
stereoisomer 1
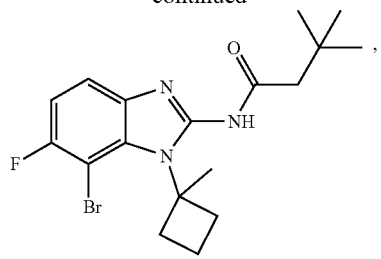
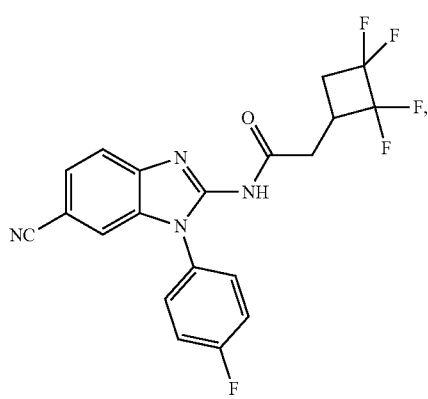
stereoisomer 2
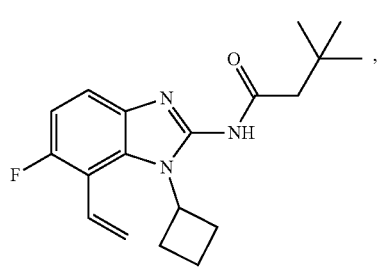
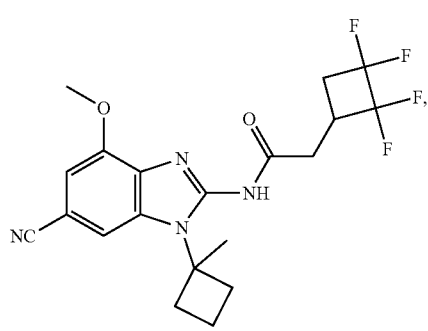
stereoisomer 2
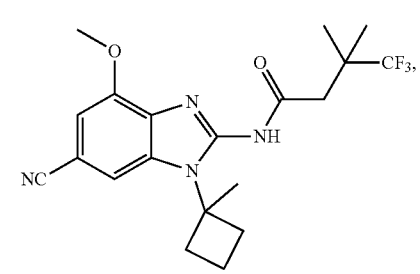

-continued

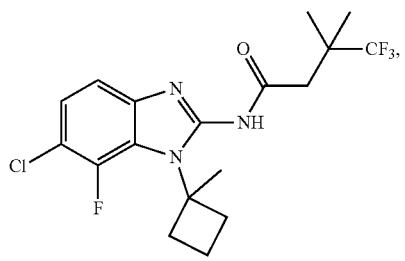

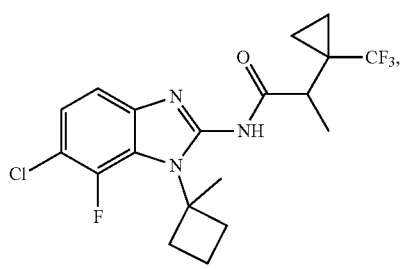

stereoisomer 1

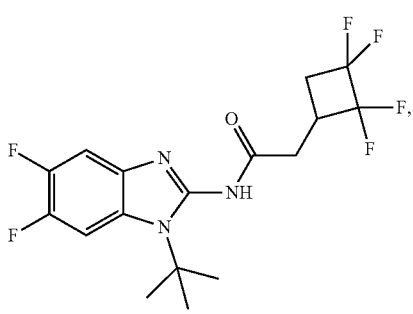

stereoisomer 2

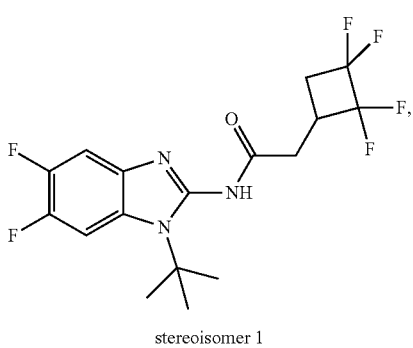

stereoisomer 1

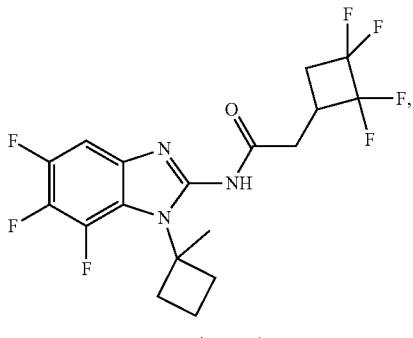

stereoisomer 1

-continued

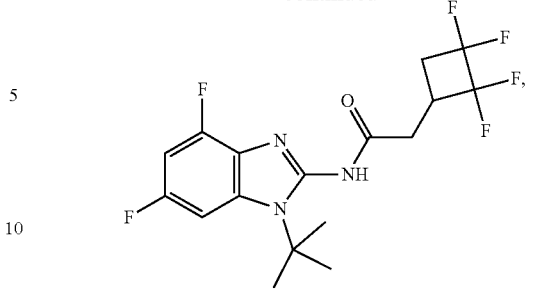

stereoisomer 2

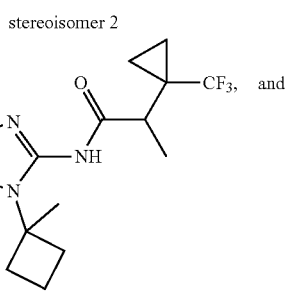

and

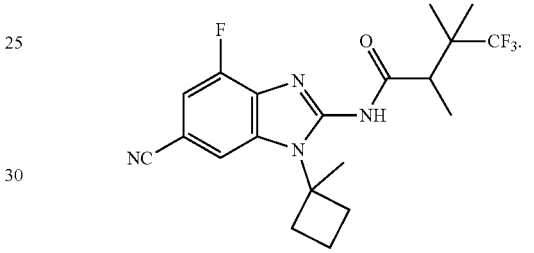

stereoisomer 1

Methods of Use

Embodiments of the present invention relate to a method of treating a Kv7 associated disorder comprising administering a therapeutically effective amount of a compound of formula 1C, 2C, 8a, 8b, 8c, 9, 10, 11, 12, 13, or 14, a compound of Group I, Group II, Group III, or Table 1, or a pharmaceutically acceptable salt thereof, to a subject in need thereof. The disorder is selected from the group consisting of epilepsy, neonatal spasms, pain, migraine, a disorder of neurotransmitter release, a smooth muscle contractility disorder, a dyskinesia, dystonia, mania, a hearing disorder, neuropathic pain, inflammatory pain, persistent pain, cancer pain, postoperative pain, anxiety, substance abuse, schizophrenia, a bladder disorder, a vasculature disorder, tinnitus, benign familial neonatal seizures, epilepsy, neurological disease via reduced basal M-current (and subsequent neuronal hyperexcitability), sensorineural hearing impairment, intellectual disability, epileptic encephalopathy, treatment-resistant epilepsy, cortical atrophy, neurological impairment, infantile spasms with hypsarrhythmia, myoclonic-tonic seizures, myoclonic seizures, tonic seizures, absence and focal-onset seizures with impaired awareness, congenital neurological disorder with intellectual disability or epileptic encephalopathy, benign familial neonatal convulsions, severe epileptic encephalopathies, congenital neurodevelopmental disorder with phenotypes of nonsyndromic intellectual disability or epileptic encephalopathy, neonatal spasms, neonatal seizures, epileptic encephalopathy, benign familial neonatal convulsions type 1, benign familial neonatal seizures 1, neonatal seizures associated with hypoxic-ischemic injury, epileptic spasms, epileptic encephalopathy, early infantile epileptic encephalopathy 7, early infantile epileptic encephalopathy with delayed psychomotor development, generalized tonic seizures, abnormal globus pallidus morphology, apnea, cerebral edema, dystonia, facial erythema, muscular hypotonia, febrile seizures, hypoplasia of the corpus callosum, hypsarrhythmia, focal clonic seizure, generalized tonic-clonic seizures, myokymia, spastic tetraparesis, myokymia, gynecological system disorders, and combinations thereof. In embodiments, such compound may be administered in a pharmaceutical composition as described herein.

In some embodiments, the gynecological system disorders are selected from the group consisting of pre-term labor, post-partum hemorrhage, uterine atony, uterine perforation, uterine hyper-stimulation, menorrhagia, metrorrhagia, menometrorrhagia, dysmenorrhea and endometriosis.

KCNQ genes encode five Kv7 potassium channel subunits (1-5). A functional Kv7 potassium channel can be assembled using a combination of these five subunits arranged as homotetramers or heterotetramers. KCNQ2, KCNQ3, KCNQ4, and KCNQ5 are expressed in the nervous system and have been associated with a range of disorders involving neuronal excitability.

Embodiments herein are directed to methods of treating a disorder associated with a KCNQ subunit comprising administering a therapeutically effective amount of a compound of formula 1C, 2C, 8a, 8b, 8c, 9, 10, 11, 12, 13, or 14, or a compound of Group I, Group II, Group III, or Table 1, or a pharmaceutically acceptable salt thereof, to a subject in need thereof. Embodiments herein are directed to methods of treating a disorder associated with a KCNQ2 subunit comprising administering a therapeutically effective amount of a compound of formula 1C, 2C, 8a, 8b, 8c, 9, 10, 11, 12, 13, or 14, or a compound of Group I, Group II, Group III, or Table 1, or a pharmaceutically acceptable salt thereof, to a subject in need thereof. Embodiments herein are directed to methods of treating a disorder associated with a KCNQ3 subunit comprising administering a therapeutically effective amount of a compound of formula 1C, 2C, 8a, 8b, 8c, 9, 10, 11, 12, 13, or 14, or a compound of Group I, Group II, Group III, or Table 1, or a pharmaceutically acceptable salt thereof, to a subject in need thereof. Embodiments herein are directed to methods of treating a disorder associated with a KCNQ4 subunit comprising administering a therapeutically effective amount of a compound of formula 1C, 2C, 8a, 8b, 8c, 9, 10, 11, 12, 13, or 14, or a compound of Group I, Group II, Group III, or Table 1, or a pharmaceutically acceptable salt thereof, to a subject in need thereof. Embodiments herein are directed to methods of treating a disorder associated with a KCNQ5 subunit comprising administering a therapeutically effective amount of a compound of formula 1C, 2C, 8a, 8b, 8c, 9, 10, 11, 12, 13, or 14, or a compound of Group I, Group II, Group III, or Table 1, or a pharmaceutically acceptable salt thereof, to a subject in need thereof.

Embodiments herein are directed to methods of treating a disorder associated with a mutation in a KCNQ subunit comprising administering a therapeutically effective amount of a compound of formula 1C, 2C, 8a, 8b, 8c, 9, 10, 11, 12, 13, or 14, or a compound of Group I, Group II, Group III, or Table 1, or a pharmaceutically acceptable salt thereof, to a subject in need thereof. Embodiments herein are directed to methods of treating a disorder associated with a mutation in a KCNQ2 subunit comprising administering a therapeutically effective amount of a compound of formula 1C, 2C, 8a, 8b, 8c, 9, 10, 11, 12, 13, or 14, or a compound of Group I, Group II, Group III, or Table 1, or a pharmaceutically acceptable salt thereof, to a subject in need thereof. Embodiments herein are directed to methods of treating a disorder associated with a mutation in a KCNQ3 subunit comprising administering a therapeutically effective amount of a compound of formula 1C, 2C, 8a, 8b, 8c, 9, 10, 11, 12, 13, or 14, or a compound of Group I, Group II, Group III, or Table 1, or a pharmaceutically acceptable salt thereof, to a subject in need thereof. Embodiments herein are directed to methods of treating a disorder associated with a mutation in a KCNQ4 subunit comprising administering a therapeutically effective amount of a compound of formula 1C, 2C, 8a, 8b, 8c, 9, 10, 11, 12, 13, or 14, or a compound of Group I, Group II, Group III, or Table 1, or a pharmaceutically acceptable salt thereof, to a subject in need thereof. Embodiments herein are directed to methods of treating a disorder associated with a mutation in a KCNQ5 subunit comprising administering a therapeutically effective amount of a compound of formula 1C, 2C, 8a, 8b, 8c, 9, 10, 11, 12, 13, or 14, or a compound of Group I, Group II, Group III, or Table 1, or a pharmaceutically acceptable salt thereof, to a subject in need thereof.

Compounds described herein have been shown to activate the Kv7 potassium channel. Mutations in the gene, KCNQ3, which encodes the Kv7 potassium channel result in a wide range of disorders. Embodiments herein are directed to methods of treating a disorder associated with a KCNQ3 mutation comprising administering a therapeutically effective amount of a compound of formula 1C, 2C, 8a, 8b, 8c, 9, 10, 11, 12, 13, or 14, a compound of Group I, Group II, Group III, or Table 1, or a pharmaceutically acceptable salt thereof, to a subject in need thereof. The disorder associated with a KCNQ3 mutation is selected from the group consisting of benign familial neonatal seizures, epilepsy, neurological disease via reduced basal M-current (and subsequent neuronal hyperexcitability), and any combination thereof.

Compounds described herein have been shown to activate the Kv7 potassium channel. Mutations in the gene, KCNQ4, which encodes the Kv7 potassium channel result in a wide range of disorders. Embodiments herein are directed to methods of treating a disorder associated with a KCNQ4 mutation comprising administering a therapeutically effective amount of a compound of formula 1C, 2C, 8a, 8b, 8c, 9, 10, 11, 12, 13, or 14, a compound of Group I, Group II, Group III, or Table 1, or a pharmaceutically acceptable salt thereof, to a subject in need thereof. The disorder associated with a KCNQ4 mutation is sensorineural hearing impairment.

Compounds described herein have been shown to activate the Kv7 potassium channel. Mutations in the gene, KCNQ5, which encodes the Kv7 potassium channel result in a wide range of disorders. Embodiments herein are directed to methods of treating a disorder associated with a KCNQ5 mutation comprising administering a therapeutically effective amount of a compound of formula 1C, 2C, 8a, 8b, 8c, 9, 10, 11, 12, 13, or 14, a compound of Group I, Group II, Group III, or Table 1, or a pharmaceutically acceptable salt thereof, to a subject in need thereof. The disorder associated with a KCNQ5 mutation is selected from the group consisting of intellectual disability, epileptic encephalopathy, treatment-resistant epilepsy, cortical atrophy, neurological impairment, infantile spasms with hypsarrhythmia, myoclonic-tonic seizures, myoclonic seizures, tonic seizures, absence and focal-onset seizures with impaired awareness, congenital neurological disorder with intellectual disability or epileptic encephalopathy, benign familial neonatal convulsions, severe epileptic encephalopathies, congenital neurodevelopmental disorder with phenotypes of nonsyndromic intellectual disability or epileptic encephalopathy, and any combination thereof.

Compounds described herein have been shown to activate the Kv7 potassium channel. Mutations in the gene, KCNQ2, which encodes the Kv7 potassium channel result in a wide range of disorders. Embodiments herein are directed to methods of treating a disorder associated with a KCNQ2 mutation comprising administering a therapeutically effective amount of a compound of formula 1C, 2C, 8a, 8b, 8c, 9, 10, 11, 12, 13, or 14, a compound of Group I, Group II, Group III, or Table 1, or a pharmaceutically acceptable salt thereof, to a subject in need thereof. The disorder associated with a KCNQ2 mutation is selected from the group consisting of neonatal spasms, neonatal seizures, epilepsy, benign familial neonatal epilepsy (KCNQ2-BFNE), epileptic encephalopathy (KCNQ2-NEE), benign familial neonatal convulsions type 1 (BFNC), benign familial neonatal seizures 1 (BFNS1), neonatal seizures associated with hypoxic-ischemic injury, epileptic spasms, epileptic encephalopathy, early infantile epileptic encephalopathy 7 (EIEE7), early infantile epileptic encephalopathy with delayed psychomotor development, generalized tonic seizures, abnormal globus pallidus morphology, apnea, cerebral edema, dystonia, facial erythema, muscular hypotonia, febrile seizures, hypoplasia of the corpus callosum, hypsarrhythmia, focal clonic seizure, generalized tonic-clonic seizures, myokymia, spastic tetraparesis, myokymia and combinations thereof. In embodiments, such compound may be administered in a pharmaceutical composition as described herein.

Embodiments are directed to methods for treating conditions associated with hyperexcitability of cells in a subject comprising administering to the subject a therapeutically effective amount of a compound of Group I, Group II, Group III, or Table 1 or Formulas 1C, 2C, 8a, 8b, 8c, 9, 10, 11, 12, 13, or 14, or a pharmaceutically acceptable salt thereof, wherein the hyperexcitability is treated.

Embodiments are directed to methods for treating a Kv7 associated disorder in a subject comprising administering to the subject a therapeutically effective amount of a compound of Group I, Group II, Group III, or Table 1 or Formulas 1C, 2C, 8a, 8b, 8c, 9, 10, 11, 12, 13, or 14, or a pharmaceutically acceptable salt thereof, wherein the symptoms of the disorder are alleviated or improved due to the activation of Kv7 potassium channel.

Embodiments are directed to methods for treating neurodegenerative disease in a subject comprising administering to the subject a therapeutically effective amount of a compound of Group I, Group II, Group III, or Table 1 or Formulas 1C, 2C, 8a, 8b, 8c, 9, 10, 11, 12, 13, or 14, or a pharmaceutically acceptable salt thereof, wherein the neurodegenerative disease is treated. The compound of Group I, Group II, Group III, or Table 1 or Formulas 1C, 2C, 8a, 8b, 8c, 9, 10, 11, 12, 13, or 14, may be administered to any individual exhibiting the symptoms of a neurodegenerative disease or to individuals predisposed to a neurodegenerative disease. Non-limiting examples of neurodegenerative diseases that may be treated using a compound of Group I, Group II, Group III, or Table 1 or Formulas 1C, 2C, 8a, 8b, 8c, 9, 10, 11, 12, 13, or 14, include amyotrophic lateral sclerosis (ALS), Huntington's disease, metabolically induced neurological damage, Alzheimer's disease, Pick's disease, senile dementia, age associated cognitive dysfunction, vascular dementia, multi-infarct dementia, Lewy body dementia, neurodegenerative dementia, frontotemporal dementia (FTD), familial FTD, neurodegenerative movement disorder, ataxia, Friedreich's ataxia, multiple sclerosis, spinal muscular atrophy, primary lateral sclerosis, seizure disorders, motor neuron disorder or disease, inflammatory demyelinating disorder, Parkinson's disease, hepatic encephalopathy, chronic encephalopathy, chronic encephalitis, or any combination thereof.

Embodiments are directed to methods for treating neurodegenerative disease, such as amyotrophic lateral sclerosis, in a subject in need thereof comprising: administering to the subject a therapeutically effective amount of a compound of Group I, Group II, Group III, or Table 1 or Formulas 1C, 2C, 8a, 8b, 8c, 9, 10, 11, 12, 13, or 14, or a pharmaceutically acceptable salt thereof, wherein the neurodegenerative disease is treated. In embodiments, the subject is a subject with definite ALS, has amyotrophic lateral sclerosis symptom onset duration of less than about 18 months, plasma creatinine levels of about 72 µM/L or greater, concomitant riluzole administration, concomitant dexpramipexole administration, and combinations thereof.

Embodiments are directed to methods for treating amyotrophic lateral sclerosis in a subject in need thereof comprising: administering to the subject a therapeutically effective amount of a compound of Group I, Group II, Group III, or Table 1 or Formulas 1C, 2C, 8a, 8b, 8c, 9, 10, 11, 12, 13, or 14, or a pharmaceutically acceptable salt thereof, wherein the amyotrophic lateral sclerosis is treated.

Embodiments are directed to methods for treating amyotrophic lateral sclerosis in a subject diagnosed with definite amyotrophic lateral sclerosis comprising administering to the subject a therapeutically effective amount of a compound of Group I, Group II, Group III, or Table 1 or Formulas 1C, 2C, 8a, 8b, 8c, 9, 10, 11, 12, 13, or 14, or a pharmaceutically acceptable salt thereof, wherein the amyotrophic lateral sclerosis is treated. In embodiments, the definite amyotrophic lateral sclerosis is as defined by the El Escorial diagnosis criteria. In embodiments, the subject is a subject with definite ALS, amyotrophic lateral sclerosis symptom onset duration of less than about 18 months, plasma creatinine levels of about 72 µM/L or greater, concomitant riluzole administration, concomitant dexpramipexole administration, and combinations thereof.

Embodiments are directed to methods for treating amyotrophic lateral sclerosis in a subject in need thereof comprising administering to the subject a therapeutically effective amount of a compound of Group I, Group II, Group III, or Table 1 or Formulas 1C, 2C, 8a, 8b, 8c, 9, 10, 11, 12, 13, or 14, or a pharmaceutically acceptable salt thereof, wherein the subject is selected from a subject with definite amyotrophic lateral sclerosis, a subject with limb-onset amyotrophic lateral sclerosis, a subject with bulbar-onset amyotrophic lateral sclerosis, a subject with amyotrophic lateral sclerosis symptom onset duration of less than about 18 months, a subject with a high level of serum creatinine, a subject with low bicarbonate levels, a subject with concomitant riluzole administration, a subject with concomitant dexpramipexole administration, and combinations thereof, and wherein the amyotrophic lateral sclerosis is treated. In certain embodiments, the method further comprises monitoring said subject for any clinical features associated with amyotrophic lateral sclerosis. In certain embodiments, the method further comprises initiating therapy with a therapeutically effective amount of a compound of Group I, Group II, Group III, or Table 1 or Formulas 1C, 2C, 8a, 8b, 8c, 9, 10, 11, 12, 13, or 14, or a pharmaceutically acceptable salt thereof upon diagnosis of amyotrophic lateral sclerosis. In certain embodiments, the subject exhibits symptoms of amyotrophic lateral sclerosis. In certain embodiments, the subject has definite amyotrophic lateral sclerosis, probable amyotrophic lateral sclerosis, possible amyotrophic lateral sclerosis or suspected amyotrophic lateral sclerosis.

Embodiments are directed to methods for treating amyotrophic lateral sclerosis in a subject diagnosed with definite amyotrophic lateral sclerosis comprising administering to the subject a therapeutically effective amount of a compound of Group I, Group II, Group III, or Table 1 or Formulas 1C, 2C, 8a, 8b, 8c, 9, 10, 11, 12, 13, or 14, or a pharmaceutically acceptable salt thereof, wherein the amyotrophic lateral sclerosis is treated. In some embodiments definite amyotrophic lateral sclerosis is the presence of the El Escorial diagnosis criteria, amyotrophic lateral sclerosis symptom onset duration of less than about 18 months, limb-onset amyotrophic lateral sclerosis, plasma creatinine levels of about 72 µM/L or greater, concomitant riluzole administration, concomitant dexpramipexole administration, an ALSFRS-R score of greater than 36.0, a pre-study progression rate greater than or equal to 0.8 points per month, a percentage predicted relaxed (slow) vital capacity (SVC) of less than or equal to 102.0, an ALSFRS-R fine motor domain score of greater than 10.0 points, ALSFRS-R bulbar domain score or greater than 9.0 points, an ALSFRS-R gross motor domain score of greater than 8.0 points, an abnormal neurological exam of the tongue, an abnormal neurological exam of the pharynx, larynx and swallowing, an abnormal neurological exam of the lower extremities, an abnormal neurological exam of the upper extremities, an abnormal neurological exam of the triceps, an abnormal neurological exam of the muscle mass and bulk, an abnormal neurological exam of the bicep, an abnormal neurological exam, a pulse rate of greater than 81.0 beats per minute, a diastolic blood pressure of greater than 82.0 mmHg, a systolic blood pressure of less than or equal to 117.0 mmHg, a creatinine value of greater than 72.0 µmol/L, a phosphorous value of less than or equal to 1.090 µmol/L, a platelet count of less than or equal to 248.0×10$^9$ cells/L, a cholesterol value of less than or equal to 5.3 mmol/L, a lactate dehydrogenase value of less than or equal to 161.0 U/L, a creatine phosphokinase value of less than or equal to 184.0 U/L, a bicarbonate value of less than or equal to 21.6 mmol/L, a triglyceride level of less than or equal to 1.4 mmol/L, a uric acid level of greater than 320.0 µmol/L, a gamma-glutamyltransferase (GGT) level of greater than 37.0 U/L, a total bilirubin level of less than or equal to 6.0 µmol/L, a urine pH of less than or equal to 5.5, or any combination thereof.

Embodiments are directed to methods for treating amyotrophic lateral sclerosis in a subject exhibiting symptoms of amyotrophic lateral sclerosis comprising administering to the subject a therapeutically effective amount of a compound of Group I, Group II, Group III, or Table 1 or Formulas 1C, 2C, 8a, 8b, 8c, 9, 10, 11, 12, 13, or 14, or a pharmaceutically acceptable salt thereof, wherein the symptoms of amyotrophic lateral sclerosis are treated. In some embodiments, the subject exhibits clinical characteristics selected from definite amyotrophic lateral sclerosis, amyotrophic lateral sclerosis symptom onset duration of less than about 18 months, limb-onset amyotrophic lateral sclerosis, plasma creatinine levels of about 72 µM/L or greater, concomitant riluzole administration, concomitant dexpramipexole administration, an ALSFRS-R score of greater than 36.0, a re-study progression rate greater than or equal to 0.8 points per month, a percentage predicted relaxed (slow) vital capacity (SVC) of less than or equal to 102.0, an ALSFRS-R fine motor domain score of greater than 10.0 points, ALSFRS-R bulbar domain score or greater than 9.0 points, an ALSFRS-R gross motor domain score of greater than 8.0 points, an abnormal neurological exam of the tongue, an abnormal neurological exam of the pharynx, larynx and swallowing, an abnormal neurological exam of the lower extremities, an abnormal neurological exam of the upper extremities, an abnormal neurological exam of the triceps, an abnormal neurological exam of the muscle mass and bulk, an abnormal neurological exam of the bicep, an abnormal neurological exam, a pulse rate of greater than 81.0 beats per minute, a diastolic blood pressure of greater than 82.0 mmHg, a systolic blood pressure of less than or equal to 117.0 mmHg, a creatinine value of greater than 72.0 µmol/L, a phosphorous value of less than or equal to 1.090 µmol/L, a platelet count of less than or equal to 248.0×109 cells/L, a cholesterol value of less than or equal to 5.3 mmol/L, a lactate dehydrogenase value of less than or equal to 161.0 U/L, a creatine phosphokinase value of less than or equal to 184.0 U/L, a bicarbonate value of less than or equal to 21.6 mmol/L, a triglyceride level of less than or equal to 1.4 mmol/L, a uric acid level of greater than 320.0 µmol/L, a gamma-glutamyltransferase (GGT) level of greater than 37.0 U/L, a total bilirubin level of less than or equal to 6.0 µmol/L, a urine pH of less than or equal to 5.5, or any combination thereof.

In some embodiments, administering a therapeutically effective amount of a compound of Group I, Group II, Group III, or Table 1 or Formulas 1C, 2C, 8a, 8b, 8c, 9, 10, 11, 12, 13, or 14, or a pharmaceutically acceptable salt thereof, may include administering daily doses of about 0.1 mg to about 1,500 mg, about 1 mg to about 1,500 mg, about 10 mg to about 1,500 mg, about 50 mg to about 1,500 mg, about 75 mg to about 1,500 mg, about 100 mg to about 1,500 mg, about 125 mg to about 1,500 mg, about 150 mg to about 1,500 mg, about 175 mg to about 1,500 mg, about 200 mg to about 1,500 mg, about 225 mg to about 1,500 mg, about 250 mg to about 1,500 mg, about 275 mg to about 1,500 mg, about 300 mg to about 1,500 mg, about 400 mg to about 1,500 mg, about 450 mg to about 1,500 mg, about 500 mg to about 1,500 mg, about 600 mg to about 1,500 mg, about 700 mg to about 1,500 mg, about 800 mg to about 1,500 mg, about 1,000 mg to about 1,500 mg, and about 1,200 mg to about 1,500 mg.

In some embodiments, the therapeutically effective amount of a compound of Group I, Group II, Group III, or Table 1 or Formulas 1C, 2C, 8a, 8b, 8c, 9, 10, 11, 12, 13, or 14, or a pharmaceutically acceptable salt thereof, is selected from the group consisting of from about 0.1 mg to about 1,000 mg, about 50 mg to about 1,000 mg per day, about 100 mg to about 1,000 mg per day, about 150 mg to about 1,000 mg per day, about 300 mg to about 1,000 mg per day, about 50 mg to about 300 mg per day, and about 150 mg to about 300 mg per day.

Such therapeutically effective amounts may be administered once a day or in equal, divided doses twice a day, three times a day, or four times a day. In some embodiments, administering a therapeutically effective amount comprises administering a dose equal to about half of a daily dose twice per day. In some embodiments, the dose is administered every about 12 hours. In some embodiments, administering a therapeutically effective amount comprises administering about 25 mg two times per day, about 75 mg two times per day, about 150 mg two times per day, or about 300 mg two times per day.

Pharmaceutical Compositions

Embodiments herein are directed to pharmaceutical compositions comprising a therapeutically effective amount of a compound described herein or acceptable salts thereof, such as a compound of Group I, Group II, Group III, Table 1, or of Formula 1C, 2C, 8a, 8b, 8c, 9, 10, 11, 12, 13, or 14, or pharmaceutically acceptable salts thereof. Pharmaceutical formulations containing such compounds and a suitable carrier can be in various forms including, but not limited to, solids, solutions, powders, fluid emulsions, fluid suspensions, semi-solids, and dry powders including an effective amount of a compound of the invention. It is also known in the art that the active ingredients can be contained in such formulations with pharmaceutically acceptable diluents, fillers, disintegrants, binders, lubricants, surfactants, hydrophobic vehicles, water soluble vehicles, emulsifiers, buffers, humectants, moisturizers, solubilizers, antioxidants, preservatives and the like. The means and methods for administration are known in the art and an artisan can refer to various pharmacologic references for guidance. For example, Modern Pharmaceutics, Banker & Rhodes, Marcel Dekker, Inc. (1979); and Goodman & Gilman's, The Pharmaceutical Basis of Therapeutics, 6th Edition, MacMillan Publishing Co., New York (1980) both of which are hereby incorporated by reference in their entireties can be consulted.

In some embodiments, a single unit dose of a compound of Group I, Group II, Group III, or Table 1 or Formulas 1C, 2C, 8a, 8b, 8c, 9, 10, 11, 12, 13, or 14 or a pharmaceutically acceptable salt thereof, is selected from the group consisting of about 0.1 mg to about 1,500 mg, about 1 mg to about 1,500 mg, about 10 mg to about 1,500 mg, about 50 mg to about 1,500 mg, about 75 mg to about 1,500 mg, about 100 mg to about 1,500 mg, about 125 mg to about 1,500 mg, about 150 mg to about 1,500 mg, about 175 mg to about 1,500 mg, about 200 mg to about 1,500 mg, about 225 mg to about 1,500 mg, about 250 mg to about 1,500 mg, about 275 mg to about 1,500 mg, about 300 mg to about 1,500 mg, about 400 mg to about 1,500 mg, about 450 mg to about 1,500 mg, about 500 mg to about 1,500 mg, about 600 mg to about 1,500 mg, about 700 mg to about 1,500 mg, about 800 mg to about 1,500 mg, about 1,000 mg to about 1,500 mg, and about 1,200 mg to about 1,500 mg.

In some embodiments, a single unit dose amount of a compound of Group I, Group II, Group III, or Table 1 or Formulas 1C, 2C, 8a, 8b, 8c, 9, 10, 11, 12, 13, or 14 or a pharmaceutically acceptable salt thereof, is selected from group consisting of about 25 mg to about 5,000 mg, about 50 mg to about 5,000 mg, about 100 mg to about 5,000 mg, about 150 mg to about 5,000 mg, about 200 mg to about 5,000 mg, about 250 mg to about 5,000 mg, about 300 mg to about 5,000 mg, about 400 mg to about 5,000 mg, about 450 mg to about 5,000 mg, about 100 mg to about 3,000 mg, about 150 mg to about 3,000 mg, about 200 mg to about 3,000 mg, about 250 mg to about 3,000 mg, about 300 mg to about 3,000 mg, about 400 mg to about 3,000 mg, 450 mg to about 3,000 mg, about 100 mg to about 1,000 mg, about 150 mg to about 1,000 mg, about 200 mg to about 1,000 mg, about 250 mg to about 1,000 mg, about 300 mg to about 1,000 mg, about 400 mg to about 1,000 mg, about 450 mg to about 1,000 mg, about 500 mg to about 1000 mg, and about 600 mg to about 1,000 mg. In some embodiments, the single unit dose amount may be 10 mg/day to 1,500 mg/day, or about 100 mg/day to 600 mg/day. In some embodiments, such single unit doses may be administered once per day or multiple times per day, such as twice per day or three times per day.

In some embodiments, the single unit dose further comprises a pharmaceutically acceptable carrier.

The compounds can be formulated for parenteral or intravenous administration by injection, e.g., by bolus injection or continuous infusion. Formulations for injection can be presented in unit dosage form, e.g., in ampoules or in multi-dose containers, with an added preservative. The compositions can take such forms as suspensions, solutions, or emulsions in oily or aqueous vehicles, and can contain formulatory agents such as suspending, stabilizing, and/or dispersing agents.

Injectable preparations may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-butanediol. Among the acceptable vehicles and solvents that may be employed are water, Ringer's solution, and isotonic sodium chloride solution.

Other embodiments include a compound prepared as described above which are formulated as a solid dosage form for oral administration including capsules, tablets, pills, powders, and granules. In such embodiments, the active compound may be admixed with one or more inert diluent such as sucrose, lactose, or starch. Such dosage forms may also comprise, as in normal practice, additional substances other than inert diluents, e.g., lubricating agents such as magnesium stearate. In the case of capsules, tablets, and pills, the dosage forms may also comprise buffering agents and can additionally be prepared with enteric coatings.

Preparation of a compound of the invention in solid dosage form may vary. For example, in one embodiment, a liquid or gelatin formulation may be prepared by combining a compound, such as those described above, and adding a thickening agent to the liquid mixture to form a gelatin. The gelatin may then be encapsulated in unit dosage form to form a capsule. In another exemplary embodiment, an oily preparation of a compound prepared as described above may be lyophilized to for a solid that may be mixed with one or more pharmaceutically acceptable excipient, carrier or diluent to form a tablet.

Further embodiments which may be useful for oral administration of a compound for the invention include liquid dosage forms. In such embodiments, a liquid dosage may include a pharmaceutically acceptable emulsion, solution, suspension, syrup, and elixir containing inert diluents commonly used in the art, such as water. Such compositions may also comprise adjuvants, such as wetting agents, emulsifying and suspending agents, and sweetening, flavoring, and perfuming agents.

In still further embodiments, the compounds described herein can be formulated as a depot preparation. Such long acting formulations can be administered by implantation (for example, subcutaneously or intramuscularly) or by intramuscular injection. Depot injections can be administered at about 1 to about 6 months or longer intervals. Thus, for example, the compounds can be formulated with suitable polymeric or hydrophobic materials (for example, as an emulsion in an acceptable oil) or ion exchange resins, or as sparingly soluble derivatives, for example, as a sparingly soluble salt.

Experimental Section

Scheme 1

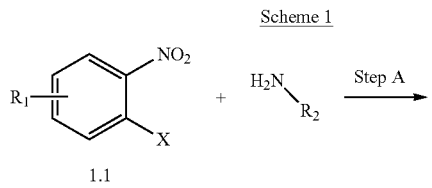

1.1

77

-continued

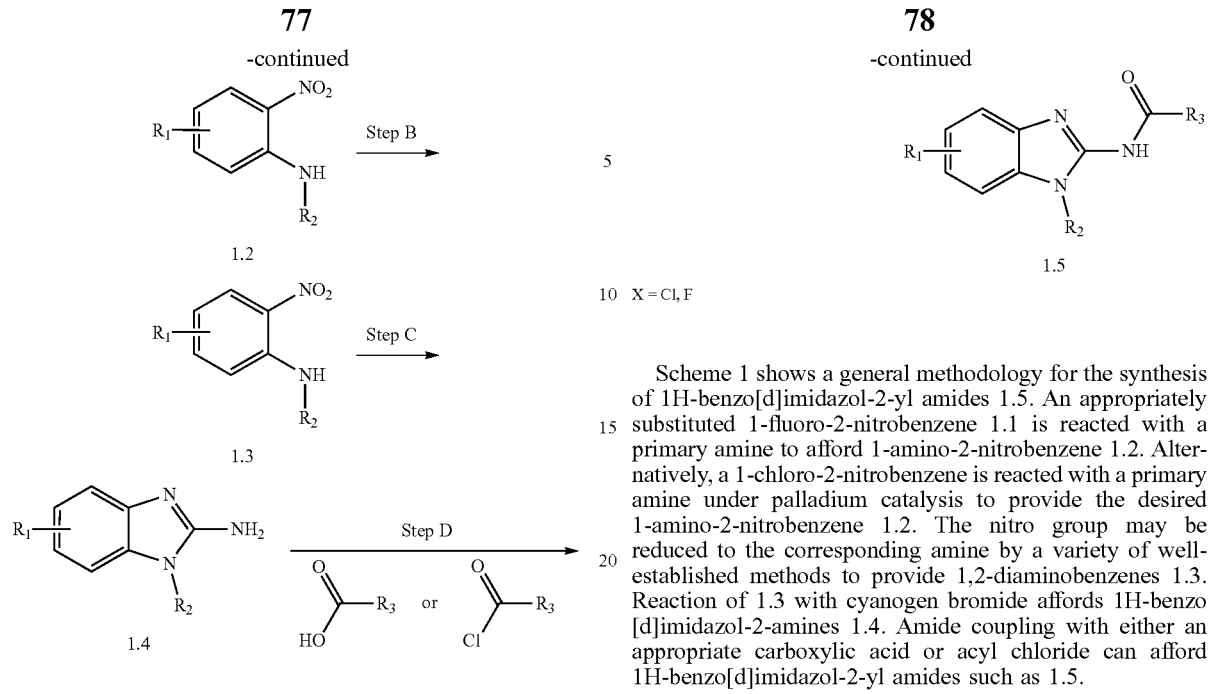

Scheme 1 shows a general methodology for the synthesis of 1H-benzo[d]imidazol-2-yl amides 1.5. An appropriately substituted 1-fluoro-2-nitrobenzene 1.1 is reacted with a primary amine to afford 1-amino-2-nitrobenzene 1.2. Alternatively, a 1-chloro-2-nitrobenzene is reacted with a primary amine under palladium catalysis to provide the desired 1-amino-2-nitrobenzene 1.2. The nitro group may be reduced to the corresponding amine by a variety of well-established methods to provide 1,2-diaminobenzenes 1.3. Reaction of 1.3 with cyanogen bromide affords 1H-benzo[d]imidazol-2-amines 1.4. Amide coupling with either an appropriate carboxylic acid or acyl chloride can afford 1H-benzo[d]imidazol-2-yl amides such as 1.5.

TABLE 1

List of Examples with Molecular Weight Data

| Example | Structure | Name | Molecular Weight |
|---|---|---|---|
| 330 | 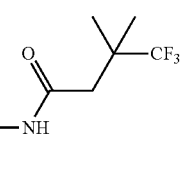 | N-(1-(tert-butyl)-7-cyano-5-fluoro-1H-benzo[d]imidazol-2-yl)-4,4,4-trifluoro-3,3-dimethylbutanamide | 384.4 |
| 331 | 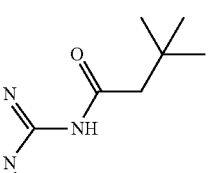 | N-(1-cyclobutyl-6-(difluoromethoxy)-4-fluoro-1H-benzo[d]imidazol-2-yl)-3,3-dimethylbutanamide | 369.4 |
| 332 | 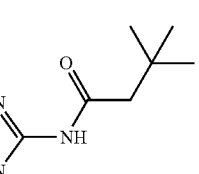 | N-(1-(3,3-difluorocyclobutyl)-6-(2-hydroxypropan-2-yl)-1H-benzo[d]imidazol-2-yl)-3,3-dimethylbutanamide | 379.5 |

TABLE 1-continued

List of Examples with Molecular Weight Data

| Example | Structure | Name | Molecular Weight |
|---|---|---|---|
| 333 | 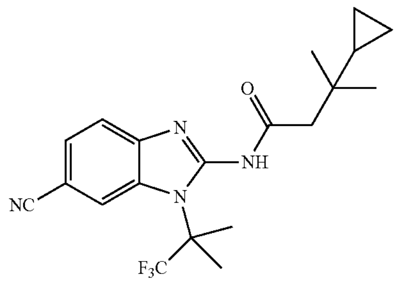 [SMILES: CC(C)(CC(=O)Nc1nc2ccc(C#N)cc2n1C(C)(C)C(F)(F)F)C1CC1] | N-(6-cyano-1-(1,1,1-trifluoro-2-methylpropan-2-yl)-1H-benzo[d]imidazol-2-yl)-3-cyclopropyl-3-methylbutanamide | 392.4 |
| 334 | 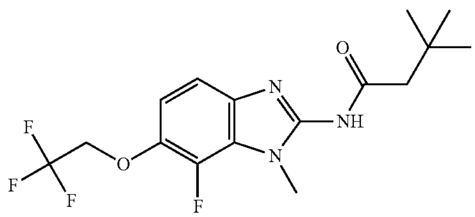 [SMILES: Cn1c(NC(=O)CC(C)(C)C)nc2ccc(OCC(F)(F)F)c(F)c21] | N-(1-cyclobutyl-7-fluoro-6-(2,2,2-trifluoroethoxy)-1H-benzo[d]imidazol-2-yl)-3,3-dimethylbutanamide | 401.4 |
| 335 | 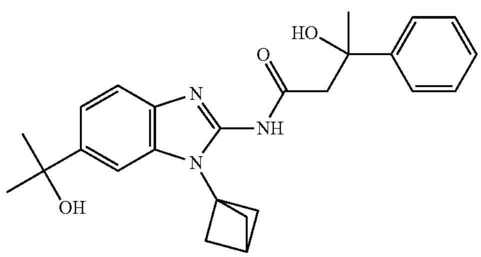 [SMILES: CC(C)(O)c1ccc2nc(NC(=O)CC(C)(O)c3ccccc3)n(C34CC(C3)C4)c2c1] | N-(1-(bicyclo[1.1.1]pentan-1-yl)-6-(2-hydroxypropan-2-yl)-1H-benzo[d]imidazol-2-yl)-3-hydroxy-3-phenylbutanamide, stereoisomer 1 | 419.5 |
| 336 | 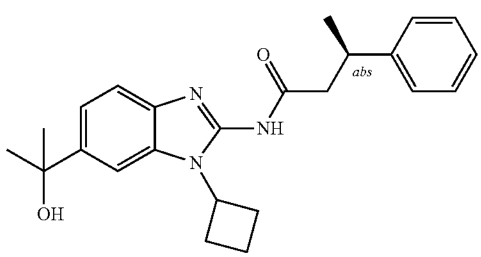 [SMILES: C[C@H](CC(=O)Nc1nc2ccc(C(C)(C)O)cc2n1C1CCC1)c1ccccc1] | (R)-N-(1-cyclobutyl-6-(2-hydroxypropan-2-yl)-1H-benzo[d]imidazol-2-yl)-3-phenylbutanamide | 391.5 |
| 337 | 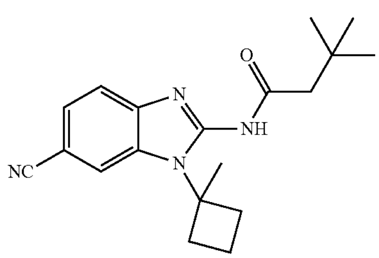 [SMILES: CC(C)(C)CC(=O)Nc1nc2ccc(C#N)cc2n1C1(C)CCC1] | N-(6-cyano-1-(1-methylcyclobutyl)-1H-benzo[d]imidazol-2-yl)-3,3-dimethylbutanamide | 324.4 |
| 338 | 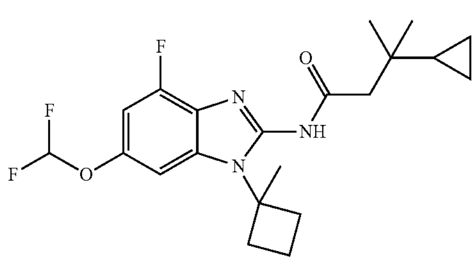 [SMILES: CC(C)(CC(=O)Nc1nc2c(F)cc(OC(F)F)cc2n1C1(C)CCC1)C1CC1] | 3-cyclopropyl-N-(6-(difluoromethoxy)-4-fluoro-1-(1-methylcyclobutyl)-1H-benzo[d]imidazol-2-yl)-3-methylbutanamide | 409.5 |

TABLE 1-continued

List of Examples with Molecular Weight Data

| Example | Structure | Name | Molecular Weight |
|---|---|---|---|
| 339 | 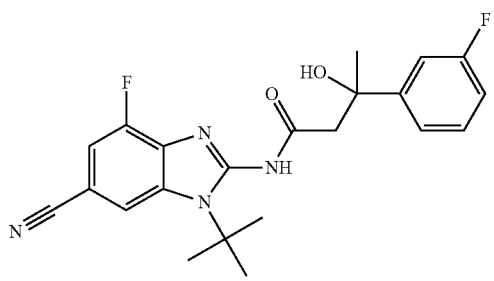 [SMILES: CC(O)(CC(=O)Nc1nc2c(F)cc(C#N)cc2n1C(C)(C)C)c1cccc(F)c1] | N-(1-(tert-butyl)-6-cyano-4-fluoro-1H-benzo[d]imidazol-2-yl)-3-(3-fluorophenyl)-3-hydroxybutanamide, stereoisomer 1 | 412.4 |
| 340 | 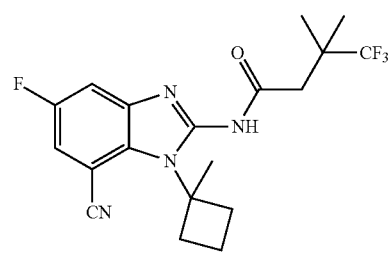 [SMILES: CC1(n2c(NC(=O)CC(C)(C)C(F)(F)F)nc3cc(F)cc(C#N)c32)CCC1] | N-(7-cyano-5-fluoro-1-(1-methylcyclobutyl)-1H-benzo[d]imidazol-2-yl)-4,4,4-trifluoro-3,3-dimethylbutanamide | 396.4 |
| 341 | 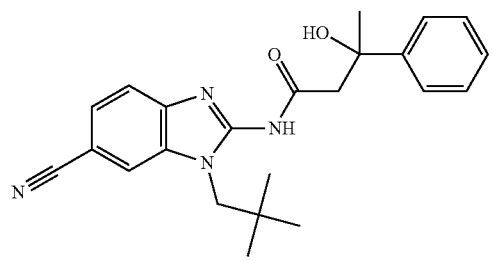 [SMILES: CC(C)(C)Cn1c(NC(=O)CC(C)(O)c2ccccc2)nc2ccc(C#N)cc21] | N-(6-cyano-1-neopentyl-1H-benzo[d]imidazol-2-yl)-3-hydroxy-3-phenylbutanamide, stereoisomer 1 | 390.5 |
| 342 | 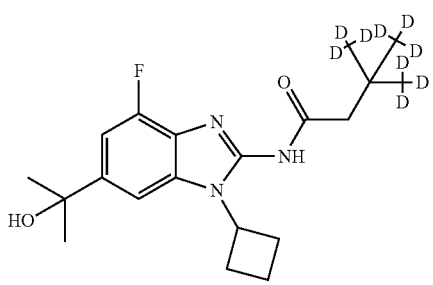 | N-(1-cyclobutyl-4-fluoro-6-(2-hydroxypropan-2-yl)-1H-benzo[d]imidazol-2-yl)-3,3-bis(methyl-d3)butanamide | 370.5 |
| 343 | 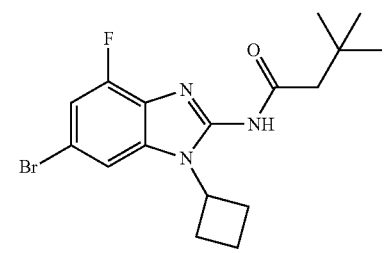 [SMILES: CC(C)(C)CC(=O)Nc1nc2c(F)cc(Br)cc2n1C1CCC1] | N-(6-bromo-1-cyclobutyl-4-fluoro-1H-benzo[d]imidazol-2-yl)-3,3-dimethylbutanamide | 382.3 |

TABLE 1-continued

List of Examples with Molecular Weight Data

| Example | Structure | Name | Molecular Weight |
|---|---|---|---|
| 344 | 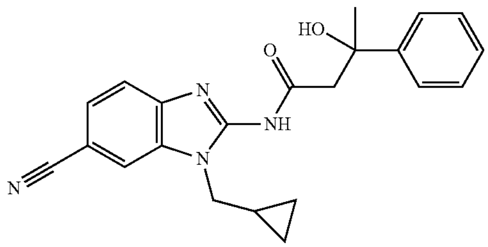 [SMILES: CC(O)(CC(=O)Nc1nc2ccc(C#N)cc2n1CC1CC1)c1ccccc1] | N-(6-cyano-1-(cyclopropylmethyl)-1H-benzo[d]imidazol-2-yl)-3-hydroxy-3-phenylbutanamide, stereoisomer 2 | 374.4 |
| 345 | 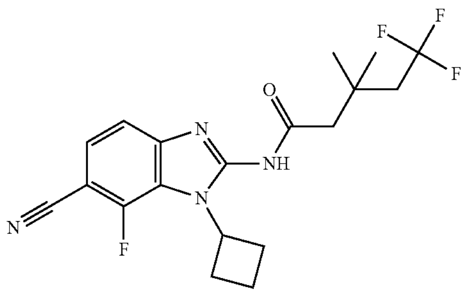 [SMILES: CC(C)(CC(=O)Nc1nc2ccc(C#N)c(F)c2n1C1CCC1)CC(F)(F)F] | N-(6-cyano-1-cyclobutyl-7-fluoro-1H-benzo[d]imidazol-2-yl)-5,5,5-trifluoro-3,3-dimethylpentanamide | 396.4 |
| 346 | 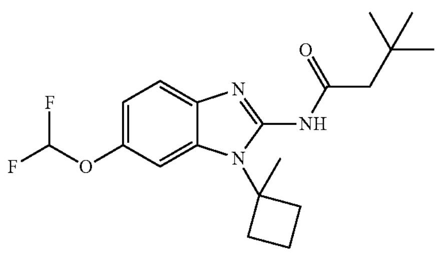 [SMILES: CC(C)(C)CC(=O)Nc1nc2ccc(OC(F)F)cc2n1C1(C)CCC1] | N-(6-(difluoromethoxy)-1-(1-methylcyclobutyl)-1H-benzo[d]imidazol-2-yl)-3,3-dimethylbutanamide | 365.4 |
| 347 | 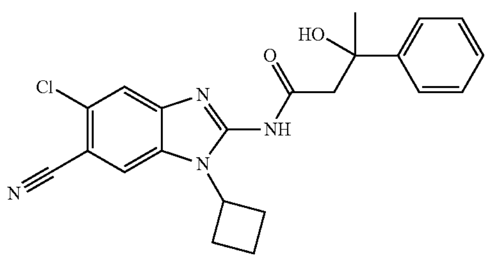 [SMILES: CC(O)(CC(=O)Nc1nc2cc(Cl)c(C#N)cc2n1C1CCC1)c1ccccc1] | N-(5-chloro-6-cyano-1-cyclobutyl-1H-benzo[d]imidazol-2-yl)-3-hydroxy-3-phenylbutanamide, stereoisomer 1 | 408.9 |
| 348 | 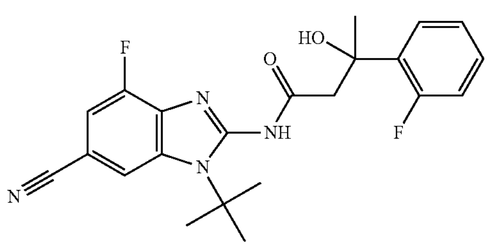 [SMILES: CC(O)(CC(=O)Nc1nc2c(F)cc(C#N)cc2n1C(C)(C)C)c1ccccc1F] | N-(1-(tert-butyl)-6-cyano-4-fluoro-1H-benzo[d]imidazol-2-yl)-3-(2-fluorophenyl)-3-hydroxybutanamide, stereoisomer 1 | 412.4 |
| 349 | 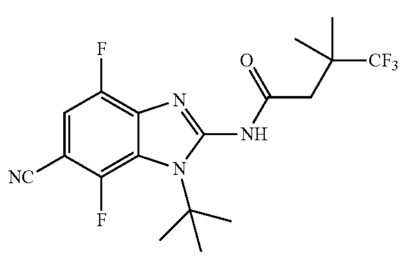 [SMILES: CC(C)(C)n1c(NC(=O)CC(C)(C)C(F)(F)F)nc2c(F)cc(C#N)c(F)c21] | N-(1-(tert-butyl)-6-cyano-4,7-difluoro-1H-benzo[d]imidazol-2-yl)-4,4,4-trifluoro-3,3-dimethylbutanamide | 402.4 |

TABLE 1-continued

List of Examples with Molecular Weight Data

| Example | Structure | Name | Molecular Weight |
|---|---|---|---|
| 350 | 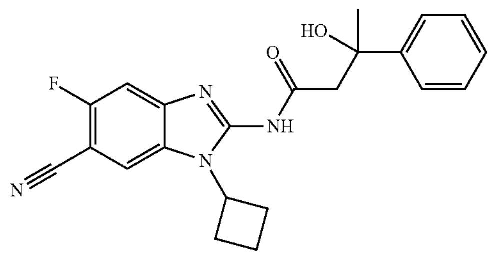 [SMILES: CC(O)(CC(=O)Nc1nc2cc(F)c(C#N)cc2n1C1CCC1)c1ccccc1] | N-(6-cyano-1-cyclobutyl-5-fluoro-1H-benzo[d]imidazol-2-yl)-3-hydroxy-3-phenylbutanamide, stereoisomer 1 | 392.4 |
| 351 | 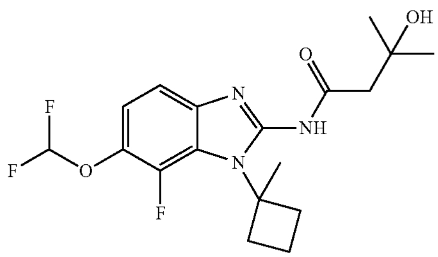 [SMILES: CC(C)(O)CC(=O)Nc1nc2ccc(OC(F)F)c(F)c2n1C1(C)CCC1] | N-(6-(difluoromethoxy)-7-fluoro-1-(1-methylcyclobutyl)-1H-benzo[d]imidazol-2-yl)-3-hydroxy-3-methylbutanamide | 385.4 |
| 352 | 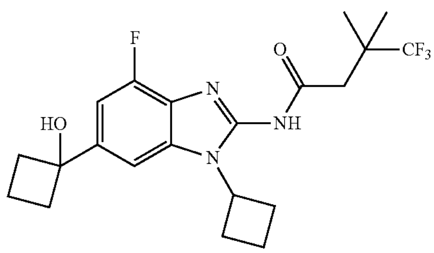 [SMILES: CC(C)(CC(=O)Nc1nc2c(F)cc(C3(O)CCC3)cc2n1C1CCC1)C(F)(F)F] | N-(1-cyclobutyl-4-fluoro-6-(1-hydroxycyclobutyl)-1H-benzo[d]imidazol-2-yl)-4,4,4-trifluoro-3,3-dimethylbutanamide | 427.4 |
| 353 | 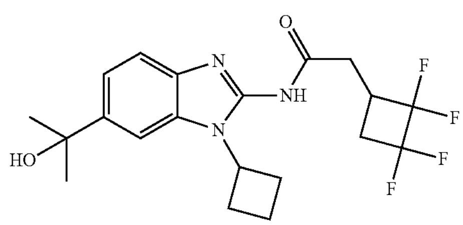 [SMILES: CC(C)(O)c1ccc2nc(NC(=O)CC3CC(F)(F)C3(F)F)n(C3CCC3)c2c1] | N-(1-cyclobutyl-6-(2-hydroxypropan-2-yl)-1H-benzo[d]imidazol-2-yl)-2-(2,2,3,3-tetrafluorocyclobutyl)acetamide | 413.4 |
| 354 | 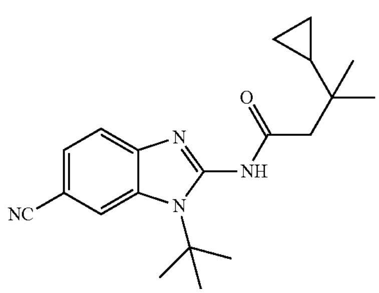 [SMILES: CC(C)(CC(=O)Nc1nc2ccc(C#N)cc2n1C(C)(C)C)C1CC1] | N-(1-(tert-butyl)-6-cyano-1H-benzo[d]imidazol-2-yl)-3-cyclopropyl-3-methylbutanamide | 338.5 |
| 355 | 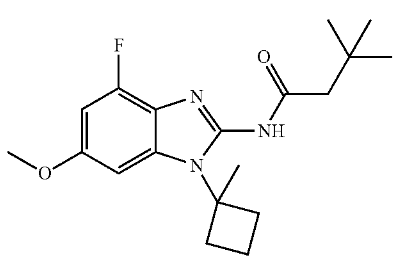 [SMILES: COc1cc(F)c2nc(NC(=O)CC(C)(C)C)n(C3(C)CCC3)c2c1] | N-(4-fluoro-6-methoxy-1-(1-methylcyclobutyl)-1H-benzo[d]imidazol-2-yl)-3,3-dimethylbutanamide | 347.4 |

TABLE 1-continued

List of Examples with Molecular Weight Data

| Example | Structure | Name | Molecular Weight |
|---|---|---|---|
| 356 | 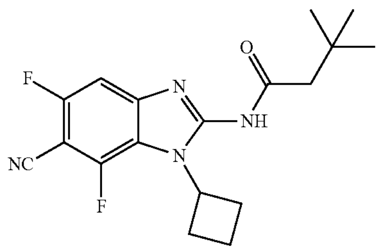 [SMILES: CC(C)(C)CC(=O)Nc1nc2cc(F)c(C#N)c(F)c2n1C1CCC1] | N-(6-cyano-1-cyclobutyl-5,7-difluoro-1H-benzo[d]imidazol-2-yl)-3,3-dimethylbutanamide | 346.4 |
| 357 | 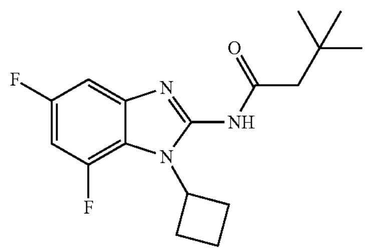 [SMILES: CC(C)(C)CC(=O)Nc1nc2cc(F)cc(F)c2n1C1CCC1] | N-(1-cyclobutyl-5,7-difluoro-1H-benzo[d]imidazol-2-yl)-3,3-dimethylbutanamide | 321.4 |
| 358 | 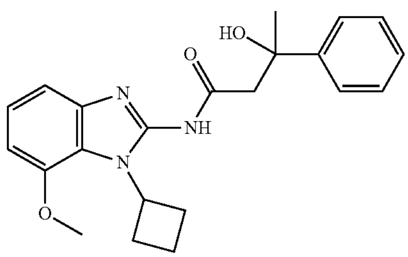 [SMILES: COc1cccc2nc(NC(=O)CC(C)(O)c3ccccc3)n(C3CCC3)c12] | N-(1-cyclobutyl-7-methoxy-1H-benzo[d]imidazol-2-yl)-3-hydroxy-3-phenylbutanamide, stereoisomer 2 | 379.5 |
| 359 | 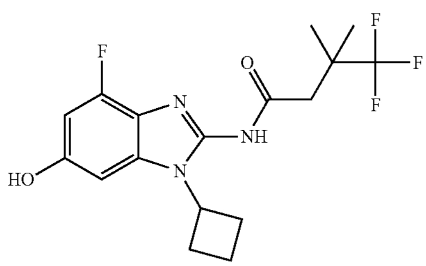 [SMILES: CC(C)(CC(=O)Nc1nc2c(F)cc(O)cc2n1C1CCC1)C(F)(F)F] | N-(1-cyclobutyl-4-fluoro-6-hydroxy-1H-benzo[d]imidazol-2-yl)-4,4,4-trifluoro-3,3-dimethylbutanamide | 373.4 |
| 360 | 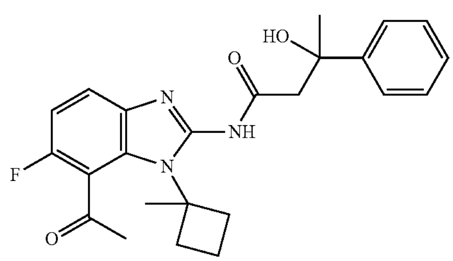 [SMILES: CC(=O)c1c(F)ccc2nc(NC(=O)CC(C)(O)c3ccccc3)n(C3(C)CCC3)c12] | N-(7-acetyl-6-fluoro-1-(1-methylcyclobutyl)-1H-benzo[d]imidazol-2-yl)-3-hydroxy-3-phenylbutanamide, stereoisomer 2 | 423.5 |
| 361 | 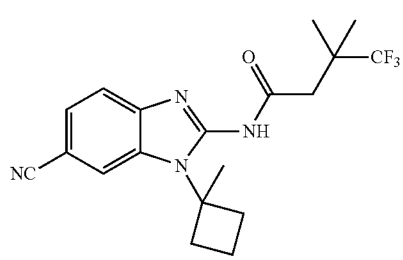 [SMILES: CC1(n2c(NC(=O)CC(C)(C)C(F)(F)F)nc3ccc(C#N)cc32)CCC1] | N-(6-cyano-1-(1-methylcyclobutyl)-1H-benzo[d]imidazol-2-yl)-4,4,4-trifluoro-3,3-dimethylbutanamide | 378.4 |

TABLE 1-continued

List of Examples with Molecular Weight Data

| Example | Structure | Name | Molecular Weight |
|---|---|---|---|
| 362 | 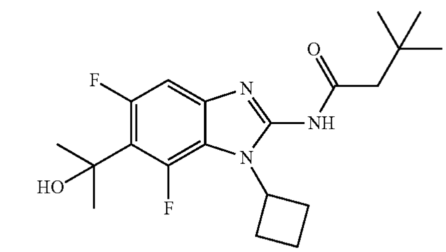 [SMILES: CC(C)(C)CC(=O)Nc1nc2cc(F)c(C(C)(C)O)c(F)c2n1C1CCC1] | N-(1-cyclobutyl-5,7-difluoro-6-(2-hydroxypropan-2-yl)-1H-benzo[d]imidazol-2-yl)-3,3-dimethylbutanamide | 379.5 |
| 363 | 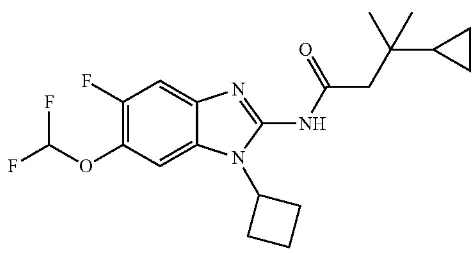 [SMILES: CC(C)(CC(=O)Nc1nc2cc(F)c(OC(F)F)cc2n1C1CCC1)C1CC1] | N-(1-cyclobutyl-6-(difluoromethoxy)-5-fluoro-1H-benzo[d]imidazol-2-yl)-3-cyclopropyl-3-methylbutanamide | 395.4 |
| 364 | 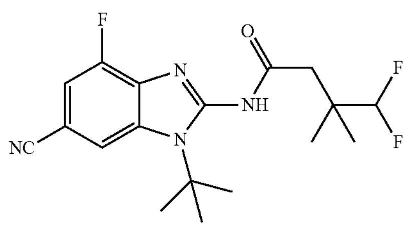 [SMILES: CC(C)(CC(=O)Nc1nc2c(F)cc(C#N)cc2n1C(C)(C)C)C(F)F] | N-(1-(tert-butyl)-6-cyano-4-fluoro-1H-benzo[d]imidazol-2-yl)-4,4-difluoro-3,3-dimethylbutanamide | 366.4 |
| 365 | 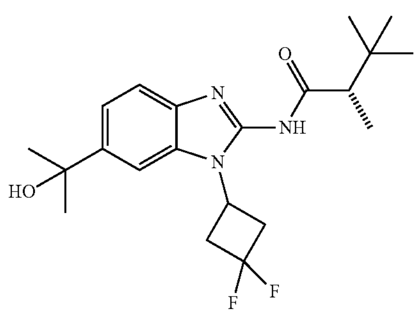 [SMILES: C[C@H](C(=O)Nc1nc2ccc(C(C)(C)O)cc2n1C1CC(F)(F)C1)C(C)(C)C] | (S)-N-(1-(3,3-difluorocyclobutyl)-6-(2-hydroxypropan-2-yl)-1H-benzo[d]imidazol-2-yl)-2,3,3-trimethylbutanamide | 393.5 |
| 366 | 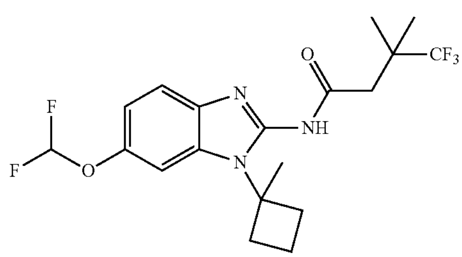 [SMILES: CC1(n2c(NC(=O)CC(C)(C)C(F)(F)F)nc3ccc(OC(F)F)cc32)CCC1] | N-(6-(difluoromethoxy)-1-(1-methylcyclobutyl)-1H-benzo[d]imidazol-2-yl)-4,4,4-trifluoro-3,3-dimethylbutanamide | 419.4 |
| 367 | 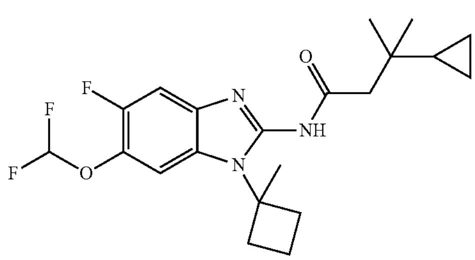 [SMILES: CC(C)(CC(=O)Nc1nc2cc(F)c(OC(F)F)cc2n1C1(C)CCC1)C1CC1] | 3-cyclopropyl-N-(6-(difluoromethoxy)-5-fluoro-1-(1-methylcyclobutyl)-1H-benzo[d]imidazol-2-yl)-3-methylbutanamide | 409.5 |

TABLE 1-continued

List of Examples with Molecular Weight Data

| Example | Structure | Name | Molecular Weight |
|---------|-----------|------|------------------|
| 368 | 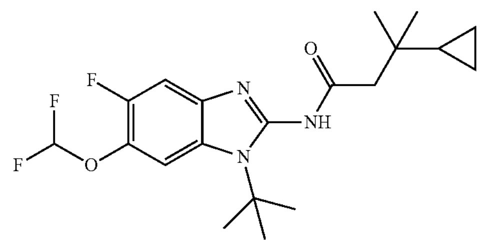 [SMILES: CC(C)(CC(=O)Nc1nc2cc(F)c(OC(F)F)cc2n1C(C)(C)C)C1CC1] | N-(1-(tert-butyl)-6-(difluoromethoxy)-5-fluoro-1H-benzo[d]imidazol-2-yl)-3-cyclopropyl-3-methylbutanamide | 397.4 |
| 369 | 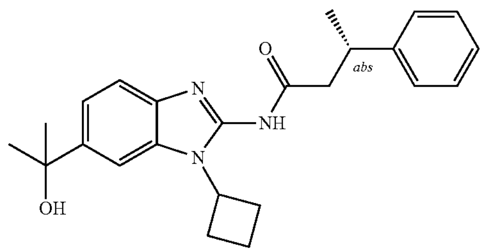 [SMILES: C[C@@H](CC(=O)Nc1nc2ccc(C(C)(C)O)cc2n1C1CCC1)c1ccccc1] | (S)-N-(1-cyclobutyl-6-(2-hydroxypropan-2-yl)-1H-benzo[d]imidazol-2-yl)-3-phenylbutanamide | 391.5 |
| 370 | 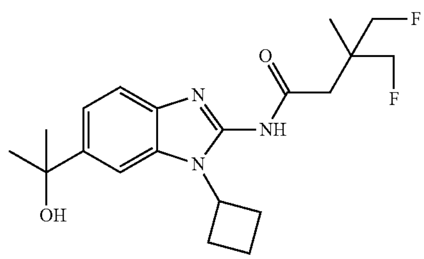 [SMILES: CC(CF)(CF)CC(=O)Nc1nc2ccc(C(C)(C)O)cc2n1C1CCC1] | N-(1-cyclobutyl-6-(2-hydroxypropan-2-yl)-1H-benzo[d]imidazol-2-yl)-4-fluoro-3-(fluoromethyl)-3-methylbutanamide | 379.5 |
| 371 | 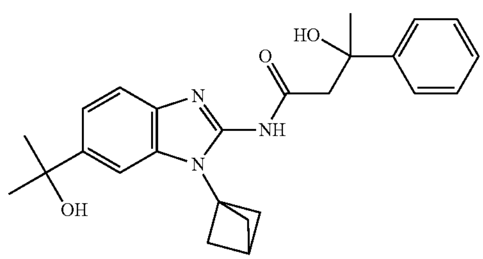 [SMILES: CC(C)(O)c1ccc2nc(NC(=O)CC(C)(O)c3ccccc3)n(C34CC(C3)C4)c2c1] | N-(1-(bicyclo[1.1.1]pentan-1-yl)-6-(2-hydroxypropan-2-yl)-1H-benzo[d]imidazol-2-yl)-3-hydroxy-3-phenylbutanamide, stereoisomer 2 | 419.5 |
| 372 | 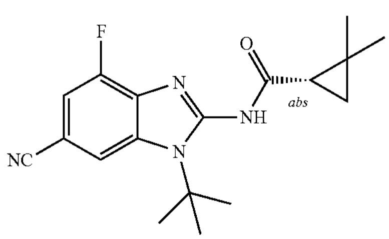 [SMILES: CC1(C)C[C@@H]1C(=O)Nc1nc2c(F)cc(C#N)cc2n1C(C)(C)C] | (S)-N-(1-(tert-butyl)-6-cyano-4-fluoro-1H-benzo[d]imidazol-2-yl)-2,2-dimethylcyclopropane-1-carboxamide | 328.4 |
| 373 | 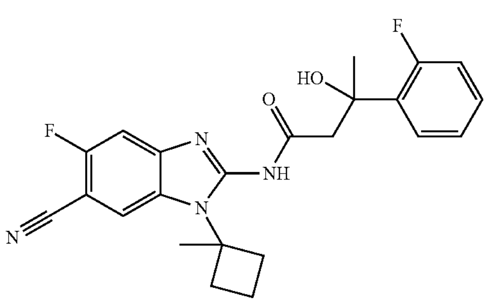 [SMILES: CC(O)(CC(=O)Nc1nc2cc(F)c(C#N)cc2n1C1(C)CCC1)c1ccccc1F] | N-(6-cyano-5-fluoro-1-(1-methylcyclobutyl)-1H-benzo[d]imidazol-2-yl)-3-(2-fluorophenyl)-3-hydroxybutanamide, stereoisomer 2 | 424.5 |

TABLE 1-continued

List of Examples with Molecular Weight Data

| Example | Structure | Name | Molecular Weight |
|---|---|---|---|
| 374 | 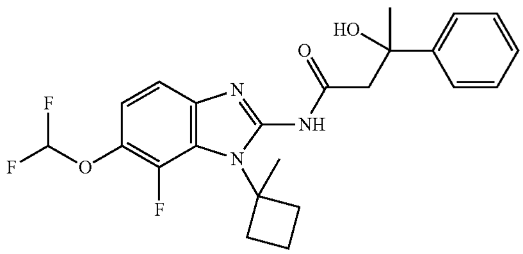 [SMILES: CC(O)(CC(=O)Nc1nc2ccc(OC(F)F)c(F)c2n1C1(C)CCC1)c1ccccc1] | N-(6-(difluoromethoxy)-7-fluoro-1-(1-methylcyclobutyl)-1H-benzo[d]imidazol-2-yl)-3-hydroxy-3-phenylbutanamide, stereoisomer 2 | 447.5 |
| 375 | 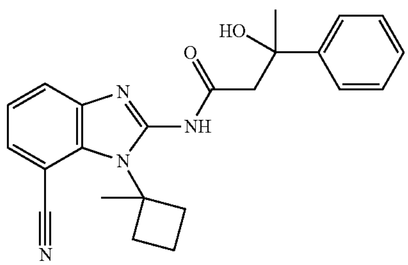 [SMILES: CC(O)(CC(=O)Nc1nc2cccc(C#N)c2n1C1(C)CCC1)c1ccccc1] | N-(7-cyano-1-(1-methylcyclobutyl)-1H-benzo[d]imidazol-2-yl)-3-hydroxy-3-phenylbutanamide, stereoisomer 2 | 388.5 |
| 376 | 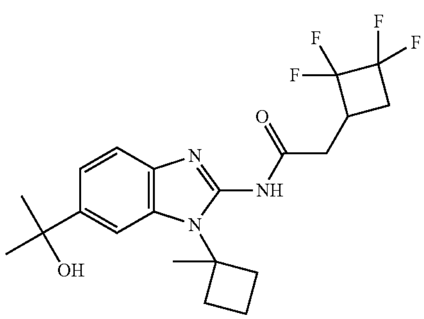 | N-(6-(2-hydroxypropan-2-yl)-1-(1-methylcyclobutyl)-1H-benzo[d]imidazol-2-yl)-2-(2,2,3,3-tetrafluorocyclobutyl)acetamide, stereoisomer 1 | 427.4 |
| 377 | 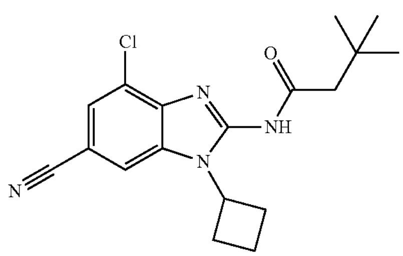 [SMILES: CC(C)(C)CC(=O)Nc1nc2c(Cl)cc(C#N)cc2n1C1CCC1] | N-(4-chloro-6-cyano-1-cyclobutyl-1H-benzo[d]imidazol-2-yl)-3,3-dimethylbutanamide | 344.8 |
| 378 | 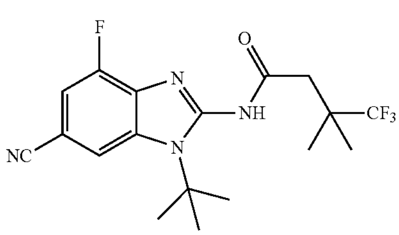 [SMILES: CC(C)(C)n1c(NC(=O)CC(C)(C)C(F)(F)F)nc2c(F)cc(C#N)cc21] | N-(1-(tert-butyl)-6-cyano-4-fluoro-1H-benzo[d]imidazol-2-yl)-4,4,4-trifluoro-3,3-dimethylbutanamide | 384.4 |

TABLE 1-continued

List of Examples with Molecular Weight Data

| Example | Structure | Name | Molecular Weight |
|---|---|---|---|
| 379 | 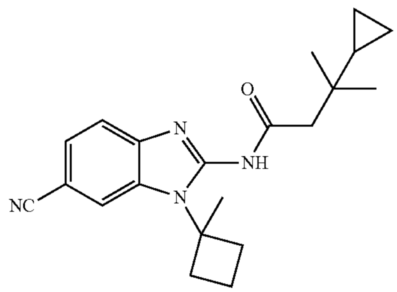 [SMILES: CC(C)(CC(=O)Nc1nc2ccc(C#N)cc2n1C1(C)CCC1)C1CC1] | N-(6-cyano-1-(1-methylcyclobutyl)-1H-benzo[d]imidazol-2-yl)-3-cyclopropyl-3-methylbutanamide | 350.5 |
| 380 | 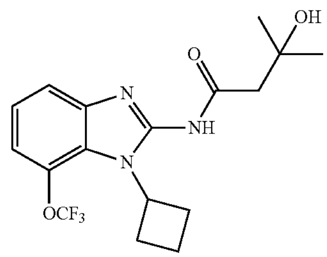 [SMILES: CC(C)(O)CC(=O)Nc1nc2cccc(OC(F)(F)F)c2n1C1CCC1] | N-(1-cyclobutyl-7-(trifluoromethoxy)-1H-benzo[d]imidazol-2-yl)-3-hydroxy-3-methylbutanamide | 371.4 |
| 381 | 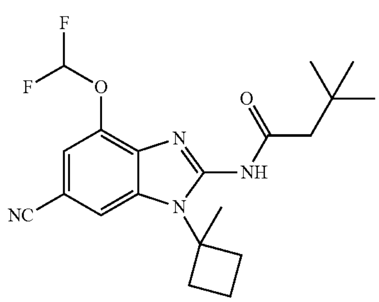 [SMILES: CC(C)(C)CC(=O)Nc1nc2c(OC(F)F)cc(C#N)cc2n1C1(C)CCC1] | N-(6-cyano-4-(difluoromethoxy)-1-(1-methylcyclobutyl)-1H-benzo[d]imidazol-2-yl)-3,3-dimethylbutanamide | 390.4 |
| 382 | 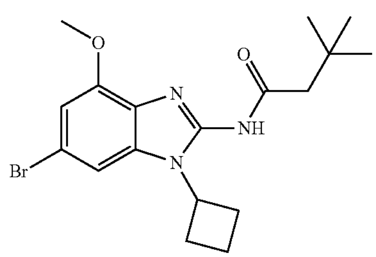 [SMILES: COc1cc(Br)cc2c1nc(NC(=O)CC(C)(C)C)n2C1CCC1] | N-(6-bromo-1-cyclobutyl-4-methoxy-1H-benzo[d]imidazol-2-yl)-3,3-dimethylbutanamide | 394.3 |
| 383 | 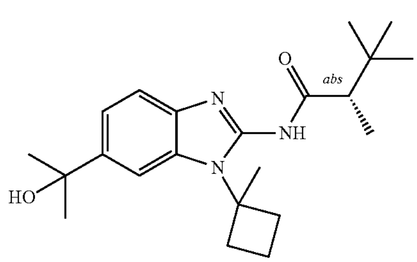 [SMILES: C[C@H](C(=O)Nc1nc2ccc(C(C)(C)O)cc2n1C1(C)CCC1)C(C)(C)C] | (S)-N-(6-(2-hydroxypropan-2-yl)-1-(1-methylcyclobutyl)-1H-benzo[d]imidazol-2-yl)-2,3,3-trimethylbutanamide | 371.5 |

US 11,261,162 B2

TABLE 1-continued

List of Examples with Molecular Weight Data

| Example | Structure | Name | Molecular Weight |
|---|---|---|---|
| 384 | 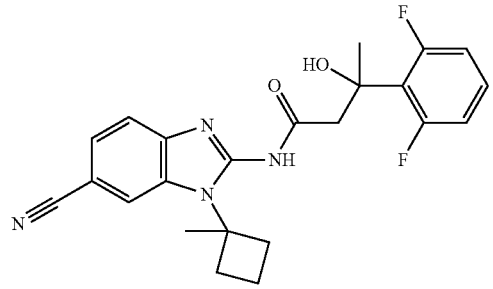 [SMILES: CC(O)(CC(=O)Nc1nc2ccc(C#N)cc2n1C1(C)CCC1)c1c(F)cccc1F] | N-(6-cyano-1-(1-methylcyclobutyl)-1H-benzo[d]imidazol-2-yl)-3-(2,6-difluorophenyl)-3-hydroxybutanamide, stereoisomer 2 | 424.5 |
| 385 | 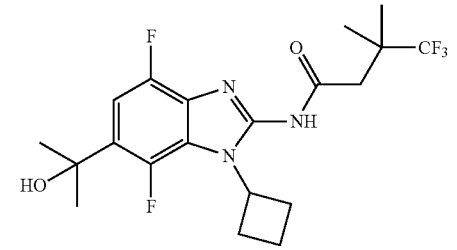 [SMILES: CC(C)(O)c1cc(F)c2nc(NC(=O)CC(C)(C)C(F)(F)F)n(C3CCC3)c2c1F] | N-(1-cyclobutyl-4,7-difluoro-6-(2-hydroxypropan-2-yl)-1H-benzo[d]imidazol-2-yl)-4,4,4-trifluoro-3,3-dimethylbutanamide | 433.4 |
| 386 | 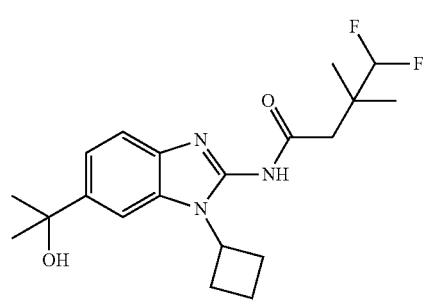 [SMILES: CC(C)(O)c1ccc2nc(NC(=O)CC(C)(C)C(F)F)n(C3CCC3)c2c1] | N-(1-cyclobutyl-6-(2-hydroxypropan-2-yl)-1H-benzo[d]imidazol-2-yl)-4,4-difluoro-3,3-dimethylbutanamide | 379.5 |
| 387 | 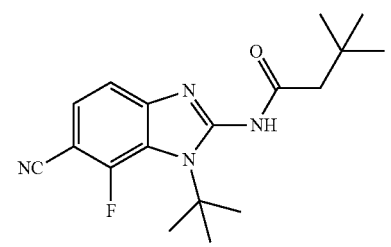 [SMILES: CC(C)(C)CC(=O)Nc1nc2ccc(C#N)c(F)c2n1C(C)(C)C] | N-(1-(tert-butyl)-6-cyano-7-fluoro-1H-benzo[d]imidazol-2-yl)-3,3-dimethylbutanamide | 330.4 |
| 388 | 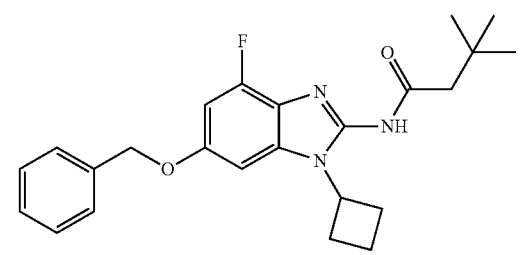 [SMILES: CC(C)(C)CC(=O)Nc1nc2c(F)cc(OCc3ccccc3)cc2n1C1CCC1] | N-(6-(benzyloxy)-1-cyclobutyl-4-fluoro-1H-benzo[d]imidazol-2-yl)-3,3-dimethylbutanamide | 409.5 |

TABLE 1-continued

List of Examples with Molecular Weight Data

| Example | Structure | Name | Molecular Weight |
|---|---|---|---|
| 389 | 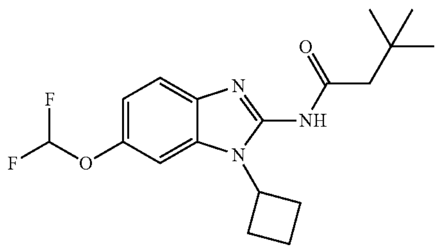 [SMILES: CC(C)(C)CC(=O)Nc1nc2ccc(OC(F)F)cc2n1C1CCC1] | N-(1-cyclobutyl-6-(difluoromethoxy)-1H-benzo[d]imidazol-2-yl)-3,3-dimethylbutanamide | 351.4 |
| 390 | 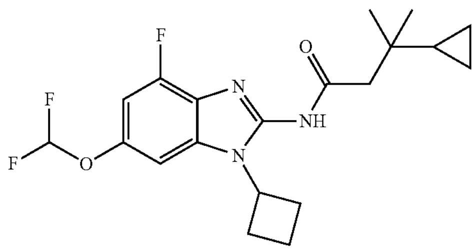 [SMILES: CC(C)(CC(=O)Nc1nc2c(F)cc(OC(F)F)cc2n1C1CCC1)C1CC1] | N-(1-cyclobutyl-6-(difluoromethoxy)-4-fluoro-1H-benzo[d]imidazol-2-yl)-3-cyclopropyl-3-methylbutanamide | 395.4 |
| 391 | 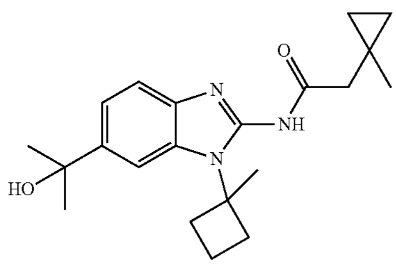 [SMILES: CC1(CC(=O)Nc2nc3ccc(C(C)(C)O)cc3n2C2(C)CCC2)CC1] | N-(6-(2-hydroxypropan-2-yl)-1-(1-methylcyclobutyl)-1H-benzo[d]imidazol-2-yl)-2-(1-methylcyclopropyl)acetamide | 355.5 |
| 392 | 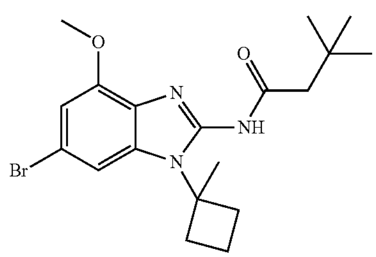 [SMILES: COc1cc(Br)cc2c1nc(NC(=O)CC(C)(C)C)n2C1(C)CCC1] | N-(6-bromo-4-methoxy-1-(1-methylcyclobutyl)-1H-benzo[d]imidazol-2-yl)-3,3-dimethylbutanamide | 408.3 |
| 393 | 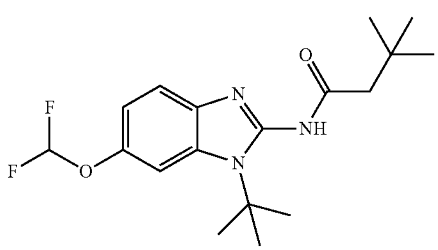 [SMILES: CC(C)(C)CC(=O)Nc1nc2ccc(OC(F)F)cc2n1C(C)(C)C] | N-(1-(tert-butyl)-6-(difluoromethoxy)-1H-benzo[d]imidazol-2-yl)-3,3-dimethylbutanamide | 353.4 |
| 394 | 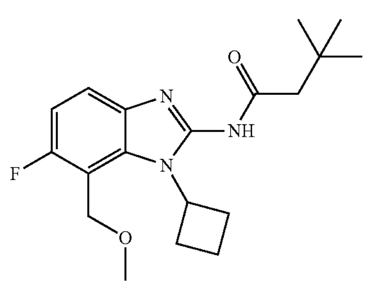 [SMILES: COCc1c(F)ccc2nc(NC(=O)CC(C)(C)C)n(C3CCC3)c12] | N-(1-cyclobutyl-6-fluoro-7-(methoxymethyl)-1H-benzo[d]imidazol-2-yl)-3,3-dimethylbutanamide | 347.4 |

TABLE 1-continued

List of Examples with Molecular Weight Data

| Example | Structure | Name | Molecular Weight |
|---|---|---|---|
| 395 | 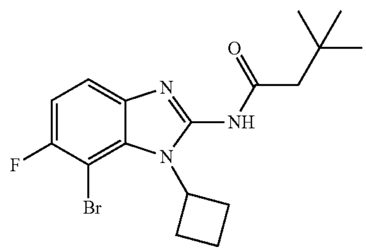 [SMILES: CC(C)(C)CC(=O)Nc1nc2ccc(F)c(Br)c2n1C1CCC1] | N-(7-bromo-1-cyclobutyl-6-fluoro-1H-benzo[d]imidazol-2-yl)-3,3-dimethylbutanamide | 382.3 |
| 396 | 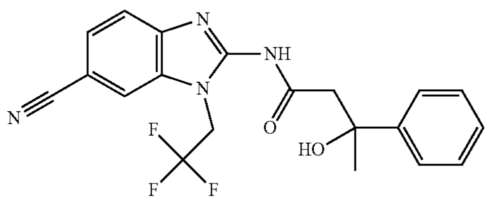 [SMILES: CC(O)(CC(=O)Nc1nc2ccc(C#N)cc2n1CC(F)(F)F)c1ccccc1] | N-(6-cyano-1-(2,2,2-trifluoroethyl)-1H-benzo[d]imidazol-2-yl)-3-hydroxy-3-phenylbutanamide, stereoisomer 1 | 402.4 |
| 397 | 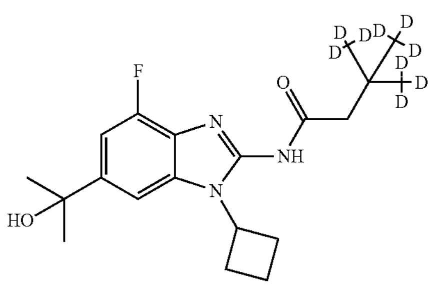 | N-(1-cyclobutyl-4-fluoro-6-(2-hydroxypropan-2-yl)-1H-benzo[d]imidazol-2-yl)-3,3-bis(methyl-d3)butanamide | 370.5 |
| 398 | 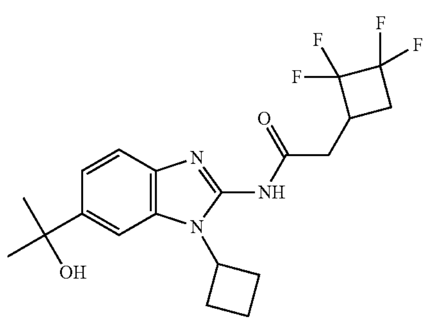 [SMILES: CC(C)(O)c1ccc2nc(NC(=O)CC3CC(F)(F)C3(F)F)n(C3CCC3)c2c1] | N-(1-cyclobutyl-6-(2-hydroxypropan-2-yl)-1H-benzo[d]imidazol-2-yl)-2-(2,2,3,3-tetrafluorocyclobutyl)acetamide, stereoisomer 1 | 413.4 |
| 399 | 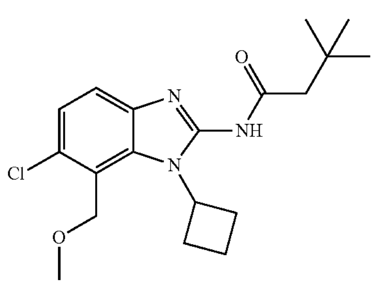 [SMILES: COCc1c(Cl)ccc2nc(NC(=O)CC(C)(C)C)n(C3CCC3)c12] | N-(6-chloro-1-cyclobutyl-7-(methoxymethyl)-1H-benzo[d]imidazol-2-yl)-3,3-dimethylbutanamide | 363.9 |

TABLE 1-continued

List of Examples with Molecular Weight Data

| Example | Structure | Name | Molecular Weight |
|---|---|---|---|
| 400 | 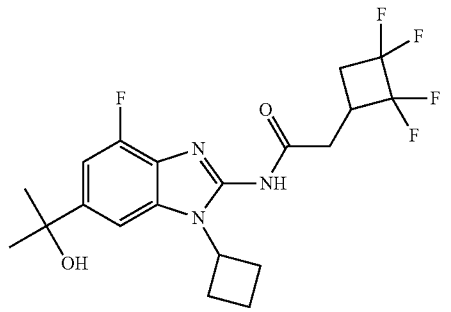 | N-(1-cyclobutyl-4-fluoro-6-(2-hydroxypropan-2-yl)-1H-benzo[d]imidazol-2-yl)-2-(2,2,3,3-tetrafluorocyclobutyl)acetamide, stereoisomer 1 | 431.4 |
| 401 | 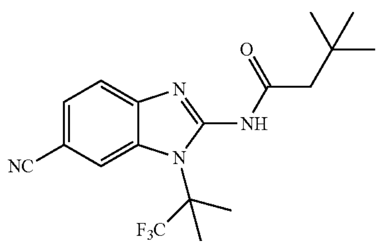 [SMILES: CC(C)(C)CC(=O)Nc1nc2ccc(C#N)cc2n1C(C)(C)C(F)(F)F] | N-(6-cyano-1-(1,1,1-trifluoro-2-methylpropan-2-yl)-1H-benzo[d]imidazol-2-yl)-3,3-dimethylbutanamide | 366.4 |
| 402 | 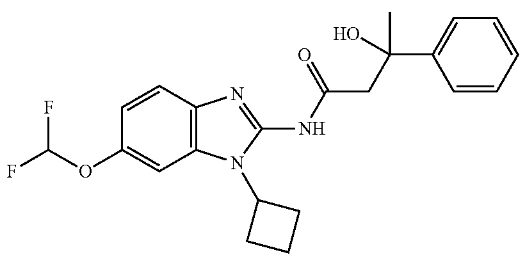 [SMILES: CC(O)(CC(=O)Nc1nc2ccc(OC(F)F)cc2n1C1CCC1)c1ccccc1] | N-(1-cyclobutyl-6-(difluoromethoxy)-1H-benzo[d]imidazol-2-yl)-3-hydroxy-3-phenylbutanamide, stereoisomer 1 | 415.4 |
| 403 | 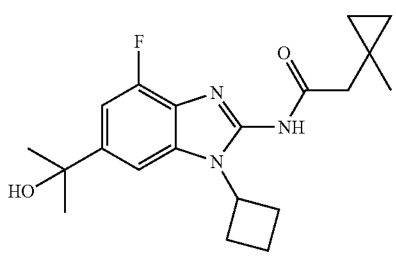 [SMILES: CC1(CC(=O)Nc2nc3c(F)cc(C(C)(C)O)cc3n2C2CCC2)CC1] | N-(1-cyclobutyl-4-fluoro-6-(2-hydroxypropan-2-yl)-1H-benzo[d]imidazol-2-yl)-2-(1-methylcyclopropyl)acetamide | 359.4 |
| 404 | 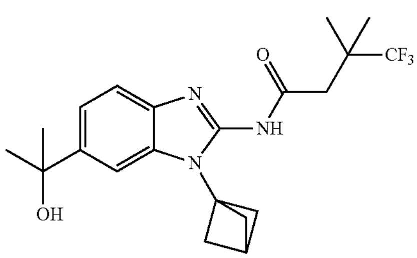 [SMILES: CC(C)(O)c1ccc2nc(NC(=O)CC(C)(C)C(F)(F)F)n(C34CC(C3)C4)c2c1] | N-(1-(bicyclo[1.1.1]pentan-1-yl)-6-(2-hydroxypropan-2-yl)-1H-benzo[d]imidazol-2-yl)-4,4,4-trifluoro-3,3-dimethylbutanamide | 409.5 |
| 405 | 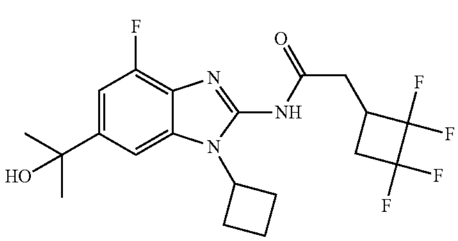 [SMILES: CC(C)(O)c1cc(F)c2nc(NC(=O)CC3CC(F)(F)C3(F)F)n(C3CCC3)c2c1] | N-(1-cyclobutyl-4-fluoro-6-(2-hydroxypropan-2-yl)-1H-benzo[d]imidazol-2-yl)-2-(2,2,3,3-tetrafluorocyclobutyl)acetamide | 431.4 |

TABLE 1-continued

List of Examples with Molecular Weight Data

| Example | Structure | Name | Molecular Weight |
|---|---|---|---|
| 406 | 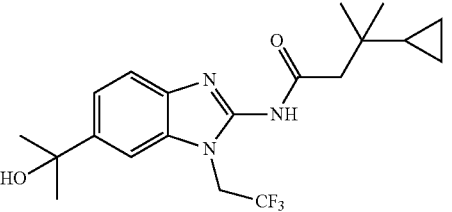 [SMILES: CC(C)(O)c1ccc2nc(NC(=O)CC(C)(C)C3CC3)n(CC(F)(F)F)c2c1] | 3-cyclopropyl-N-(6-(2-hydroxypropan-2-yl)-1-(2,2,2-trifluoroethyl)-1H-benzo[d]imidazol-2-yl)-3-methylbutanamide | 397.4 |
| 407 | 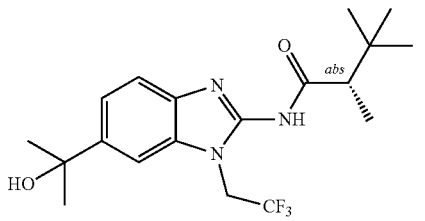 [SMILES: C[C@H](C(=O)Nc1nc2ccc(C(C)(C)O)cc2n1CC(F)(F)F)C(C)(C)C] | (S)-N-(6-(2-hydroxypropan-2-yl)-1-(2,2,2-trifluoroethyl)-1H-benzo[d]imidazol-2-yl)-2,3,3-trimethylbutanamide | 385.4 |
| 408 | 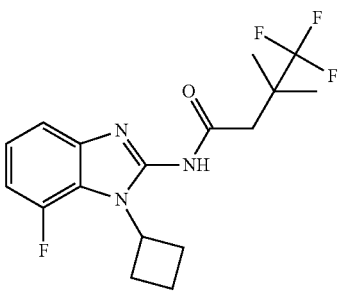 [SMILES: CC(C)(CC(=O)Nc1nc2cccc(F)c2n1C1CCC1)C(F)(F)F] | N-(1-cyclobutyl-7-fluoro-1H-benzo[d]imidazol-2-yl)-4,4,4-trifluoro-3,3-dimethylbutanamide | 357.4 |
| 409 | 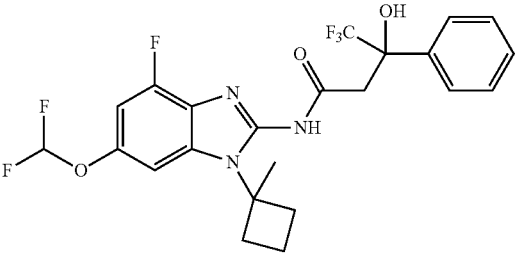 [SMILES: CC1(n2c(NC(=O)CC(O)(c3ccccc3)C(F)(F)F)nc3c(F)cc(OC(F)F)cc32)CCC1] | N-(6-(difluoromethoxy)-4-fluoro-1-(1-methylcyclobutyl)-1H-benzo[d]imidazol-2-yl)-4,4,4-trifluoro-3-hydroxy-3-phenylbutanamide | 501.4 |
| 410 | 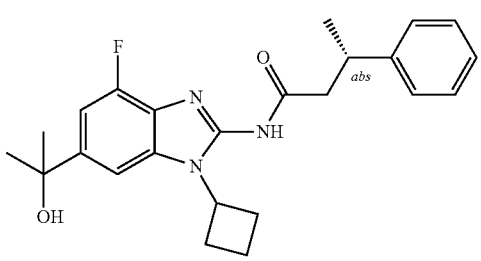 [SMILES: C[C@@H](CC(=O)Nc1nc2c(F)cc(C(C)(C)O)cc2n1C1CCC1)c1ccccc1] | (S)-N-(1-cyclobutyl-4-fluoro-6-(2-hydroxypropan-2-yl)-1H-benzo[d]imidazol-2-yl)-3-phenylbutanamide | 409.5 |
| 411 | 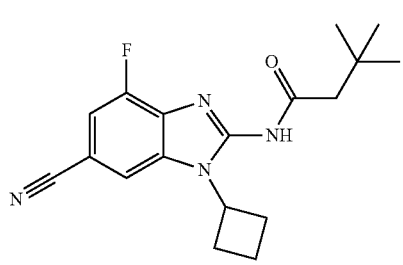 | N-(6-cyano-1-cyclobutyl-4-fluoro-1H-benzo[d]imidazol-2-yl)-3,3-dimethylbutanamide | 328.4 |

TABLE 1-continued

List of Examples with Molecular Weight Data

| Example | Structure | Name | Molecular Weight |
|---|---|---|---|
| 412 | 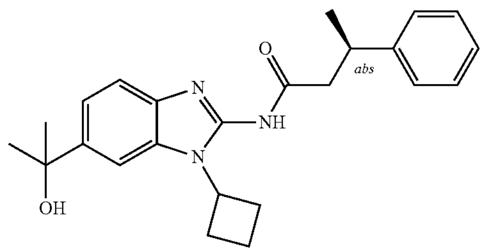 [SMILES: C[C@H](CC(=O)Nc1nc2ccc(C(C)(C)O)cc2n1C1CCC1)c1ccccc1] | (R)-N-(1-cyclobutyl-4-fluoro-6-(2-hydroxypropan-2-yl)-1H-benzo[d]imidazol-2-yl)-3-phenylbutanamide | 409.5 |
| 413 | 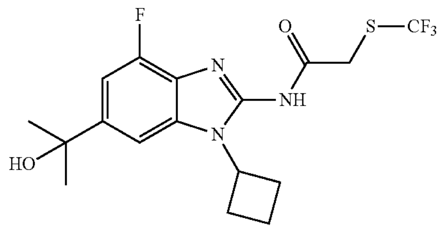 [SMILES: CC(C)(O)c1cc(F)c2nc(NC(=O)CSC(F)(F)F)n(C3CCC3)c2c1] | N-(1-cyclobutyl-4-fluoro-6-(2-hydroxypropan-2-yl)-1H-benzo[d]imidazol-2-yl)-2-((trifluoromethyl)thio)acetamide | 405.4 |
| 414 | 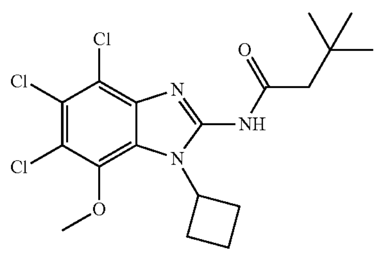 [SMILES: COc1c(Cl)c(Cl)c(Cl)c2nc(NC(=O)CC(C)(C)C)n(C3CCC3)c12] | 3,3-dimethyl-N-(4,5,6-trichloro-1-cyclobutyl-7-methoxy-1H-benzo[d]imidazol-2-yl)butanamide | 418.7 |
| 415 | 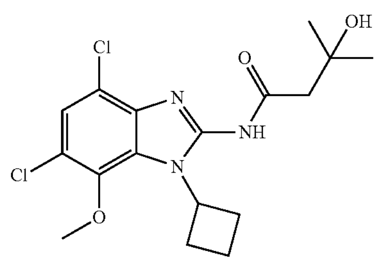 [SMILES: COc1c(Cl)cc(Cl)c2nc(NC(=O)CC(C)(C)O)n(C3CCC3)c12] | N-(4,6-dichloro-1-cyclobutyl-7-methoxy-1H-benzo[d]imidazol-2-yl)-3-hydroxy-3-methylbutanamide | 386.3 |
| 416 | 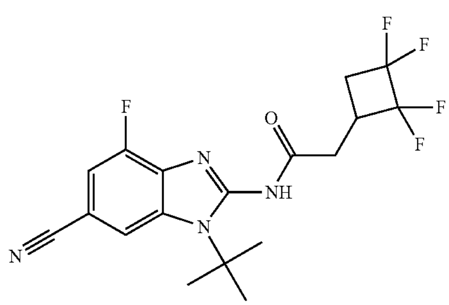 [SMILES: CC(C)(C)n1c(NC(=O)CC2CC(F)(F)C2(F)F)nc2c(F)cc(C#N)cc21] | N-(1-(tert-butyl)-6-cyano-4-fluoro-1H-benzo[d]imidazol-2-yl)-2-(2,2,3,3-tetrafluorocyclobutyl)acetamide, stereoisomer 2 | 400.4 |
| 417 | 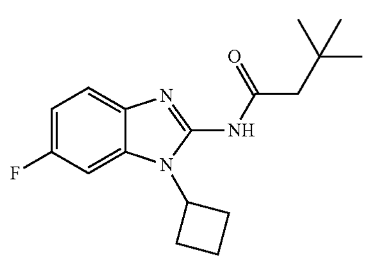 [SMILES: CC(C)(C)CC(=O)Nc1nc2ccc(F)cc2n1C1CCC1] | N-(1-cyclobutyl-6-fluoro-1H-benzo[d]imidazol-2-yl)-3,3-dimethylbutanamide | 303.4 |

TABLE 1-continued

List of Examples with Molecular Weight Data

| Example | Structure | Name | Molecular Weight |
|---|---|---|---|
| 418 | 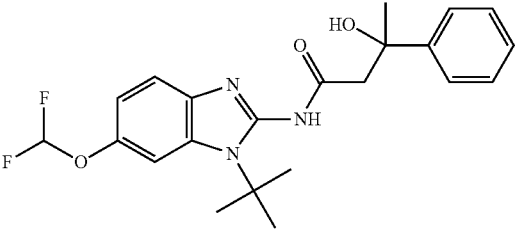 [SMILES: CC(O)(CC(=O)Nc1nc2ccc(OC(F)F)cc2n1C(C)(C)C)c1ccccc1] | N-(1-(tert-butyl)-6-(difluoromethoxy)-1H-benzo[d]imidazol-2-yl)-3-hydroxy-3-phenylbutanamide, stereoisomer 1 | 417.5 |
| 419 | 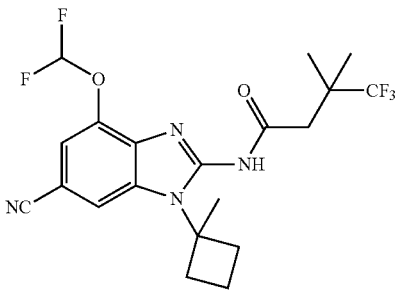 [SMILES: CC1(n2c(NC(=O)CC(C)(C)C(F)(F)F)nc3c(OC(F)F)cc(C#N)cc32)CCC1] | N-(6-cyano-4-(difluoromethoxy)-1-(1-methylcyclobutyl)-1H-benzo[d]imidazol-2-yl)-4,4,4-trifluoro-3,3-dimethylbutanamide | 444.4 |
| 420 | 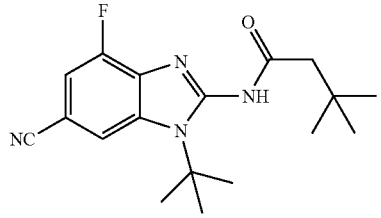 [SMILES: CC(C)(C)CC(=O)Nc1nc2c(F)cc(C#N)cc2n1C(C)(C)C] | N-(1-(tert-butyl)-6-cyano-4-fluoro-1H-benzo[d]imidazol-2-yl)-3,3-dimethylbutanamide | 330.4 |
| 421 | 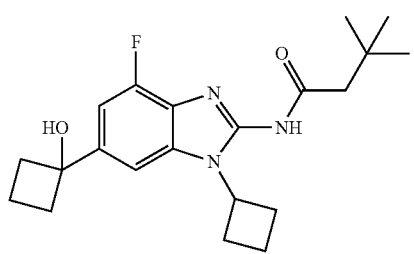 [SMILES: CC(C)(C)CC(=O)Nc1nc2c(F)cc(C3(O)CCC3)cc2n1C1CCC1] | N-(1-cyclobutyl-4-fluoro-6-(1-hydroxycyclobutyl)-1H-benzo[d]imidazol-2-yl)-3,3-dimethylbutanamide | 373.5 |
| 422 | 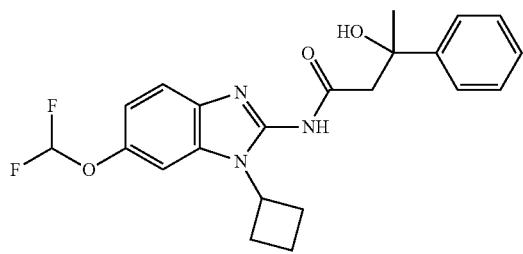 [SMILES: CC(O)(CC(=O)Nc1nc2ccc(OC(F)F)cc2n1C1CCC1)c1ccccc1] | N-(1-cyclobutyl-6-(difluoromethoxy)-1H-benzo[d]imidazol-2-yl)-3-hydroxy-3-phenylbutanamide, stereoisomer 2 | 415.4 |

TABLE 1-continued

List of Examples with Molecular Weight Data

| Example | Structure | Name | Molecular Weight |
|---|---|---|---|
| 423 | 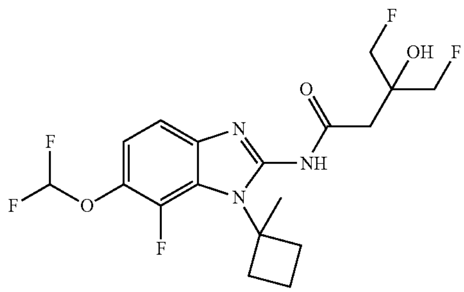 [SMILES: CC1(n2c(NC(=O)CC(O)(CF)CF)nc3ccc(OC(F)F)c(F)c32)CCC1] | N-(6-(difluoromethoxy)-7-fluoro-1-(1-methylcyclobutyl)-1H-benzo[d]imidazol-2-yl)-4-fluoro-3-(fluoromethyl)-3-hydroxybutanamide | 421.4 |
| 424 | 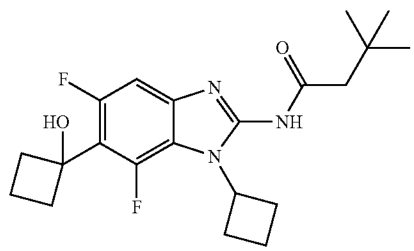 [SMILES: CC(C)(C)CC(=O)Nc1nc2cc(F)c(C3(O)CCC3)c(F)c2n1C1CCC1] | N-(1-cyclobutyl-5,7-difluoro-6-(1-hydroxycyclobutyl)-1H-benzo[d]imidazol-2-yl)-3,3-dimethylbutanamide | 391.5 |
| 425 | 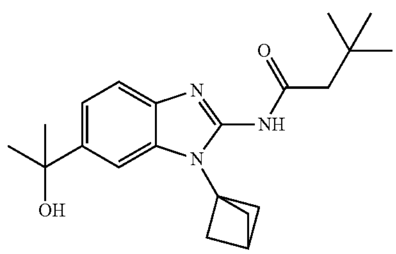 [SMILES: CC(C)(C)CC(=O)Nc1nc2ccc(C(C)(C)O)cc2n1C12CC(C1)C2] | N-(1-(bicyclo[1.1.1]pentan-1-yl)-6-(2-hydroxypropan-2-yl)-1H-benzo[d]imidazol-2-yl)-3,3-dimethylbutanamide | 355.5 |
| 426 | 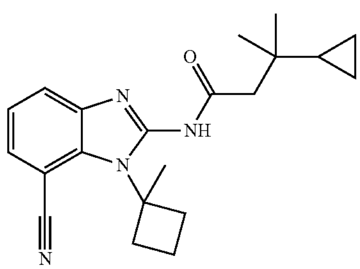 [SMILES: CC(C)(CC(=O)Nc1nc2cccc(C#N)c2n1C1(C)CCC1)C1CC1] | N-(7-cyano-1-(1-methylcyclobutyl)-1H-benzo[d]imidazol-2-yl)-3-cyclopropyl-3-methylbutanamide | 350.5 |
| 427 | 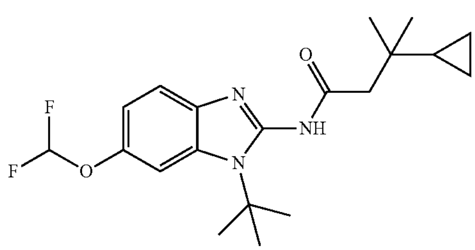 [SMILES: CC(C)(CC(=O)Nc1nc2ccc(OC(F)F)cc2n1C(C)(C)C)C1CC1] | N-(1-(tert-butyl)-6-(difluoromethoxy)-1H-benzo[d]imidazol-2-yl)-3-cyclopropyl-3-methylbutanamide | 379.5 |
| 428 | 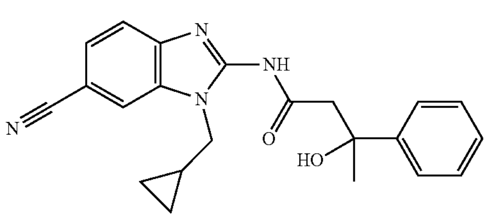 [SMILES: CC(O)(CC(=O)Nc1nc2ccc(C#N)cc2n1CC1CC1)c1ccccc1] | N-(6-cyano-1-(cyclopropylmethyl)-1H-benzo[d]imidazol-2-yl)-3-hydroxy-3-phenylbutanamide, stereoisomer 1 | 374.4 |

TABLE 1-continued

List of Examples with Molecular Weight Data

| Example | Structure | Name | Molecular Weight |
|---|---|---|---|
| 429 | 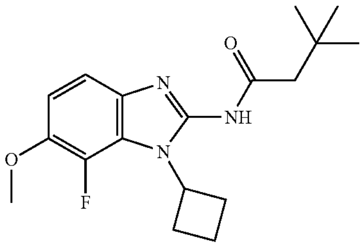 [SMILES: COc1ccc2nc(NC(=O)CC(C)(C)C)n(C3CCC3)c2c1F] | N-(1-cyclobutyl-7-fluoro-6-methoxy-1H-benzo[d]imidazol-2-yl)-3,3-dimethylbutanamide | 333.4 |
| 430 | 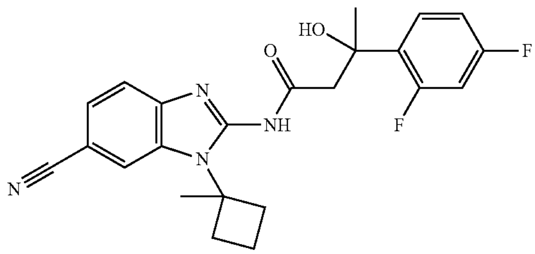 [SMILES: CC(O)(CC(=O)Nc1nc2ccc(C#N)cc2n1C1(C)CCC1)c1ccc(F)cc1F] | N-(6-cyano-1-(1-methylcyclobutyl)-1H-benzo[d]imidazol-2-yl)-3-(2,4-difluorophenyl)-3-hydroxybutanamide, stereoisomer 1 | 424.5 |
| 431 | 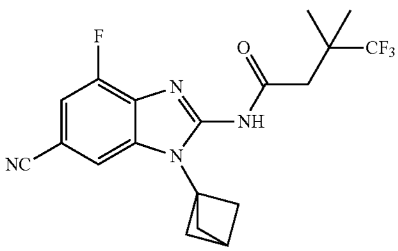 [SMILES: CC(C)(CC(=O)Nc1nc2c(F)cc(C#N)cc2n1C12CC(C1)C2)C(F)(F)F] | N-(1-(bicyclo[1.1.1]pentan-1-yl)-6-cyano-4-fluoro-1H-benzo[d]imidazol-2-yl)-4,4,4-trifluoro-3,3-dimethylbutanamide | 394.4 |
| 432 | 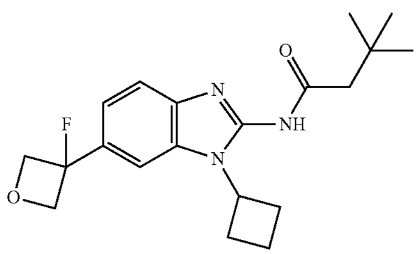 [SMILES: CC(C)(C)CC(=O)Nc1nc2ccc(C3(F)COC3)cc2n1C1CCC1] | N-(1-cyclobutyl-6-(3-fluorooxetan-3-yl)-1H-benzo[d]imidazol-2-yl)-3,3-dimethylbutanamide | 359.4 |
| 433 | 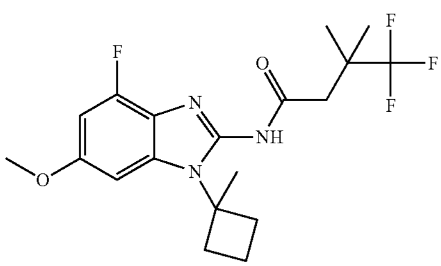 [SMILES: COc1cc(F)c2nc(NC(=O)CC(C)(C)C(F)(F)F)n(C3(C)CCC3)c2c1] | 4,4,4-trifluoro-N-(4-fluoro-6-methoxy-1-(1-methylcyclobutyl)-1H-benzo[d]imidazol-2-yl)-3,3-dimethylbutanamide | 401.4 |
| 434 | 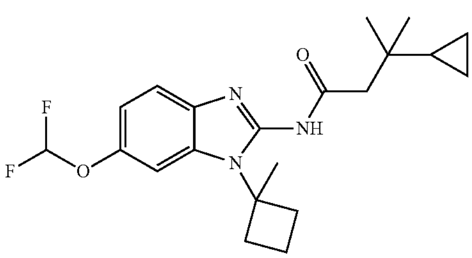 [SMILES: CC(C)(CC(=O)Nc1nc2ccc(OC(F)F)cc2n1C1(C)CCC1)C1CC1] | 3-cyclopropyl-N-(6-(difluoromethoxy)-1-(1-methylcyclobutyl)-1H-benzo[d]imidazol-2-yl)-3-methylbutanamide | 391.5 |

TABLE 1-continued

List of Examples with Molecular Weight Data

| Example | Structure | Name | Molecular Weight |
|---|---|---|---|
| 435 | 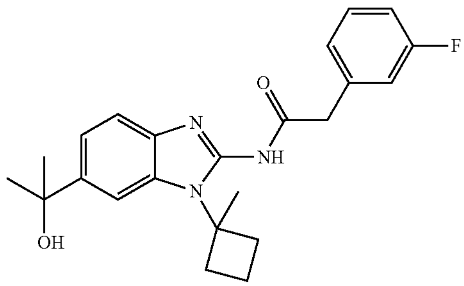 [SMILES: CC(C)(O)c1ccc2nc(NC(=O)Cc3cccc(F)c3)n(C3(C)CCC3)c2c1] | 2-(3-fluorophenyl)-N-(6-(2-hydroxypropan-2-yl)-1-(1-methylcyclobutyl)-1H-benzo[d]imidazol-2-yl)acetamide | 395.5 |
| 436 | 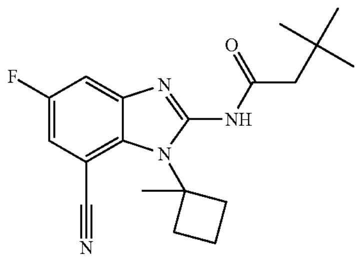 [SMILES: CC(C)(C)CC(=O)Nc1nc2cc(F)cc(C#N)c2n1C1(C)CCC1] | N-(7-cyano-5-fluoro-1-(1-methylcyclobutyl)-1H-benzo[d]imidazol-2-yl)-3,3-dimethylbutanamide | 342.4 |
| 437 | 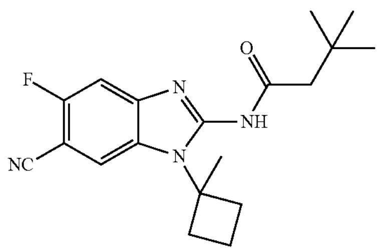 [SMILES: CC(C)(C)CC(=O)Nc1nc2cc(F)c(C#N)cc2n1C1(C)CCC1] | N-(6-cyano-5-fluoro-1-(1-methylcyclobutyl)-1H-benzo[d]imidazol-2-yl)-3,3-dimethylbutanamide | 342.4 |
| 438 | 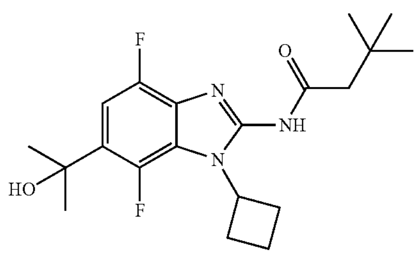 [SMILES: CC(C)(C)CC(=O)Nc1nc2c(F)cc(C(C)(C)O)c(F)c2n1C1CCC1] | N-(1-cyclobutyl-4,7-difluoro-6-(2-hydroxypropan-2-yl)-1H-benzo[d]imidazol-2-yl)-3,3-dimethylbutanamide | 379.5 |
| 439 | 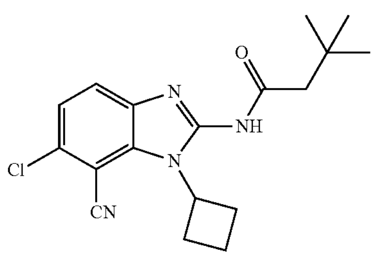 [SMILES: CC(C)(C)CC(=O)Nc1nc2ccc(Cl)c(C#N)c2n1C1CCC1] | N-(6-chloro-7-cyano-1-cyclobutyl-1H-benzo[d]imidazol-2-yl)-3,3-dimethylbutanamide | 344.8 |
| 440 | 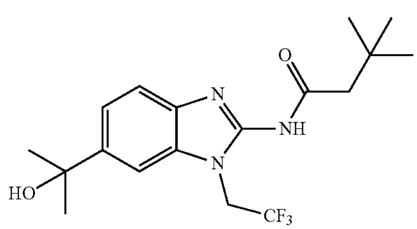 [SMILES: CC(C)(C)CC(=O)Nc1nc2ccc(C(C)(C)O)cc2n1CC(F)(F)F] | N-(6-(2-hydroxypropan-2-yl)-1-(2,2,2-trifluoroethyl)-1H-benzo[d]imidazol-2-yl)-3,3-dimethylbutanamide | 371.4 |

TABLE 1-continued

List of Examples with Molecular Weight Data

| Example | Structure | Name | Molecular Weight |
|---|---|---|---|
| 441 | 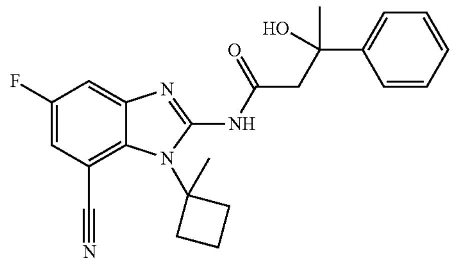 [SMILES: CC(O)(CC(=O)Nc1nc2cc(F)cc(C#N)c2n1C1(C)CCC1)c1ccccc1] | N-(7-cyano-5-fluoro-1-(1-methylcyclobutyl)-1H-benzo[d]imidazol-2-yl)-3-hydroxy-3-phenylbutanamide, stereoisomer 1 | 406.5 |
| 442 | 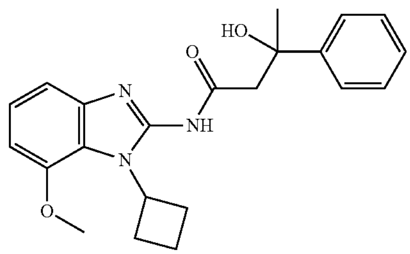 [SMILES: COc1cccc2nc(NC(=O)CC(C)(O)c3ccccc3)n(C3CCC3)c12] | N-(1-cyclobutyl-7-methoxy-1H-benzo[d]imidazol-2-yl)-3-hydroxy-3-phenylbutanamide, stereoisomer 1 | 379.5 |
| 443 | 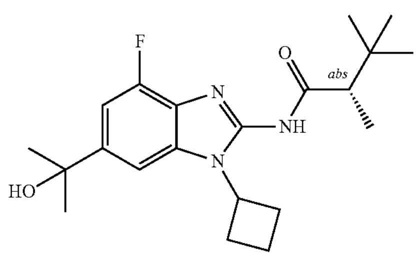 [SMILES: C[C@H](C(=O)Nc1nc2c(F)cc(C(C)(C)O)cc2n1C1CCC1)C(C)(C)C] | (S)-N-(1-cyclobutyl-4-fluoro-6-(2-hydroxypropan-2-yl)-1H-benzo[d]imidazol-2-yl)-2,3,3-trimethylbutanamide | 375.5 |
| 444 | 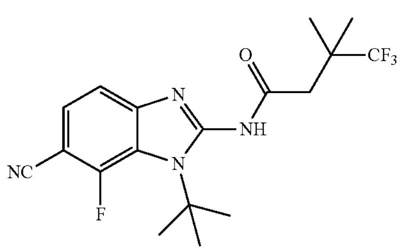 [SMILES: CC(C)(C)n1c(NC(=O)CC(C)(C)C(F)(F)F)nc2ccc(C#N)c(F)c21] | N-(1-(tert-butyl)-6-cyano-7-fluoro-1H-benzo[d]imidazol-2-yl)-4,4,4-trifluoro-3,3-dimethylbutanamide | 384.4 |
| 445 | 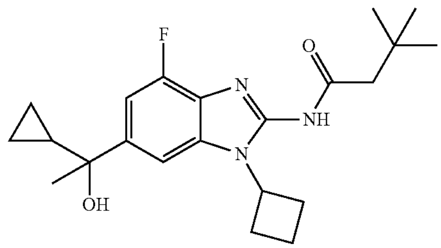 [SMILES: CC(C)(C)CC(=O)Nc1nc2c(F)cc(C(C)(O)C3CC3)cc2n1C1CCC1] | N-(1-cyclobutyl-6-(1-cyclopropyl-1-hydroxyethyl)-4-fluoro-1H-benzo[d]imidazol-2-yl)-3,3-dimethylbutanamide | 387.5 |

TABLE 1-continued

List of Examples with Molecular Weight Data

| Example | Structure | Name | Molecular Weight |
|---|---|---|---|
| 446 | 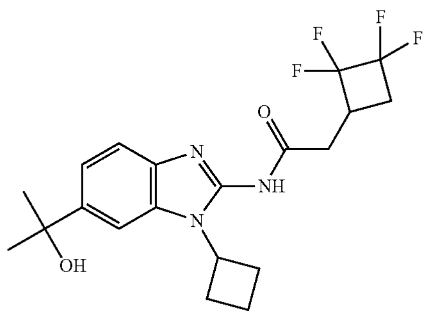 [SMILES: CC(C)(O)c1ccc2nc(NC(=O)CC3CC(F)(F)C3(F)F)n(C3CCC3)c2c1] | N-(1-cyclobutyl-6-(2-hydroxypropan-2-yl)-1H-benzo[d]imidazol-2-yl)-2-(2,2,3,3-tetrafluorocyclobutyl)acetamide, stereoisomer 2 | 413.4 |
| 447 | 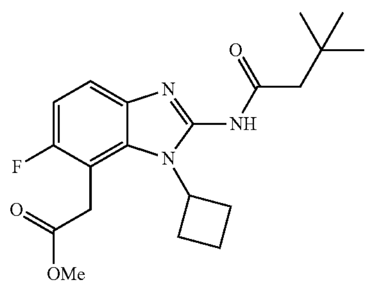 [SMILES: COC(=O)Cc1c(F)ccc2nc(NC(=O)CC(C)(C)C)n(C3CCC3)c12] | methyl 2-(1-cyclobutyl-2-(3,3-dimethylbutanamido)-6-fluoro-1H-benzo[d]imidazol-7-yl)acetate | 375.4 |
| 448 | 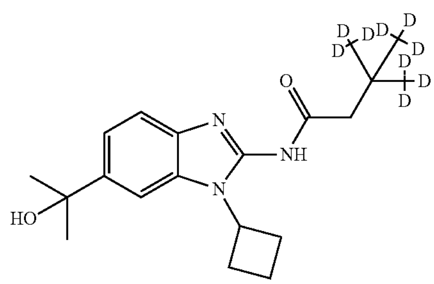 | N-(1-cyclobutyl-6-(2-hydroxypropan-2-yl)-1H-benzo[d]imidazol-2-yl)-3,3-bis(methyl-d3)butanamide | 352.5 |
| 449 | 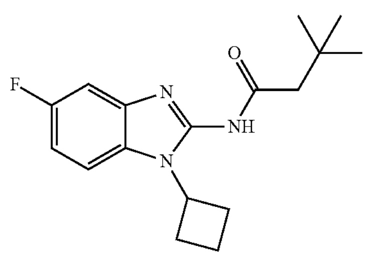 [SMILES: CC(C)(C)CC(=O)Nc1nc2cc(F)ccc2n1C1CCC1] | N-(1-cyclobutyl-5-fluoro-1H-benzo[d]imidazol-2-yl)-3,3-dimethylbutanamide | 303.4 |
| 450 | 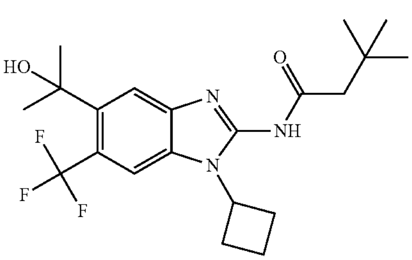 [SMILES: CC(C)(C)CC(=O)Nc1nc2cc(C(C)(C)O)c(C(F)(F)F)cc2n1C1CCC1] | N-(1-cyclobutyl-5-(2-hydroxypropan-2-yl)-6-(trifluoromethyl)-1H-benzo[d]imidazol-2-yl)-3,3-dimethylbutanamide | 411.5 |

TABLE 1-continued

List of Examples with Molecular Weight Data

| Example | Structure | Name | Molecular Weight |
|---|---|---|---|
| 451 | 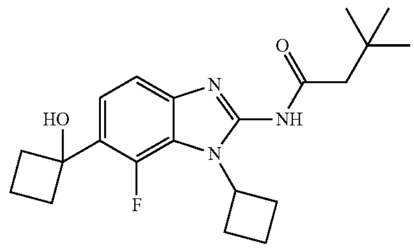 [SMILES: CC(C)(C)CC(=O)Nc1nc2ccc(C3(O)CCC3)c(F)c2n1C1CCC1] | N-(1-cyclobutyl-7-fluoro-6-(1-hydroxycyclobutyl)-1H-benzo[d]imidazol-2-yl)-3,3-dimethylbutanamide | 373.5 |
| 452 | 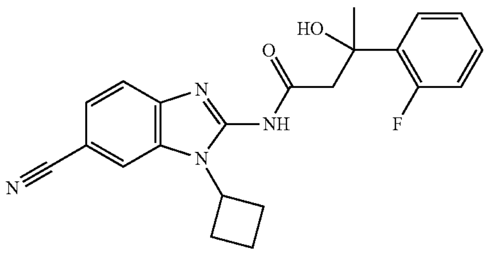 [SMILES: CC(O)(CC(=O)Nc1nc2ccc(C#N)cc2n1C1CCC1)c1ccccc1F] | N-(6-cyano-1-cyclobutyl-1H-benzo[d]imidazol-2-yl)-3-(2-fluorophenyl)-3-hydroxybutanamide, stereoisomer 1 | 392.4 |
| 453 | 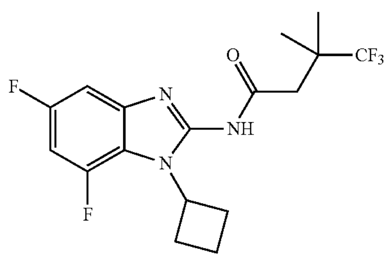 [SMILES: CC(C)(CC(=O)Nc1nc2cc(F)cc(F)c2n1C1CCC1)C(F)(F)F] | N-(1-cyclobutyl-5,7-difluoro-1H-benzo[d]imidazol-2-yl)-4,4,4-trifluoro-3,3-dimethylbutanamide | 375.3 |
| 454 | 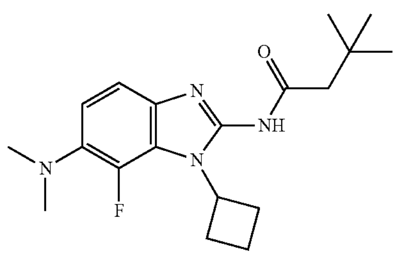 [SMILES: CN(C)c1ccc2nc(NC(=O)CC(C)(C)C)n(C3CCC3)c2c1F] | N-(1-cyclobutyl-6-(dimethylamino)-7-fluoro-1H-benzo[d]imidazol-2-yl)-3,3-dimethylbutanamide | 346.5 |
| 455 | 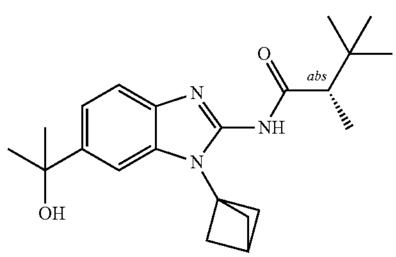 [SMILES: C[C@H](C(=O)Nc1nc2ccc(C(C)(C)O)cc2n1C12CC(C1)C2)C(C)(C)C] | (S)-N-(1-(bicyclo[1.1.1]pentan-1-yl)-6-(2-hydroxypropan-2-yl)-1H-benzo[d]imidazol-2-yl)-2,3,3-trimethylbutanamide | 369.5 |
| 456 | 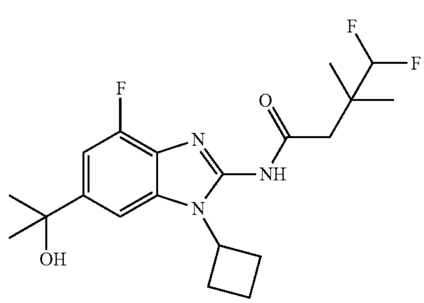 [SMILES: CC(C)(O)c1cc(F)c2nc(NC(=O)CC(C)(C)C(F)F)n(C3CCC3)c2c1] | N-(1-cyclobutyl-4-fluoro-6-(2-hydroxypropan-2-yl)-1H-benzo[d]imidazol-2-yl)-4,4-difluoro-3,3-dimethylbutanamide | 397.4 |

TABLE 1-continued

List of Examples with Molecular Weight Data

| Example | Structure | Name | Molecular Weight |
|---|---|---|---|
| 457 | 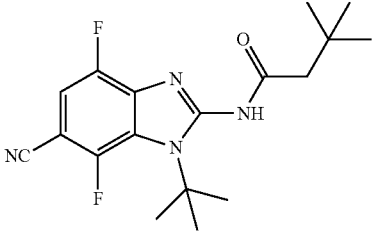 [SMILES: CC(C)(C)CC(=O)Nc1nc2c(F)cc(C#N)c(F)c2n1C(C)(C)C] | N-(1-(tert-butyl)-6-cyano-4,7-difluoro-1H-benzo[d]imidazol-2-yl)-3,3-dimethylbutanamide | 348.4 |
| 458 | 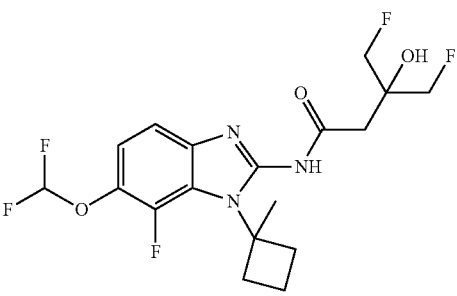 [SMILES: CC1(n2c(NC(=O)CC(O)(CF)CF)nc3ccc(OC(F)F)c(F)c32)CCC1] | N-(1-cyclobutyl-7-methoxy-1H-benzo[d]imidazol-2-yl)-3-cyclopropyl-3-methylbutanamide | 341.5 |
| 459 | 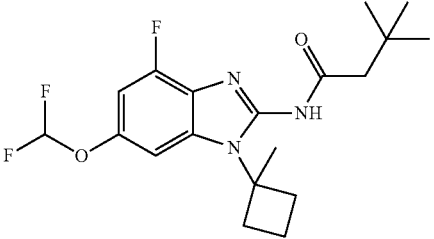 [SMILES: CC(C)(C)CC(=O)Nc1nc2c(F)cc(OC(F)F)cc2n1C1(C)CCC1] | N-(6-(difluoromethoxy)-4-fluoro-1-(1-methylcyclobutyl)-1H-benzo[d]imidazol-2-yl)-3,3-dimethylbutanamide | 383.4 |
| 460 | 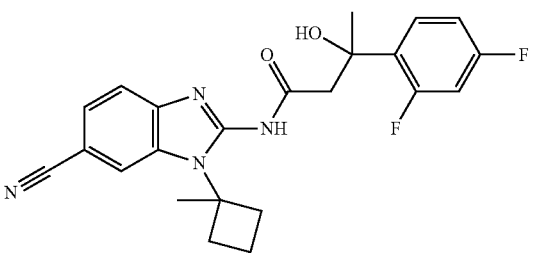 [SMILES: CC(O)(CC(=O)Nc1nc2ccc(C#N)cc2n1C1(C)CCC1)c1ccc(F)cc1F] | N-(6-cyano-1-(1-methylcyclobutyl)-1H-benzo[d]imidazol-2-yl)-3-(2,4-difluorophenyl)-3-hydroxybutanamide, stereoisomer 2 | 424.5 |
| 461 | 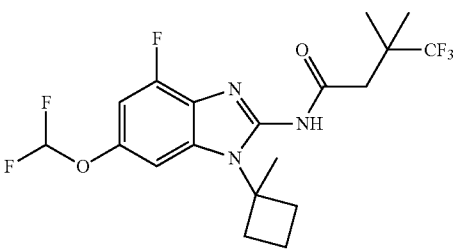 [SMILES: CC1(n2c(NC(=O)CC(C)(C)C(F)(F)F)nc3c(F)cc(OC(F)F)cc32)CCC1] | N-(6-(difluoromethoxy)-4-fluoro-1-(1-methylcyclobutyl)-1H-benzo[d]imidazol-2-yl)-4,4,4-trifluoro-3,3-dimethylbutanamide | 437.4 |

TABLE 1-continued

List of Examples with Molecular Weight Data

| Example | Structure | Name | Molecular Weight |
|---|---|---|---|
| 462 | 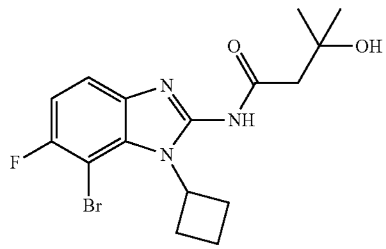 [SMILES: CC(C)(O)CC(=O)Nc1nc2ccc(F)c(Br)c2n1C1CCC1] | N-(7-bromo-1-cyclobutyl-6-fluoro-1H-benzo[d]imidazol-2-yl)-3-hydroxy-3-methylbutanamide | 384.2 |
| 463 | 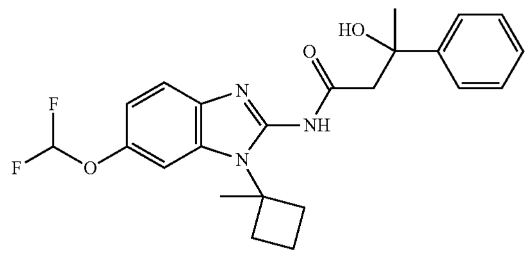 [SMILES: CC(O)(CC(=O)Nc1nc2ccc(OC(F)F)cc2n1C1(C)CCC1)c1ccccc1] | N-(6-(difluoromethoxy)-1-(1-methylcyclobutyl)-1H-benzo[d]imidazol-2-yl)-3-hydroxy-3-phenylbutanamide, stereoisomer 1 | 429.5 |
| 464 | 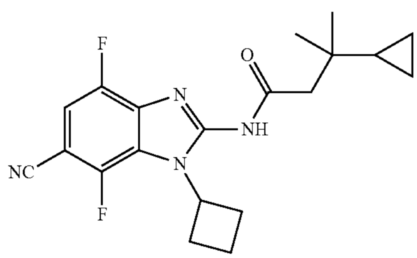 [SMILES: CC(C)(CC(=O)Nc1nc2c(F)cc(C#N)c(F)c2n1C1CCC1)C1CC1] | N-(6-cyano-1-cyclobutyl-4,7-difluoro-1H-benzo[d]imidazol-2-yl)-3-cyclopropyl-3-methylbutanamide | 372.4 |
| 465 | 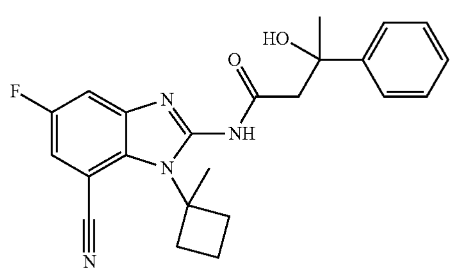 [SMILES: CC(O)(CC(=O)Nc1nc2cc(F)cc(C#N)c2n1C1(C)CCC1)c1ccccc1] | N-(7-cyano-5-fluoro-1-(1-methylcyclobutyl)-1H-benzo[d]imidazol-2-yl)-3-hydroxy-3-phenylbutanamide, stereoisomer 2 | 406.5 |
| 466 | 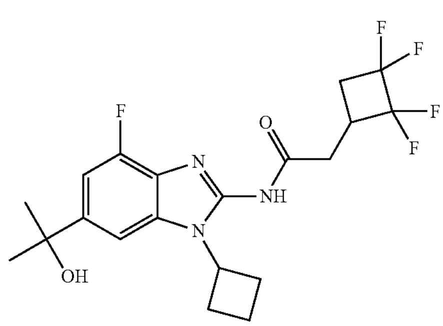 [SMILES: CC(C)(O)c1cc(F)c2nc(NC(=O)CC3CC(F)(F)C3(F)F)n(C3CCC3)c2c1] | N-(1-cyclobutyl-4-fluoro-6-(2-hydroxypropan-2-yl)-1H-benzo[d]imidazol-2-yl)-2-(2,2,3,3-tetrafluorocyclobutyl)acetamide, stereoisomer 2 | 431.4 |

TABLE 1-continued

List of Examples with Molecular Weight Data

| Example | Structure | Name | Molecular Weight |
|---|---|---|---|
| 467 | 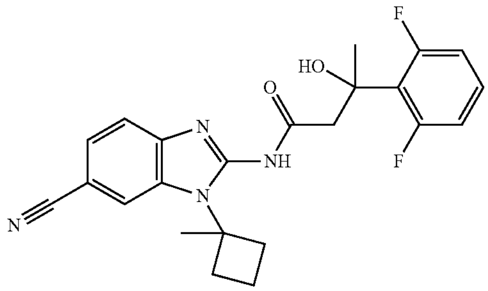 [SMILES: CC(O)(CC(=O)Nc1nc2ccc(C#N)cc2n1C1(C)CCC1)c1c(F)cccc1F] | N-(6-cyano-1-(1-methylcyclobutyl)-1H-benzo[d]imidazol-2-yl)-3-(2,6-difluorophenyl)-3-hydroxybutanamide, stereoisomer 1 | 424.5 |
| 468 | 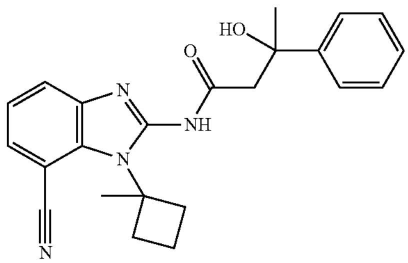 [SMILES: CC(O)(CC(=O)Nc1nc2cccc(C#N)c2n1C1(C)CCC1)c1ccccc1] | N-(7-cyano-1-(1-methylcyclobutyl)-1H-benzo[d]imidazol-2-yl)-3-hydroxy-3-phenylbutanamide, stereoisomer 1 | 388.5 |
| 469 | 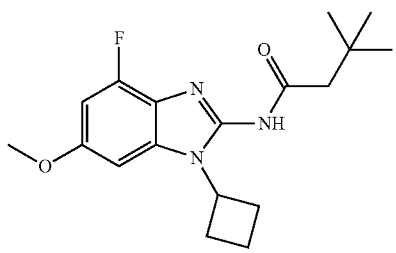 [SMILES: COc1cc(F)c2nc(NC(=O)CC(C)(C)C)n(C3CCC3)c2c1] | N-(1-cyclobutyl-4-fluoro-6-methoxy-1H-benzo[d]imidazol-2-yl)-3,3-dimethylbutanamide | 333.4 |
| 470 | 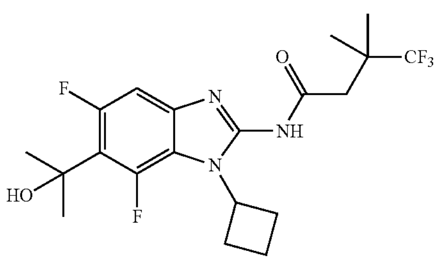 [SMILES: CC(C)(O)c1c(F)cc2nc(NC(=O)CC(C)(C)C(F)(F)F)n(C3CCC3)c2c1F] | N-(1-cyclobutyl-5,7-difluoro-6-(2-hydroxypropan-2-yl)-1H-benzo[d]imidazol-2-yl)-4,4,4-trifluoro-3,3-dimethylbutanamide | 433.4 |
| 471 | 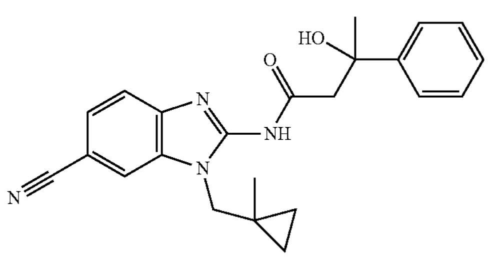 [SMILES: CC1(Cn2c(NC(=O)CC(C)(O)c3ccccc3)nc3ccc(C#N)cc32)CC1] | N-(6-cyano-1-((1-methylcyclopropyl)methyl)-1H-benzo[d]imidazol-2-yl)-3-hydroxy-3-phenylbutanamide, stereoisomer 1 | 388.5 |

TABLE 1-continued

List of Examples with Molecular Weight Data

| Example | Structure | Name | Molecular Weight |
|---|---|---|---|
| 472 | 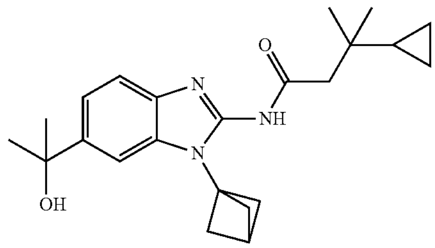 [SMILES: CC(C)(O)c1ccc2nc(NC(=O)CC(C)(C)C3CC3)n(C34CC(C3)C4)c2c1] | N-(1-(bicyclo[1.1.1]pentan-1-yl)-6-(2-hydroxypropan-2-yl)-1H-benzo[d]imidazol-2-yl)-3-cyclopropyl-3-methylbutanamide | 381.5 |
| 473 | 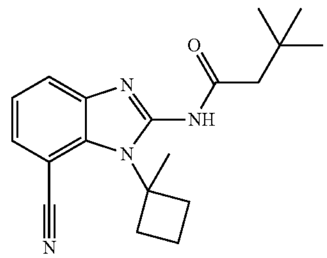 [SMILES: CC(C)(C)CC(=O)Nc1nc2cccc(C#N)c2n1C1(C)CCC1] | N-(7-cyano-1-(1-methylcyclobutyl)-1H-benzo[d]imidazol-2-yl)-3,3-dimethylbutanamide | 324.4 |
| 474 | 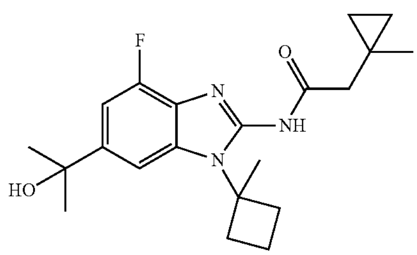 [SMILES: CC1(CC(=O)Nc2nc3c(F)cc(C(C)(C)O)cc3n2C2(C)CCC2)CC1] | N-(4-fluoro-6-(2-hydroxypropan-2-yl)-1-(1-methylcyclobutyl)-1H-benzo[d]imidazol-2-yl)-2-(1-methylcyclopropyl)acetamide | 373.5 |
| 475 | 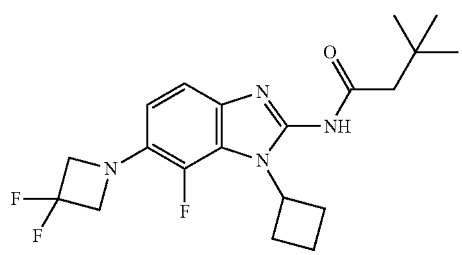 [SMILES: CC(C)(C)CC(=O)Nc1nc2ccc(N3CC(F)(F)C3)c(F)c2n1C1CCC1] | N-(1-cyclobutyl-6-(3,3-difluoroazetidin-1-yl)-7-fluoro-1H-benzo[d]imidazol-2-yl)-3,3-dimethylbutanamide | 394.4 |
| 476 | 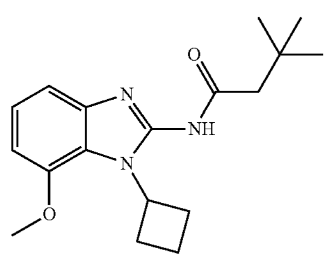 [SMILES: COc1cccc2nc(NC(=O)CC(C)(C)C)n(C3CCC3)c12] | N-(1-cyclobutyl-7-methoxy-1H-benzo[d]imidazol-2-yl)-3,3-dimethylbutanamide | 315.4 |
| 477 | 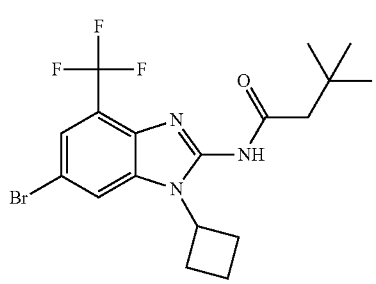 [SMILES: CC(C)(C)CC(=O)Nc1nc2c(C(F)(F)F)cc(Br)cc2n1C1CCC1] | N-(6-bromo-1-cyclobutyl-4-(trifluoromethyl)-1H-benzo[d]imidazol-2-yl)-3,3-dimethylbutanamide | 432.3 |

TABLE 1-continued

List of Examples with Molecular Weight Data

| Example | Structure | Name | Molecular Weight |
|---|---|---|---|
| 478 | 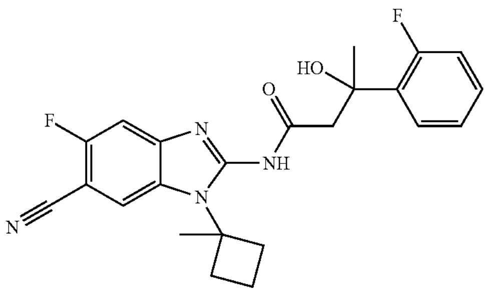 [SMILES: CC(O)(CC(=O)Nc1nc2cc(F)c(C#N)cc2n1C1(C)CCC1)c1ccccc1F] | N-(6-cyano-5-fluoro-1-(1-methylcyclobutyl)-1H-benzo[d]imidazol-2-yl)-3-(2-fluorophenyl)-3-hydroxybutanamide, stereoisomer 1 | 424.5 |
| 479 | 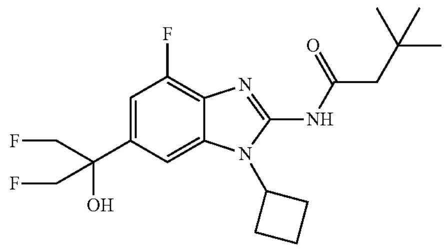 [SMILES: CC(C)(C)CC(=O)Nc1nc2c(F)cc(C(O)(CF)CF)cc2n1C1CCC1] | N-(1-cyclobutyl-6-(1,3-difluoro-2-hydroxypropan-2-yl)-4-fluoro-1H-benzo[d]imidazol-2-yl)-3,3-dimethylbutanamide | 397.4 |
| 480 | 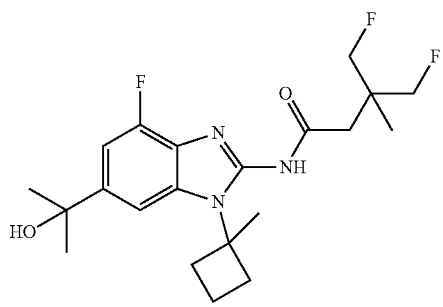 [SMILES: CC(CF)(CF)CC(=O)Nc1nc2c(F)cc(C(C)(C)O)cc2n1C1(C)CCC1] | 4-fluoro-N-(4-fluoro-6-(2-hydroxypropan-2-yl)-1-(1-methylcyclobutyl)-1H-benzo[d]imidazol-2-yl)-3-(fluoromethyl)-3-methylbutanamide | 411.5 |
| 481 | 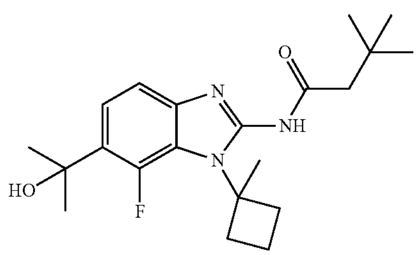 [SMILES: CC(C)(C)CC(=O)Nc1nc2ccc(C(C)(C)O)c(F)c2n1C1(C)CCC1] | N-(7-fluoro-6-(2-hydroxypropan-2-yl)-1-(1-methylcyclobutyl)-1H-benzo[d]imidazol-2-yl)-3,3-dimethylbutanamide | 375.5 |
| 482 | 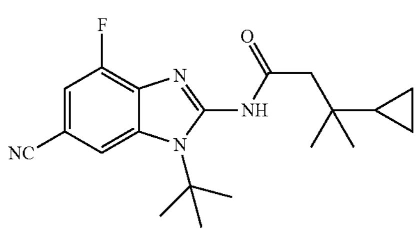 [SMILES: CC(C)(CC(=O)Nc1nc2c(F)cc(C#N)cc2n1C(C)(C)C)C1CC1] | N-(1-(tert-butyl)-6-cyano-4-fluoro-1H-benzo[d]imidazol-2-yl)-3-cyclopropyl-3-methylbutanamide | 356.4 |
| 483 | 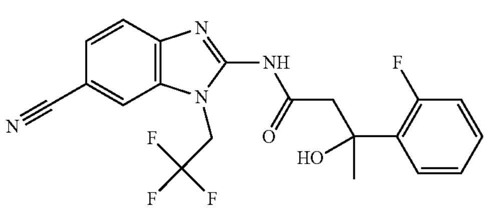 [SMILES: CC(O)(CC(=O)Nc1nc2ccc(C#N)cc2n1CC(F)(F)F)c1ccccc1F] | N-(6-cyano-1-(2,2,2-trifluoroethyl)-1H-benzo[d]imidazol-2-yl)-3-(2-fluorophenyl)-3-hydroxybutanamide, stereoisomer 1 | 420.4 |

TABLE 1-continued

List of Examples with Molecular Weight Data

| Example | Structure | Name | Molecular Weight |
|---|---|---|---|
| 484 | 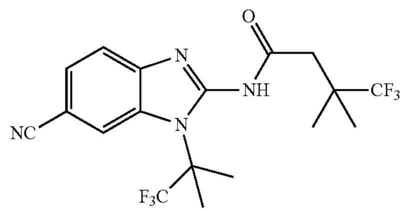 [SMILES: CC(C)(CC(=O)Nc1nc2ccc(C#N)cc2n1C(C)(C)C(F)(F)F)C(F)(F)F] | N-(6-cyano-1-(1,1,1-trifluoro-2-methylpropan-2-yl)-1H-benzo[d]imidazol-2-yl)-4,4,4-trifluoro-3,3-dimethylbutanamide | 420.4 |
| 485 | 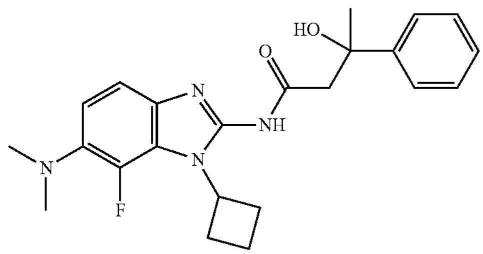 [SMILES: CN(C)c1ccc2nc(NC(=O)CC(C)(O)c3ccccc3)n(C3CCC3)c2c1F] | N-(1-cyclobutyl-6-(dimethylamino)-7-fluoro-1H-benzo[d]imidazol-2-yl)-3-hydroxy-3-phenylbutanamide, stereoisomer 1 | 410.5 |
| 486 | 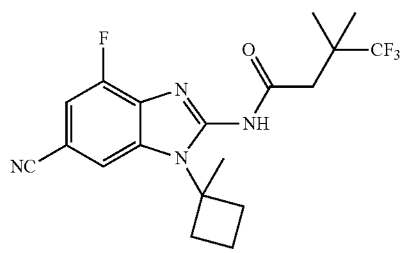 [SMILES: CC1(n2c(NC(=O)CC(C)(C)C(F)(F)F)nc3c(F)cc(C#N)cc32)CCC1] | N-(6-cyano-4-fluoro-1-(1-methylcyclobutyl)-1H-benzo[d]imidazol-2-yl)-4,4,4-trifluoro-3,3-dimethylbutanamide | 396.4 |
| 487 | 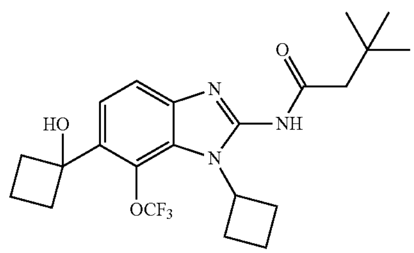 [SMILES: CC(C)(C)CC(=O)Nc1nc2ccc(C3(O)CCC3)c(OC(F)(F)F)c2n1C1CCC1] | N-(1-cyclobutyl-6-(1-hydroxycyclobutyl)-7-(trifluoromethoxy)-1H-benzo[d]imidazol-2-yl)-3,3-dimethylbutanamide | 439.5 |
| 488 | 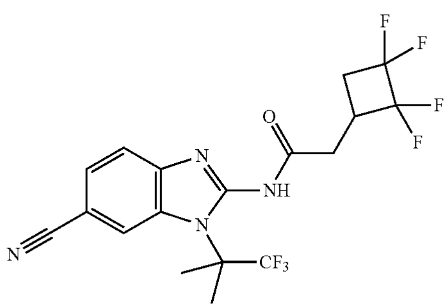 [SMILES: CC(C)(n1c(NC(=O)CC2CC(F)(F)C2(F)F)nc2ccc(C#N)cc21)C(F)(F)F] | N-(6-cyano-1-(1,1,1-trifluoro-2-methylpropan-2-yl)-1H-benzo[d]imidazol-2-yl)-2-(2,2,3,3-tetrafluorocyclobutyl)acetamide, stereoisomer 2 | 436.3 |
| 489 | 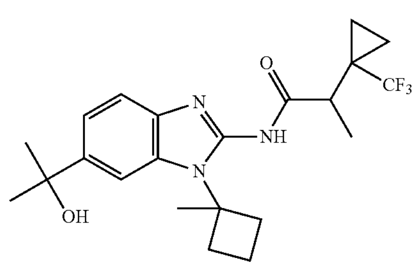 [SMILES: CC(C(=O)Nc1nc2ccc(C(C)(C)O)cc2n1C1(C)CCC1)C1(C(F)(F)F)CC1] | N-(6-(2-hydroxypropan-2-yl)-1-(1-methylcyclobutyl)-1H-benzo[d]imidazol-2-yl)-2-(1-(trifluoromethyl)cyclopropyl)propanamide, stereoisomer 1 | 423.5 |

TABLE 1-continued

List of Examples with Molecular Weight Data

| Example | Structure | Name | Molecular Weight |
|---|---|---|---|
| 490 | 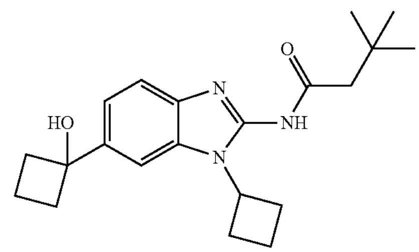 [SMILES: CC(C)(C)CC(=O)Nc1nc2ccc(C3(O)CCC3)cc2n1C1CCC1] | N-(1-cyclobutyl-6-(1-hyd roxycyclobutyl)-7-(trifluoromethyl)-1H-benzo[d]imidazol-2-yl)-3,3-dimethylbutanamide | 423.5 |
| 491 | 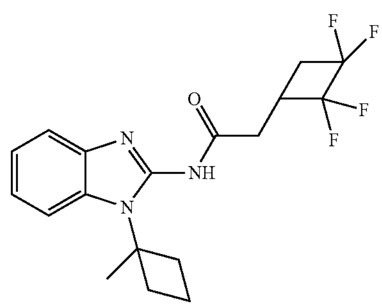 [SMILES: CC1(n2c(NC(=O)CC3CC(F)(F)C3(F)F)nc3ccccc32)CCC1] | N-(6-(2-hydroxypropan-2-yl)-1-(1-methylcyclobutyl)-1H-benzo[d]imidazol-2-yl)-2-(2,2,3,3-tetrafluorocyclobutyl)acetamide | 427.4 |
| 492 | 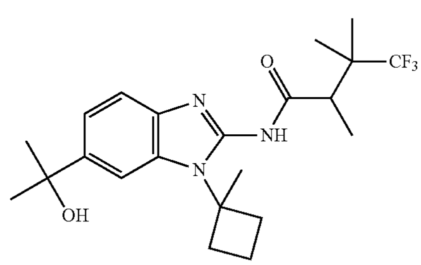 [SMILES: CC(C(=O)Nc1nc2ccc(C(C)(C)O)cc2n1C1(C)CCC1)C(C)(C)C(F)(F)F] | 4,4,4-trifluoro-N-(6-(2-hydroxypropan-2-yl)-1-(1-methylcyclobutyl)-1H-benzo[d]imidazol-2-yl)-2,3,3-trimethylbutanamide, stereoisomer 1 | 425.5 |
| 493 | 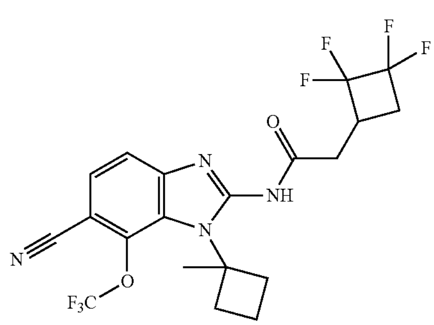 [SMILES: CC1(n2c(NC(=O)CC3CC(F)(F)C3(F)F)nc3ccc(C#N)c(OC(F)(F)F)c32)CCC1] | N-(6-cyano-1-(1-methylcyclobutyl)-7-(trifluoromethoxy)-1H-benzo[d]imidazol-2-yl)-2-(2,2,3,3-tetrafluorocyclobutyl)acetamide, stereoisomer 1 | 478.4 |
| 494 | 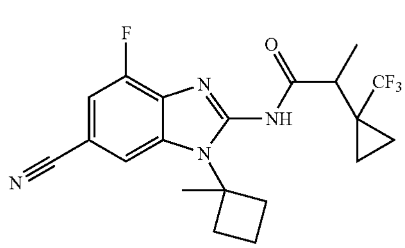 [SMILES: CC(C(=O)Nc1nc2c(F)cc(C#N)cc2n1C1(C)CCC1)C1(C(F)(F)F)CC1] | N-(6-cyano-4-fluoro-1-(1-methylcyclobutyl)-1H-benzo[d]imidazol-2-yl)-2-(1-(trifluoromethyl)cyclopropyl)propanamide, stereoisomer 1 | 408.4 |

TABLE 1-continued

List of Examples with Molecular Weight Data

| Example | Structure | Name | Molecular Weight |
|---|---|---|---|
| 495 | 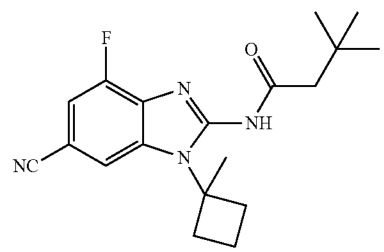 [SMILES: CC(C)(C)CC(=O)Nc1nc2c(F)cc(C#N)cc2n1C1(C)CCC1] | N-(6-cyano-4-fluoro-1-(1-methylcyclobutyl)-1H-benzo[d]imidazol-2-yl)-3,3-dimethylbutanamide | 342.4 |
| 496 | 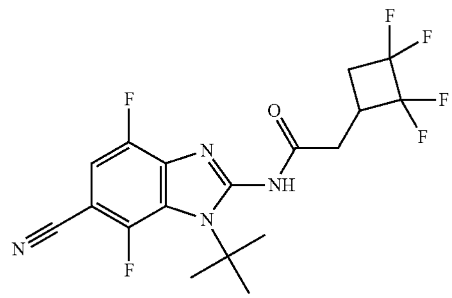 [SMILES: CC(C)(C)n1c(NC(=O)CC2CC(F)(F)C2(F)F)nc2c(F)cc(C#N)c(F)c21] | N-(1-(tert-butyl)-6-cyano-4,7-difluoro-1H-benzo[d]imidazol-2-yl)-2-(2,2,3,3-tetrafluorocyclobutyl)acetamide, stereoisomer 1 | 418.3 |
| 497 | 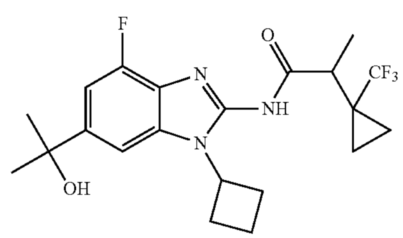 [SMILES: CC(C(=O)Nc1nc2c(F)cc(C(C)(C)O)cc2n1C1CCC1)C1(C(F)(F)F)CC1] | N-(1-cyclobutyl-4-fluoro-6-(2-hydroxypropan-2-yl)-1H-benzo[d]imidazol-2-yl)-2-(1-(trifluoromethyl)cyclopropyl)propanamide, stereoisomer 1 | 427.4 |
| 498 | 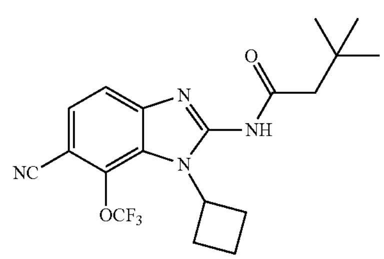 [SMILES: CC(C)(C)CC(=O)Nc1nc2ccc(C#N)c(OC(F)(F)F)c2n1C1CCC1] | N-(6-cyano-1-cyclobutyl-7-(trifluoromethoxy)-1H-benzo[d]imidazol-2-yl)-3,3-dimethylbutanamide | 394.4 |
| 499 | 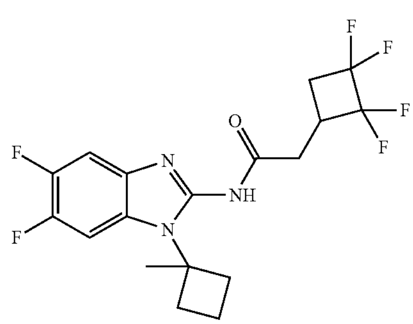 [SMILES: CC1(n2c(NC(=O)CC3CC(F)(F)C3(F)F)nc3cc(F)c(F)cc32)CCC1] | N-(5,6-difluoro-1-(1-methylcyclobutyl)-1H-benzo[d]imidazol-2-yl)-2-(2,2,3,3-tetrafluorocyclobutyl)acetamide, stereoisomer 2 | 405.3 |

TABLE 1-continued

List of Examples with Molecular Weight Data

| Example | Structure | Name | Molecular Weight |
|---|---|---|---|
| 500 | 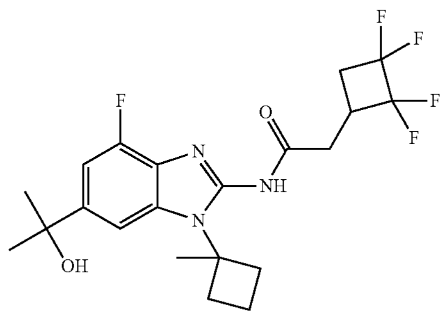 [SMILES: CC(C)(O)c1cc(F)c2nc(NC(=O)CC3CC(F)(F)C3(F)F)n(C3(C)CCC3)c2c1] | N-(4-fluoro-6-(2-hydroxypropan-2-yl)-1-(1-methylcyclobutyl)-1H-benzo[d]imidazol-2-yl)-2-(2,2,3,3-tetrafluorocyclobutyl)acetamide, stereoisomer 2 | 445.4 |
| 501 | 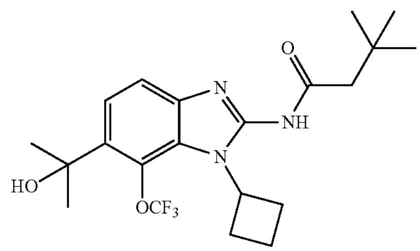 [SMILES: CC(C)(C)CC(=O)Nc1nc2ccc(C(C)(C)O)c(OC(F)(F)F)c2n1C1CCC1] | N-(1-cyclobutyl-6-(2-hydroxypropan-2-yl)-7-(trifluoromethoxy)-1H-benzo[d]imidazol-2-yl)-3,3-dimethylbutanamide | 427.5 |
| 502 | 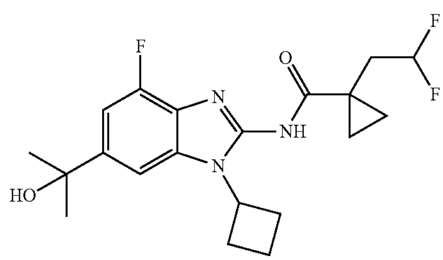 [SMILES: CC(C)(O)c1cc(F)c2nc(NC(=O)C3(CC(F)F)CC3)n(C3CCC3)c2c1] | N-(1-cyclobutyl-4-fluoro-6-(2-hydroxypropan-2-yl)-1H-benzo[d]imidazol-2-yl)-1-(2,2-difluoroethyl)cyclopropane-1-carboxamide | 395.4 |
| 503 | 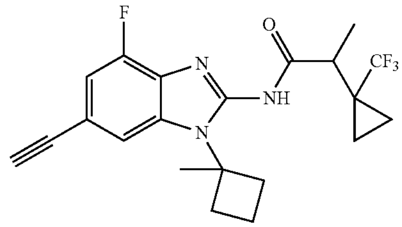 [SMILES: C#Cc1cc(F)c2nc(NC(=O)C(C)C3(C(F)(F)F)CC3)n(C3(C)CCC3)c2c1] | N-(6-cyano-4-fluoro-1-(1-methylcyclobutyl)-1H-benzo[d]imidazol-2-yl)-2-(1-(trifluoromethyl)cyclopropyl)propanamide, stereoisomer 2 | 408.4 |
| 504 | 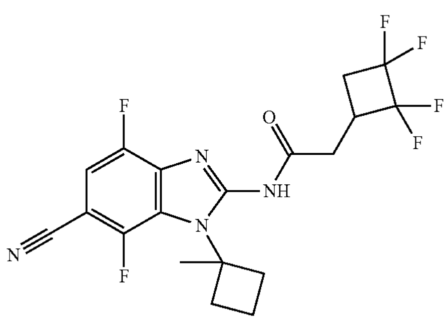 [SMILES: CC1(n2c(NC(=O)CC3CC(F)(F)C3(F)F)nc3c(F)cc(C#N)c(F)c32)CCC1] | N-(6-cyano-4,7-difluoro-1-(1-methylcyclobutyl)-1H-benzo[d]imidazol-2-yl)-2-(2,2,3,3-tetrafluorocyclobutyl)acetamide, stereoisomer 1 | 430.4 |

TABLE 1-continued

List of Examples with Molecular Weight Data

| Example | Structure | Name | Molecular Weight |
|---|---|---|---|
| 505 | 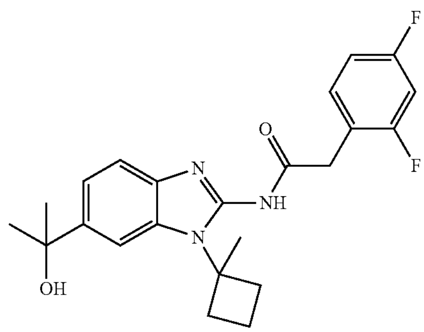 [SMILES: CC(C)(O)c1ccc2nc(NC(=O)Cc3ccc(F)cc3F)n(C3(C)CCC3)c2c1] | 2-(2,4-difluorophenyl)-N-(6-(2-hydroxypropan-2-yl)-1-(1-methylcyclobutyl)-1H-benzo[d]imidazol-2-yl)acetamide | 413.5 |
| 506 | 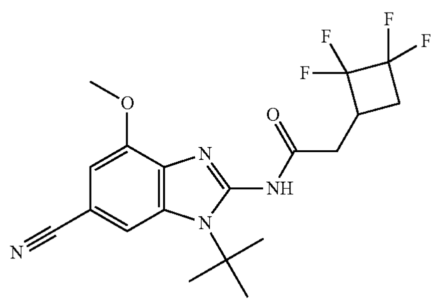 [SMILES: COc1cc(C#N)cc2c1nc(NC(=O)CC1CC(F)(F)C1(F)F)n2C(C)(C)C] | N-(1-(tert-butyl)-6-cyano-4-methoxy-1H-benzo[d]imidazol-2-yl)-2-(2,2,3,3-tetrafluorocyclobutyl)acetamide, stereoisomer 2 | 412.4 |
| 507 | 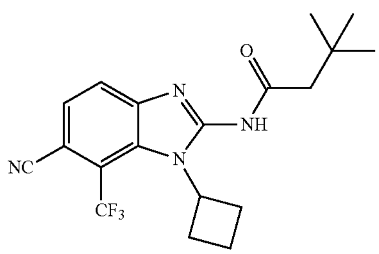 [SMILES: CC(C)(C)CC(=O)Nc1nc2ccc(C#N)c(C(F)(F)F)c2n1C1CCC1] | N-(6-cyano-1-cyclobutyl-7-(trifluoromethyl)-1H-benzo[d]imidazol-2-yl)-3,3-dimethylbutanamide | 378.4 |
| 508 | 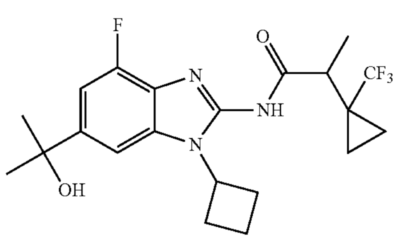 [SMILES: CC(C(=O)Nc1nc2c(F)cc(C(C)(C)O)cc2n1C1CCC1)C1(C(F)(F)F)CC1] | N-(1-cyclobutyl-4-fluoro-6-(2-hydroxypropan-2-yl)-1H-benzo[d]imidazol-2-yl)-2-(1-(trifluoromethyl)cyclopropyl)propanamide, stereoisomer 2 | 427.4 |
| 509 | 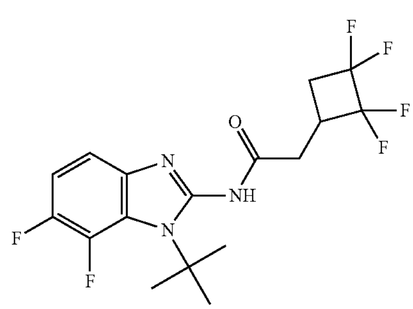 [SMILES: CC(C)(C)n1c(NC(=O)CC2CC(F)(F)C2(F)F)nc2ccc(F)c(F)c21] | N-(1-(tert-butyl)-6,7-difluoro-1H-benzo[d]imidazol-2-yl)-2-(2,2,3,3-tetrafluorocyclobutyl)acetamide, stereoisomer 2 | 393.3 |

TABLE 1-continued

List of Examples with Molecular Weight Data

| Example | Structure | Name | Molecular Weight |
|---|---|---|---|
| 510 | 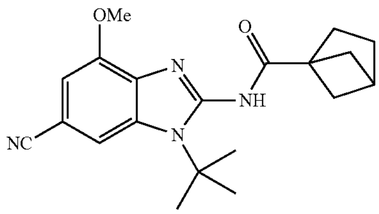 [SMILES: COc1cc(C#N)cc2c1nc(NC(=O)C13CCC(C1)C3)n2C(C)(C)C] | N-(1-(tert-butyl)-6-cyano-4-methoxy-1H-benzo[d]imidazol-2-yl)bicyclo[2.1.1]hexane-1-carboxamide | 352.4 |
| 511 | 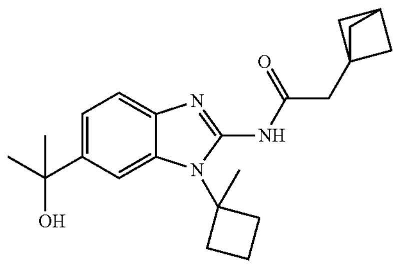 [SMILES: CC(C)(O)c1ccc2nc(NC(=O)CC34CC(C3)C4)n(C3(C)CCC3)c2c1] | 2-(bicyclo[1.1.1]pentan-1-yl)-N-(6-(2-hydroxypropan-2-yl)-1-(1-methylcyclobutyl)-1H-benzo[d]imidazol-2-yl)acetamide | 367.5 |
| 512 | 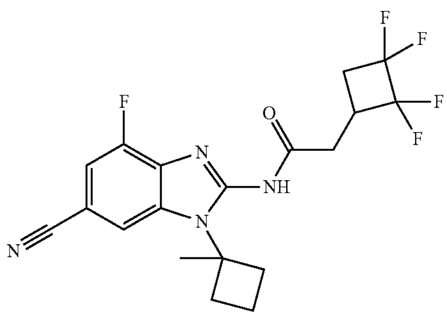 [SMILES: CC1(n2c(NC(=O)CC3CC(F)(F)C3(F)F)nc3c(F)cc(C#N)cc32)CCC1] | N-(6-cyano-4-fluoro-1-(1-methylcyclobutyl)-1H-benzo[d]imidazol-2-yl)-2-(2,2,3,3-tetrafluorocyclobutyl)acetamide, stereoisomer 2 | 412.4 |
| 513 | 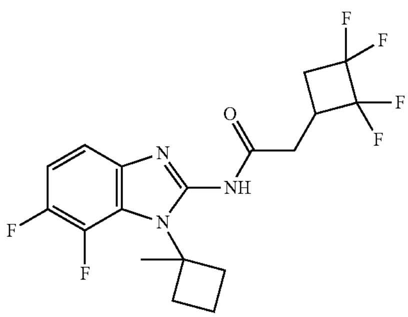 [SMILES: CC1(n2c(NC(=O)CC3CC(F)(F)C3(F)F)nc3ccc(F)c(F)c32)CCC1] | N-(6,7-difluoro-1-(1-methylcyclobutyl)-1H-benzo[d]imidazol-2-yl)-2-(2,2,3,3-tetrafluorocyclobutyl)acetamide, stereoisomer 2 | 405.3 |
| 514 | 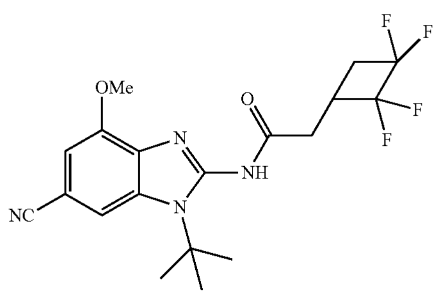 [SMILES: COc1cc(C#N)cc2c1nc(NC(=O)CC1CC(F)(F)C1(F)F)n2C(C)(C)C] | N-(1-(tert-butyl)-6-cyano-4-methoxy-1H-benzo[d]imidazol-2-yl)-2-(2,2,3,3-tetrafluorocyclobutyl)acetamide | 412.4 |

TABLE 1-continued

List of Examples with Molecular Weight Data

| Example | Structure | Name | Molecular Weight |
|---|---|---|---|
| 515 | 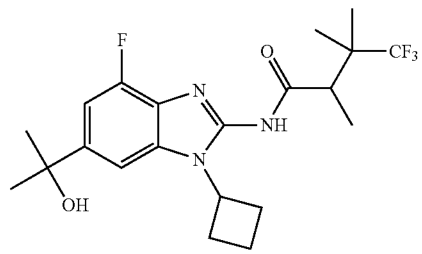 [SMILES: CC(C(=O)Nc1nc2c(F)cc(C(C)(C)O)cc2n1C1CCC1)C(C)(C)C(F)(F)F] | N-(1-cyclobutyl-4-fluoro-6-(2-hydroxypropan-2-yl)-1H-benzo[d]imidazol-2-yl)-4,4,4-trifluoro-2,3,3-trimethylbutanamide, stereoisomer 1 | 429.5 |
| 516 | 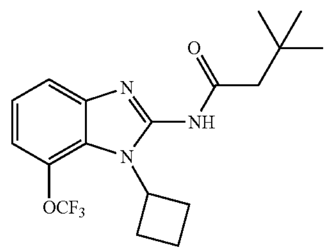 [SMILES: CC(C)(C)CC(=O)Nc1nc2cccc(OC(F)(F)F)c2n1C1CCC1] | N-(1-cyclobutyl-7-(trifluoromethoxy)-1H-benzo[d]imidazol-2-yl)-3,3-dimethylbutanamide | 369.4 |
| 517 | 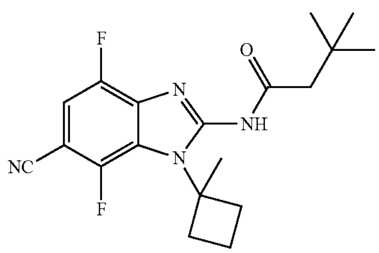 [SMILES: CC(C)(C)CC(=O)Nc1nc2c(F)cc(C#N)c(F)c2n1C1(C)CCC1] | N-(6-cyano-4,7-difluoro-1-(1-methylcyclobutyl)-1H-benzo[d]imidazol-2-yl)-3,3-dimethylbutanamide | 360.4 |
| 518 | 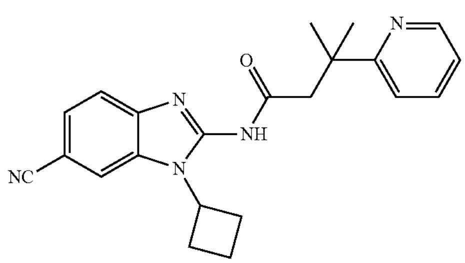 [SMILES: CC(C)(CC(=O)Nc1nc2ccc(C#N)cc2n1C1CCC1)c1ccccn1] | N-(6-cyano-1-cyclobutyl-1H-benzo[d]imidazol-2-yl)-3-methyl-3-(pyridin-2-yl)butanamide | 373.5 |
| 519 | 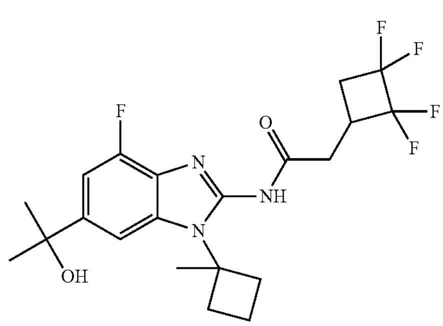 [SMILES: CC(C)(O)c1cc(F)c2nc(NC(=O)CC3CC(F)(F)C3(F)F)n(C3(C)CCC3)c2c1] | N-(4-fluoro-6-(2-hydroxypropan-2-yl)-1-(1-methylcyclobutyl)-1H-benzo[d]imidazol-2-yl)-2-(2,2,3,3-tetrafluorocyclobutyl)acetamide, stereoisomer 1 | 445.4 |

TABLE 1-continued

List of Examples with Molecular Weight Data

| Example | Structure | Name | Molecular Weight |
|---|---|---|---|
| 520 | 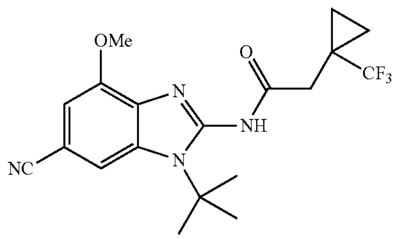 [SMILES: COc1cc(C#N)cc2c1nc(NC(=O)CC1(C(F)(F)F)CC1)n2C(C)(C)C] | N-(1-(tert-butyl)-6-cyano-4-methoxy-1H-benzo[d]imidazol-2-yl)-2-(1-(trifluoromethyl)cyclopropyl)acetamide | 394.4 |
| 521 | 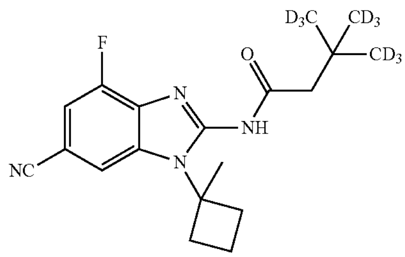 [SMILES: [2H]C([2H])([2H])C(CC(=O)Nc1nc2c(F)cc(C#N)cc2n1C1(C)CCC1)(C([2H])([2H])[2H])C([2H])([2H])[2H]] | N-(6-cyano-4-fluoro-1-(1-methylcyclobutyl)-1H-benzo[d]imidazol-2-yl)-3,3-bis(methyl-d3)butanamide | 351.5 |
| 522 | 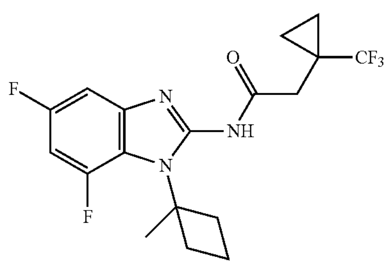 [SMILES: CC1(n2c(NC(=O)CC3(C(F)(F)F)CC3)nc3cc(F)cc(F)c32)CCC1] | N-(5,7-difluoro-1-(1-methylcyclobutyl)-1H-benzo[d]imidazol-2-yl)-2-(1-(trifluoromethyl)cyclopropyl)acetamide | 387.4 |
| 523 | 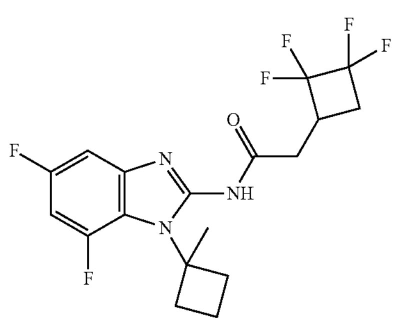 | N-(5,7-difluoro-1-(1-methylcyclobutyl)-1H-benzo[d]imidazol-2-yl)-2-(2,2,3,3-tetrafluorocyclobutyl)acetamide, stereoisomer 1 | 405.3 |
| 524 | 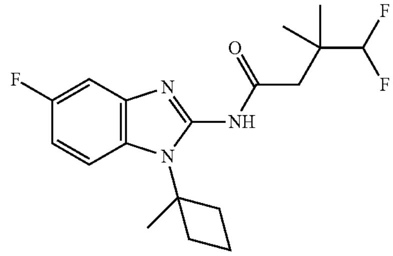 [SMILES: CC(C)(CC(=O)Nc1nc2cc(F)ccc2n1C1(C)CCC1)C(F)F] | 4,4-difluoro-N-(5-fluoro-1-(1-methylcyclobutyl)-1H-benzo[d]imidazol-2-yl)-3,3-dimethylbutanamide | 353.4 |

TABLE 1-continued

List of Examples with Molecular Weight Data

| Example | Structure | Name | Molecular Weight |
|---|---|---|---|
| 525 | 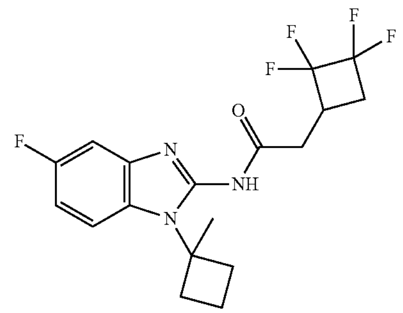 [SMILES: CC1(n2c(NC(=O)CC3CC(F)(F)C3(F)F)nc3cc(F)ccc32)CCC1] | N-(5-fluoro-1-(1-methylcyclobutyl)-1H-benzo[d]imidazol-2-yl)-2-(2,2,3,3-tetrafluorocyclobutyl)acetamide, stereoisomer 1 | 387.4 |
| 526 | 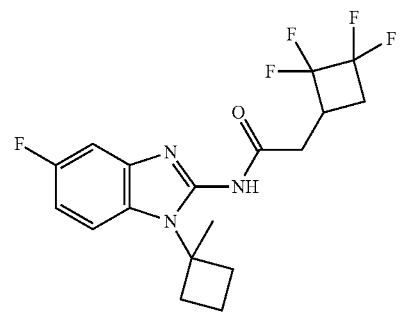 [SMILES: CC1(n2c(NC(=O)CC3CC(F)(F)C3(F)F)nc3cc(F)ccc32)CCC1] | N-(5-fluoro-1-(1-methylcyclobutyl)-1H-benzo[d]imidazol-2-yl)-2-(2,2,3,3-tetrafluorocyclobutyl)acetamide, stereoisomer 2 | 387.4 |
| 527 | 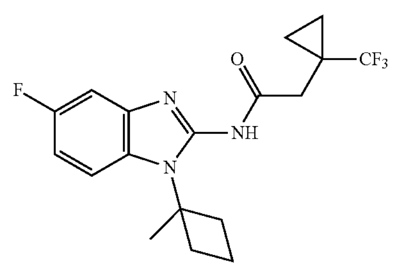 [SMILES: CC1(n2c(NC(=O)CC3(C(F)(F)F)CC3)nc3cc(F)ccc32)CCC1] | N-(5-fluoro-1-(1-methylcyclobutyl)-1H-benzo[d]imidazol-2-yl)-2-(1-(trifluoromethyl)cyclopropyl)acetamide | 369.4 |
| 528 | 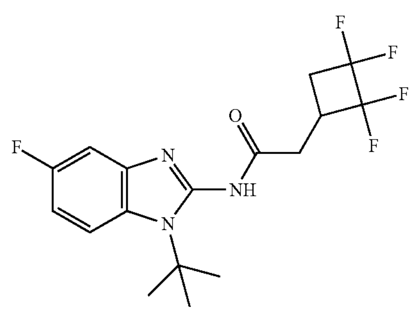 [SMILES: CC(C)(C)n1c(NC(=O)CC2CC(F)(F)C2(F)F)nc2cc(F)ccc21] | N-(1-(tert-butyl)-5-fluoro-1H-benzo[d]imidazol-2-yl)-2-(2,2,3,3-tetrafluorocyclobutyl)acetamide, stereoisomer 1 | 375.3 |
| 529 | 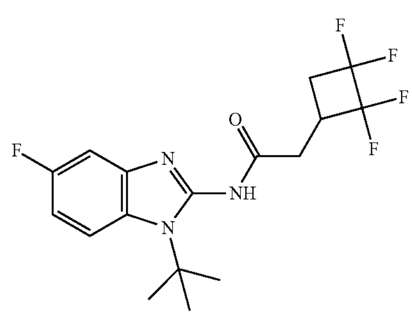 [SMILES: CC(C)(C)n1c(NC(=O)CC2CC(F)(F)C2(F)F)nc2cc(F)ccc21] | N-(1-(tert-butyl)-5-fluoro-1H-benzo[d]imidazol-2-yl)-2-(2,2,3,3-tetrafluorocyclobutyl)acetamide, stereoisomer 2 | 375.3 |

TABLE 1-continued

List of Examples with Molecular Weight Data

| Example | Structure | Name | Molecular Weight |
|---|---|---|---|
| 530 | 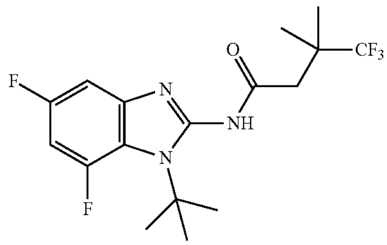 [SMILES: CC(C)(C)n1c(NC(=O)CC(C)(C)C(F)(F)F)nc2cc(F)cc(F)c21] | N-(1-(tert-butyl)-5,7-difluoro-1H-benzo[d]imidazol-2-yl)-4,4,4-trifluoro-3,3-dimethylbutanamide | 377.4 |
| 531 | 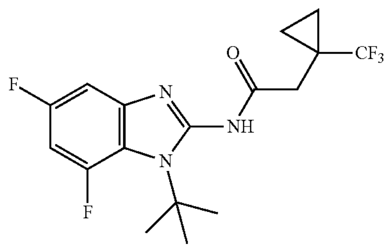 [SMILES: CC(C)(C)n1c(NC(=O)CC2(C(F)(F)F)CC2)nc2cc(F)cc(F)c21] | N-(1-(tert-butyl)-5,7-difluoro-1H-benzo[d]imidazol-2-yl)-2-(1-(trifluoromethyl)cyclopropyl)acetamide | 375.3 |
| 532 | 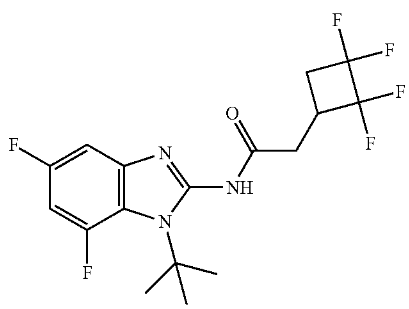 [SMILES: CC(C)(C)n1c(NC(=O)CC2CC(F)(F)C2(F)F)nc2cc(F)cc(F)c21] | N-(1-(tert-butyl)-5,7-difluoro-1H-benzo[d]imidazol-2-yl)-2-(2,2,3,3-tetrafluorocyclobutyl)acetamide, stereoisomer 2 | 393.3 |
| 533 | 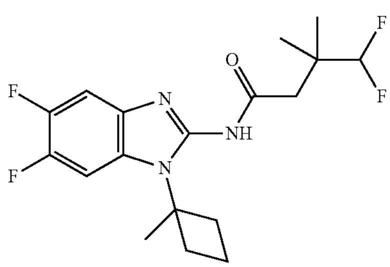 [SMILES: CC(C)(CC(=O)Nc1nc2cc(F)c(F)cc2n1C1(C)CCC1)C(F)F] | N-(5,6-difluoro-1-(1-methylcyclobutyl)-1H-benzo[d]imidazol-2-yl)-4,4-difluoro-3,3-dimethylbutanamide | 371.4 |
| 534 | 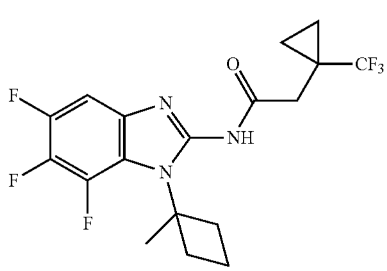 [SMILES: CC1(n2c(NC(=O)CC3(C(F)(F)F)CC3)nc3cc(F)c(F)c(F)c32)CCC1] | N-(5,6,7-trifluoro-1-(1-methylcyclobutyl)-1H-benzo[d]imidazol-2-yl)-2-(1-(trifluoromethyl)cyclopropyl)acetamide | 405.3 |

TABLE 1-continued

List of Examples with Molecular Weight Data

| Example | Structure | Name | Molecular Weight |
|---|---|---|---|
| 535 | 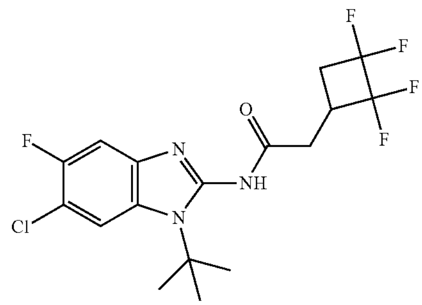 [SMILES: CC(C)(C)n1c(NC(=O)CC2CC(F)(F)C2(F)F)nc2cc(F)c(Cl)cc21] | N-(1-(tert-butyl)-6-chloro-5-fluoro-1H-benzo[d]imidazol-2-yl)-2-(2,2,3,3-tetrafluorocyclobutyl)acetamide, stereoisomer 2 | 409.8 |
| 536 | 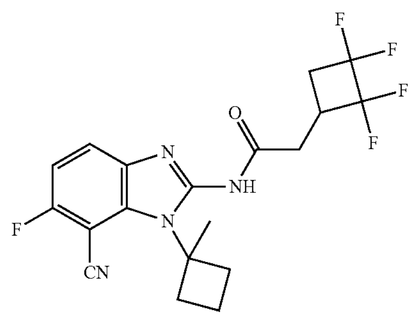 [SMILES: CC1(n2c(NC(=O)CC3CC(F)(F)C3(F)F)nc3ccc(F)c(C#N)c32)CCC1] | N-(7-cyano-6-fluoro-1-(1-methylcyclobutyl)-1H-benzo[d]imidazol-2-yl)-2-(2,2,3,3-tetrafluorocyclobutyl)acetamide, stereoisomer 1 | 412.4 |
| 537 | 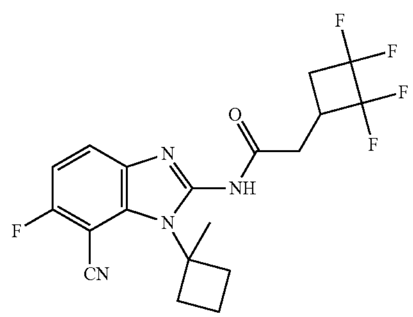 [SMILES: CC1(n2c(NC(=O)CC3CC(F)(F)C3(F)F)nc3ccc(F)c(C#N)c32)CCC1] | N-(7-cyano-6-fluoro-1-(1-methylcyclobutyl)-1H-benzo[d]imidazol-2-yl)-2-(2,2,3,3-tetrafluorocyclobutyl)acetamide, stereoisomer 2 | 412.4 |
| 538 | 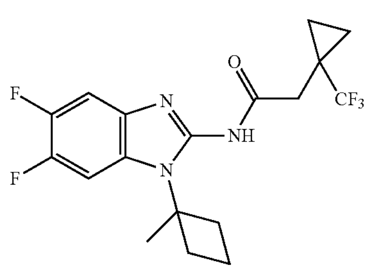 [SMILES: CC1(n2c(NC(=O)CC3(C(F)(F)F)CC3)nc3cc(F)c(F)cc32)CCC1] | N-(5,6-difluoro-1-(1-methylcyclobutyl)-1H-benzo[d]imidazol-2-yl)-2-(1-(trifluoromethyl)cyclopropyl)acetamide | 387.4 |
| 539 | 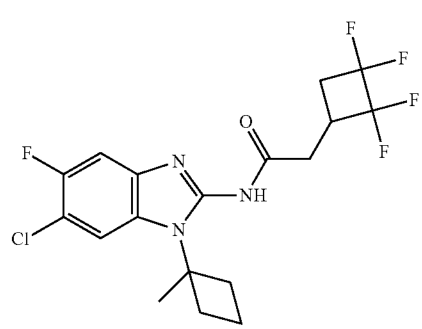 [SMILES: CC1(n2c(NC(=O)CC3CC(F)(F)C3(F)F)nc3cc(F)c(Cl)cc32)CCC1] | N-(6-chloro-5-fluoro-1-(1-methylcyclobutyl)-1H-benzo[d]imidazol-2-yl)-2-(2,2,3,3-tetrafluorocyclobutyl)acetamide, stereoisomer 2 | 421.8 |

TABLE 1-continued

List of Examples with Molecular Weight Data

| Example | Structure | Name | Molecular Weight |
|---|---|---|---|
| 540 | 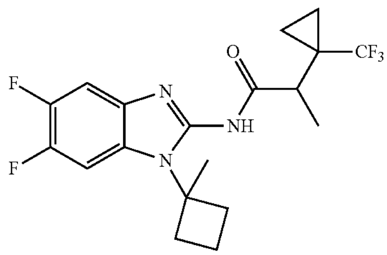 [SMILES: CC(C(=O)Nc1nc2cc(F)c(F)cc2n1C1(C)CCC1)C1(C(F)(F)F)CC1] | N-(5,6-difluoro-1-(1-methylcyclobutyl)-1H-benzo[d]imidazol-2-yl)-2-(1-(trifluoromethyl)cyclopropyl)propanamide, stereoisomer 1 | 401.4 |
| 541 | 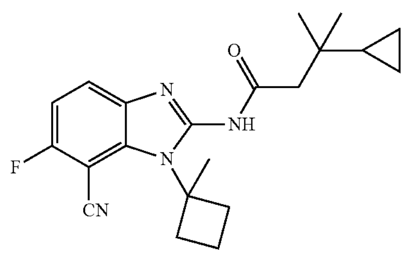 [SMILES: CC(C)(CC(=O)Nc1nc2ccc(F)c(C#N)c2n1C1(C)CCC1)C1CC1] | N-(7-cyano-6-fluoro-1-(1-methylcyclobutyl)-1H-benzo[d]imidazol-2-yl)-3-cyclopropyl-3-methylbutanamide | 368.5 |
| 542 | 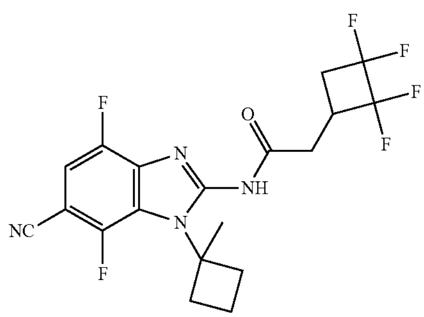 [SMILES: CC1(n2c(NC(=O)CC3CC(F)(F)C3(F)F)nc3c(F)cc(C#N)c(F)c32)CCC1] | N-(6-cyano-4,7-difluoro-1-(1-methylcyclobutyl)-1H-benzo[d]imidazol-2-yl)-2-(2,2,3,3-tetrafluorocyclobutyl)acetamide, stereoisomer 2 | 430.4 |
| 543 | 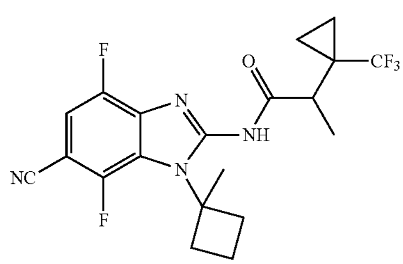 [SMILES: CC(C(=O)Nc1nc2c(F)cc(C#N)c(F)c2n1C1(C)CCC1)C1(C(F)(F)F)CC1] | N-(6-cyano-4,7-difluoro-1-(1-methylcyclobutyl)-1H-benzo[d]imidazol-2-yl)-2-(1-(trifluoromethyl)cyclopropyl)propanamide, stereoisomer 2 | 426.4 |
| 544 | 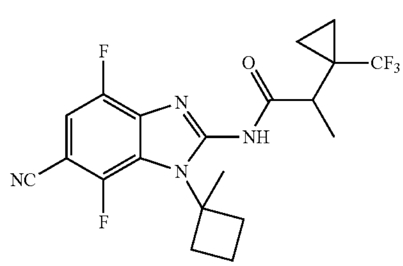 [SMILES: CC(C(=O)Nc1nc2c(F)cc(C#N)c(F)c2n1C1(C)CCC1)C1(C(F)(F)F)CC1] | N-(6-cyano-4,7-difluoro-1-(1-methylcyclobutyl)-1H-benzo[d]imidazol-2-yl)-2-(1-(trifluoromethyl)cyclopropyl)propanamide, stereoisomer 1 | 426.4 |

TABLE 1-continued

List of Examples with Molecular Weight Data

| Example | Structure | Name | Molecular Weight |
|---|---|---|---|
| 545 | 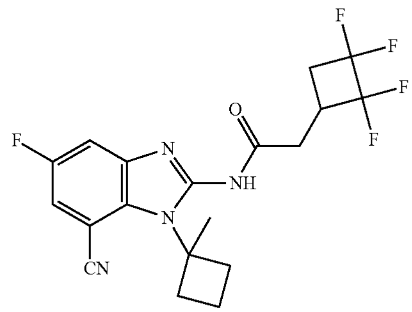 [SMILES: CC1(n2c(NC(=O)CC3CC(F)(F)C3(F)F)nc3cc(F)cc(C#N)c32)CCC1] | N-(7-cyano-5-fluoro-1-(1-methylcyclobutyl)-1H-benzo[d]imidazol-2-yl)-2-(2,2,3,3-tetrafluorocyclobutyl)acetamide, stereoisomer 1 | 412.4 |
| 546 | 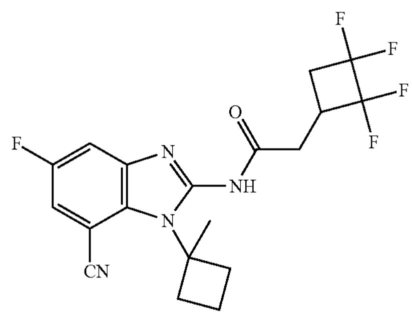 [SMILES: CC1(n2c(NC(=O)CC3CC(F)(F)C3(F)F)nc3cc(F)cc(C#N)c32)CCC1] | N-(7-cyano-5-fluoro-1-(1-methylcyclobutyl)-1H-benzo[d]imidazol-2-yl)-2-(2,2,3,3-tetrafluorocyclobutyl)acetamide, stereoisomer 2 | 412.4 |
| 547 | 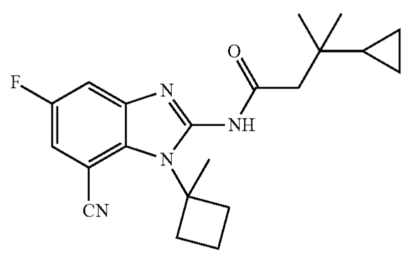 [SMILES: CC(C)(CC(=O)Nc1nc2cc(F)cc(C#N)c2n1C1(C)CCC1)C1CC1] | N-(7-cyano-5-fluoro-1-(1-methylcyclobutyl)-1H-benzo[d]imidazol-2-yl)-3-cyclopropyl-3-methylbutanamide | 368.5 |
| 548 | 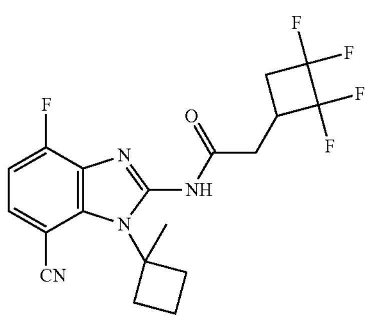 [SMILES: CC1(n2c(NC(=O)CC3CC(F)(F)C3(F)F)nc3c(F)ccc(C#N)c32)CCC1] | N-(7-cyano-4-fluoro-1-(1-methylcyclobutyl)-1H-benzo[d]imidazol-2-yl)-2-(2,2,3,3-tetrafluorocyclobutyl)acetamide, stereoisomer 2 | 412.4 |
| 549 | 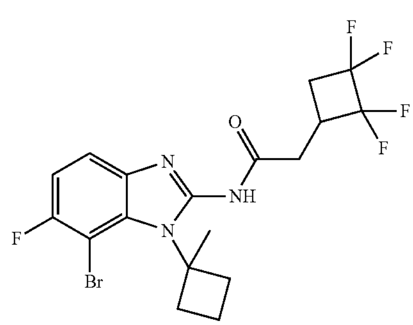 [SMILES: CC1(n2c(NC(=O)CC3CC(F)(F)C3(F)F)nc3ccc(F)c(Br)c32)CCC1] | N-(7-bromo-6-fluoro-1-(1-methylcyclobutyl)-1H-benzo[d]imidazol-2-yl)-2-(2,2,3,3-tetrafluorocyclobutyl)acetamide, stereoisomer 1 | 466.3 |

TABLE 1-continued

List of Examples with Molecular Weight Data

| Example | Structure | Name | Molecular Weight |
|---|---|---|---|
| 550 | 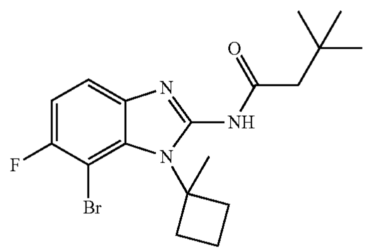 [SMILES: CC(C)(C)CC(=O)Nc1nc2ccc(F)c(Br)c2n1C1(C)CCC1] | N-(7-bromo-6-fluoro-1-(1-methylcyclobutyl)-1H-benzo[d]imidazol-2-yl)-3,3-dimethylbutanamide | 396.3 |
| 551 | 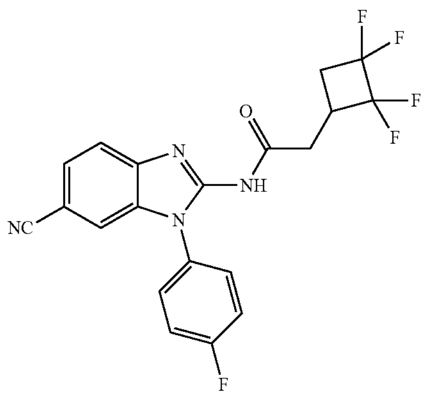 [SMILES: N#Cc1ccc2nc(NC(=O)CC3CC(F)(F)C3(F)F)n(-c3ccc(F)cc3)c2c1] | N-(6-cyano-1-(4-fluorophenyl)-1H-benzo[d]imidazol-2-yl)-2-(2,2,3,3-tetrafluorocyclobutyl)acetamide, stereoisomer 2 | 420.3 |
| 552 | 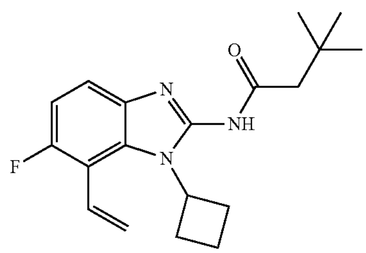 [SMILES: C=Cc1c(F)ccc2nc(NC(=O)CC(C)(C)C)n(C3CCC3)c12] | N-(1-cyclobutyl-6-fluoro-7-vinyl-1H-benzo[d]imidazol-2-yl)-3,3-dimethylbutanamide | 329.4 |
| 553 | 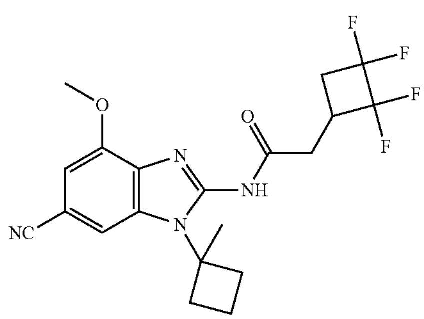 [SMILES: COc1cc(C#N)cc2c1nc(NC(=O)CC1CC(F)(F)C1(F)F)n2C1(C)CCC1] | N-(6-cyano-4-methoxy-1-(1-methylcyclobutyl)-1H-benzo[d]imidazol-2-yl)-2-(2,2,3,3-tetrafluorocyclobutyl)acetamide, stereoisomer 2 | 424.4 |
| 554 | 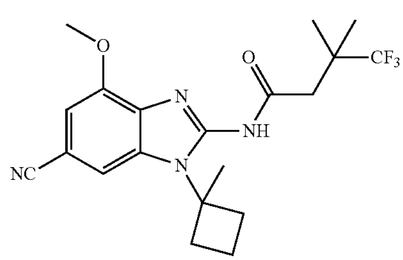 [SMILES: COc1cc(C#N)cc2c1nc(NC(=O)CC(C)(C)C(F)(F)F)n2C1(C)CCC1] | N-(6-cyano-4-methoxy-1-(1-methylcyclobutyl)-1H-benzo[d]imidazol-2-yl)-4,4,4-trifluoro-3,3-dimethylbutanamide | 408.4 |

TABLE 1-continued

List of Examples with Molecular Weight Data

| Example | Structure | Name | Molecular Weight |
|---|---|---|---|
| 555 | 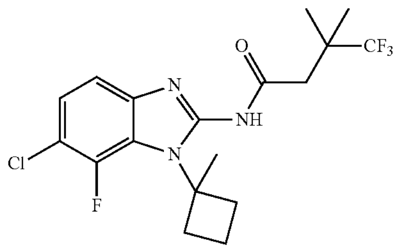 [SMILES: CC1(n2c(NC(=O)CC(C)(C)C(F)(F)F)nc3ccc(Cl)c(F)c32)CCC1] | N-(6-chloro-7-fluoro-1-(1-methylcyclobutyl)-1H-benzo[d]imidazol-2-yl)-4,4,4-trifluoro-3,3-dimethylbutanamide | 405.8 |
| 556 | 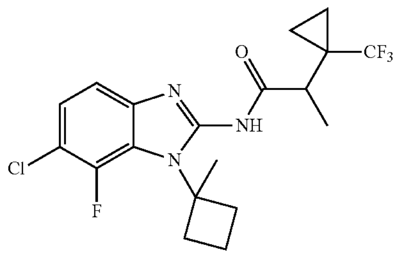 [SMILES: CC(C(=O)Nc1nc2ccc(Cl)c(F)c2n1C1(C)CCC1)C1(C(F)(F)F)CC1] | N-(6-chloro-7-fluoro-1-(1-methylcyclobutyl)-1H-benzo[d]imidazol-2-yl)-2-(1-(trifluoromethyl)cyclopropyl)propanamide, stereoisomer 1 | 417.8 |
| 557 | 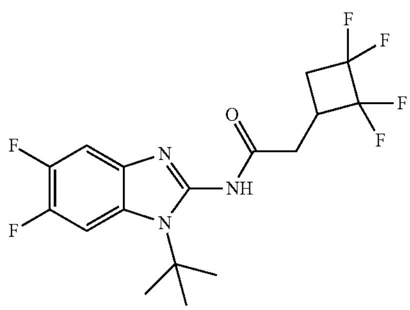 [SMILES: CC(C)(C)n1c(NC(=O)CC2CC(F)(F)C2(F)F)nc2cc(F)c(F)cc21] | N-(1-(tert-butyl)-5,6-difluoro-1H-benzo[d]imidazol-2-yl)-2-(2,2,3,3-tetrafluorocyclobutyl)acetamide, stereoisomer 2 | 393.3 |
| 558 | 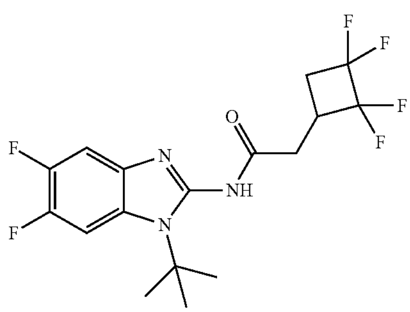 [SMILES: CC(C)(C)n1c(NC(=O)CC2CC(F)(F)C2(F)F)nc2cc(F)c(F)cc21] | N-(1-(tert-butyl)-5,6-difluoro-1H-benzo[d]imidazol-2-yl)-2-(2,2,3,3-tetrafluorocyclobutyl)acetamide, stereoisomer 1 | 393.3 |
| 559 | 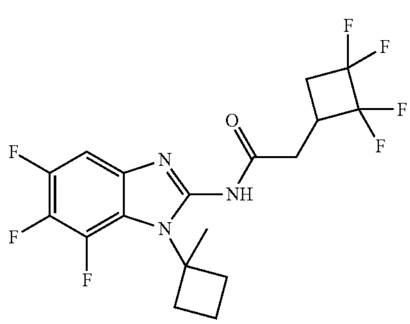 [SMILES: CC1(n2c(NC(=O)CC3CC(F)(F)C3(F)F)nc3cc(F)c(F)c(F)c32)CCC1] | 2-(2,2,3,3-tetrafluorocyclobutyl)-N-(5,6,7-trifluoro-1-(1-methylcyclobutyl)-1H-benzo[d]imidazol-2-yl)acetamide, stereoisomer 2 | 423.3 |

TABLE 1-continued

List of Examples with Molecular Weight Data

| Example | Structure | Name | Molecular Weight |
|---|---|---|---|
| 560 | 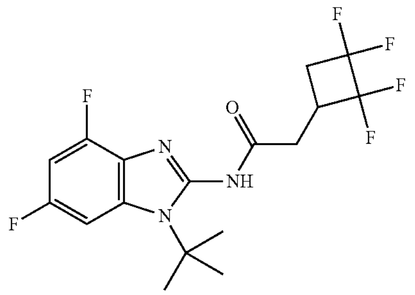 [SMILES: CC(C)(C)n1c(NC(=O)CC2CC(F)(F)C2(F)F)nc2c(F)cc(F)cc21] | N-(1-(tert-butyl)-4,6-difluoro-1H-benzo[d]imidazol-2-yl)-2-(2,2,3,3-tetrafluorocyclobutyl)acetamide, stereoisomer 2 | 393.3 |
| 561 | 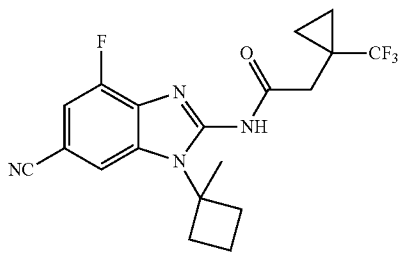 [SMILES: CC1(n2c(NC(=O)CC3(C(F)(F)F)CC3)nc3c(F)cc(C#N)cc32)CCC1] | N-(6-cyano-4-fluoro-1-(1-methylcyclobutyl)-1H-benzo[d]imidazol-2-yl)-2-(1-(trifluoromethyl)cyclopropyl)acetamide | 394.4 |
| 562 | 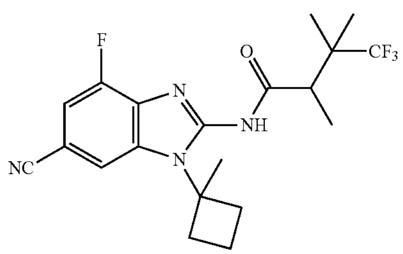 [SMILES: CC(C(=O)Nc1nc2c(F)cc(C#N)cc2n1C1(C)CCC1)C(C)(C)C(F)(F)F] | N-(6-cyano-4-fluoro-1-(1-methylcyclobutyl)-1H-benzo[d]imidazol-2-yl)-4,4,4-trifluoro-2,3,3-trimethylbutanamide, stereoisomer 1 | 410.4 |

Biological Assay Methods

Kv7.2/7.3 Activation Assay

The ability of compounds to potentiate K-currents in Kv7.2/7.3 containing HEK cells was assessed using planar patch-clamp on the QPatch automated screening platform.

Cell Line: The hKv7.2/7.3 cell line was obtained from Chantest (Cleveland, Ohio 44128) cat. #CT6147. These HEK cells will express the Kv7.2/7.3 ion channels when induced.

Cell Culture: Cells were maintained in a media containing DMEM/F12; 50/50 (GIBCO cat. #11330), 10% Fetal Bovine Serum (FBS) (GIBCO cat. #26140), 100 units/mL Penicillin-Streptomycin (GIBCO cat. #15140), 0.005 mg/mL Blasticidin (INVIVOGEN cat. #ant-bl-1), 0.5 mg/mL Geneticin (GIBCO cat. #10131), 0.1 mg/mL Zeocin (GIBCO cat. #R25001). Cells used in the electrophysiology assay were maintained in a media without Blasticidin, Geneticin and Zeocin for 2 days and channel expression was induced by adding tetracycline (BIOLINE cat. #BIO-87030) at a final concentration of 1 mg/mL. Cells were grown in T-175 flask to ~75% confluency. Currents were recorded 24 hours after channel induction.

Compound Plates: Test compounds were prepared by performing serial dilutions on a Biomek NX$^P$ (BECKMAN COULTER). Final dilutions were made in external recording solution with a final DMSO concentration of 0.1% DMSO. For single concentration screens each plate had 10 M retigabine as a positive control and 0.1% DMSO as a negative control.

Electrophysiology: On the day of the experiment cells were washed with Hank's Balanced Salt Solution (HBBS) (GIBCO cat. #14175) and harvested with Tryple (GIBCO cat. #12604). Cells were then centrifuged at 2000 rpm for 5 minutes and resuspended in CHO-S-SFM (GIBCO cat. #12052) at ~3×10$^6$ cells/mL. Cells were stirred for 30 minutes before experiments were started. External recording solution contained (in mM): NaCl (145), KCl (4), CaCl$_2$) (2), MgCl$_2$ (1), HEPES (10) and Glucose (10); pH was adjusted to 7.4 with NaOH and the osmolarity was adjusted to 300-305 mOsM with sucrose if necessary. Internal solution contained (in mM): KCl (125), KF (10), EGTA (5), Na$_2$ATP (5), MgCl$_2$ (3.2), HEPES (5); pH was adjusted to 7.2 with KOH and the osmolarity was adjusted to 298-302 mOsM with sucrose.

Potassium channel activity was measured on the QPatch HTX (Sophion Bioscience) using QPlates with 48-wells/plate. Each cell was taken as an independent experiment and only one compound was tested per well. Potassium channel activity was elicited by holding at −80 mV and stepping to −30 mV for 2 s followed by a 100 ms pulse to −120 mV.

Single concentration screen: Baseline conditions were obtained by recording 5 sweeps in the external solution only, this was repeated for three applications of the external solution. The effect of test compounds on elicited current was then assessed by recording 5 sweeps in the presence of a 3 M compound solution. The steady-state current at the end of the 2 s pulse to −30 mV was measured to determine the fold increase from baseline.

Data of the Kv7.2/7.3 Activation Assay is summarized in Table 2

TABLE 2

Kv7.2/7.3 QPatch Single Concentration Screen Results.

| Example | HPLC Retention time (min)[a] | MS (ESI) m/z (M + H)+ | Kv7.2/7.3 Activity[b] |
|---|---|---|---|
| 330 | 3.5 | 383.2 (M − H)− | ++ |
| 331 | 3.8 | 370.4 | +++ |
| 332 | 3.1 | 380.4 | + |
| 333 | 4.0 | 393.2 | ++ |
| 334 | 3.9 | 402.4 | ++ |
| 335 | 2.9 | 420.4 | O |
| 336 | 2.9 | 392.4 | + |
| 337 | 3.7 | 325.2 | ++ |
| 338 | 4.1 | 410.4 | +++ |
| 339 | 3.4 | 413.2 | O |
| 340 | 4.0 | 397.2 | + |
| 341 | 3.7 | 391.2 | + |
| 342 | 3.1 | 371.2 | +++ |
| 343 | 4.1 | 382.0 | +++ |
| 344 | 3.4 | 375.2 | + |
| 345 | 3.9 | 397.2 | + |
| 346 | 3.7 | 366.4 | ++ |
| 347 | 3.5 | 409.2 | + |
| 348 | 3.4 | 413.2 | O |
| 349 | 3.8 | 403.2 | ++ |
| 350 | 3.5 | 393.2 | + |
| 351 | 3.2 | 386.4 | + |
| 352 | 3.6 | 428.4 | ++ |
| 353 | 2.9 | 414.4 | + |
| 354 | 3.9 | 339.2 | ++ |
| 355 | 3.6 | 348.4 | +++ |
| 356 | 3.8 | 347.2 | + |
| 357 | 3.9 | 322.4 | +++ |
| 358 | 3.3 | 380.4 | + |
| 359 | 3.2 | 374.4 | ++ |
| 360 | 3.6 | 424.4 | O |
| 361 | 4.1 | 379.2 | ++ |
| 362 | 3.4 | 380.4 | ++ |
| 363 | 3.8 | 396.4 | + |
| 364 | 3.4 | 367.2 | ++ |
| 365 | 3.3 | 394.4 | + |
| 366 | 4.3 | 420.4 | + |
| 367 | 4.0 | 410.4 | ++ |
| 368 | 3.9 | 398.4 | + |
| 369 | 2.9 | 392.4 | O |
| 370 | 2.6 | 380.4 | ++ |
| 371 | 2.9 | 420.4 | O |
| 372 | 3.3 | 329.2 | ++ |
| 373 | 3.8 | 425.2 | ++ |
| 374 | 3.8 | 448.4 | ++ |
| 375 | 3.6 | 389.2 | + |
| 376 | 3.3 | 428.4 | + |
| 377 | 3.7 | 345.2 | +++ |
| 378 | 3.6 | 385.2 | +++ |
| 379 | 3.9 | 351.2 | ++ |
| 380 | 3.4 | 372.4 | + |
| 381 | 3.8 | 391.2 | ++ |
| 382 | 3.8 | 394.0 | +++ |
| 383 | 2.9 | 372.4 | ++ |
| 384 | 3.6 | 425.2 | ++ |
| 385 | 3.7 | 434.4 | O |
| 386 | 2.7 | 380.4 | + |
| 387 | 3.5 | 331.2 | ++ |
| 388 | 4.1 | 410.4 | +++ |
| 389 | 3.3 | 352.4 | ++ |
| 390 | 4.0 | 396.4 | + |
| 391 | 2.6 | 356.4 | + |
| 392 | 4.0 | 408.0 | +++ |
| 393 | 3.8 | 354.4 | +++ |
| 394 | 4.0 | 348.4 | O |
| 395 | 4.2 | 383.2 | O |
| 396 | 3.4 | 403.2 | + |
| 397 | 3.1 | 371.2 | +++ |
| 398 | 3.1 | 414.4 | + |
| 399 | 4.3 | 364.4 | +++ |
| 400 | 3.3 | 432.4 | +++ |
| 401 | 3.7 | 367.2 | ++ |
| 402 | 3.5 | 416.4 | ++ |
| 403 | 3.0 | 360.4 | ++ |
| 404 | 3.8 | 410.4 | + |
| 405 | 3.1 | 432.4 | ++ |
| 406 | 3.3 | 398.4 | +++ |
| 407 | 3.4 | 386.4 | ++ |
| 408 | 4.3 | 358.4 | ++ |
| 409 | 4.3 | 502.4 | + |
| 410 | 3.3 | 410.4 | O |
| 411 | 3.6 | 329.2 | +++ |
| 412 | 3.3 | 410.4 | ++ |
| 413 | 3.6 | 406.0 | +++ |
| 414 | 4.5 | 418.0 (M − H)− | ++ |
| 415 | 3.5 | 384.0 (M − H)− | O |
| 416 | 3.4 | 401.2 | ++ |
| 417 | 3.2 | 304.4 | ++ |
| 418 | 3.7 | 418.4 | ++ |
| 419 | 3.9 | 445.2 | + |
| 420 | 3.4 | 331.2 | + |
| 421 | 3.3 | 374.4 | +++ |
| 422 | 3.5 | 416.4 | + |
| 423 | 3.5 | 422.4 | + |
| 424 | 3.6 | 392.4 | O |
| 425 | 3.0 | 356.4 | ++ |
| 426 | 3.9 | 351.2 | +++ |
| 427 | 4.0 | 380.4 | ++ |
| 428 | 3.4 | 375.2 | ++ |
| 429 | 3.5 | 334.4 | +++ |
| 430 | 3.9 | 425.2 | ++ |
| 431 | 3.7 | 395.2 | ++ |
| 432 | 3.2 | 360.4 | +++ |
| 433 | 3.9 | 402.4 | ++ |
| 434 | 3.9 | 392.4 | +++ |
| 435 | 3.1 | 396.4 | O |
| 436 | 3.8 | 343.2 | ++ |
| 437 | 3.8 | 343.2 | ++ |
| 438 | 3.6 | 380.4 | O |
| 439 | 3.9 | 345.2 | + |
| 440 | 3.1 | 372.4 | + |
| 441 | 3.6 | 407.2 | ++ |
| 442 | 3.3 | 380.4 | + |
| 443 | 3.3 | 376.4 | ++ |
| 444 | 3.7 | 385.2 | ++ |
| 445 | 3.4 | 388.4 | ++ |
| 446 | 3.1 | 414.4 | ++ |
| 447 | 3.6 | 376.4 | +++ |
| 448 | 2.6 | 353.6 | ++ |
| 449 | 3.2 | 304.4 | ++ |
| 450 | 3.8 | 412.4 | + |
| 451 | 3.3 | 374.4 | O |
| 452 | 3.5 | 393.2 | O |
| 453 | 4.2 | 376.0 | ++ |
| 454 | 3.0 | 347.2 | +++ |
| 455 | 3.3 | 370.4 | ++ |
| 456 | 3.2 | 398.4 | ++ |
| 457 | 3.6 | 349.2 | ++ |
| 458 | 3.6 | 342.4 | +++ |
| 459 | 4.0 | 384.4 | +++ |
| 460 | 3.9 | 425.2 | ++ |
| 461 | 4.2 | 438.4 | + |
| 462 | 3.3 | 385.2 | ++ |
| 463 | 3.6 | 430.4 | + |
| 464 | 4.0 | 373.2 | ++ |
| 465 | 3.6 | 407.2 | ++ |
| 466 | 3.3 | 432.4 | ++ |
| 467 | 3.6 | 425.2 | + |
| 468 | 3.6 | 389.2 | + |
| 469 | 3.4 | 334.4 | +++ |
| 470 | 3.8 | 434.4 | + |
| 471 | 3.6 | 389.2 | + |
| 472 | 3.2 | 382.4 | +++ |
| 473 | 3.7 | 325.2 | ++ |
| 474 | 3.1 | 374.4 | O |
| 475 | 3.8 | 395.4 | ++ |

TABLE 2-continued

Kv7.2/7.3 QPatch Single Concentration Screen Results.

| Example | HPLC Retention time (min)[a] | MS (ESI) m/z (M + H)+ | Kv7.2/7.3 Activity[b] |
|---|---|---|---|
| 476 | 3.0 | 316.4 | + |
| 477 | 4.4 | 432.0 | +++ |
| 478 | 3.8 | 425.2 | + |
| 479 | 3.2 | 398.4 | ++ |
| 480 | 3.2 | 412.4 | O |
| 481 | 3.4 | 376.4 | O |
| 482 | 3.6 | 357.2 | +++ |
| 483 | 3.5 | 421.2 | ++ |
| 484 | 4.0 | 421.2 | + |
| 485 | 3.1 | 411.2 | +++ |

[a]HPLC Method B
[b]Increase over baseline in current from Kv7.2/Kv7.3 co-expressing HEK cells, using Kv7.2/7.3 Activation Assay as described in Biological Assay Methods section, measured at compound concentration of 3 µM described as a range from 1.2-2.9 (+), 3-3.9 (++), and >4 (+++) fold increase over baseline; O represents open channel at holding potential.

The Thallium Flux Assay is used as a surrogate indicator of potassium channel activity.

The experimental protocol was adapted from the FluxOR™ II Green Potassium Ion Channel Assay User Guide (Pub. No. MAN0016084, Invitrogen). Conditions were optimized for the Kv7.2/7.3 cell line.

Cell Line: The hKV7.2/7.3 cell line was obtained from Chantest (Cleveland, Ohio 44128) cat. #CT6147.

Cell Culture: Kv7.2/7.3 cells were maintained in a media containing DMEM/F12; 50/50 (GIBCO cat. #11330), 10% Fetal Bovine Serum (FBS) (GIBCO cat. #26140), 100 units/mL Penicillin-Streptomycin (GIBCO cat. #15140), 0.005 mg/ml Blasticidin (SIGMA 15205), 0.5 mg/mL Geneticin (GIBCO cat. #10131), and 0.1 mg/mL Zeocin (GIBCO cat. #R25001). One day prior to experimentation, cells were plated in 96 well clear bottom plates (Corning cat. #353219) in a media without Blasticidin, Geneticin, or Zeocin. Channel expression was induced by adding tetracycline (Bioline cat. #BIO87030) at a final concentration of 10 ng/mL.

Compound Plates: The test compound is diluted in a mixture of 0.1% DMSO/extracellular solution with an eight-point concentration range from 0.014 µM to 30 µM. Serial dilutions were made on a Biomek NXP (BECKMAN COULTER).

Measurement and data analysis: A plate reader (Enspire, Perkin Elmer) is used to characterize the ion-channel modulating properties of novel compounds using an excitation wavelength of 475 nm and an emission wavelength of 530 nm. After a 15 sec baseline measurement, the stimulus buffer containing thallium and potassium is injected. A final endpoint measure is taken after 90 sec. Responses are normalized to positive control (retigabine, 30 µM max). Mean normalized responses at each concentration tested are fit to the standard Hill equation to generate an EC50 and maximal response.

Data of the Thallium Flux Assay is summarized in Table 3

TABLE 3

Kv7.2/7.3 Thallium Flux Assay Results.

| Example | HPLC Retention time (min)[a] | MS (ESI) m/z (M + H)+ | Kv7.2/7.3 Activity[c] |
|---|---|---|---|
| 486 | 3.8 | 397.2 | *** |
| 487 | 4.0 | 440.4 | *** |
| 488 | 3.8 | 437.2 | *** |
| 489 | 3.8 | 424.4 | *** |
| 490 | 4.0 | 424.4 | *** |
| 491 | 3.4 | 428.4 | *** |
| 492 | 3.8 | 426.4 | *** |
| 493 | 4.1 | 479.2 | *** |
| 494 | 3.8 | 409.2 | *** |
| 495 | 3.6 | 343.2 | *** |
| 496 | 3.6 | 419.2 | *** |
| 497 | 3.5 | 428.4 | *** |
| 498 | 4.0 | 395.2 | *** |
| 499 | 3.9 | 406.0 | *** |
| 500 | 3.4 | 446.4 | *** |
| 501 | 3.7 | 428.4 | ** |
| 502 | 3.9 | 396.4 | * |
| 503 | 3.9 | 409.2 | *** |
| 504 | 3.7 | 431.2 | *** |
| 505 | 3.3 | 414.4 | *** |
| 506 | 3.6 | 413.2 | *** |
| 507 | 4.0 | 379.2 | *** |
| 508 | 3.5 | 428.4 | ** |
| 509 | 3.6 | 394.4 | *** |
| 510 | 3.4 | 353.2 | ** |
| 511 | 2.7 | 368.4 | *** |
| 512 | 3.6 | 413.2 | *** |
| 513 | 4.0 | 406.0 | *** |
| 514 | 3.6 | 413.2 | *** |
| 515 | 3.6 | 430.4 | *** |
| 516 | 4.3 | 370.4 | *** |
| 517 | 3.8 | 361.2 | *** |
| 518 | 2.4 | 374.4 | ** |
| 519 | 3.4 | 446.4 | *** |
| 520 | 3.6 | 395.2 | * |
| 521 | 3.6 | 352.4 | *** |
| 522 | 4.1 | 388.4 | *** |
| 523 | 4.1 | 406.4 | *** |
| 524 | 3.9 | 354.4 | *** |
| 525 | 4.0 | 388.4 | *** |
| 526 | 4.0 | 388.4 | *** |
| 527 | 4.1 | 370.4 | *** |
| 528 | 3.9 | 376.4 | *** |
| 529 | 3.9 | 376.4 | *** |
| 530 | 3.9 | 378.4 | *** |
| 531 | 3.7 | 376.4 | *** |
| 532 | 3.7 | 394.4 | *** |
| 533 | 3.9 | 372.4 | *** |
| 534 | 4.0 | 406.4 | *** |
| 535 | 4.1 | 410.0 | *** |
| 536 | 3.7 | 413.2 | *** |
| 537 | 3.7 | 413.2 | *** |
| 538 | 4.0 | 388.4 | *** |
| 539 | 4.2 | 422.0 | *** |
| 540 | 4.4 | 402.4 | *** |
| 541 | 3.9 | 369.2 | *** |
| 542 | 3.7 | 431.2 | *** |
| 543 | 3.9 | 427.2 | *** |
| 544 | 3.9 | 427.2 | *** |
| 545 | 3.8 | 413.2 | *** |
| 546 | 3.8 | 413.2 | *** |
| 547 | 4.0 | 369.2 | *** |
| 548 | 3.6 | 413.2 | *** |
| 549 | 4.1 | 466.0 | *** |
| 550 | 4.1 | 396.0 | *** |
| 551 | 3.6 | 421.4 | *** |
| 552 | 3.8 | 330.4 | *** |
| 553 | 3.7 | 425.2 | *** |
| 554 | 4.0 | 409.2 | *** |
| 555 | 4.6 | 406.0 | *** |
| 556 | 4.8 | 418.0 | *** |
| 557 | 3.8 | 394.4 | *** |
| 558 | 3.8 | 394.4 | ** |
| 559 | 4.0 | 424.0 | *** |
| 560 | 3.6 | 394.4 | *** |

TABLE 3-continued

Kv7.2/7.3 Thallium Flux Assay Results.

| Example | HPLC Retention time (min)[a] | MS (ESI) m/z (M + H)+ | Kv7.2/7.3 Activity[c] |
|---|---|---|---|
| 561 | 3.5 | 395.2 | *** |
| 562 | 3.9 | 411.2 | *** |

[a]HPLC Method B
[c]Measured EC50 of Kv7.2/Kv7.3 activation using thallium flux assay as described in Biological Assay Methods section, described as a range from 3-10 μM (*), 1-3 μM (), and <1 μM (*).

Groupings of alternative elements or embodiments disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, the claims include all modifications and equivalents of the subject matter recited in the claims as permitted by applicable law. Moreover, any combination of the above-described elements in all possible variations thereof is contemplated unless otherwise indicated herein or otherwise clearly contradicted by context.

In closing, it is to be understood that the embodiments disclosed herein are illustrative of the principles of the claims. Other modifications that may be employed are within the scope of the claims. Thus, by way of example, but not of limitation, alternative embodiments may be utilized in accordance with the teachings herein. Accordingly, the claims are not limited to embodiments precisely as shown and described.

KV7 Activators and Methods of Treating ALS

In embodiments, this disclosure relates to methods for treating neurodegenerative disease, such as amyotrophic lateral sclerosis, in a subject in need thereof comprising: administering to the subject a therapeutically effective amount of a compound of formula A-1 through A-44 or B-1 through B-7, or a pharmaceutically acceptable salt thereof, wherein the neurodegenerative disease is treated.

In embodiments, the subject is a subject with definite ALS, has amyotrophic lateral sclerosis symptom onset duration of less than about 18 months, plasma creatinine levels of about 72 μM/L or greater, concomitant riluzole administration, concomitant dexpramipexole administration, and combinations thereof.

It has been demonstrated that the motor neurons of ALS patients have reduced delayed-rectifier potassium current amplitudes, which may underlie the hyperexcitability seen in these diseased neurons. Embodiments described herein are directed to compounds of formula A-1 through A-44 or B-1 through B-7, or a pharmaceutically acceptable salt thereof, which activate Kv7 channels to block the hyperexcitability associated with ALS and improve motor neuron function and/or survival.

Embodiments are directed to methods for treating neurodegenerative disease in a subject comprising administering to the subject a therapeutically effective amount of a compound of formula A-1 through A-44 or B-1 through B-7, or a pharmaceutically acceptable salt thereof, wherein the neurodegenerative disease is treated. The compounds of formula A-1 through A-44 or B-1 through B-7, or a pharmaceutically acceptable salt thereof, may be administered to any individual exhibiting the symptoms of a neurodegenerative disease or to individuals predisposed to a neurodegenerative disease. Non-limiting examples of neurodegenerative diseases that may be treated using a compound of formula A-1 through A-44 or B-1 through B-7, or a pharmaceutically acceptable salt thereof, include amyotrophic lateral sclerosis (ALS), Huntington's disease, metabolically induced neurological damage, Alzheimer's disease, Pick's disease, senile dementia, age associated cognitive dysfunction, vascular dementia, multi-infarct dementia, Lewy body dementia, neurodegenerative dementia, frontotemporal dementia (FTD), familial FTD, neurodegenerative movement disorder, ataxia, Friedreich's ataxia, multiple sclerosis, spinal muscular atrophy, primary lateral sclerosis, seizure disorders, motor neuron disorder or disease, inflammatory demyelinating disorder, Parkinson's disease, hepatic encephalopathy, chronic encephalopathy, chronic encephalitis, or any combination thereof.

Embodiments are directed to methods for treating neurodegenerative disease, such as amyotrophic lateral sclerosis, in a subject in need thereof comprising: administering to the subject a therapeutically effective amount of a compound of formula A-1 through A-44 or B-1 through B-7, or a pharmaceutically acceptable salt thereof, wherein the neurodegenerative disease is treated. In embodiments, the subject is a subject with definite ALS, has amyotrophic lateral sclerosis symptom onset duration of less than about 18 months, plasma creatinine levels of about 72 μM/L or greater, concomitant riluzole administration, concomitant dexpramipexole administration, and combinations thereof.

Embodiments are directed to methods for treating amyotrophic lateral sclerosis in a subject in need thereof comprising: administering to the subject a therapeutically effective amount of a compound of formula A-1 through A-44 or B-1 through B-7, or a pharmaceutically acceptable salt thereof, wherein the amyotrophic lateral sclerosis is treated.

Embodiments are directed to methods for treating amyotrophic lateral sclerosis in a subject diagnosed with definite amyotrophic lateral sclerosis comprising administering to the subject a therapeutically effective amount of a compound of formula A-1 through A-44 or B-1 through B-7, or a pharmaceutically acceptable salt thereof, wherein the amyotrophic lateral sclerosis is treated. In embodiments, the definite amyotrophic lateral sclerosis is as defined by the El Escorial diagnosis criteria. In embodiments, the subject is a subject with definite ALS, amyotrophic lateral sclerosis symptom onset duration of less than about 18 months, plasma creatinine levels of about 72 μM/L or greater, concomitant riluzole administration, concomitant dexpramipexole administration, and combinations thereof.

Amyotrophic lateral sclerosis (ALS; Lou Gehrig's disease) is a progressively debilitating motor neuron disease, characterized by degeneration and dysfunction/death of upper and lower motor neurons. ALS is universally fatal but the rate of disease progression may not be linear.

In accordance with embodiments described herein, the El Escorial World Federation of Neurology's Criteria for the Diagnosis of ALS is as follows (See also Brooks, B. R., R. G. Miller, et al. (2000). "El Escorial revisited: revised criteria for the diagnosis of amyotrophic lateral sclerosis." *Amyotrophic Lateral Sclerosis Other Motor Neuron Disord* 1(5): 293-9, which is incorporated by reference in its entirety). As used in the El Escorial World Federation of Neurology's Criteria for the Diagnosis of ALS, the term "definite" is intended to mean specific clinical exclusionary criteria met, no other diagnosis possible on basis of clinical distribution or laboratory findings; the term "dementia" is intended to mean progressive deterioration of specific cognitive functions; the term "onset" is intended to mean time of first subjective symptom noticed by patient which later is confirmed by examination; the term "possible" is intended to mean specific clinical and exclusionary criteria met; the term "probable" is intended to mean specific clinical and exclusionary criteria; and the term "worsening" is intended to mean increased weakness of muscles in a previously affected segment or new weakness in a previously unaffected segment.

The diagnoses of ALS requires the presence of: 1) signs of lower motor neuron (LMN) degeneration by clinical, electrophysiological or neuropathologic examination, 2) signs of upper motor neuron (UMN) degeneration by clinical examination, and 3) progressive spread of signs within a region or to other regions, together with the absence of electrophysiological evidence of other disease processes that might explain the signs of LMN and/or UMN degenerations; and neuroimaging evidence of other disease processes that might explain the observed clinical and electrophysiological signs.

Furthermore, the El Escorial World Federation of Neurology's Criteria for the Diagnosis of ALS set forth the following steps in the diagnosis of Amyotrophic Lateral Sclerosis. The diagnoses of ALS is made possible by 1) history, physical and appropriate neurological examinations to ascertain clinical finding which may suggest suspected, possible, probable or definite ALS, 2) electrophysiological examinations to ascertain findings which confirm LMN degeneration in clinically involved regions, identify LMN degeneration in clinically uninvolved regions and exclude other disorders, 3) neuroimaging examinations to ascertain findings which may exclude other disease processes, 4) clinical laboratory examinations, determined by clinical judgment, to ascertain possible ALS-related syndromes, 5) neuropathologic examinations, where appropriate, to ascertain findings which may confirm or exclude sporadic ALS, coexistent sporadic ALS, ALS-related syndromes or ALS variants, 6) repetition of clinical and electrophysiological examinations at least six months apart to ascertain evidence of progression.

Definite ALS is defined on clinical grounds alone by the presence of UMN as well as LMN signs in the bulbar region and at least two of the other spinal regions or the presence of UMN and LMN signs in three spinal regions. The important determinants of diagnosis of definite ALS in the absence of electrophysiological, neuroimaging and laboratory examinations are the presence of UMN and LMN signs together in multiple regions.

Probable ALS is defined on clinical grounds alone by UMN and LMN signs in at least two regions. While the regions may be different, some UMN signs must be rostral (above) the LMN signs. Multiple different combinations of UMN and LMN signs may be present in patients with probable ALS.

Possible ALS is defined on clinical grounds alone when the UMN and LMN signs are in only one region or UMN signs alone are present in 2 or more regions or LMN signs are rostral to UMN signs (the latter distribution of signs needs to be differentiated from multiple non-ALS processes). Monomelic ALS, progressive bulbar palsy without spinal UMN and/or LMN signs and progressive primary lateral sclerosis without spinal LMN signs and progressive primary lateral sclerosis without spinal LMN signs constitute special cases which may develop LMN or UMN signs to meet the criteria for probable ALS with time or be subsequently confirmed at autopsy by specific LMN and UMN neuropathologic findings.

Suspected ALS will manifest only LMN signs in 2 or more regions, although UMN pathology might be demonstrated at autopsy. However, only clinical signs are considered pertinent to this classification at the time of diagnostic evaluation.

The clinical signs of progressive LMN and UMN degeneration seen in ALS may 1) occur alone (sporadic ALS), 2) be present incidentally with other pre-existing disease processes that have not developed in parallel with the ALS (coexistent sporadic ALS), 3) Occur in association with laboratory-defined or epidemiologically defined abnormalities that are time-linked to the ALS (ALS-related syndromes), or 4) Occur in association with clinical, genetic or epidemiological features which develop in parallel with the ALS (ALS variants).

The physical and neurological examinations will allow for the clinical diagnosis of ALS to a particular degree of certainty as defined above; however, the history of the disease onset, toxic exposures, past medical history, injuries, family history, geographic location, etc., must be incorporated with the clinical examinations in determining whether the patient may have an ALS related syndrome or an ALS variant.

ALS-related syndromes must meet the clinical, electrophysiological and neuroimaging criteria for possible, probable or definite ALS. ALS-related syndromes have unique laboratory-defined or epidemiologically defined features which are time-linked to the development of the ALS phenotype. If correction of the associated laboratory-defined feature does not result in correction of the ALS phenotype, then the patient with an ALS-related syndrome should be considered in the same way as a patient with sporadic ALS.

ALS-related syndromes include: 1) monoclonal gammopathy (monoclonal gammopathy of unknown significance, Waldenstroms's macroglobulinemia, osteosclerotic myeloma, etc.), 2) dysimmune motor system degeneration (autoimmune; high-titer GMI ganglioside antibody; etc.), 3) nonmalignant endocrine abnormalities (hyperthyroidism, hyperparathyroidism, hypogonadism, etc.), 4) lymphoma (Hodgkin's and non-Hodgkin's lymphoma). 5) infection (HIV-1, HTLV-I, encephalitis lethargica, varicella-zoster, brucellosis, cat-scratch disease, Creutzfeldt-Jakob disease, syphilis, delayed post-poliomyelitis, etc.), 6) acquired enzyme defects (detoxification enzymes, etc.), 7) exogenous toxins (lead, mercury, arsenic, thallium, cadmium, manganese, aluminum, organic pesticides, lupin seeds, etc.), 8) physical injury (electric shock, radiation therapy, etc.), 9) vascular (vasculitis; ischemic (Dejerine anterior bulbar artery syndrome, etc.), 10) spondylotic myelopathy (painless myelopathy with no sensory signs, stabilization or progression post-surgery).

ALS Variants must meet the clinical, electrophysiological and neuroimaging criteria for possible, probable or definite ALS. The predominant presentation is that seen in sporadic ALS, but includes one or more features such as: multiple phenotypes characterized by age of onset; site of onset; length of survival; and presumed type of inheritance.

Familial ALS variants in genetic linkage studies should be characterized by an established genetic mode of inheritance over at least two generations and at least one clinically definite or autopsy confirmed case and compelling evidence excluding other possible causes. Affected sub pairs occurring in one generation alone may not result from a single gene effect.

Examples: a) ALS with defined inheritance and known gene product (hexosaminidase A/B deficiency, superoxide dismutase deficiency); b) ALS with defined inheritance and chromosome linkage but no gene product (chromosome 21 associated familial ALS or chromosome 2 associated juvenile familial ALS); c) ALS with defined inheritance and no known linkage or gene product (most cases or familial ALS); d) geographic clustering (including disorders seen in the Western Pacific, Guam, Kii Peninsula, North Africa, Madras, etc.); e) Eetrapyramidal signs (bradykinesia; cogwheel rigidity; tremor; clinically significant onset of supranuclear eye signs (pursuit abnormalities); familial or sporadic); f) cerebellar degeneration (spinocerebellar abnormalities; familial or sporadic); g) dementia (progressive cognitive abnormalities; familial or sporadic); h) autonomic nervous system involvement (clinically significant abnormal cardiovascular reflexes; bowel or bladder control problems; familial or sporadic); i) objective sensory abnormalities (decreased vibration; sharp-dull discrimination; blunting of cold sensation; familial or sporadic); j) electrophysiological features in the diagnoses of ALS Embodiments are directed to methods for treating amyotrophic lateral sclerosis in a subject in need thereof comprising administering to the subject a therapeutically effective amount of a compound of formula A-1 through A-44 or B-1 through B-7, or a pharmaceutically acceptable salt thereof, wherein the subject is selected from a subject with definite amyotrophic lateral sclerosis, a subject with limb-onset amyotrophic lateral sclerosis, a subject with bulbar-onset amyotrophic lateral sclerosis, a subject with amyotrophic lateral sclerosis symptom onset duration of less than about 18 months, a subject with a high level of serum creatinine, a subject with low bicarbonate levels, a subject with concomitant riluzole administration, a subject with concomitant dexpramipexole administration, and combinations thereof, and wherein the amyotrophic lateral sclerosis is treated. In certain embodiments, the method further comprises monitoring said subject for any clinical features associated with amyotrophic lateral sclerosis. In certain embodiments, the method further comprises initiating therapy with a therapeutically effective amount of a compound of formula A-1 through A-44 or B-1 through B-7, or a pharmaceutically acceptable salt thereof upon diagnosis of amyotrophic lateral sclerosis. In certain embodiments, the subject exhibits symptoms of amyotrophic lateral sclerosis. In certain embodiments, the subject has definite amyotrophic lateral sclerosis, probable amyotrophic lateral sclerosis, possible amyotrophic lateral sclerosis or suspected amyotrophic lateral sclerosis.

In certain embodiments, the subject has upper motor neuron degeneration and lower motor neuron degeneration in the bulbar region and two other spinal regions. In certain embodiments, the subject has upper motor neuron degeneration and lower motor neuron degeneration in three spinal regions. In certain embodiments, the subject is selected from a subject with symptom onset duration of less than about 18 months, a subject with a high level of serum creatinine, a subject with low levels of serum sodium bicarbonate, a subject with concomitant riluzole administration, a subject concomitant dexpramipexole administration, and combinations thereof. In certain embodiments, a subject with a high level of serum creatinine is a subject with greater than about 72 μmol/L serum creatinine.

In embodiments, the subject with definite amyotrophic lateral sclerosis is a subject diagnosed with definite ALS as defined by the El Escorial criteria. In certain embodiments, the subject with definite amyotrophic lateral sclerosis is a subject with upper motor neuron degeneration and lower motor neuron degeneration in the bulbar region and two other spinal regions. In certain embodiments, the subject with definite amyotrophic lateral sclerosis is a subject with upper motor neuron degeneration and lower motor neuron degeneration in three spinal regions.

Embodiments are directed to methods for treating amyotrophic lateral sclerosis in a subject diagnosed with definite amyotrophic lateral sclerosis comprising administering to the subject a therapeutically effective amount of a compound of formula A-1 through A-44 or B-1 through B-7, or a pharmaceutically acceptable salt thereof, wherein the amyotrophic lateral sclerosis is treated. In some embodiments definite amyotrophic lateral sclerosis is the presence of the El Escorial diagnosis criteria, amyotrophic lateral sclerosis symptom onset duration of less than about 18 months, limb-onset amyotrophic lateral sclerosis, plasma creatinine levels of about 72 μM/L or greater, concomitant riluzole administration, concomitant dexpramipexole administration, an ALSFRS-R score of greater than 36.0, a pre-study progression rate greater than or equal to 0.8 points per month, a percentage predicted relaxed (slow) vital capacity (SVC) of less than or equal to 102.0, an ALSFRS-R fine motor domain score of greater than 10.0 points, ALSFRS-R bulbar domain score or greater than 9.0 points, an ALSFRS-R gross motor domain score of greater than 8.0 points, an abnormal neurological exam of the tongue, an abnormal neurological exam of the pharynx, larynx and swallowing, an abnormal neurological exam of the lower extremities, an abnormal neurological exam of the upper extremities, an abnormal neurological exam of the triceps, an abnormal neurological exam of the muscle mass and bulk, an abnormal neurological exam of the bicep, an abnormal neurological exam, a pulse rate of greater than 81.0 beats per minute, a diastolic blood pressure of greater than 82.0 mmHg, a systolic blood pressure of less than or equal to 117.0 mmHg, a creatinine value of greater than 72.0 μmol/L, a phosphorous value of less than or equal to 1.090 μmol/L, a platelet count of less than or equal to $248.0 \times 10^9$ cells/L, a cholesterol value of less than or equal to 5.3 mmol/L, a lactate dehydrogenase value of less than or equal to 161.0 U/L, a creatine phosphokinase value of less than or equal to 184.0 U/L, a bicarbonate value of less than or equal to 21.6 mmol/L, a triglyceride level of less than or equal to 1.4 mmol/L, a uric acid level of greater than 320.0 μmol/L, a gamma-glutamyltransferase (GGT) level of greater than 37.0 U/L, a total bilirubin level of less than or equal to 6.0 μmol/L, a urine pH of less than or equal to 5.5, or any combination thereof.

Embodiments are directed to methods for treating amyotrophic lateral sclerosis in a subject exhibiting symptoms of amyotrophic lateral sclerosis comprising administering to the subject a therapeutically effective amount of a compound of formula A-1 through A-44 or B-1 through B-7, or a pharmaceutically acceptable salt thereof, wherein the symptoms of amyotrophic lateral sclerosis are treated. In some embodiments, the subject exhibits clinical characteristics selected from definite amyotrophic lateral sclerosis, amyotrophic lateral sclerosis symptom onset duration of less than about 18 months, limb-onset amyotrophic lateral sclerosis, plasma creatinine levels of about 72 µM/L or greater, concomitant riluzole administration, concomitant dexpramipexole administration, an ALSFRS-R score of greater than 36.0, a re-study progression rate greater than or equal to 0.8 points per month, a percentage predicted relaxed (slow) vital capacity (SVC) of less than or equal to 102.0, an ALSFRS-R fine motor domain score of greater than 10.0 points, ALSFRS-R bulbar domain score or greater than 9.0 points, an ALSFRS-R gross motor domain score of greater than 8.0 points, an abnormal neurological exam of the tongue, an abnormal neurological exam of the pharynx, larynx and swallowing, an abnormal neurological exam of the lower extremities, an abnormal neurological exam of the upper extremities, an abnormal neurological exam of the triceps, an abnormal neurological exam of the muscle mass and bulk, an abnormal neurological exam of the bicep, an abnormal neurological exam, a pulse rate of greater than 81.0 beats per minute, a diastolic blood pressure of greater than 82.0 mmHg, a systolic blood pressure of less than or equal to 117.0 mmHg, a creatinine value of greater than 72.0 µmol/L, a phosphorous value of less than or equal to 1.090 µmol/L, a platelet count of less than or equal to 248.0×109 cells/L, a cholesterol value of less than or equal to 5.3 mmol/L, a lactate dehydrogenase value of less than or equal to 161.0 U/L, a creatine phosphokinase value of less than or equal to 184.0 U/L, a bicarbonate value of less than or equal to 21.6 mmol/L, a triglyceride level of less than or equal to 1.4 mmol/L, a uric acid level of greater than 320.0 µmol/L, a gamma-glutamyltransferase (GGT) level of greater than 37.0 U/L, a total bilirubin level of less than or equal to 6.0 µmol/L, a urine pH of less than or equal to 5.5, or any combination thereof.

In certain embodiments, the subject with amyotrophic lateral sclerosis symptom onset duration of less than about 18 months is a subject with symptom onset selected from less than 18 months, less than about 17 months, less than about 16 months, less than about 15 months, less than about 14 months, less than about 13 months, less than about 12 months, less than about 11 months, less than about 10 months, less than about 9 months, less than about 8 months, less than about 7 months, less than about 6 months, less than about 5 months, less than about 4 months, less than about 3 months, less than about 2 months, and less than about 1 month. In certain embodiments, the subject with amyotrophic lateral sclerosis symptom onset duration of less than about 18 months is a subject with symptom onset selected from about 18 months, about 17 months, about 16 months, about 15 months about 14 months, about 13 months, about 12 months, about 11 months, about 10 months, about 9 months, about 8 months, about 7 months, about 6 months, about 5 months, about 4 months, about 3 months, about 2 months, and about 1 month.

In certain embodiments, the subject with a high level of serum creatinine is a subject with serum creatinine level selected from greater than about 40 µmol/L, greater than about 45 µmol/L, greater than about 50 µmol/L, greater than about 55 µmol/L, greater than about 60 µmol/L, greater than about 65 µmol/L, greater than about 70 µmol/L, greater than about 72 µmol/L of serum creatinine. In certain embodiments, the subject with a high level of serum creatinine is a subject with serum creatinine level selected from about 40 µmol/L, about 45 µmol/L, about 50 µmol/L, about 55 µmol/L, about 60 µmol/L, about 65 µmol/L, about 70 µmol/L, about 72 µmol/L of serum creatinine.

In certain embodiments, the subject with concomitant riluzole administration is a subject on a stable dosing regimen of riluzole. In certain embodiments, the subject with concomitant riluzole administration is a subject receiving about 50 milligrams of riluzole twice daily. In certain embodiments, the subject with concomitant riluzole administration is a subject who has been receiving riluzole for more than about thirty days. In certain embodiments, the subject with concomitant riluzole administration is a subject who has been receiving riluzole for about sixty days or more. In certain embodiments, the subject with concomitant dexpramipexole administration is a subject on a stable dosing regimen of dexpramipexole. In certain embodiments, the subject with concomitant dexpramipexole administration is a subject receiving about 75 milligrams of dexpramipexole twice daily. In certain embodiments, the subject with concomitant dexpramipexole administration is a subject receiving about 150 milligrams of dexpramipexole twice daily. In certain embodiments, the subject with concomitant dexpramipexole administration is a subject receiving about 300 milligrams of dexpramipexole twice daily.

In certain embodiments, treating amyotrophic lateral sclerosis in said subject is selected from improved ALSFRS-R score, improved CAFS rank, decreased mortality, increased life expectancy, and combinations thereof. In some embodiments, the subject exhibits a greater than 20% improvement in ALS Functional Rating Scale, Revised (ALSFRS-R) score when compared to baseline. In particular embodiments, the subject exhibits a greater than 30% improvement in ALS Functional Rating Scale, Revised (ALSFRS-R) score when compared to baseline. The ALSFRS-R measures 4 domains: pulmonary function, bulbar function, and gross and fine motor skills. There are a total of 12 questions, each scored from 0 to 4 for a total possible score of 48. The twelve questions and rating scale are provided in Cederbaum, et al., 169 J. NEUROL. SCI., 13-21 (1999) which is incorporated herein in its entirety.

In some embodiments, treating ALS can include slowing progression of ALS, reducing intensity of symptoms associated with ALS, reducing onset of symptoms associated with ALS, reducing weight loss associated with ALS, reversing weight loss associated with ALS, delaying mortality, and combinations thereof. In particular embodiments, the symptoms associated with ALS may be, for example, decreases in fine motor function, decreases in gross motor function, decreases in bulbar function, decreases in respiratory function, and combinations thereof. Further, in other embodiments, the symptoms associated with ALS can include difficulty with daily activities, such as, for example, difficulty with walking, speech, eating, swallowing, writing, climbing stairs, cutting food, turning in bed, dressing, maintaining hygiene, and combinations thereof, and may experience other symptoms, such as, for example, difficulty breathing, dyspnea, orthopnea, respiratory insufficiency, increased salivation and combinations thereof. In particular embodiments of the various methods, a compound of formula A-1 through A-44 or B-1 through B-7, or a pharmaceutically acceptable salt thereof, may be used to treat ALS. For example, in some embodiments, individuals diagnosed with ALS within two years or less may be treated with a compound of formula A-1 through A-44 or B-1 through B-7, or a pharmaceutically acceptable salt thereof, to reduce, eliminate, or slow advancement of ALS or symptoms associated with ALS such as, for example, fine motor function loss, gross motor function loss, loss of bulbar function, and loss of respiratory function. In other embodiments, a compound of formula A-1 through A-44 or B-1 through B-7, or a pharmaceutically acceptable salt thereof, may be administered to reduce or slow the advancement of symptoms including, but not limited to, trembling, loss of muscle control, loss of ability to write, loss of ability to move or roll over, loss of speech, inability to swallow, difficulty breathing, and so on. In other embodiments, individuals with advanced symptoms or individuals who were diagnosed with ALS more than two years before beginning treatment may be treated with a compound of formula A-1 through A-44 or B-1 through B-7, or a pharmaceutically acceptable salt thereof, and such individuals may respond to treatment by exhibiting a reduction or elimination of one or more symptoms related to ALS, or in certain embodiments, the rate of symptom onset or advancement may be reduced, for example; the rate of motor function loss, the rate of loss of speech, and/or difficulty swallowing may be slowed and/or reduced.

In embodiments, the subject is administered a therapeutically effective amount of a compound of formula A-1 through A-44 or B-1 through B-7, or a pharmaceutically acceptable salt thereof, and the decline of muscle loss is reduced. In embodiments, the subject is administered a therapeutically effective amount of a compound of formula A-1 through A-44 or B-1 through B-7, or a pharmaceutically acceptable salt thereof, and the decline of serum creatinine is reduced. In additional embodiments of the various methods, compound of formula A-1 through A-44 or B-1 through B-7, or a pharmaceutically acceptable salt thereof, may be administered to subjects in need of treatment for excessive weight loss associated with ALS. Without wishing to be bound by theory, the precipitous weight loss that is a cardinal symptom of ALS may be associated with increased energy expenditure, skeletal muscle hypermetabolism, and the systematic wasting of muscle tissue known as cachexia.

In some embodiments, the method is carried out for a time period selected from at least about twelve months, at least about eighteen months, at least about two years, at least about four years, at least about six years, at least about eight years, at least about ten years, at least about twenty years, and until the subject dies. In other embodiments, the method is carried out at least daily for an indefinite amount of time.

The present application provides for a method of identifying a patient who will respond to treatment with a compound of formula A-1 through A-44 or B-1 through B-7, or a pharmaceutically acceptable salt thereof, comprising: diagnosing a patient with EEC definite ALS; measuring the serum creatinine levels of the patient; and identifying the patient as a responder if the serum creatinine levels are greater than about 72 µmol/L. Some embodiments include methods of identifying a subject that will likely respond to treatments described herein. In some embodiments, the subject will exhibit one or more of the following characteristics: definite ALS as defined by the El Escorial diagnosis criteria, amyotrophic lateral sclerosis symptom onset duration of less than about 18 months, limb-onset amyotrophic lateral sclerosis, plasma creatinine levels of about 72 µM/L or greater, concomitant riluzole administration, concomitant dexpramipexole administration, an ALSFRS-R score of greater than 36.0, a re-study progression rate greater than or equal to 0.8 points per month, a percentage predicted relaxed (slow) vital capacity (SVC) of less than or equal to 102.0, an ALSFRS-R fine motor domain score of greater than 10.0 points, ALSFRS-R bulbar domain score or greater than 9.0 points, an ALSFRS-R gross motor domain score of greater than 8.0 points, an abnormal neurological exam of the tongue, an abnormal neurological exam of the pharynx, larynx and swallowing, an abnormal neurological exam of the lower extremities, an abnormal neurological exam of the upper extremities, an abnormal neurological exam of the triceps, an abnormal neurological exam of the muscle mass and bulk, an abnormal neurological exam of the bicep, an abnormal neurological exam, a pulse rate of greater than 81.0 beats per minute, a diastolic blood pressure of greater than 82.0 mmHg, a systolic blood pressure of less than or equal to 117.0 mmHg, a creatinine value of greater than 72.0 µmol/L, a phosphorous value of less than or equal to 1.090 µmol/L, a platelet count of less than or equal to $248.0 \times 10^9$ cells/L, a cholesterol value of less than or equal to 5.3 mmol/L, a lactate dehydrogenase value of less than or equal to 161.0 U/L, a creatine phosphokinase value of less than or equal to 184.0 U/L, a bicarbonate value of less than or equal to 21.6 mmol/L, a triglyceride level of less than or equal to 1.4 mmol/L, a uric acid level of greater than 320.0 µmol/L, a gamma-glutamyltransferase (GGT) level of greater than 37.0 U/L, a total bilirubin level of less than or equal to 6.0 µmol/L, a urine pH of less than or equal to 5.5, or any combination thereof. In some embodiments, the subject will have at least one of the above characteristics. In some embodiments, the subject will have more than one of the above characteristics. In embodiments, the method further comprises monitoring said subject for any clinical features associated with amyotrophic lateral sclerosis. In embodiments, the method further comprises initiating therapy with a therapeutically effective amount of (6R)-2-amino-4,5,6,7-tetrahydro-6-(propylamino)benzothiazole or a pharmaceutically acceptable salt thereof upon diagnosis of amyotrophic lateral sclerosis. In certain embodiments, the subject exhibits symptoms of amyotrophic lateral sclerosis. In certain embodiments, the subject has definite amyotrophic lateral sclerosis, probable amyotrophic lateral sclerosis, possible amyotrophic lateral sclerosis or suspected amyotrophic lateral sclerosis.

The structures associated with some of the chemical names referred to herein are depicted below. These structures may be unsubstituted, as shown below, or a substituent may independently be in any position normally occupied by a hydrogen atom when the structure is unsubstituted. Unless a point of attachment is indicated by

attachment may occur at any position normally occupied by a hydrogen atom.

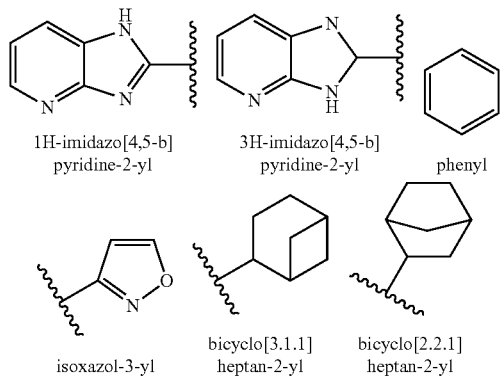

179

-continued

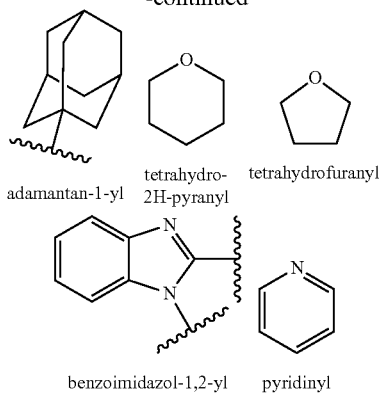

adamantan-1-yl  tetrahydro-2H-pyranyl  tetrahydrofuranyl benzoimidazol-1,2-yl  pyridinyl Formulas A and B Some embodiments include a compound represented by Formula A-1:

Formula A-1

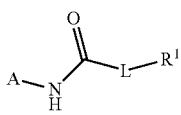

With respect to Formula A-1 or any embodiments of Formula A-1, A is optionally substituted imidazo[4,5-b]pyridin-2-yl, such as optionally substituted 1H-imidazo[4,5-b]pyridin-2-yl or optionally substituted 3H-imidazo[4,5-b]pyridin-2-yl. If the imidazo[4,5-b]pyridin-2-yl is substituted, it may have 1, 2, 3, or 4 substituents. Any substituent may be included on the imidazo[4,5-b]pyridin-2-yl. In some embodiments, some or all of the substituents on the imidazo[4,5-b]pyridin-2-yl may have: from 0 to 10 carbon atoms and from 0 to 10 heteroatoms, wherein each heteroatom is independently: O, N, S, F, Cl, Br, or I (provided that there is at least 1 non-hydrogen atom); and/or a molecular weight of 15 g/mol to 500 g/mol. For example, the substituents may be $C_{1-10}$ optionally substituted alkyl, such as $CH_3$, $C_2H_5$, $C_3H_7$, cyclic $C_3H_5$, $C_4H_9$, cyclic $C_4H_7$, $C_5H_{11}$, cyclic $C_5H_9$, $C_6H_{13}$, cyclic $C_6H_{11}$, etc., which may be optionally substituted; $C_{1-10}$ optionally substituted alkoxy such as $OCH_3$, $OC_2H_5$, $OC_3H_7$, cyclic $OC_3H_5$, $OC_4H_9$, cyclic $OC_4H_7$, $OC_5H_{11}$, cyclic $OC_5H_9$, $OC_6H_{13}$, cyclic $OC_6H_{11}$, etc.; halo, such as F, Cl, Br, I; OH; CN; $NO_2$; $C_{1-6}$ fluoroalkyl, such as $CF_3$, $CF_2H$, $C_2F5$, etc.; $C_{1-6}$ fluoroalkoxy, such as $OCF_3$, $OCF_2H$, $OC_2F_5$, etc.; a $C_{1-10}$ ester such as —$O_2CCH_3$, —$CO_2CH_3$, —$O_2CC_2H_5$, —$CO_2C_2H_5$, —$O_2C$-phenyl, —$CO_2$-phenyl, etc.; a $C_{1-10}$ ketone such as —$COCH_3$, —$COC_2H_5$, —$COC_3H_7$, —CO-phenyl, etc.; or a $C_{1-10}$ amine such as $NH_2$, $NH(CH_3)$, $N(CH_3)_2$, $N(CH_3)C_2H_5$, etc.

In some embodiments, any or all of the substituents of 1H-imidazo[4,5-b]pyridin-2-yl or 3H-imidazo[4,5-b]pyridin-2-yl are independently $CF_3$, Cl, CN, or $OCH_3$. In some embodiments, A has a $CF_3$ substituent. In some embodiments, A has a Cl substituent. In some embodiments, A has a CN substituent. In some embodiments, A has an $OCH_3$ substituent.

180

In some embodiments of Formula A-1, A may be:

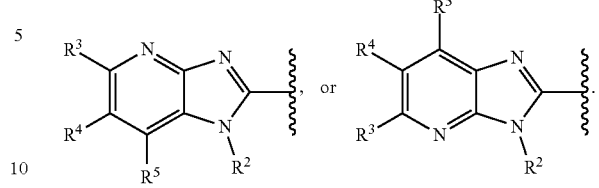

Some embodiments of Formula A-1 may include a compound represented by one or more of Formulas A-2 through A-42 or a pharmaceutically acceptable salt thereof:

Formula A-2

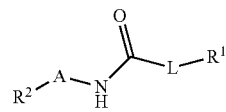

Formula A-3

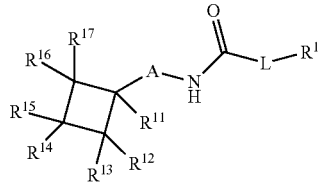

Formula A-4

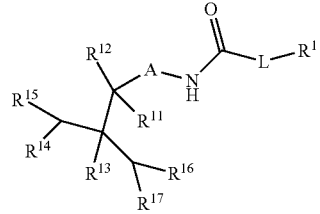

Formula A-5

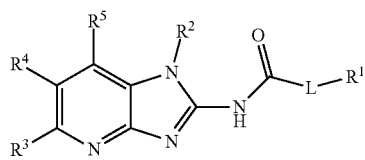

Formula A-6

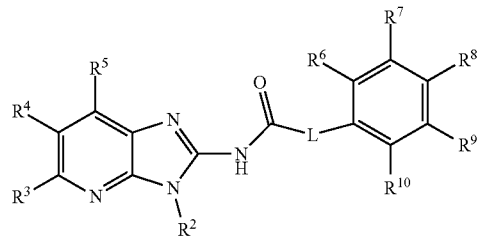

Formula A-7

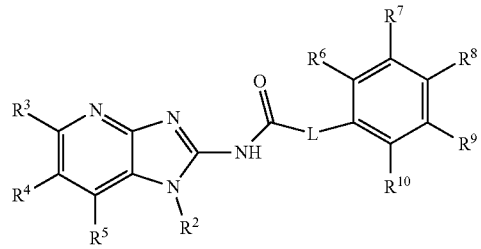

Formula A-8
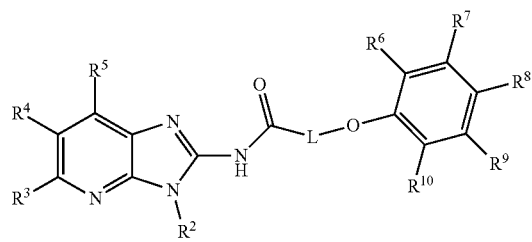
Formula A-9
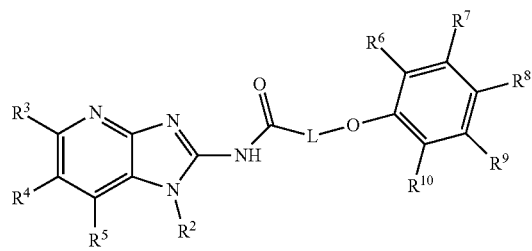
Formula A-10
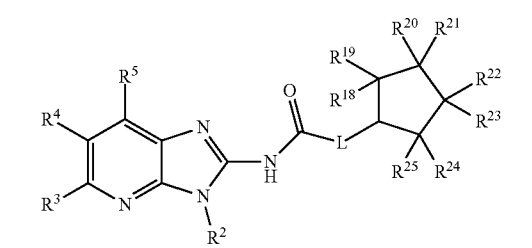
Formula A-11
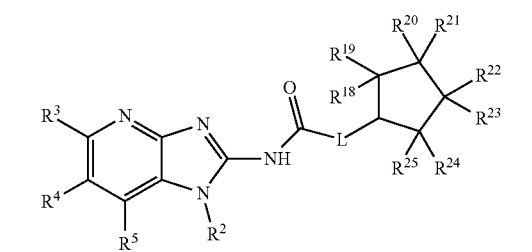
Formula A-12
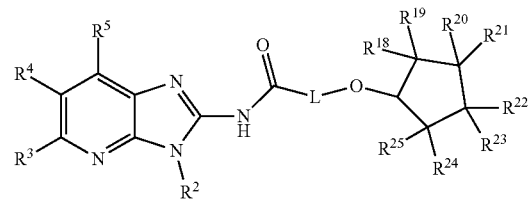
Formula A-13
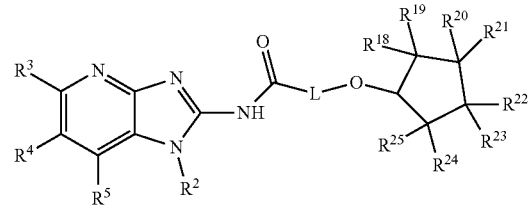
Formula A-14
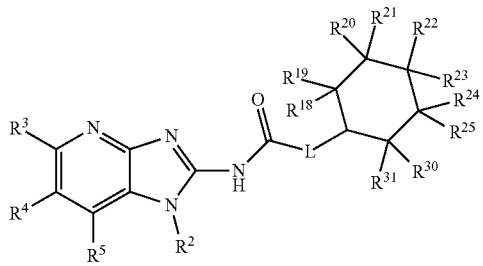
Formua A-15
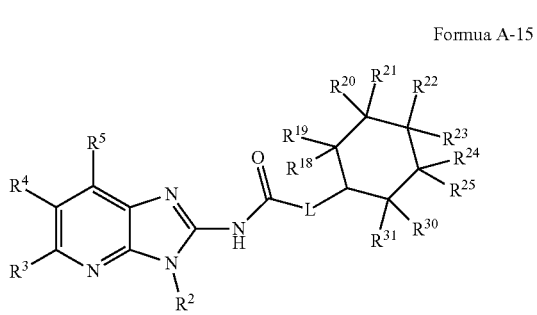
Formula A-16
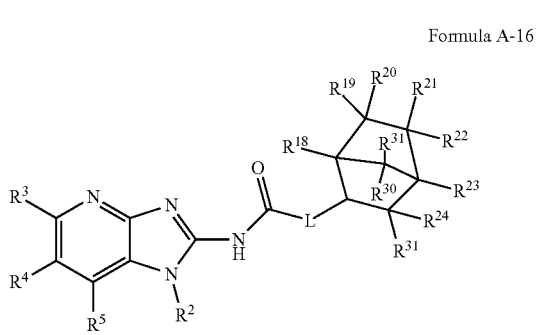
Formula A-17
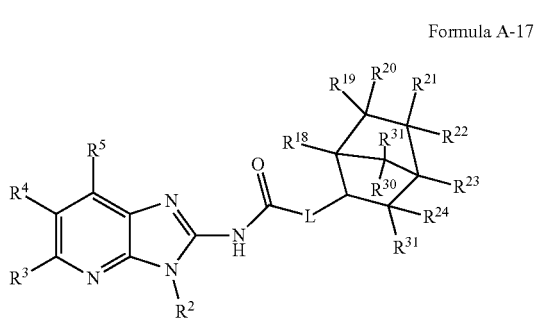
Formula A-18
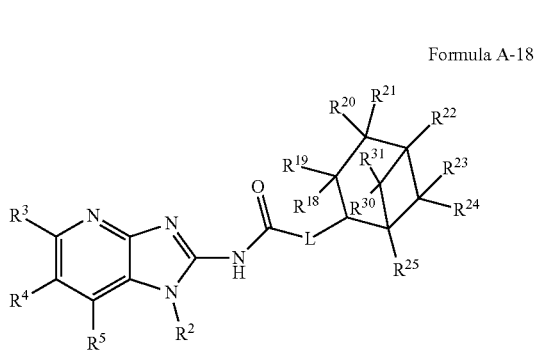

Formula A-19
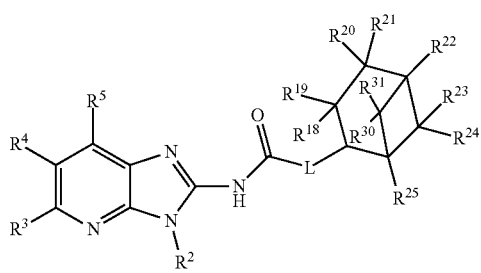
Formula A-20
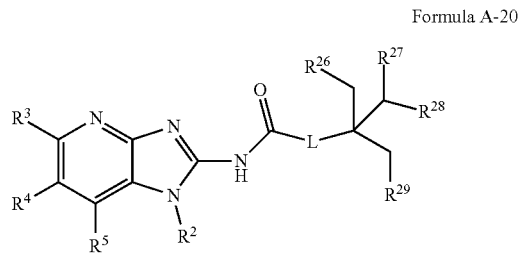
Formula A-21

Formula A-22
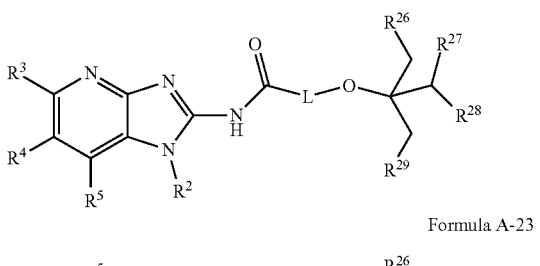
Formula A-23
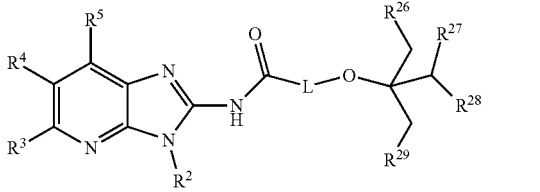
Formula A-24
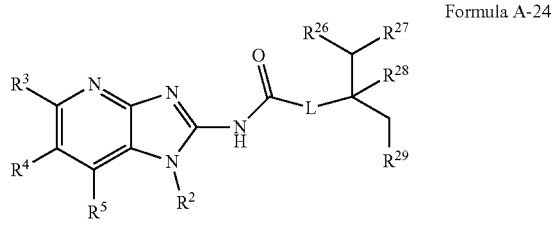
Formula A-25
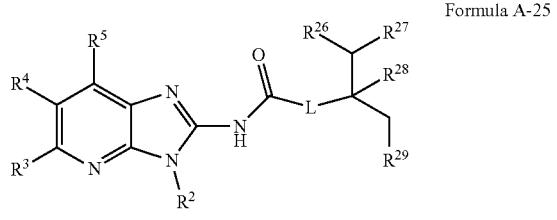
Formula A-26
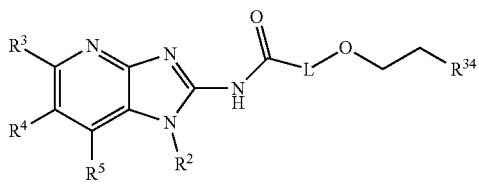
Formula A-27
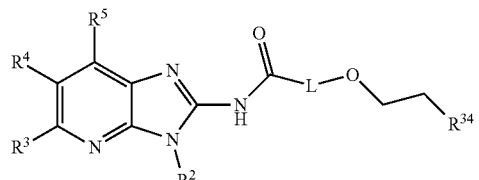
Formula A-28
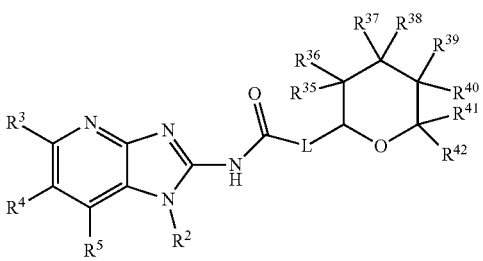
Formula A-29
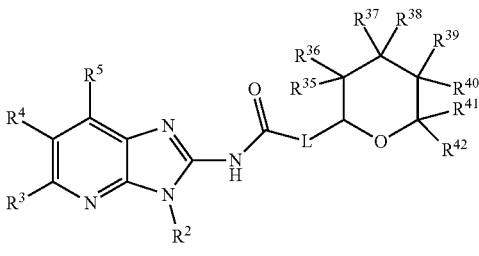
Formula A-30
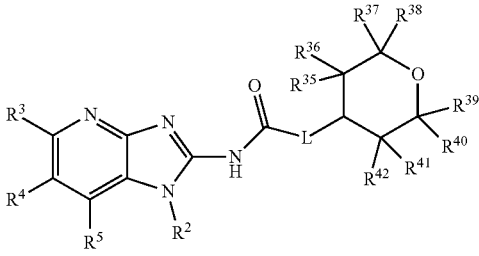
Formula A-31
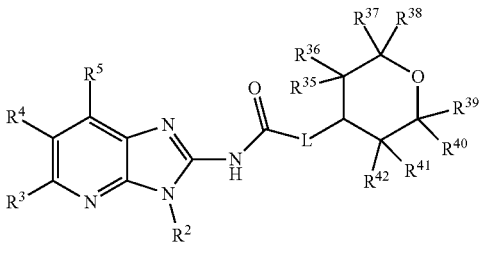

Formula A-32
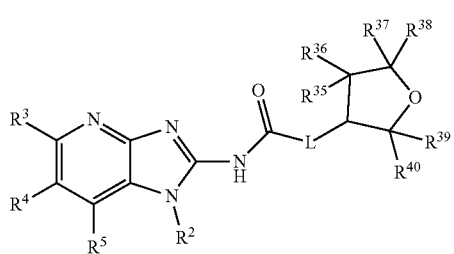

Formula A-33
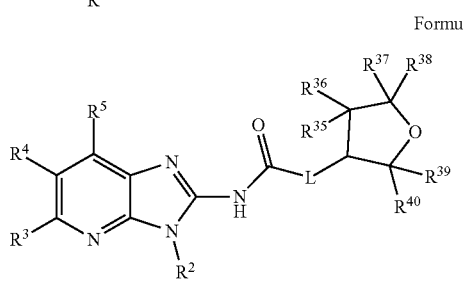

Formula A-34
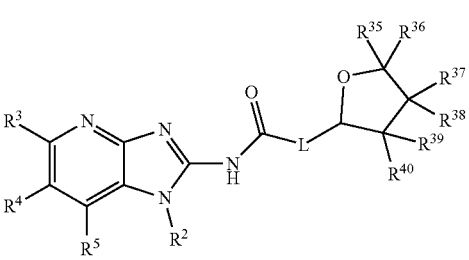

Formula A-35
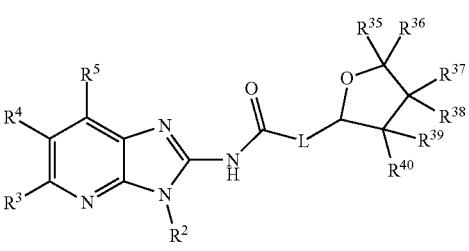

Formula A-36
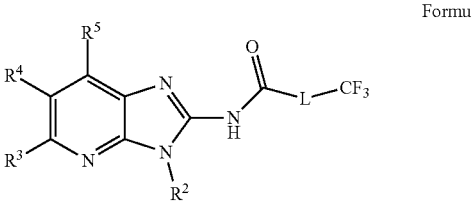

Formula A-37
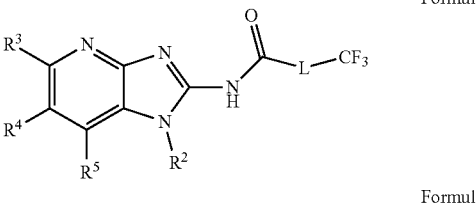

Formula A-38
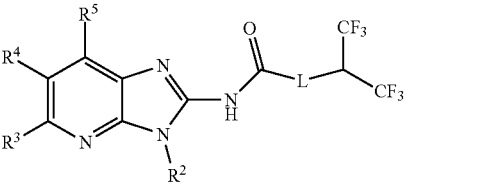

Formula A-39
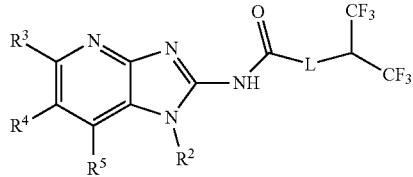

Formula A-40
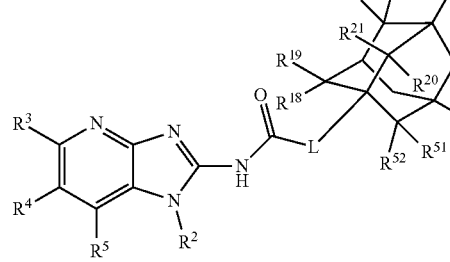

Formula A-41
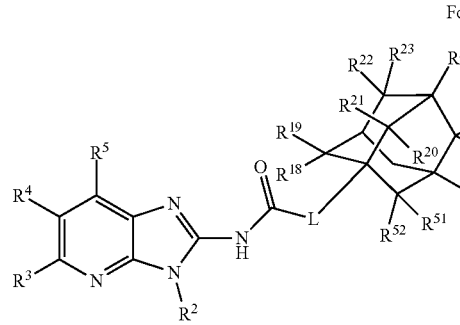

Formula A-42
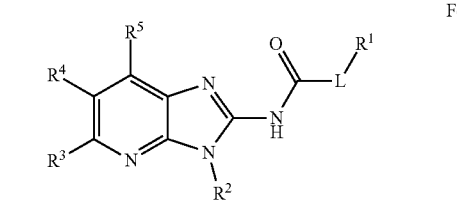

With respect to any relevant embodiment or structural representation of Formula A-1 herein, such as Formulas A-1 through A-42, L is $CH_2$, $CF_2$, $C_2H_4$ (such as $CH_2CH_2$, $CH(CH_3)$, etc.), $C_3H_6$ (such as $CH_2CH_2CH_2$, $CH_2CH(CH_3)$, $CH(CH_3)CH_2$, $CH(CH_3)_2$, etc.), O, $CH_2O$, $C_2H_4O$ (such as $OCH_2CH_2$ (where the O atom may be on either side of the $CH_2CH_2$), $CH_2OCH_2$, $OCH(CH_3)$, etc.), or $C_3H_6O$.

In some embodiments of Formula A-1, such as Formulas A-1 through A-42, L is $CH_2$, $CF_2$, $CH_2CH_2$, $CH(CH_3)_2$, or $CH(CH_3)$.

In some embodiments of Formula A-1, such as Formulas A-1 through A-42, L is $CH_2$.

In some embodiments of Formula A-1, such as Formulas A-1 through A-42, L is $CH_2CH_2$.

In some embodiments of Formula A-1, such as Formulas A-1 through A-42, L is $CH(CH_3)_2$.

In some embodiments of Formula A-1, such as Formulas A-1 through A-42, L is $CH(CH_3)$.

With respect to any relevant embodiment or structural representation of Formula A-1 herein, such as Formulas A-1 through A-42, $R^1$ may be $C_{1-12}$ optionally substituted alkyl, such as optionally substituted $CH_3$, optionally substituted $C_2H_5$, optionally substituted $C_3H_7$, optionally substituted cyclic $C_3H_5$, optionally substituted $C_4H_9$, optionally substituted cyclic C₄H₇, optionally substituted C₅H₁₁, optionally substituted cyclic C₅H₉, optionally substituted C₆H₁₃, optionally substituted cyclic C₆H₁₁, optionally substituted bicyclo[2.2.1]heptan-2-yl, optionally substituted bicyclo [3.1.1]heptan-2-yl, etc.; C$_{1-12}$ optionally substituted —O— alkyl, such as optionally substituted —O—CH₃, optionally substituted —O—C₂H₅, optionally substituted —O—C₃H₇, optionally substituted cyclic —O—C₃H₅, optionally substituted —O—C₄H₉, optionally substituted cyclic —O—C₄H₇, optionally substituted —O—C₅H₁₁, optionally substituted cyclic —O—C₅H₉, optionally substituted —O—C₆H₁₃, optionally substituted cyclic —O—C₆H₁₁, optionally substituted (2,3-dihydro-1H-inden-1-yl)oxy, etc.; optionally substituted C$_{6-10}$ aryl, such as optionally substituted phenyl; optionally substituted C$_{6-10}$—O-aryl, such as optionally substituted —O-phenyl; or optionally substituted C$_{2-9}$ heterocyclyl, such as optionally substituted isoxazolyl, optionally substituted tetrahydropyranyl, optionally substituted tetrahydrofuryanyl, etc. In some embodiments, $R^1$ is CH₃, C$_{2-12}$ optionally substituted alkyl, C$_{1-12}$ optionally substituted —O-alkyl, optionally substituted C$_{6-10}$ aryl, optionally substituted C$_{6-10}$ O-aryl, or optionally substituted C$_{2-9}$ heterocyclyl.

With respect to any relevant embodiment or structural representation of Formula A-1 herein, such as Formulas A-1 through A-42, in some embodiments, $R^1$ is optionally substituted phenyl. In some embodiments, $R^1$ is C$_{3-4}$ alkyl. In some embodiments, $R^1$ is optionally substituted bicyclo [2.2.1]heptan-2-yl. In some embodiments, $R^1$ is optionally substituted isoxazol-3-yl. In some embodiments, $R^1$ is CF₃. In some embodiments, $R^1$ is optionally substituted cyclopentyl. In some embodiments, $R^1$ is optionally substituted cyclohexyl. In some embodiments, $R^1$ is methyl. In some embodiments, $R^1$ is optionally substituted bicyclo[3.1.1] heptan-2-yl. In some embodiments, $R^1$ is optionally substituted —O— phenyl. In some embodiments, $R^1$ is optionally substituted CH(CF₃)₂. In some embodiments, $R^1$ is C$_{2-4}$— O-alkyl. In some embodiments, $R^1$ is optionally substituted adamantan-1-yl. In some embodiments, $R^1$ is optionally substituted tetrahydro-2H-pyranyl. In some embodiments, $R^1$ is optionally substituted (2,3-dihydro-1H-inden-1-yl)oxy. In some embodiments, $R^1$ is optionally substituted tetrahydrofuranyl.

With respect to any relevant embodiment or structural representation of Formula A-1 herein, such as Formulas A-1 through A-42, in some embodiments, $R^1$ can be one of the following:

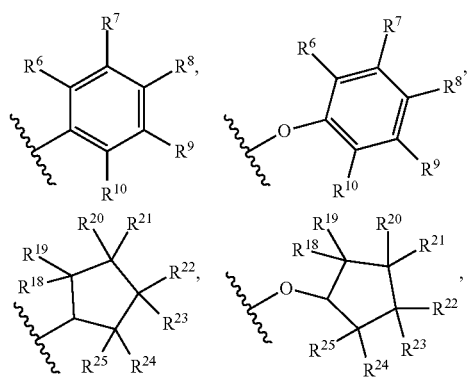

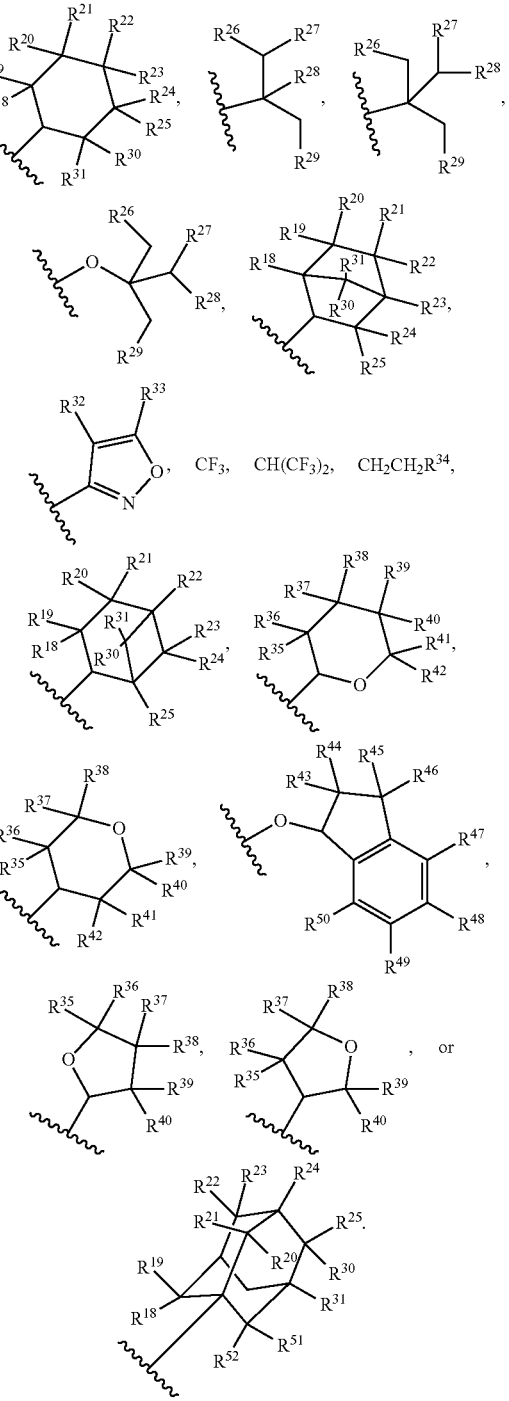

With respect to any relevant embodiment or structural representation of Formula A-1 herein, such as Formulas A-2 and A-42 through A-42, $R^2$ is —R$^\alpha$-Cy. R$^\alpha$ is a bond or C$_{1-12}$ optionally substituted alkyl, such as CH₂, C₂H₄, C₃H₆, C₄H₈, C₅H₁₀, C₆H₁₂, cyclic C₃H₅, cyclic C₄H₇, cyclic C₅H₉, cyclic C₆H₁₁, etc. Cy is H; optionally substituted C$_{6-10}$ aryl, such as optionally substituted phenyl; or optionally substituted C$_{2-9}$ heterocyclyl, such as optionally substituted azetidinyl, optionally substituted oxatanyl, optionally substituted thietanyl, etc. In some embodiments, $R^2$ is optionally substituted cyclobutyl or optionally substituted 2-methylpropyl. In some embodiments, $R^2$ is:

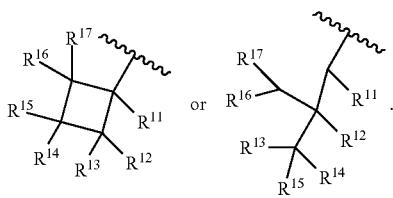

In some embodiments of Formula A-1 through A-44, $R^2$ is cyclobutyl. In some embodiments, $R^2$ is 2-methylpropyl.

To any relevant embodiment or structural representation of Formula A-1 through A-44 herein the following applies. Generally $R^3$-$R^{52}$, may be H or any substituent, such as a substituent having 0 to 12 atoms or 0 to 6 carbon atoms and 0 to 5 heteroatoms, wherein each heteroatom is independently: O, N, S, F, Cl, Br, or I, and/or having a molecular weight of 15 g/mol to 300 g/mol. Any of $R^3$-$R^{52}$ may comprise: a) 1 or more alkyl moieties optionally substituted with, or optionally connected by or to, b) 1 or more functional groups, such as C=C, C≡C, CO, $CO_2$, CON, $NCO_2$, OH, SH, O, S, N, N=C, F, Cl, Br, I, CN, $NO_2$, $CO_2H$, $NH_2$, etc.; or may be a substituent having no alkyl portion, such as F, Cl, Br, I, $NO_2$, CN, $NH_2$, OH, COH, $CO_2H$, etc.

With respect to any relevant embodiment or structural representation of Formula A-1 through A-44 herein, some non-limiting examples of $R^3$ may include $R^A$, F, Cl, CN, $OR^A$, $CF_3$, $NO_2$, $NR^AR^B$, $COR^A$, $CO_2R^A$, $OCOR^A$, $NR^A\text{-}COR^B$, $CONR^AR^B$, etc. In some embodiments, $R^3$ may be H; F; Cl; CN; $CF_3$; OH; $NH_2$; $C_{1-6}$ alkyl, such as methyl, ethyl, propyl isomers (e.g. n-propyl and isopropyl), cyclopropyl, butyl isomers, cyclobutyl isomers (e.g. cyclobutyl and methylcyclopropyl), pentyl isomers, cyclopentyl isomers, hexyl isomers, cyclohexyl isomers, etc.; or $C_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^3$ may be H, F, Cl, Br, I, CN, $C_{1-12}$ optionally substituted alkyl, $C_{1-12}$ optionally substituted —O-alkyl, optionally substituted $C_{2-9}$ heterocyclyl, optionally substituted $C_{6-10}$ aryl, optionally substituted $C_{2-9}$—O-heterocyclyl, optionally substituted $C_{6-10}$—O-aryl, $C_{1-12}$ optionally substituted acylamino, $C_{1-12}$ optionally substituted aminoacyl, or optionally substituted $C_{1-12}$ aminoalkyl (or alkyl with an amino substituent). In some embodiments, $R^3$ may be H, $CH_3$, OH, $OCH_3$, $NH_2$, $NHCH_3$, $N(CH_3)_2$, COH, $COCH_3$, $CF_3$, Cl, CN, or $OCH_3$. In some embodiments, $R^3$ may be H, $CF_3$, Cl, CN, or $OCH_3$. In some embodiments, $R^3$ is H. In some embodiments, $R^3$ is $CF_3$. In some embodiments, $R^3$ is Cl. In some embodiments, $R^3$ is CN. In some embodiments, $R^3$ is $OCH_3$.

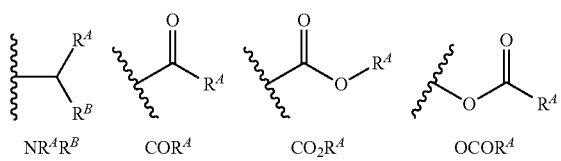

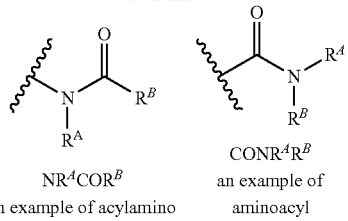

NR$^A$COR$^B$
an example of acylamino

CONR$^A$R$^B$
an example of aminoacyl

To any relevant embodiment or structural representation of Formula A-1 through A-44 herein the following applies. Each $R^A$ may independently be H, or $C_{1-12}$ alkyl, including: linear or branched alkyl having a formula $C_aH_{a+1}$, or cycloalkyl having a formula $C_aH_{a-1}$, wherein a is 1, 2, 3, 4, 5, 6, 7, 8, 9, 10, 11, or 12, such as linear or branched alkyl of a formula: $CH_3$, $C_2H_5$, $C_3H_7$, $C_4H_9$, $C_5H_{11}$, $C_6H_{13}$, $C_7H_{15}$, $C_8H_{17}$, $C_9H_{19}$, $C_{10}H_{21}$, etc., or cycloalkyl of a formula: $C_3H_5$, $C_4H_7$, $C_5H_9$, $C_6H_{11}$, $C_7H_{13}$, $C_8H_{15}$, $C_9H_{17}$, $C_{10}H_{19}$, etc. In some embodiments, $R^A$ may be H or $C_{1-6}$ alkyl. In some embodiments, $R^A$ may be H or $C_{1-3}$ alkyl. In some embodiments, $R^A$ may be H or $CH_3$. In some embodiments, $R^A$ may be H.

To any relevant embodiment or structural representation of Formula A-1 through A-44 herein the following applies. Each $R^B$ may independently be H, or $C_{1-12}$ alkyl, including: linear or branched alkyl having a formula $C_aH_{a+1}$, or cycloalkyl having a formula $C_aH_a$, wherein a is 1, 2, 3, 4, 5, 6, 7, 8, 9, 10, 11, or 12, such as linear or branched alkyl of a formula: $CH_3$, $C_2H_5$, $C_3H_7$, $C_4H_9$, $C_5H_{11}$, $C_6H_{13}$, $C_8H_{17}$, $C_7H_{15}$, $C_9H_{19}$, $C_{10}H_{21}$, etc., or cycloalkyl of a formula: $C_3H_5$, $C_4H_7$, $C_5H_9$, $C_6H_{11}$, $C_7H_{13}$, $C_8H_{15}$, $C_9H_{17}$, $C_{10}H_{19}$, etc. In some embodiments, $R^B$ may be H or $C_{1-3}$ alkyl. In some embodiments, $R^B$ may be H or $CH_3$. In some embodiments, $R^B$ may be H.

With respect to any relevant embodiment or structural representation of Formula A-1 through A-44 herein, some non-limiting examples of $R^4$ may include $R^A$, F, Cl, CN, $OR^A$, $CF_3$, $NO_2$, $NR^AR^B$, $COR^A$, $CO_2R^A$, $OCOR^A$, $NR^A\text{-}COR^B$, $CONR^AR^B$, etc. In some embodiments, $R^4$ may be H; F; Cl; CN; $CF_3$; OH; $NH_2$; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc., or —O—$C_{1-6}$ alkyl, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^4$ may be H, F, Cl, Br, I, CN, $C_{1-12}$ optionally substituted alkyl, $C_{1-12}$ optionally substituted —O-alkyl, optionally substituted $C_{2-9}$ heterocyclyl, optionally substituted $C_{6-10}$ aryl, optionally substituted $C_{2-9}$—O-heterocyclyl, optionally substituted $C_{6-10}$—O-aryl, $C_{1-12}$ optionally substituted acylamino, $C_{1-12}$ optionally substituted aminoacyl, or optionally substituted $C_{1-12}$ aminoalkyl. In some embodiments, $R^4$ may be H, $CF_3$, or Cl. In some embodiments, $R^4$ is H. In some embodiments, $R^4$ is $CF_3$. In some embodiments, $R^4$ is Cl.

With respect to any relevant embodiment or structural representation of Formula A-1 through A-44 herein, some non-limiting examples of $R^5$ may include $R^A$, F, Cl, CN, $OR^A$, $CF_3$, $NO_2$, $NR^AR^B$, $COR^A$, $CO_2R^A$, $OCOR^A$, $NR^A\text{-}COR^B$, $CONR^AR^B$, etc. In some embodiments, $R^5$ may be H; F; Cl; CN; $CF_3$; OH; $NH_2$; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or $C_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^6$ may be H, F, Cl, Br, I, CN, $C_{1-12}$ optionally substituted alkyl, $C_{1-12}$ optionally substituted —O-alkyl, optionally substituted $C_{2-9}$ heterocyclyl, optionally substituted $C_{6-10}$ aryl, optionally substituted $C_{2-9}$—O-heterocyclyl, optionally substituted $C_{6-10}$—O-aryl, $C_{1-12}$ optionally substituted acylamino, $C_{1-12}$ optionally substituted aminoacyl, or optionally substituted $C_{1-12}$ aminoalkyl. In some embodiments, $R^5$ may be H, F, Cl, CN, $CF_3$, OH; $NH_2$, $CH_3$, $CH_2CH_3$, $CH_2CH_2CH_3$, $CH(CH_3)_2$, —$OCH_3$, —$OCH_2CH_3$, —$OCH_2CH_2CH_3$, or —$OCH(CH_3)_2$. In some embodiments, $R^5$ may be H.

With respect to any relevant embodiment or structural representation of Formula A-1 through A-44 herein, some non-limiting examples of $R^6$ may include $R^A$, F, Cl, CN, $OR^A$, $CF_3$, $NO_2$, $NR^AR^B$, $COR^A$, $CO_2R^A$, $OCOR^A$, $NR^A$-$COR^B$, $CONR^AR^B$, etc. In some embodiments, $R^6$ may be H; F; Cl; CN; $CF_3$; OH; $NH_2$; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or $C_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^6$ may be H, F, Cl, CN, $CF_3$, OH; $NH_2$, $CH_3$, $CH_2CH_3$, $CH_2CH_2CH_3$, $CH(CH_3)_2$, —$OCH_3$, —$OCH_2CH_3$, —$OCH_2CH_2CH_3$, or —$OCH(CH_3)_2$. In some embodiments, $R^6$ may be H.

With respect to any relevant embodiment or structural representation of Formula A-1 through A-44 herein, some non-limiting examples of $R^7$ may include $R^A$, F, Cl, CN, $OR^A$, $CF_3$, $NO_2$, $NR^AR^B$, $COR^A$, $CO_2R^A$, $OCOR^A$, $NR^A$-$COR^B$, $CONR^AR^B$, etc. In some embodiments, $R^7$ may be H; F; Cl; CN; $CF_3$; OH; $NH_2$; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or $C_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^7$ may be H, F, Cl, CN, $CF_3$, OH; $NH_2$, $CH_3$, $CH_2CH_3$, $CH_2CH_2CH_3$, $CH(CH_3)_2$, —$OCH_3$, —$OCH_2CH_3$, —$OCH_2CH_2CH_3$, or —$OCH(CH_3)_2$. In some embodiments, $R^7$ may be H.

With respect to any relevant embodiment or structural representation of Formula A-1 through A-44 herein, some non-limiting examples of $R^8$ may include $R^A$, F, Cl, CN, $OR^A$, $CF_3$, $NO_2$, $NR^AR^B$, $COR^A$, $CO_2R^A$, $OCOR^A$, $NR^A$-$COR^B$, $CONR^AR^B$, etc. In some embodiments, $R^8$ may be H; F; Cl; CN; $CF_3$; OH; $NH_2$; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or $C_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^8$ may be H, F, Cl, CN, $CF_3$, OH; $NH_2$, $CH_3$, $CH_2CH_3$, $CH_2CH_2CH_3$, $CH(CH_3)_2$, —$OCH_3$, —$OCH_2CH_3$, —$OCH_2CH_2CH_3$, or —$OCH(CH_3)_2$. In some embodiments, $R^8$ is H. In some embodiments, $R^8$ is F.

With respect to any relevant embodiment or structural representation of Formula A-1 through A-44 herein, some non-limiting examples of $R^9$ may include $R^A$, F, Cl, CN, $OR^A$, $CF_3$, $NO_2$, $NR^AR^B$, $COR^A$, $CO_2R^A$, $OCOR^A$, $NR^A$-$COR^B$, $CONR^AR^B$, etc. In some embodiments, $R^9$ may be H; F; Cl; CN; $CF_3$; OH; $NH_2$; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or $C_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^9$ may be H, F, Cl, CN, $CF_3$, OH; $NH_2$, $CH_3$, $CH_2CH_3$, $CH_2CH_2CH_3$, $CH(CH_3)_2$, —$OCH_3$, —$OCH_2CH_3$, —$OCH_2CH_2CH_3$, or —$OCH(CH_3)_2$. In some embodiments, $R^9$ may be H.

With respect to any relevant embodiment or structural representation of Formula A-1 through A-44 herein, some non-limiting examples of $R^{10}$ may include $R^A$, F, Cl, CN, $OR^A$, $CF_3$, $NO_2$, $NR^AR^B$, $COR^A$, $CO_2R^A$, $OCOR^A$, $NR^A$-$COR^B$, $CONR^AR^B$, etc. In some embodiments, $R^{10}$ may be H; F; Cl; CN; $CF_3$; OH; $NH_2$; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or $C_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^{10}$ may be H, F, Cl, CN, $CF_3$, OH; $NH_2$, $CH_3$, $CH_2CH_3$, $CH_2CH_2CH_3$, $CH(CH_3)_2$, —$OCH_3$, —$OCH_2CH_3$, —$OCH_2CH_2CH_3$, or —$OCH(CH_3)_2$. In some embodiments, $R^{10}$ may be H.

With respect to any relevant embodiment or structural representation of Formula A-1 through A-44 herein, some non-limiting examples of $R^{10}$ may include $R^A$, F, Cl, CN, $OR^A$, $CF_3$, $NO_2$, $NR^AR^B$, $COR^A$, $CO_2R^A$, $OCOR^A$, $NR^A$-$COR^B$, $CONR^AR^B$, etc. In some embodiments, $R^{10}$ may be H; F; Cl; CN; $CF_3$; OH; $NH_2$; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or $C_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^{11}$ is H, $CH_3$, F, Cl, or $CF_3$. In some embodiments, $R^{11}$ may be H.

With respect to any relevant embodiment or structural representation of Formula A-1 through A-44 herein, some non-limiting examples of $R^{12}$ may include $R^A$, F, Cl, CN, $OR^A$, $CF_3$, $NO_2$, $NR^AR^B$, $COR^A$, $CO_2R^A$, $OCOR^A$, $NR^A$-$COR^B$, $CONR^AR^B$, etc. In some embodiments, $R^{12}$ may be H; F; Cl; CN; $CF_3$; OH; $NH_2$; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or $C_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^{12}$ is H, $CH_3$, F, Cl, or $CF_3$. In some embodiments, $R^{12}$ may be H.

With respect to any relevant embodiment or structural representation of Formula A-1 through A-44 herein, some non-limiting examples of $R^{13}$ may include $R^A$, F, Cl, CN, $OR^A$, $CF_3$, $NO_2$, $NR^AR^B$, $COR^A$, $CO_2R^A$, $OCOR^A$, $NR^A\text{-}COR^B$, $CONR^AR^B$, etc. In some embodiments, $R^{13}$ may be H; F; Cl; CN; $CF_3$; OH; $NH_2$; $C_{1\text{-}6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or $C_{1\text{-}6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^{13}$ is H, $CH_3$, F, Cl, or $CF_3$. In some embodiments, $R^{13}$ may be H.

With respect to any relevant embodiment or structural representation of Formula A-1 through A-44 herein, some non-limiting examples of $R^{14}$ may include $R^A$, F, Cl, CN, $OR^A$, $CF_3$, $NO_2$, $NR^AR^B$, $COR^A$, $CO_2R^A$, $OCOR^A$, $NR^A\text{-}COR^B$, $CONR^AR^B$, etc. In some embodiments, $R^{14}$ may be H; F; Cl; CN; $CF_3$; OH; $NH_2$; $C_{1\text{-}6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or $C_{1\text{-}6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^{14}$ is H, $CH_3$, F, Cl, or $CF_3$. In some embodiments, $R^{14}$ may be H.

With respect to any relevant embodiment or structural representation of Formula A-1 through A-44 herein, some non-limiting examples of $R^{14}$ may include $R^A$, F, Cl, CN, $OR^A$, $CF_3$, $NO_2$, $NR^AR^B$, $COR^A$, $CO_2R^A$, $OCOR^A$, $NR^A\text{-}COR^B$, $CONR^AR^B$, etc. In some embodiments, $R^{14}$ may be H; F; Cl; CN; $CF_3$; OH; $NH_2$; $C_{1\text{-}6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or $C_{1\text{-}6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^{15}$ is H, $CH_3$, F, Cl, or $CF_3$. In some embodiments, $R^{15}$ may be H.

With respect to any relevant embodiment or structural representation of Formula A-1 through A-44 herein, some non-limiting examples of $R^{16}$ may include $R^A$, F, Cl, CN, $OR^A$, $CF_3$, $NO_2$, $NR^AR^B$, $COR^A$, $CO_2R^A$, $OCOR^A$, $NR^A\text{-}COR^B$, $CONR^AR^B$, etc. In some embodiments, $R^{16}$ may be H; F; Cl; CN; $CF_3$; OH; $NH_2$; $C_{1\text{-}6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or $C_{1\text{-}6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^{16}$ is H, $CH_3$, F, Cl, or $CF_3$. In some embodiments, $R^{16}$ may be H.

With respect to any relevant embodiment or structural representation of Formula A-1 through A-44 herein, some non-limiting examples of $R^{17}$ may include $R^A$, F, Cl, CN, $OR^A$, $CF_3$, $NO_2$, $NR^AR^B$, $COR^A$, $CO_2R^A$, $OCOR^A$, $NR^A\text{-}COR^B$, $CONR^AR^B$, etc. In some embodiments, $R^{17}$ may be H; F; Cl; CN; $CF_3$; OH; $NH_2$; $C_{1\text{-}6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or $C_{1\text{-}6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^{17}$ is H, $CH_3$, F, Cl, or $CF_3$. In some embodiments, $R^{17}$ may be H.

With respect to any relevant embodiment or structural representation of Formula A-1 through A-44 herein, some non-limiting examples of $R^{17}$ may include $R^A$, F, Cl, CN, $OR^A$, $CF_3$, $NO_2$, $NR^AR^B$, $COR^A$, $CO_2R^A$, $OCOR^A$, $NR^A\text{-}COR^B$, $CONR^AR^B$, etc. In some embodiments, $R^{17}$ may be H; F; Cl; CN; $CF_3$; OH; $NH_2$; $C_{1\text{-}6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or $C_{1\text{-}6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^{18}$ may be H, F, Cl, OH, CN, $CF_3$, $CH_3$, $CH_2CH_3$, —$OCH_3$, or —$OCH_2CH_3$. In some embodiments, $R^{18}$ may be H.

With respect to any relevant embodiment or structural representation of Formula A-1 through A-44 herein, some non-limiting examples of $R^{19}$ may include $R^A$, F, Cl, CN, $OR^A$, $CF_3$, $NO_2$, $NR^AR^B$, $COR^A$, $CO_2R^A$, $OCOR^A$, $NR^A\text{-}COR^B$, $CONR^AR^B$, etc. In some embodiments, $R^{19}$ may be H; F; Cl; CN; $CF_3$; OH; $NH_2$; $C_{1\text{-}6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or $C_{1\text{-}6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^{19}$ may be H, OH, CN, $CF_3$, $CH_3$, $CH_2CH_3$, —$OCH_3$, or —$OCH_2CH_3$. In some embodiments, $R^{19}$ may be H.

With respect to any relevant embodiment or structural representation of Formula A-1 through A-44 herein, some non-limiting examples of $R^{20}$ may include $R^A$, F, Cl, CN, $OR^A$, $CF_3$, $NO_2$, $NR^AR^B$, $COR^A$, $CO_2R^A$, $OCOR^A$, $NR^A\text{-}COR^B$, $CONR^AR^B$, etc. In some embodiments, $R^{20}$ may be H; F; Cl; CN; $CF_3$; OH; $NH_2$; $C_{1\text{-}6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or $C_{1\text{-}6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^{20}$ may be H, F, Cl, OH, CN, $CF_3$, $CH_3$, $CH_2CH_3$, —$OCH_3$, or —$OCH_2CH_3$. In some embodiments, $R^{20}$ may be H.

With respect to any relevant embodiment or structural representation of Formula A-1 through A-44 herein, some non-limiting examples of $R^{21}$ may include $R^A$, F, Cl, CN, $OR^A$, $CF_3$, $NO_2$, $NR^AR^B$, $COR^A$, $CO_2R^A$, $OCOR^A$, $NR^A\text{-}COR^B$, $CONR^AR^B$, etc. In some embodiments, $R^{21}$ may be H; F; Cl; CN; $CF_3$; OH; $NH_2$; $C_{1\text{-}6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or $C_{1\text{-}6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc.

In some embodiments, $R^{21}$ may be H, OH, CN, $CF_3$, $CH_3$, $CH_2CH_3$, —$OCH_3$, or —$OCH_2CH_3$. In some embodiments, $R^{21}$ may be H.

With respect to any relevant embodiment or structural representation of Formula A-1 through A-44 herein, some non-limiting examples of $R^{22}$ may include $R^A$, F, Cl, CN, $OR^A$, $CF_3$, $NO_2$, $NR^AR^B$, $COR^A$, $CO_2R^A$, $OCOR^A$, $NR^A$-$COR^B$, $CONR^AR^B$, etc. In some embodiments, $R^{22}$ may be H; F; Cl; CN; $CF_3$; OH; $NH_2$; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or $C_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^{22}$ may be H, F, Cl, OH, CN, $CF_3$, $CH_3$, $CH_2CH_3$, —$OCH_3$, or —$OCH_2CH_3$. In some embodiments, $R^{22}$ may be H.

With respect to any relevant embodiment or structural representation of Formula A-1 through A-44 herein, some non-limiting examples of $R^{23}$ may include $R^A$, F, Cl, CN, $OR^A$, $CF_3$, $NO_2$, $NR^AR^B$, $COR^A$, $CO_2R^A$, $OCOR^A$, $NR^A$-$COR^B$, $CONR^AR^B$, etc. In some embodiments, $R^{23}$ may be H; F; Cl; CN; $CF_3$; OH; $NH_2$; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or $C_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^{23}$ may be H, OH, CN, $CF_3$, $CH_3$, $CH_2CH_3$, —$OCH_3$, or —$OCH_2CH_3$. In some embodiments, $R^{23}$ is H. In some embodiments, $R^{23}$ is $CH_3$.

With respect to any relevant embodiment or structural representation of Formula A-1 through A-44 herein, some non-limiting examples of $R^{24}$ may include $R^A$, F, Cl, CN, $OR^A$, $CF_3$, $NO_2$, $NR^AR^B$, $COR^A$, $CO_2R^A$, $OCOR^A$, $NR^A$-$COR^B$, $CONR^AR^B$, etc. In some embodiments, $R^{24}$ may be H; F; Cl; CN; $CF_3$; OH; $NH_2$; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or $C_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^{24}$ may be H, F, Cl, OH, CN, $CF_3$, $CH_3$, $CH_2CH_3$, —$OCH_3$, or —$OCH_2CH_3$. In some embodiments, $R^{24}$ is H. In some embodiments, $R^{24}$ is $CH_3$.

With respect to any relevant embodiment or structural representation of Formula A-1 through A-44 herein, some non-limiting examples of $R^{25}$ may include $R^A$, F, Cl, CN, $OR^A$, $CF_3$, $NO_2$, $NR^AR^B$, $COR^A$, $CO_2R^A$, $OCOR^A$, $NR^A$-$COR^B$, $CONR^AR^B$, etc. In some embodiments, $R^{25}$ may be H; F; Cl; CN; $CF_3$; OH; $NH_2$; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or $C_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^{25}$ may be H, OH, CN, $CF_3$, $CH_3$, $CH_2CH_3$, —$OCH_3$, or —$OCH_2CH_3$. In some embodiments, $R^{25}$ may be H.

With respect to any relevant embodiment or structural representation of Formula A-1 through A-44 herein, some non-limiting examples of $R^{26}$ may include $R^A$, F, Cl, CN, $OR^A$, $CF_3$, $NO_2$, $NR^AR^B$, $COR^A$, $CO_2R^A$, $OCOR^A$, $NR^A$-$COR^B$, $CONR^AR^B$, etc. In some embodiments, $R^{26}$ may be H; F; Cl; CN; $CF_3$; OH; $NH_2$; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or $C_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^{26}$ may be H, F, Cl, OH, CN, $CF_3$, $CH_3$, or —$OCH_3$. In some embodiments, $R^{26}$ may be H.

With respect to any relevant embodiment or structural representation of Formula A-1 through A-44 herein, some non-limiting examples of $R^{27}$ may include $R^A$, F, Cl, CN, $OR^A$, $CF_3$, $NO_2$, $NR^AR^B$, $COR^A$, $CO_2R^A$, $OCOR^A$, $NR^A$-$COR^B$, $CONR^AR^B$, etc. In some embodiments, $R^{27}$ may be H; F; Cl; CN; $CF_3$; OH; $NH_2$; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or $C_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^{27}$ may be H, F, Cl, OH, CN, $CF_3$, $CH_3$, or —$OCH_3$. In some embodiments, $R^{27}$ may be H.

With respect to any relevant embodiment or structural representation of Formula A-1 through A-44 herein, some non-limiting examples of $R^{28}$ may include $R^A$, F, Cl, CN, $OR^A$, $CF_3$, $NO_2$, $NR^AR^B$, $COR^A$, $CO_2R^A$, $OCOR^A$, $NR^A$-$COR^B$, $CONR^AR^B$, etc. In some embodiments, $R^{28}$ may be H; F; Cl; CN; $CF_3$; OH; $NH_2$; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or $C_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^{28}$ may be H, F, CN, $CF_3$, or $CH_3$. In some embodiments, $R^{28}$ may be H.

With respect to any relevant embodiment or structural representation of Formula A-1 through A-44 herein, some non-limiting examples of $R^{29}$ may include $R^A$, F, Cl, CN, $OR^A$, $CF_3$, $NO_2$, $NR^AR^B$, $COR^A$, $CO_2R^A$, $OCOR^A$, $NR^A$-$COR^B$, $CONR^AR^B$, etc. In some embodiments, $R^{29}$ may be H; F; Cl; CN; $CF_3$; OH; $NH_2$; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or $C_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^{29}$ may be H, F, Cl, OH, CN, $CF_3$, $CH_3$, or —$OCH_3$. In some embodiments, $R^{29}$ may be H.

With respect to any relevant embodiment or structural representation of Formula A-1 through A-44 herein, some non-limiting examples of $R^{30}$ may include $R^A$, F, Cl, CN, $OR^A$, $CF_3$, $NO_2$, $NR^AR^B$, $COR^A$, $CO_2R^A$, $OCOR^A$, $NR^A$-$COR^B$, $CONR^AR^B$, etc. In some embodiments, $R^{30}$ may be H; F; Cl; CN; $CF_3$; OH; $NH_2$; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or $C_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^{30}$ may be H, F, Cl, OH, CN, $CF_3$, $CH_3$, $CH_2CH_3$, —$OCH_3$, or —$OCH_2CH_3$. In some embodiments, $R^{30}$ may be H.

With respect to any relevant embodiment or structural representation of Formula A-1 through A-44 herein, some non-limiting examples of $R^{31}$ may include $R^A$, F, Cl, CN, $OR^A$, $CF_3$, $NO_2$, $NR^AR^B$, $COR^A$, $CO_2R^A$, $OCOR^A$, $NR^A$-$COR^B$, $CONR^AR^B$, etc. In some embodiments, $R^{31}$ may be H; F; Cl; CN; $CF_3$; OH; $NH_2$; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or $C_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^{31}$ may be H, OH, CN, $CF_3$, $CH_3$, $CH_2CH_3$, —$OCH_3$, or —$OCH_2CH_3$. In some embodiments, $R^{31}$ may be H.

With respect to any relevant embodiment or structural representation of Formula A-1 through A-44 herein, some non-limiting examples of $R^{32}$ may include $R^A$, F, Cl, CN, $OR^A$, $CF_3$, $NO_2$, $NR^AR^B$, $COR^A$, $CO_2R^A$, $OCOR^A$, $NR^A$-$COR^B$, $CONR^AR^B$, etc. In some embodiments, $R^{32}$ may be H; F; Cl; CN; $CF_3$; OH; $NH_2$; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or $C_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^{32}$ may be H, F, Cl, CN, $CF_3$, $CH_3$, $CH_2CH_3$, $CH_2CH_2CH_3$, $CH(CH_3)_2$, —$OCH_3$, —$OCH_2CH_3$, —$OCH_2CH_2CH_3$, or —$OCH(CH_3)_2$. In some embodiments, $R^{32}$ may be H.

With respect to any relevant embodiment or structural representation of Formula A-1 through A-44 herein, some non-limiting examples of $R^{33}$ may include $R^A$, F, Cl, CN, $OR^A$, $CF_3$, $NO_2$, $NR^AR^B$, $COR^A$, $CO_2R^A$, $OCOR^A$, $NR^A$-$COR^B$, $CONR^AR^B$, etc. In some embodiments, $R^{33}$ may be H; F; Cl; CN; $CF_3$; OH; $NH_2$; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or $C_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^{33}$ may be H, F, Cl, CN, $CF_3$, $CH_3$, $CH_2CH_3$, $CH_2CH_2CH_3$, $CH(CH_3)_2$, —$OCH_3$, —$OCH_2CH_3$, —$OCH_2CH_2CH_3$, or —$OCH(CH_3)_2$. In some embodiments, $R^{33}$ is H. In some embodiments, $R^{33}$ is $CH_3$.

With respect to any relevant embodiment or structural representation of Formula A-1 through A-44 herein, some non-limiting examples of $R^{34}$ may include $R^A$, F, Cl, CN, $OR^A$, $CF_3$, $NO_2$, $NR^AR^B$, $COR^A$, $CO_2R^A$, $OCOR^A$, $NR^A$-$COR^B$, $CONR^AR^B$, etc. In some embodiments, $R^{34}$ may be H; F; Cl; CN; $CF_3$; OH; $NH_2$; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or $C_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^{34}$ may be H, F, Cl, OH, CN, $CF_3$, $CH_3$, $NH_2$, $NHCH_3$, $N(CH_3)_2$, or —$OCH_3$. In some embodiments, $R^{34}$ may be H.

With respect to any relevant embodiment or structural representation of Formula A-1 through A-44 herein, some non-limiting examples of $R^{35}$ may include $R^A$, F, Cl, CN, $OR^A$, $CF_3$, $NO_2$, $NR^AR^B$, $COR^A$, $CO_2R^A$, $OCOR^A$, $NR^A$-$COR^B$, $CONR^AR^B$, etc. In some embodiments, $R^{35}$ may be H; F; Cl; CN; $CF_3$; OH; $NH_2$; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or $C_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^{35}$ may be H, F, CN, $CF_3$, $CH_3$, $CH_2CH_3$, $CH_2CH_2CH_3$, or $CH(CH_3)_2$. In some embodiments, $R^{35}$ is H. In some embodiments, $R^{35}$ is $CH_3$.

With respect to any relevant embodiment or structural representation of Formula A-1 through A-44 herein, some non-limiting examples of $R^{36}$ may include $R^A$, F, Cl, CN, $OR^A$, $CF_3$, $NO_2$, $NR^AR^B$, $COR^A$, $CO_2R^A$, $OCOR^A$, $NR^A$-$COR^B$, $CONR^AR^B$, etc. In some embodiments, $R^{36}$ may be H; F; Cl; CN; $CF_3$; OH; $NH_2$; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or $C_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^{36}$ may be H, F, CN, $CF_3$, $CH_3$, $CH_2CH_3$, $CH_2CH_2CH_3$, or $CH(CH_3)_2$. In some embodiments, $R^{36}$ is H. In some embodiments, $R^{36}$ is $CH_3$.

With respect to any relevant embodiment or structural representation of Formula A-1 through A-44 herein, some non-limiting examples of $R^{37}$ may include $R^A$, F, Cl, CN, $OR^A$, $CF_3$, $NO_2$, $NR^AR^B$, $COR^A$, $CO_2R^A$, $OCOR^A$, $NR^A$-$COR^B$, $CONR^AR^B$, etc. In some embodiments, $R^{37}$ may be H; F; Cl; CN; $CF_3$; OH; $NH_2$; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or $C_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^{37}$ may be H, F, CN, $CF_3$, $CH_3$, $CH_2CH_3$, $CH_2CH_2CH_3$, or $CH(CH_3)_2$. In some embodiments, $R^{37}$ is H. In some embodiments, $R^{37}$ is $CH_3$.

With respect to any relevant embodiment or structural representation of Formula A-1 through A-44 herein, some non-limiting examples of $R^{38}$ may include $R^A$, F, Cl, CN, $OR^A$, $CF_3$, $NO_2$, $NR^AR^B$, $COR^A$, $CO_2R^A$, $OCOR^A$, $NR^A$-$COR^B$, $CONR^AR^B$, etc. In some embodiments, $R^{38}$ may be H; F; Cl; CN; $CF_3$; OH; $NH_2$; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or $C_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^{38}$ may be H, F, CN, $CF_3$, $CH_3$, $CH_2CH_3$, $CH_2CH_2CH_3$, or $CH(CH_3)_2$. In some embodiments, $R^{38}$ is H. In some embodiments, $R^{38}$ is $CH_3$.

With respect to any relevant embodiment or structural representation of Formula A-1 through A-44 herein, some non-limiting examples of $R^{39}$ may include $R^A$, F, Cl, CN, $OR^A$, $CF_3$, $NO_2$, $NR^AR^B$, $COR^A$, $CO_2R^A$, $OCOR^A$, $NR^A\text{-}COR^B$, $CONR^AR^B$, etc. In some embodiments, $R^{39}$ may be H; F; Cl; CN; $CF_3$; OH; $NH_2$; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or $C_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^{39}$ may be H, F, CN, $CF_3$, $CH_3$, $CH_2CH_3$, $CH_2CH_2CH_3$, or $CH(CH_3)_2$. In some embodiments, $R^{39}$ may be H.

With respect to any relevant embodiment or structural representation of Formula A-1 through A-44 herein, some non-limiting examples of $R^{40}$ may include $R^A$, F, Cl, CN, $OR^A$, $CF_3$, $NO_2$, $NR^AR^B$, $COR^A$, $CO_2R^A$, $OCOR^A$, $NR^A\text{-}COR^B$, $CONR^AR^B$, etc. In some embodiments, $R^{40}$ may be H; F; Cl; CN; $CF_3$; OH; $NH_2$; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or $C_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^{40}$ may be H, F, CN, $CF_3$, $CH_3$, $CH_2CH_3$, $CH_2CH_2CH_3$, or $CH(CH_3)_2$. In some embodiments, $R^{40}$ may be H.

With respect to any relevant embodiment or structural representation of Formula A-1 through A-44 herein, some non-limiting examples of $R^{41}$ may include $R^A$, F, Cl, CN, $OR^A$, $CF_3$, $NO_2$, $NR^AR^B$, $COR^A$, $CO_2R^A$, $OCOR^A$, $NR^A\text{-}COR^B$, $CONR^AR^B$, etc. In some embodiments, $R^{41}$ may be H; F; Cl; CN; $CF_3$; OH; $NH_2$; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or $C_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^{41}$ may be H, F, CN, $CF_3$, $CH_3$, $CH_2CH_3$, $CH_2CH_2CH_3$, or $CH(CH_3)_2$. In some embodiments, $R^{41}$ is H. In some embodiments, $R^{41}$ is $CH_3$.

With respect to any relevant embodiment or structural representation of Formula A-1 through A-44 herein, some non-limiting examples of $R^{42}$ may include $R^A$, F, Cl, CN, $OR^A$, $CF_3$, $NO_2$, $NR^AR^B$, $COR^A$, $CO_2R^A$, $OCOR^A$, $NR^A\text{-}COR^B$, $CONR^AR^B$, etc. In some embodiments, $R^{42}$ may be H; F; Cl; CN; $CF_3$; OH; $NH_2$; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or $C_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^{42}$ may be H, CN, $CF_3$, $CH_3$, $CH_2CH_3$, $CH_2CH_2CH_3$, or $CH(CH_3)_2$. In some embodiments, $R^{42}$ is H. In some embodiments, $R^{42}$ is $CH_3$.

With respect to any relevant embodiment or structural representation of Formula A-1 through A-44 herein, some non-limiting examples of $R^{43}$ may include $R^A$, F, Cl, CN, $OR^A$, $CF_3$, $NO_2$, $NR^AR^B$, $COR^A$, $CO_2R^A$, $OCOR^A$, $NR^A\text{-}COR^B$, $CONR^AR^B$, etc. In some embodiments, $R^{43}$ may be H; F; Cl; CN; $CF_3$; OH; $NH_2$; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or $C_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^{43}$ may be H, F, Cl, CN, $CF_3$, $CH_3$, $CH_2CH_3$, $CH_2CH_2CH_3$, $CH(CH_3)_2$, —$OCH_3$, —$OCH_2CH_3$, —$OCH_2CH_2CH_3$, or —$OCH(CH_3)_2$. In some embodiments, $R^{43}$ may be H.

With respect to any relevant embodiment or structural representation of Formula A-1 through A-44 herein, some non-limiting examples of $R^{44}$ may include $R^A$, F, Cl, CN, $OR^A$, $CF_3$, $NO_2$, $NR^AR^B$, $COR^A$, $CO_2R^A$, $OCOR^A$, $NR^A\text{-}COR^B$, $CONR^AR^B$, etc. In some embodiments, $R^{44}$ may be H; F; Cl; CN; $CF_3$; OH; $NH_2$; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or $C_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^{44}$ may be H, F, Cl, CN, $CF_3$, $CH_3$, $CH_2CH_3$, $CH_2CH_2CH_3$, $CH(CH_3)_2$, —$OCH_3$, —$OCH_2CH_3$, —$OCH_2CH_2CH_3$, or —$OCH(CH_3)_2$. In some embodiments, $R^{44}$ may be H.

With respect to any relevant embodiment or structural representation of Formula A-1 through A-44 herein, some non-limiting examples of $R^{45}$ may include $R^A$, F, Cl, CN, $OR^A$, $CF_3$, $NO_2$, $NR^AR^B$, $COR^A$, $CO_2R^A$, $OCOR^A$, $NR^A\text{-}COR^B$, $CONR^AR^B$, etc. In some embodiments, $R^{45}$ may be H; F; Cl; CN; $CF_3$; OH; $NH_2$; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or $C_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^{45}$ may be H, F, Cl, CN, $CF_3$, $CH_3$, $CH_2CH_3$, $CH_2CH_2CH_3$, $CH(CH_3)_2$, —$OCH_3$, —$OCH_2CH_3$, —$OCH_2CH_2CH_3$, or —$OCH(CH_3)_2$. In some embodiments, $R^{45}$ may be H.

With respect to any relevant embodiment or structural representation of Formula A-1 through A-44 herein, some non-limiting examples of $R^{46}$ may include $R^A$, F, Cl, CN, $OR^A$, $CF_3$, $NO_2$, $NR^AR^B$, $COR^A$, $CO_2R^A$, $OCOR^A$, $NR^A\text{-}COR^B$, $CONR^AR^B$, etc. In some embodiments, $R^{46}$ may be H; F; Cl; CN; $CF_3$; OH; $NH_2$; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or $C_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^{46}$ may be H, F, Cl, CN, $CF_3$, $CH_3$, $CH_2CH_3$, $CH_2CH_2CH_3$, $CH(CH_3)_2$, —$OCH_3$, —$OCH_2CH_3$, —$OCH_2CH_2CH_3$, or —$OCH(CH_3)_2$. In some embodiments, $R^{46}$ may be H.

With respect to any relevant embodiment or structural representation of Formula A-1 through A-44 herein, some non-limiting examples of $R^{47}$ may include $R^A$, F, Cl, CN, $OR^A$, $CF_3$, $NO_2$, $NR^AR^B$, $COR^A$, $CO_2R^A$, $OCOR^A$, $NR^A$-$COR^B$, $CONR^AR^B$, etc. In some embodiments, $R^{47}$ may be H; F; Cl; CN; $CF_3$; OH; $NH_2$; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or $C_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^{47}$ may be H, F, Cl, CN, $CF_3$, OH; $NH_2$, $CH_3$, $CH_2CH_3$, $CH_2CH_2CH_3$, $CH(CH_3)_2$, —$OCH_3$, —$OCH_2CH_3$, —$OCH_2CH_2CH_3$, or —$OCH(CH_3)_2$. In some embodiments, $R^{47}$ may be H.

With respect to any relevant embodiment or structural representation of Formula A-1 through A-44 herein, some non-limiting examples of $R^{48}$ may include $R^A$, F, Cl, CN, $OR^A$, $CF_3$, $NO_2$, $NR^AR^B$, $COR^A$, $CO_2R^A$, $OCOR^A$, $NR^A$-$COR^B$, $CONR^AR^B$, etc. In some embodiments, $R^{48}$ may be H; F; Cl; CN; $CF_3$; OH; $NH_2$; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or $C_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^{48}$ may be H, F, Cl, CN, $CF_3$, OH; $NH_2$, $CH_3$, $CH_2CH_3$, $CH_2CH_2CH_3$, $CH(CH_3)_2$, —$OCH_3$, —$OCH_2CH_3$, —$OCH_2CH_2CH_3$, or —$OCH(CH_3)_2$. In some embodiments, $R^{48}$ may be H.

With respect to any relevant embodiment or structural representation of Formula A-1 through A-44 herein, some non-limiting examples of $R^{49}$ may include $R^A$, F, Cl, CN, $OR^A$, $CF_3$, $NO_2$, $NR^AR^B$, $COR^A$, $CO_2R^A$, $OCOR^A$, $NR^A$-$COR^B$, $CONR^AR^B$, etc. In some embodiments, $R^{49}$ may be H; F; Cl; CN; $CF_3$; OH; $NH_2$; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or $C_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^{49}$ may be H, F, Cl, CN, $CF_3$, OH; $NH_2$, $CH_3$, $CH_2CH_3$, $CH_2CH_2CH_3$, $CH(CH_3)_2$, —$OCH_3$, —$OCH_2CH_3$, —$OCH_2CH_2CH_3$, or —$OCH(CH_3)_2$. In some embodiments, $R^{49}$ may be H.

With respect to any relevant embodiment or structural representation of Formula A-1 through A-44 herein, some non-limiting examples of $R^{50}$ may include $R^A$, F, Cl, CN, $OR^A$, $CF_3$, $NO_2$, $NR^AR^B$, $COR^A$, $CO_2R^A$, $OCOR^A$, $NR^A$-$COR^B$, $CONR^AR^B$, etc. In some embodiments, $R^{50}$ may be H; F; Cl; CN; $CF_3$; OH; $NH_2$; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or $C_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^{50}$ may be H, F, Cl, CN, $CF_3$, OH; $NH_2$, $CH_3$, $CH_2CH_3$, $CH_2CH_2CH_3$, $CH(CH_3)_2$, —$OCH_3$, —$OCH_2CH_3$, —$OCH_2CH_2CH_3$, or —$OCH(CH_3)_2$. In some embodiments, $R^{50}$ may be H.

With respect to any relevant embodiment or structural representation of Formula A-1 through A-44 herein, some non-limiting examples of $R^{51}$ may include $R^A$, F, Cl, CN, $OR^A$, $CF_3$, $NO_2$, $NR^AR^B$, $COR^A$, $CO_2R^A$, $OCOR^A$, $NR^A$-$COR^B$, $CONR^AR^B$, etc. In some embodiments, $R^{51}$ may be H; F; Cl; CN; $CF_3$; OH; $NH_2$; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or $C_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^{51}$ may be H, F, Cl, CN, $CF_3$, $CH_3$, $CH_2CH_3$, $CH_2CH_2CH_3$, $CH(CH_3)_2$, —$OCH_3$, —$OCH_2CH_3$, —$OCH_2CH_2CH_3$, or —$OCH(CH_3)_2$. In some embodiments, $R^{51}$ may be H.

With respect to any relevant embodiment or structural representation of Formula A-1 through A-44 herein, some non-limiting examples of $R^{52}$ may include $R^A$, F, Cl, CN, $OR^A$, $CF_3$, $NO_2$, $NR^AR^B$, $COR^A$, $CO_2R^A$, $OCOR^A$, $NR^A$-$COR^B$, $CONR^AR^B$, etc. In some embodiments, $R^{52}$ may be H; F; Cl; CN; $CF_3$; OH; $NH_2$; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or $C_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^{52}$ may be H, F, Cl, CN, $CF_3$, $CH_3$, $CH_2CH_3$, $CH_2CH_2CH_3$, $CH(CH_3)_2$, —$OCH_3$, —$OCH_2CH_3$, —$OCH_2CH_2CH_3$, or —$OCH(CH_3)_2$. In some embodiments, $R^{52}$ may be H.

Some embodiments of Formula A-1 may include a compound represented by Formula A-43:

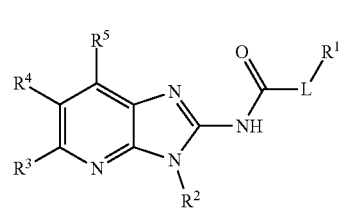

Formula A-43 wherein

L is $CH_2$;

$R^1$ is optionally substituted cyclic $C_3H_5$, wherein the optional substituent of $R^1$ is $CF_3$;

$R^2$ is optionally substituted cyclobutyl;

$R^3$ is optionally substituted $C_3$ alkyl, wherein the optional substituents of $R^3$ is OH;

$R^4$ is H; and $R^5$ is H;

or a pharmaceutically acceptable salt thereof.

Some embodiments of Formula A-1 may include a compound represented by Formula A-44:

Formula A-44

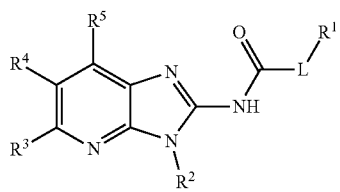

wherein

L is CH$_2$;

R$^1$ is optionally substituted C$_2$ alkyl, wherein the optional substituents of R$^1$ are independently CF$_3$ or CH$_3$;

R$^2$ is optionally substituted cyclobutyl;

R$^3$ is optionally substituted C$_3$ alkyl, wherein the optional substituents of R$^3$ is OH;

R$^4$ is H; and

R$^5$ is H;

or a pharmaceutically acceptable salt thereof.

Some embodiments of Formula A-1 include a compound represented by the following structures or a pharmaceutically acceptable salt thereof:

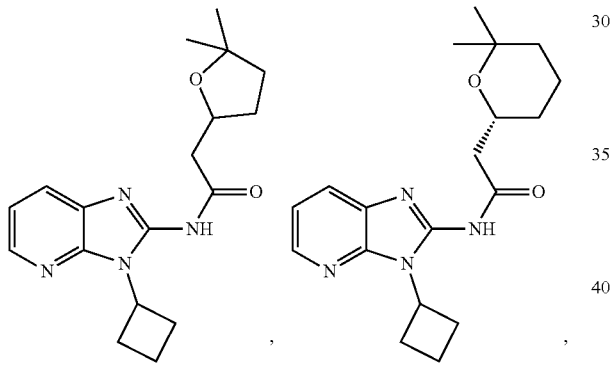

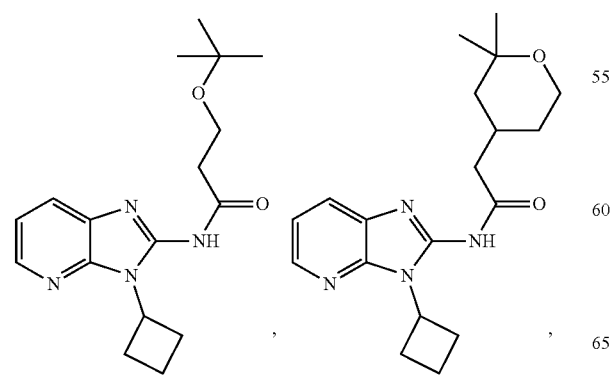

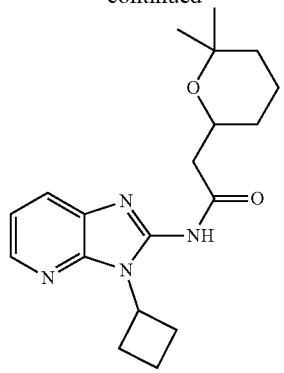

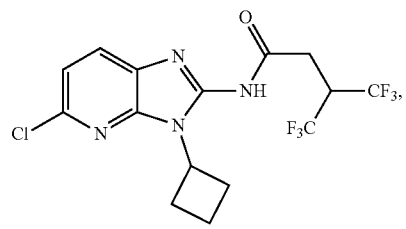

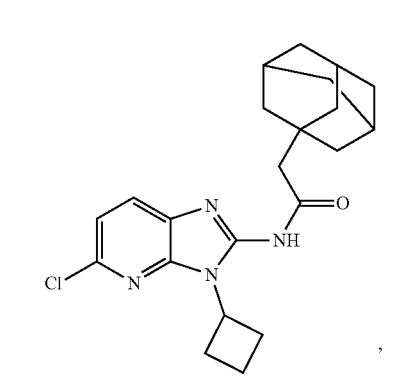

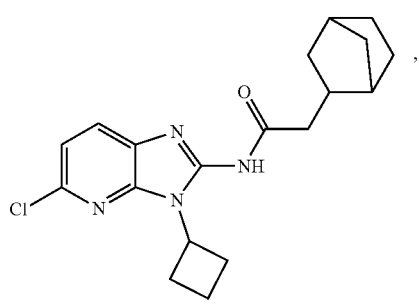

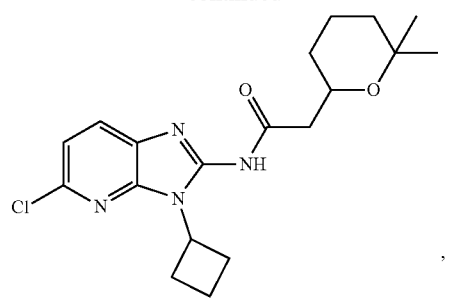
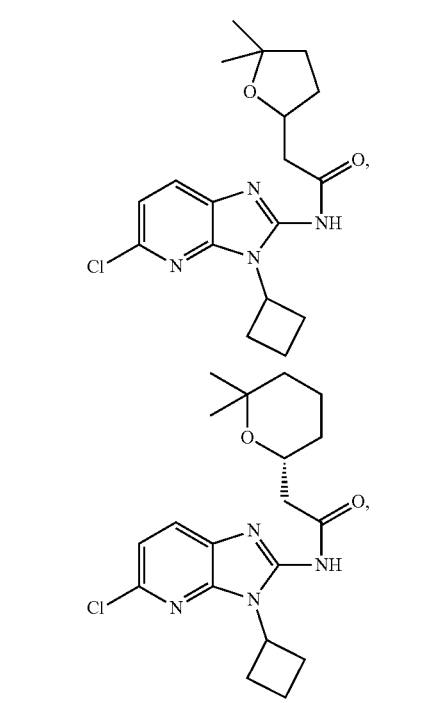
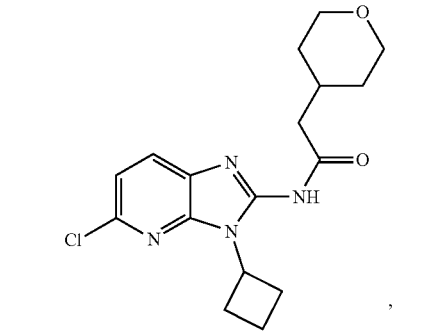
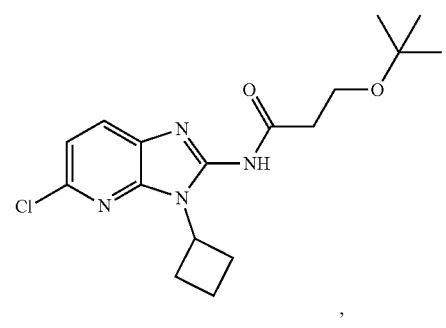
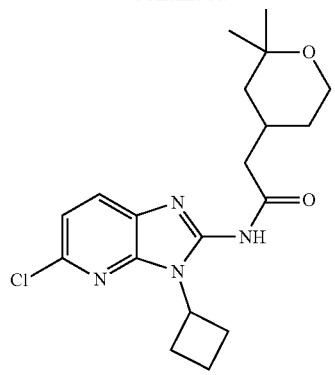
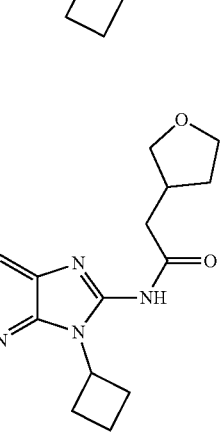
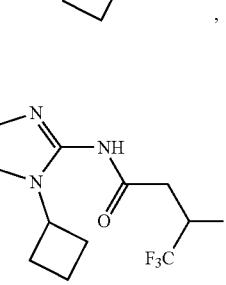
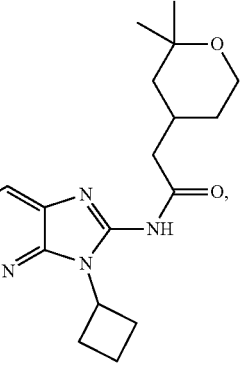
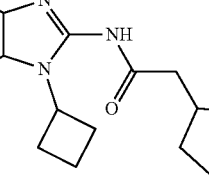

207
-continued
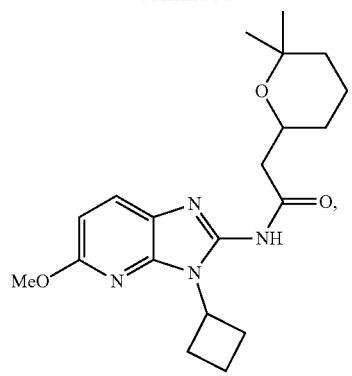
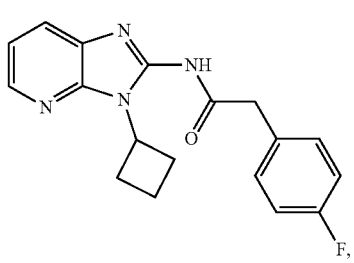
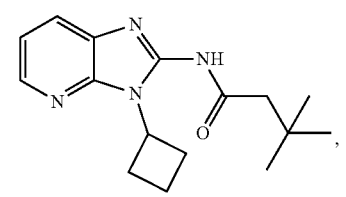
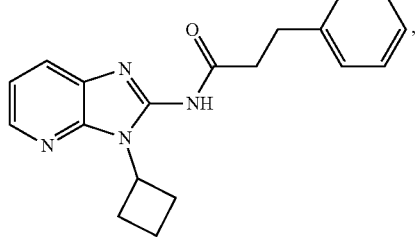
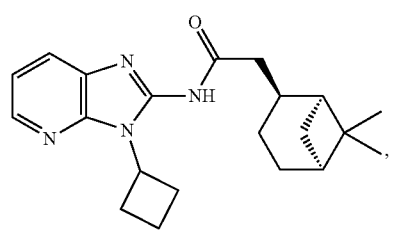
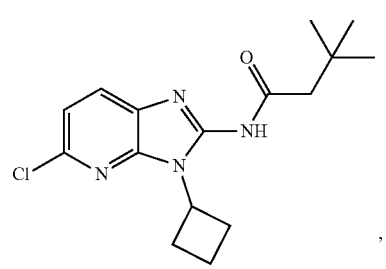
208
-continued
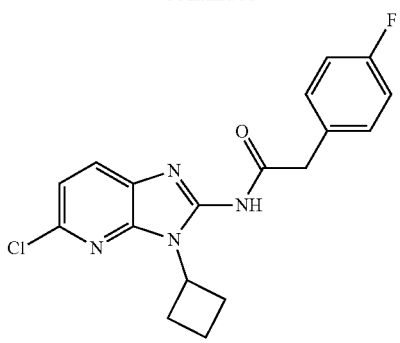
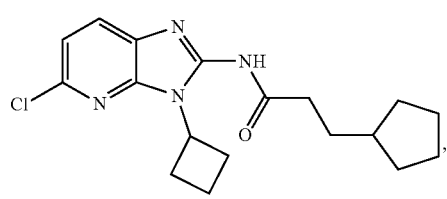
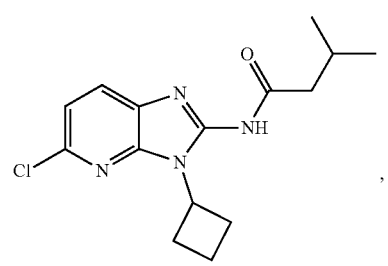
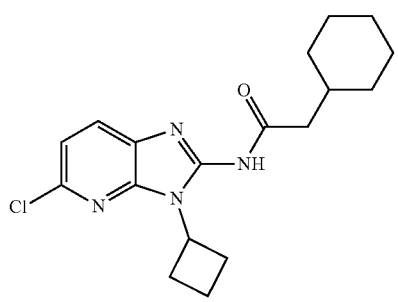
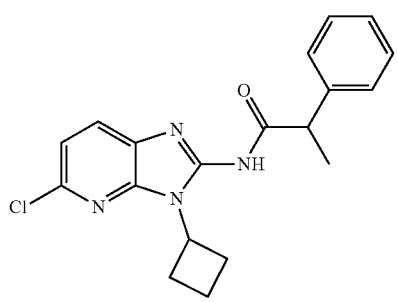
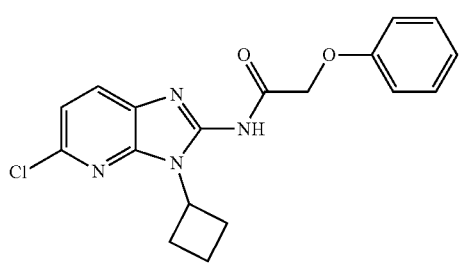

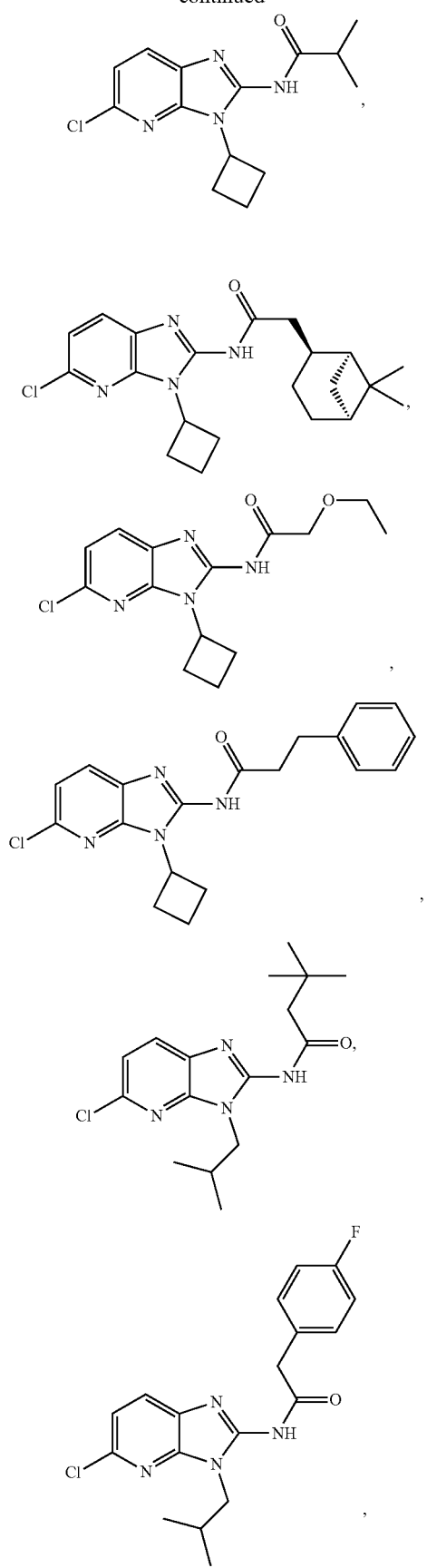
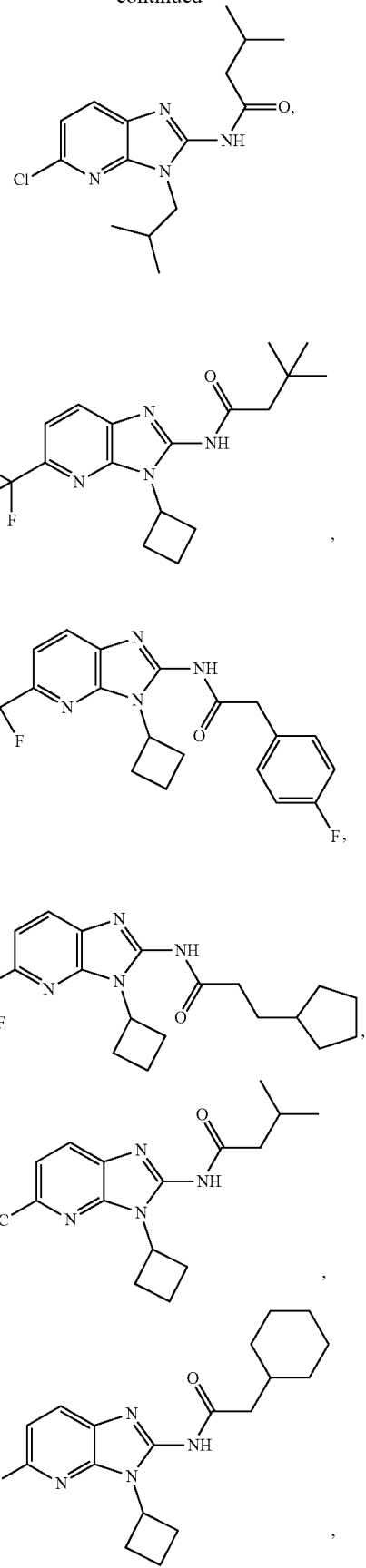

211
-continued
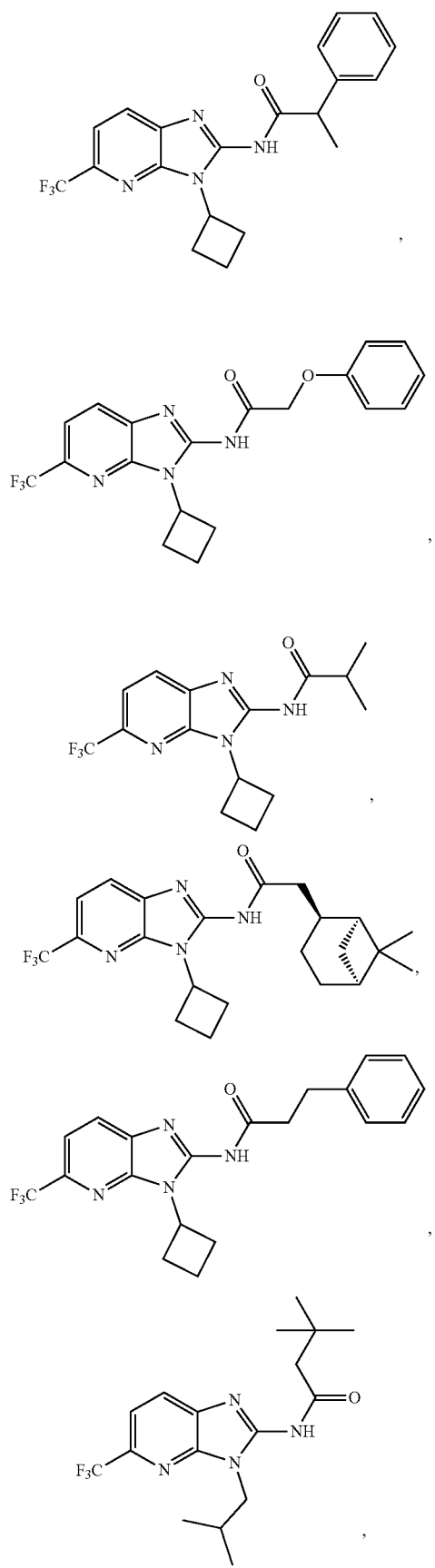
212
-continued
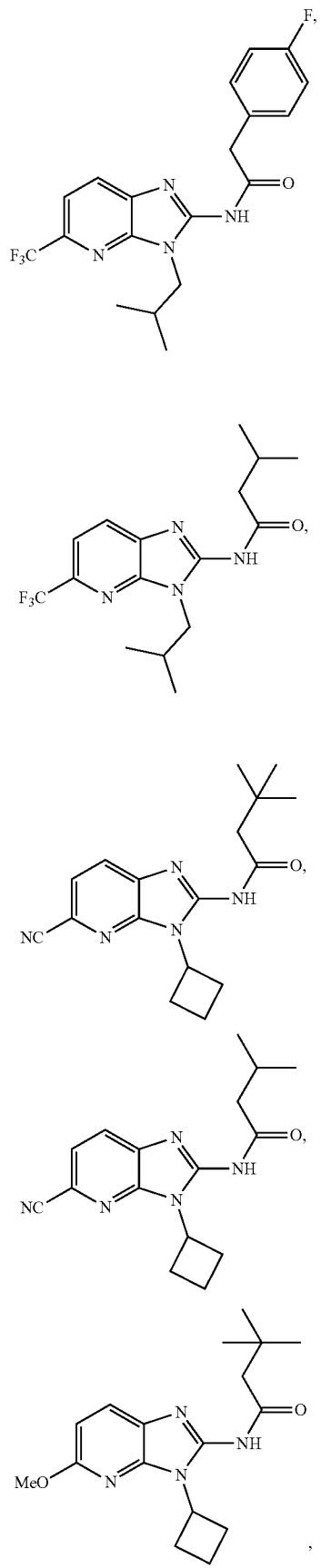

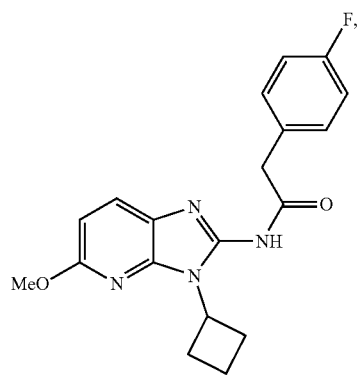
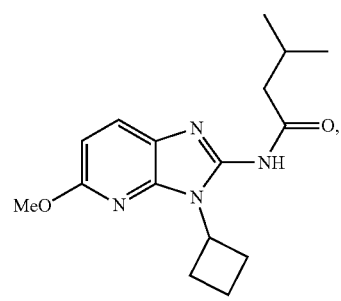
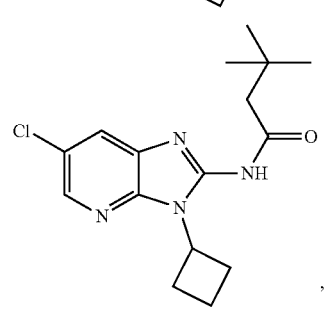
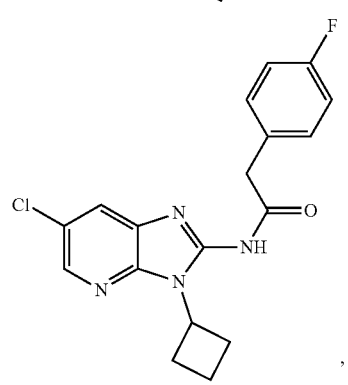
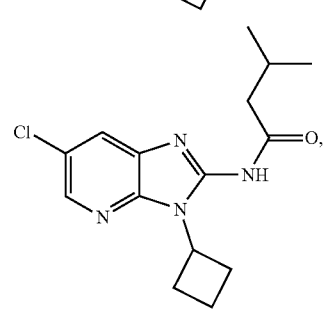
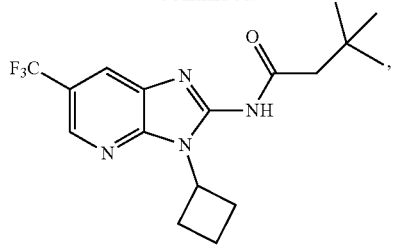
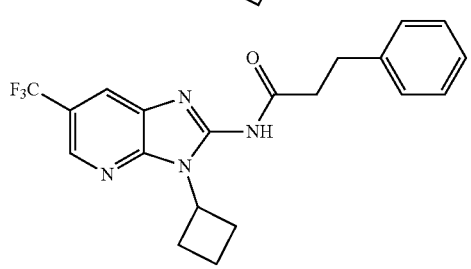
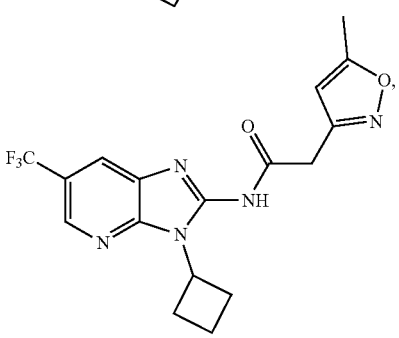
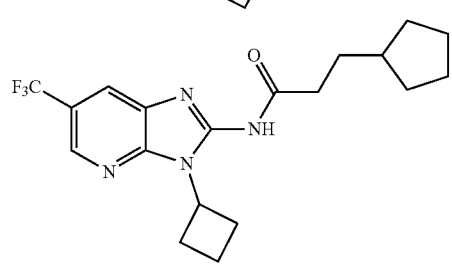
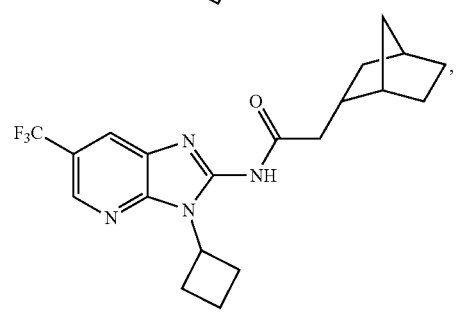
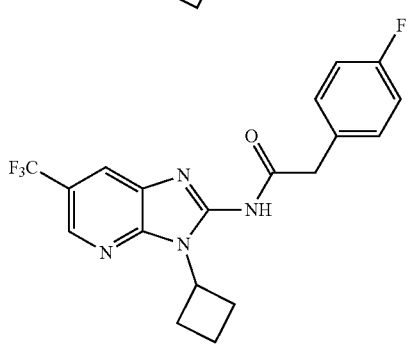

215
-continued
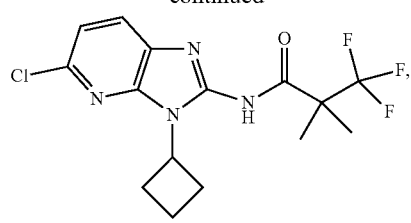
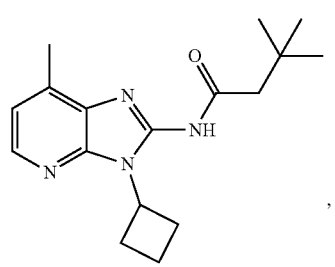
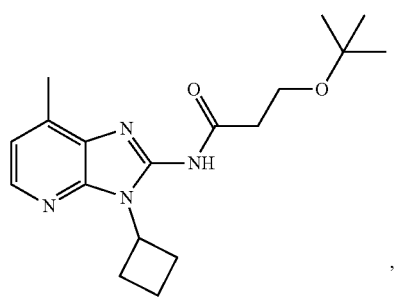
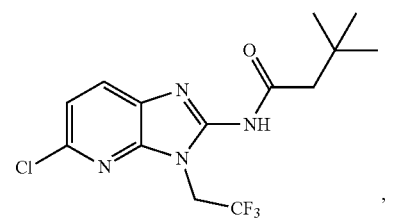
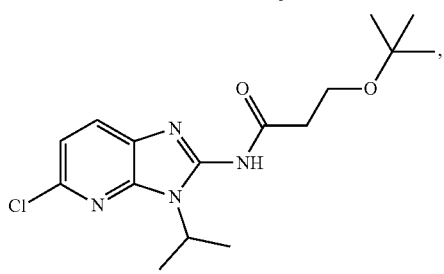
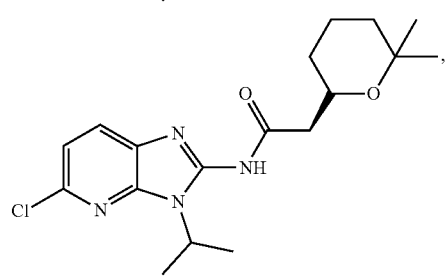
216
-continued
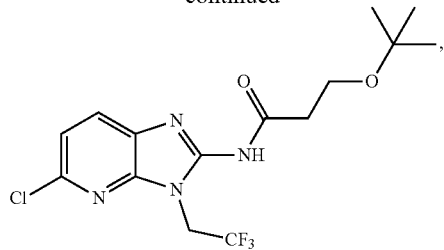
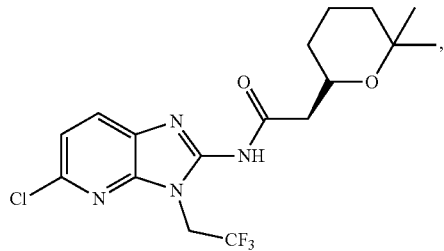
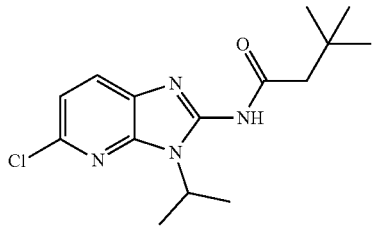
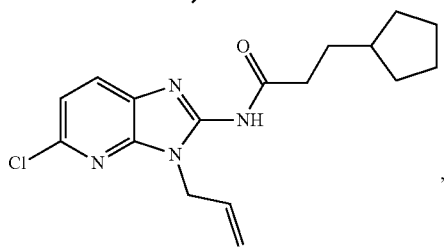
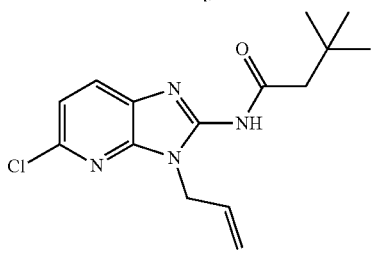
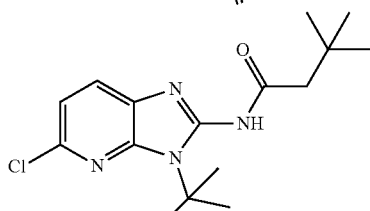
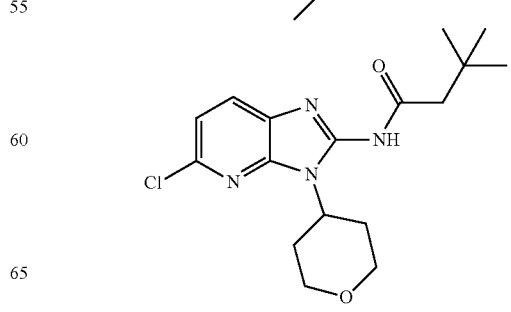

217
-continued
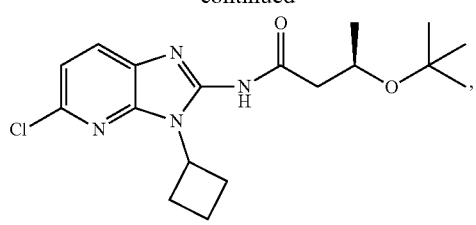
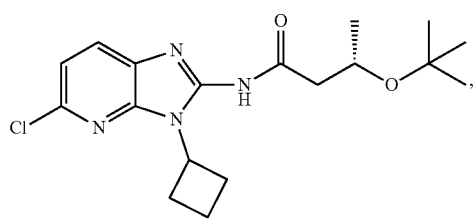
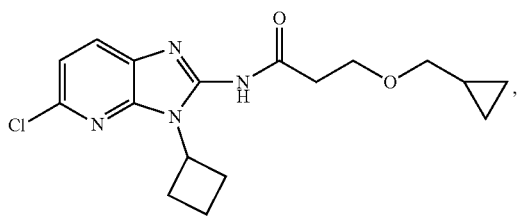
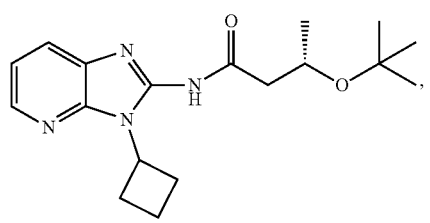
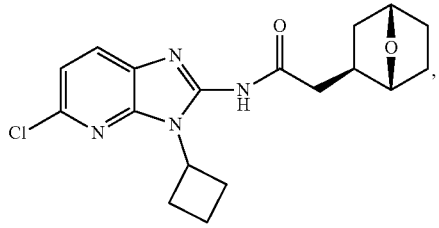
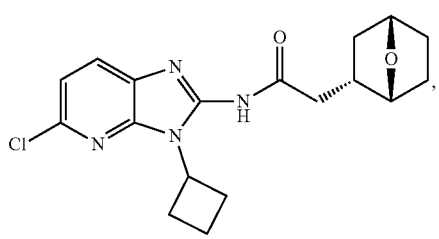
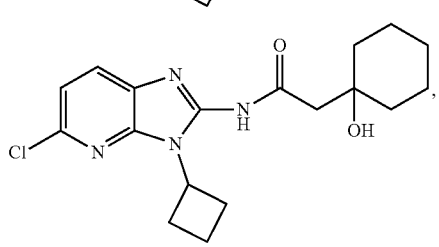
218
-continued
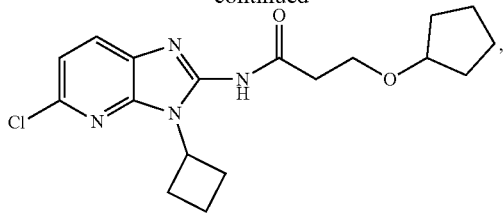
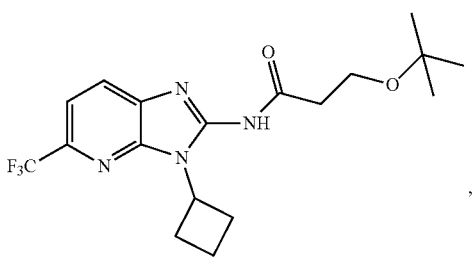
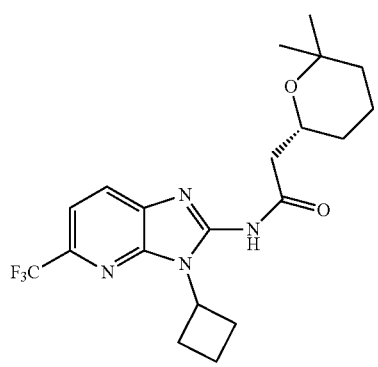
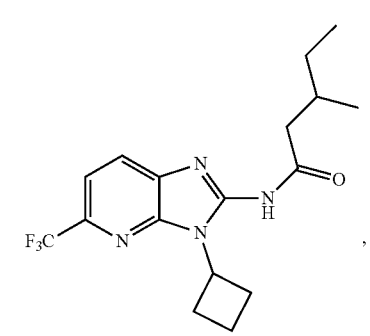
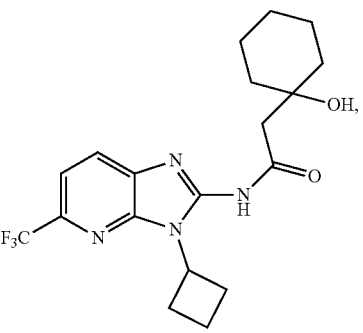

219
-continued
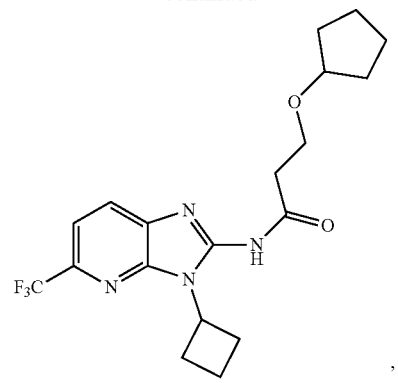
,
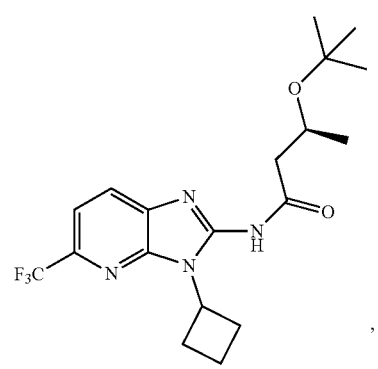
,
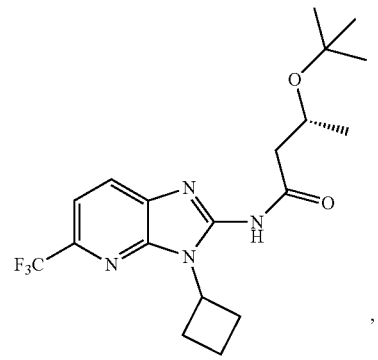
,
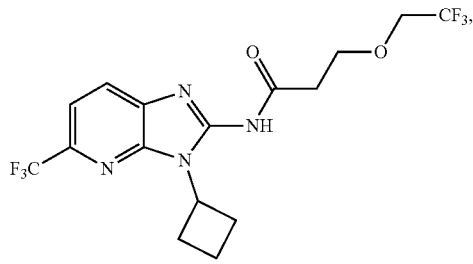
,
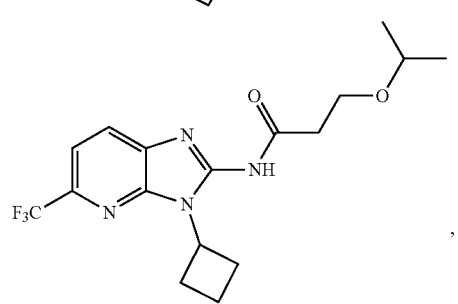
,
220
-continued
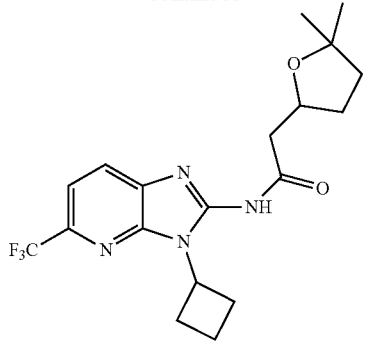
,
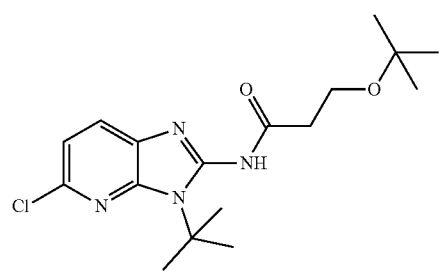
,
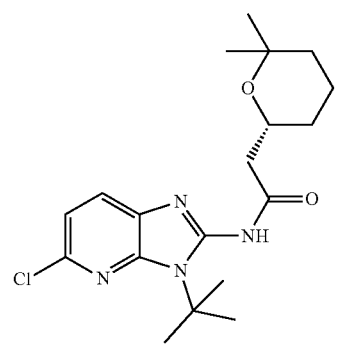
,
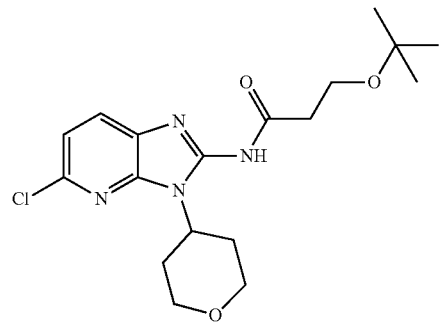
,
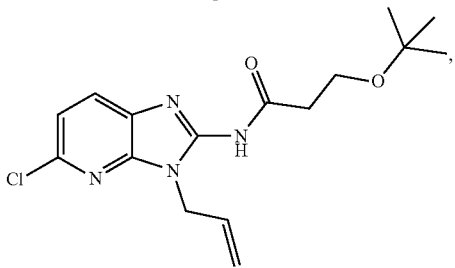
, 221
-continued
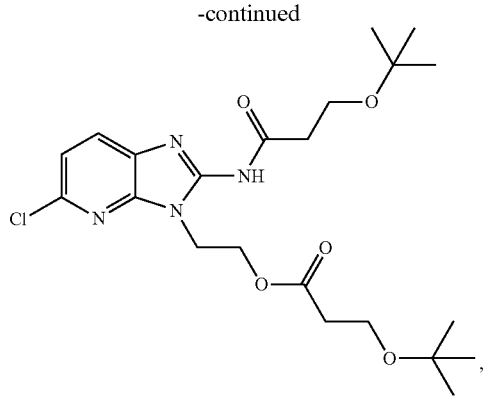
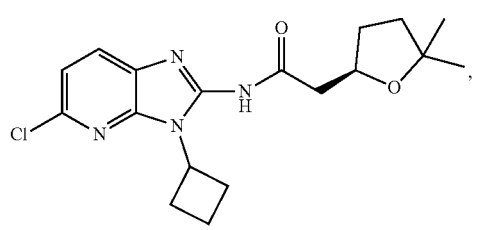
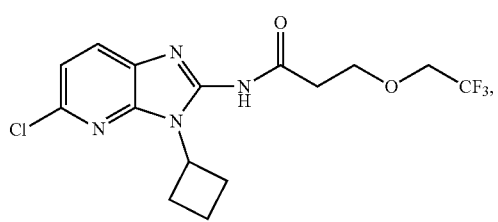
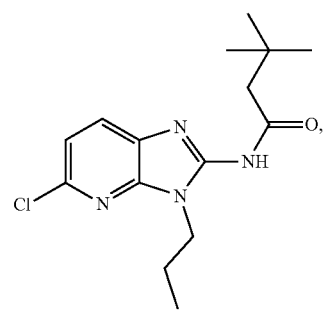
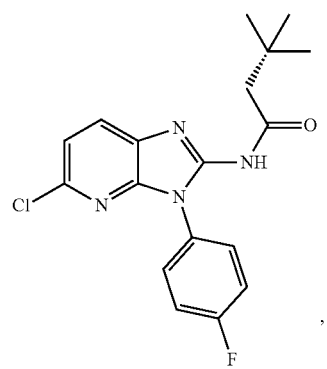
222
-continued
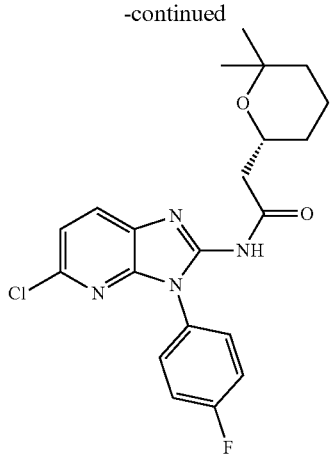
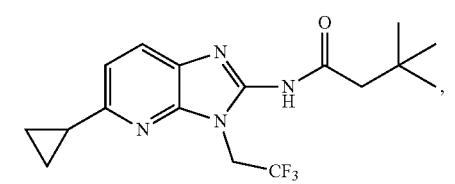
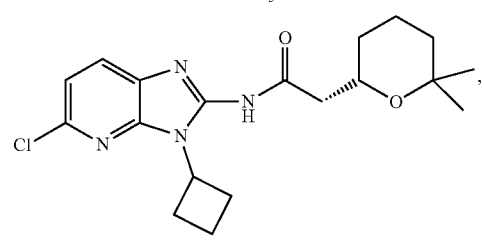
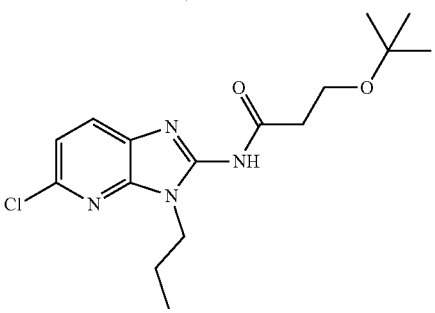
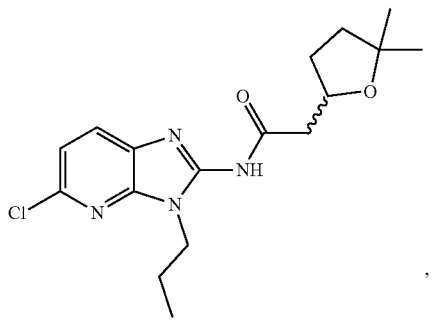

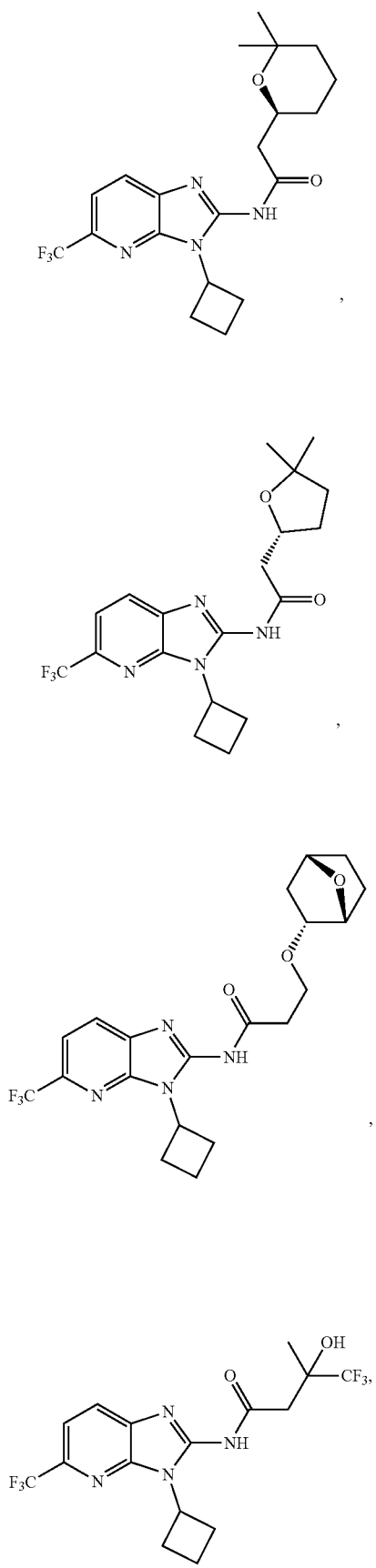
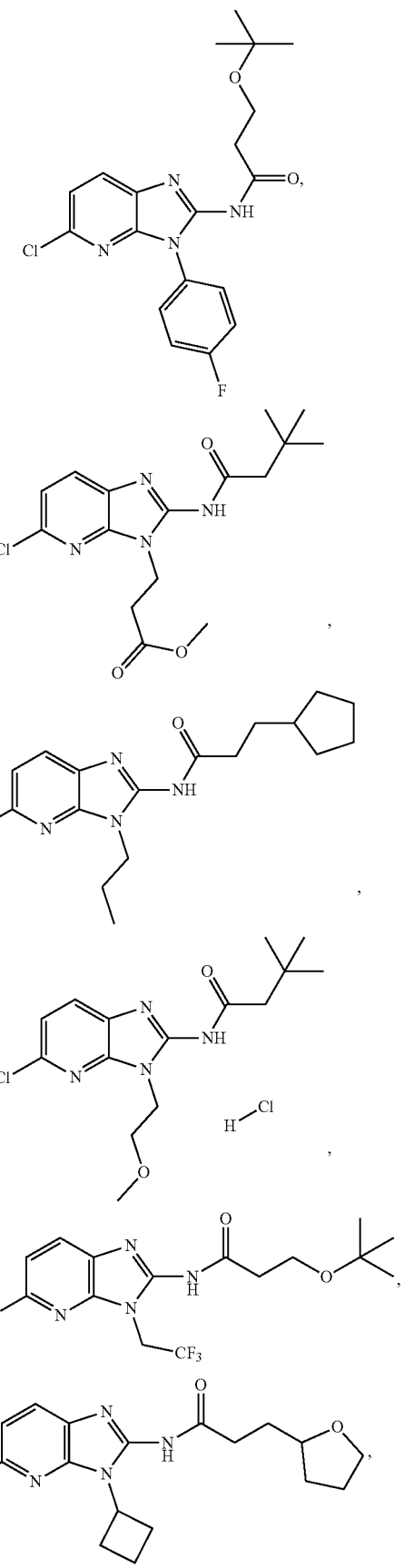

225
-continued
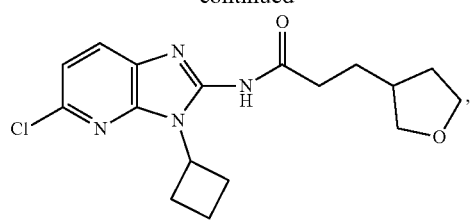
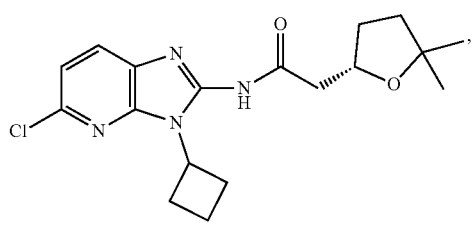
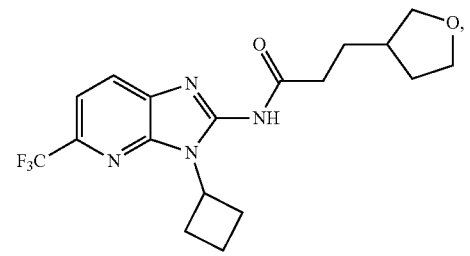
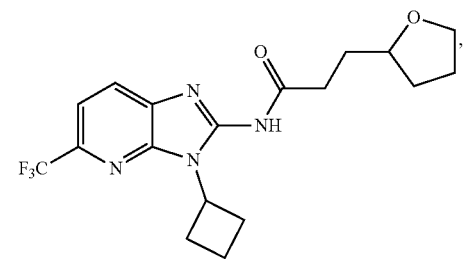
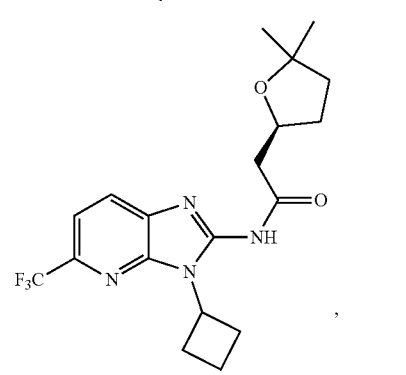
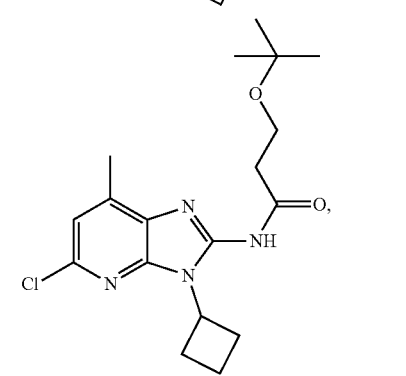
226
-continued
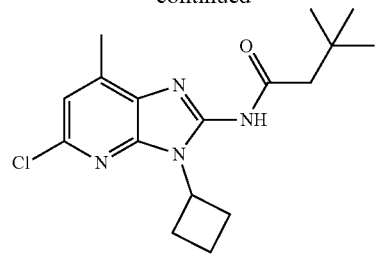
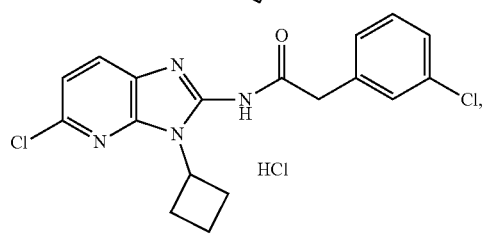
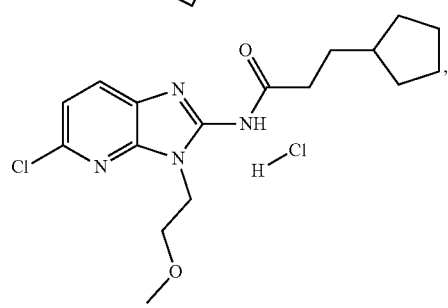
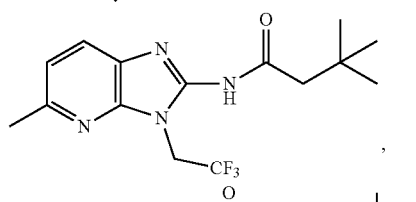
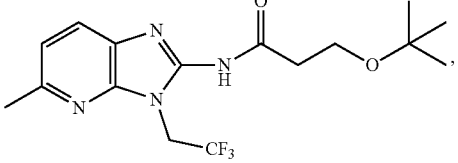
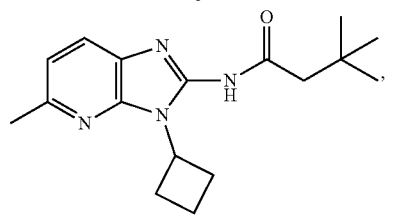
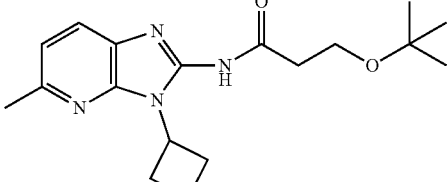
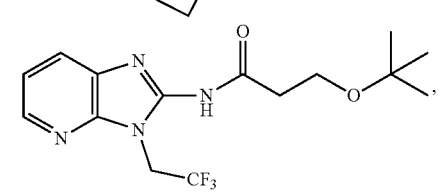

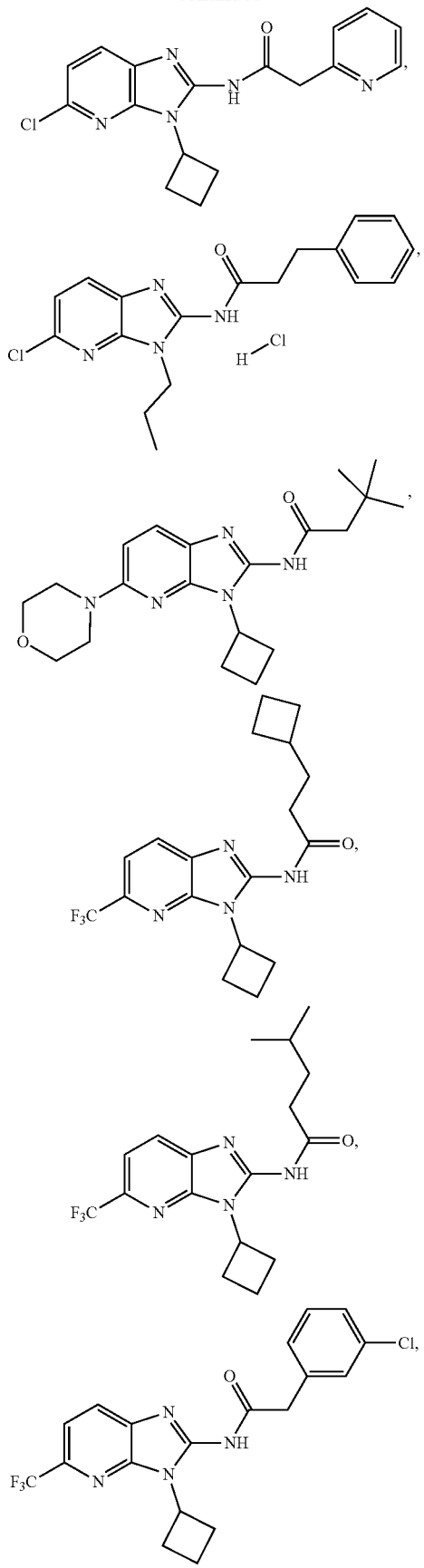
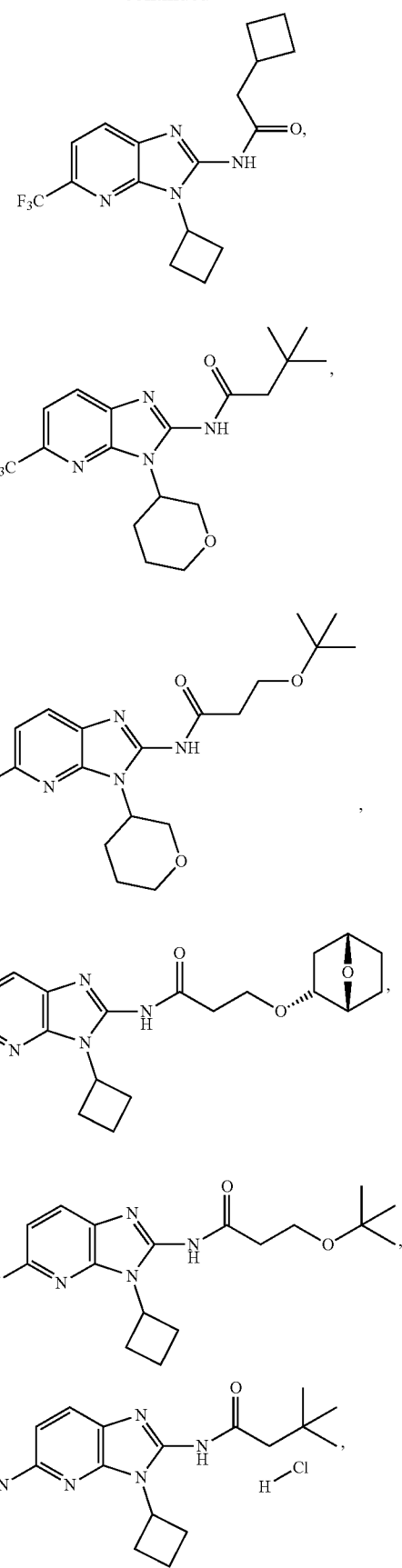

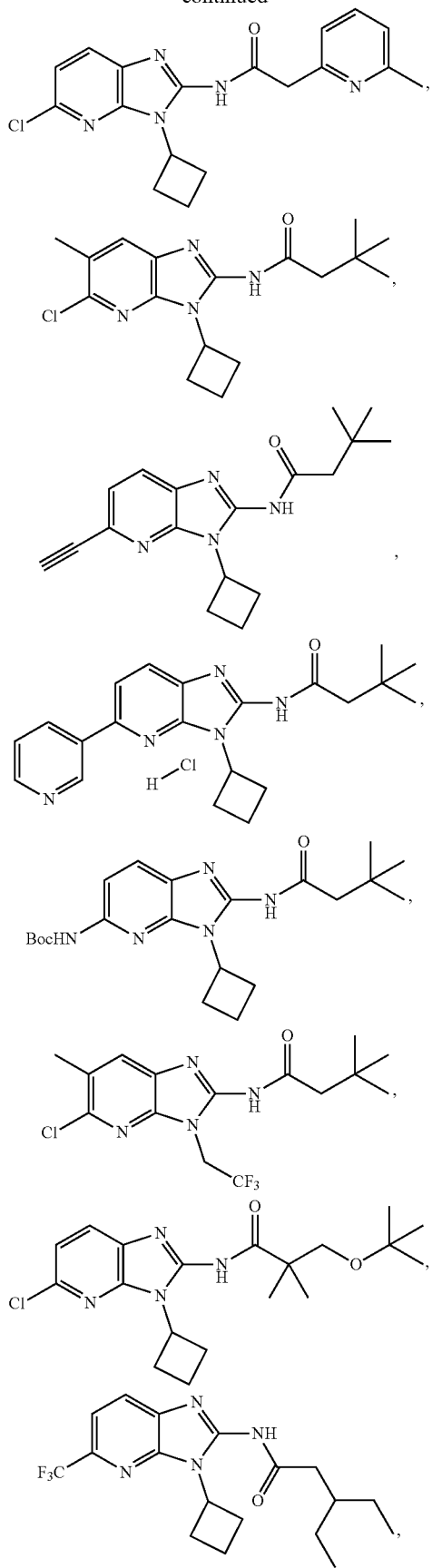
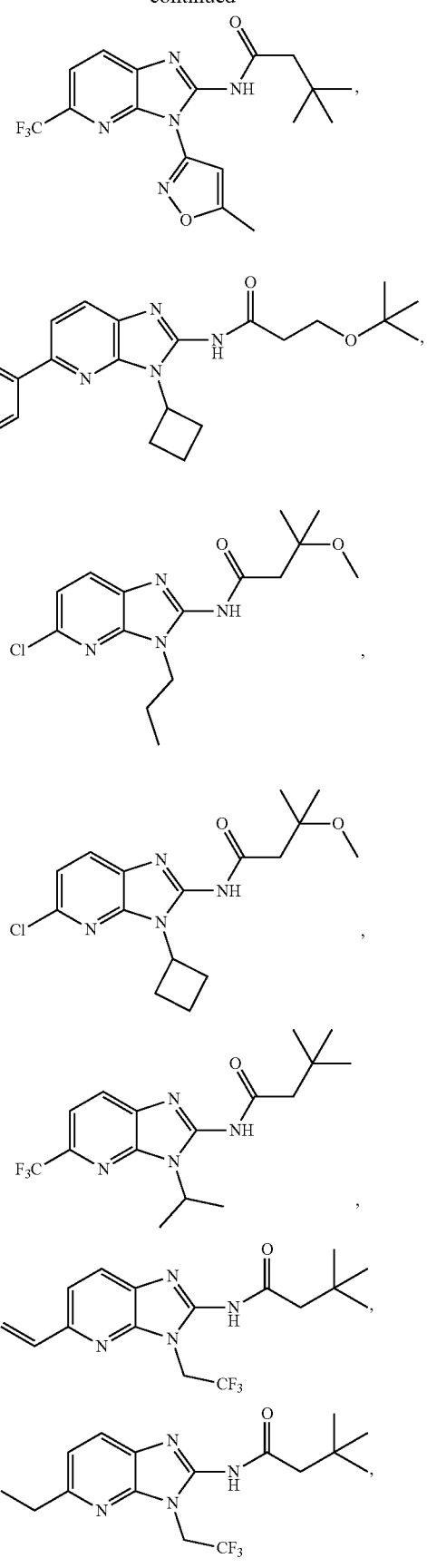

231
-continued
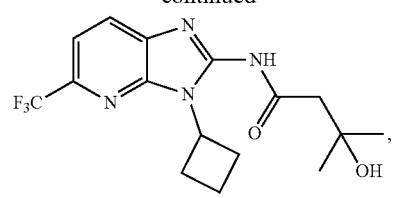
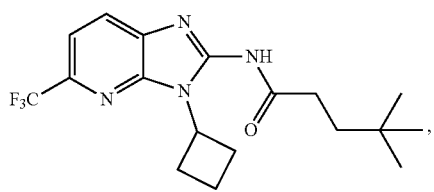
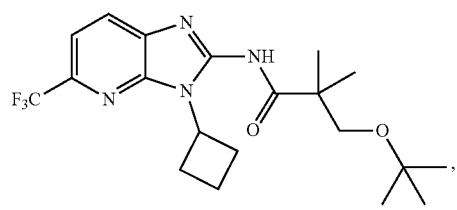
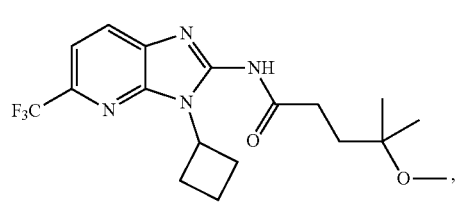
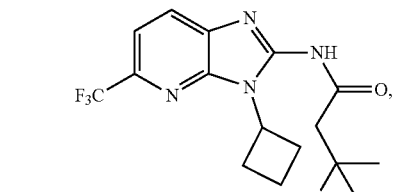
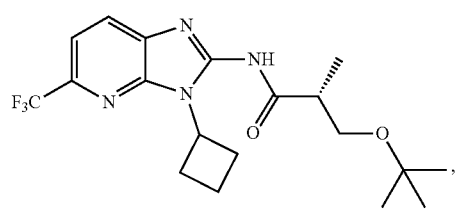
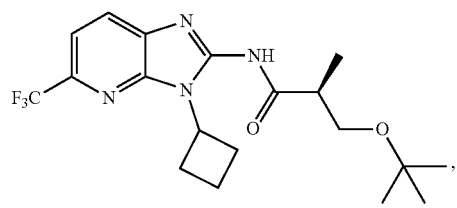
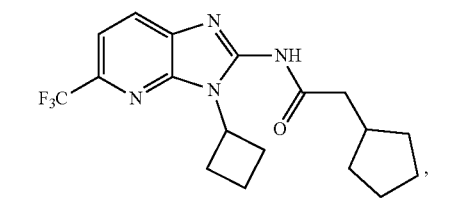
232
-continued
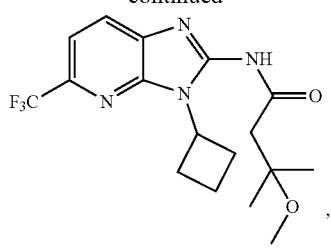
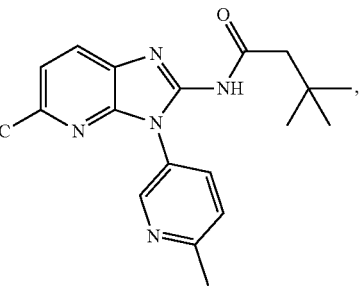
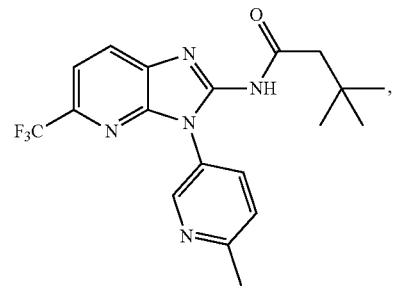
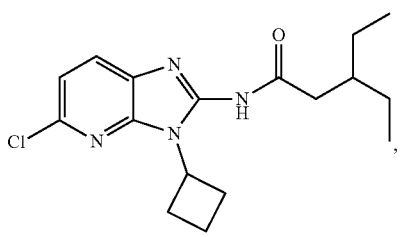
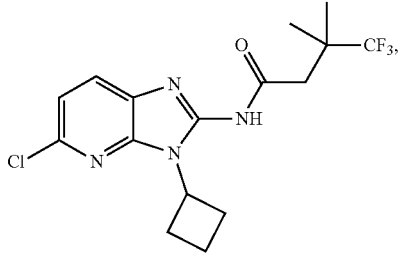
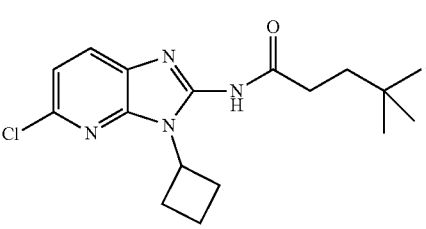
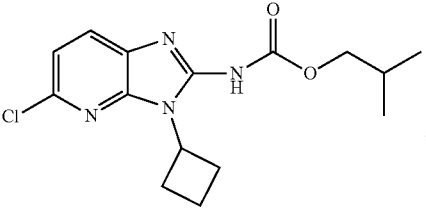

-continued
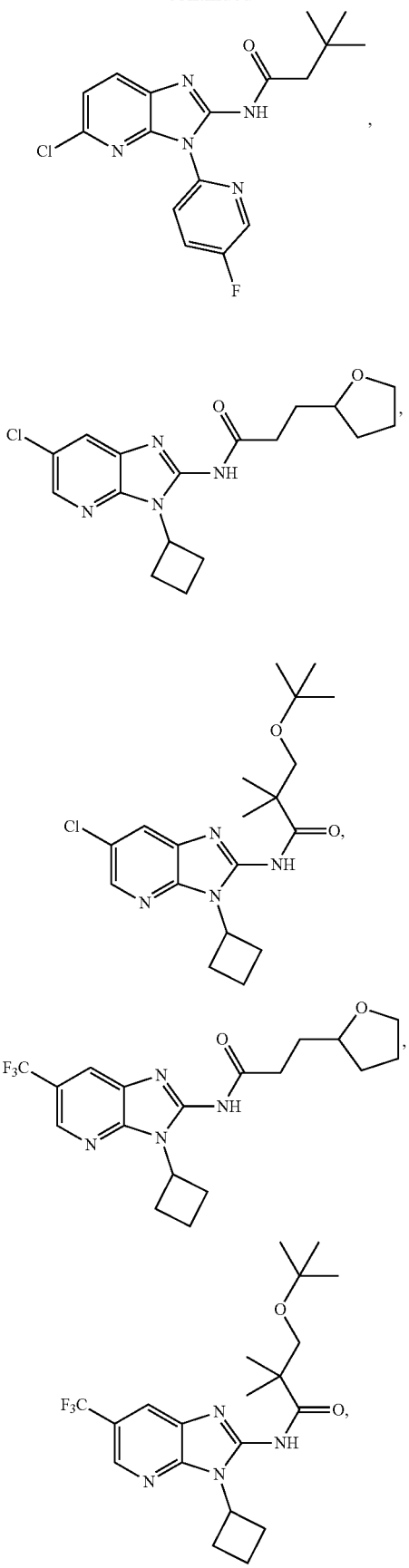
-continued
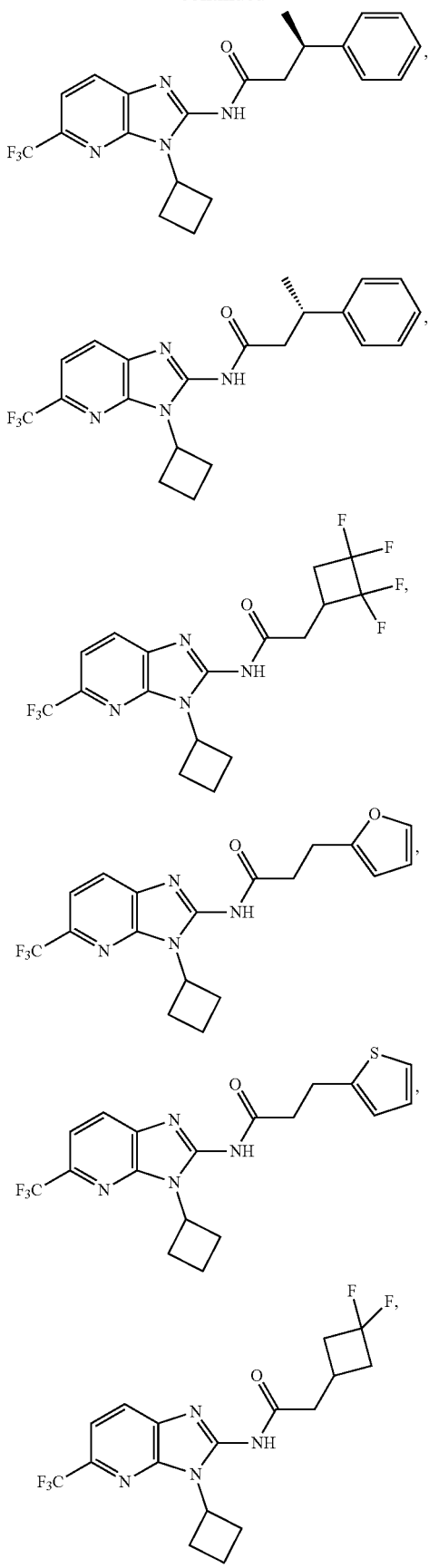

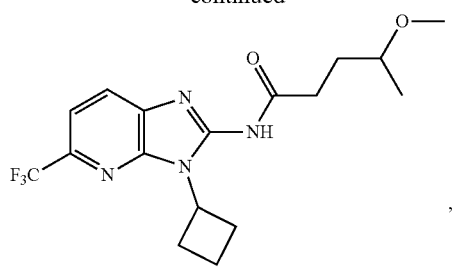,
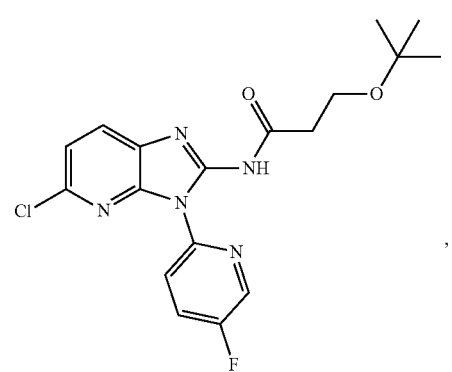,
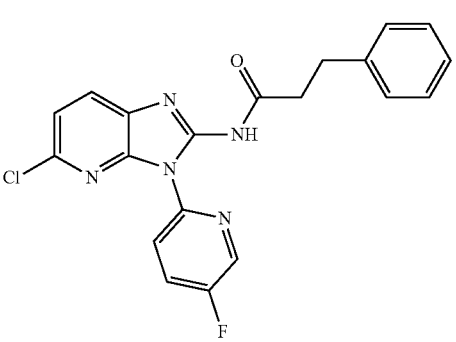,
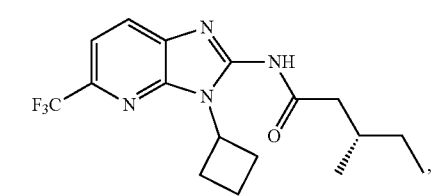,
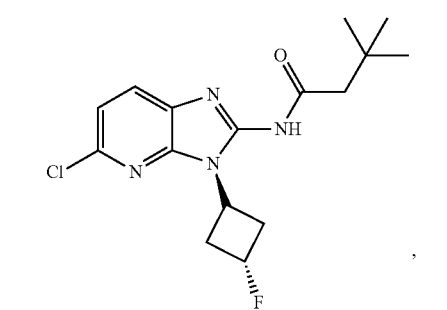,
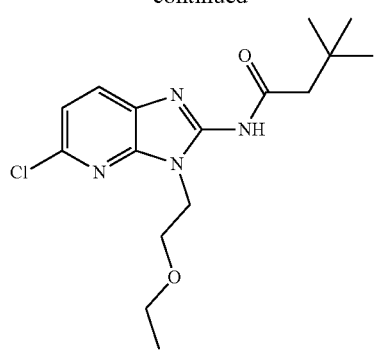,
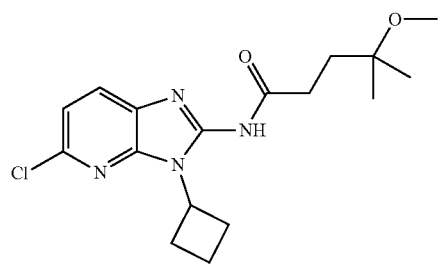,
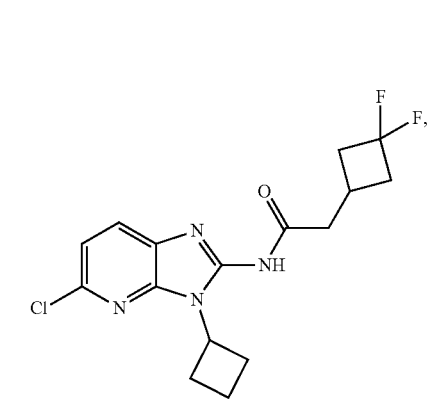,
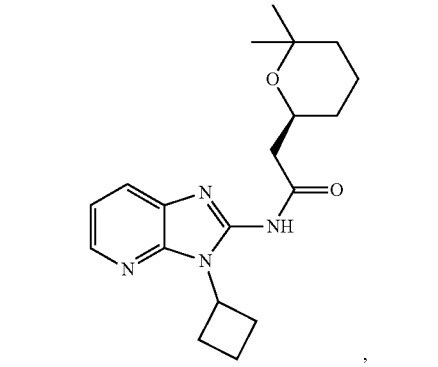,
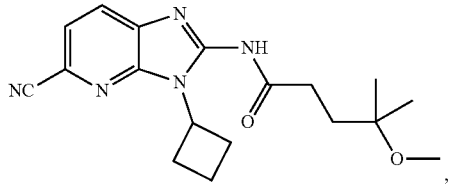, 237
-continued
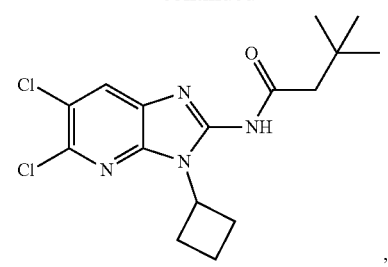
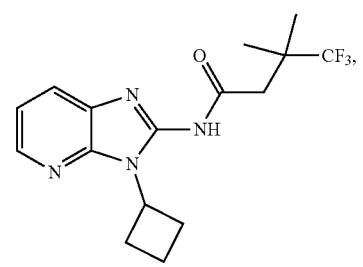
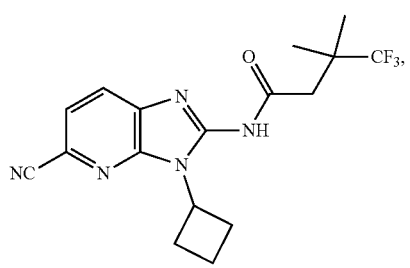
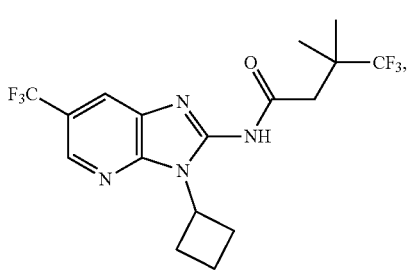
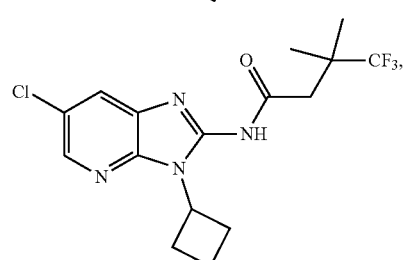
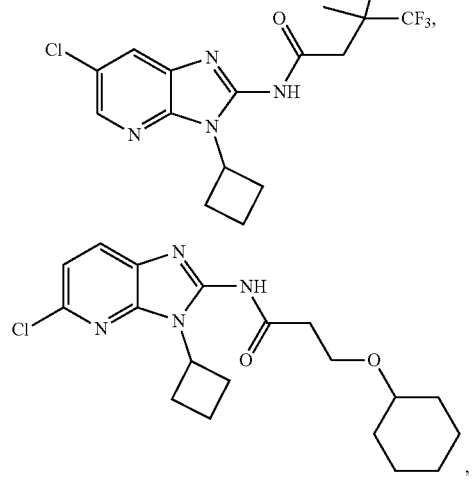
238
-continued
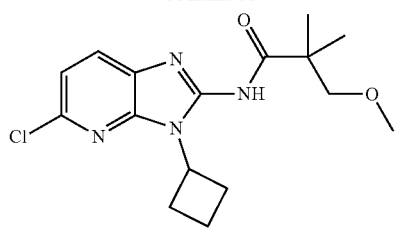
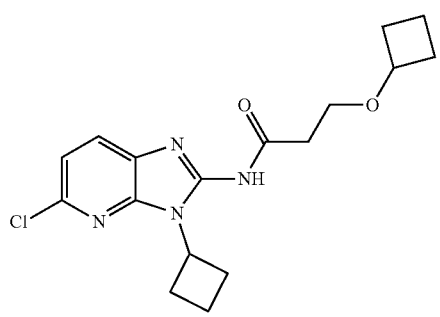
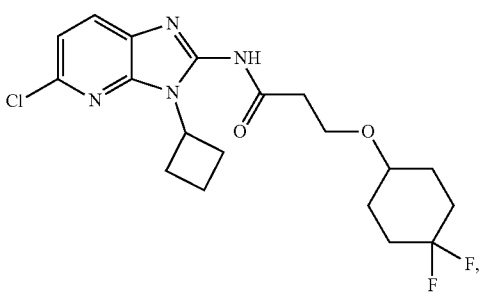
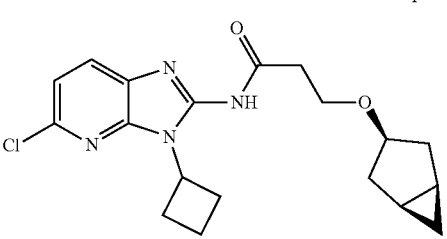
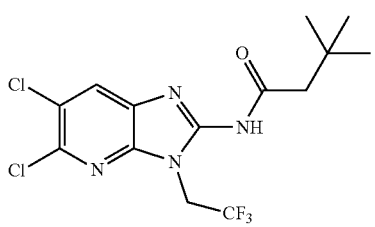
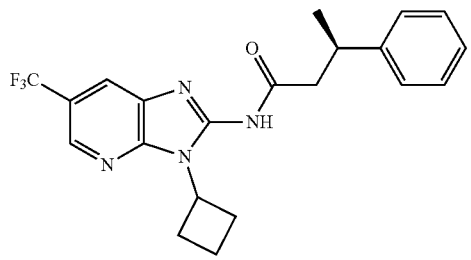

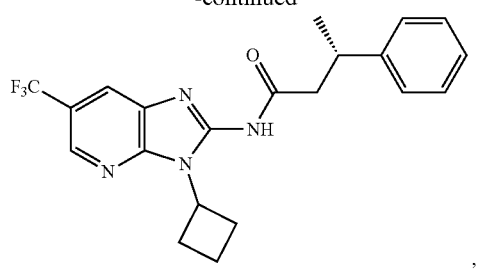
,
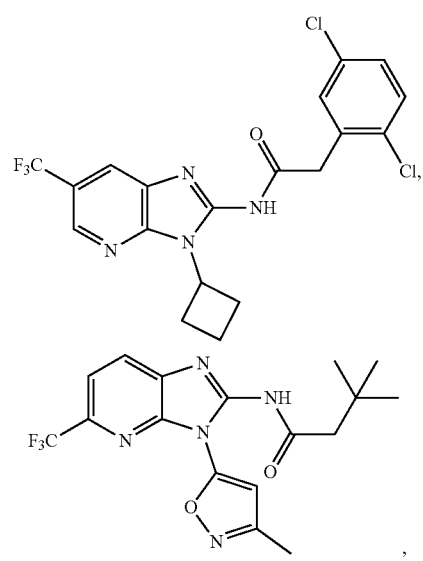
,
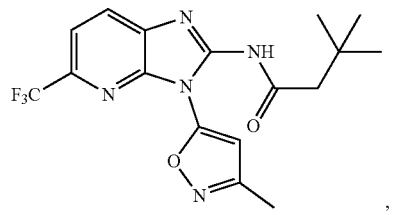
,
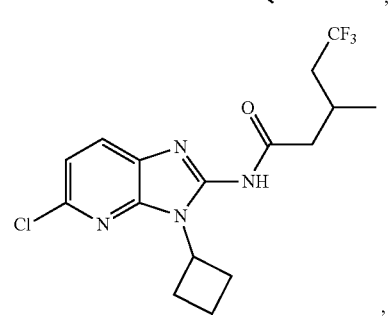
,
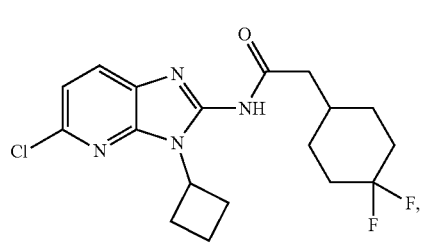
,
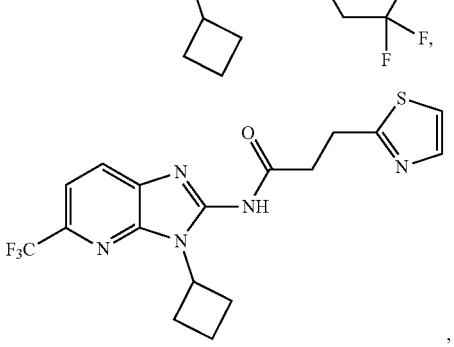
,
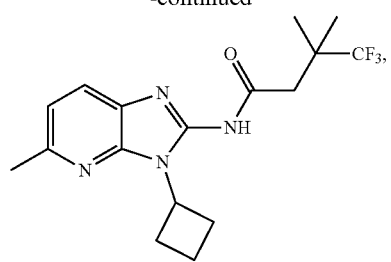
,
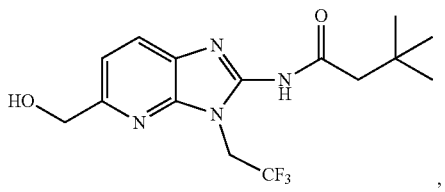
,
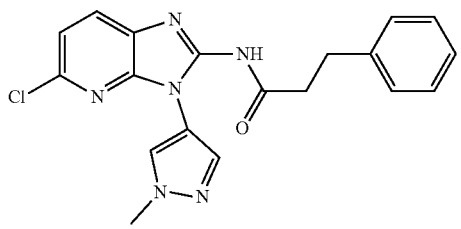
,
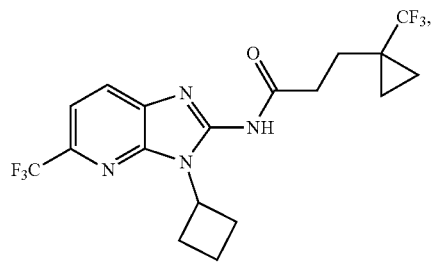
,
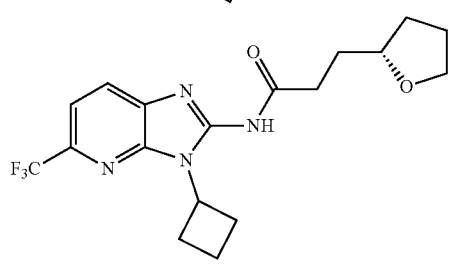
,
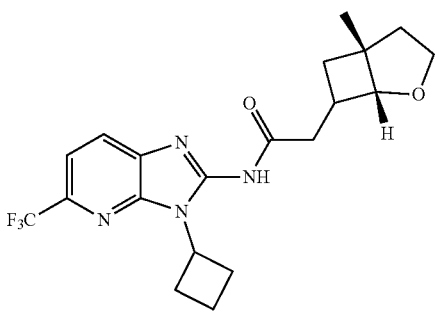
, 241
-continued
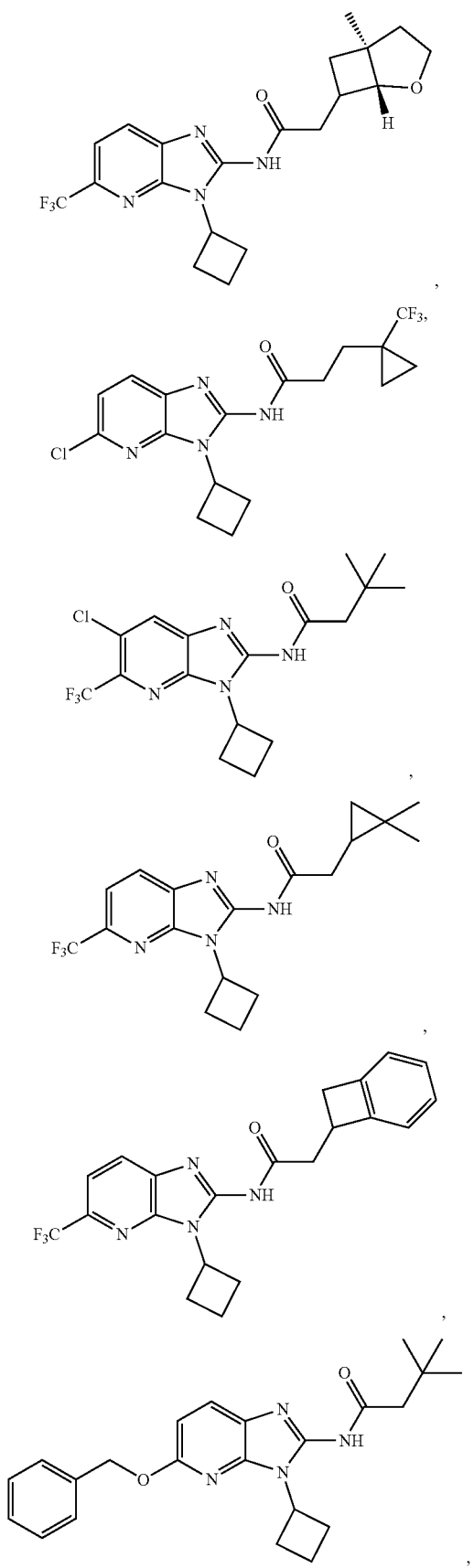
242
-continued
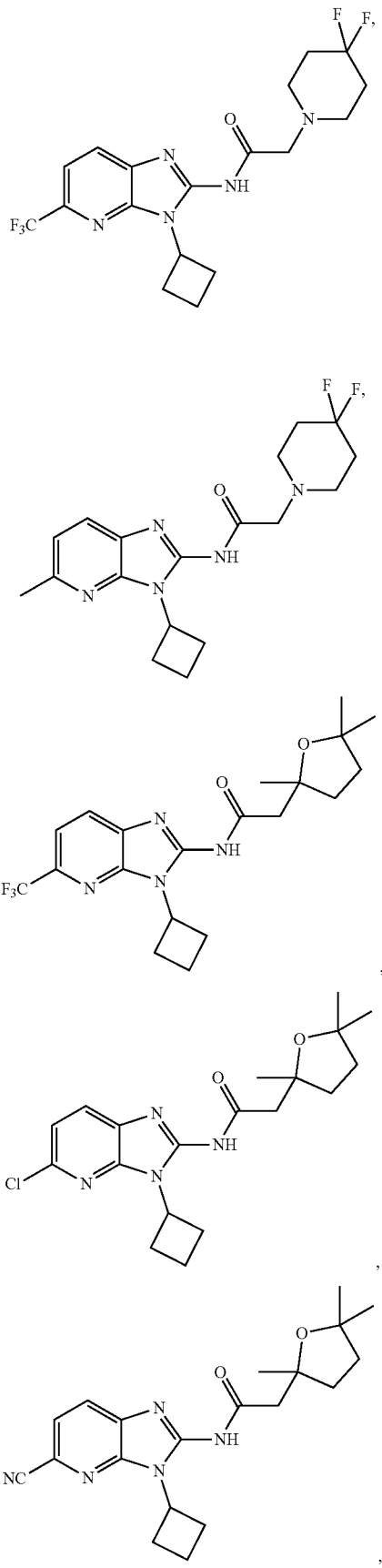

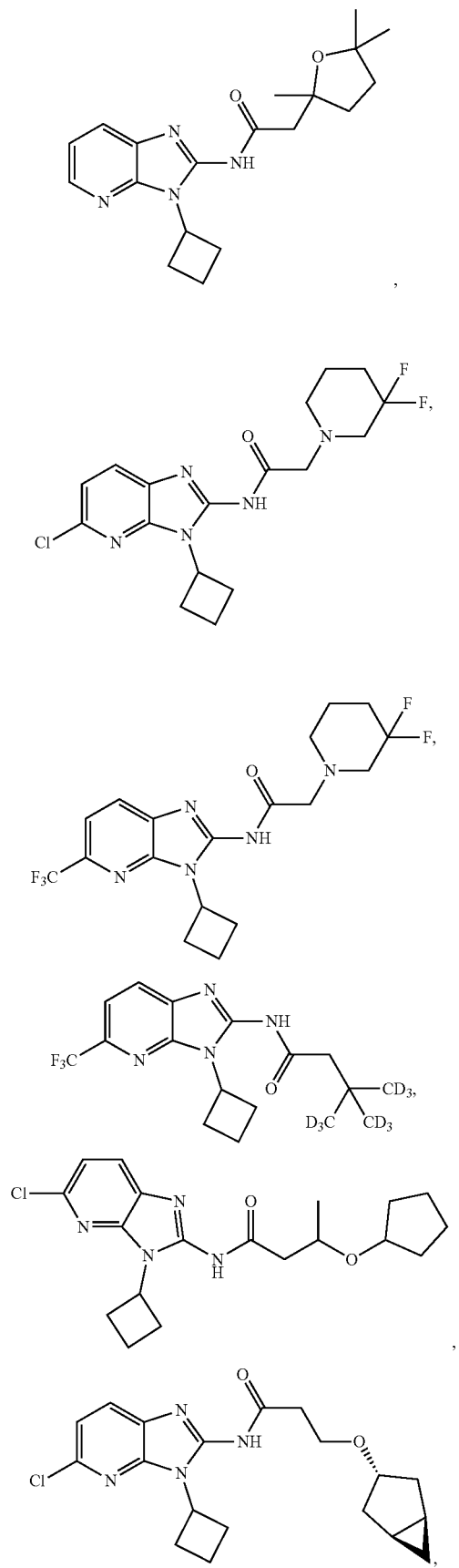
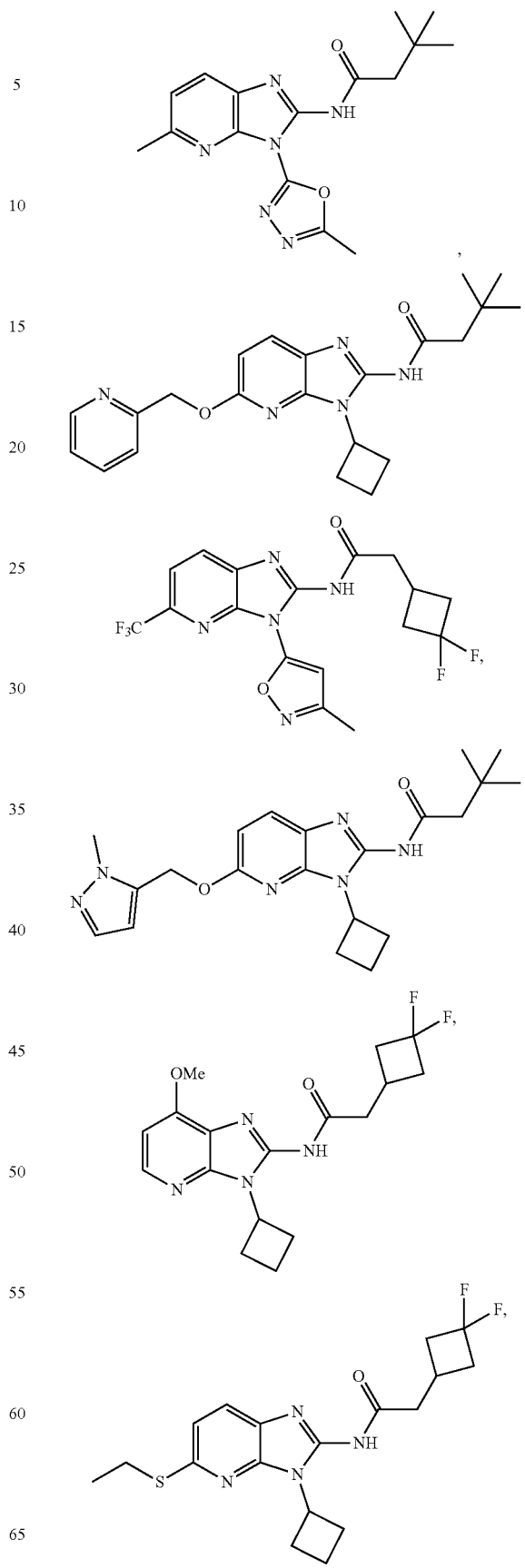

-continued
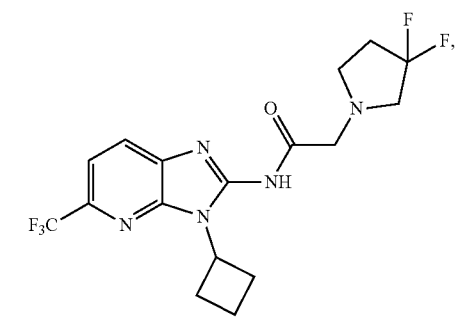
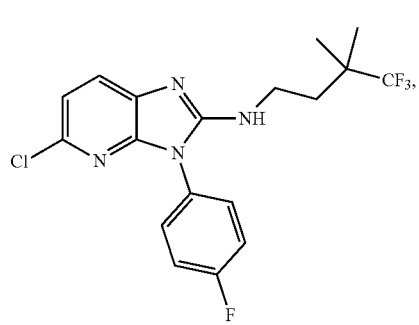
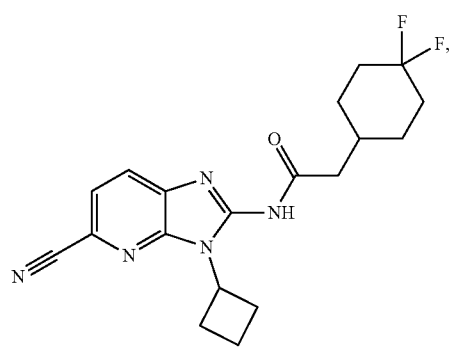
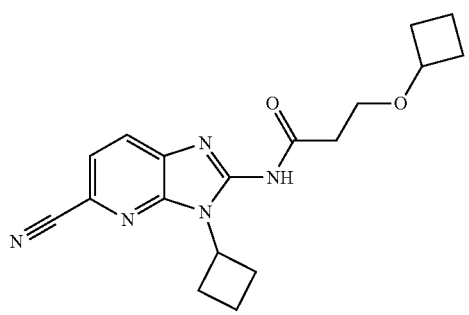
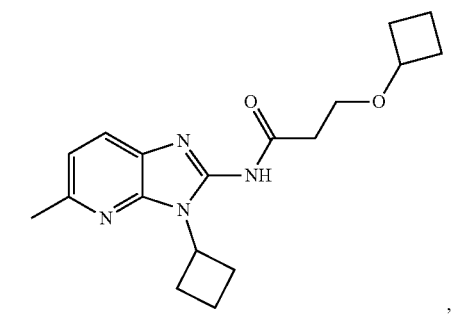
-continued
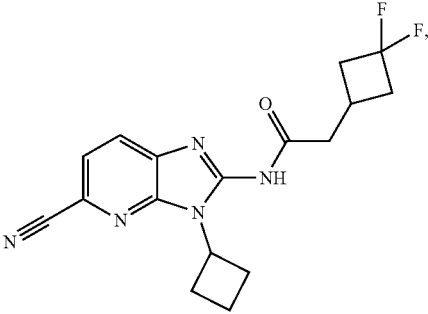
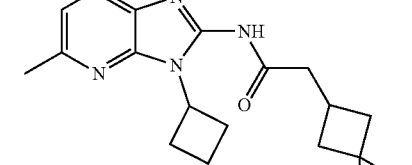
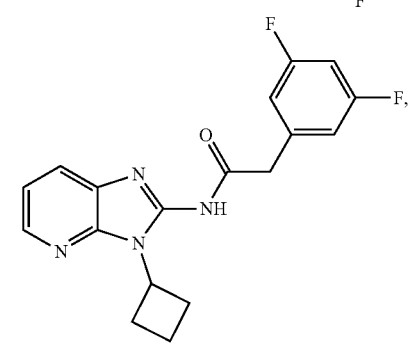
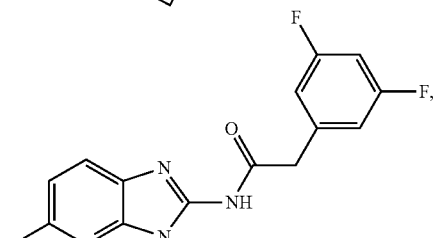
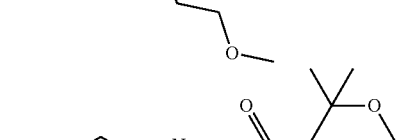
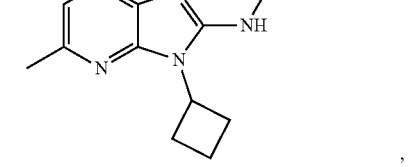
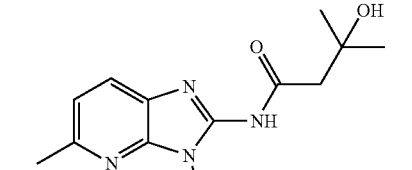
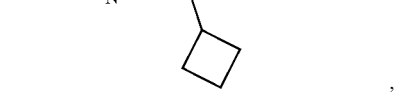

247
-continued
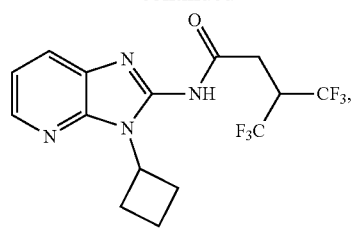
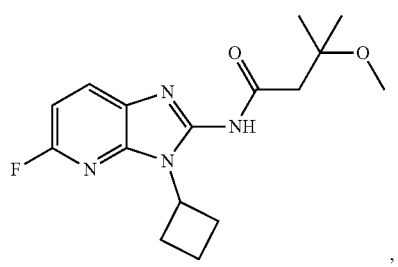
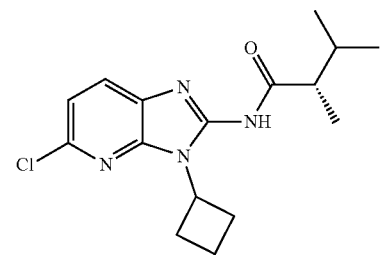
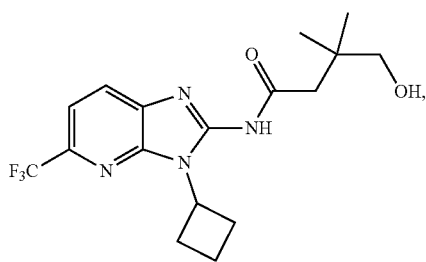
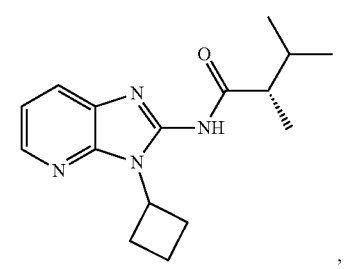
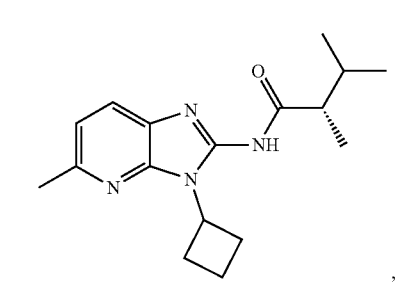
248
-continued
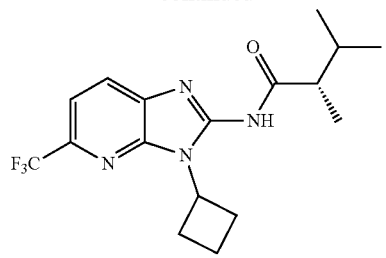
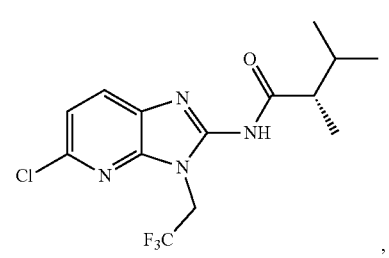
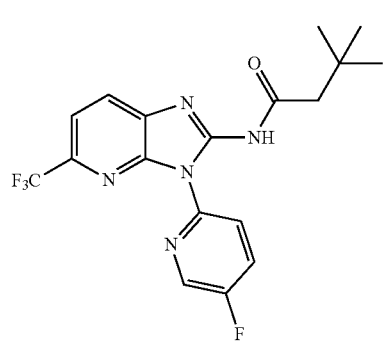
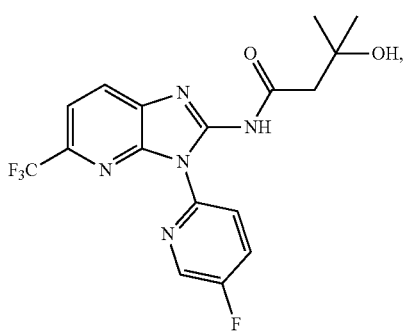
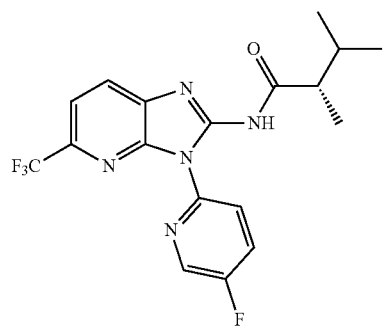

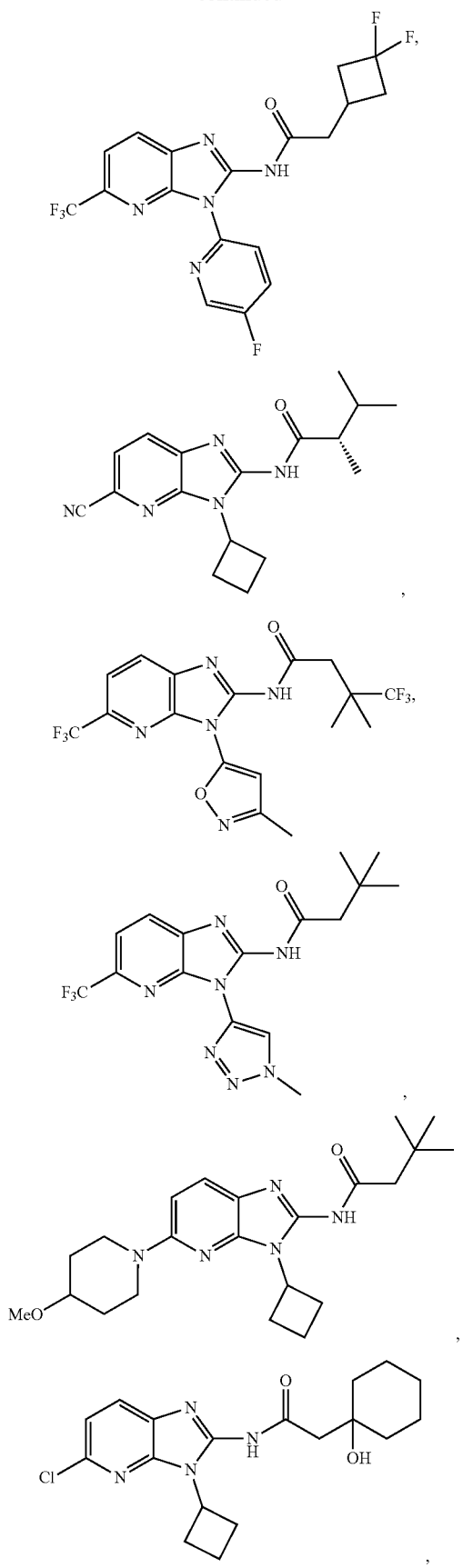
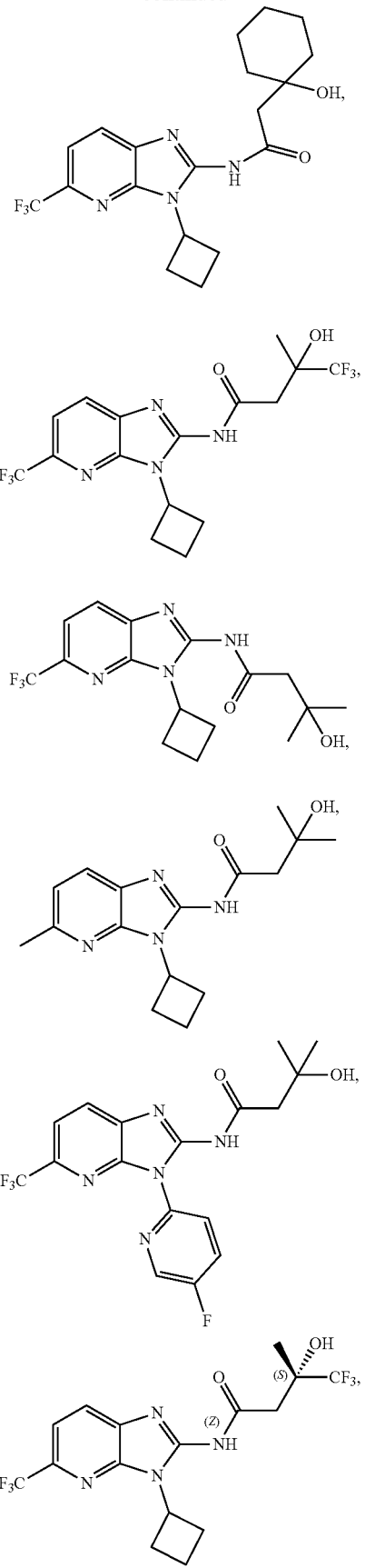

-continued
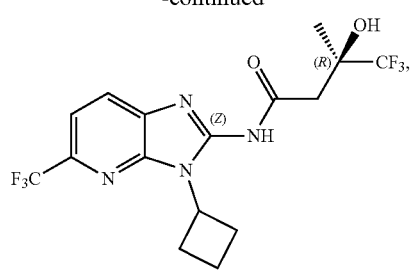
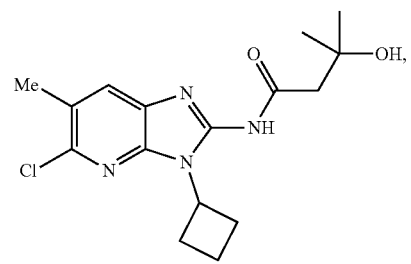
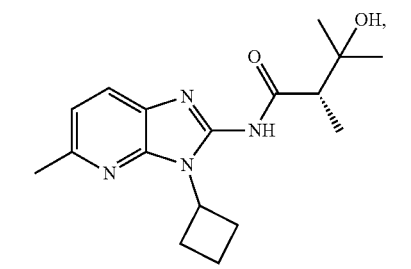
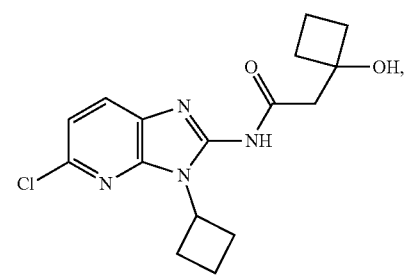
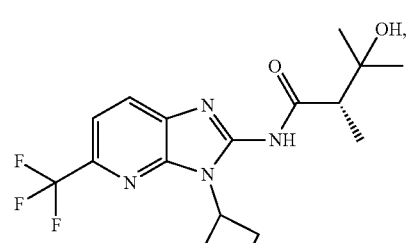
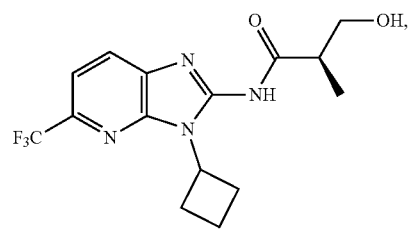
-continued
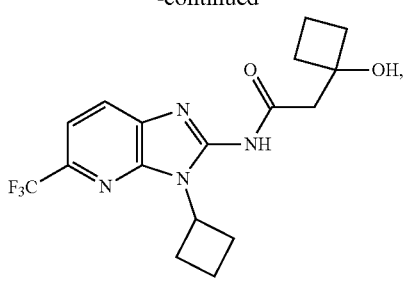
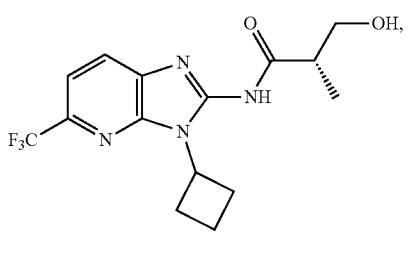
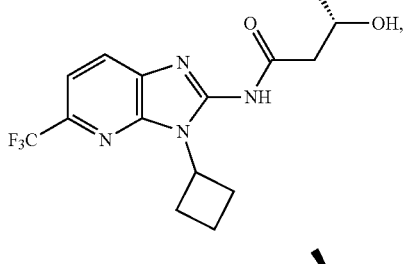
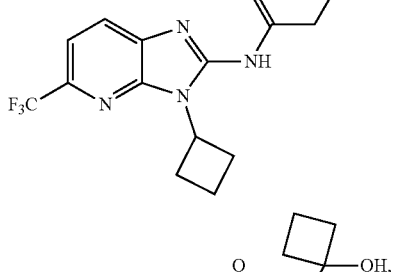
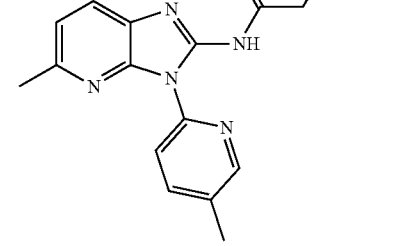
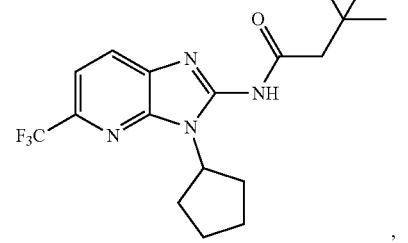

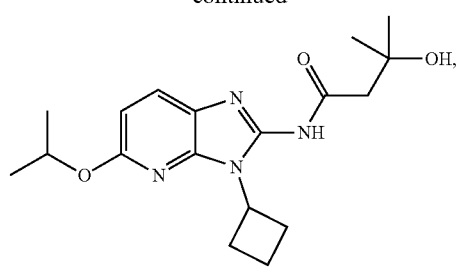
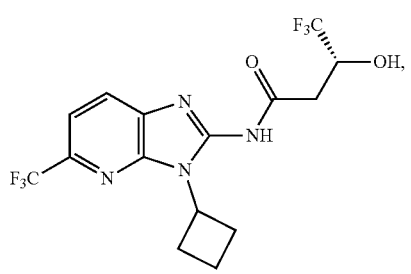
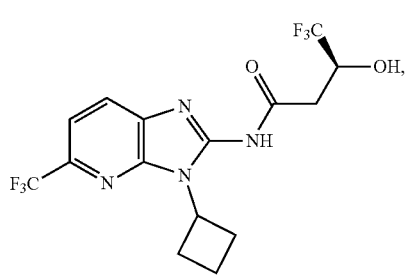
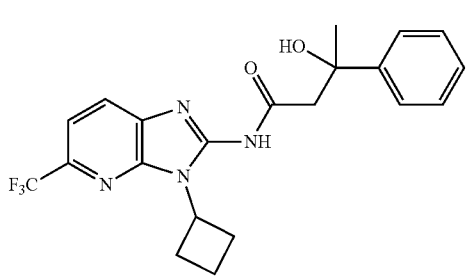
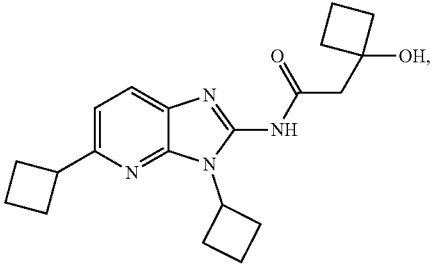
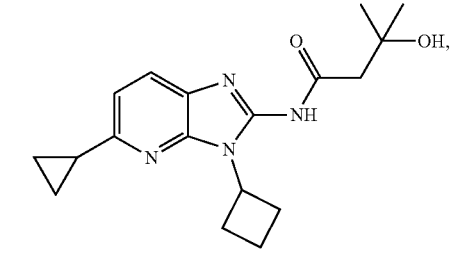
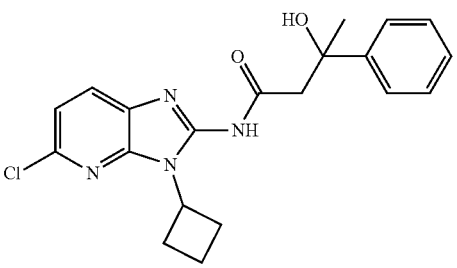
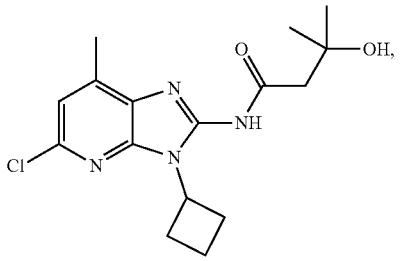
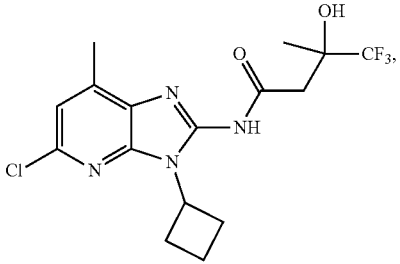
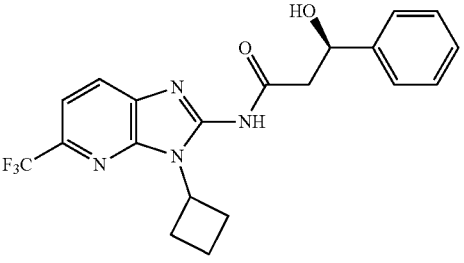
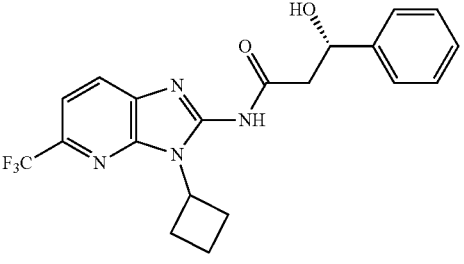

255
-continued
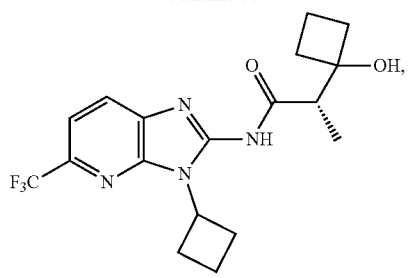
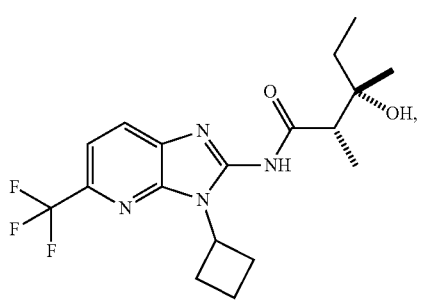
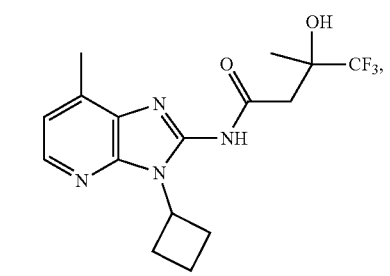
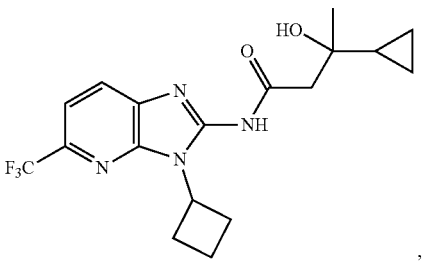
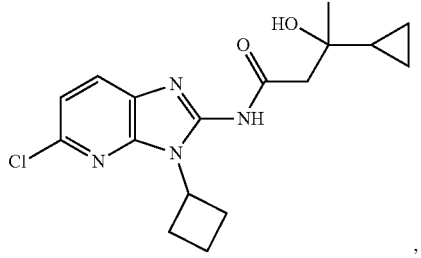
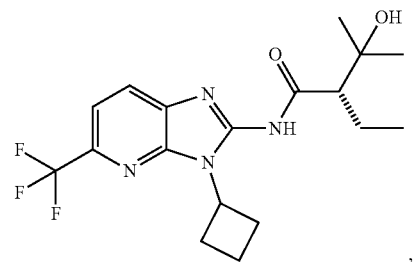
256
-continued
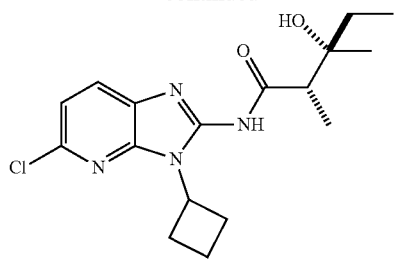
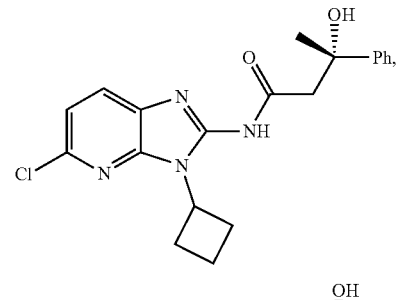
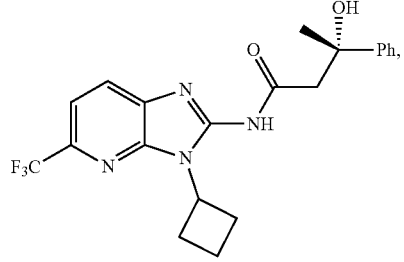
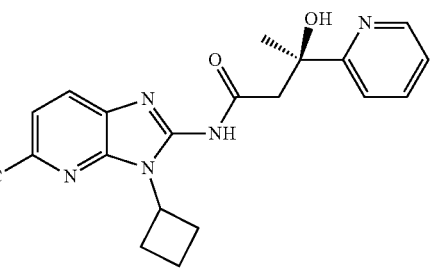
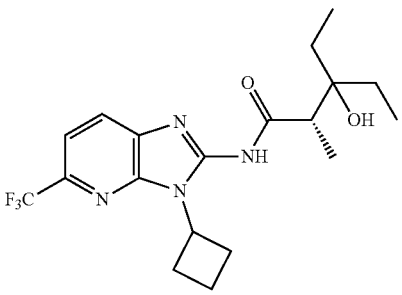
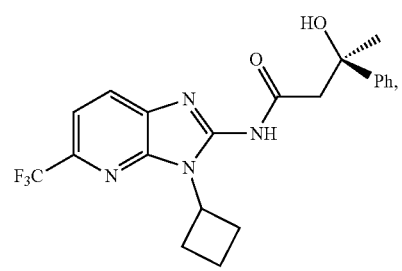

257
-continued
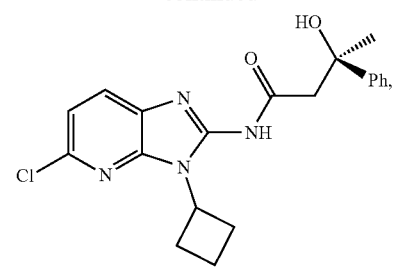
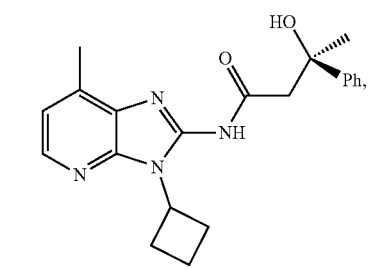
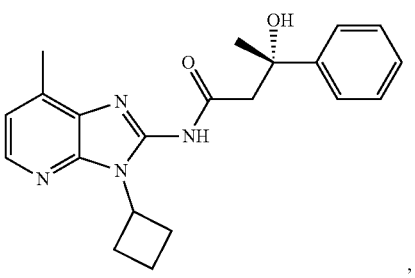
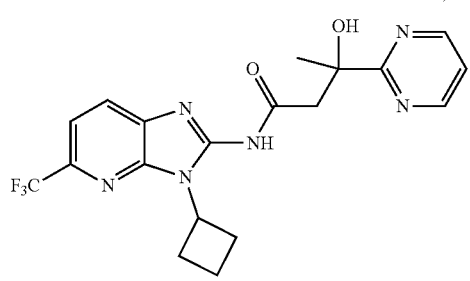
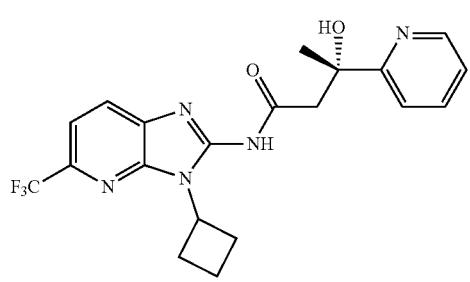
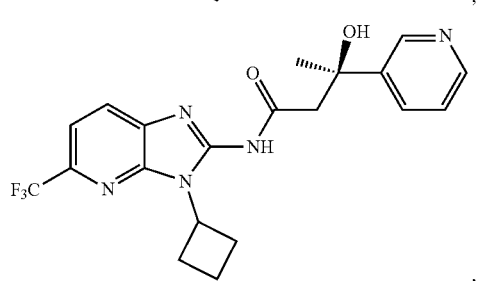
258
-continued
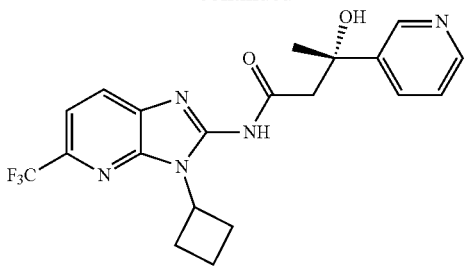
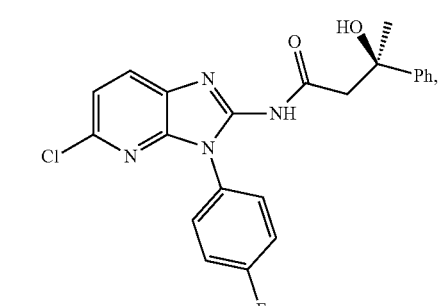
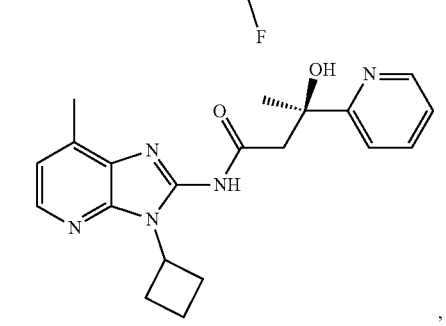
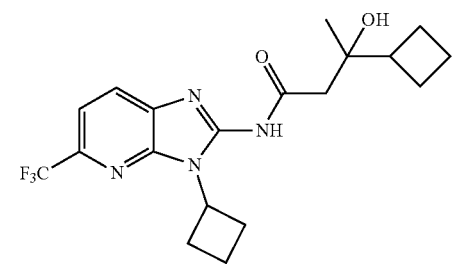
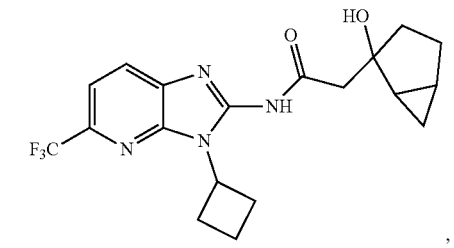
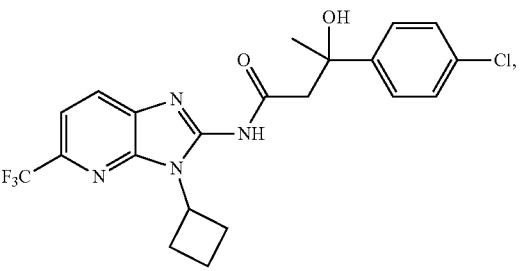

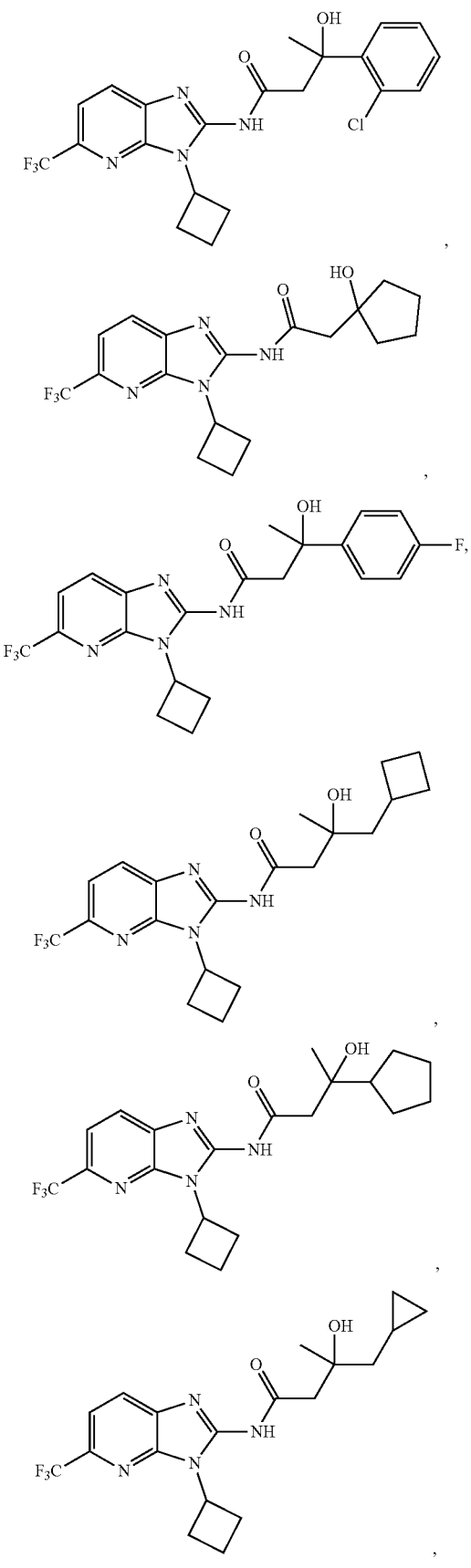
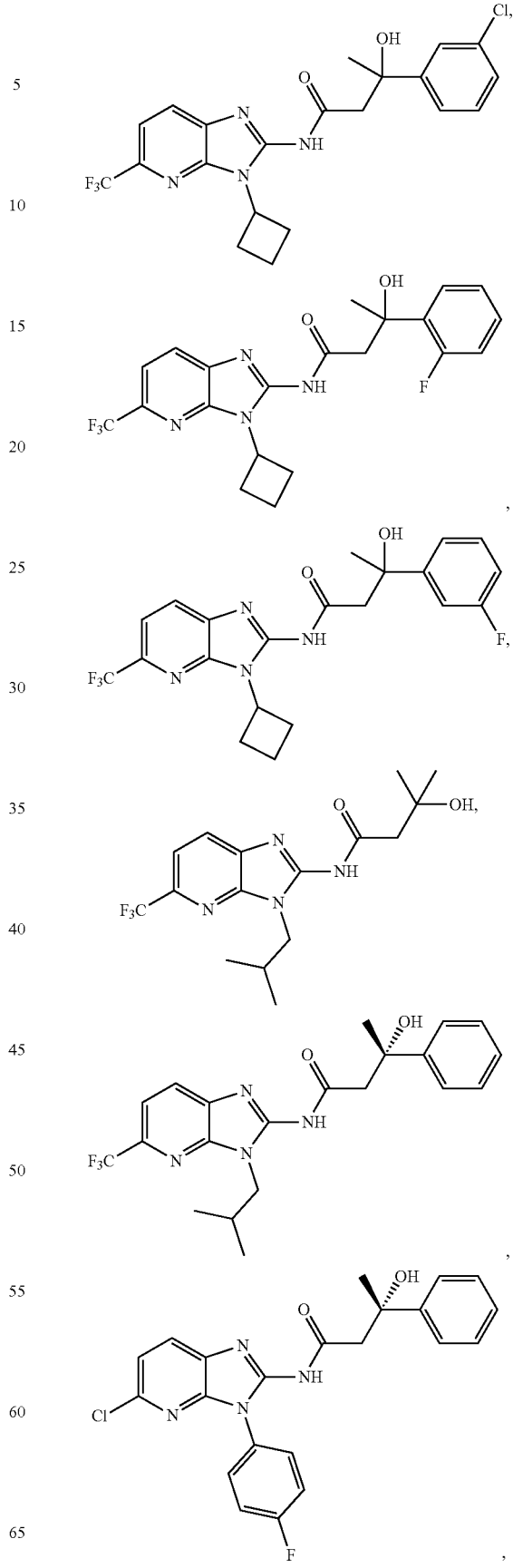

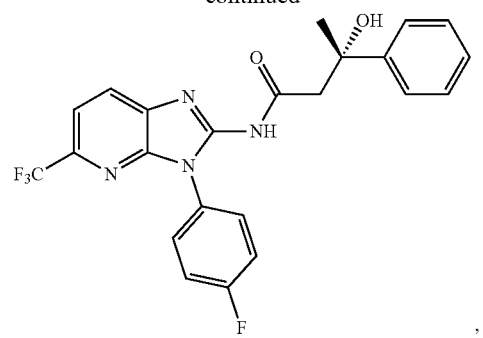
,
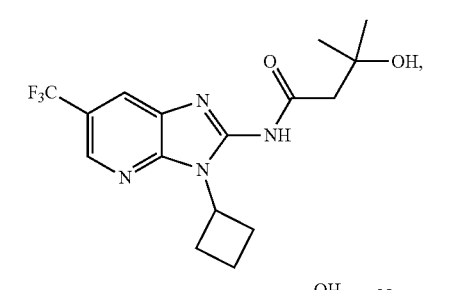
,
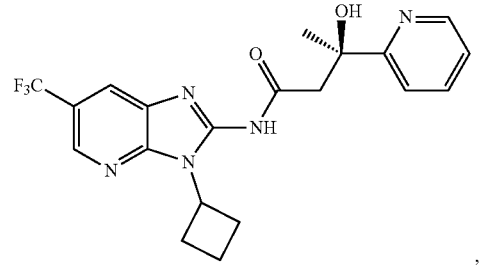
,
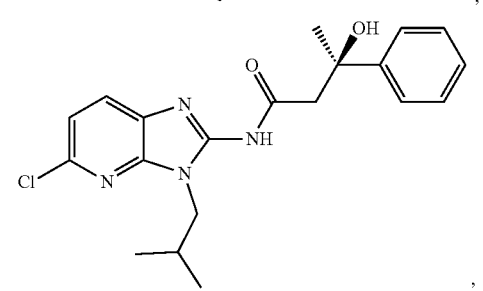
,
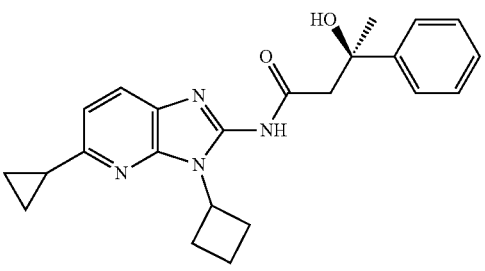
,
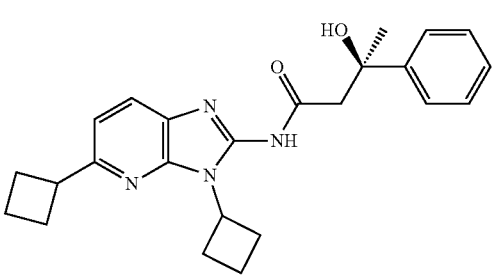
,
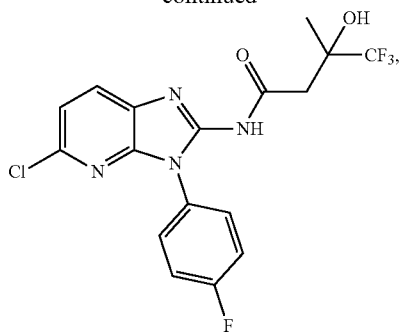
,
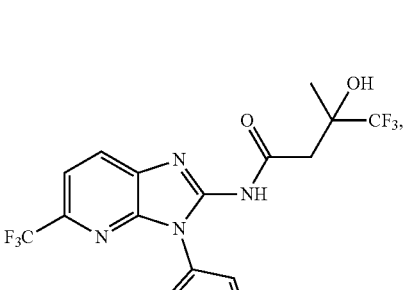
,
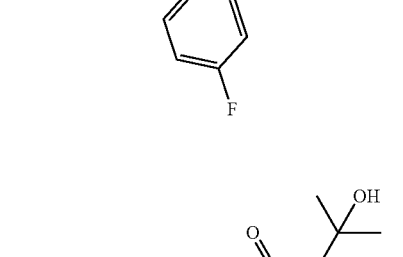
,
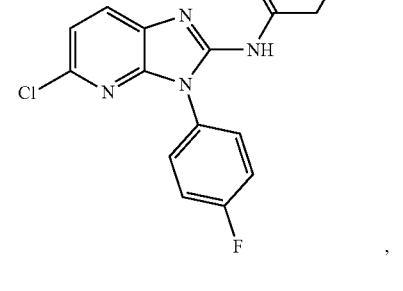
,
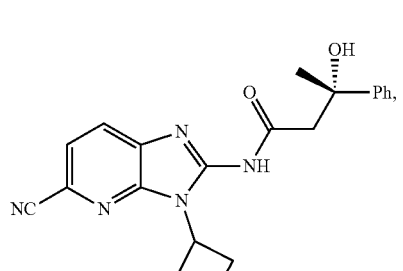
,
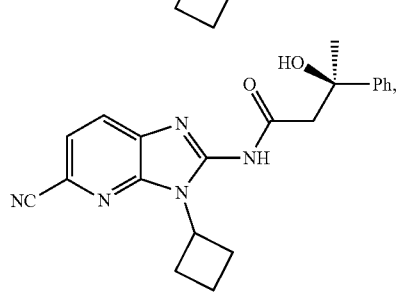
, 263
-continued
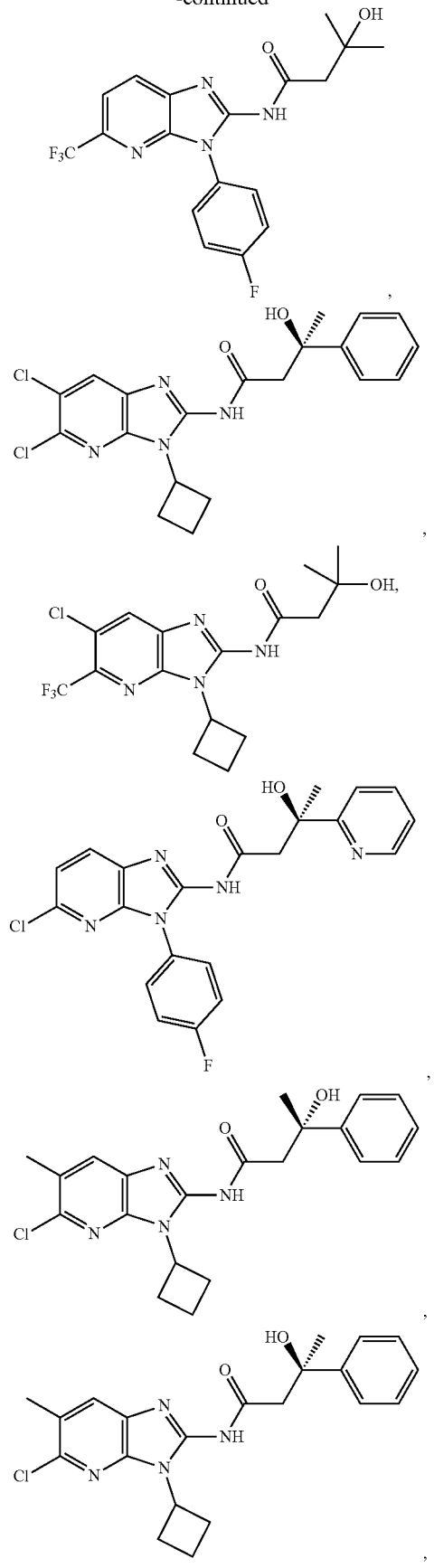
264
-continued
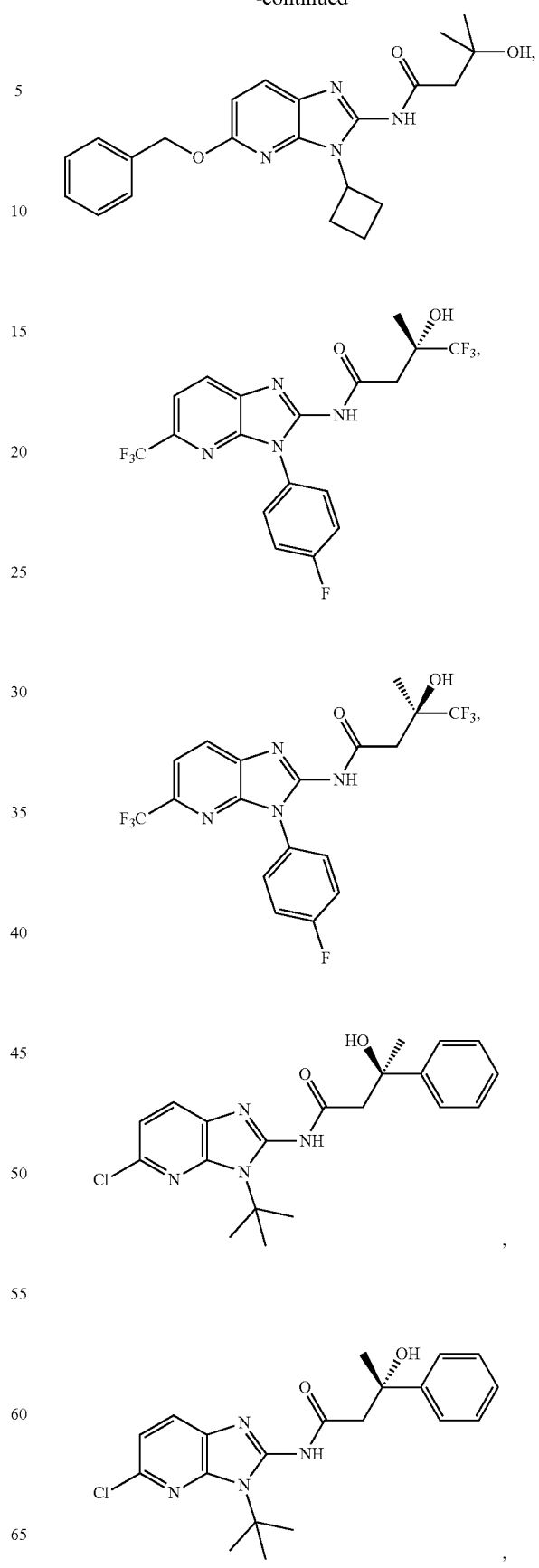

265
-continued
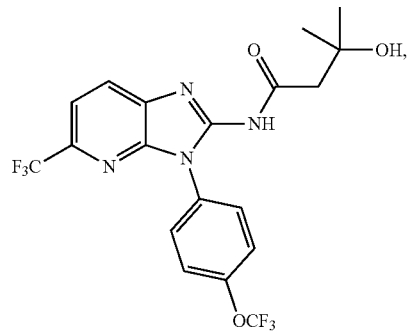
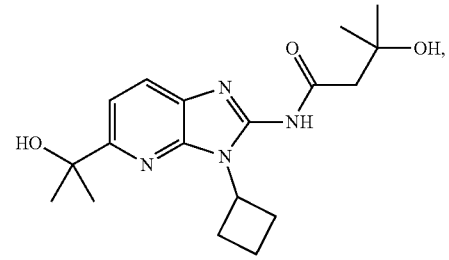
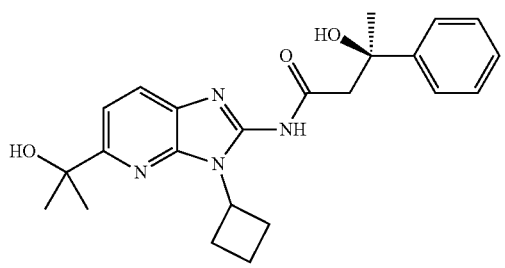
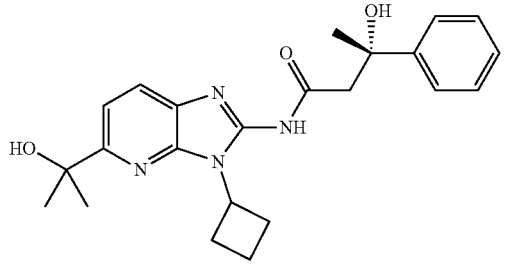
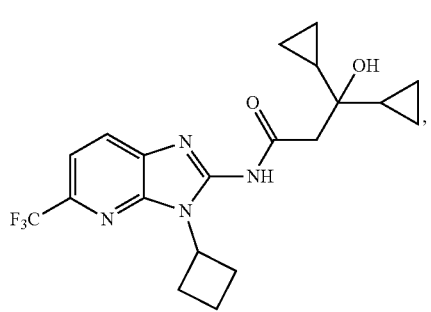
266
-continued
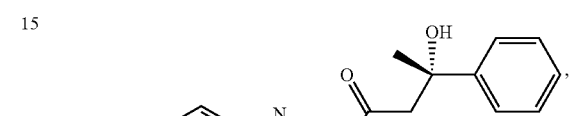
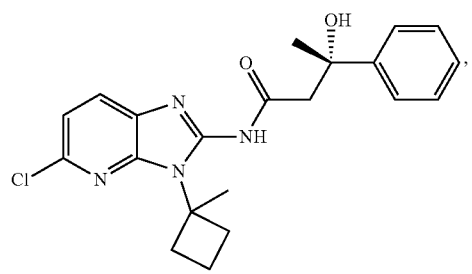
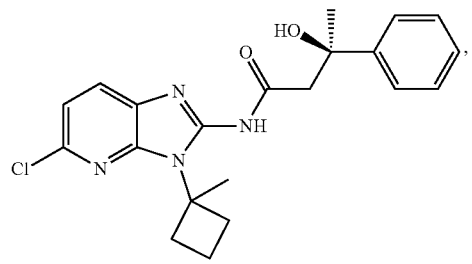
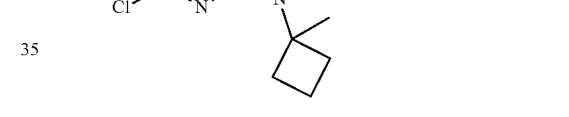
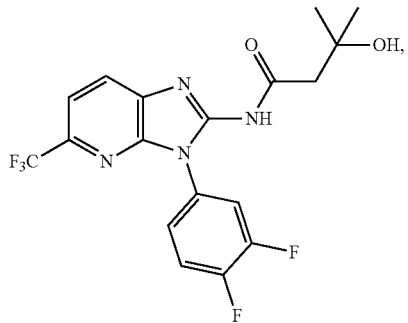
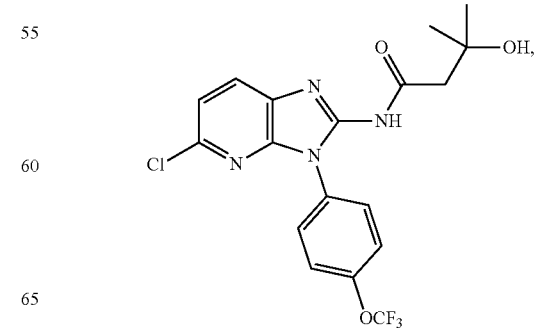

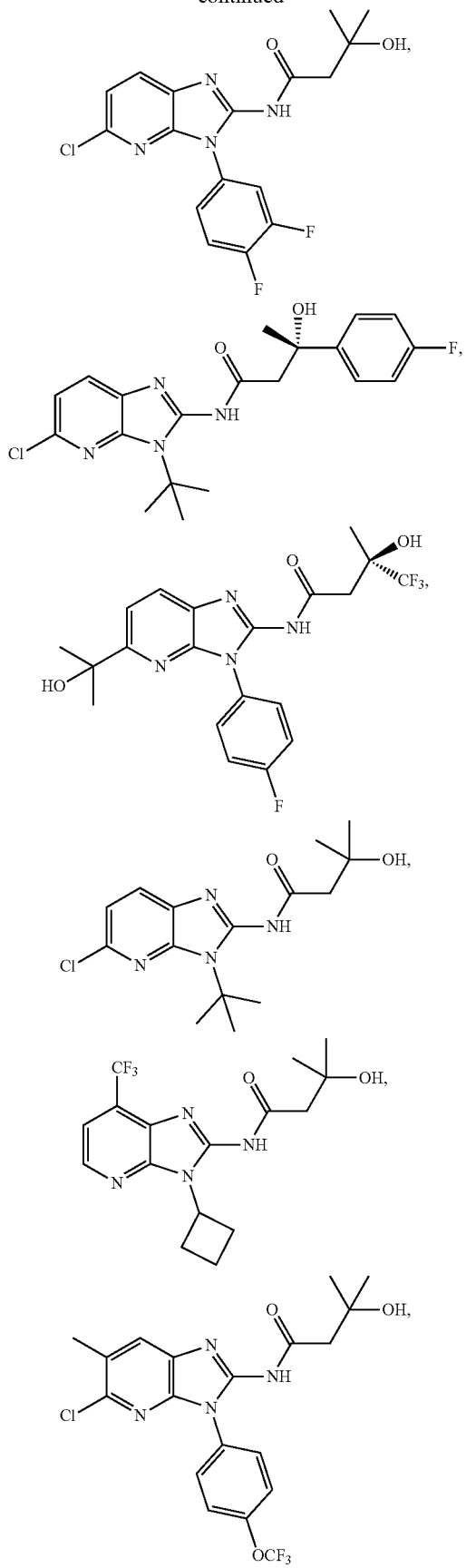
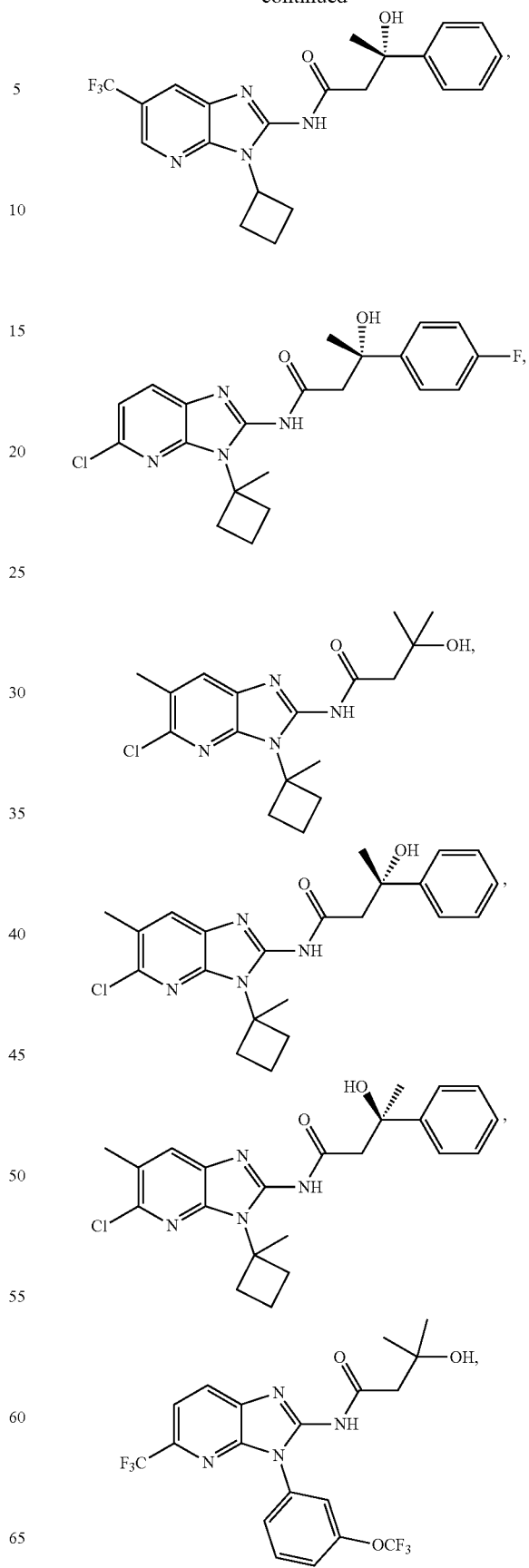

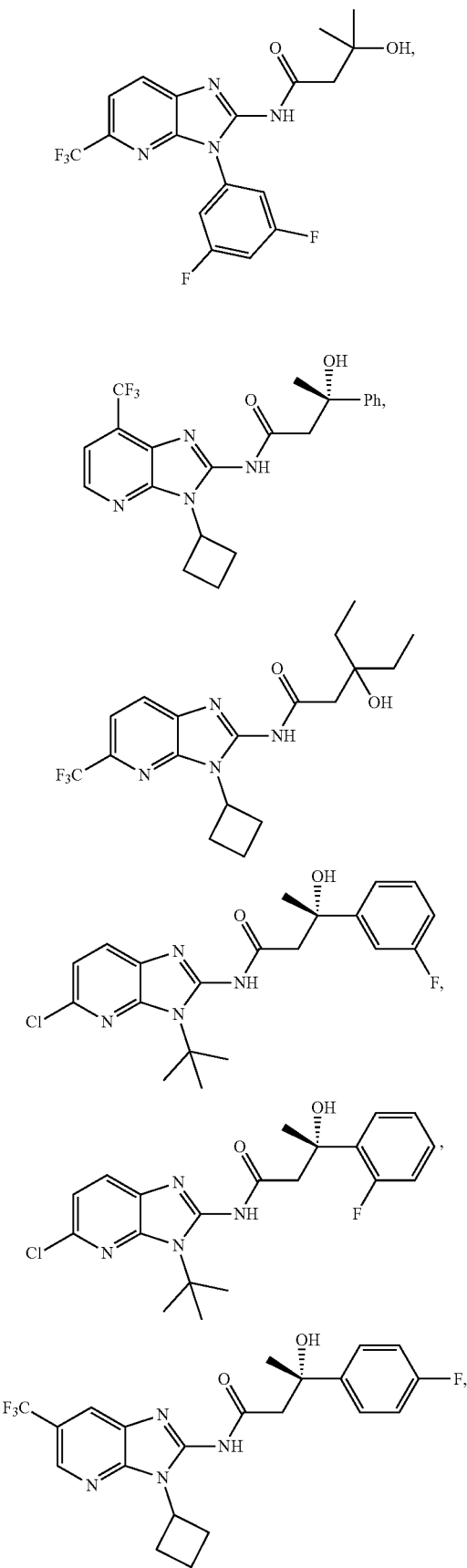
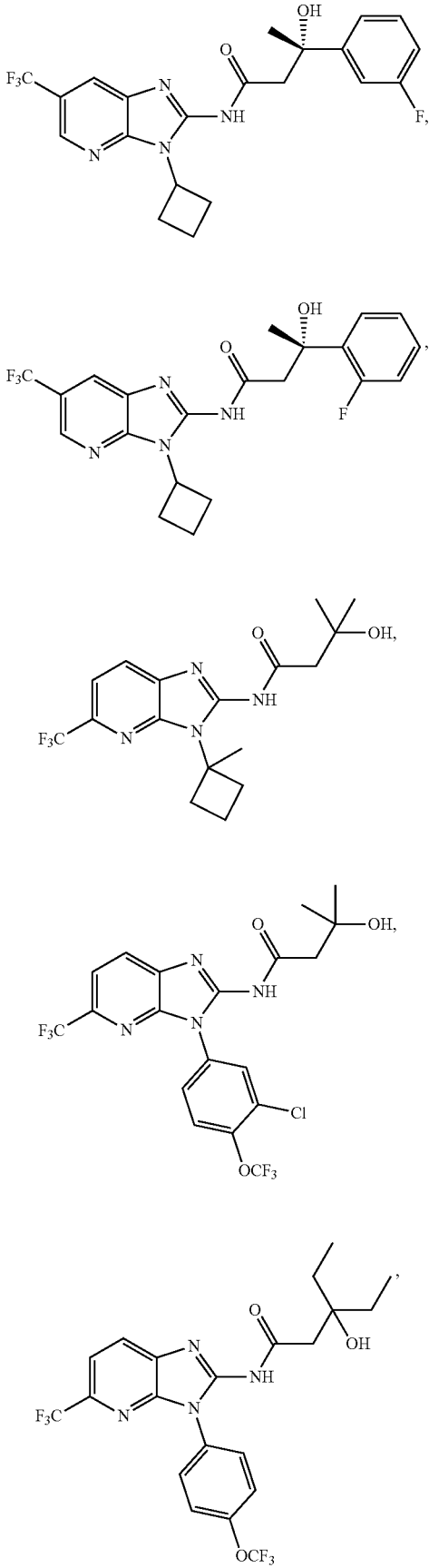

271
-continued
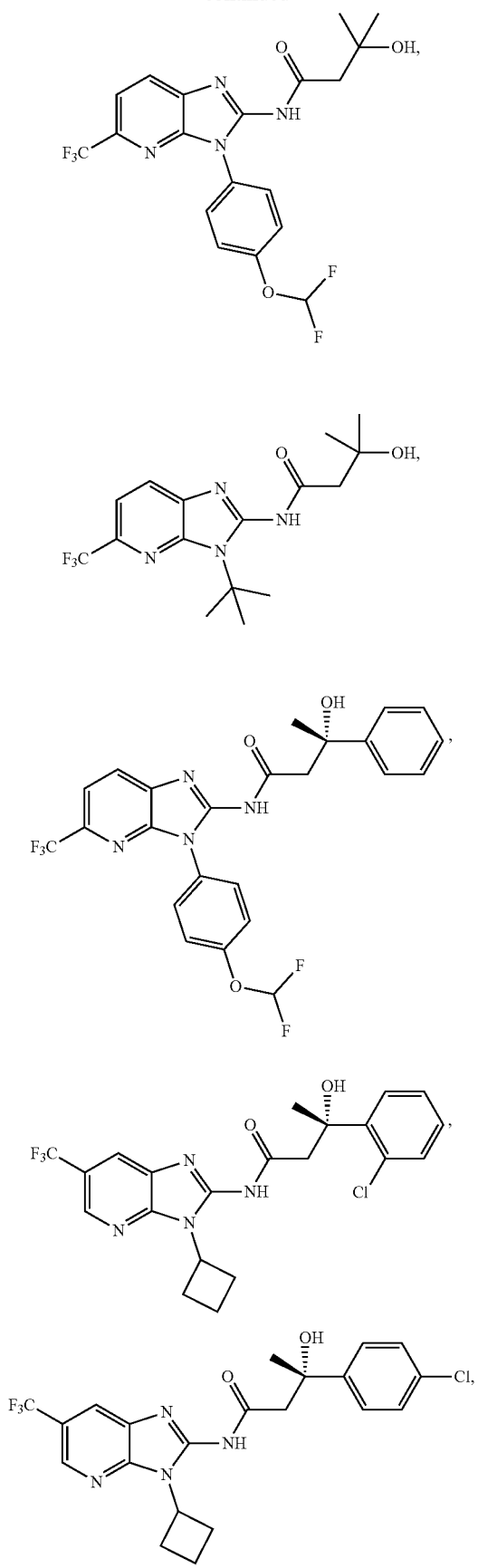
272
-continued
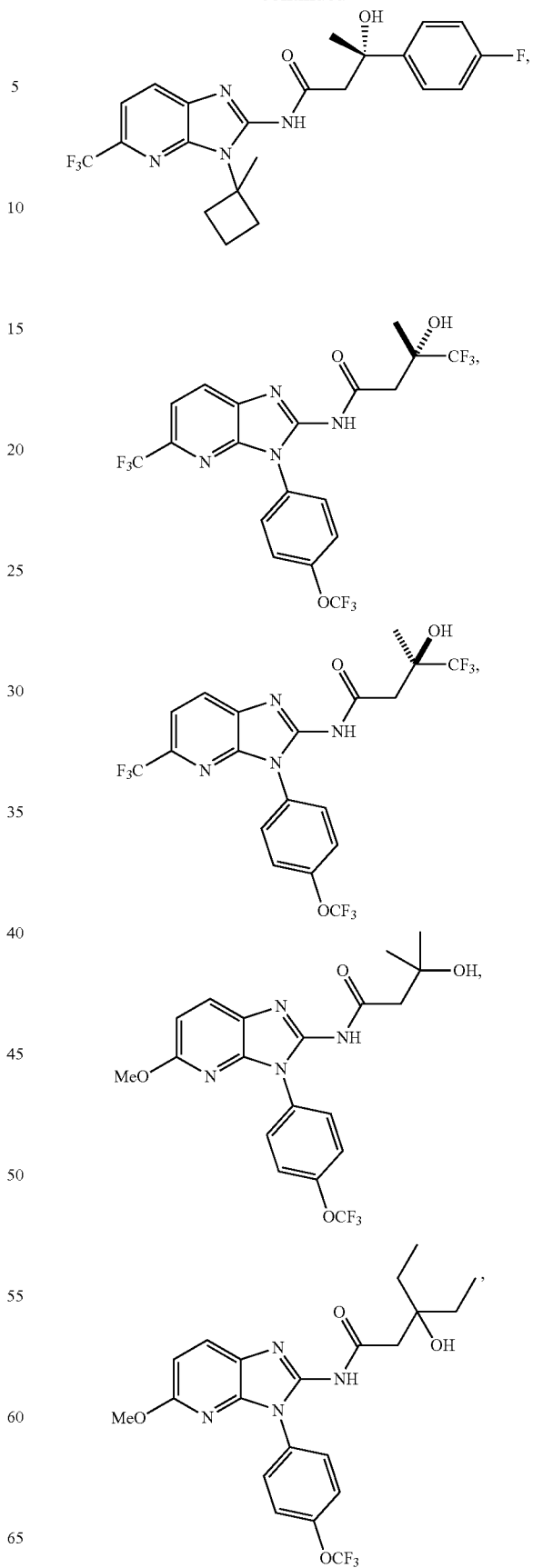

273
-continued
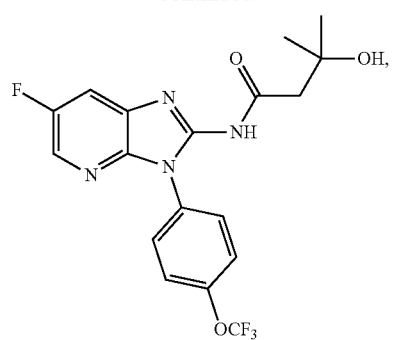
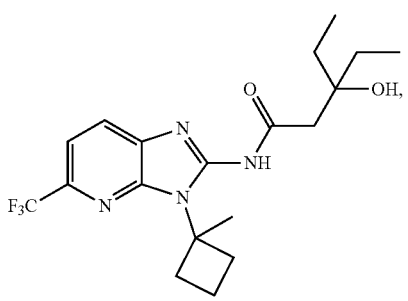
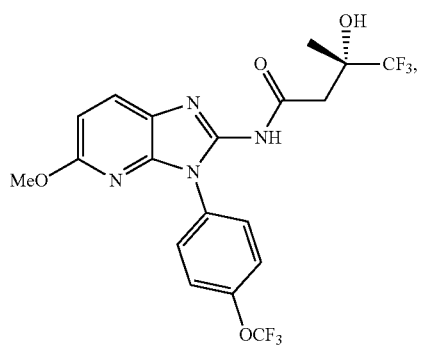
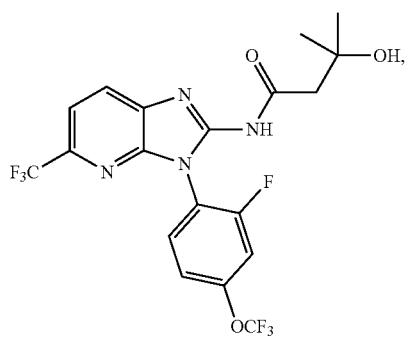
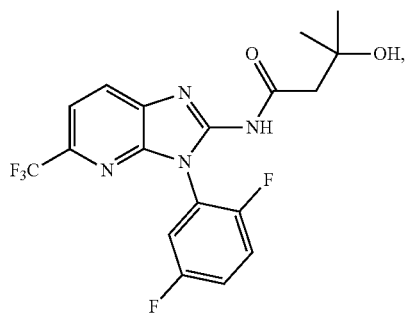
274
-continued
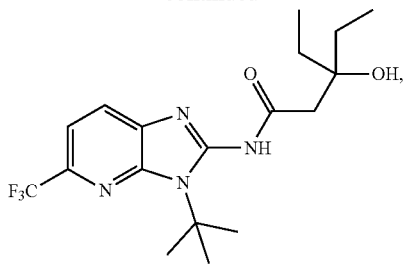
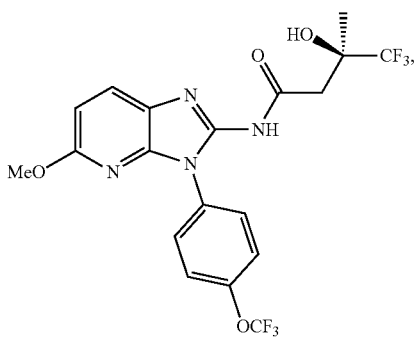
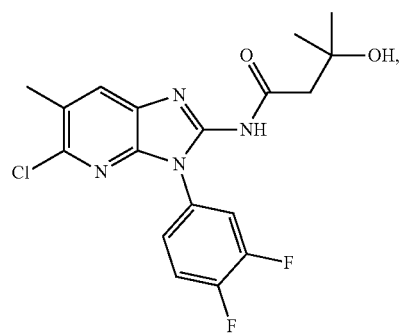
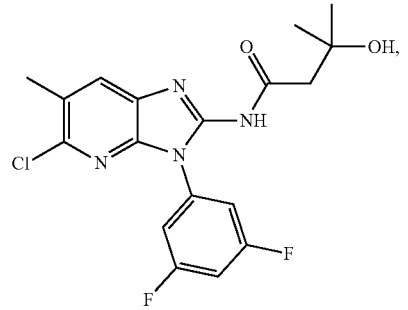
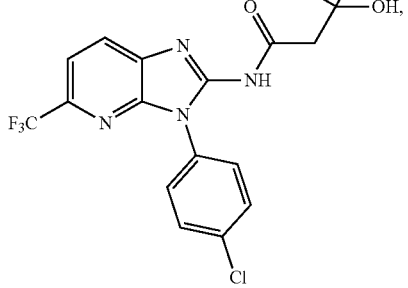

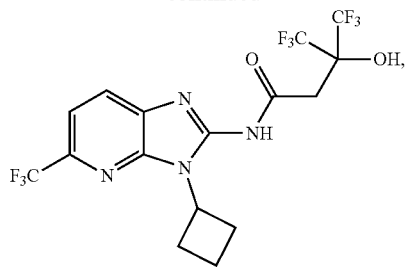
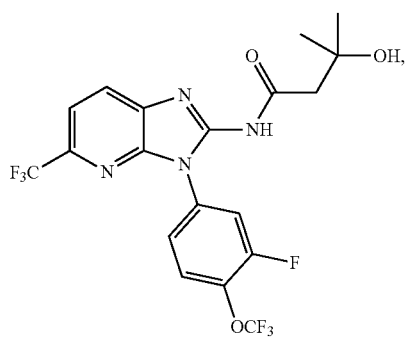
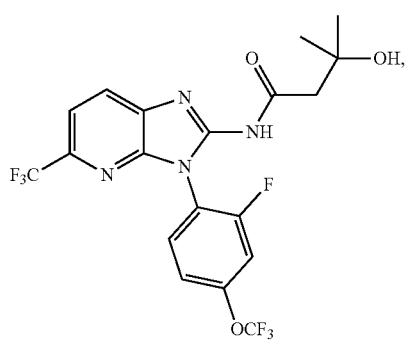
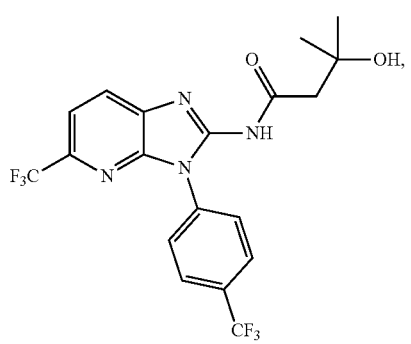
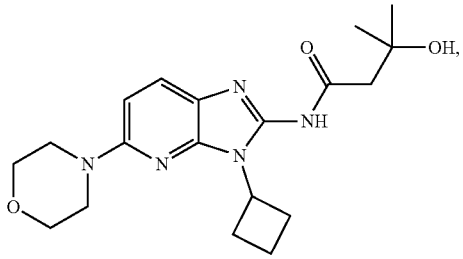
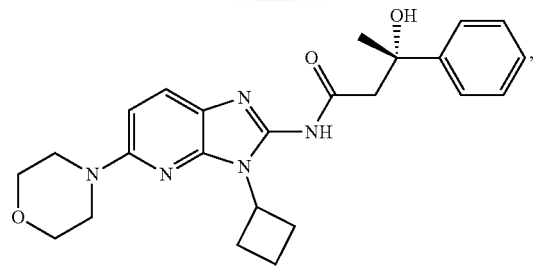
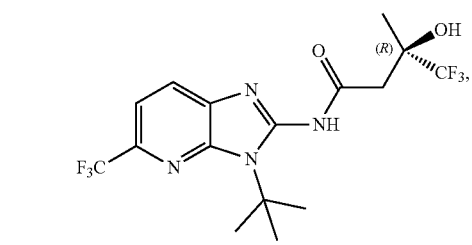
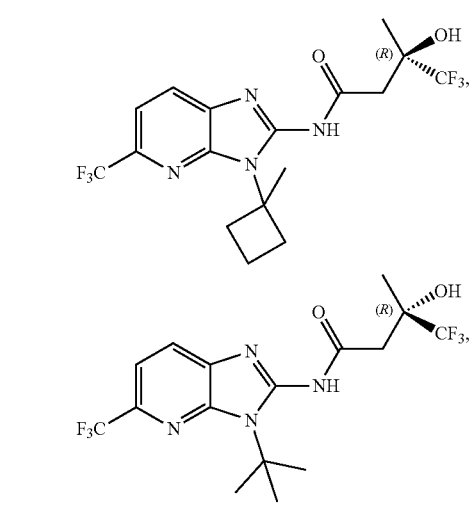
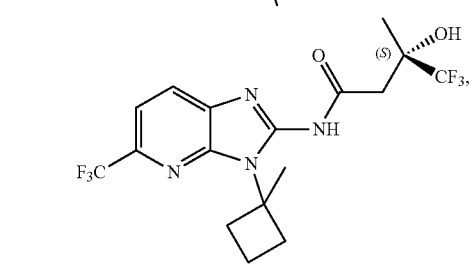
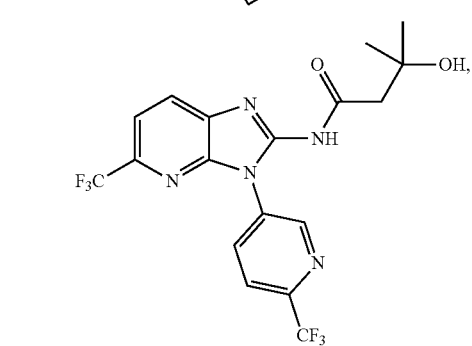

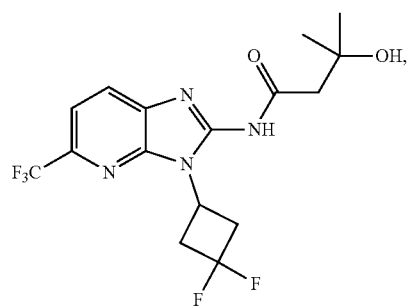
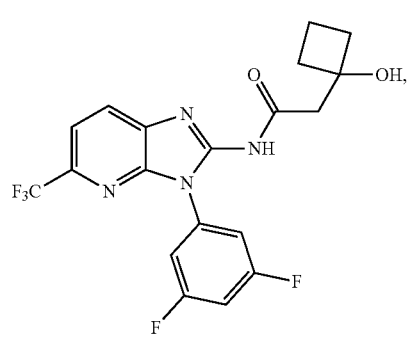
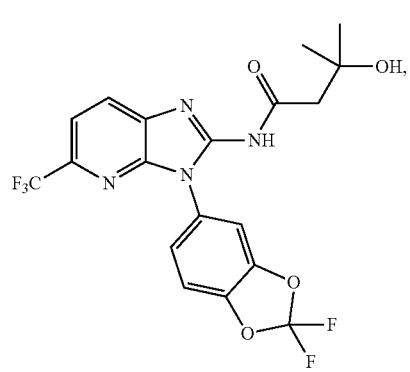
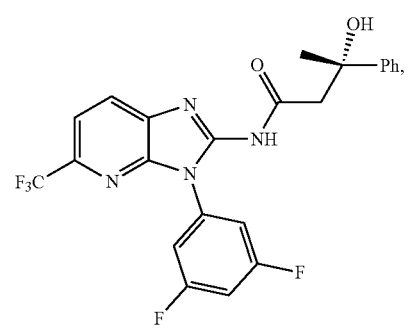
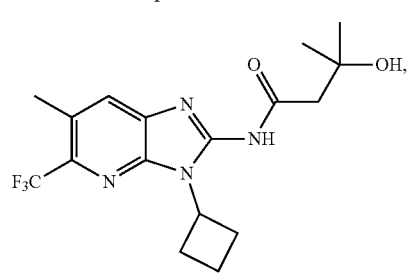
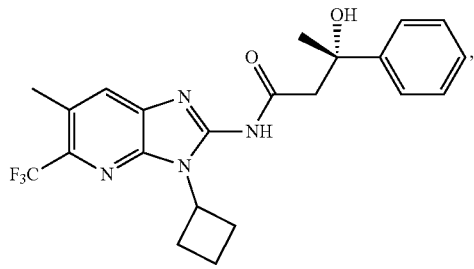
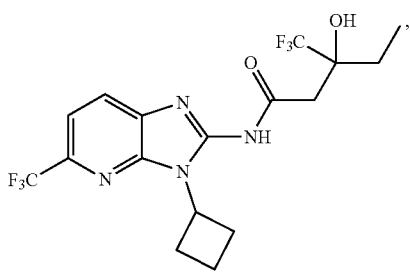
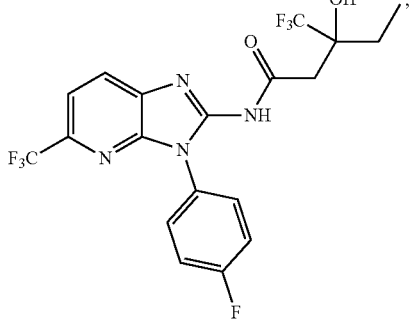
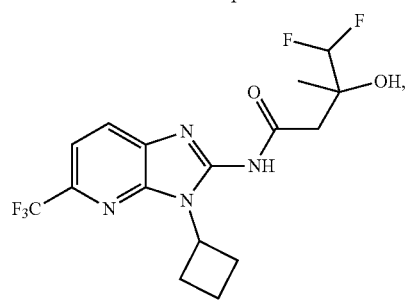
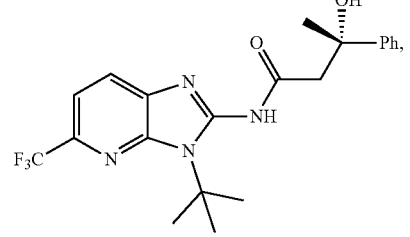
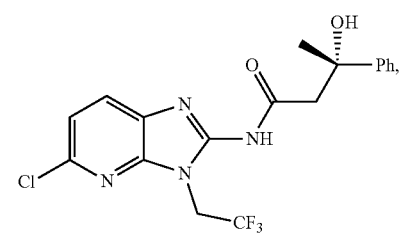

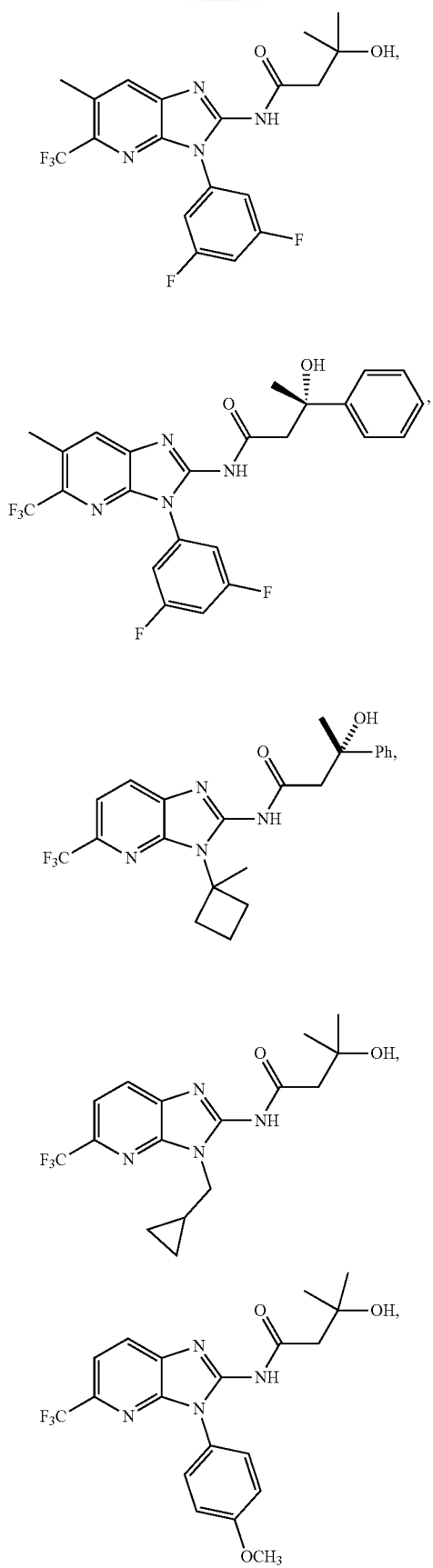
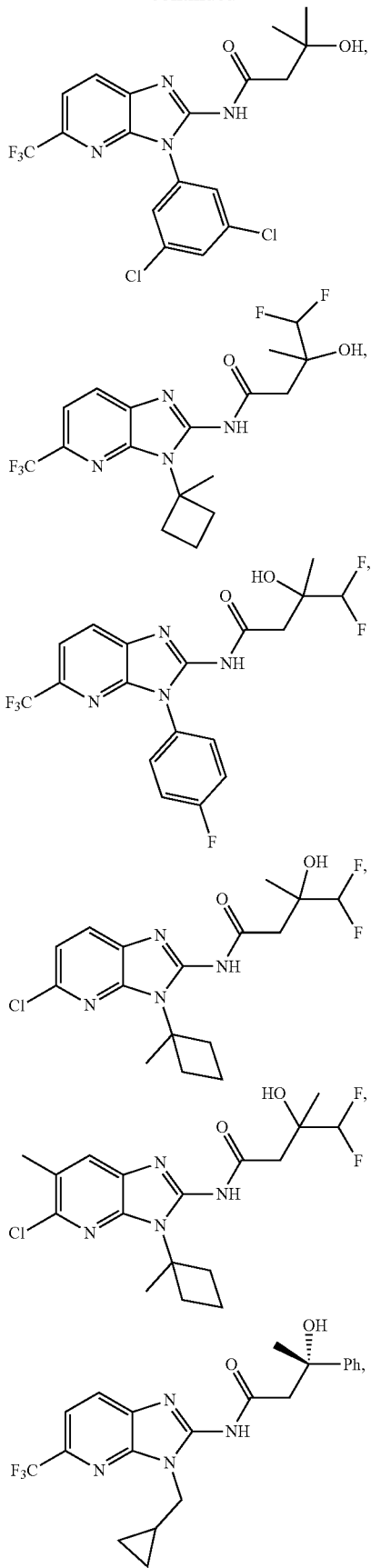

281
-continued
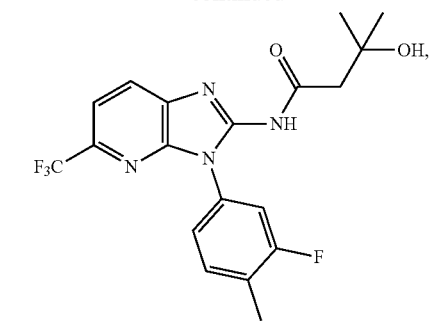
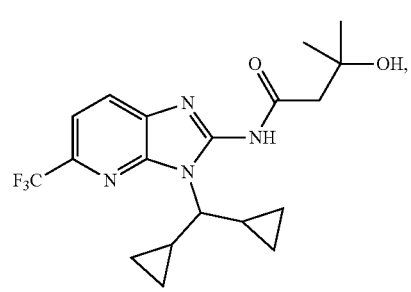
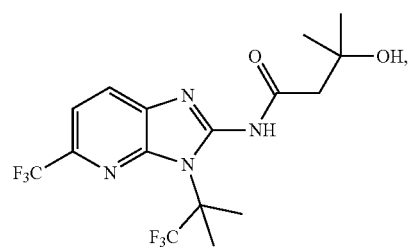
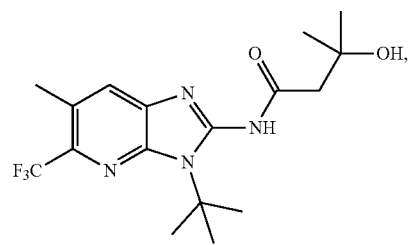
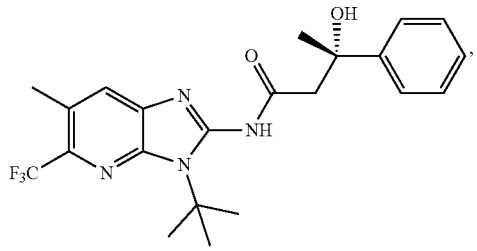
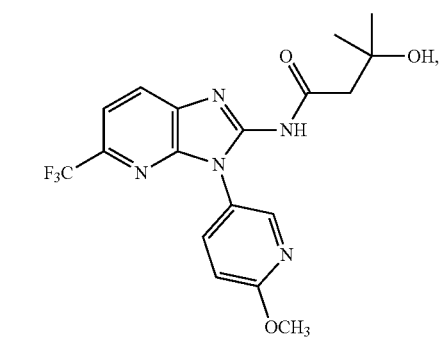
282
-continued
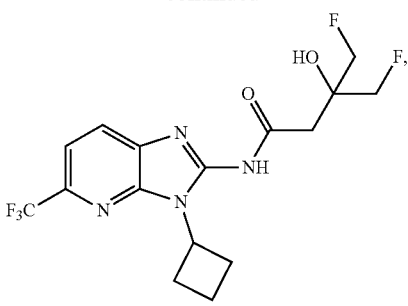
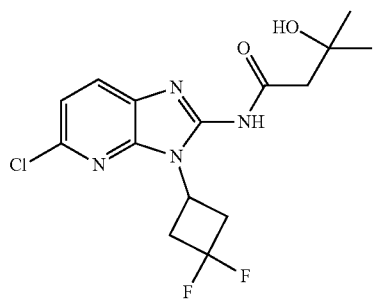
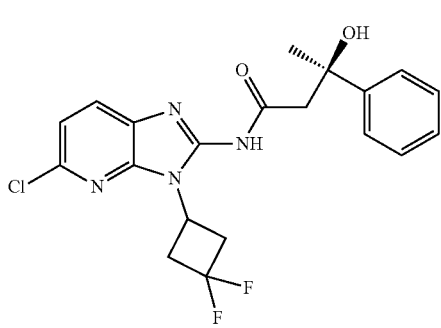
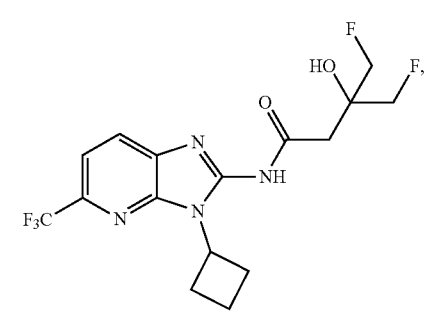
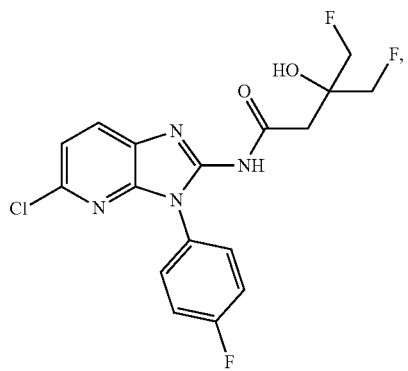

283
-continued
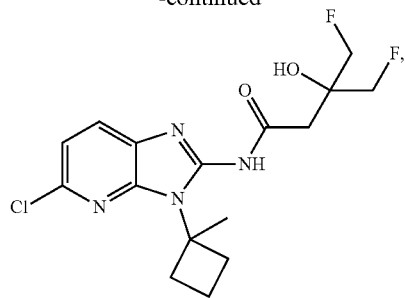
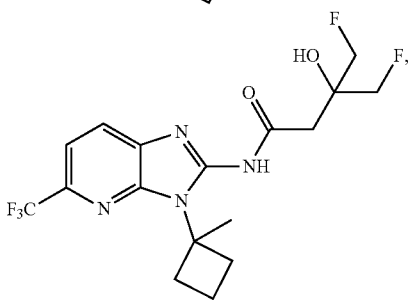
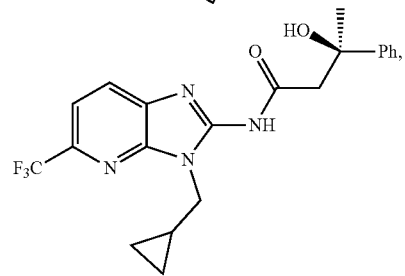
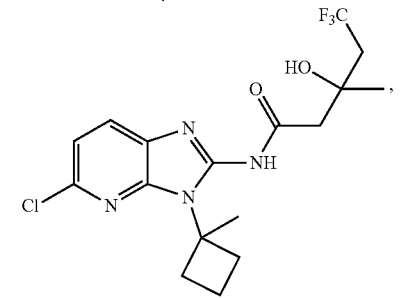
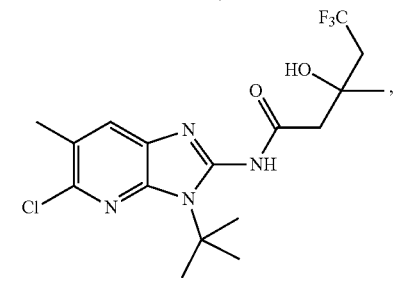
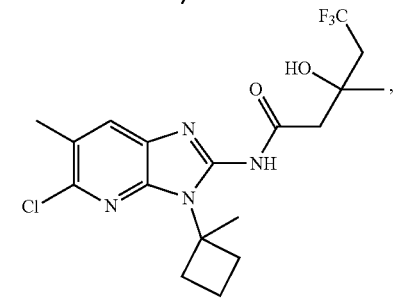
284
-continued
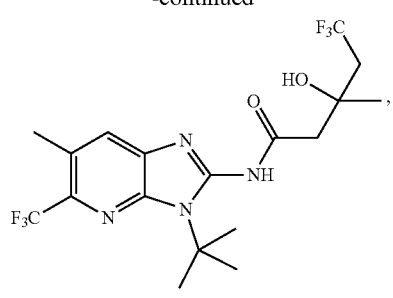
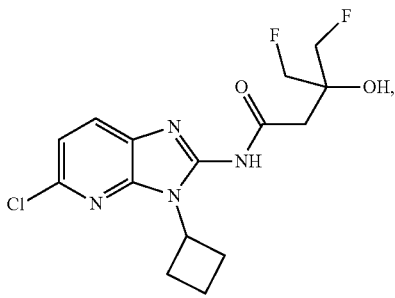
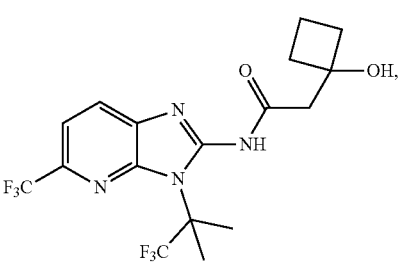
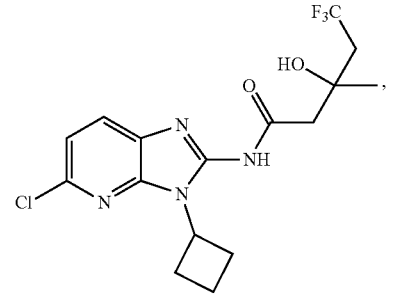
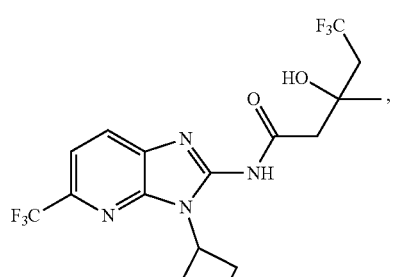
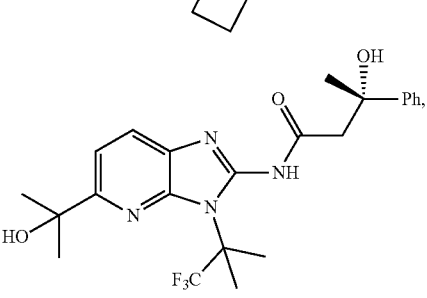

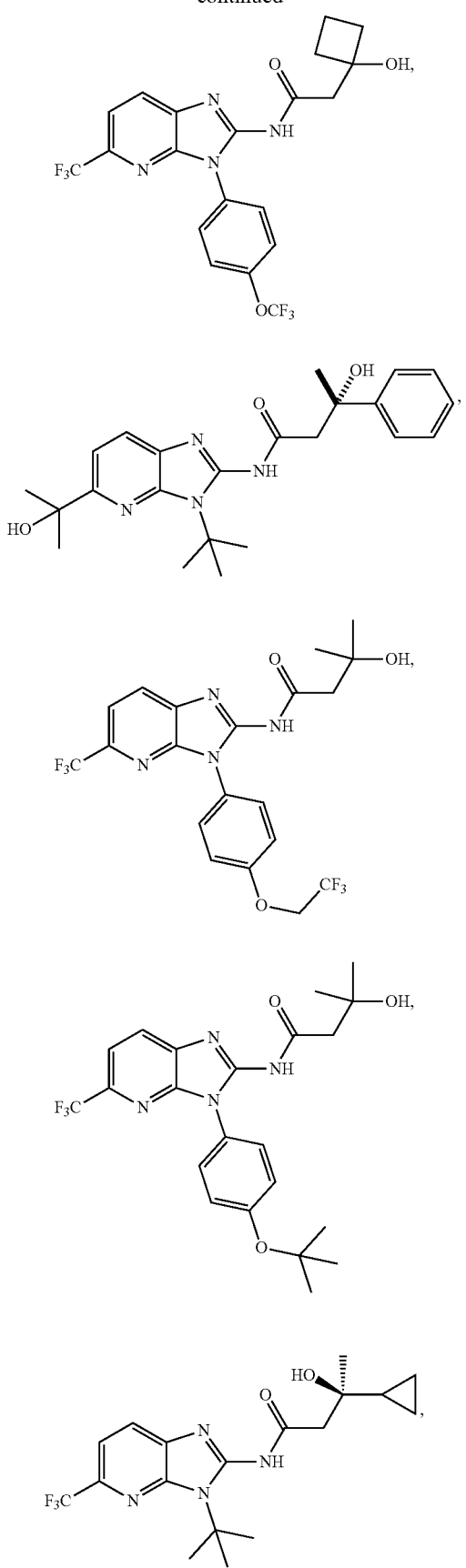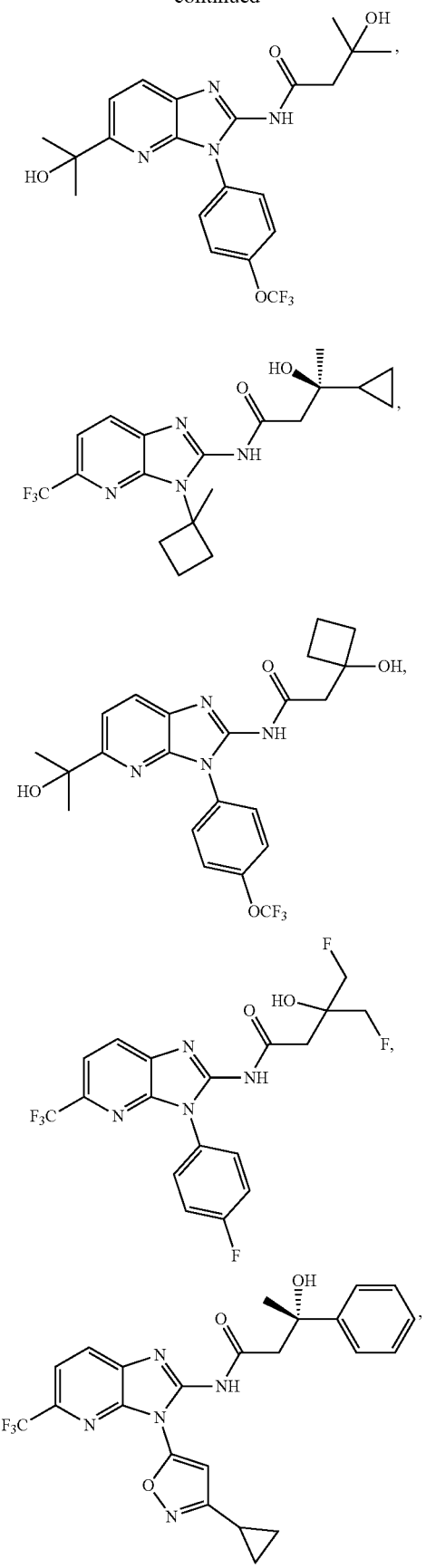

287
-continued
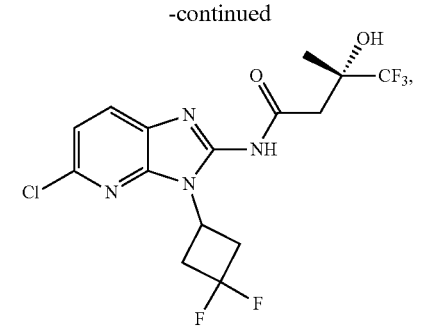
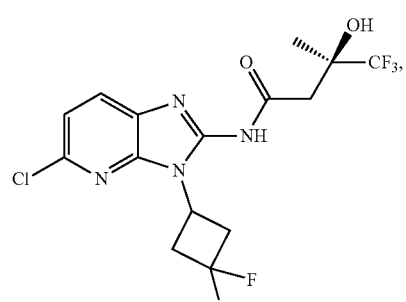
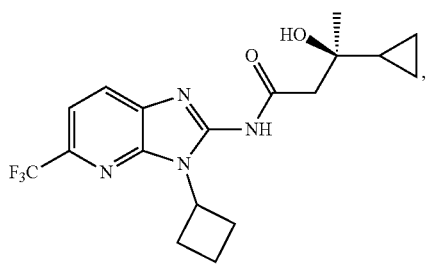
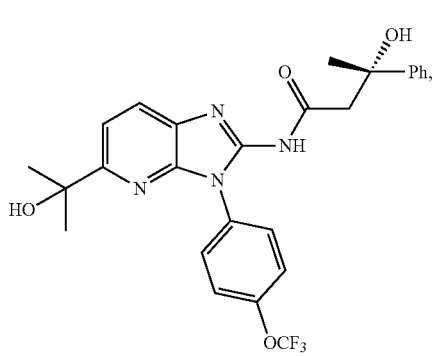
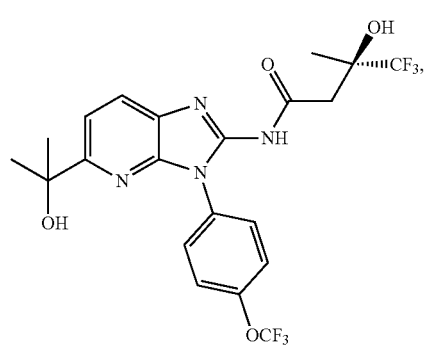
288
-continued
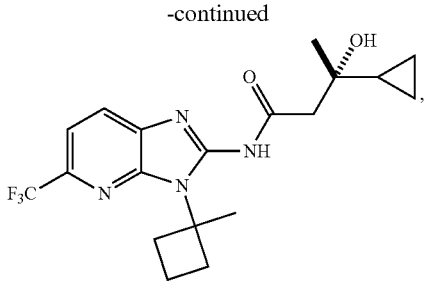
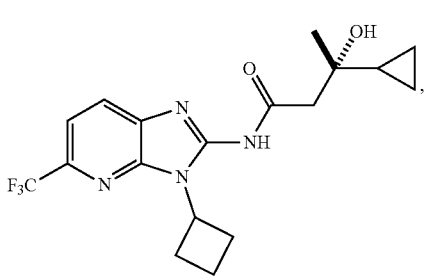
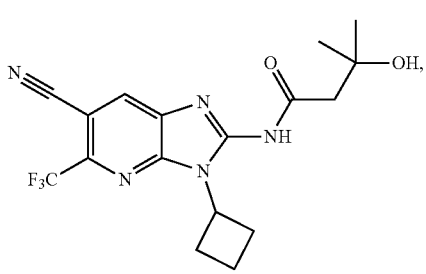
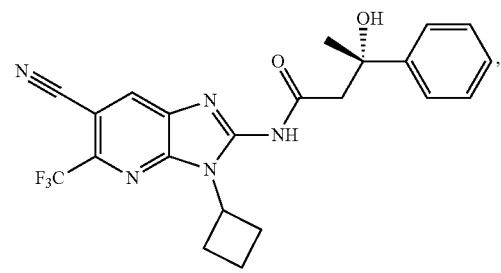
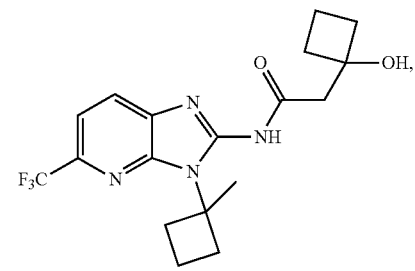
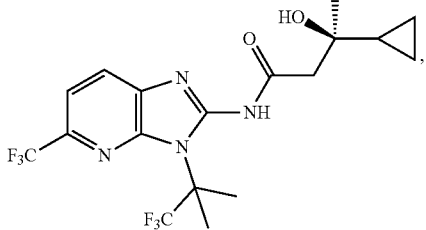

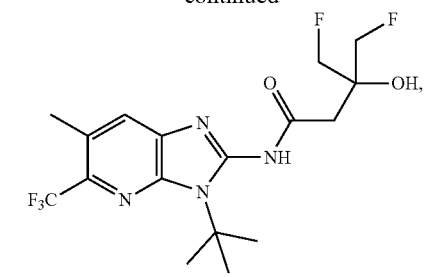
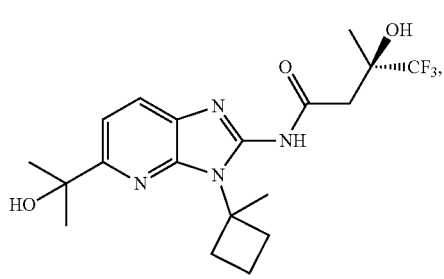
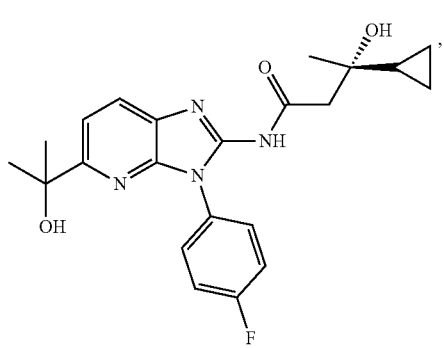
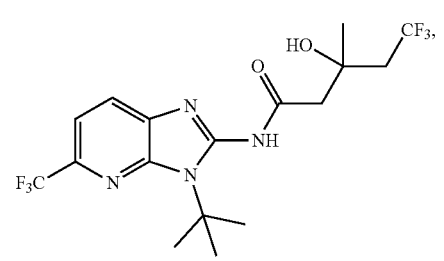
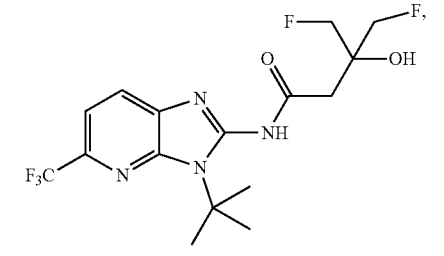
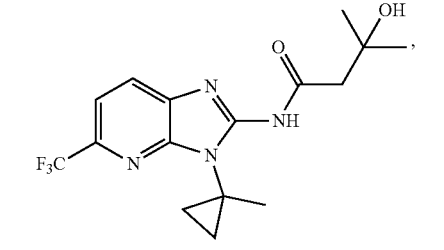
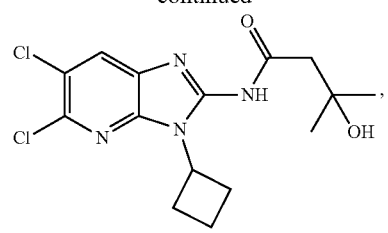
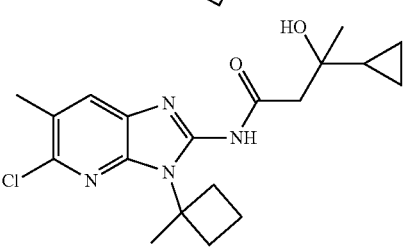
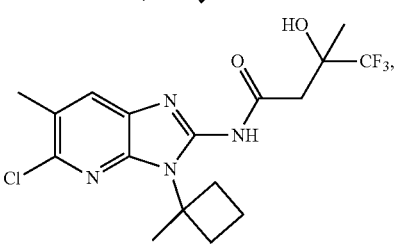
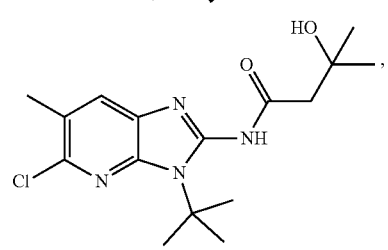
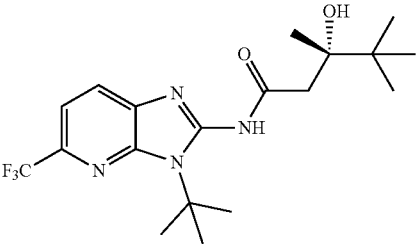
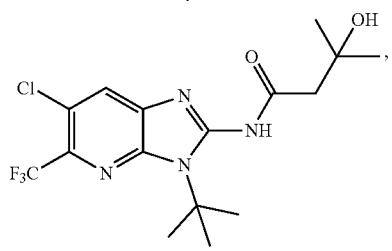
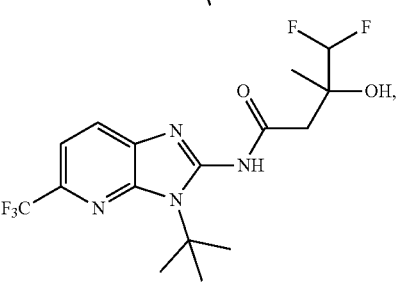

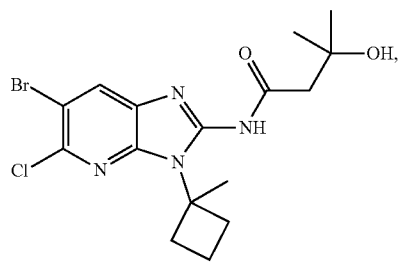
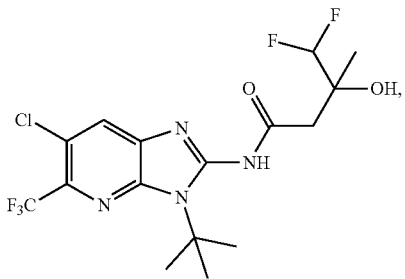
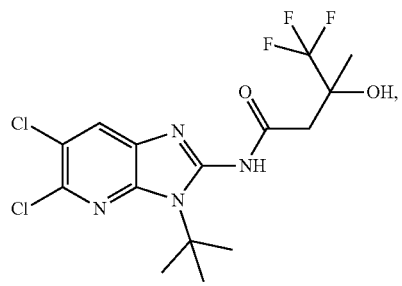
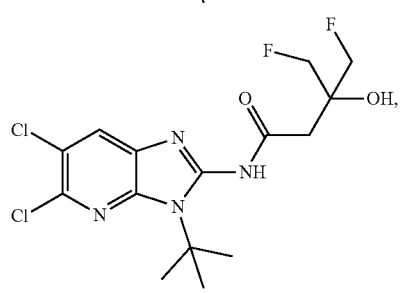
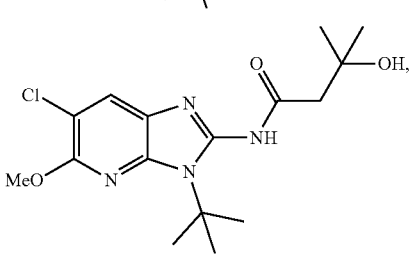
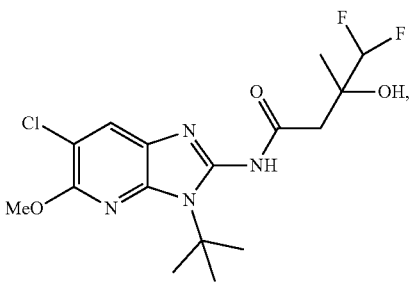
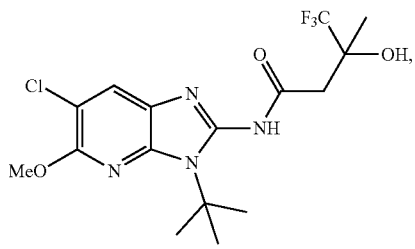
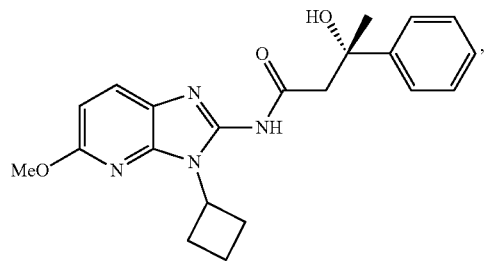
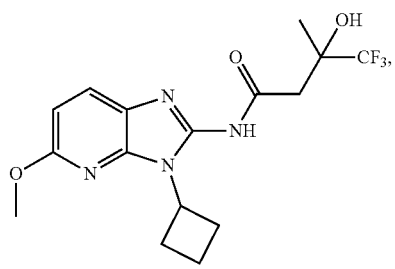
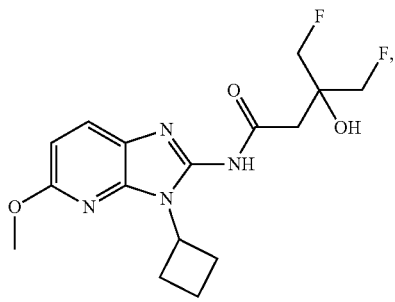
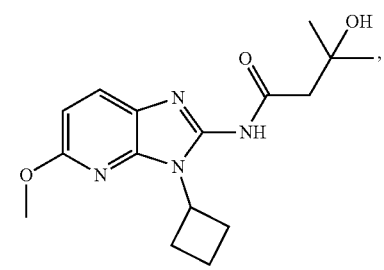
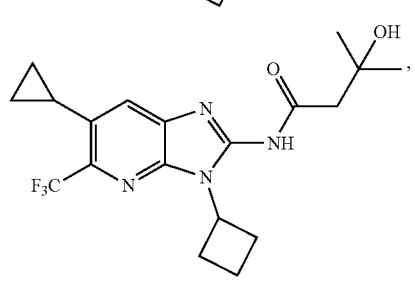

293
-continued
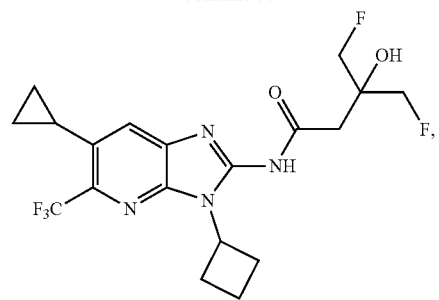
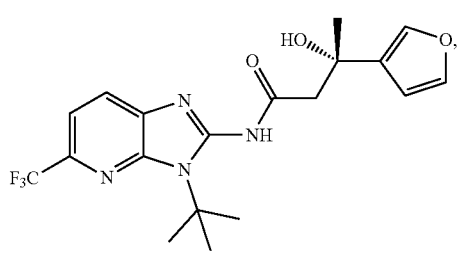
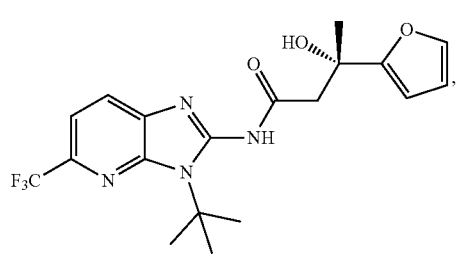
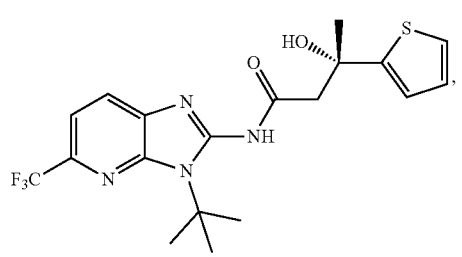
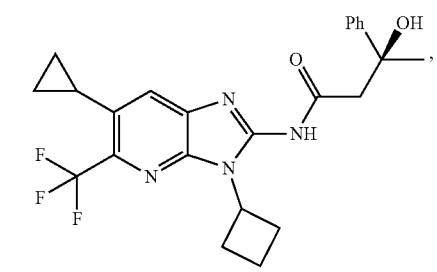
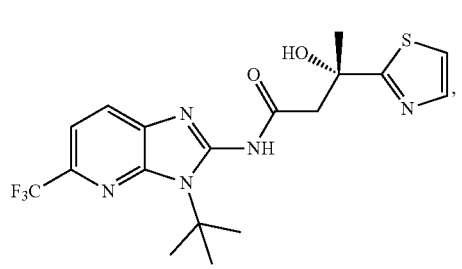
294
-continued
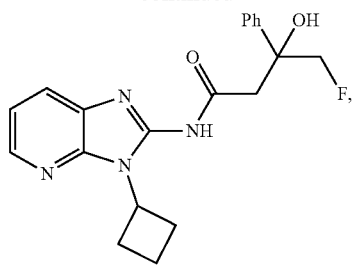
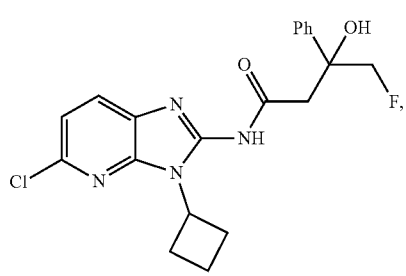
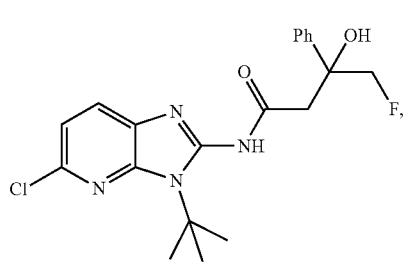
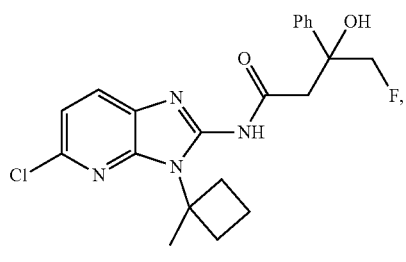
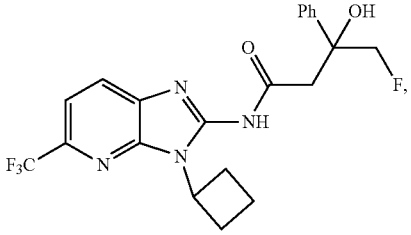
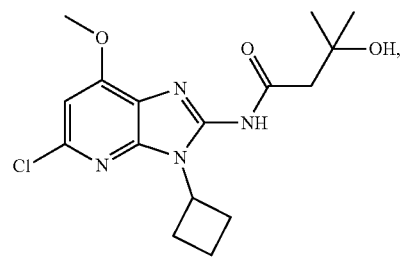

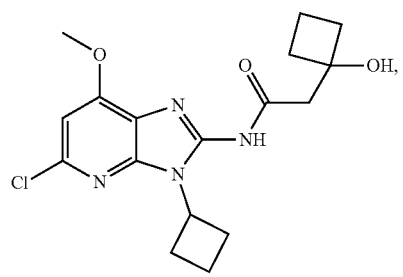
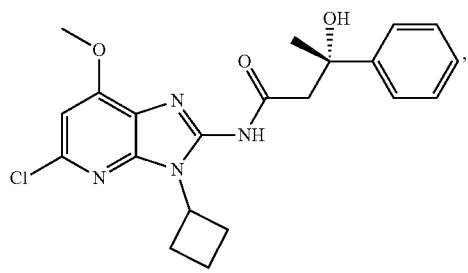
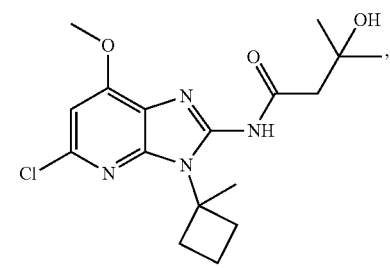
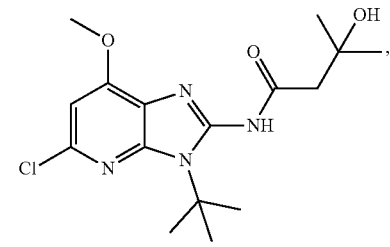
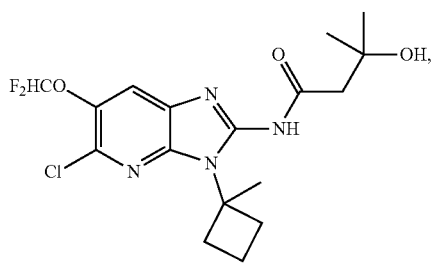
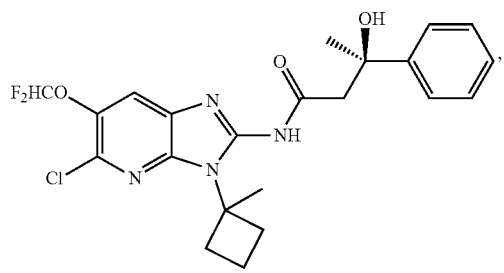
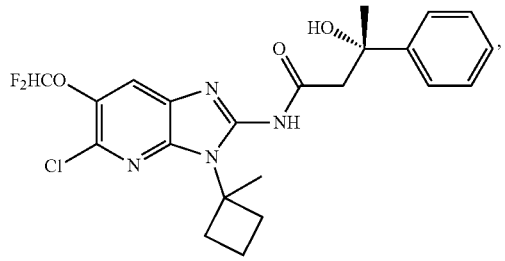
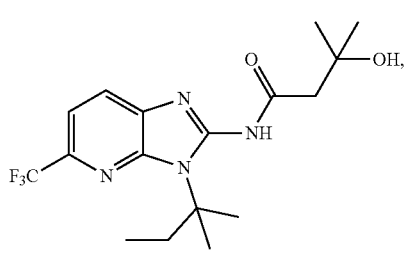
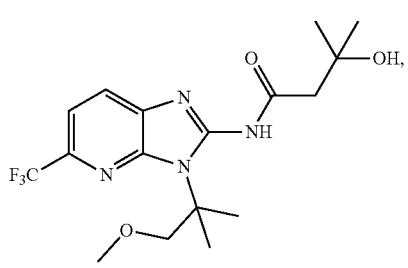
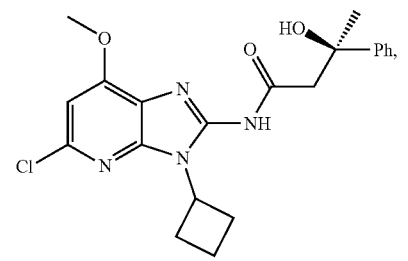
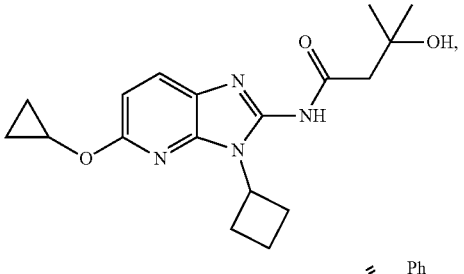
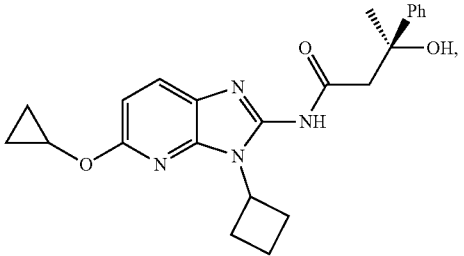

297
-continued
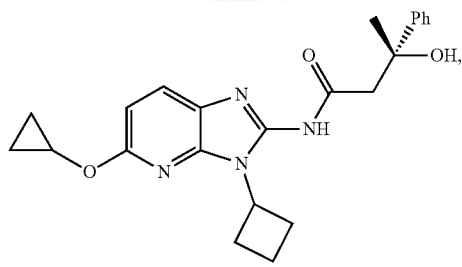
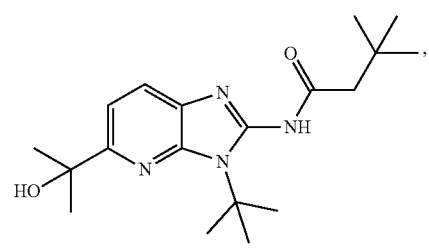
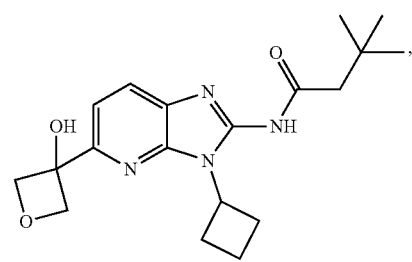
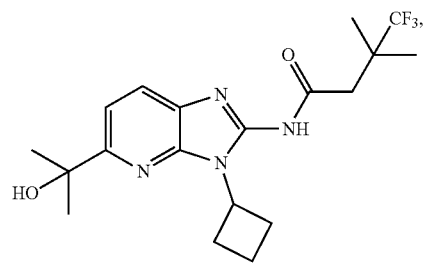
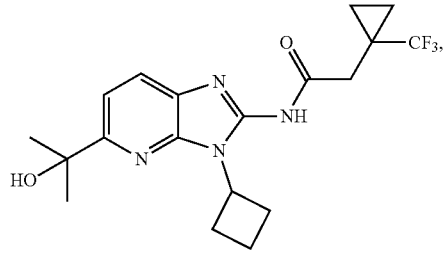
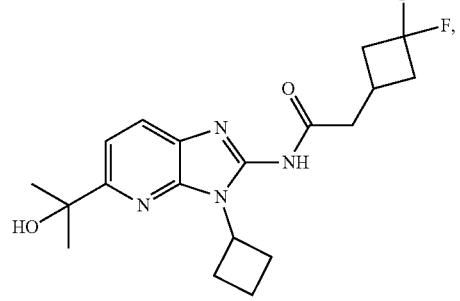
298
-continued
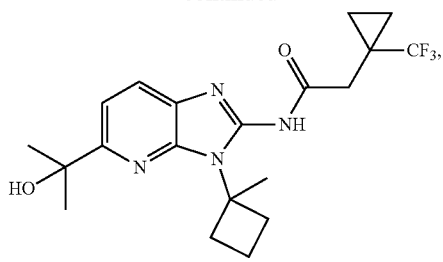
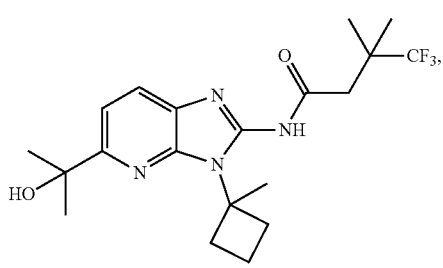
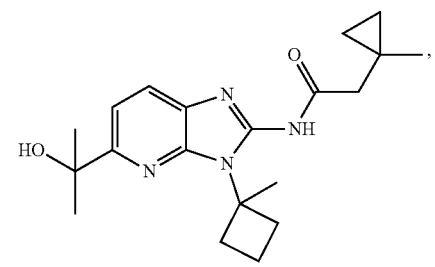
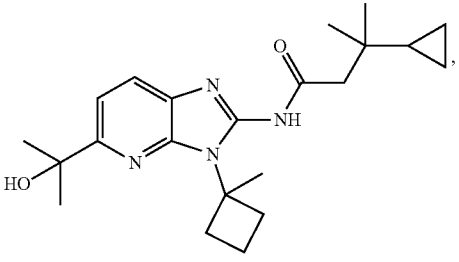
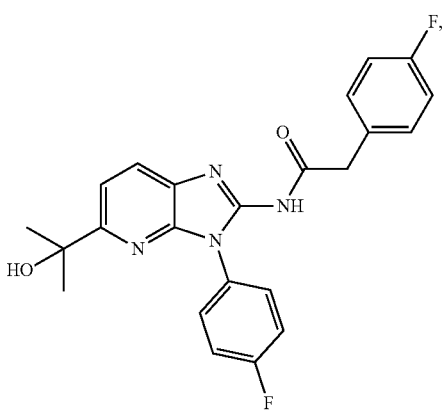

299
-continued
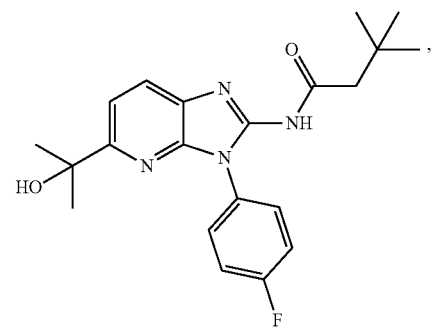
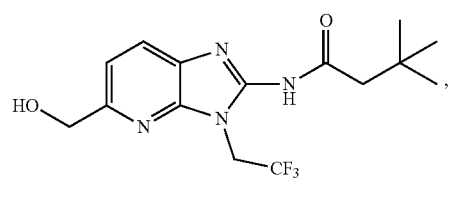
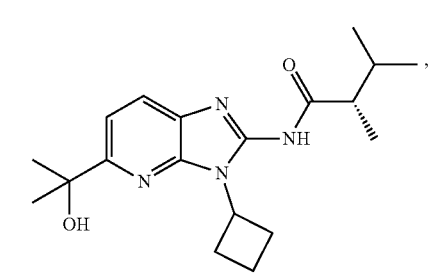
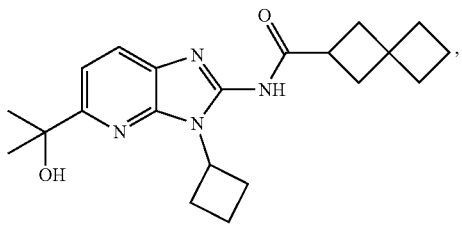
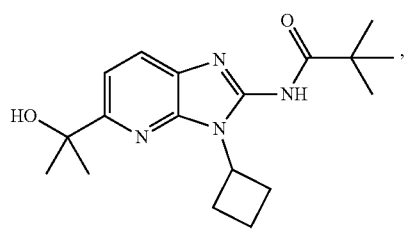
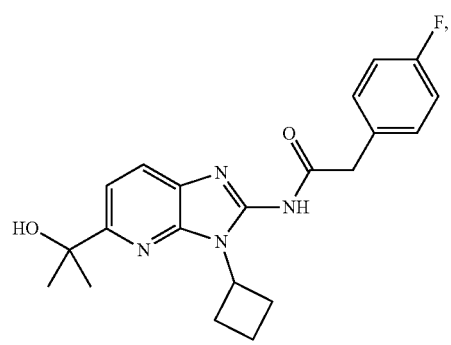
300
-continued
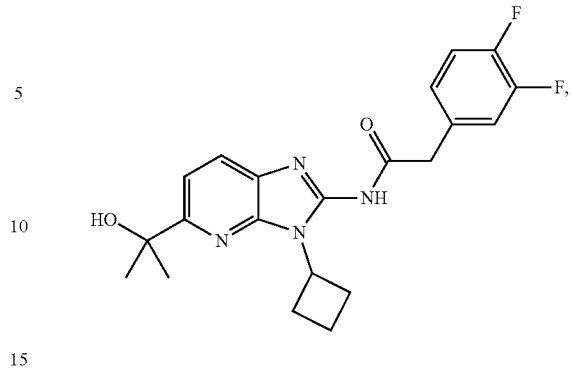
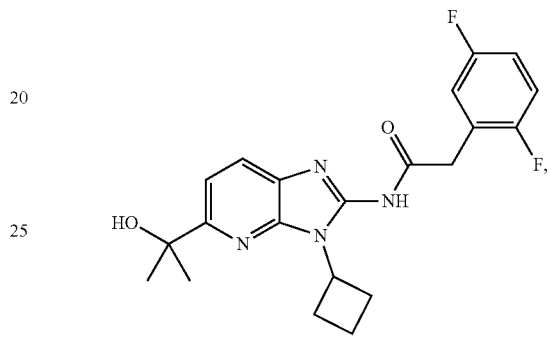
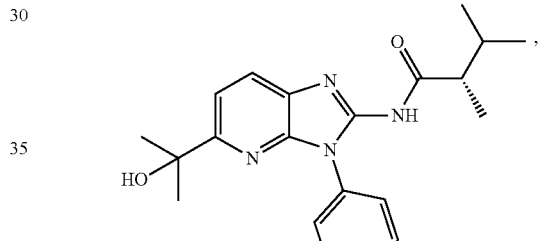
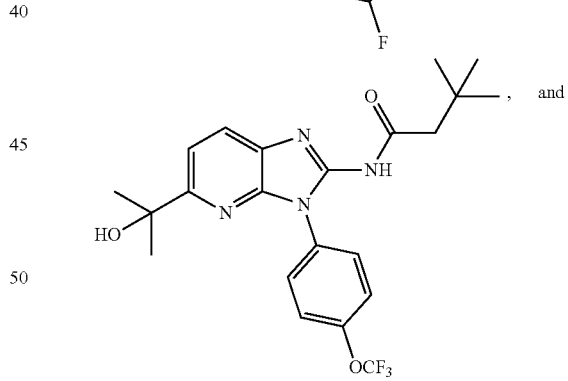
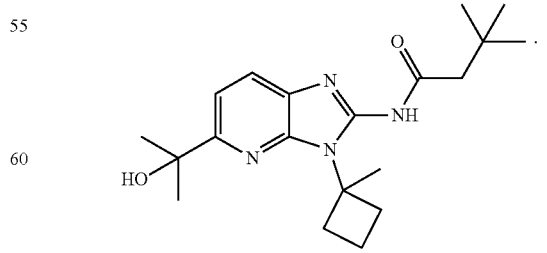
Some embodiments include a compound represented by Formula B-1:

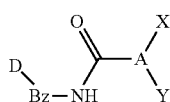

Formula B-1

With respect to Formula B-1, or any embodiments of Formula B-1, Bz can be optionally substituted benzoimidazol-1,2-yl. If the benzoimidazol-1,2-yl is substituted, it may have 1, 2, 3, or 4 substituents. Any substituent may be included on the benzoimidazol-1,2-yl. In some embodiments, some or all of the substituents on the benzoimidazol-1,2-yl may have: from 0 to 10 carbon atoms and from 0 to 10 heteroatoms, wherein each heteroatom is independently: O, N, S, F, Cl, Br, or I (provided that there is at least 1 non-hydrogen atom); and/or a molecular weight of 15 g/mol to 500 g/mol. In some embodiments, some or all of the substituents may each have a molecular weight of 15 Da to 200 Da, 15 Da to 100 Da, or 15 Da to 50 Da, and consist of 2 to 5 chemical elements, wherein the chemical elements are independently C, H, O, N, S, F, Cl, or Br. In some embodiments, Bz can be optionally substituted benzoimidazol-1,2-diyl. In some embodiments, Bz can be optionally substituted benzoimidazol-1, 2, 6-triyl.

For example, with respect to Formula B-1, or any embodiments of Formula B-1, the substituents of Bz may be $C_{1-10}$ optionally substituted alkyl, such as $CH_3$, $C_2H_5$, $C_3H_7$, cyclic $C_3H_5$, $C_4H_9$, cyclic $C_4H_7$, $C_5H_{11}$, cyclic $C_5H_9$, $C_6H_{13}$, cyclic $C_6H_{11}$, etc., which may be optionally substituted; $C_{1-10}$ optionally substituted alkoxy such as $OCH_3$, $OC_2H_5$, $OC_3H_7$, cyclic $OC_3H_5$, $OC_4H_9$, cyclic $OC_4H_7$, $OC_5H_{11}$, cyclic $OC_5H_9$, $OC_6H_{13}$, cyclic $OC_6H_{11}$, etc.; halo, such as F, Cl, Br, I; OH; CN; $NO_2$; $C_{1-6}$ fluoroalkyl, such as $CF_3$, $CF_2H$, $C_2F_5$, etc.; $C_{1-6}$ fluoroalkoxy, such as $OCF_3$, $OCF_2H$, $OC_2F_5$, etc.; a $C_{1-10}$ ester such as $—O_2CCH_3$, $—CO_2CH_3$, $—O_2CC_2H_5$, $—CO_2C_2H_5$, $—O_2C$-phenyl, $—CO_2$-phenyl, etc.; a $C_{1-10}$ ketone such as $—COCH_3$, $—COC_2H_5$, $—COC_3H_7$, $—CO$-phenyl, etc.; or a $C_{1-10}$ amine such as $NH_2$, $NH(CH_3)$, $N(CH_3)_2$, $N(CH_3)C_2H_5$, etc. In some embodiments, a substituent of Bz may be F, Cl, Br, I, CN, $NO_2$, $C_{1-4}$ alkyl, $C_{1-4}$ alkyl-OH, $C_{1-3}$ O-alkyl, $CF_3$, COH, $C_{1-4}$ CO-alkyl, $CO_2H$, $C_{1-4}$ $CO_2$-alkyl, $NH_2$, or $C_{1-4}$ alkylamino.

Some embodiments of Formula B-1 may include a compound represented by Formulas B-2:

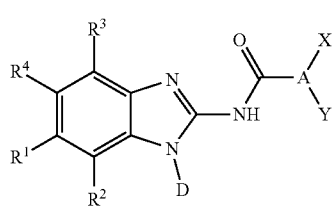

Formula B-2

To any relevant embodiment or structural representation of Formula B-1 or B-2 or B-3 through B-7 herein the following applies, D is optionally substituted $C_{3-6}$ carbocyclyl or $C_{2-5}$ heterocyclyl. If D is substituted cyclobutyl, it may have 1, 2, 3, 4, 5, 6, or 7 substituents. If D is substituted phenyl, it may have 1, 2, 3, 4, or 5 substituents. If D is substituted isoxazolyl, it may have 1 or 2. D may include any substituent. In some embodiments, some or all of the substituents of D may have: from 0 to 10 carbon atoms and from 0 to 10 heteroatoms, wherein each heteroatom is independently: O, N, S, F, Cl, Br, or I (provided that there is at least 1 non-hydrogen atom); and/or a molecular weight of 15 g/mol to 500 g/mol. In some embodiments, some or all of the substituents may each have a molecular weight of 15 Da to 200 Da, 15 Da to 100 Da, or 15 Da to 50 Da, and consist of 2 to 5 chemical elements, wherein the chemical elements are independently C, H, O, N, S, F, Cl, or Br.

To any relevant embodiment or structural representation of Formula B-1 or B-2 or B-3 through B-7 herein the following applies, the substituents of D may be $C_{1-10}$ optionally substituted alkyl, such as $CH_3$, $C_2H_5$, $C_3H_7$, cyclic $C_3H_5$, $C_4H_9$, cyclic $C_4H_7$, $C_5H_{11}$, cyclic $CH_9$, $C_6H_{13}$, cyclic $C_6H_{11}$, etc., which may be optionally substituted; $C_{1-10}$ optionally substituted alkoxy such as $OCH_3$, $OC_2H_5$, $OC_3H_7$, cyclic $OC_3H_5$, $OC_4H_9$, cyclic $OC_4H_7$, $OC_5H_{11}$, cyclic $OC_5H_9$, $OC_6H_{13}$, cyclic $OC_6H_{11}$, etc.; halo, such as F, Cl, Br, I; OH; CN; $NO_2$; $C_{1-6}$ fluoroalkyl, such as $CF_3$, $CF_2H$, $C_2F_5$, etc.; $C_{1-6}$ fluoroalkoxy, such as $OCF_3$, $OCF_2H$, $OC_2F_5$, etc.; a $C_{1-10}$ ester such as $—O_2CCH_3$, $—CO_2CH_3$, $—O_2CC_2H_5$, $—CO_2C_2H_5$, $—O_2C$-phenyl, $—CO_2$-phenyl, etc.; a $C_{1-10}$ ketone such as $—COCH_3$, $—COC_2H_5$, $—COC_3H_7$, $—CO$-phenyl, etc.; or a $C_{1-10}$ amine such as $NH_2$, $NH(CH_3)$, $N(CH_3)_2$, $N(CH_3)C_2H_5$, etc. In some embodiments, a substituent of D may be F, Cl, Br, I, CN, $NO_2$, $C_{1-4}$ alkyl, $C_{1-4}$ alkyl-OH, $C_{1-3}$ O-alkyl, $CF_3$, COH, $C_{1-4}$ CO-alkyl, $CO_2H$, $C_{1-4}$ $CO_2$-alkyl, $NH_2$, or $C_{1-4}$ alkylamino.

To any relevant embodiment or structural representation of Formula B-1 or B-2 or B-3 through B-7 herein the following applies, in some embodiments, D is:

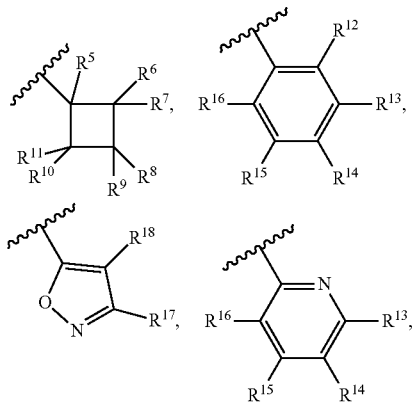

optionally substituted $C_{2-4}$ alkyl.

To any relevant embodiment or structural representation of Formula B-1 or B-2 or B-3 through B-7 herein the following applies, in some embodiments, D is optionally substituted cyclobutyl, optionally substituted phenyl, optionally substituted isoxazolyl, or isopropyl.

To any relevant embodiment or structural representation of Formula B-1 or B-2 or B-3 through B-7 herein the following applies, in some embodiments, D is optionally substituted cyclobutyl. In some embodiments, D is cyclobutyl. In some embodiments, D is

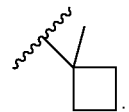

To any relevant embodiment or structural representation of Formula B-1 or B-2 or B-3 through B-7 herein the following applies, in some embodiments, D is isopropyl.

To any relevant embodiment or structural representation of Formula B-1 or B-2 or B-3 through B-7 herein the following applies, in some embodiments, D is t-butyl, or tert-butyl.

To any relevant embodiment or structural representation of Formula B-1 or B-2 or B-3 through B-7 herein the following applies, in some embodiments, D is optionally substituted phenyl. In some embodiments D is

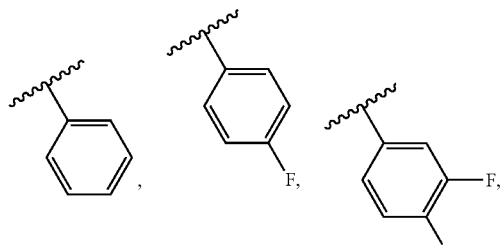

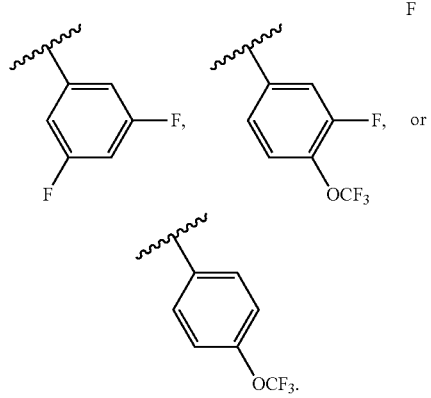

To any relevant embodiment or structural representation of Formula B-1 or B-2 or B-3 through B-7 herein the following applies, in some embodiments, D is optionally substituted pyridinyl, such as optionally substituted pyridiny-2-yl, pyridin-3-yl, or pyridin-4-yl.

In some embodiments, D is

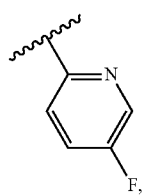

To any relevant embodiment or structural representation of Formula B-1 or B-2 or B-3 through B-7 herein the following applies, in some embodiments, D is optionally substituted isoxazolyl. In some embodiments, D is

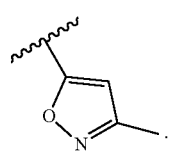 [SMILES: *c1cc(C)no1]

To any relevant embodiment or structural representation of Formula B-1 or B-2 or B-3 through B-7 herein the following applies, A is $C_{2-8}$ alkyl, such as linear or branched

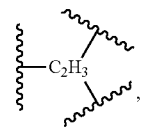

linear or branched

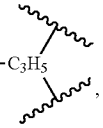

linear or branched

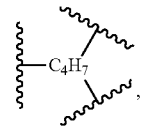

linear or branched

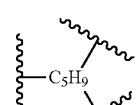

linear or branched

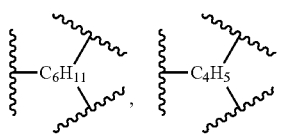

containing one ring,

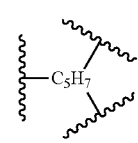

containing one ring,

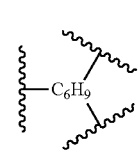

containing one ring,

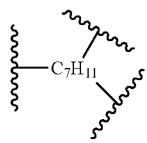

containing one ring, or

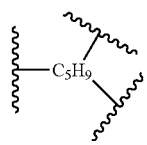

containing a bicyclic ring system.

To any relevant embodiment or structural representation of Formula B-1 or B-2 or B-3 through B-7 herein the following applies, X is H, F, $CF_3$, optionally substituted phenyl, or optionally substituted pyridinyl. In some embodiments, X is H. In some embodiments, X is F. In some embodiments, X is $CF_3$.

To any relevant embodiment or structural representation of Formula B-1 or B-2 or B-3 through B-7 herein the following applies, if X is substituted phenyl, it may have 1, 2, 3, 4, or 5, substituents. If X is substituted pyridinyl, it may have 1, 2, 3, or 4 substituents. In some embodiments, some or all of the substituents of X may have: from 0 to 10 carbon atoms and from 0 to 10 heteroatoms, wherein each heteroatom is independently: O, N, S, F, Cl, Br, or I (provided that there is at least 1 non-hydrogen atom); and/or a molecular weight of 15 g/mol to 500 g/mol. In some embodiments, some or all of the substituents may each have a molecular weight of 15 Da to 200 Da, 15 Da to 100 Da, or 15 Da to 50 Da, and consist of 2 to 5 chemical elements, wherein the chemical elements are independently C, H, O, N, S, F, Cl, or Br.

To any relevant embodiment or structural representation of Formula B-1 or B-2 or B-3 through B-7 herein the following applies, the substituents of X may be $C_{1-10}$ optionally substituted alkyl, such as $CH_3$, $C_2H_5$, $C_3H_7$, cyclic $C_3H_5$, $C_4H_9$, cyclic $C_4H_7$, $C_5H_{11}$, cyclic $CH_9$, $C_6H_{13}$, cyclic $C_6H_{11}$, etc., which may be optionally substituted; $C_{1-10}$ optionally substituted alkoxy such as $OCH_3$, $OC_2H_5$, $OC_3H_7$, cyclic $OC_3H_5$, $OC_4H_9$, cyclic $OC_4H_7$, $OCH_{11}$, cyclic $OC_5H_9$, $OC_6H_{13}$, cyclic $OC_6H_{11}$, etc.; halo, such as F, Cl, Br, I; OH; CN; $NO_2$; $C_{1-6}$ fluoroalkyl, such as $CF_3$, $CF_2H$, $C_2F_5$, etc.; $C_{1-6}$ fluoroalkoxy, such as $OCF_3$, $OCF_2H$, $OC_2F_5$, etc.; a $C_{1-10}$ ester such as $-O_2CCH_3$, $-CO_2CH_3$, $-O_2CC_2H_5$, $-CO_2C_2H_5$, $-O_2C$-phenyl, $-CO_2$-phenyl, etc.; a $C_{1-10}$ ketone such as $-COCH_3$, $-COC_2H_5$, $-COC_3H_7$, $-CO$-phenyl, etc.; or a $C_{1-10}$ amine such as $NH_2$, $NH(CH_3)$, $N(CH_3)_2$, $N(CH_3)C_2H_5$, etc. In some embodiments, a substituent of X may be F, Cl, Br, I, CN, $NO_2$, $C_{1-4}$ alkyl, $C_{1-4}$ alkyl-OH, $C_{1-3}$ O-alkyl, $CF_3$, COH, $C_{1-4}$ CO-alkyl, $CO_2H$, $C_{1-4}$ $CO_2$-alkyl, $NH_2$, or $C_{1-4}$ alkylamino.

To any relevant embodiment or structural representation of Formula B-1 or B-2 or B-3 through B-7 herein the following applies, Y is H, F, Cl, Br, I, or a moiety having a molecular weight of 15 Da to 300 Da and consisting of 2 to 5 chemical elements, wherein the chemical elements are independently C, H, O, N, S, F, Cl, or Br. In some embodiments, Y is H, F, Cl, Br, I, CN, $-COH$, $C_{1-6}$—CO-alkyl, $CF_3$, OH, $C_{1-5}$ O-alkyl, $C_{0-6}$ amino, or $C_{0-6}$ fluoroamino. In some embodiments, Y is H, F, $CF_3$, OH, $C_{1-5}$ O-alkyl, $C_{0-6}$ amino, or $C_{0-6}$ fluoroamino. In some embodiments, Y is H. In some embodiments, Y is OH. In some embodiments, Y is F. In some embodiments, Y is $CF_3$. In some embodiments, Y is $C_{1-3}$ O-alkyl, such as $-OCH_3$, $OC_2H_5$, $OC_3H_7$, etc. In some embodiments, Y is $C_{0-6}$ fluoroamino. In some embodiments, Y is optionally substituted tetrahydropyranyl, such as

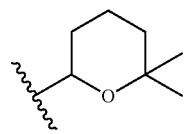

In some embodiments Y may include a $C_{1-8}$ alkyl that may include one or two $C_{3-6}$ carbocyclyl rings. In some embodiments, wherein Y includes at least one carbocyclyl rings, the rings may be connected to each other. In some embodiments, Y is $-C(CF_3)_2OH$ (or 1,1,1,3,3,3-hexafluoro-2-hydroxypropan-2-yl). In some embodiments Y is

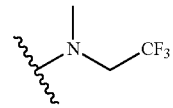

(or methyl(2,2,2-trifluoroethyl)amino). In some embodiments, Y is dimethylamino.

To any relevant embodiment or structural representation of Formula B-1 or B-2 or B-3 through B-7 herein the following applies, in some embodiments

is $C_{2-8}$ alkyl, such as

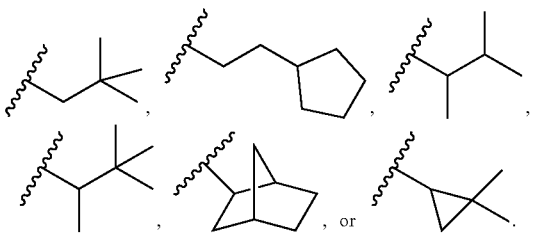

To any relevant embodiment or structural representation of Formula B-1 or B-2 or B-3 through B-7 herein the following applies, in some embodiments

is C$_{2-8}$ hydroxyalkyl, such as

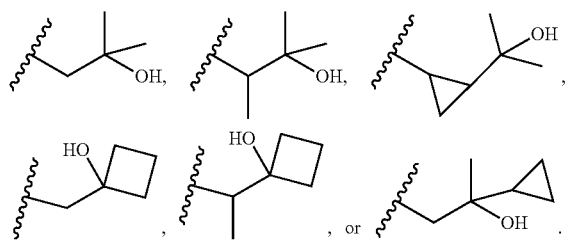

To any relevant embodiment or structural representation of Formula B-1 or B-2 or B-3 through B-7 herein the following applies, in some embodiments

is C$_{2-8}$ fluoroalkyl such as

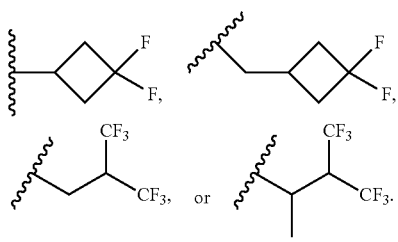

To any relevant embodiment or structural representation of Formula B-1 or B-2 or B-3 through B-7 herein the following applies, in some embodiments

is C$_{2-8}$ alkoxyalkyl, such as

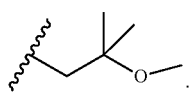 [SMILES: *CC(C)(C)OC]

To any relevant embodiment or structural representation of Formula B-1 or B-2 or B-3 through B-7 herein the following applies, in some embodiments is C$_{2-8}$ hydroxyfluoroalkyl, such as

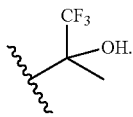

To any relevant embodiment or structural representation of Formula B-1 or B-2 or B-3 through B-7 herein the following applies, in some embodiments

is optionally substituted 2-hydroxy-2-phenylethyl, such as

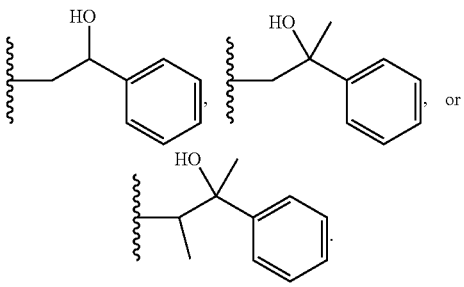

To any relevant embodiment or structural representation of Formula B-1 or B-2 or B-3 through B-7 herein the following applies, in some embodiments

is optionally substituted 2-hydroxy-2-phenylpyridinyl, such as

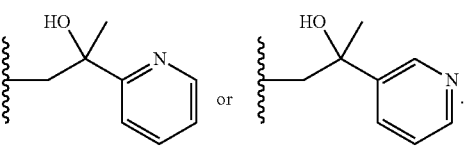 [SMILES: *CC(C)(O)c1ccccn1 ; *CC(C)(O)c1cccnc1]

To any relevant embodiment or structural representation of Formula B-1 or B-2 or B-3 through B-7 herein the following applies, in some embodiments

is optionally substituted $C_{2-8}$ fluoroaminoalkyl, such as

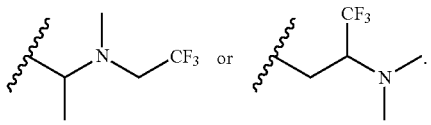

To any relevant embodiment or structural representation of Formula B-1 or B-2 or B-3 through B-7 herein the following applies. Generally $R^{1-18}$, may be H or any substituent, such as a substituent having 0 to 12 atoms or 0 to 6 carbon atoms and 0 to 5 heteroatoms, wherein each heteroatom is independently: O, N, S, F, Cl, Br, or I, and/or having a molecular weight of 15 g/mol to 300 g/mol. Any of $R^{1-18}$ may comprise: a) 1 or more alkyl moieties optionally substituted with, or optionally connected by or to, b) 1 or more functional groups, such as C=C, C≡C, CO, $CO_2$, CON, $NCO_2$, OH, SH, O, S, N, N=C, F, Cl, Br, I, CN, $NO_2$, $CO_2H$, $NH_2$, etc.; or may be a substituent having no alkyl portion, such as F, Cl, Br, I, $NO_2$, CN, $NH_2$, OH, COH, $CO_2H$, etc. In some embodiments, each of $R^{1-18}$ is independently H, F, Cl, Br, I, or a substituent having a molecular weight of 15 Da to 300 Da, 15 Da to 200 Da, 15 Da to 100 Da, or 15 Da to 60 Da, and consisting of 2 to 5 chemical elements, wherein the chemical elements are independently C, H, O, N, S, F, Cl, or Br.

With respect to any relevant structural representation of Formula B-1 or B-2 or B-3 through B-7, some non-limiting examples of $R^1$-18 may include $R^A$, F, Cl, Br, CN, $OR^A$, $C_{1-3}$ fluoroalkyl, $C_{1-4}$ hydroxyalkyl, $NO_2$, $NR^AR^B$, $COR^A$, $CO_2R^A$, $OCOR^A$, $NR^ACOR^B$, $CONR^AR^B$, etc. In some embodiments, $R^{1-18}$ may be H; F; Cl; Br; CN; $C_{1-3}$ fluoroalkyl, such as $CHF_2$, $CF_3$, etc; OH; $NH_2$; $C_{1-6}$ alkyl, such as methyl, ethyl, propyl isomers (e.g. n-propyl and isopropyl), cyclopropyl, butyl isomers, cyclobutyl isomers (e.g. cyclobutyl and methylcyclopropyl), pentyl isomers, cyclopentyl isomers, hexyl isomers, cyclohexyl isomers, etc.; $C_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc.; $C_{1-4}$ hydroxyalkyl, such as —$CH_2OH$, —$C_2H_4$—OH, —$C_3H_6$—OH, $C_4H_8$—OH, etc.; $C_{2-5}$—$CO_2$-alkyl, such as —$CO_2$—$CH_3$, —$CO_2$—$C_2H_5$, —$CO_2$—$C_3H_7$, —$CO_2$—$C_4H_9$, etc.

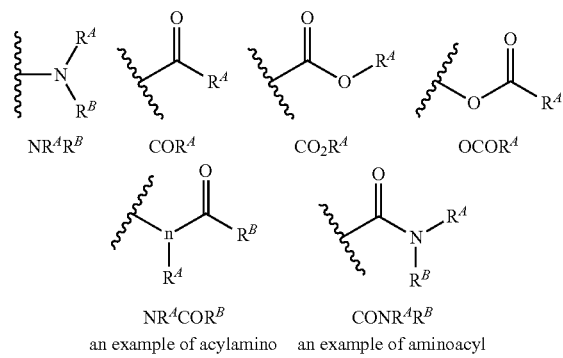

NR$^A$R$^B$  COR$^A$  CO$_2$R$^A$  OCOR$^A$

NR$^A$COR$^B$  CONR$^A$R$^B$
an example of acylamino  an example of aminoacyl

With respect to any relevant structural representation of Formula B-1 or B-2 or B-3 through B-7, each $R^A$ may independently be H, or $C_{1-12}$ alkyl, including: linear or branched alkyl having a formula $C_aH_{a+1}$, or cycloalkyl having a formula $C_aH_{a-1}$, wherein a is 1, 2, 3, 4, 5, 6, 7, 8, 9, 10, 11, or 12, such as linear or branched alkyl of a formula: $CH_3$, $C_2H_5$, $C_3H_7$, $C_4H_9$, $C_5H_{11}$, $C_6H_{13}$, $C_7H_{15}$, $C_8H_{17}$, $C_9H_{19}$, $C_{10}H_{21}$, etc., or cycloalkyl of a formula: $C_3H_5$, $C_4H_7$, $C_5H_9$, $C_6H_{11}$, $C_7H_{13}$, $C_8H_{15}$, $C_9H_{17}$, $C_{10}H_{19}$, etc. In some embodiments, $R^A$ may be H or $C_{1-6}$ alkyl. In some embodiments, $R^A$ may be H or $C_{1-3}$ alkyl. In some embodiments, $R^A$ may be H or $CH_3$. In some embodiments, $R^A$ may be H.

With respect to any relevant structural representation of Formula B-1 or B-2 or B-3 through B-7, each $R^B$ may independently be H, or $C_{1-12}$ alkyl, including: linear or branched alkyl having a formula $C_aH_{a+1}$, or cycloalkyl having a formula $C_aH_{a-1}$, wherein a is 1, 2, 3, 4, 5, 6, 7, 8, 9, 10, 11, or 12, such as linear or branched alkyl of a formula: $CH_3$, $C_2H_5$, $C_3H_7$, $C_4H_9$, $C_5H_{11}$, $C_6H_{13}$, $C_7H_{15}$, $C_8H_{17}$, $C_9H_{19}$, $C_{10}H_{21}$, etc., or cycloalkyl of a formula: $C_3H_5$, $C_4H_7$, $C_5H_9$, $C_6H_{11}$, $C_7H_{13}$, $C_8H_{15}$, $C_9H_{17}$, $C_{10}H_{19}$, etc. In some embodiments, $R^B$ may be H or $C_{1-3}$ alkyl. In some embodiments, $R^B$ may be H or $CH_3$. In some embodiments, $R^B$ may be H.

With respect to any relevant structural representation of Formula B-1 or B-2 or B-3 through B-7, such as Formula B-2, in some embodiments $R^1$ is H, F, Cl, Br, CN, $OCH_3$, $CHF_2$, $CF_3$, $C_{1-4}$—$CO_2$-alkyl, $C_{1-4}$ alkyl, or $C_{1-4}$ hydroxyalkyl. In some embodiments, $R^1$ is H, Cl, Br, CN, $OCH_3$, $CHF_2$, $CF_3$, —$CO_2CH_2CH_3$, —$CH_2OH$,

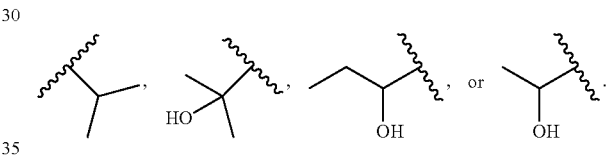

In some embodiments, $R^1$ is H. In some embodiments, $R^1$ is Cl. In some embodiments, $R^1$ is Br. In some embodiments, $R^1$ is CN. In some embodiments, R is $OCH_3$. In some embodiments, $R^1$ is $CHF_2$. In some embodiments, $R^1$ is $CF_3$. In some embodiments, $R^1$ is —$CO_2CH_2CH_3$. In some embodiments, $R^1$ is —$CH_2OH$. In some embodiments, $R^1$ is

In some embodiments, $R^1$ is

In some embodiments, $R^1$ is

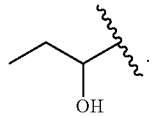

In some embodiments, $R^1$ is

[structure: a carbon with two wavy-line bonds and an OH group]

In some embodiments, $R^1$ is —OCH$_3$, —CN, —CF$_3$, —CH$_2$OH, —COOCH$_2$CH$_3$, —C(CH$_3$)$_2$OH, —CHOHCH$_2$CH$_3$, —CHOHCH$_3$, —CHF$_2$, —CH(CH$_3$)$_2$, —C(CH$_2$CH$_3$)OH, —CH$_2$COOC H$_2$CH$_3$, —CH$_2$C(CH$_3$)$_2$OH, —CH$_2$COOH, or —CH$_2$CON(CH$_3$)$_2$. With respect to the embodiments recited in this paragraph, in some embodiments, the remaining groups of $R^{1-18}$ may independently be $R^A$, F, Cl, Br, CN, OR$^A$, C$_{1-3}$ fluoroalkyl, C$_{1-4}$ hydroxyalkyl, NO$_2$, NR$^A$R$^B$ COR$^A$, CO$_2$R$^A$, OCOR$^A$, NR$^A$COR$^B$, CONR$^A$R$^B$, etc. In some embodiments, the remaining groups of $R^{1-18}$ may be H, F, Cl, Br, CN, C$_{1-3}$ fluoroalkyl, OH, NH$_2$, C$_{1-6}$ alkyl, C$_{1-6}$ alkoxy, C$_{1-4}$—CO$_2$-alkyl, or C$_{1-5}$ hydroxyalkyl.

With respect to any relevant structural representation of Formula B-1 or B-2 or B-3 through B-7, in some embodiments $R^2$ is H, F, Cl, Br, CN, OCH$_3$, CHF$_2$, CF$_3$, C$_{1-4}$—CO$_2$-alkyl, C$_{1-4}$ alkyl, or C$_{1-4}$ hydroxyalkyl. In some embodiments, $R^2$ is H. In some embodiments, $R^2$ is CH$_2$OH. In some embodiments, $R^2$ is —CO$_2$CH$_3$. With respect to the embodiments recited in this paragraph, in some embodiments, the remaining groups of $R^{1-18}$ may independently be $R^A$F, Cl, Br, CN, OR$^A$, C$_{1-3}$ fluoroalkyl, C$_{1-4}$ hydroxyalkyl, NO$_2$, NR$^A$R$^B$, COR$^A$, CO$_2$R$^A$, OCOR$^A$NR$^A$COR$^B$, CONR$^A$R$^B$, etc. In some embodiments, the remaining groups of $R^{1-18}$ may be H, F, Cl, Br, CN, C$_{1-3}$ fluoroalkyl, OH, NH$_2$, C$_{1-6}$ alkyl, C$_{1-6}$ alkoxy, C$_{1-4}$—CO$_2$-alkyl, or C$_{1-4}$ hydroxyalkyl. In some embodiments, $R^2$ is —CH$_2$OH, —CO$_2$Me, or —C(CH$_3$)$_2$OH.

With respect to any relevant structural representation of Formula B-1 or B-2 or B-3 through B-7, in some embodiments $R^3$ is H, F, Cl, Br, CN, OCH$_3$, CHF$_2$, CF$_3$, C$_{1-4}$—CO$_2$-alkyl, C$_{1-4}$ alkyl, or C$_{1-4}$ hydroxyalkyl. In some embodiments, $R^3$ is H. With respect to the embodiments recited in this paragraph, in some embodiments, the remaining groups of $R^{1-18}$ may independently be $R^A$, F, Cl, Br, CN, OR$^A$, C$_{1-3}$ fluoroalkyl, C$_{1-4}$ hydroxyalkyl, NO$_2$, NR$^A$R$^B$ COR$^A$, CO$_2$R$^A$, OCOR$^A$, NR$^A$COR$^B$, CONR$^A$R$^B$, etc. In some embodiments, the remaining groups of $R^{1-18}$ may be H, F, Cl, Br, CN, C$_{1-3}$ fluoroalkyl, OH, NH$_2$, C$_{1-6}$ alkyl, C$_{1-6}$ alkoxy, C$_{1-4}$—CO$_2$-alkyl, or C$_{1-4}$ hydroxyalkyl.

With respect to any relevant structural representation of Formula B-1 or B-2 or B-3 through B-7, in some embodiments $R^4$ is H, F, Cl, Br, CN, OCH$_3$, CHF$_2$, CF$_3$, C$_{1-4}$—CO$_2$-alkyl, C$_{1-4}$ alkyl, or C$_{1-4}$ hydroxyalkyl. In some embodiments, $R^4$ is H. In some embodiments, $R^4$ is CH$_3$. In some embodiments, $R^4$ is CF$_3$. With respect to the embodiments recited in this paragraph, in some embodiments, the remaining groups of $R^{1-18}$ may independently be $R^A$, F, Cl, Br, CN, OR$^A$, 1-3 fluoroalkyl, C$_{1-4}$ hydroxyalkyl, NO$_2$, NR$^A$R$^B$, COR$^A$, CO$_2$R$^A$, OCOR$^A$, NR$^A$COR$^B$, CONR$^A$R$^B$, etc. In some embodiments, the remaining groups of $R^{1-18}$ may be H, F, Cl, Br, CN, C$_3$ fluoroalkyl, OH, NH$_2$, C$_{1-6}$ alkyl, C$_{1-6}$ alkoxy, C$_{1-4}$—CO$_2$-alkyl, or C$_{1-4}$ hydroxyalkyl.

With respect to any relevant structural representation of Formula B-1 or B-2 or B-3 through B-7, in some embodiments $R^5$ is H, F, Cl, Br, CN, OCH$_3$, CHF$_2$, CF$_3$, C$_{1-4}$—CO$_2$-alkyl, C$_{1-4}$ alkyl, or C$_{1-4}$ hydroxyalkyl. In some embodiments, $R^5$ is H. With respect to the embodiments recited in this paragraph, in some embodiments, the remaining groups of $R^{1-18}$ may independently be $R^A$, F, Cl, Br, CN, OR$^A$, C$_{1-3}$ fluoroalkyl, C$_{1-4}$ hydroxyalkyl, NO$_2$, NR$^A$R$^B$ COR$^A$, CO$_2$R$^A$, OCOR$^A$, NR$^A$COR$^B$, CONR$^A$R$^B$, etc. In some embodiments, the remaining groups of $R^{1-18}$ may be H, F, Cl, Br, CN, C$_3$ fluoroalkyl, OH, NH$_2$, C$_{1-6}$ alkyl, C$_{1-6}$ alkoxy, C$_{1-4}$—CO$_2$-alkyl, or C$_{1-4}$ hydroxyalkyl.

With respect to any relevant structural representation of Formula B-1 or B-2 or B-3 through B-7, in some embodiments $R^6$ is H, F, Cl, Br, CN, OCH$_3$, CHF$_2$, CF$_3$, C$_{1-4}$—CO$_2$-alkyl, C$_{1-4}$ alkyl, or C$_{1-4}$ hydroxyalkyl. In some embodiments, $R^6$ is H. With respect to the embodiments recited in this paragraph, in some embodiments, the remaining groups of $R^{1-18}$ may independently be $R^A$, F, Cl, Br, CN, OR$^A$, C$_{1-3}$ fluoroalkyl, C$_{1-4}$ hydroxyalkyl, NO$_2$, NR$^A$R$^B$ COR$^A$, CO$_2$R$^A$, OCOR$^A$, NR$^A$COR$^B$, CONR$^A$R$^B$, etc. In some embodiments, the remaining groups of $R^{1-18}$ may be H, F, Cl, Br, CN, C$_3$ fluoroalkyl, OH, NH$_2$, C$_{1-6}$ alkyl, C$_{1-6}$ alkoxy, C$_{1-4}$—CO$_2$-alkyl, or C$_{1-4}$ hydroxyalkyl.

With respect to any relevant structural representation of Formula B-1 or B-2 or B-3 through B-7, in some embodiments $R^7$ is H, F, Cl, Br, CN, OCH$_3$, CHF$_2$, CF$_3$, C$_{1-4}$—CO$_2$-alkyl, C$_{1-4}$ alkyl, or C$_{1-4}$ hydroxyalkyl. In some embodiments, $R^7$ is H. With respect to the embodiments recited in this paragraph, in some embodiments, the remaining groups of $R^{1-18}$ may independently be $R^A$, F, Cl, Br, CN, OR$^A$, C$_{1-3}$ fluoroalkyl, C$_{1-4}$ hydroxyalkyl, NO$_2$, NR$^A$R$^B$ COR$^A$, CO$_2$R$^A$, OCOR$^A$, NR$^A$COR$^B$, CONR$^A$R$^B$, etc. In some embodiments, the remaining groups of $R^{1-18}$ may be H, F, Cl, Br, CN, C$_3$ fluoroalkyl, OH, NH$_2$, C$_{1-6}$ alkyl, C$_{1-6}$ alkoxy, C$_{1-4}$—CO$_2$-alkyl, or C$_{1-4}$ hydroxyalkyl.

With respect to any relevant structural representation of Formula B-1 or B-2 or B-3 through B-7, in some embodiments $R^8$ is H, F, Cl, Br, CN, OCH$_3$, CHF$_2$, CF$_3$, C$_{1-4}$—CO$_2$-alkyl, C$_{1-4}$ alkyl, or C$_{1-4}$ hydroxyalkyl. In some embodiments, $R^8$ is H. With respect to the embodiments recited in this paragraph, in some embodiments, the remaining groups of $R^{1-18}$ may independently be $R^A$, F, Cl, Br, CN, OR$^A$, C$_{1-3}$ fluoroalkyl, C$_{1-4}$ hydroxyalkyl, NO$_2$, NR$^A$R$^B$ COR$^A$, CO$_2$R$^A$, OCOR$^A$, NR$^A$COR$^B$, CONR$^A$R$^B$, etc. In some embodiments, the remaining groups of $R^{1-18}$ may be H, F, Cl, Br, CN, C$_3$ fluoroalkyl, OH, NH$_2$, C$_{1-6}$ alkyl, C$_{1-6}$ alkoxy, C$_{1-4}$—CO$_2$-alkyl, or C$_{1-4}$ hydroxyalkyl.

With respect to any relevant structural representation of Formula B-1 or B-2 or B-3 through B-7, in some embodiments $R^9$ is H, F, Cl, Br, CN, OCH$_3$, CHF$_2$, CF$_3$, C$_{1-4}$—CO$_2$-alkyl, C$_{1-4}$ alkyl, or C$_{1-4}$ hydroxyalkyl. In some embodiments, $R^9$ is H. With respect to the embodiments recited in this paragraph, in some embodiments, the remaining groups of $R^{1-18}$ may independently be $R^A$, F, Cl, Br, CN, OR$^A$, C$_{1-3}$ fluoroalkyl, C$_{1-4}$ hydroxyalkyl, NO$_2$, NR$^A$R$^B$ COR$^A$, CO$_2$R$^A$, OCOR$^A$, NR$^A$COR$^B$, CONR$^A$R$^B$, etc. In some embodiments, the remaining groups of $R^{1-18}$ may be H, F, Cl, Br, CN, C$_{1-3}$ fluoroalkyl, OH, NH$_2$, C$_{1-6}$ alkyl, C$_{1-6}$ alkoxy, C$_{1-4}$—CO$_2$-alkyl, or C$_{1-4}$ hydroxyalkyl.

With respect to any relevant structural representation of Formula B-1 or B-2 or B-3 through B-7, in some embodiments $R^{10}$ is H, F, Cl, Br, CN, OCH$_3$, CHF$_2$, CF$_3$, C$_{1-4}$—CO$_2$-alkyl, C$_{1-4}$ alkyl, or C$_{1-4}$ hydroxyalkyl. In some embodiments, $R^{10}$ is H. With respect to the embodiments recited in this paragraph, in some embodiments, the remaining groups of $R^{1-18}$ may independently be $R^A$, F, Cl, Br, CN, OR$^A$, C$_{1-3}$ fluoroalkyl, C$_{1-4}$ hydroxyalkyl, NO$_2$, NR$^A$R$^B$ COR$^A$, CO$_2$R$^A$, OCOR$^A$, NR$^A$COR$^B$, CONR$^A$R$^B$, etc. In some embodiments, the remaining groups of $R^{1-18}$ may be H, F, Cl, Br, CN, C$_3$ fluoroalkyl, OH, NH$_2$, C$_{1-6}$ alkyl, C$_{1-6}$ alkoxy, C$_{1-4}$—CO$_2$-alkyl, or C$_{1-4}$ hydroxyalkyl.

With respect to any relevant structural representation of Formula B-1 or B-2 or B-3 through B-7, in some embodiments $R^{11}$ is H, F, Cl, Br, CN, $OCH_3$, $CHF_2$, $CF_3$, $C_{1-4}$—$CO_2$-alkyl, $C_{1-4}$ alkyl, or $C_{1-4}$ hydroxyalkyl. In some embodiments, $R^{12}$ is H. With respect to the embodiments recited in this paragraph, in some embodiments, the remaining groups of $R^{1-18}$ may independently be $R^A$, F, Cl, Br, CN, $OR^A$, $C_{1-3}$ fluoroalkyl, $C_{1-4}$ hydroxyalkyl, $NO_2$, $NR^AR^B$, $COR^A$, $CO_2R^A$, $OCOR^A$, $NR^ACOR^B$, $CONR^AR^B$, etc. In some embodiments, the remaining groups of $R^{1-18}$ may be H, F, Cl, Br, CN, $C_3$ fluoroalkyl, OH, $NH_2$, $C_{1-6}$ alkyl, $C_{1-6}$ alkoxy, $C_{1-4}$—$CO_2$-alkyl, or $C_{1-4}$ hydroxyalkyl.

With respect to any relevant structural representation of Formula B-1 or B-2 or B-3 through B-7, in some embodiments $R^{12}$ is H, F, Cl, Br, CN, $OCH_3$, $CHF_2$, $CF_3$, $C_{1-4}$—$CO_2$-alkyl, $C_{1-4}$ alkyl, or $C_{1-4}$ hydroxyalkyl. In some embodiments, $R^{12}$ is H. With respect to the embodiments recited in this paragraph, in some embodiments, the remaining groups of $R^{1-18}$ may independently be $R^A$, F, Cl, Br, CN, $OR^A$, $C_{1-3}$ fluoroalkyl, $C_{1-4}$ hydroxyalkyl, $NO_2$, $NR^AR^B$, $COR^A$, $CO_2R^A$, $OCOR^A$, $NR^ACOR^B$, $CONR^AR^B$, etc. In some embodiments, the remaining groups of $R^{1-18}$ may be H, F, Cl, Br, CN, $C_3$ fluoroalkyl, OH, $NH_2$, $C_{1-6}$ alkyl, $C_{1-6}$ alkoxy, $C_{1-4}$—$CO_2$-alkyl, or $C_{1-4}$ hydroxyalkyl.

With respect to any relevant structural representation of Formula B-1 or B-2 or B-3 through B-7, in some embodiments $R^{13}$ is H, F, Cl, Br, CN, $OCH_3$, $CHF_2$, $CF_3$, $C_{1-4}$—$CO_2$-alkyl, $C_{1-4}$ alkyl, or $C_{1-4}$ hydroxyalkyl. In some embodiments, $R^{13}$ is H. With respect to the embodiments recited in this paragraph, in some embodiments, the remaining groups of $R^{1-18}$ may independently be $R^A$, F, Cl, Br, CN, $OR^A$, $C_{1-3}$ fluoroalkyl, $C_{1-4}$ hydroxyalkyl, $NO_2$, $NR^AR^B$, $COR^A$, $CO_2R^A$, $OCOR^A$, $NR^ACOR^B$, $CONR^AR^B$, etc. In some embodiments, the remaining groups of $R^{1-18}$ may be H, F, Cl, Br, CN, $C_3$ fluoroalkyl, OH, $NH_2$, $C_{1-6}$ alkyl, $C_{1-6}$ alkoxy, $C_{1-4}$—$CO_2$-alkyl, or $C_{1-4}$ hydroxyalkyl.

With respect to any relevant structural representation of Formula B-1 or B-2 or B-3 through B-7, in some embodiments $R^{14}$ is H, F, Cl, Br, CN, $OCH_3$, $CHF_2$, $CF_3$, $C_{1-4}$—$CO_2$-alkyl, $C_{1-4}$ alkyl, or $C_{1-4}$ hydroxyalkyl. In some embodiments, $R^{14}$ is H. In some embodiments, $R^{14}$ is F. With respect to the embodiments recited in this paragraph, in some embodiments, the remaining groups of $R^{1-18}$ may independently be $R^A$, F, Cl, Br, CN, $OR^A$, $C_{1-3}$ fluoroalkyl, $C_{1-4}$ hydroxyalkyl, $NO_2$, $NR^AR^B$, $COR^A$, $CO_2R^A$, $OCOR^A$, $NR^ACOR^B$, $CONR^AR^B$, etc. In some embodiments, the remaining groups of $R^{1-18}$ may be H, F, Cl, Br, CN, $C_{1-3}$ fluoroalkyl, OH, $NH_2$, $C_{1-6}$ alkyl, $C_{1-6}$ alkoxy, $C_{1-4}$—$CO_2$-alkyl, or $C_{1-4}$ hydroxyalkyl.

In some embodiments of the invention, one or more hydrogen atoms is replaced by a deuterium. It is well established that deuteration of physiologically active compounds offer the advantage of retaining the pharmacological profile of their hydrogen counterparts while positively impacting their metabolic outcome. Selective replacement of one or more hydrogen with deuterium, in a compound of the present invention, could improve the safety, tolerability and efficacy of the compound when compared to its all hydrogen counterpart.

Methods for incorporation of deuterium into compounds is well established. Using metabolic studies establish in the art, the compound of the present invention can be tested to identify sites for selective placement of a deuterium isotope, wherein the isotope will not be metabolized. Moreover these studies identify sites of metabolism as the location where a deuterium atom would be placed.

Some embodiments of Formula B-1 may include a compound represented by Formula B-3:

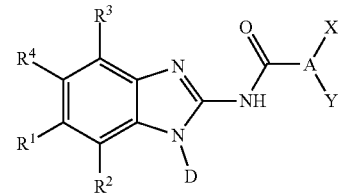

Formula B-3 wherein
D is optionally substituted cyclobutyl;
A is $C_4$ alkyl;
X is $CF_3$;
Y is H;
$R^1$ is $C_3$ hydroxyalkyl;
$R^2$ and $R^4$ are H; and
$R^3$ is F;
or a pharmaceutically acceptable salt thereof.

Some embodiments of Formula B-1 may include a compound represented by Formula B-4:

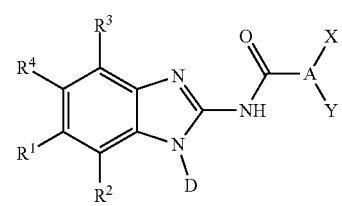

Formula B-4 wherein
D is optionally substituted cyclobutyl;
A is $C_4$ alkyl;
X is $CF_3$;
Y is H;
$R^1$ is $C_3$ hydroxyalkyl; and
$R^2$, $R^3$ and $R^4$ are H;
or a pharmaceutically acceptable salt thereof.

Some embodiments of Formula B-1 may include a compound represented by Formula B-5:

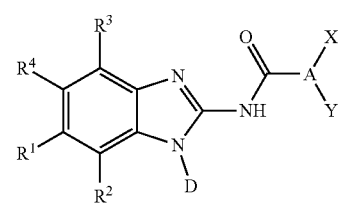

Formula B-5 wherein
D is t-butyl;
A is $C_5$ alkyl;
X is H;
Y is H;
$R^1$ is CN;
$R^2$ and $R^4$ are H; and
$R^3$ is F;
or a pharmaceutically acceptable salt thereof.

Some embodiments of Formula B-1 may include a compound represented by Formula B-6:

Formula B-6

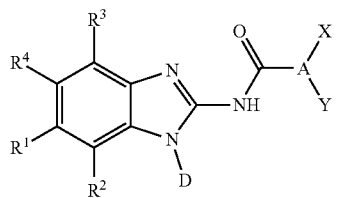

wherein
D is t-butyl;
A is C₄ alkyl;
X is CF₃;
Y is H;
R¹ is CN;
R² and R⁴ are H; and
R³ is F;
or a pharmaceutically acceptable salt thereof.

Some embodiments of Formula B-1 may include a compound represented by Formula B-7:

Formula B-7

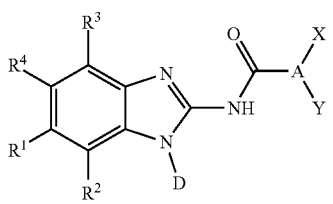

wherein
D is t-butyl;
A is C₅ alkyl;
X is H;
Y is H;
R¹ is CN;
R² and R³ are F; and
R⁴ is H;
or a pharmaceutically acceptable salt thereof.

Some embodiments of Formula B-1 include a compound represented by the following structures or a pharmaceutically acceptable salt thereof:

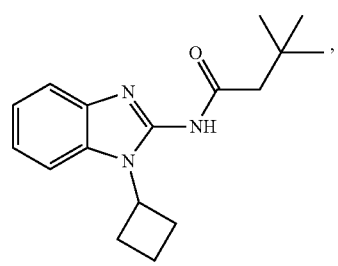

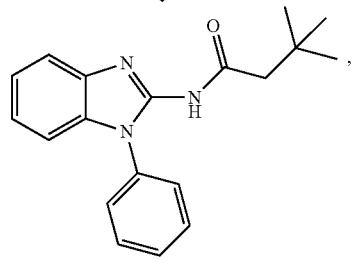

-continued

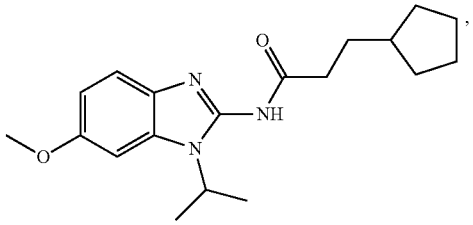

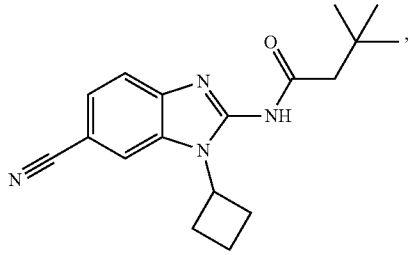

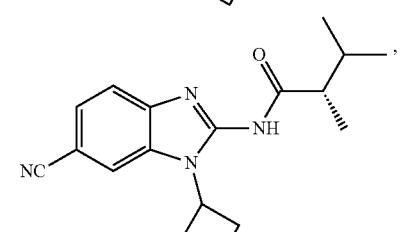

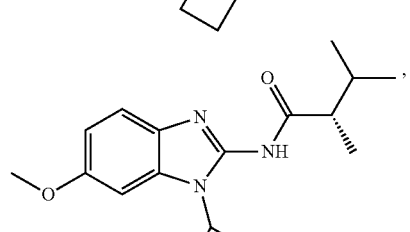

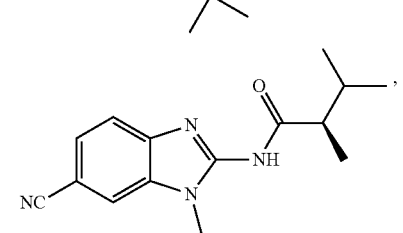

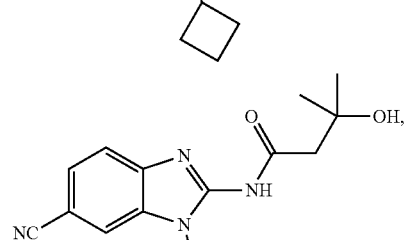

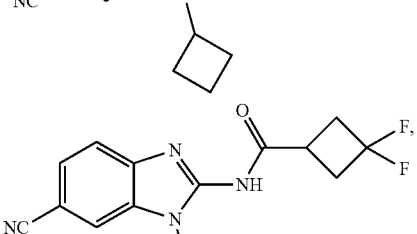

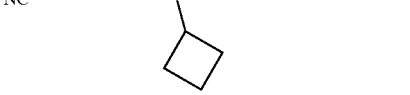

317
-continued
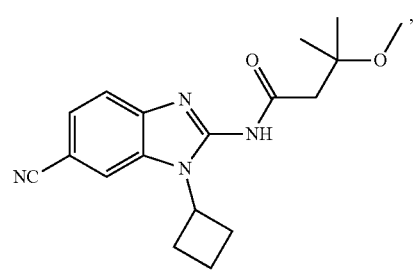
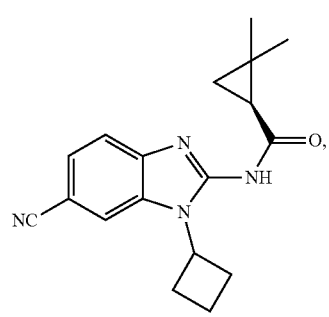
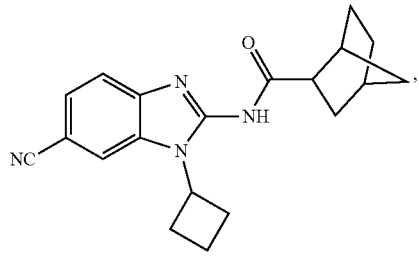
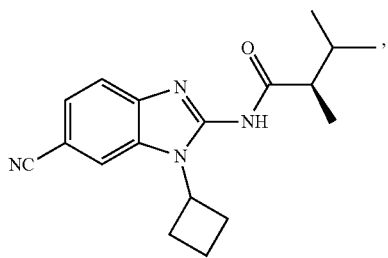
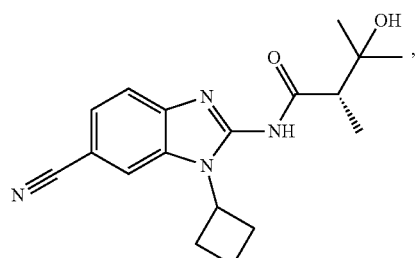
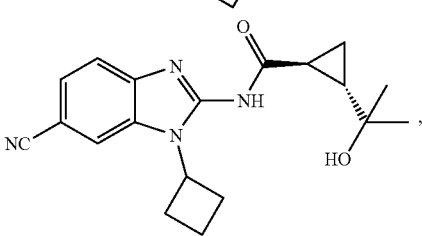
318
-continued
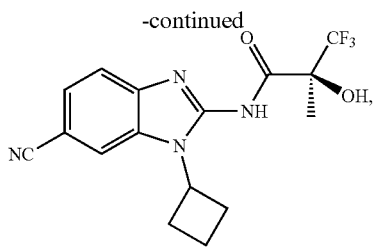
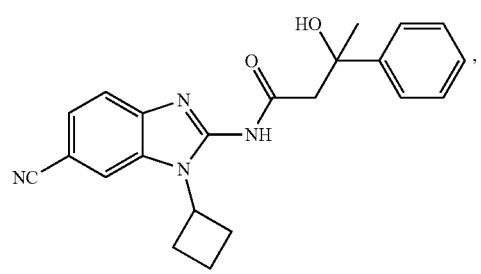
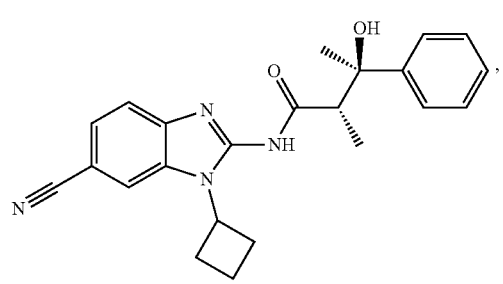
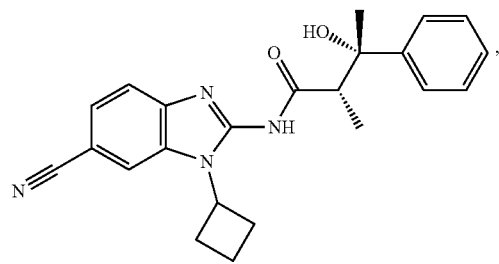
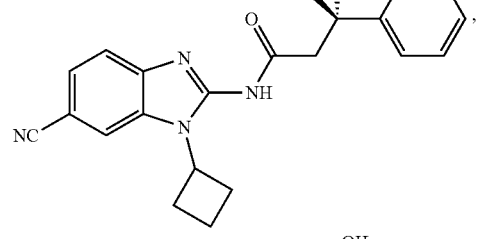
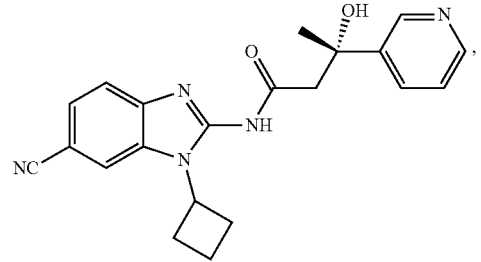

319
-continued
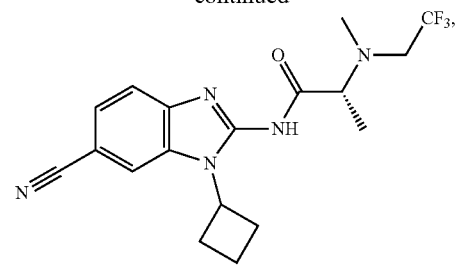
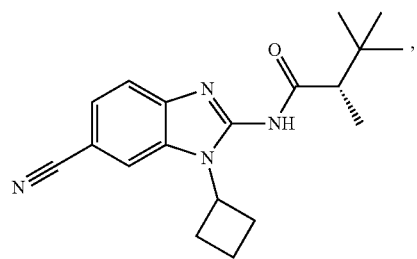
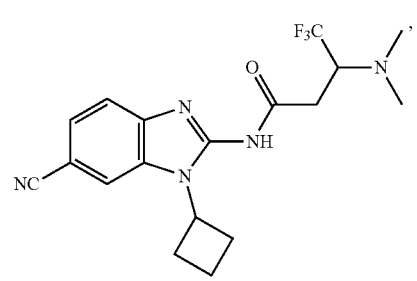
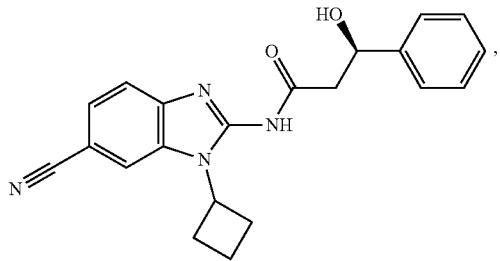
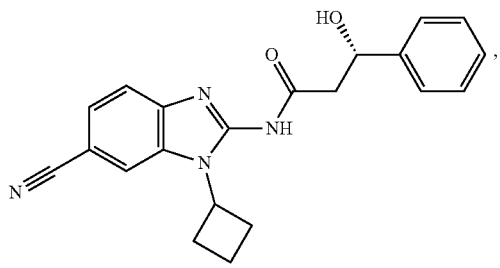
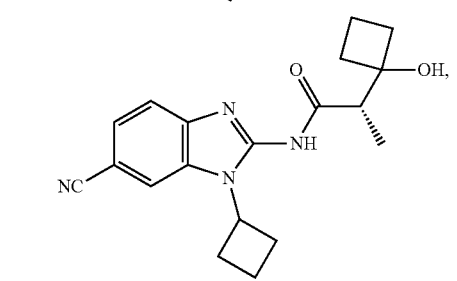
320
-continued
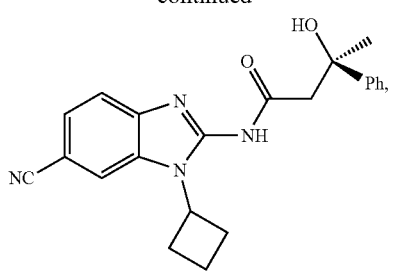
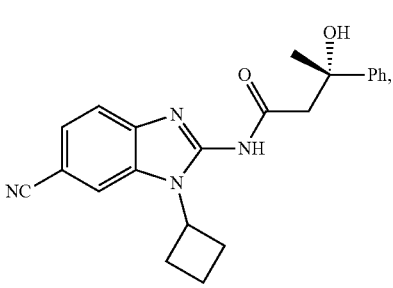
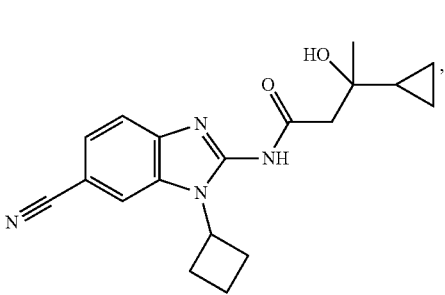
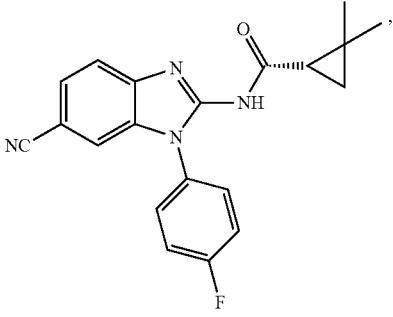
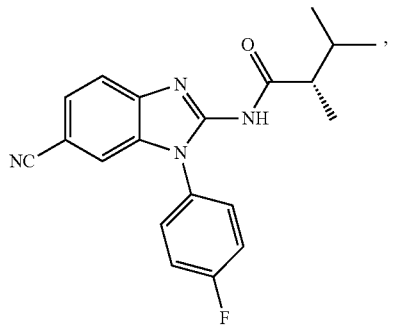

321
-continued
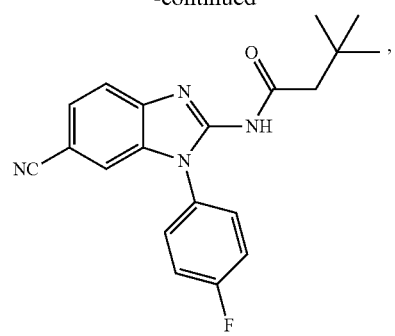
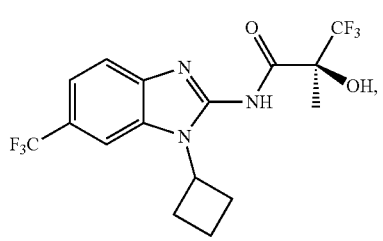
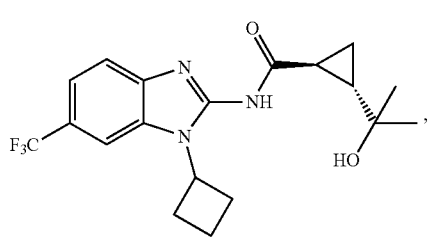
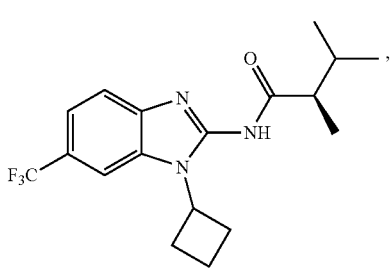
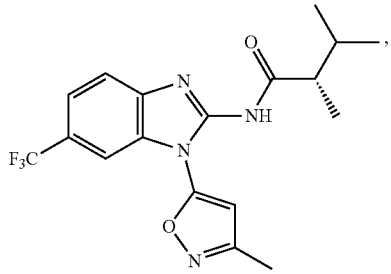
322
-continued
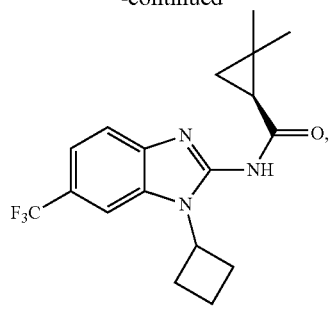
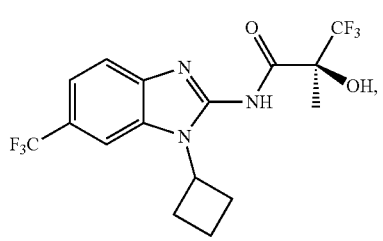
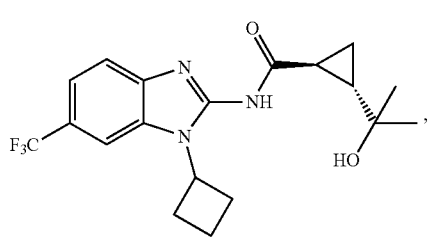
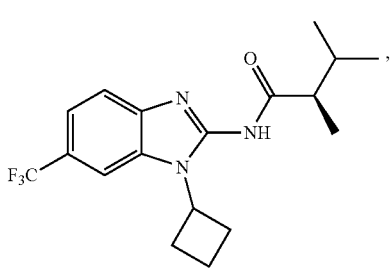
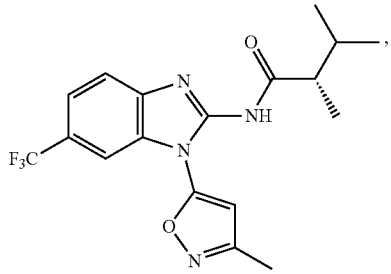
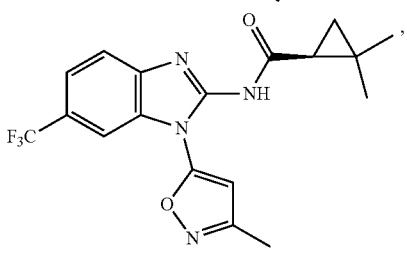

323
-continued
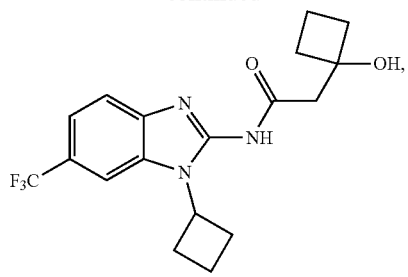
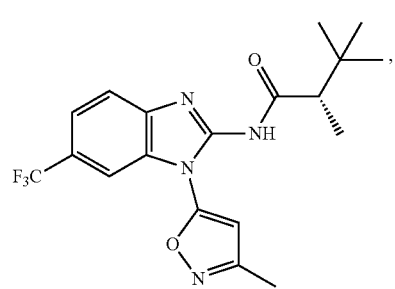
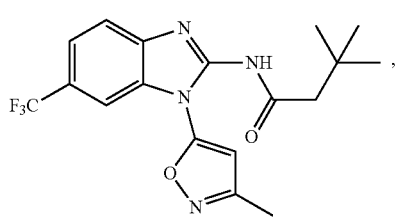
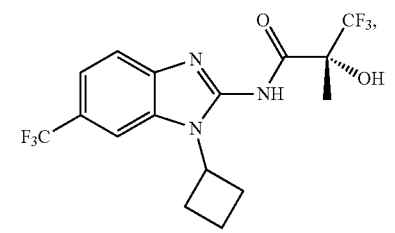
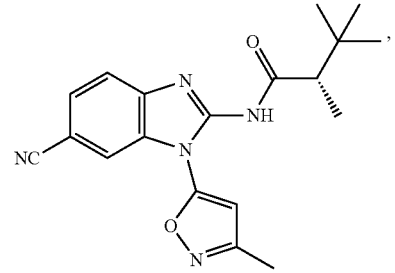
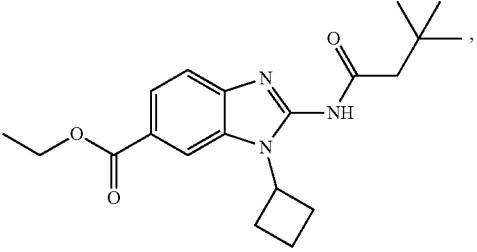
324
-continued
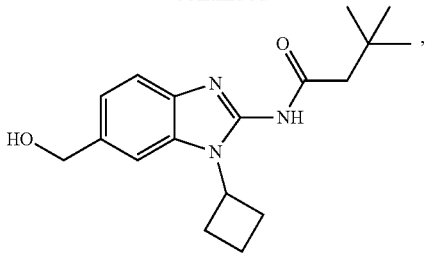
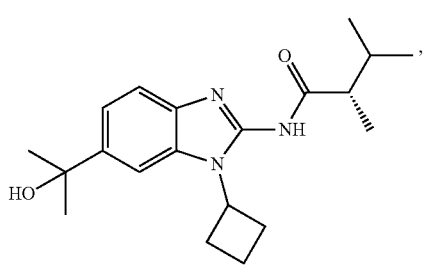
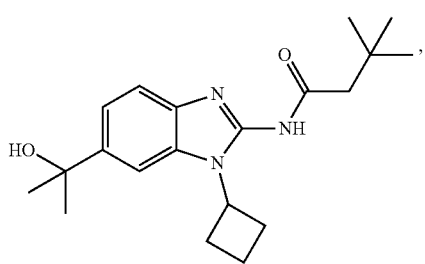
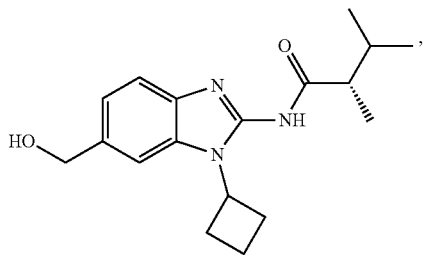
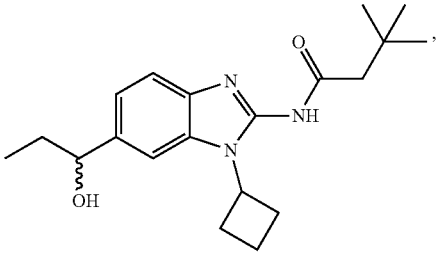
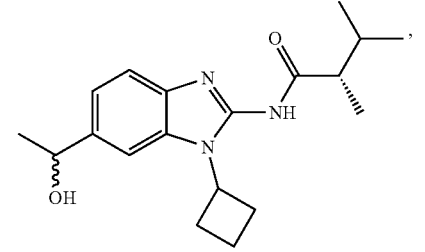

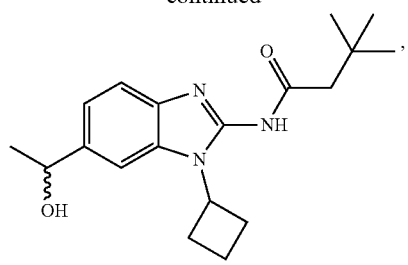
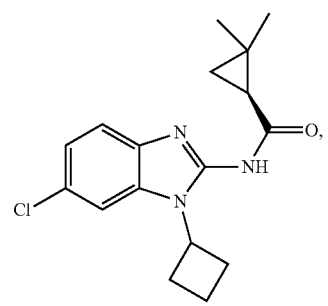
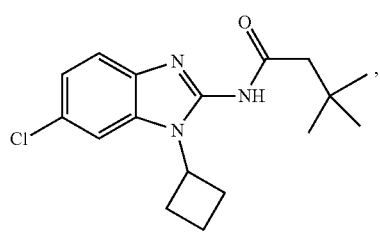
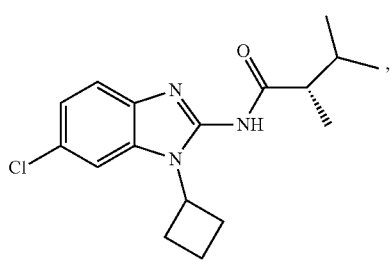
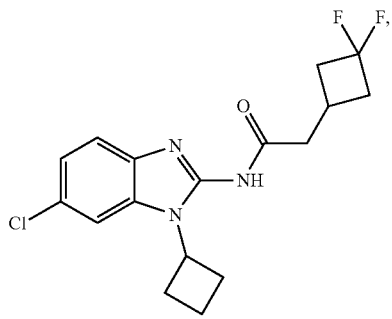
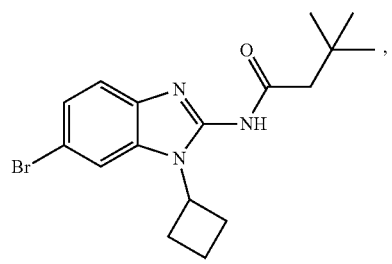
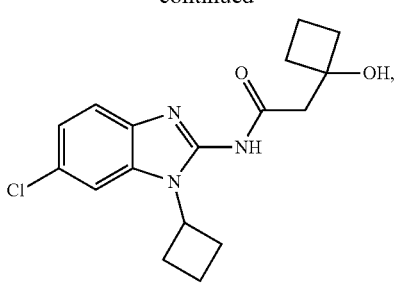
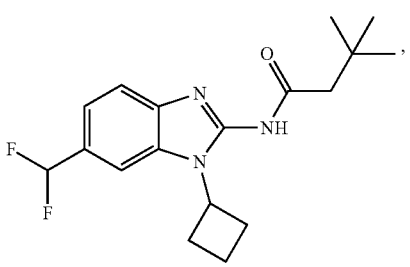
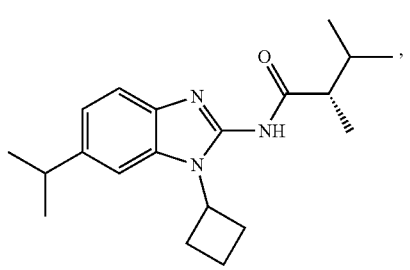
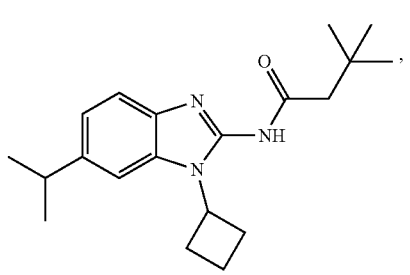
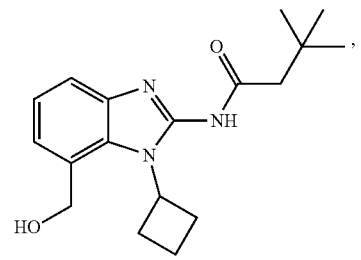
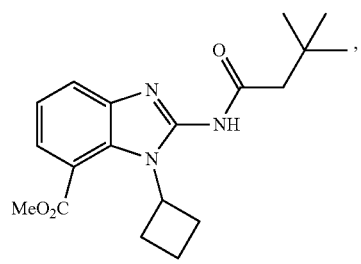

327
-continued
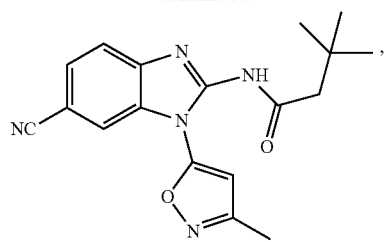
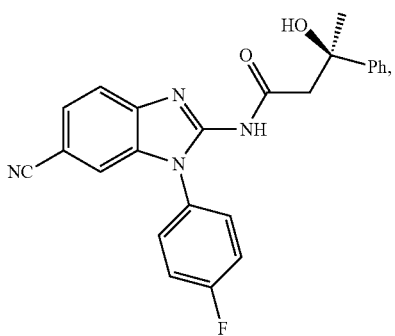
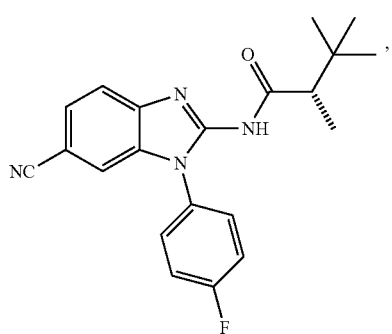
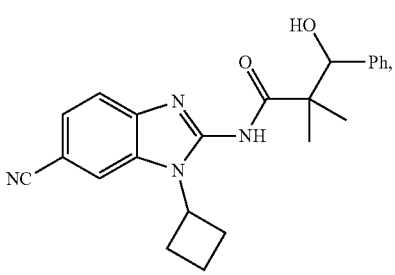
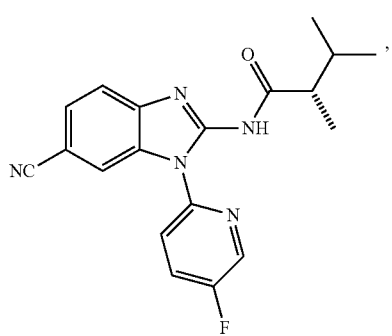
328
-continued
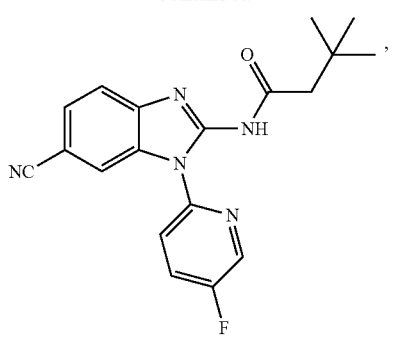
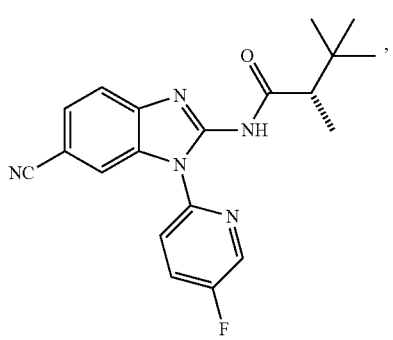
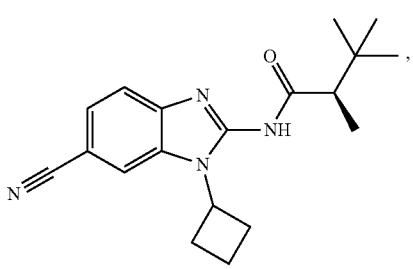
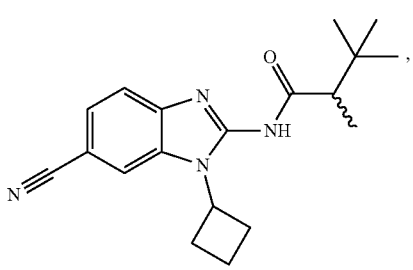
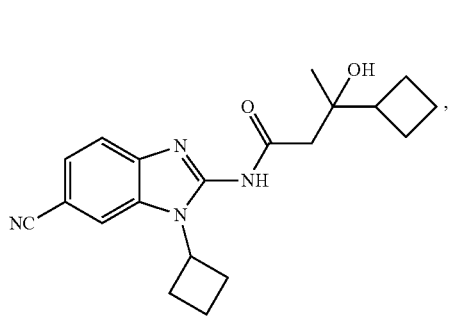

329
-continued
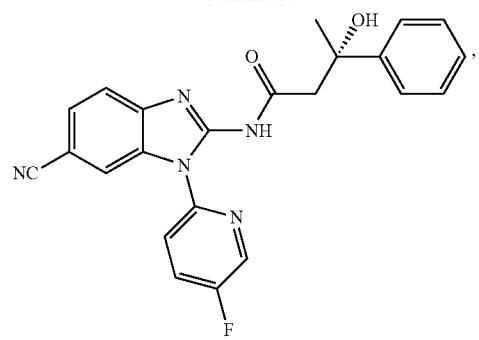
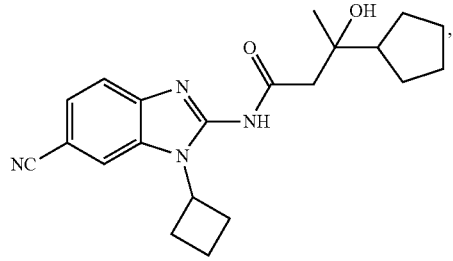
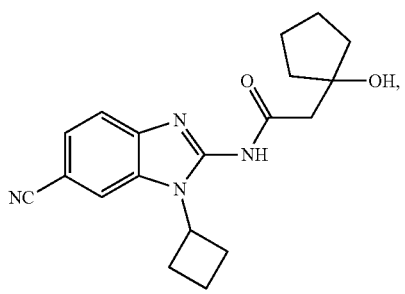
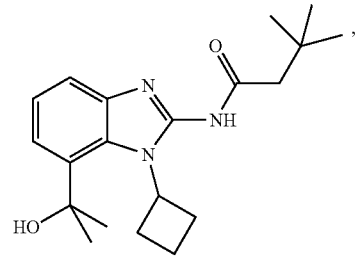
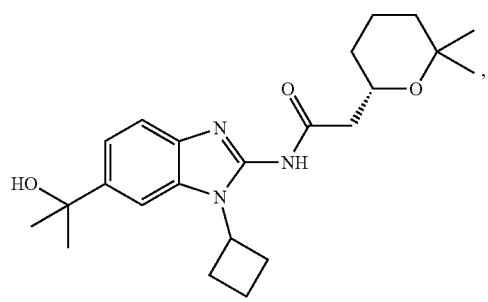
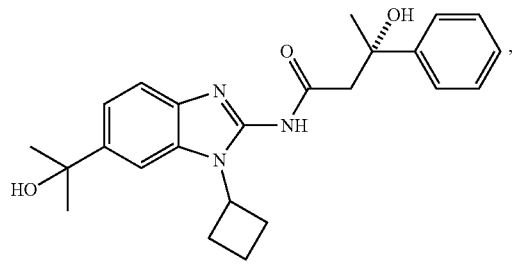
330
-continued
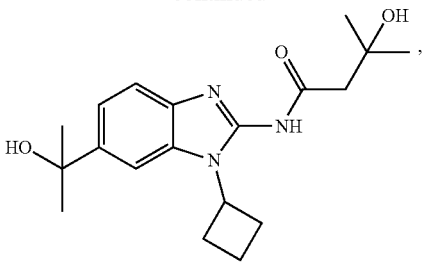
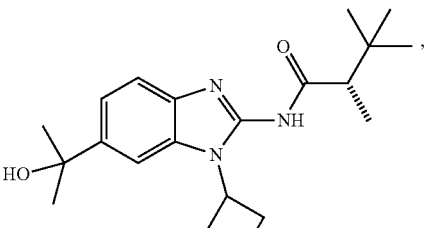
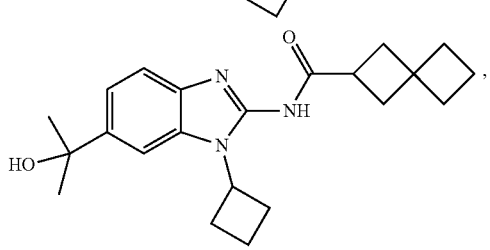
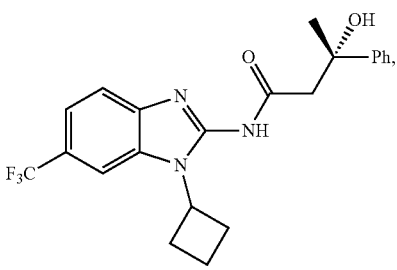
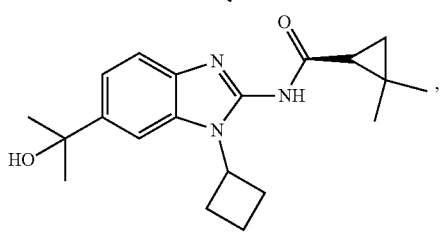
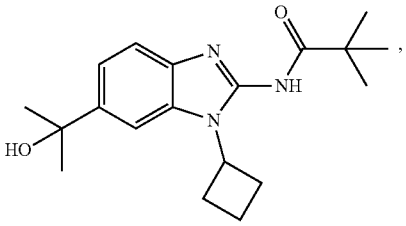
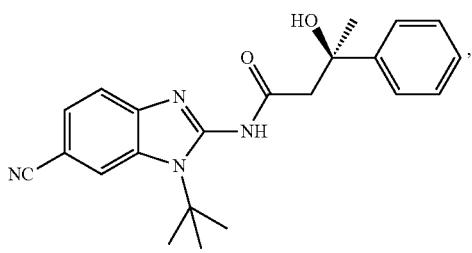

331
-continued
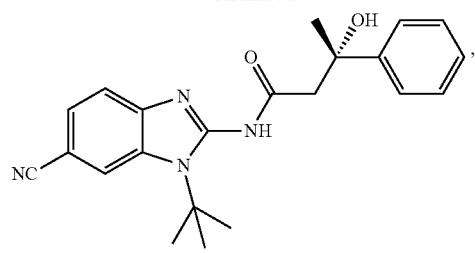
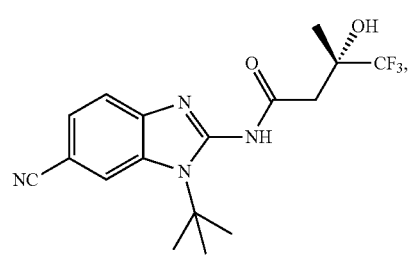
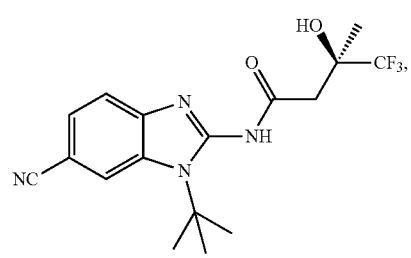
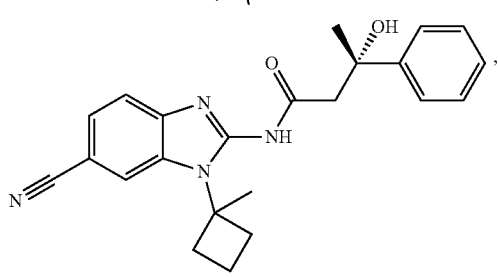
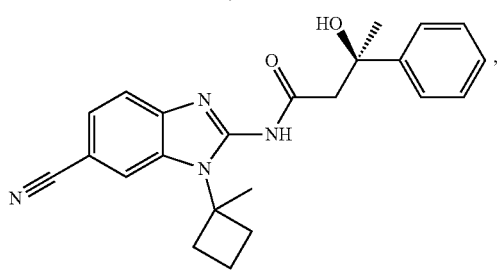
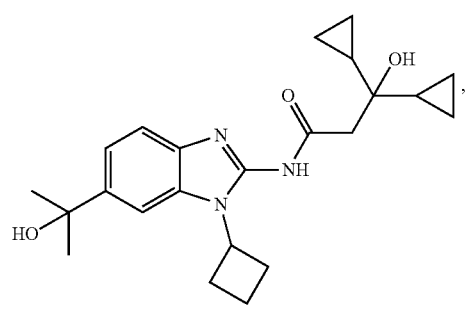
332
-continued
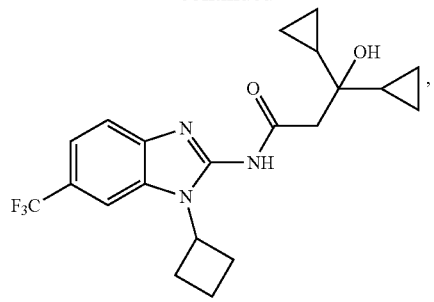
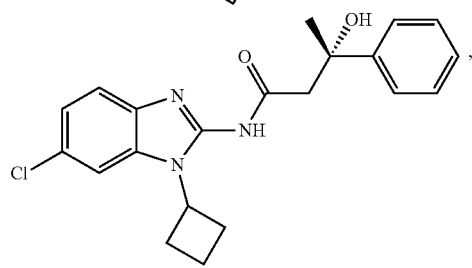
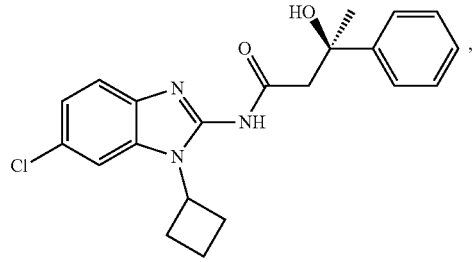
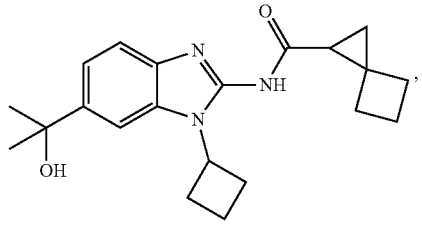
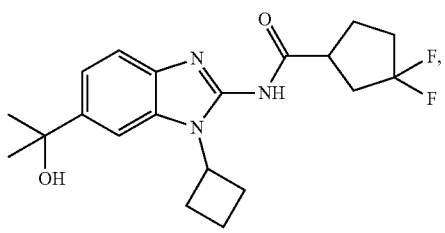
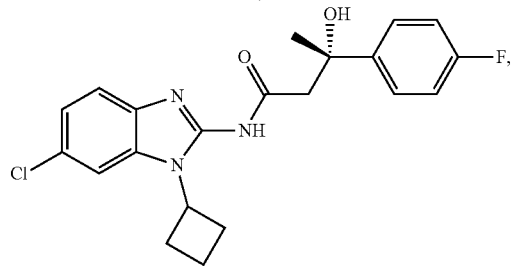

333
-continued
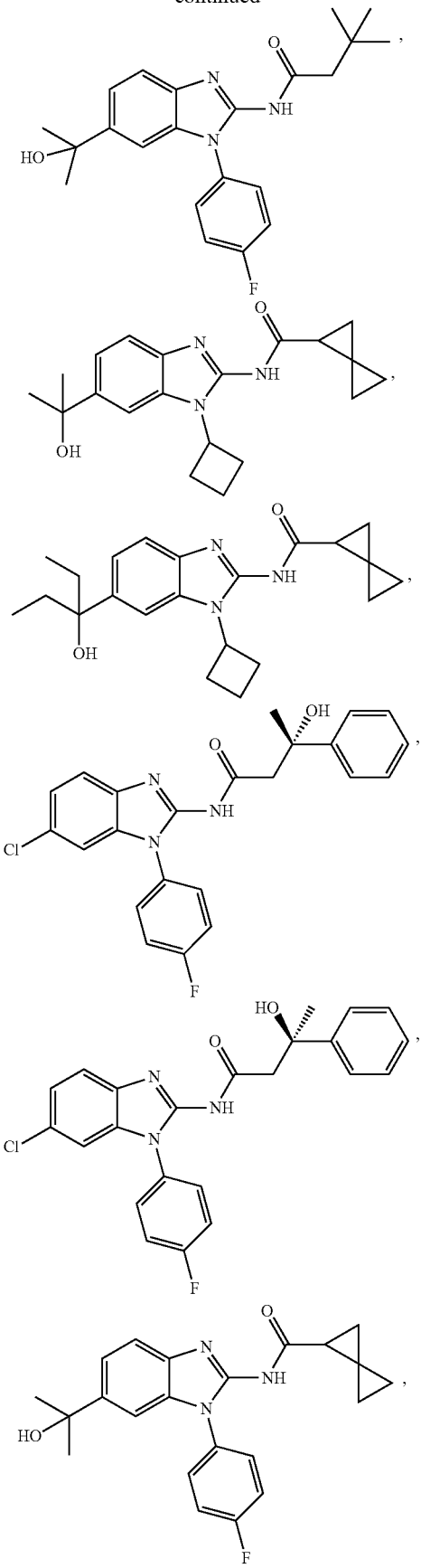
334
-continued
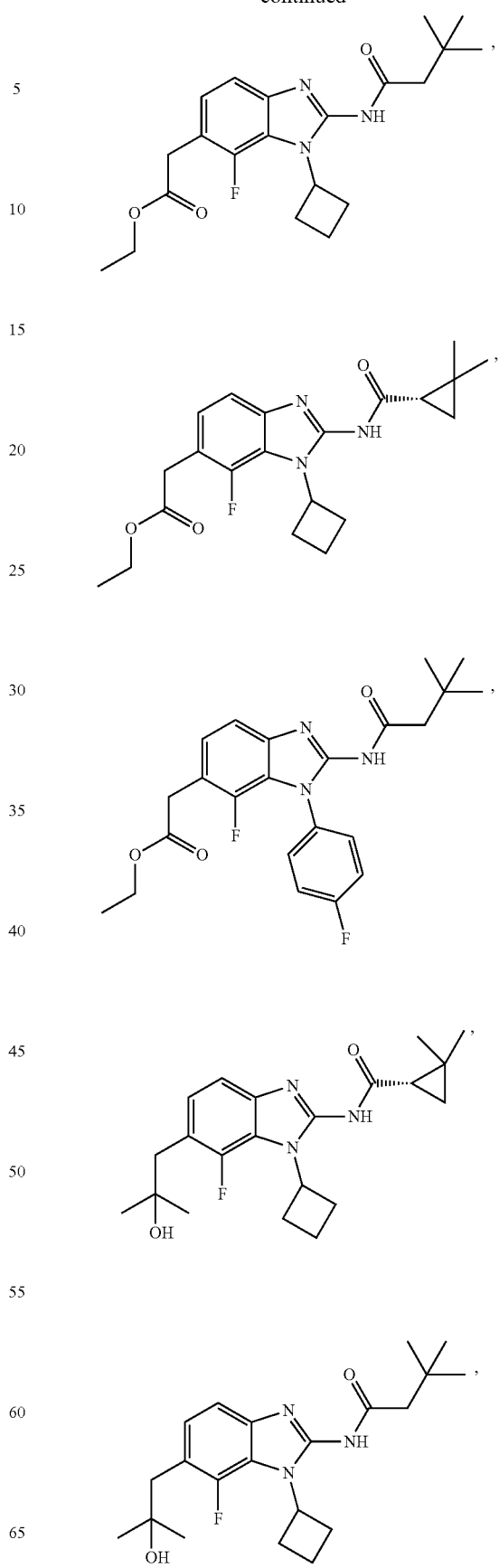

335
-continued
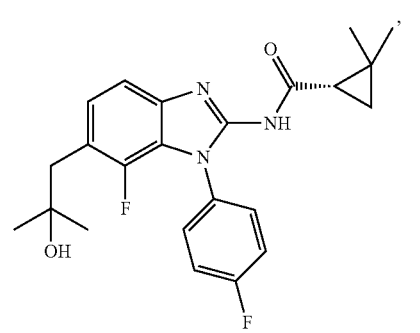
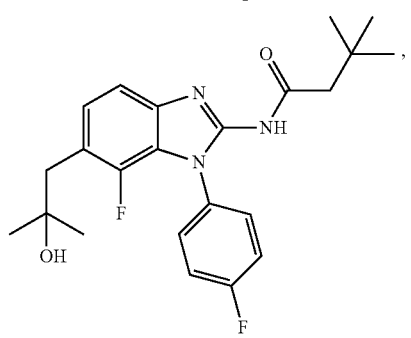
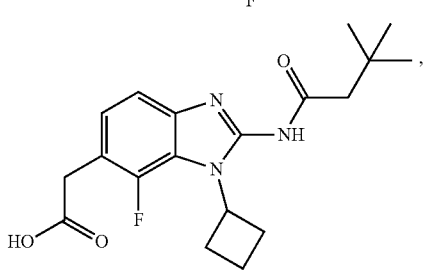
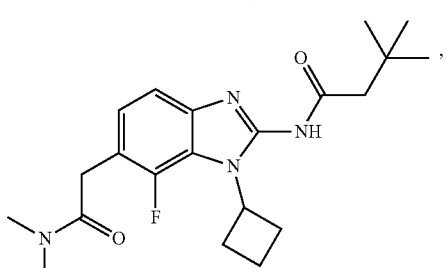
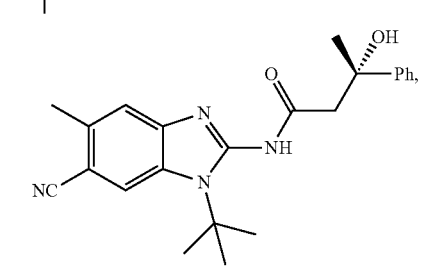
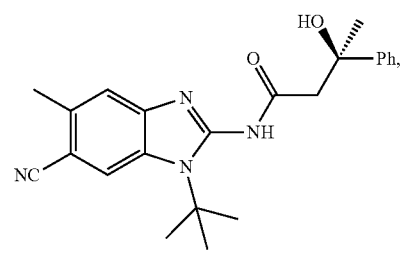
336
-continued
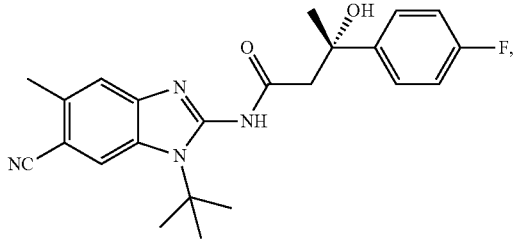
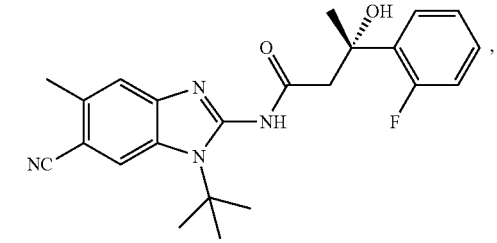
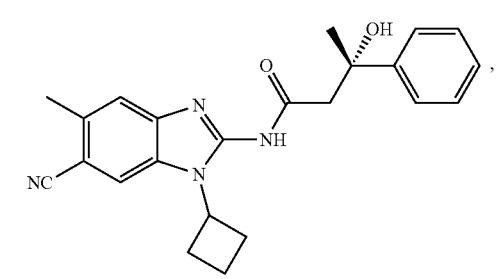
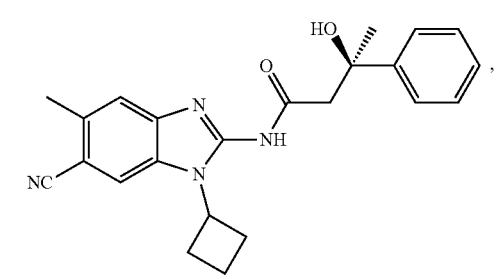
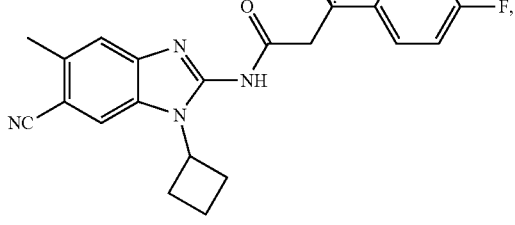
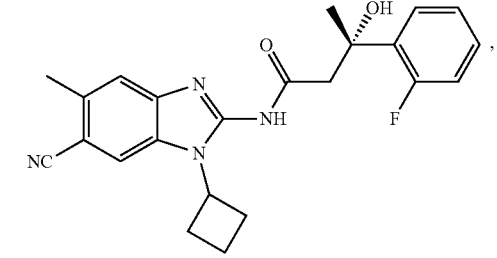

337
-continued
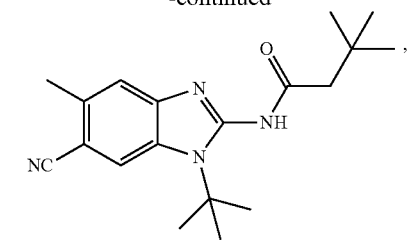
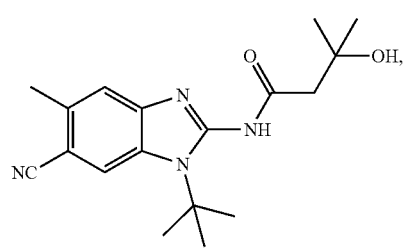
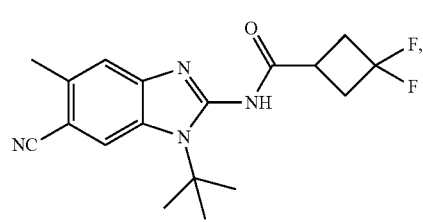
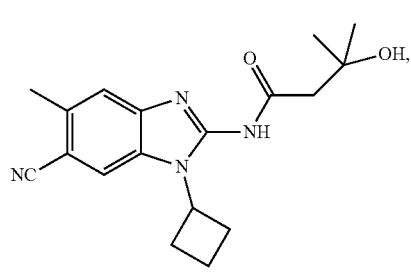
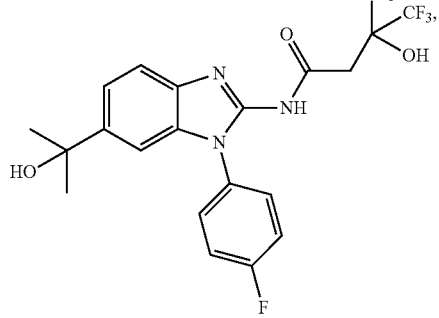
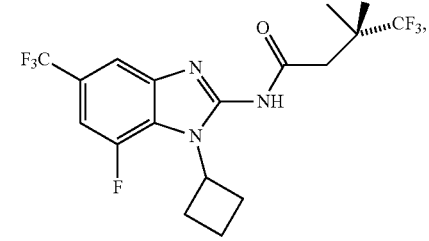
338
-continued
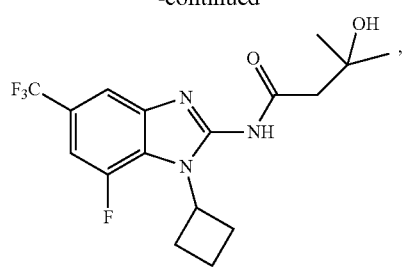
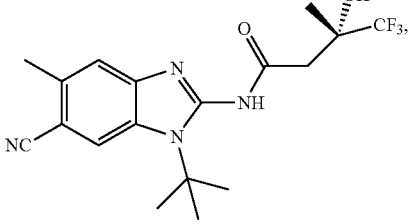
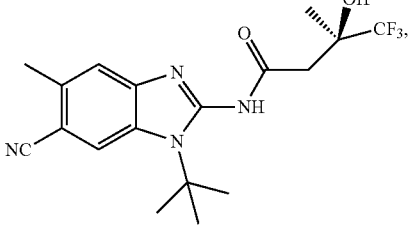
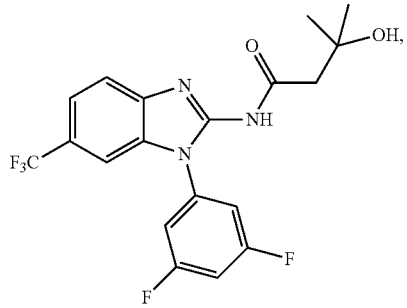
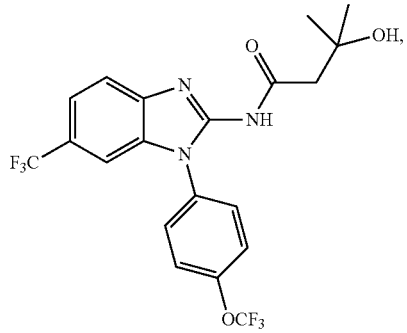
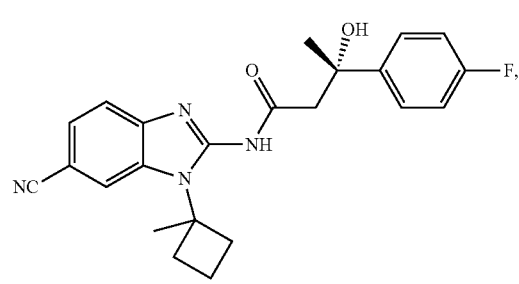

339
-continued
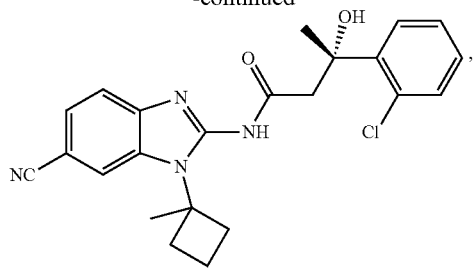
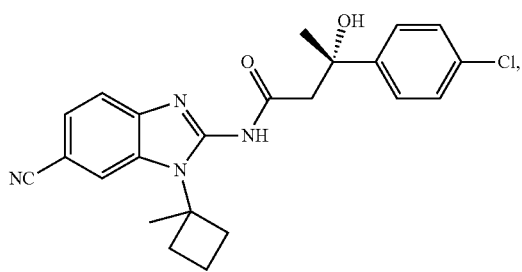
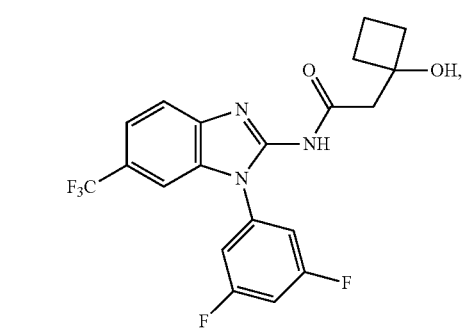
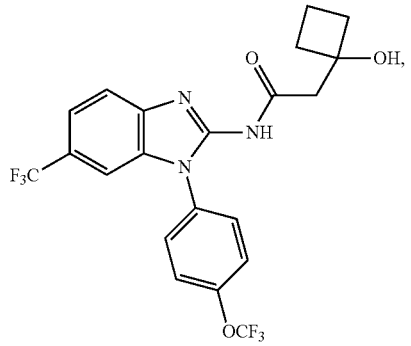
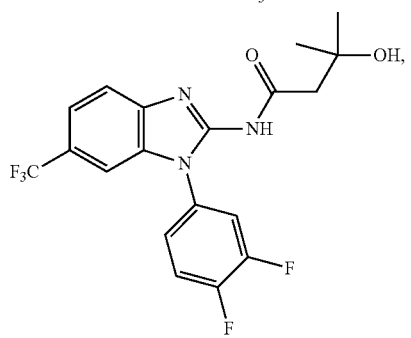
340
-continued
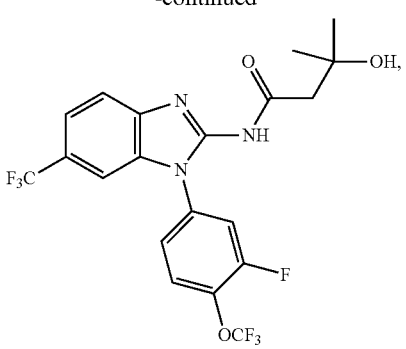
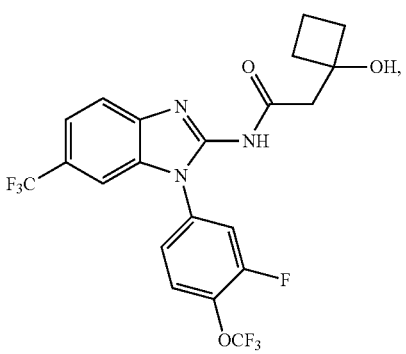
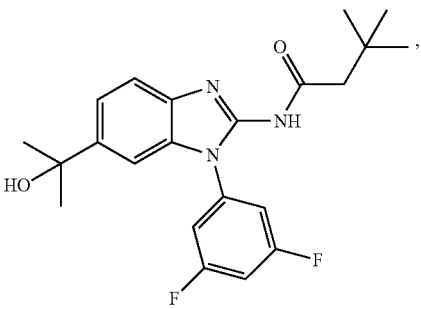
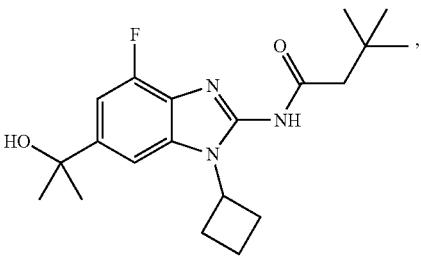
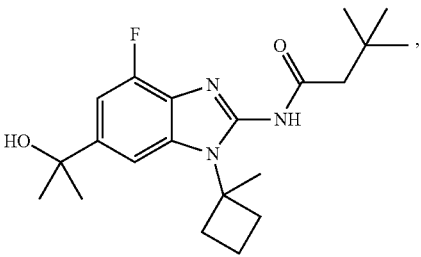

-continued
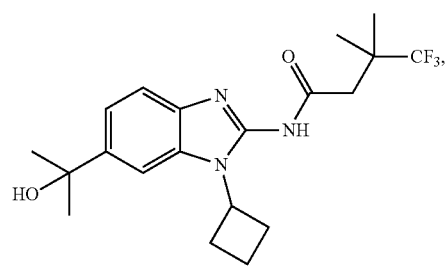
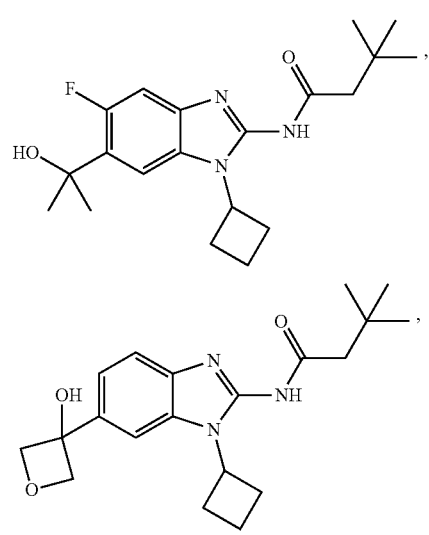
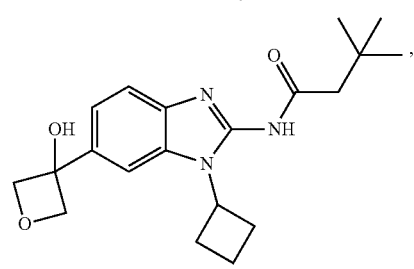
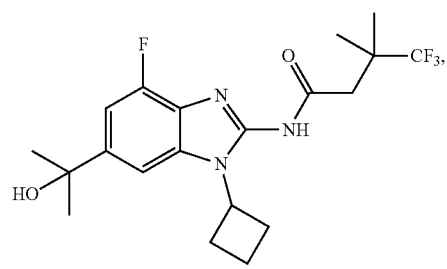
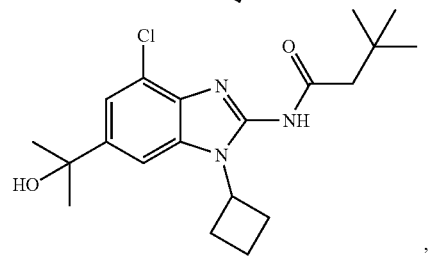
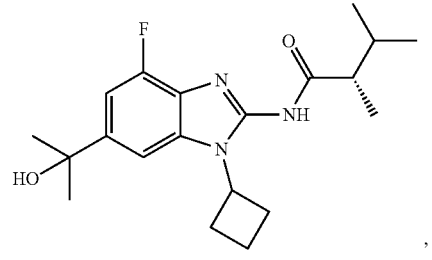
-continued
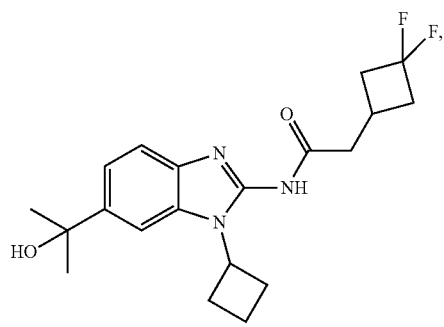
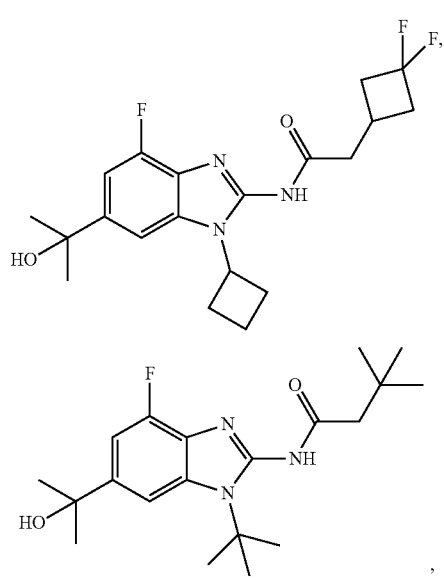
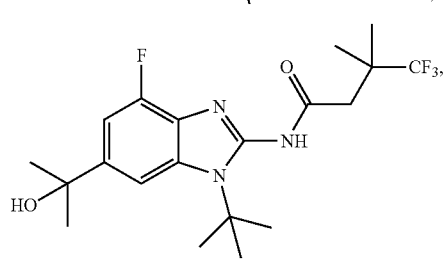
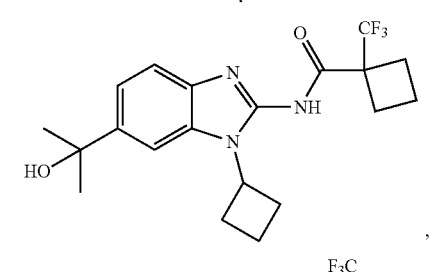
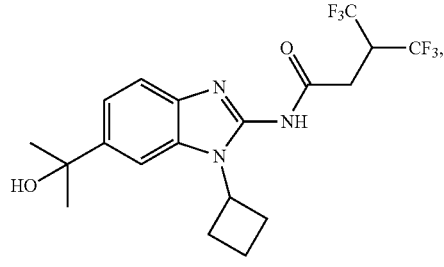

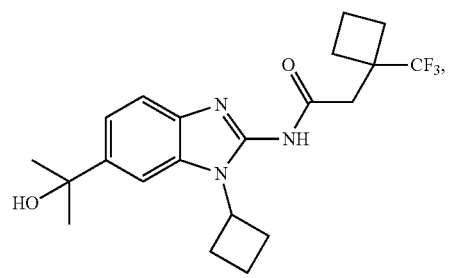
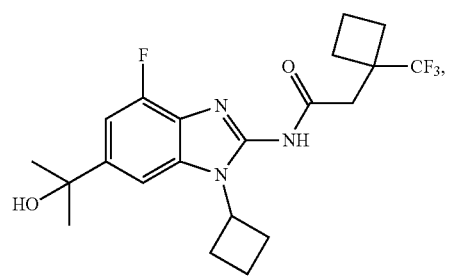
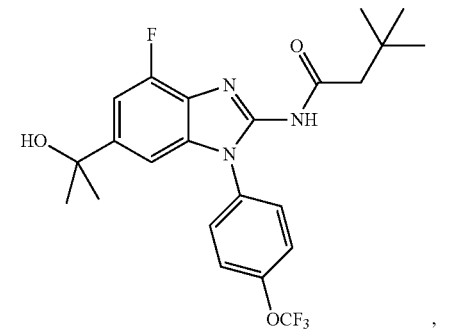
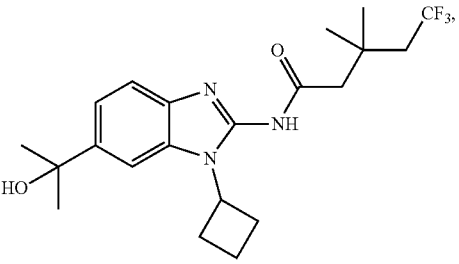
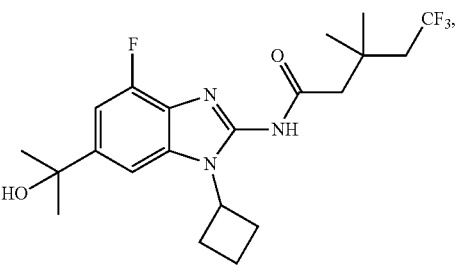
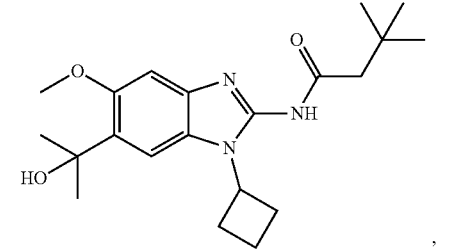
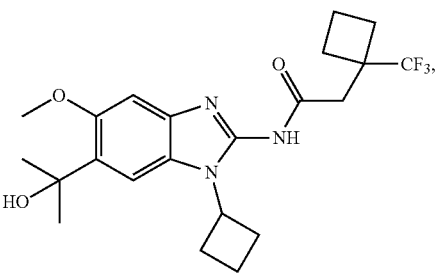
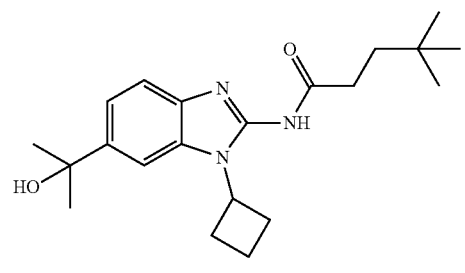
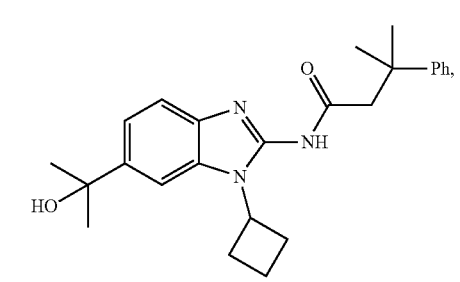
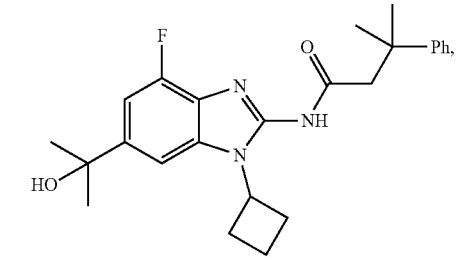
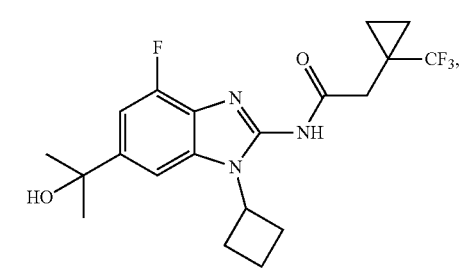
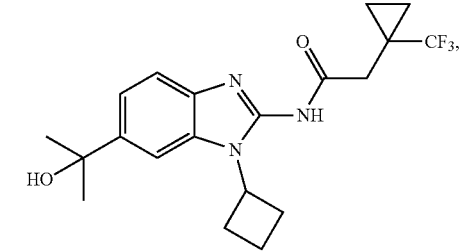

345
-continued
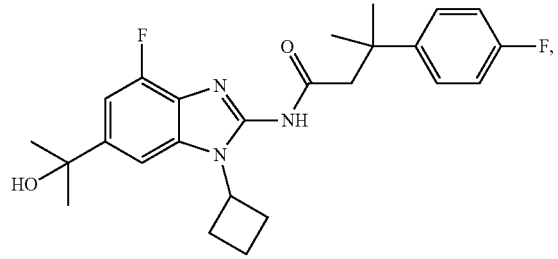
,
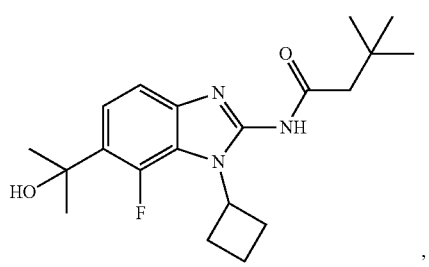
,
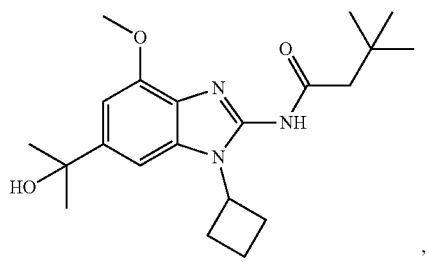
,
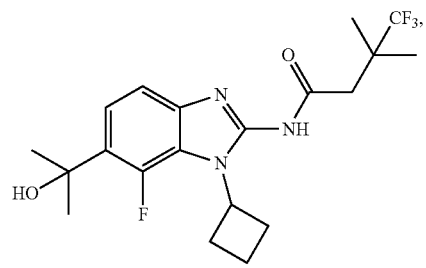
,
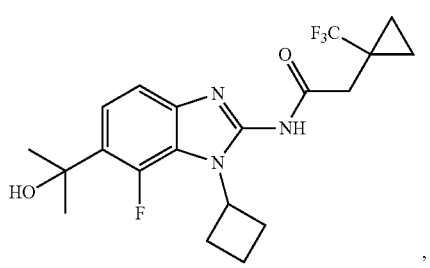
,
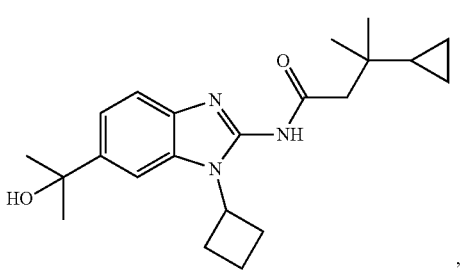
,
346
-continued
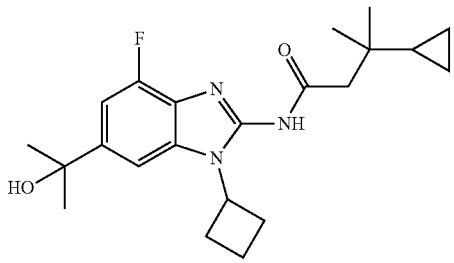
,
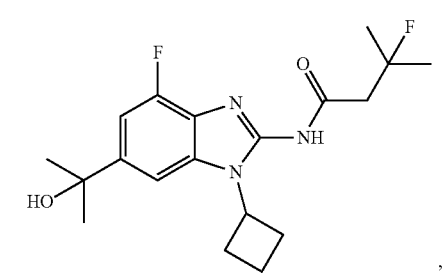
,
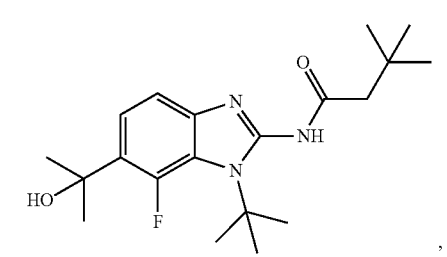
,
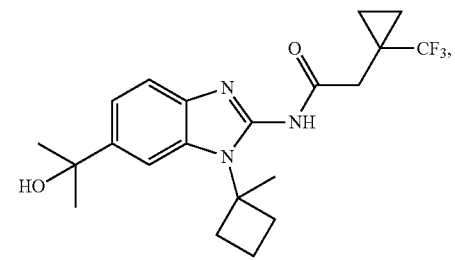
,
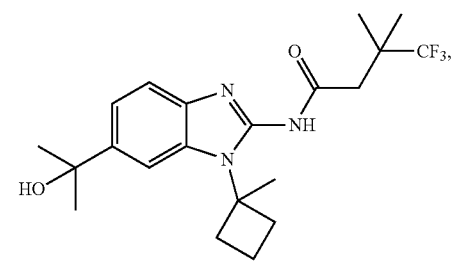
,
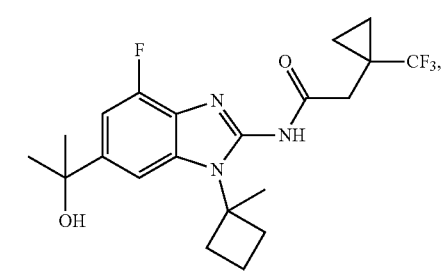
,

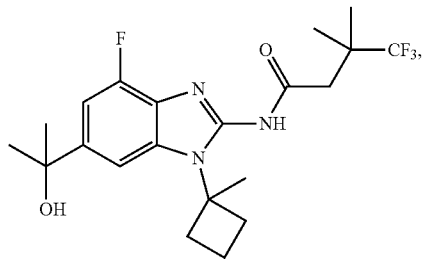
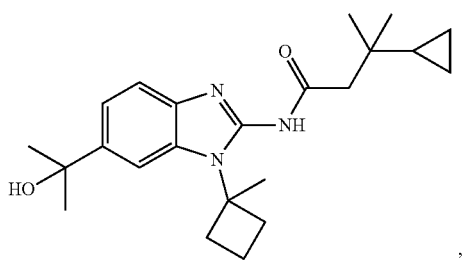
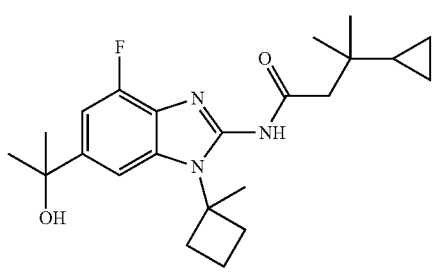
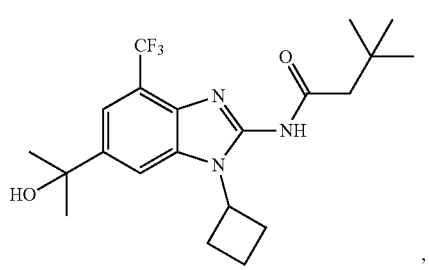
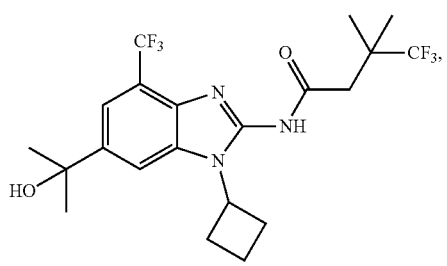
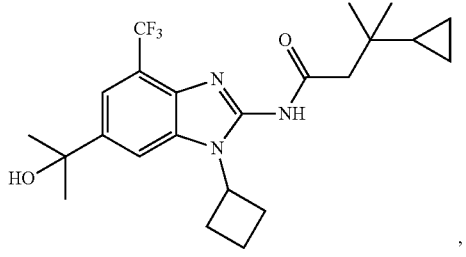
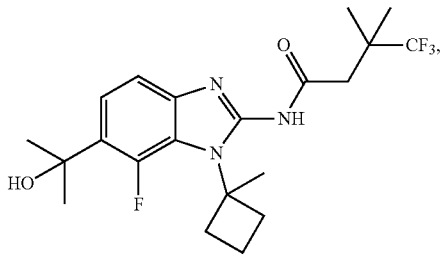
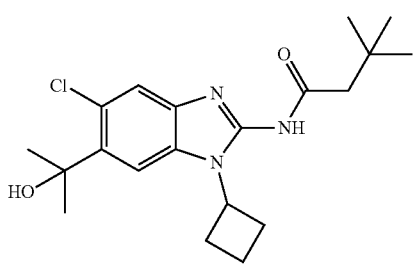
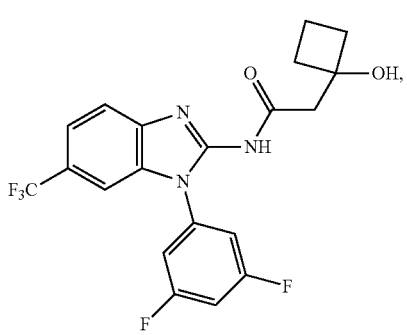
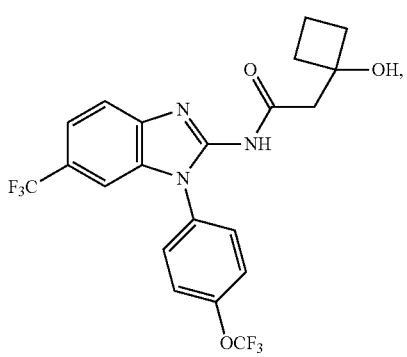
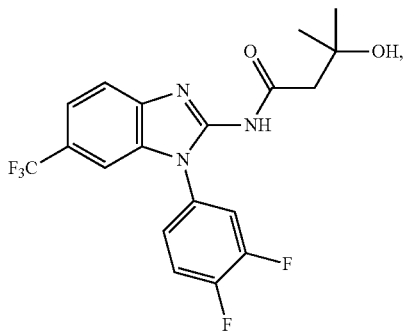

349
-continued
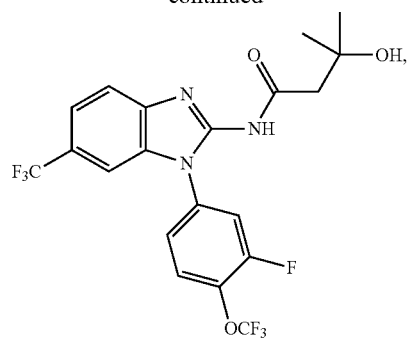
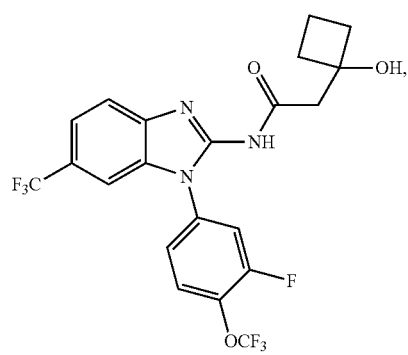
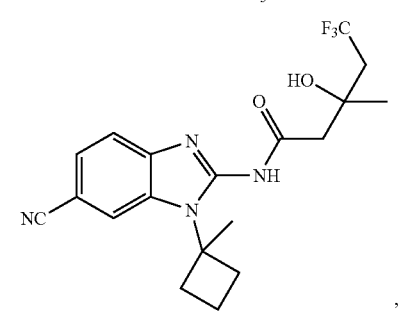
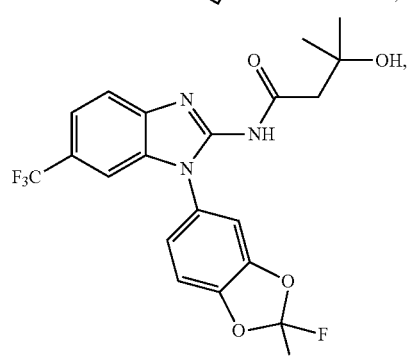
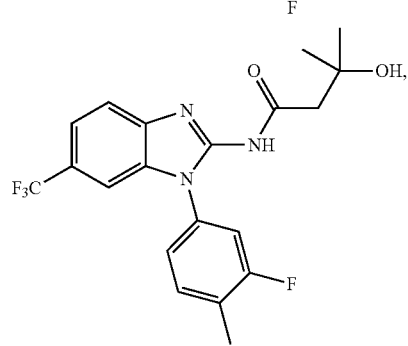
350
-continued
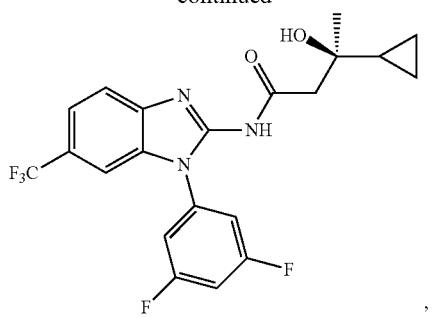
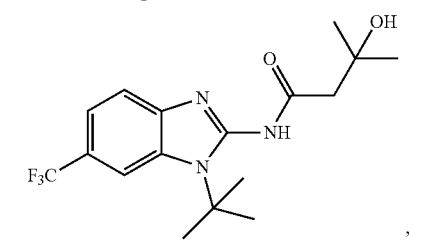
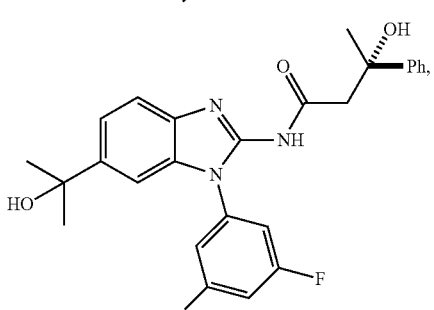
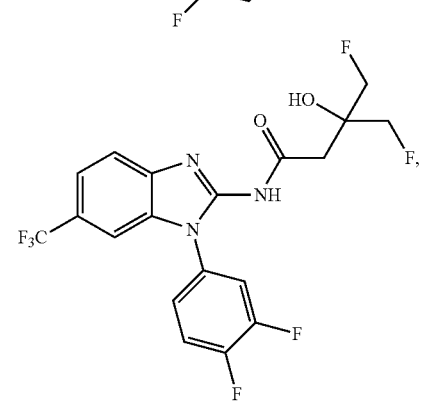
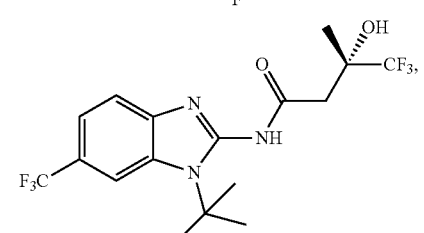
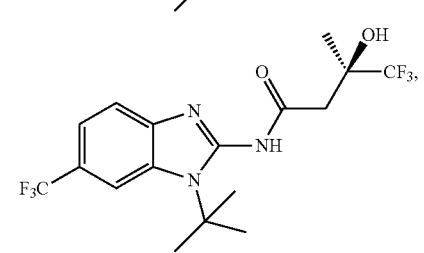

351
-continued
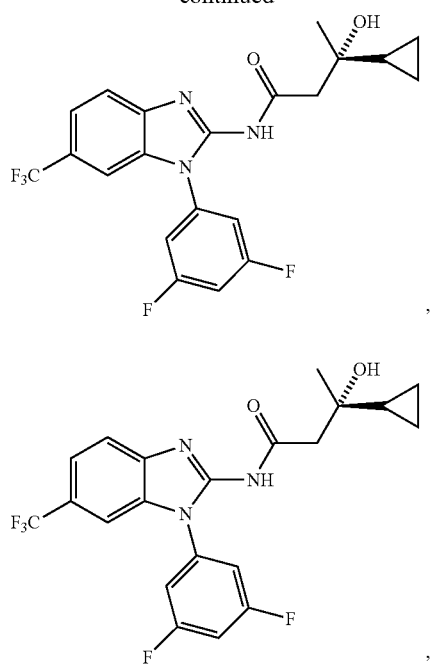
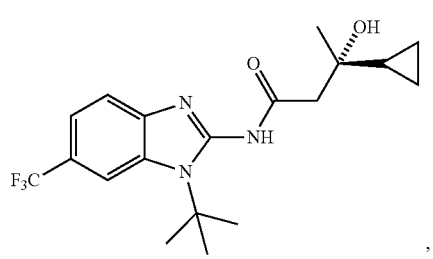
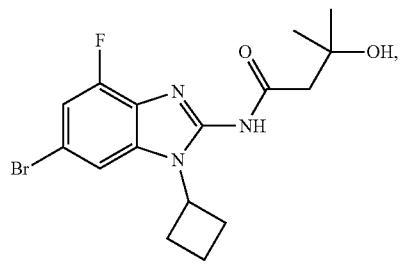
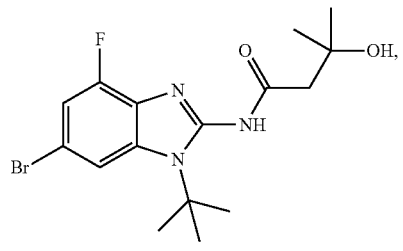
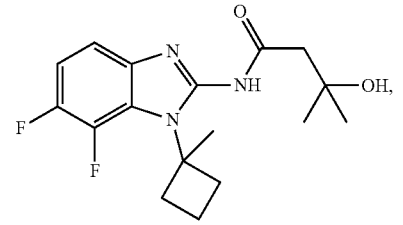
352
-continued
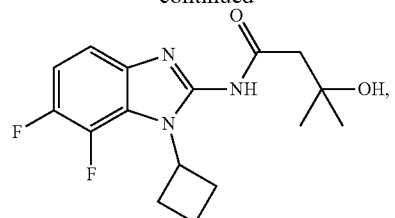
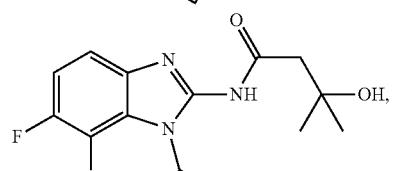
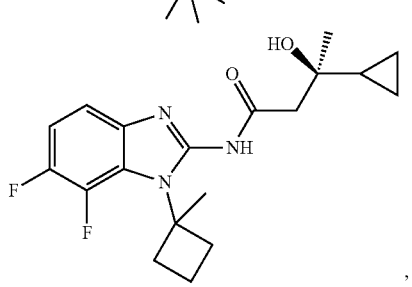
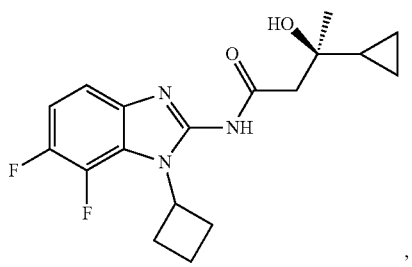
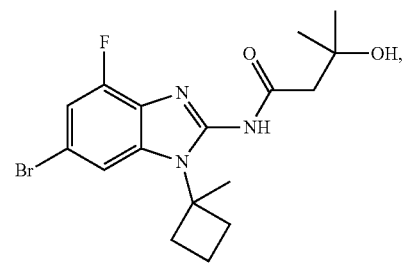
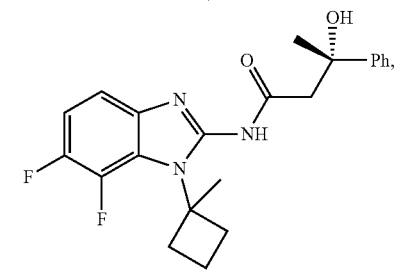
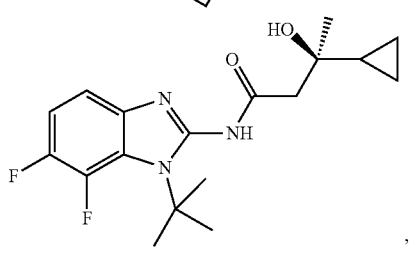

-continued
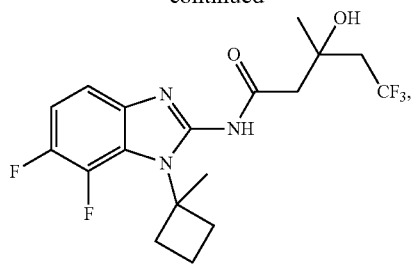
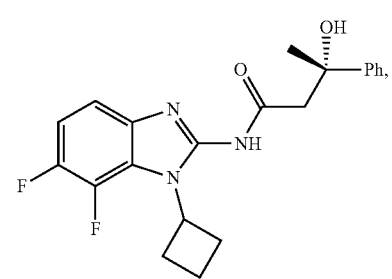
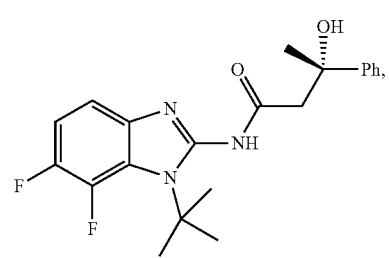
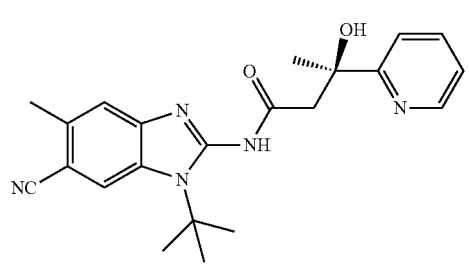
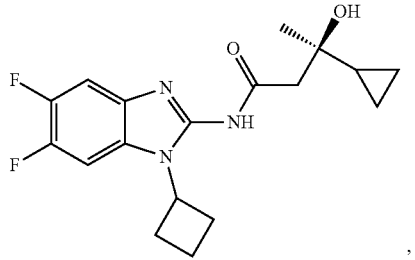
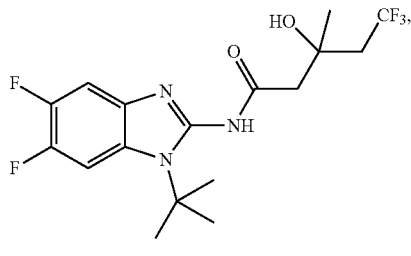
-continued
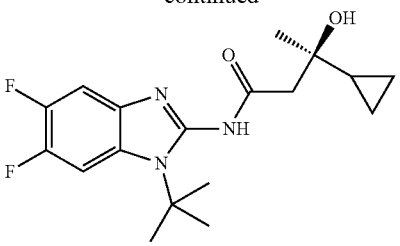
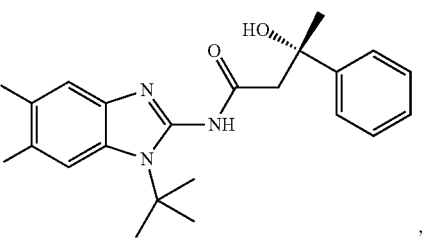
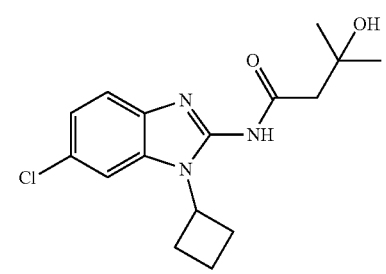
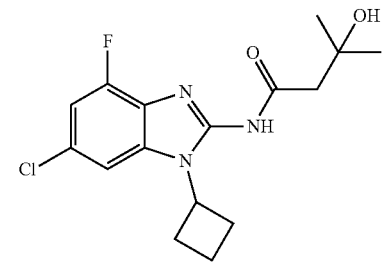
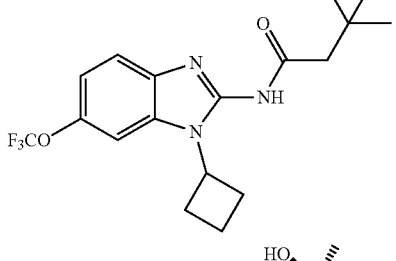
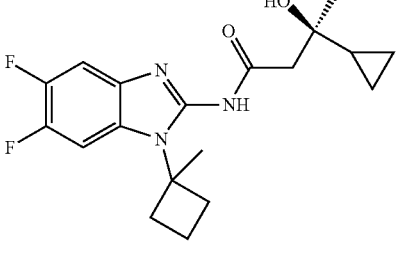

355
-continued
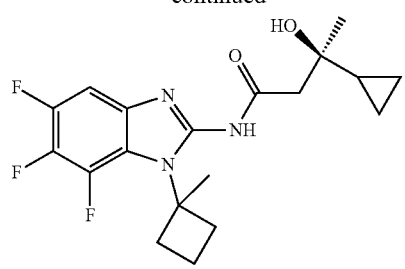
,
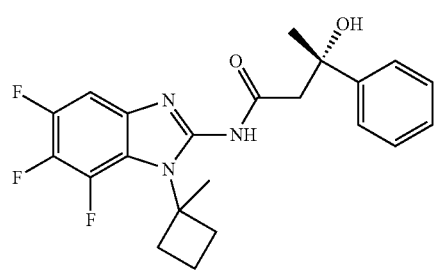
,
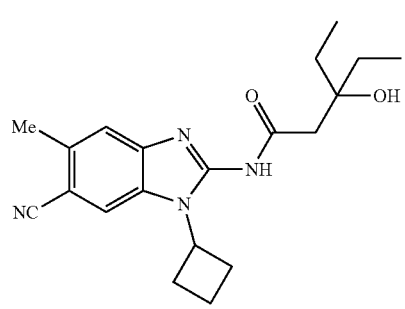
,
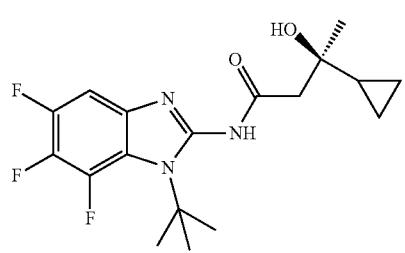
,
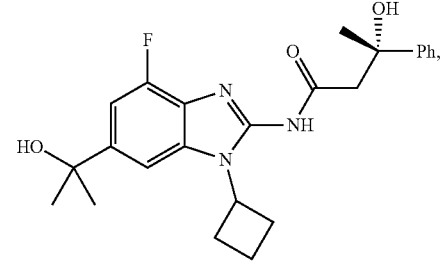
,
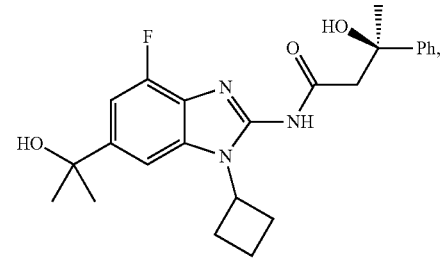
,
356
-continued
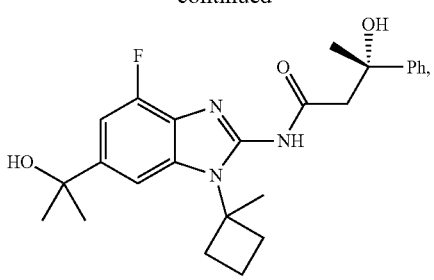
,
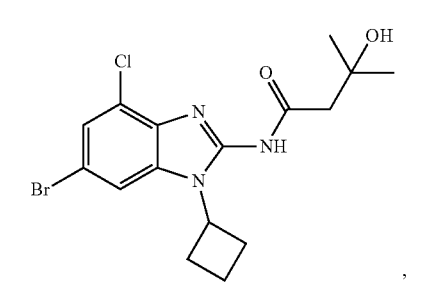
,
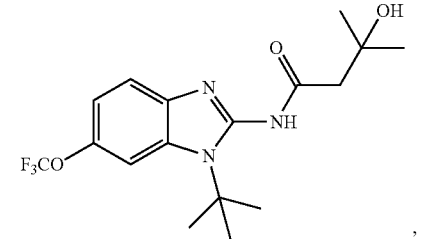
,
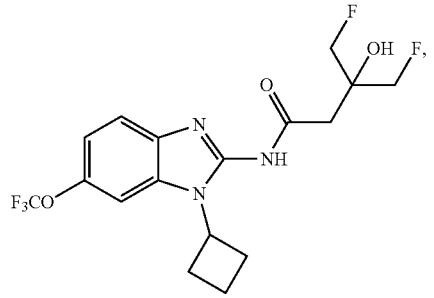
,
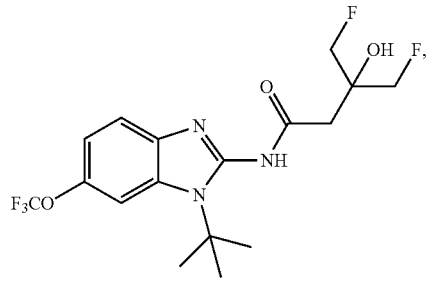
,
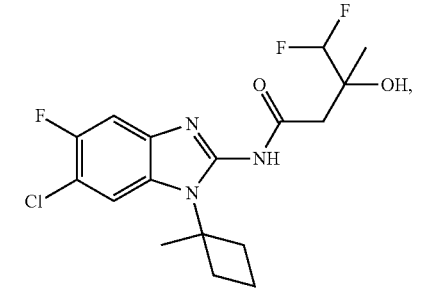
, 357
-continued
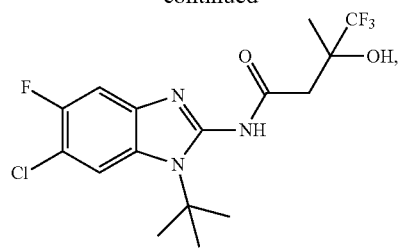
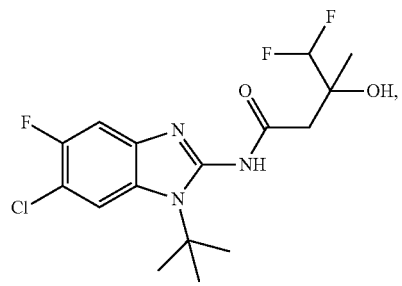
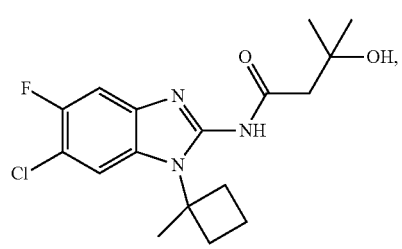
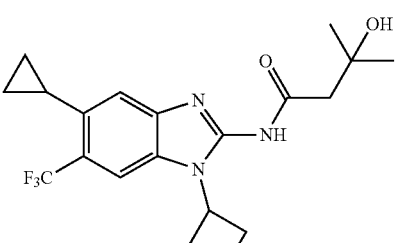
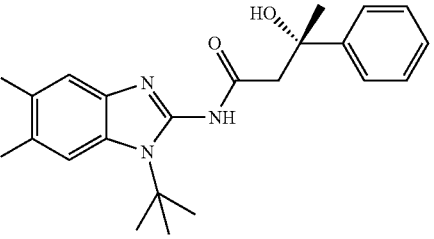
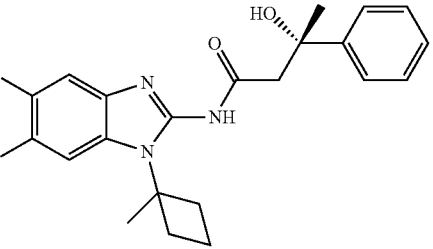
358
-continued
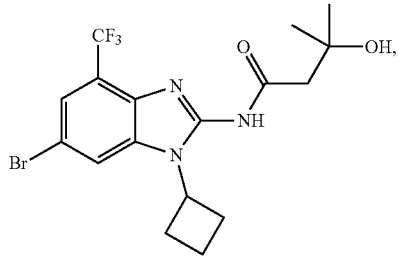
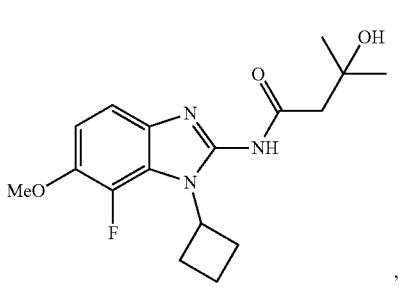
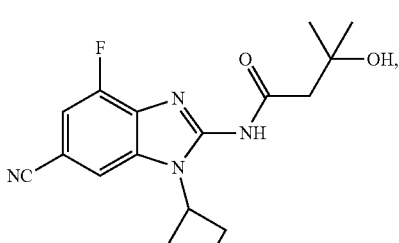
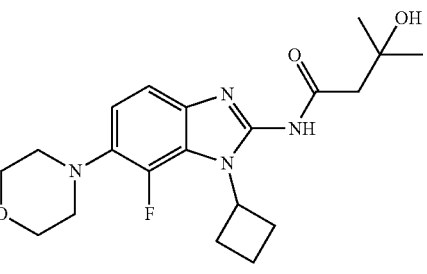
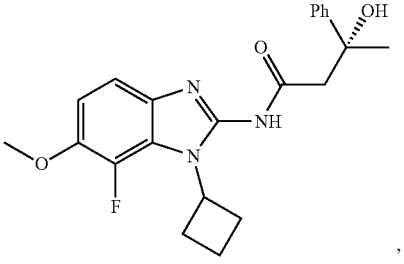
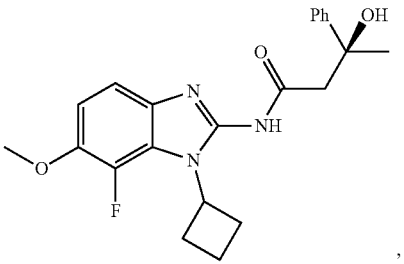

359
-continued
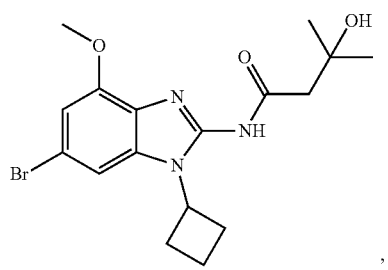
,
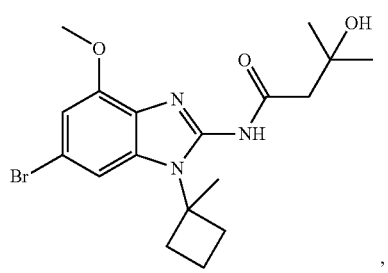
,
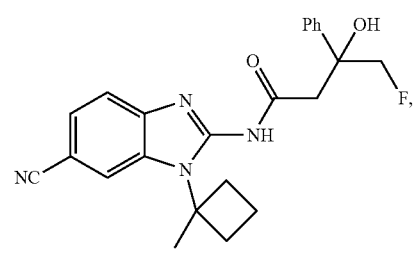
,
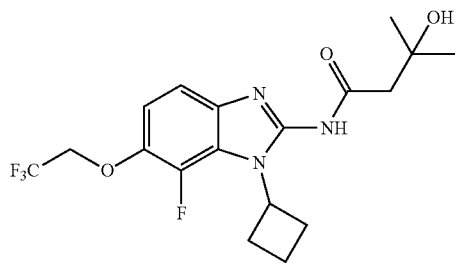
,
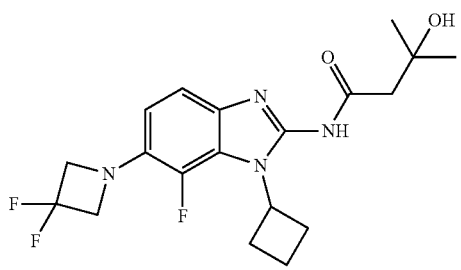
,
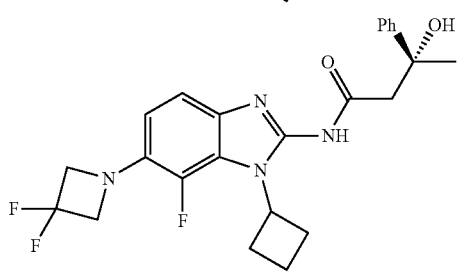
,
360
-continued
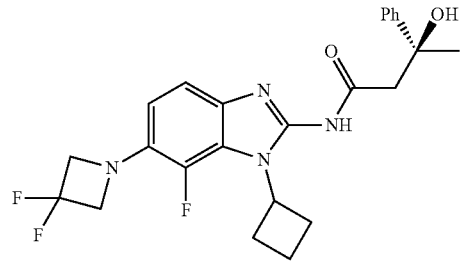
,
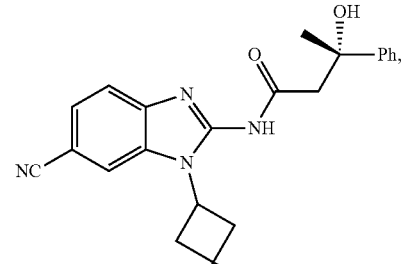
,
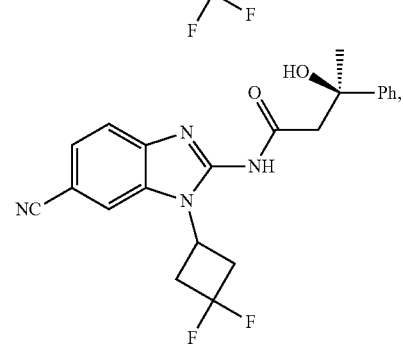
,
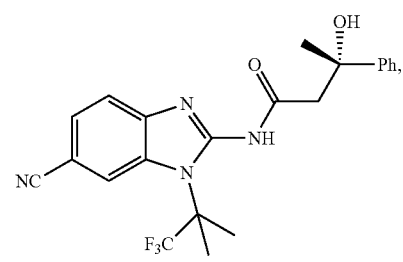
,
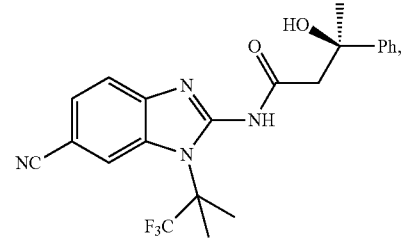
,
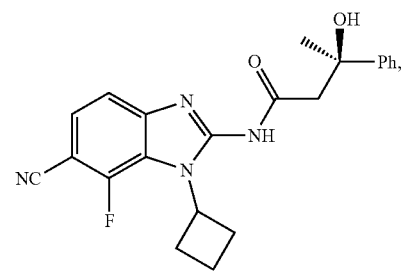
, 361
-continued
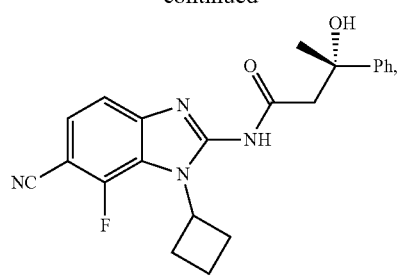
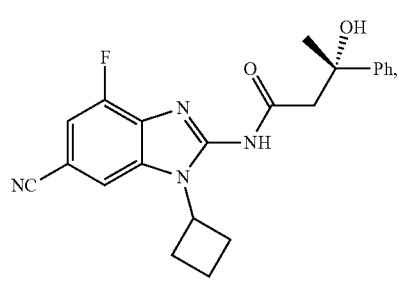
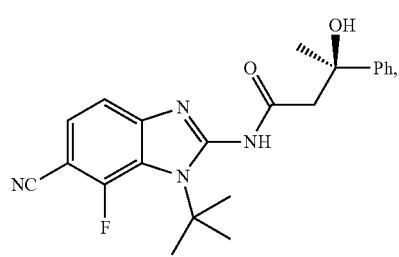
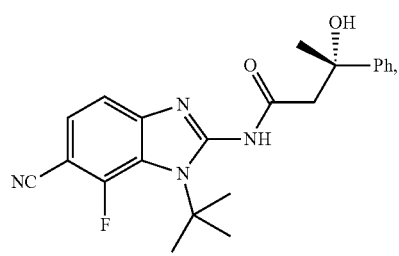
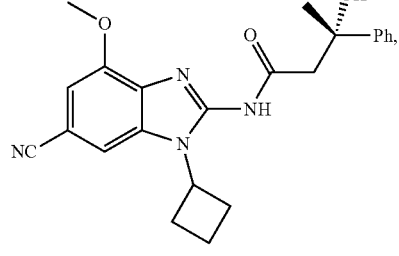
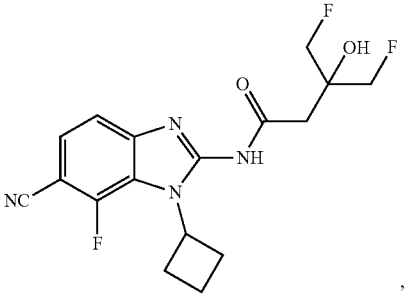
362
-continued
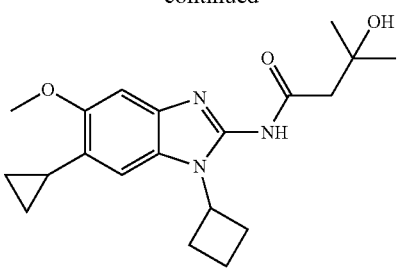
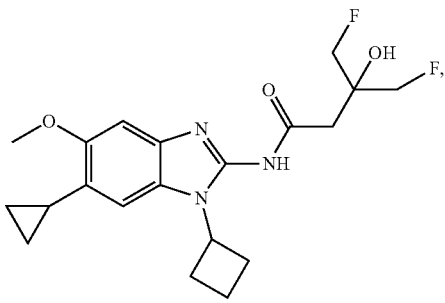
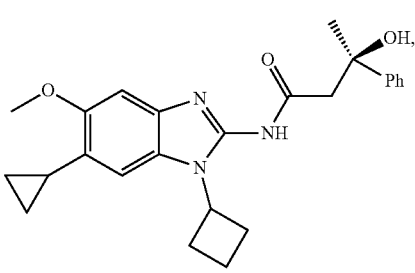
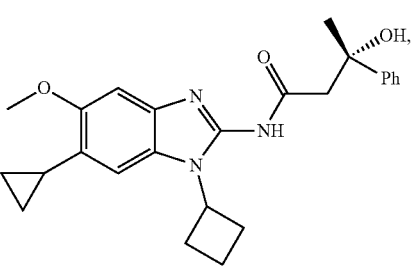
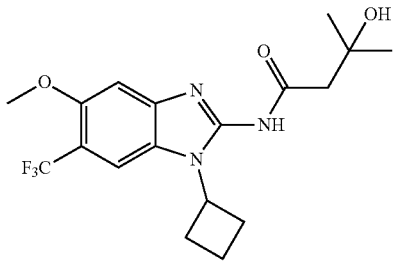

363
-continued
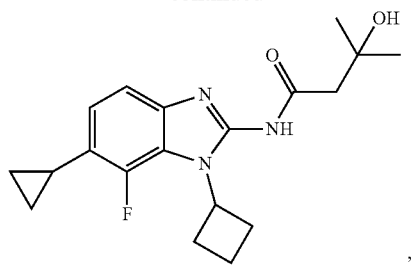
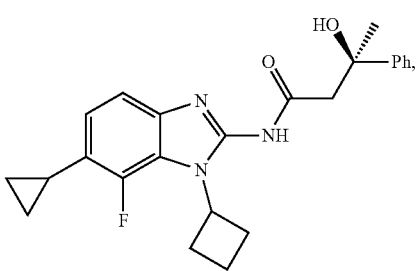
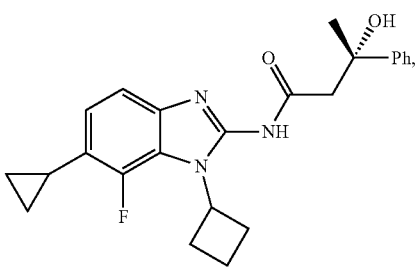
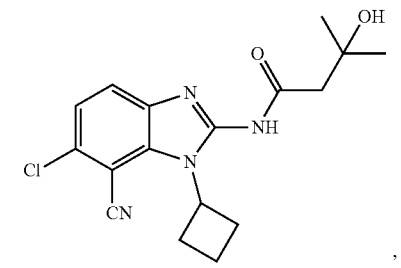
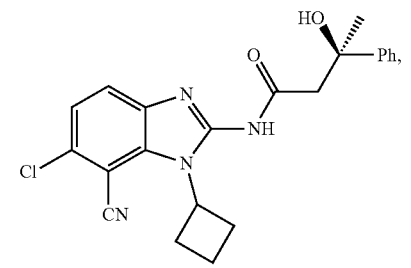
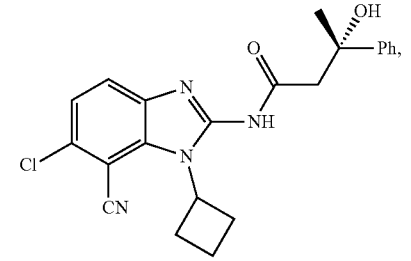
364
-continued
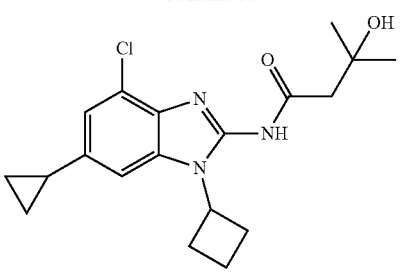
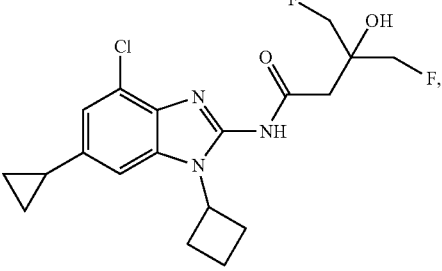
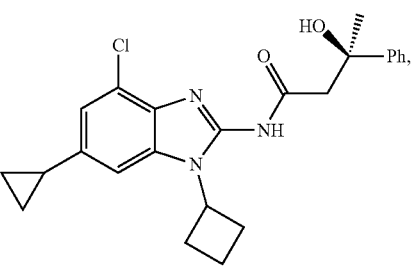
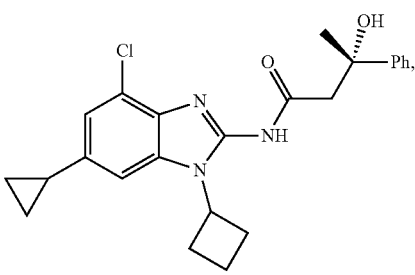
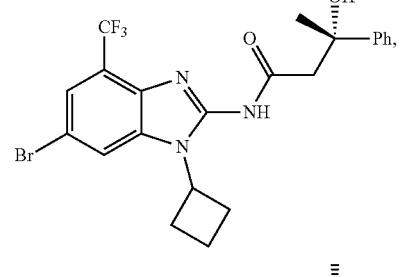
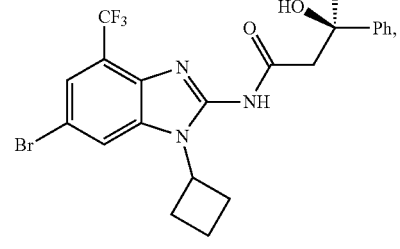

365
-continued
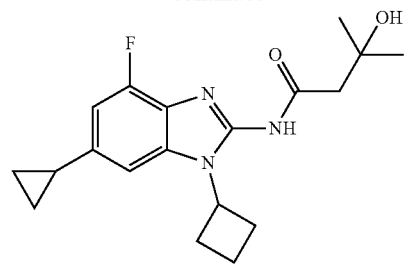
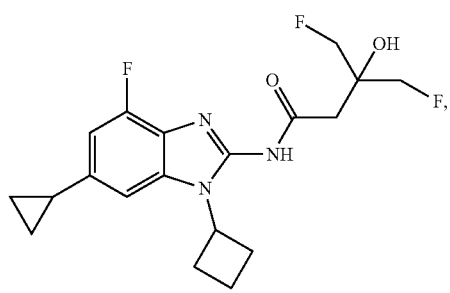
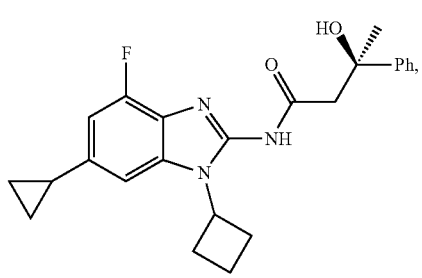
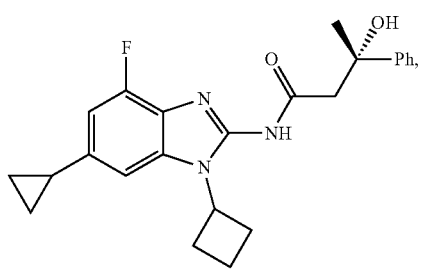
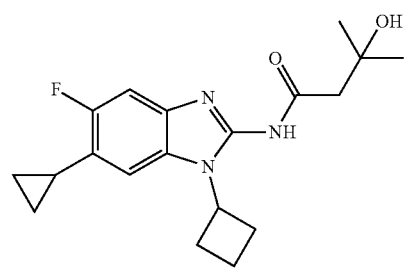
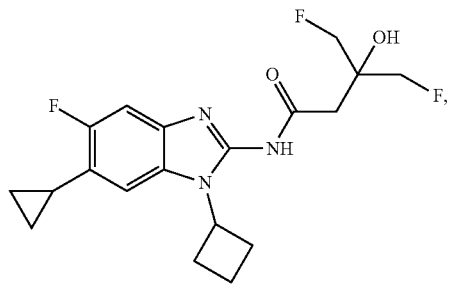
366
-continued
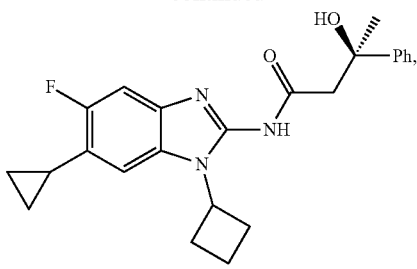
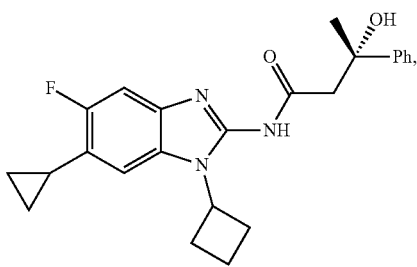
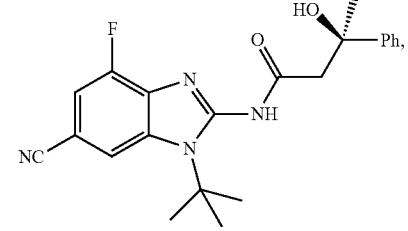
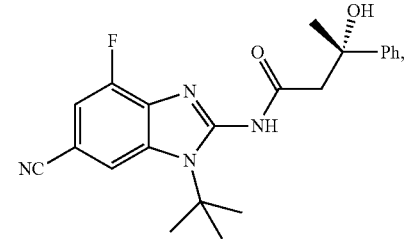
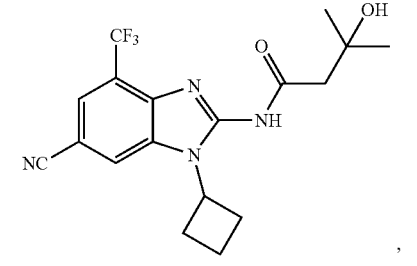
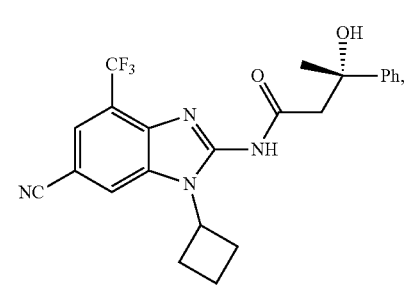

367
-continued
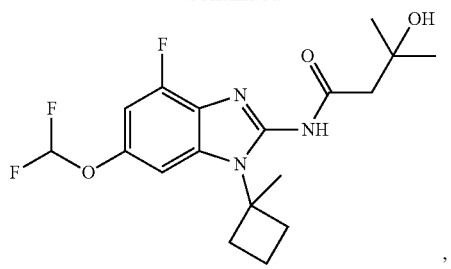
,
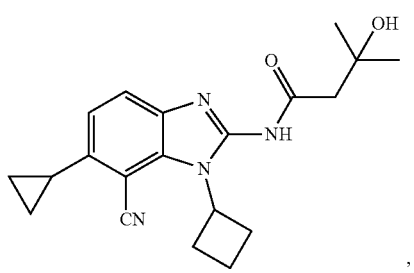
,
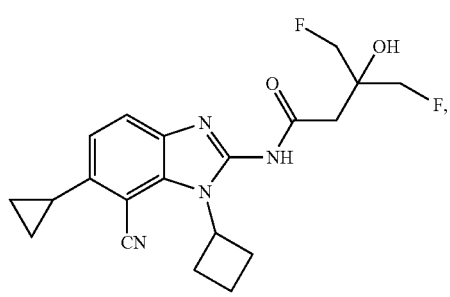
,
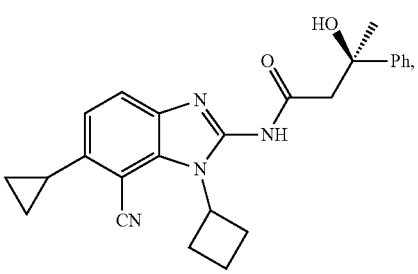
,
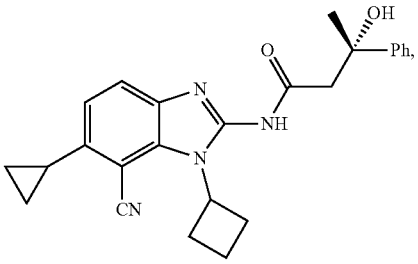
,
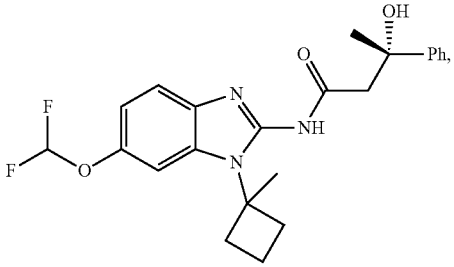
368
-continued
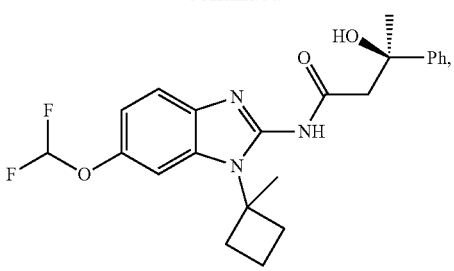
,
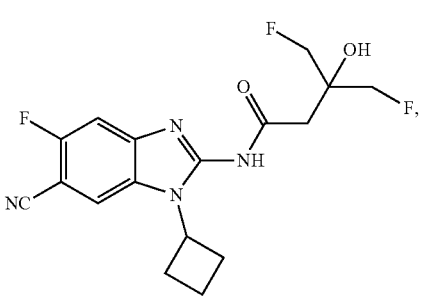
,
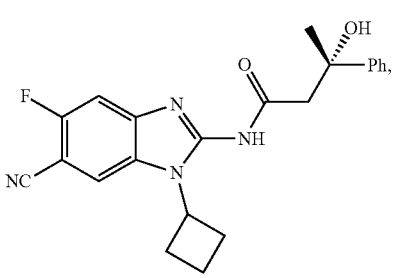
,
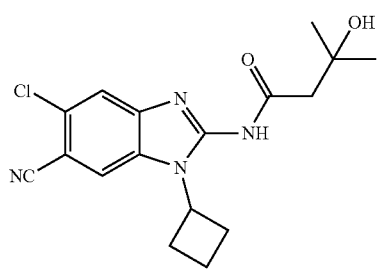
,
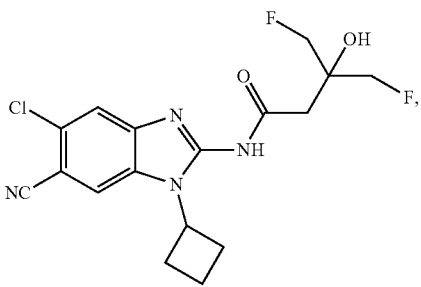
,
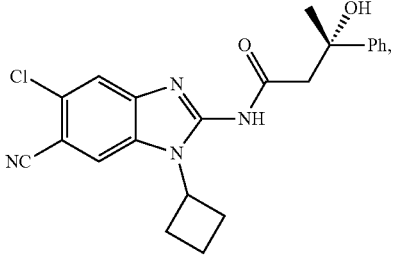

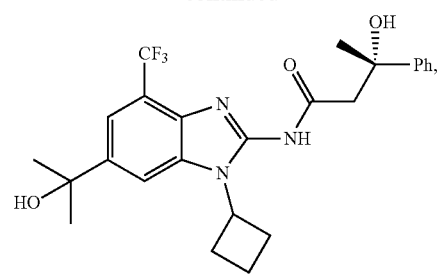
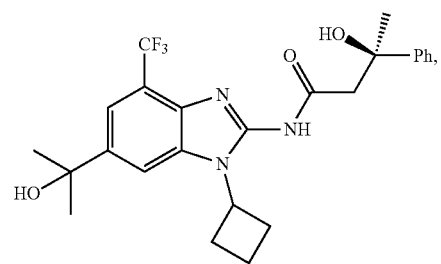
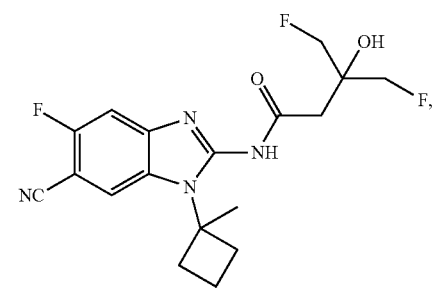
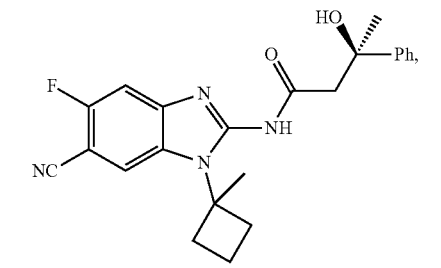
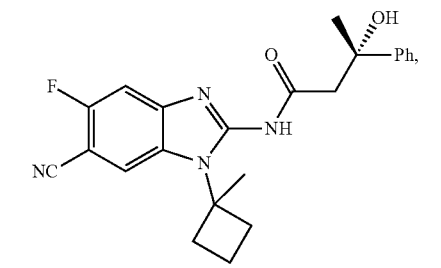
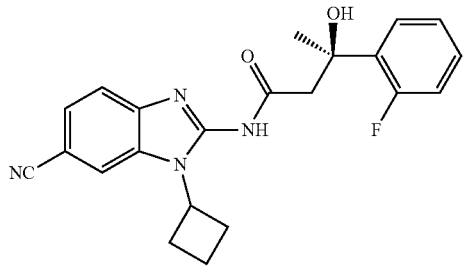
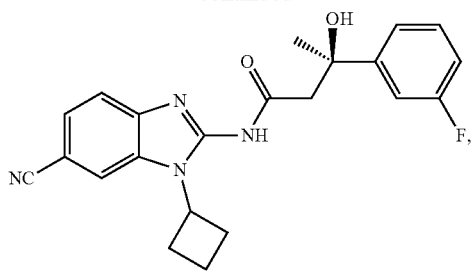
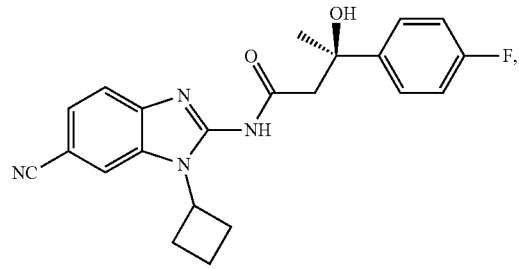
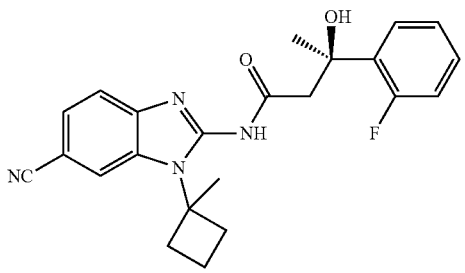
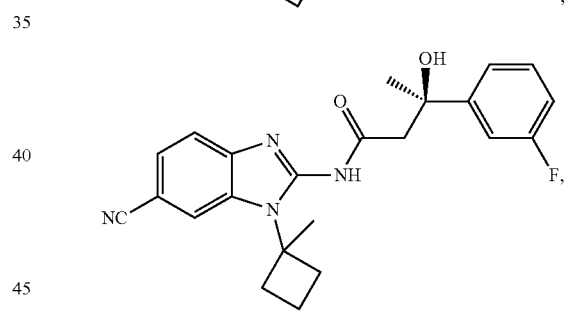
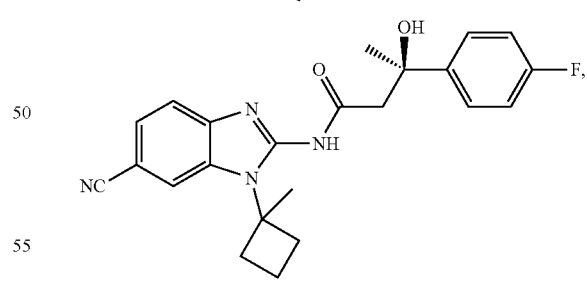
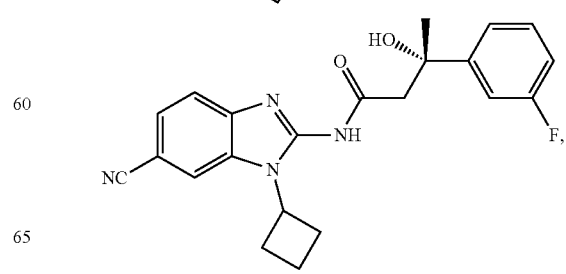

371
-continued
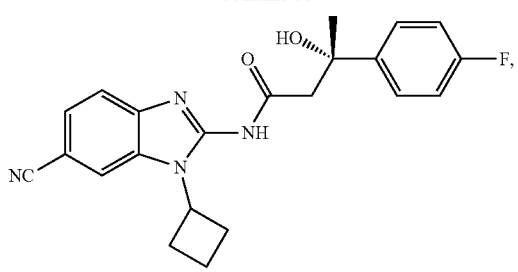
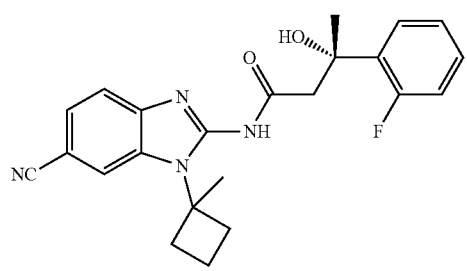
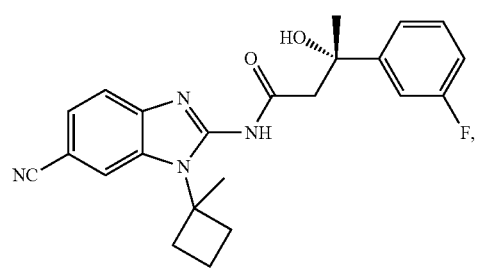
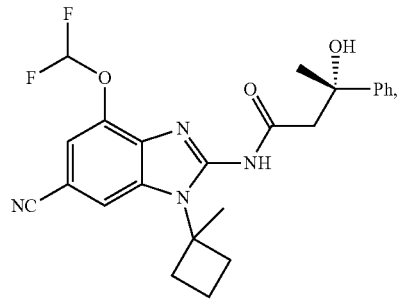
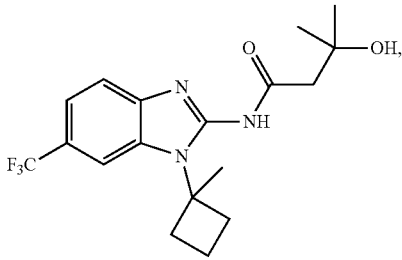
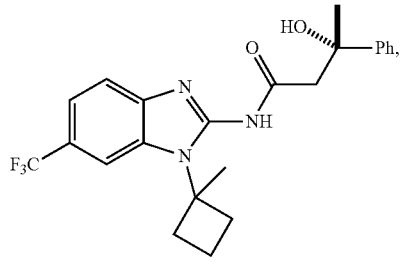
372
-continued
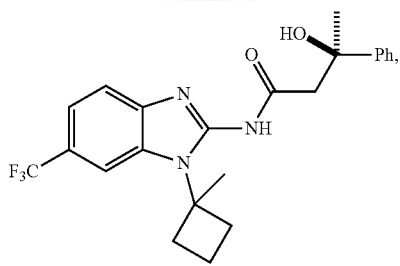
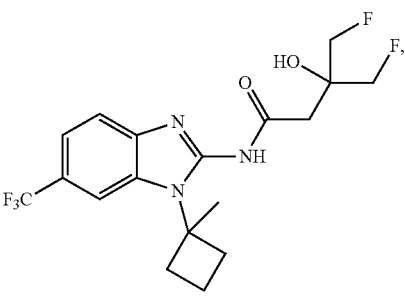
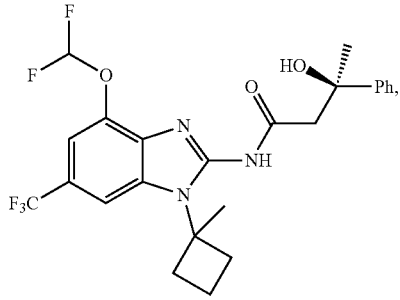
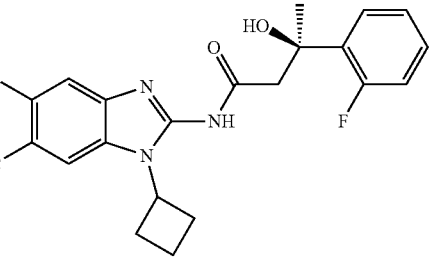
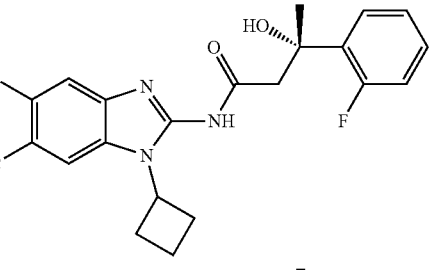
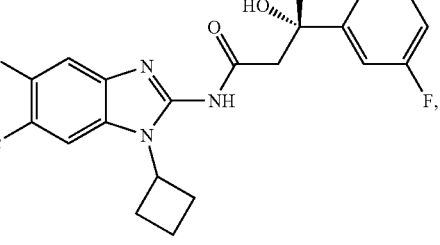

Compounds disclosed herein may be synthesized by the methods disclosed in U.S. Pat. Nos. 9,650,376 and 9,481,653, which are incorporated by reference herein.

In embodiments described herein, the therapeutically effective amount of a compound of formula A-1 through A-44 or B-1 through B-7, or a pharmaceutically acceptable salt thereof, may be from about 0.1 mg/day to about 3,000 mg/day. In such embodiments of the various methods, the pharmaceutical composition suitable for oral administration may include at least about 50 milligrams of a compound of formula A-1 through A-44 or B-1 through B-7, or a pharmaceutically acceptable salt thereof, and in some embodiments, such pharmaceutical compositions may include at least about 75 milligrams of a compound of formula A-1 through A-44 or B-1, at least about 100 milligrams of a compound of formula A-1 through A-44 or B-1 through B-7, or a pharmaceutically acceptable salt thereof, at least about 150 milligrams of a compound of formula A-1 through A-44 or B-1 through B-7, or a pharmaceutically acceptable salt thereof, at least about 200 milligrams of a compound of formula A-1 through A-44 or B-1 through B-7, or a pharmaceutically acceptable salt thereof, at least about 250 milligrams of a compound of formula A-1 through A-44 or B-1 through B-7, or a pharmaceutically acceptable salt thereof, at least about 300 milligrams of a compound of formula A-1 through A-44 or B-1 through B-7, or a pharmaceutically acceptable salt thereof, at least about 500 milligrams of a compound of formula A-1 through A-44 or B-1 through B-7, or a pharmaceutically acceptable salt thereof, at least about 600 milligrams of a compound of formula A-1 through A-44 or B-1 through B-7, or a pharmaceutically acceptable salt thereof, at least about 750 milligrams of a compound of formula A-1 through A-44 or B-1 through B-7, or a pharmaceutically acceptable salt thereof, or at least about 1000 milligrams of a compound of formula A-1 through A-44 or B-1 through B-7, or a pharmaceutically acceptable salt thereof.

In embodiments, the compound of formula A-1 through A-44 or B-1 through B-7, or a pharmaceutically acceptable salt thereof, may be administered in a pharmaceutical composition. The pharmaceutical compositions of the various methods may be prepared, packaged, sold in bulk, as a single unit dose, or as multiple unit doses, and can be administered in the conventional manner by any route where they are active. For example, the compositions may be administered orally, ophthalmically, intravenously, intramuscularly, intra-arterially, intramedullary, intrathecally, intraventricularly, transdermally, subcutaneously, intraperitoneally, intravesicularly, intranasally, enterally, topically, sublingually, rectally by inhalation, by depot injections, or by implants or by use of vaginal creams, suppositories, pessaries, vaginal rings, rectal suppositories, intrauterine devices, and transdermal forms such as patches and creams. Specific modes of administration will depend on the indication. The selection of the specific route of administration and the dose regimen may be adjusted or titrated by the clinician according to known methods in order to obtain the optimal clinical response. All of the methods described herein may be carried out by administering a compound of formula A-1 through A-44 or B-1 through B-7, or a pharmaceutically acceptable salt thereof, by any such route for administration described herein. Additionally, a compound of formula A-1 through A-44 or B-1 through B-7, or a pharmaceutically acceptable salt thereof, may be delivered by using any such route of administration for the entire dosage regimen described herein.

Pharmaceutical compositions containing a compound of formula A-1 through A-44 or B-1 through B-7, or a pharmaceutically acceptable salt thereof, in a solid dosage may include, but are not limited to, tablets, capsules, cachets, pellets, pills, powders, and granules; topical dosage forms which include, but are not limited to, solutions, powders, fluid emulsions, fluid suspensions, semi-solids, ointments, pastes, creams, gels and jellies, and foams; and parenteral dosage forms which include, but are not limited to, solutions, suspensions, emulsions, and dry powder; comprising an effective amount of a polymer or copolymer. It is also known in the art that the active ingredients can be contained in such formulations with pharmaceutically acceptable diluents, fillers, disintegrants, binders, lubricants, surfactants, hydrophobic vehicles, water soluble vehicles, emulsifiers, buffers, humectants, moisturizers, solubilizers, preservatives and the like. The means and methods for administration are known in the art and an artisan can refer to various pharmacologic references for guidance. For example, *Modern Pharmaceutics*, Banker & Rhodes, Marcel Dekker, Inc. (1979); and *Goodman & Gilman's The Pharmaceutical Basis of Therapeutics*, 6th Edition, MacMillan Publishing Co., New York (1980) can be consulted.

For oral administration, a compound of formula A-1 through A-44 or B-1 through B-7, or a pharmaceutically acceptable salt thereof, can be formulated readily by combining these a compound of formula A-1 through A-44 or B-1 through B-7, or a pharmaceutically acceptable salt thereof, with pharmaceutically acceptable carriers well known in the art. Such carriers enable the compounds of the various methods to be formulated as tablets, pills, dragees, capsules, liquids, gels, syrups, slurries, suspensions and the like, for oral ingestion by a subject to be treated. Pharmaceutical preparations for oral use can be obtained by adding a solid excipient, optionally grinding the resulting mixture, and processing the mixture of granules, after adding suitable auxiliaries, if desired, to obtain tablets or dragee cores. Suitable excipients include, but are not limited to, fillers such as sugars, including, but not limited to, lactose, sucrose, mannitol, and sorbitol; cellulose preparations including, but not limited to, maize starch, wheat starch, rice starch, potato starch, gelatin, gum tragacanth, methyl cellulose, hydroxypropylmethyl-cellulose, sodium carboxymethylcellulose, and polyvinylpyrrolidone (PVP). If desired, disintegrating agents can be added, such as, but not limited to, the cross-linked polyvinyl pyrrolidone, agar, or alginic acid or a salt thereof such as sodium alginate.

In some embodiments of the various methods, pharmaceutical compositions may be suitable for oral administration such as, for example, a solid oral dosage form or a capsule, and in certain embodiments, the composition may be a tablet. Such tablets may include any number of additional agents such as, for example, one or more binder, one or more lubricant, one or more diluent, one or more lubricant, one or more surface active agent, one or more dispersing agent, one or more colorant, and the like. Such tablets may be prepared by any method known in the art, for example, by compression or molding. Compressed tablets may be prepared by compressing in a suitable machine the ingredients of the composition in a free-flowing form such as a powder or granules, and molded tablets may be made by molding in a suitable machine a mixture of the powdered compound moistened with an inert liquid diluent. The tablets, of some embodiments, may be uncoated and, in other embodiments, they may be coated by known techniques.

In other embodiments of the various methods prepared for oral administration, the pharmaceutical compositions of the various methods may be provided in a dragee cores with suitable coatings. In such embodiments, dragee cores may be prepared suing concentrated sugar solutions, which may optionally contain gum arabic, talc, polyvinyl pyrrolidone, carbopol gel, polyethylene glycol, and/or titanium dioxide, lacquer solutions, and suitable organic solvents or solvent mixtures. In some embodiments, dyestuffs or pigments may be added to the tablets or dragee coatings for identification or to characterize different combinations of active compound doses. In yet other embodiments, pharmaceutical compositions including an effective amount of a compound of formula A-1 through A-44 or B-1 through B-7, or a pharmaceutically acceptable salt thereof, prepared for oral administration may include, but are not limited to, push-fit capsules made of gelatin, as well as soft, sealed capsules made of gelatin and a plasticizer, such as glycerol or sorbitol. The push-fit capsules can contain the active ingredients in admixture with filler such as, for example, lactose, binders such as, for example, starches, and/or lubricants such as, for example, talc or magnesium stearate and, optionally, stabilizers. In soft capsules, the active compounds can be dissolved or suspended in suitable liquids, such as fatty oils, liquid paraffin, or liquid polyethylene glycols. In addition, stabilizers can be added. All formulations for oral administration should be in dosages suitable for such administration.

In embodiments of the various methods in which the tablets and dragee cores are coated, the coatings may delay disintegration and absorption in the gastrointestinal tract and thereby provide a sustained action over a longer period. Additionally, such coatings may be adapted for releasing a compound of formula A-1 through A-44 or B-1 through B-7, or a pharmaceutically acceptable salt thereof, in a predetermined pattern, for example, in order to achieve a controlled release formulation, or it may be adapted to not release the active compound until after passage of the stomach by including, for example, an enteric coating. Suitable coatings encompassed by such embodiments may include, but are not limited to, sugar coating, film coating, such as, for example, hydroxypropyl methylcellulose, methyl-cellulose, methyl hydroxyethylcellulose, hydroxypropylcellulose, carboxymethylcellulose, acrylate copolymers, polyethylene glycols, and/or polyvinylpyrrolidone, or an enteric coating, such as, for example, methacrylic acid copolymer, cellulose acetate phthalate, hydroxypropyl methylcellulose phthalate, hydroxypropyl methylcellulose acetate succinate, polyvinyl acetate phthalate, shellac, and/or ethylcellulose. Furthermore, a time delay material such as, for example, glyceryl monostearate or glyceryl distearate may be incorporated into the coatings of some embodiments. In still other embodiments, solid tablet compositions may include a coating adapted to protect the composition from unwanted chemical changes, for example, to reduce chemical degradation prior to the release of the active drug substance.

Pharmaceutical compositions suitable for oral administration encompassed in embodiments of the various methods may include a therapeutically effective amount of a compound of formula A-1 through A-44 or B-1 through B-7, or a pharmaceutically acceptable salt thereof, and may further include one or more diluents, one or more disintegrants, one or more lubricants, one or more pigments or colorants, one or more gelatins, one or more plasticizers, and the like. For example, in some embodiments, a tablet may include an effective amount of a compound of formula A-1 through A-44 or B-1 through B-7, or a pharmaceutically acceptable salt thereof, from about 20% to about 50% by weight of diluent in an amount, from about 10% to about 30% by weight of a second diluent, from about 2% to about 6% by weight of a disintegrant, and from about 0.01% to about 2% by weight of a lubricant, and in particular embodiments, such tablets may include an effective amount of a compound of formula A-1 through A-44 or B-1 through B-7, or a pharmaceutically acceptable salt thereof, from about 20% to about 50% by weight microcrystalline cellulose, about 10% to about 30% by weight mannitol, from about 2% to about 6% crospovidone or croscarmellose, and from about 0.01% to about 2% by weight magnesium stearate. In further embodiments, the pharmaceutical composition may include any amount or combination of microcrystalline cellulose, mannitol, sodium, crospovidone, croscarmellose magnesium stearate, or any combination thereof.

In some embodiments of the various methods, the pharmaceutical compositions including a compound of formula A-1 through A-44 or B-1 through B-7, or a pharmaceutically acceptable salt thereof, may be prepared as suspensions, solutions, or emulsions in oily or aqueous vehicles suitable for injection. In such embodiments, such liquid formulations may further include formulatory agents such as suspending, stabilizing, and/or dispersing agents formulated for parenteral administration. Such injectable formulations may be administered by any route, including but not limited to, for example, subcutaneous, intravenous, intramuscular, intraarterial, bolus injection, or continuous infusion, and in embodiments in which injectable formulations are administered by continuous infusion, such infusion may be carried out for a period of about fifteen minutes to about twenty-four hours. In certain embodiments, formulations for injection can be presented in unit dosage form, such as, for example, in ampoules or in multi-dose containers, with an added preservative.

In other embodiments of the various methods, a compound of formula A-1 through A-44 or B-1 through B-7, or a pharmaceutically acceptable salt thereof, may be formulated as a depot preparation, and such long acting formulations can be administered by implantation, such as, for example, subcutaneously or intramuscularly, or by intramuscular injection. Depot injections can be administered at about one to about six months or longer intervals. Thus, for example, the compounds can be formulated with suitable polymeric or hydrophobic materials, for example, as an emulsion in an acceptable oil, or with ion exchange resins, or as sparingly soluble derivatives, for example, as a sparingly soluble salt.

In still other embodiments, pharmaceutical compositions including a compound of formula A-1 through A-44 or B-1 through B-7, or a pharmaceutically acceptable salt thereof, may be formulated for buccal or sublingual administration. In such embodiments, the pharmaceutical compositions may be prepared as chewable tablets, flash melts, or lozenges formulated in any conventional manner known in the art.

In yet other embodiments, pharmaceutical compositions including a compound of formula A-1 through A-44 or B-1 through B-7, or a pharmaceutically acceptable salt thereof, may be formulated for administration by inhalation. In such embodiments, pharmaceutical compositions according to the various methods may be delivered in the form of an aerosol spray presentation from pressurized packs or a nebulizer with the use of a suitable propellant, such as, for example, dichlorodifluoromethane, trichlorofluoromethane, dichlorotetrafluoroethane, carbon dioxide, or other suitable gas. In the case of a pressurized aerosol pack, the dosage unit can be determined by providing a valve to deliver a metered amount. Capsules and cartridges of, for example, gelatin for use in an inhaler or insufflator can be formulated containing a powder mix of the compound and a suitable powder base such as lactose or starch.

In further embodiments, pharmaceutical compositions including a compound of formula A-1 through A-44 or B-1 through B-7, or a pharmaceutically acceptable salt thereof, can be formulated in rectal compositions such as suppositories or retention enemas, for example, containing conventional suppository bases such as cocoa butter or other glycerides.

In some embodiments, pharmaceutical compositions including a compound of formula A-1 through A-44 or B-1 through B-7, or a pharmaceutically acceptable salt thereof, may be formulated for transdermal administration. Such pharmaceutical compositions may be prepared, for example, to be applied to a plaster or applied by transdermal, therapeutic systems that are supplied to the subject. In other embodiments, pharmaceutical and therapeutic compositions including a compound of formula A-1 through A-44 or B-1 through B-7, or a pharmaceutically acceptable salt thereof, for transdermal administration may include suitable solid or gel phase carriers or excipients such as, but not limited to, calcium carbonate, calcium phosphate, various sugars, starches, cellulose derivatives, gelatin, and polymers such as, for example, polyethylene glycols.

In some embodiments, pharmaceutical compositions including a compound of formula A-1 through A-44 or B-1 through B-7, or a pharmaceutically acceptable salt thereof, may be administered alone as a single therapeutic agent. In other embodiments, pharmaceutical compositions including a compound of formula A-1 through A-44 or B-1 through B-7, or a pharmaceutically acceptable salt thereof, may be administered in combination with one or more other active ingredients, such as, for example, adjuvants, protease inhibitors, or other compatible drugs or compounds where such combination is seen to be desirable or advantageous in achieving the desired effects of the methods described herein.

In embodiments, the method further comprises administering one or more active agent simultaneously or concurrently with administering a compound of formula A-1 through A-44 or B-1 through B-7, or a pharmaceutically acceptable salt thereof. In embodiments, the one or more active agent is dexpramipexole, riluzole, baclofen, tizanidine, or edaravone. Riluzole is a neuroprotective agent that blocks sodium channels in their inactivated states. Riluzole has been shown to prolong survival in t subjects with ALS. In embodiments, riluzole is administered at 50 mg once or twice daily. In embodiments, dexpramipexole is administered at 150 mg a total daily dose of or 300 mg or 600 mg. In embodiments, baclofen is administered at 0.05 mg, 0.5 mg, 1 mg, 2 mg, 5 mg, 10 mg, or 20 mg. In embodiments, tizanidine is administered at 2 mg, 4 mg, or 6 mg. In embodiments, edaravone is administered at 30 mg. In embodiments, the one or more active agent is dexpramipexole. In embodiments, the one or more active agent is riluzole.

In embodiments, the one or more active agent is an anti-glutamatergic or ion channel blocker such as, but are not limited to, FP-0011, memantine, N-acetylated-a-linked acidic dipeptidease (NAALADase) inhibitors, nimodipine, or combination thereof. Excessive glutamate levels have been shown to be toxic to neurons, and evidence suggests that both direct and indirect glutamate toxicity may contribute to the pathogenesis of motor neuron degeneration in diseases such as ALS. FP0011 is an antiglutamatergic compound that may reduce presynaptic glutamate levels and shows strong neuroprotective properties. Memantine is a noncompetitive N-methyl-d-aspartate (NMDA) receptor antagonist that has been shown to protect neurons against NMDA or glutamate-induced toxicity in vitro and in animal models of neurodegenerative diseases. In embodiments, memantine is administered at 2 mg, 5 mg, 7 mg, 10 mg, 14 mg, 21 mg, or 28 mg. N-Acetylated-Alpha-Linked-Acidic-Dipeptidase (NAALADase) converts N-Acetyl-Aspartyl-Glutamate into glutamate during neuronal damage and may represent a new approach to block the release of excess glutamate without interfering with normal brain function in treatment of neurodegenerative disorders. Nimodipine is a dihydropyridine calcium channel blocker which may antagonize excitatory amino acid receptor activation decreasing calcium entry into damaged neurons and might help to slow or reverse ALS. In embodiments, nimodipine is administered at 30 mg or 60 mg.

In embodiments, the one or more active agent is a mitochondrial energy promoter such as, but are not limited to, resveratrol, creatine, erythropoietin, cholest-4-en-3-One, oxime (TRO-19622) and combinations thereof. Resveratrol is a powerful antioxidant found in red grape skins that has been found to suppress the influx of calcium into cells associated with glutamate-induced cell toxicity. In embodiments, resveratrol is administered at 100 mg, 500 mg, 1000 mg, or 1500 mg. Creatine aids in the formation of ATP, the primary source of cellular energy in the body, and has been shown to provide protective mechanisms against neurodegenerative disorders by stabilizing cellular membranes and mitochondrial energy-transfer complexes which may reduce motor neuron death by improving mitochondrial function. Creatine may also reduce oxidative stress and increase glutamate uptake and may help reduce the loss of muscle strength in ALS patients. In embodiments, creatine is administered at about 750 mg to about 5 grams. Erythropoietin (EPO) is a glycoprotein hormone that controls erythropoiesis, red blood cell production that has recently been identified as a cytokine with various neuroprotective effects, including, for example, reduction of inflammation, enhancement of survival signals, and prevention of neuronal cell death. Cholest-4-en-3-one, oxime (TRO-19622) is a low molecular-weight compound shown to enhance motor neuron survival and growth by interacting with protein components of the mitochondrial permeability transition pore and that may rescue motor neuron cell bodies from axonomy-induced cell death in vivo. In embodiments, the one or more active agent is creatine.

What is claimed is:

1. A compound represented by a formula:

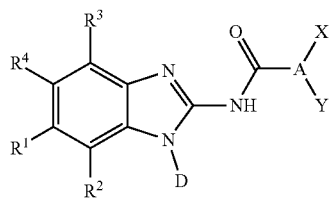

Formula 8c wherein
D is optionally substituted cyclobutyl, optionally substituted phenyl, or optionally substituted $C_{2-5}$ alkyl, wherein the optional substituents are selected from —$CH_3$ and F;
A is $C_1$ alkyl;
X is substituted cyclobutyl, wherein the substituent is F;
Y is H;
$R^1$ is selected from H, $C_3$ hydroxyalkyl, CN, F, or Cl;
$R^2$ is selected from H, CN, F, Br, or —$OCF_3$;
$R^3$ is selected from H, F, or —$OCH_3$;
$R^4$ is H or F; and
wherein when X is substituted with 2 fluorine atoms, the fluorine atoms are not geminal;
or a pharmaceutically acceptable salt thereof.

2. The compound of claim 1, wherein the compound is selected from the group consisting of:

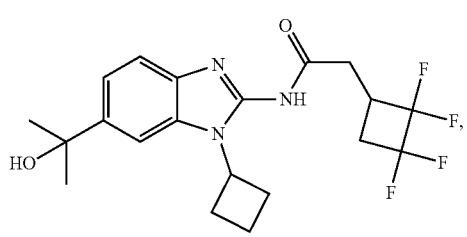

stereoisomer 1

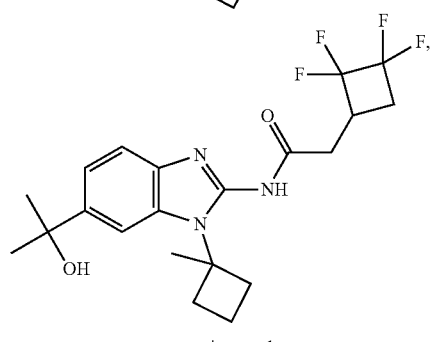

stereoisomer 1

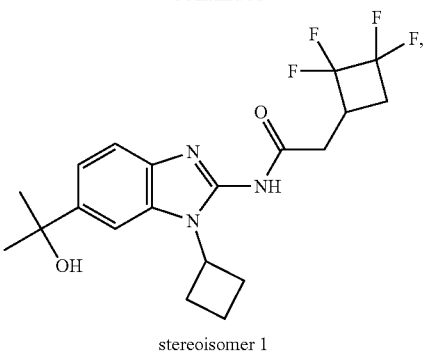 [SMILES: CC(C)(O)c1ccc2nc(NC(=O)CC3CC(F)(F)C3(F)F)n(C3CCC3)c2c1]

stereoisomer 1

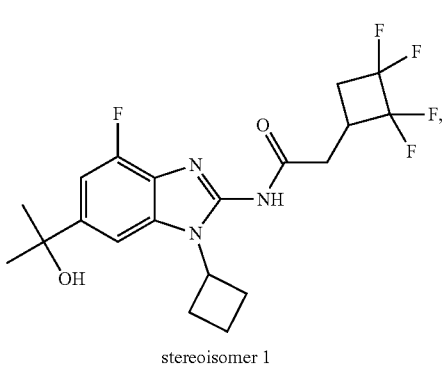

stereoisomer 1

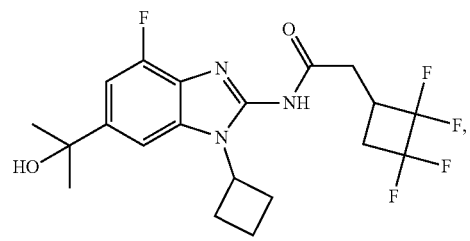

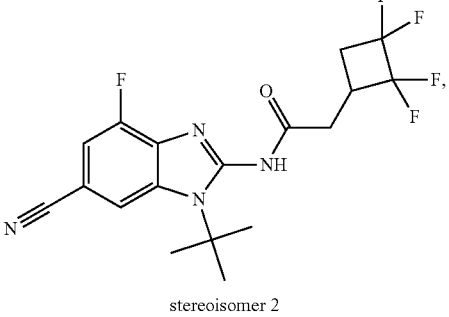

stereoisomer 2

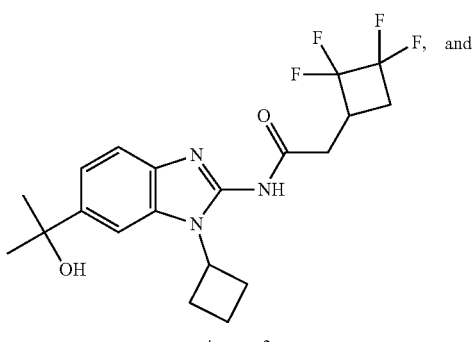

stereoisomer 2

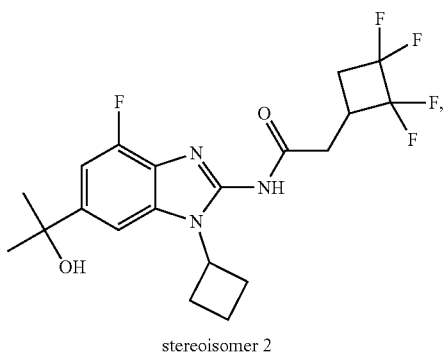 [SMILES: CC(C)(O)c1cc(F)c2nc(NC(=O)CC3CC(F)(F)C3(F)F)n(C3CCC3)c2c1]
stereoisomer 2
or a pharmaceutically acceptable salt thereof.
3. The compound of claim 1, wherein the compound is selected from the group consisting of:
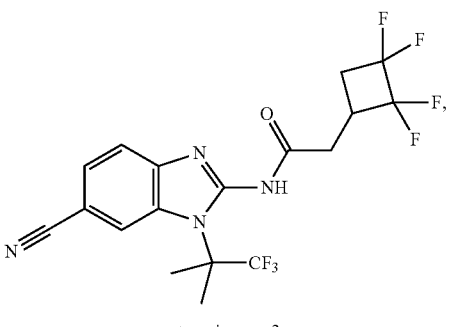
stereoisomer 2
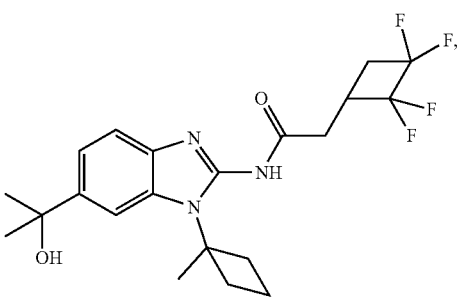
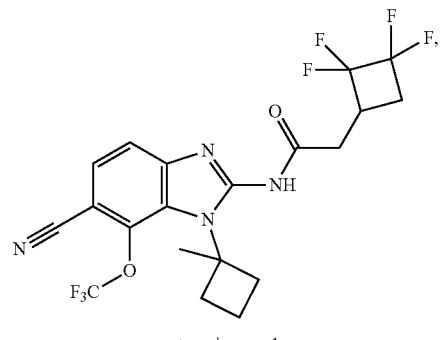
stereoisomer 1
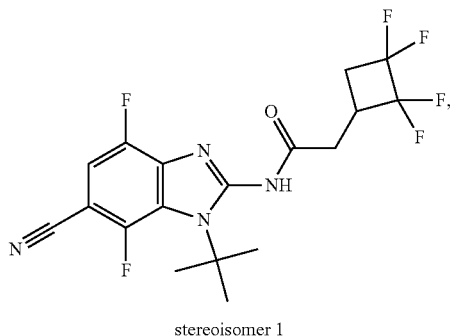
stereoisomer 1
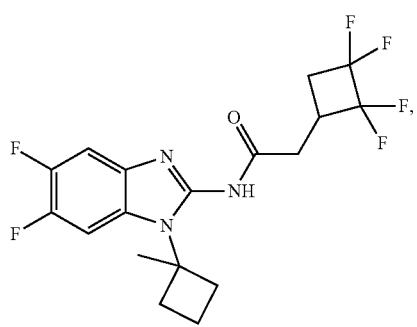
stereoisomer 2
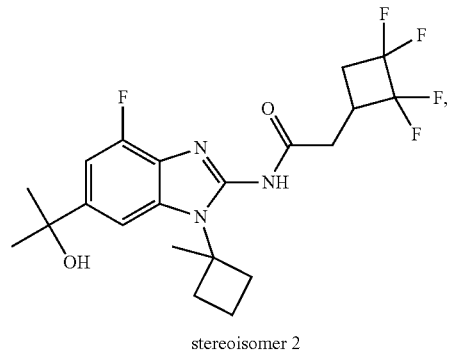
stereoisomer 2
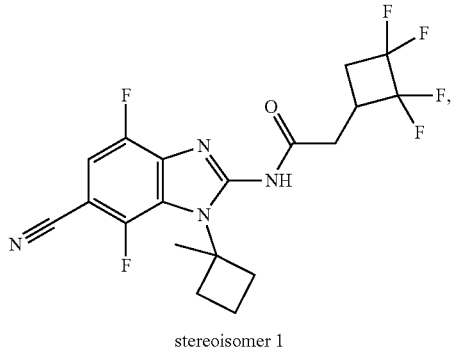
stereoisomer 1

383
-continued
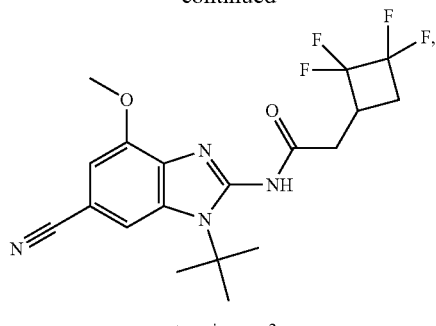
stereoisomer 2
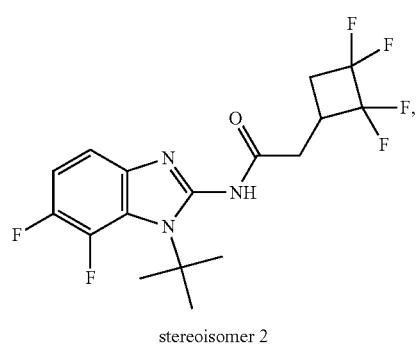
stereoisomer 2
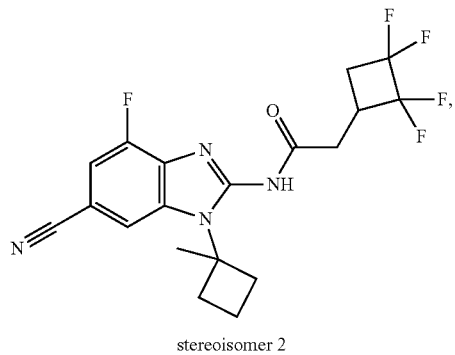
stereoisomer 2
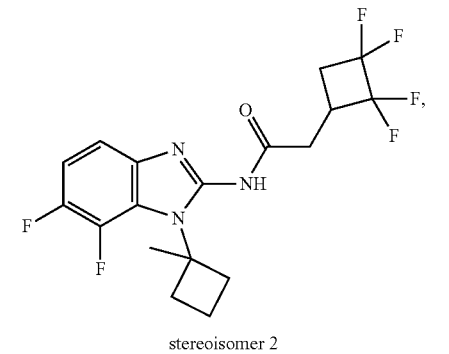
stereoisomer 2
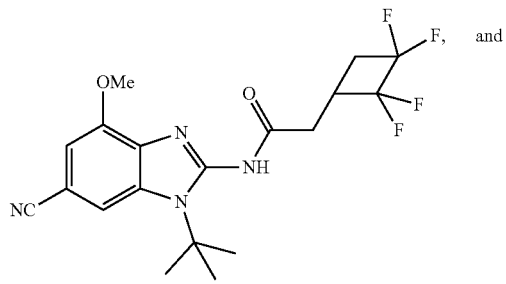
and
384
-continued
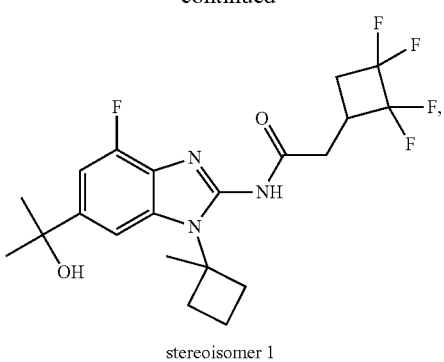
stereoisomer 1
or a pharmaceutically acceptable salt thereof.
4. The compound of claim 1, wherein the compound is selected from the group consisting of:
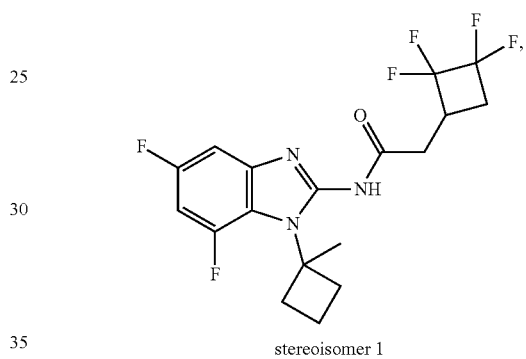
stereoisomer 1
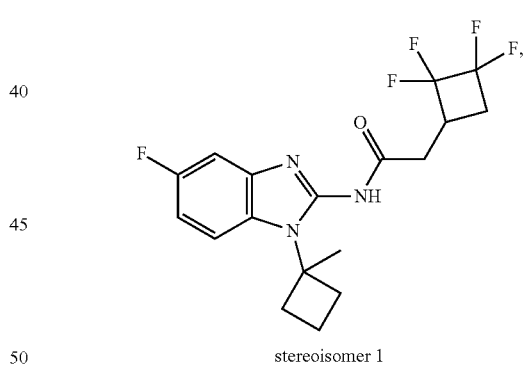
stereoisomer 1
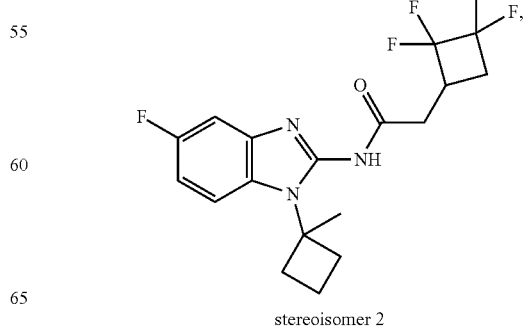
stereoisomer 2

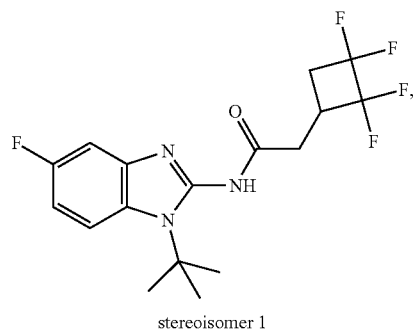
stereoisomer 1
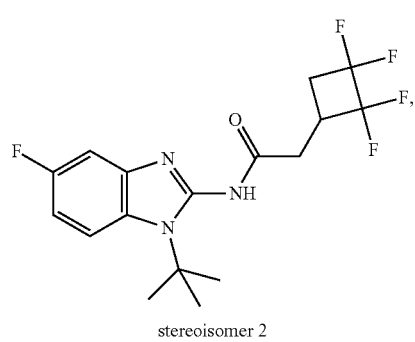
stereoisomer 2
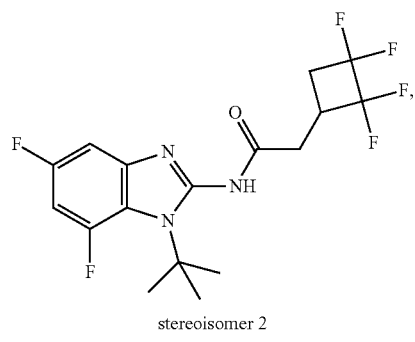
stereoisomer 2
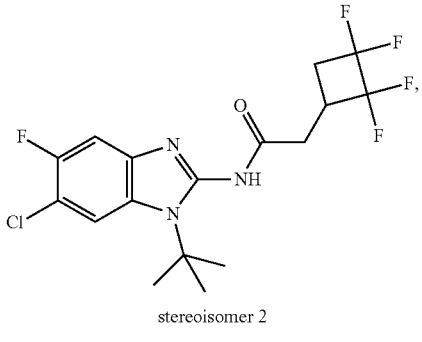
stereoisomer 2
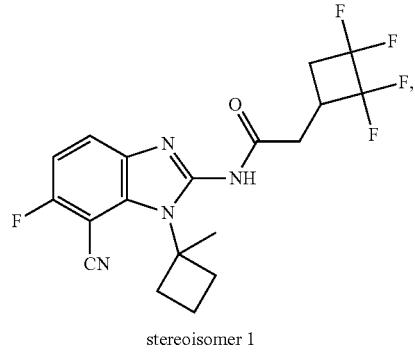
stereoisomer 1
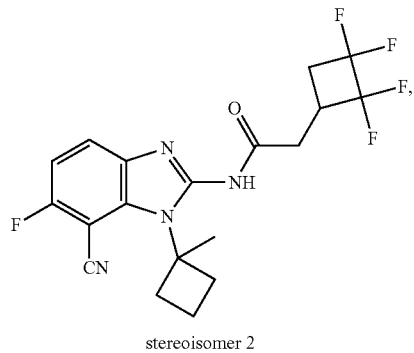
stereoisomer 2
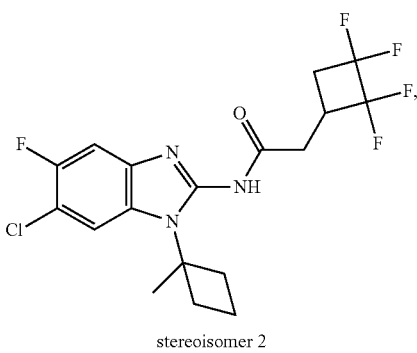
stereoisomer 2
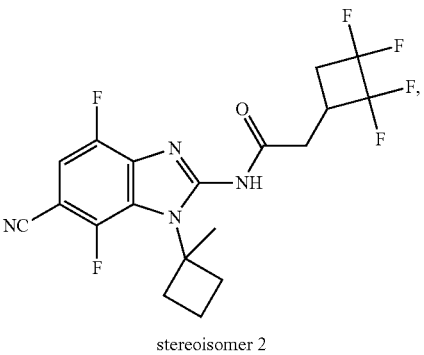
stereoisomer 2
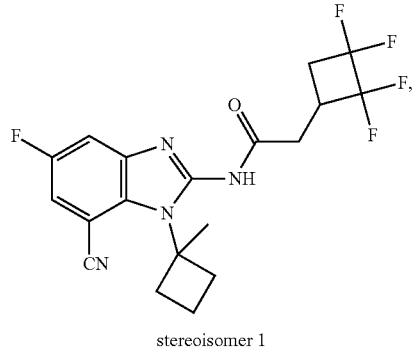
stereoisomer 1

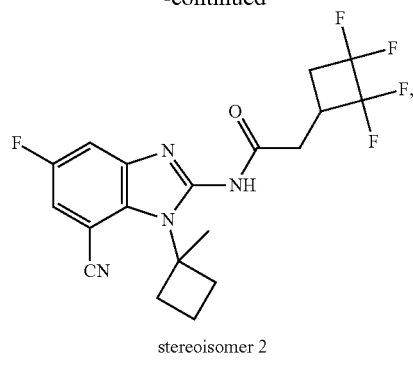
stereoisomer 2
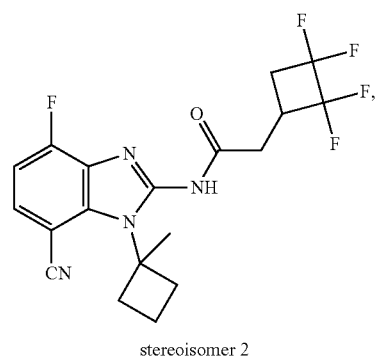
stereoisomer 2
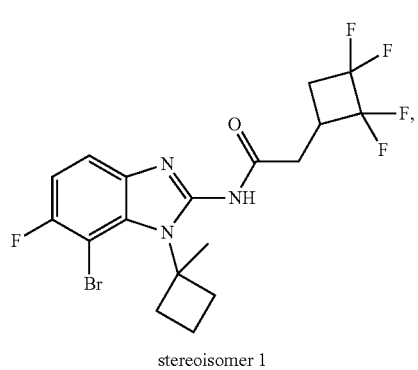
stereoisomer 1
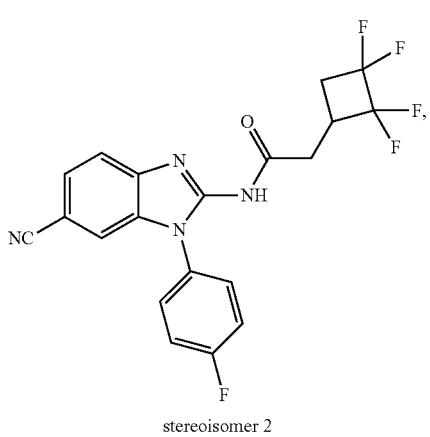
stereoisomer 2
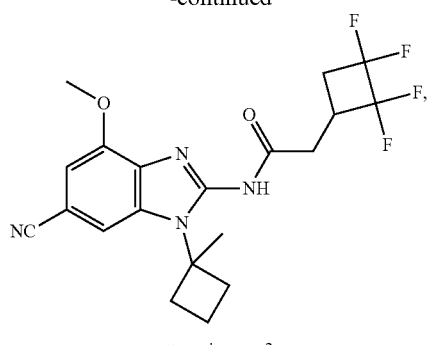
stereoisomer 2
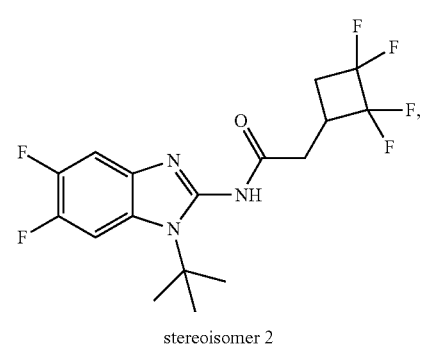
stereoisomer 2
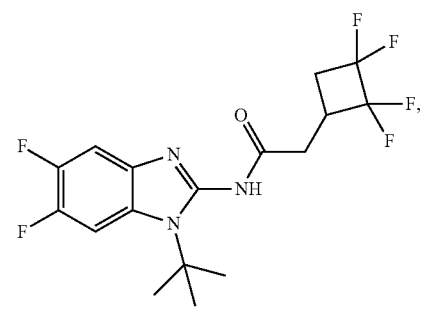
stereoisomer 1
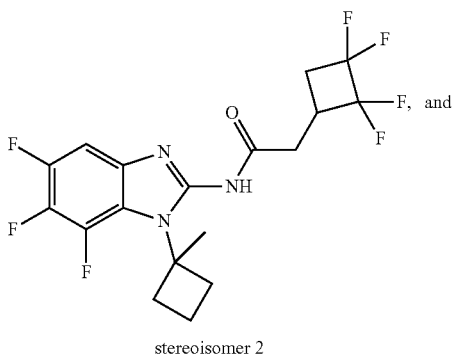
stereoisomer 2

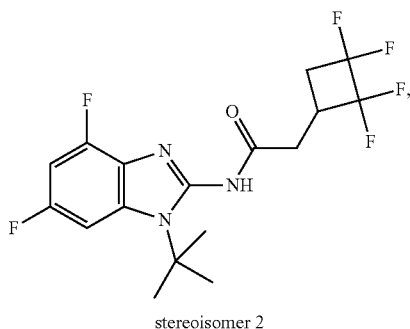

stereoisomer 2 or a pharmaceutically acceptable salt thereof.

5. A pharmaceutical composition comprising a compound of claim 1, or a pharmaceutically acceptable salt thereof.

6. A pharmaceutical composition comprising a compound of claim 2, or a pharmaceutically acceptable salt thereof.

7. A pharmaceutical composition comprising a compound of claim 3, or a pharmaceutically acceptable salt thereof.

8. A pharmaceutical composition comprising a compound of claim 4, or a pharmaceutically acceptable salt thereof.

9. The compound of claim 2, wherein the compound is

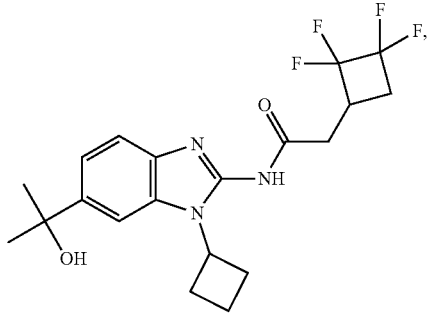

stereoisomer 1 or a pharmaceutically acceptable salt thereof.

10. The compound of claim 2, wherein the compound is

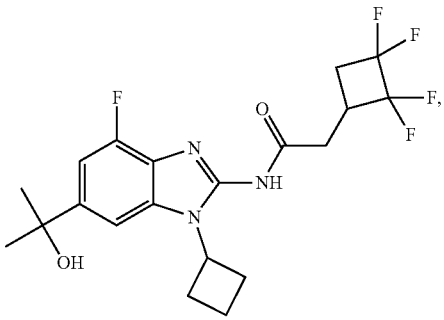

stereoisomer 1 or a pharmaceutically acceptable salt thereof.

11. The compound of claim 2, wherein the compound is

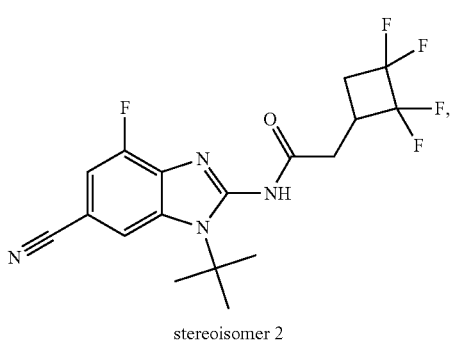 [SMILES: CC(C)(C)n1c(NC(=O)CC2CC(F)(F)C2(F)F)nc2c(F)cc(C#N)cc21]

stereoisomer 2 or a pharmaceutically acceptable salt thereof.

12. The compound of claim 3, wherein the compound is

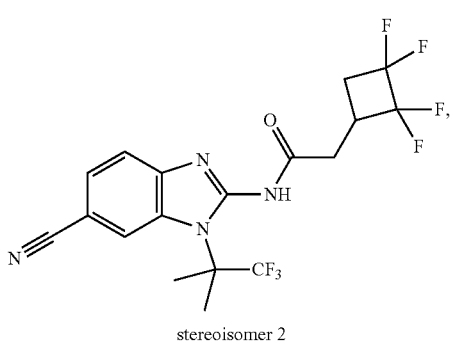 [SMILES: CC(C)(n1c(NC(=O)CC2CC(F)(F)C2(F)F)nc2ccc(C#N)cc21)C(F)(F)F]

stereoisomer 2 or a pharmaceutically acceptable salt thereof.

13. The compound of claim 3, wherein the compound is

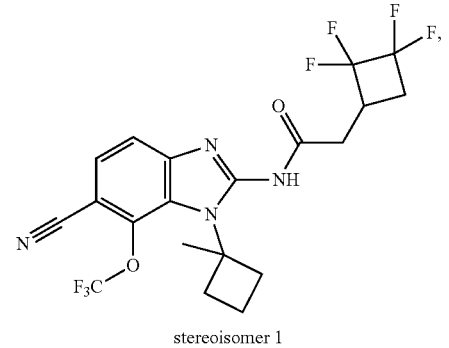 [SMILES: CC1(n2c(NC(=O)CC3CC(F)(F)C3(F)F)nc3ccc(C#N)c(OC(F)(F)F)c32)CCC1]

stereoisomer 1 or a pharmaceutically acceptable salt thereof.

14. The compound of claim 4, wherein the compound is

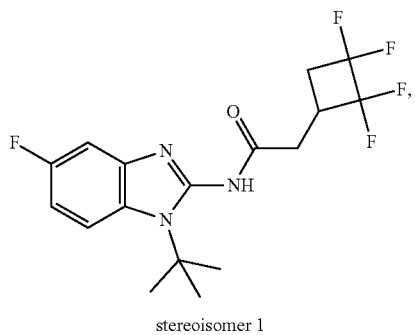 [SMILES: CC(C)(C)n1c(NC(=O)CC2CC(F)(F)C2(F)F)nc2cc(F)ccc21]

stereoisomer 1 or a pharmaceutically acceptable salt thereof.

15. The compound of claim 4, wherein the compound is

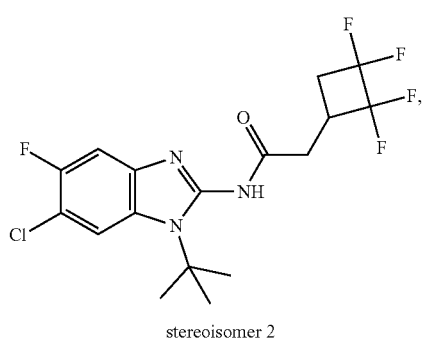 [SMILES: CC(C)(C)n1c(NC(=O)CC2CC(F)(F)C2(F)F)nc2cc(F)c(Cl)cc21]

stereoisomer 2 or a pharmaceutically acceptable salt thereof.

16. The compound of claim 4, wherein the compound is

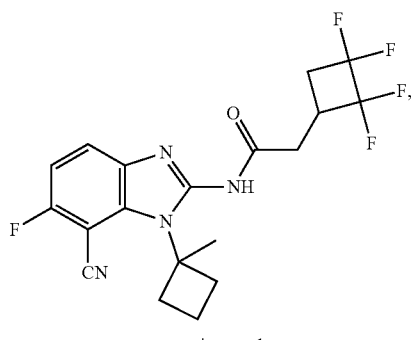

stereoisomer 1 or a pharmaceutically acceptable salt thereof.

17. The compound of claim 4, wherein the compound is

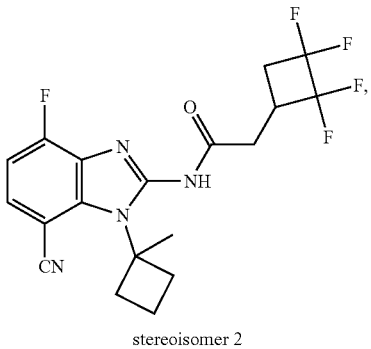 [SMILES: CC1(n2c(NC(=O)CC3CC(F)(F)C3(F)F)nc3c(F)ccc(C#N)c32)CCC1]

stereoisomer 2 or a pharmaceutically acceptable salt thereof.

18. The compound of claim 4, wherein the compound is

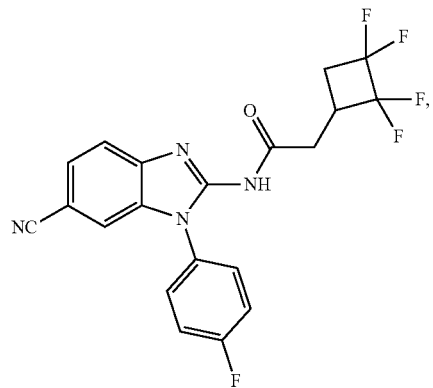

stereoisomer 2 or a pharmaceutically acceptable salt thereof.

19. The compound of claim 4, wherein the compound is

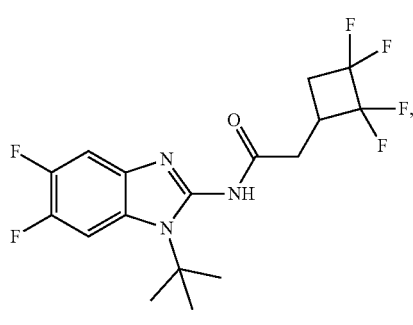

stereoisomer 2 or a pharmaceutically acceptable salt thereof.

20. The compound of claim 4, wherein the compound is
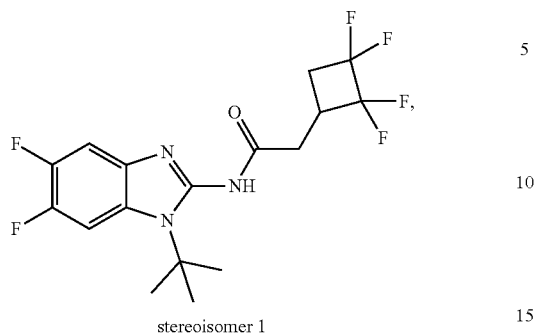
stereoisomer 1
or a pharmaceutically acceptable salt thereof.
* * * * *